US012701915B2

(12) United States Patent
Ma et al.

(10) Patent No.: US 12,701,915 B2
(45) Date of Patent: Aug. 4, 2026

(54) ORGANIC ELECTROLUMINESCENT MATERIALS AND DEVICES

(71) Applicant: UNIVERSAL DISPLAY CORPORATION, Ewing, NJ (US)

(72) Inventors: Bin Ma, Plainsboro, NJ (US); Alexey Borisovich Dyatkin, Ambler, PA (US); Bert Alleyne, Newtown, PA (US); Zhaoqun Zhou, Bedford, MA (US); Yuxin Shen, Hong Kong (CN); Lixia Zhang, Hong Kong (CN); Ting-Chih Wang, Lawrenceville, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 1049 days.

(21) Appl. No.: 17/569,691

(22) Filed: Jan. 6, 2022

(65) Prior Publication Data

US 2022/0255020 A1 Aug. 11, 2022

Related U.S. Application Data

(60) Provisional application No. 63/145,815, filed on Feb. 4, 2021.

(51) Int. Cl.

| | |
|---|---|
| ***C07D 405/10*** | (2006.01) |
| ***C07D 409/10*** | (2006.01) |
| ***C09K 11/06*** | (2006.01) |
| ***H10K 85/60*** | (2023.01) |
| *H10K 50/11* | (2023.01) |
| *H10K 101/10* | (2023.01) |

(52) U.S. Cl.

CPC ....... *H10K 85/6574* (2023.02); *C07D 405/10* (2013.01); *C07D 409/10* (2013.01); *C09K 11/06* (2013.01); *H10K 85/654* (2023.02); *H10K 85/6576* (2023.02); *C09K 2211/1018* (2013.01); *H10K 50/11* (2023.02); *H10K 2101/10* (2023.02)

(58) Field of Classification Search

None

See application file for complete search history.

(56) References Cited

U.S. PATENT DOCUMENTS

| | | | |
|---|---|---|---|
| 4,769,292 | A | 9/1988 | Tang et al. |
| 5,061,569 | A | 10/1991 | VanSlyke et al. |
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |

(Continued)

FOREIGN PATENT DOCUMENTS

| | | | |
|---|---|---|---|
| CN | 111269219 A * | 6/2020 | ........... C07D 409/14 |
| EP | 0650955 | 5/1995 | |

(Continued)

OTHER PUBLICATIONS

Machine translation of CN-111269219-A, translation generated Aug. 2025, 12 pages. (Year: 2025).*

(Continued)

*Primary Examiner* — Robert S Loewe

(74) *Attorney, Agent, or Firm* — DUANE MORRIS LLP

(57) ABSTRACT

A compound having a structure of Formula I,

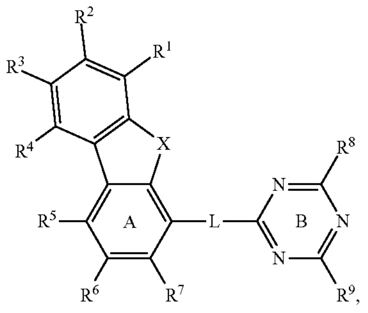

provided. In Formula I, each of $R^1$ to $R^7$ is hydrogen or phenyl or a system consisting of two to ten phenyl groups connected to each other; at least two of $R^1$ to $R^7$ are not hydrogen; each of $R^8$ and $R^9$ are phenyl or a system consisting of two to ten phenyl groups connected to each other; X is O, S, or Se; and L is a direct bond or

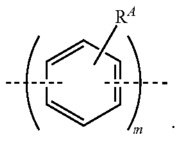

In the structure of L, m is an integer from 1 to 5, and $R^A$ is hydrogen, an aromatic or a heteroaromatic ring. Formulations, OLEDs, and consumer products containing the same are also provided.

20 Claims, 2 Drawing Sheets

(56) References Cited

U.S. PATENT DOCUMENTS

| | | | | |
|---|---|---|---|---|
| 6,468,819 | B1 | 10/2002 | Kim et al. | |
| 6,528,187 | B1 | 3/2003 | Okada | |
| 6,687,266 | B1 | 2/2004 | Ma et al. | |
| 6,835,469 | B2 | 12/2004 | Kwong et al. | |
| 6,921,915 | B2 | 7/2005 | Takiguchi et al. | |
| 7,087,321 | B2 | 8/2006 | Kwong et al. | |
| 7,090,928 | B2 | 8/2006 | Thompson et al. | |
| 7,154,114 | B2 | 12/2006 | Brooks et al. | |
| 7,250,226 | B2 | 7/2007 | Tokito et al. | |
| 7,279,704 | B2 | 10/2007 | Walters et al. | |
| 7,332,232 | B2 | 2/2008 | Ma et al. | |
| 7,338,722 | B2 | 3/2008 | Thompson et al. | |
| 7,393,599 | B2 | 7/2008 | Thompson et al. | |
| 7,396,598 | B2 | 7/2008 | Takeuchi et al. | |
| 7,431,968 | B1 | 10/2008 | Shtein et al. | |
| 7,445,855 | B2 | 11/2008 | Mackenzie et al. | |
| 7,534,505 | B2 | 5/2009 | Lin et al. | |
| 2002/0034656 | A1 | 3/2002 | Thompson et al. | |
| 2002/0134984 | A1 | 9/2002 | Igarashi | |
| 2002/0158242 | A1 | 10/2002 | Son et al. | |
| 2003/0138657 | A1 | 7/2003 | Li et al. | |
| 2003/0152802 | A1 | 8/2003 | Tsuboyama et al. | |
| 2003/0162053 | A1 | 8/2003 | Marks et al. | |
| 2003/0175553 | A1 | 9/2003 | Thompson et al. | |
| 2003/0230980 | A1 | 12/2003 | Forrest et al. | |
| 2004/0036077 | A1 | 2/2004 | Ise | |
| 2004/0137267 | A1 | 7/2004 | Igarashi et al. | |
| 2004/0137268 | A1 | 7/2004 | Garashi et al. | |
| 2004/0174116 | A1 | 9/2004 | Lu et al. | |
| 2005/0025993 | A1 | 2/2005 | Thompson et al. | |
| 2005/0112407 | A1 | 5/2005 | Ogasawara et al. | |
| 2005/0238919 | A1 | 10/2005 | Ogasawara | |
| 2005/0244673 | A1 | 11/2005 | Satoh et al. | |
| 2005/0260441 | A1 | 11/2005 | Thompson et al. | |
| 2005/0260449 | A1 | 11/2005 | Walters et al. | |
| 2006/0008670 | A1 | 1/2006 | Lin et al. | |
| 2006/0202194 | A1 | 9/2006 | Jeong et al. | |
| 2006/0240279 | A1 | 10/2006 | Adamovich et al. | |
| 2006/0251923 | A1 | 11/2006 | Lin et al. | |
| 2006/0263635 | A1 | 11/2006 | Ise | |
| 2006/0280965 | A1 | 12/2006 | Kwong et al. | |
| 2007/0190359 | A1 | 8/2007 | Knowles et al. | |
| 2007/0278938 | A1 | 12/2007 | Yabunouchi et al. | |
| 2008/0015355 | A1 | 1/2008 | Schafer et al. | |
| 2008/0018221 | A1 | 1/2008 | Egen et al. | |
| 2008/0106190 | A1 | 5/2008 | Yabunouchi et al. | |
| 2008/0124572 | A1 | 5/2008 | Mizuki et al. | |
| 2008/0220265 | A1 | 9/2008 | Xia et al. | |
| 2008/0297033 | A1 | 12/2008 | Knowles et al. | |
| 2009/0008605 | A1 | 1/2009 | Kawamura et al. | |
| 2009/0009065 | A1 | 1/2009 | Nishimura et al. | |
| 2009/0017330 | A1 | 1/2009 | Iwakuma et al. | |
| 2009/0030202 | A1 | 1/2009 | Iwakuma et al. | |
| 2009/0039776 | A1 | 2/2009 | Yamada et al. | |
| 2009/0045730 | A1 | 2/2009 | Nishimura et al. | |
| 2009/0045731 | A1 | 2/2009 | Nishimura et al. | |
| 2009/0101870 | A1 | 4/2009 | Prakash et al. | |
| 2009/0108737 | A1 | 4/2009 | Kwong et al. | |
| 2009/0115316 | A1 | 5/2009 | Zheng et al. | |
| 2009/0165846 | A1 | 7/2009 | Johannes et al. | |
| 2009/0167162 | A1 | 7/2009 | Lin et al. | |
| 2009/0179554 | A1 | 7/2009 | Kuma et al. | |
| 2016/0093808 | A1 | 3/2016 | Adamovich et al. | |
| 2017/0025618 | A1 | 1/2017 | Zheng et al. | |
| 2018/0301639 | A1 | 10/2018 | Zeng et al. | |
| 2019/0047991 | A1* | 2/2019 | Jung | C07D 411/14 |
| 2020/0079735 | A1 | 3/2020 | Ma et al. | |
| 2020/0127212 | A1 | 4/2020 | Adamovich et al. | |
| 2021/0047306 | A1* | 2/2021 | Jung | C07D 405/10 |
| 2021/0206754 | A1* | 7/2021 | Yoon | H10K 85/654 |
| 2022/0064153 | A1* | 3/2022 | Jung | C07D 409/14 |
| 2022/0199911 | A1* | 6/2022 | Lee | H10K 85/615 |
| 2022/0255020 | A1* | 8/2022 | Ma | H10K 85/6576 |

FOREIGN PATENT DOCUMENTS

| | | | |
|---|---|---|---|
| EP | 1725079 | 11/2006 | |
| EP | 2034538 | 3/2009 | |
| EP | 2966706 | 1/2016 | |
| JP | 200511610 | 1/2005 | |
| JP | 2007123392 | 5/2007 | |
| JP | 2007254297 | 10/2007 | |
| JP | 2008074939 | 4/2008 | |
| WO | 01/39234 | 5/2001 | |
| WO | 02/02714 | 1/2002 | |
| WO | 02015654 | 2/2002 | |
| WO | 03040257 | 5/2003 | |
| WO | 03060956 | 7/2003 | |
| WO | 2004093207 | 10/2004 | |
| WO | 2004107822 | 12/2004 | |
| WO | 2005014551 | 2/2005 | |
| WO | 2005019373 | 3/2005 | |
| WO | 2005030900 | 4/2005 | |
| WO | 2005089025 | 9/2005 | |
| WO | 2005123873 | 12/2005 | |
| WO | 2006009024 | 1/2006 | |
| WO | 2006056418 | 6/2006 | |
| WO | 2006072002 | 7/2006 | |
| WO | 2006082742 | 8/2006 | |
| WO | 2006098120 | 9/2006 | |
| WO | 2006100298 | 9/2006 | |
| WO | 2006103874 | 10/2006 | |
| WO | 2006114966 | 11/2006 | |
| WO | 2006132173 | 12/2006 | |
| WO | 2007002683 | 1/2007 | |
| WO | 2007004380 | 1/2007 | |
| WO | 2007063754 | 6/2007 | |
| WO | 2007063796 | 6/2007 | |
| WO | 2008056746 | 5/2008 | |
| WO | 2008101842 | 8/2008 | |
| WO | 2008132085 | 11/2008 | |
| WO | 2009000673 | 12/2008 | |
| WO | 2009003898 | 1/2009 | |
| WO | 2009008311 | 1/2009 | |
| WO | 2009018009 | 2/2009 | |
| WO | 2009021126 | 2/2009 | |
| WO | 2009050290 | 4/2009 | |
| WO | 2009062578 | 5/2009 | |
| WO | 2009063833 | 5/2009 | |
| WO | 2009066778 | 5/2009 | |
| WO | 2009066779 | 5/2009 | |
| WO | 2009086028 | 7/2009 | |
| WO | 2009100991 | 8/2009 | |
| WO | WO-2020013572 A1 * | 1/2020 | C07B 59/002 |
| WO | 2020/071863 | 4/2020 | |
| WO | WO-2020231197 A1 * | 11/2020 | C07D 251/24 |

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 1, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 1: 15-20 (2000).

(56) References Cited

OTHER PUBLICATIONS

Hamada, Yuji et al., "High Luminance in Organic Electroluminescent Devices with Bis(10-hydroxybenzo[h]quinolinato) beryllium as an Emitter," Chem. Lett., 905-906 (1993).
Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2, N)iridium(III) Derivatives," Adv. Mater., 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi et al., "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18 (21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota, Yasuhiko, "5,5'-Bis(dimesitylboryl)-2,2'-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent ridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8): 1832-1833 (2000).
Salbeck, J. et al., "Low Molecular Organic Glasses for Blue Electroluminescence," Synthetic Metals, 91: 209-215 (1997).
Shirota, Yasuhiko et al., "Starburst Molecules Based on pi-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing NCN-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 88:171-177 (1997).
Takizawa, Shin-ya et al., "Phosphorescent Iridium Complexes Based on 2-Phenylimidazo[1,2- α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69 (15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).

* cited by examiner

ORGANIC ELECTROLUMINESCENT MATERIALS AND DEVICES

CROSS-REFERENCE TO RELATED APPLICATIONS

This application claims priority under 35 U.S.C. § 119(e) to U.S. Provisional Application No. 63/145,815, filed on Feb. 4, 2021, the entire contents of which are incorporated herein by reference.

FIELD

The present disclosure generally relates to organometallic compounds and formulations and their various uses including as hosts or emitters in devices such as organic light emitting diodes and related electronic devices.

BACKGROUND

Opto-electronic devices that make use of organic materials are becoming increasingly desirable for various reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes/devices (OLEDs), organic phototransistors, organic photovoltaic cells, and organic photodetectors. For OLEDs, the organic materials may have performance advantages over conventional materials.

OLEDs make use of thin organic films that emit light when voltage is applied across the device. OLEDs are becoming an increasingly interesting technology for use in applications such as flat panel displays, illumination, and backlighting.

One application for phosphorescent emissive molecules is a full color display. Industry standards for such a display call for pixels adapted to emit particular colors, referred to as "saturated" colors. In particular, these standards call for saturated red, green, and blue pixels. Alternatively, the OLED can be designed to emit white light. In conventional liquid crystal displays emission from a white backlight is filtered using absorption filters to produce red, green and blue emission. The same technique can also be used with OLEDs. The white OLED can be either a single emissive layer (EML) device or a stack structure. Color may be measured using CIE coordinates, which are well known to the art.

SUMMARY

In one aspect, the present disclosure provides a compound having a structure of Formula I:

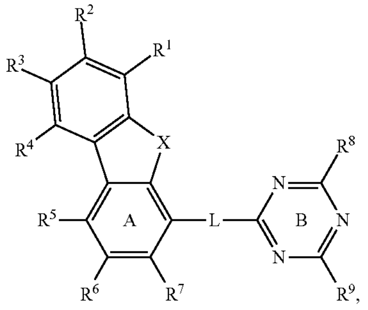

where:

each of $R^1$ to $R^7$ is independently a hydrogen or a substituent selected from the group consisting of phenyl, and a system consisting of two to ten phenyl groups connected to each other;

at least two of $R^1$ to $R^7$ are not hydrogen;

$R^8$ and $R^9$ are each independently selected from the group consisting of phenyl, and a system consisting of two to ten phenyl groups connected to each other;

X is selected from the group consisting of O, S, and Se; and

L is selected from the group consisting of direct bond and

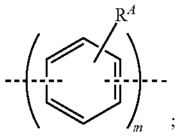
;

wherein m is an integer from 1 to 5, and $R^A$ is a hydrogen or a substituent selected from the group consisting of aromatic and heteroaromatic rings;

with the proviso that the following structures are excluded

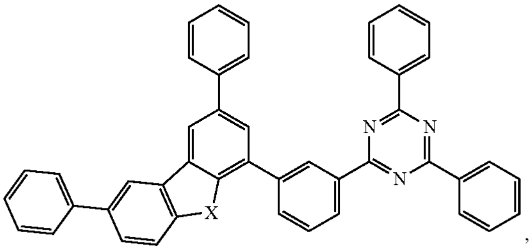
, and

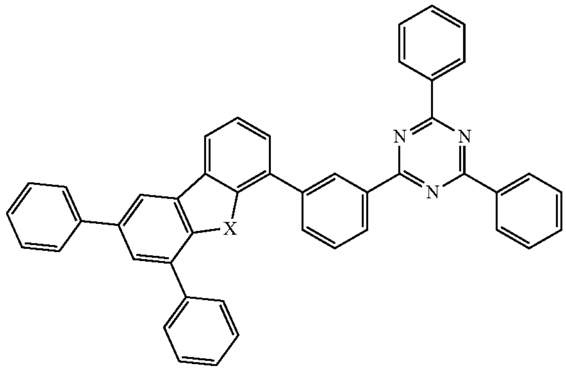
.

In another aspect, the present disclosure provides a formulation of the compound of the present disclosure.

In yet another aspect, the present disclosure provides an OLED having an organic layer comprising the compound of the present disclosure.

In yet another aspect, the present disclosure provides a consumer product comprising an OLED with an organic layer comprising the compound of the present disclosure.

DETAILED DESCRIPTION

A. Terminology

Figure 1:
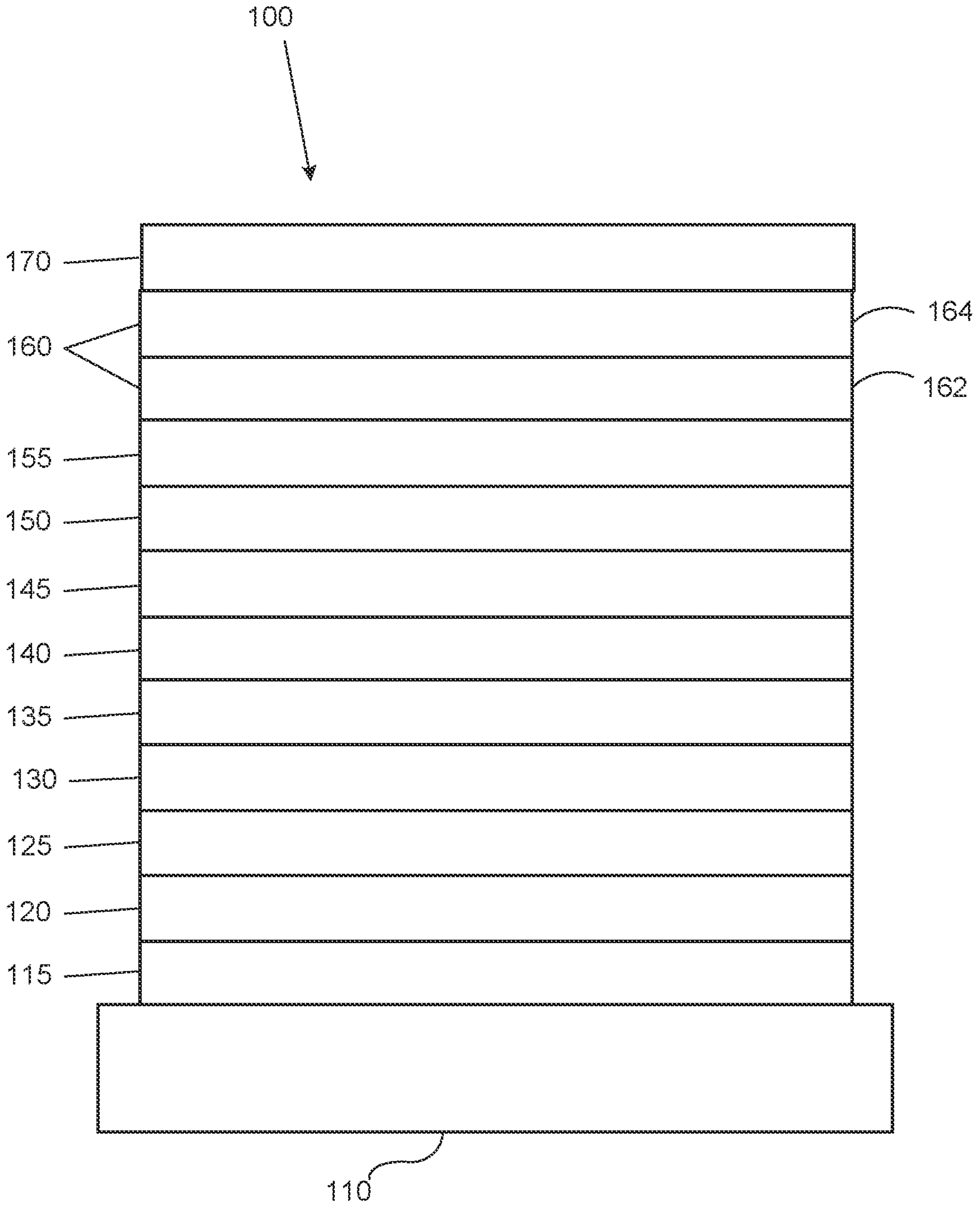
FIG. 1 shows an organic light emitting device.

Unless otherwise specified, the below terms used herein are defined as follows:

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processable" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

The terms "halo," "halogen," and "halide" are used interchangeably and refer to fluorine, chlorine, bromine, and iodine.

The term "acyl" refers to a substituted carbonyl radical ($C(O)—R_s$).

The term "ester" refers to a substituted oxycarbonyl ($—O—C(O)—R_s$ or $—C(O)—O—R_s$) radical.

The term "ether" refers to an $—OR_s$ radical.

The terms "sulfanyl" or "thio-ether" are used interchangeably and refer to a $—SR_s$ radical.

The term "selenyl" refers to a $—SeR_s$ radical.

The term "sulfinyl" refers to a $—S(O)—R_s$ radical.

The term "sulfonyl" refers to a $—SO_2—R_s$ radical.

The term "phosphino" refers to a $—P(R_s)_3$ radical, wherein each $R_s$ can be same or different.

The term "silyl" refers to a $—Si(R_s)_3$ radical, wherein each $R_s$ can be same or different.

The term "germyl" refers to a $—Ge(R_s)_3$ radical, wherein each $R_s$ can be same or different.

The term "boryl" refers to a $—B(R_s)_2$ radical or its Lewis adduct $—B(R_s)_3$ radical, wherein $R_s$ can be same or different.

In each of the above, $R_s$ can be hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, and combination thereof. Preferred $R_s$ is selected from the group consisting of alkyl, cycloalkyl, aryl, heteroaryl, and combination thereof.

The term "alkyl" refers to and includes both straight and branched chain alkyl radicals. Preferred alkyl groups are those containing from one to fifteen carbon atoms and includes methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group may be optionally substituted.

The term "cycloalkyl" refers to and includes monocyclic, polycyclic, and spiro alkyl radicals. Preferred cycloalkyl groups are those containing 3 to 12 ring carbon atoms and includes cyclopropyl, cyclopentyl, cyclohexyl, bicyclo[3.1.1]heptyl, spiro[4.5]decyl, spiro[5.5]undecyl, adamantyl, and the like. Additionally, the cycloalkyl group may be optionally substituted.

The terms "heteroalkyl" or "heterocycloalkyl" refer to an alkyl or a cycloalkyl radical, respectively, having at least one carbon atom replaced by a heteroatom. Optionally the at least one heteroatom is selected from O, S, N, P, B, Si and Se, preferably, 0, S or N. Additionally, the heteroalkyl or heterocycloalkyl group may be optionally substituted.

The term "alkenyl" refers to and includes both straight and branched chain alkene radicals. Alkenyl groups are essentially alkyl groups that include at least one carbon-carbon double bond in the alkyl chain Cycloalkenyl groups are essentially cycloalkyl groups that include at least one carbon-carbon double bond in the cycloalkyl ring. The term "heteroalkenyl" as used herein refers to an alkenyl radical having at least one carbon atom replaced by a heteroatom. Optionally the at least one heteroatom is selected from O, S, N, P, B, Si, and Se, preferably, O, S, or N. Preferred alkenyl, cycloalkenyl, or heteroalkenyl groups are those containing two to fifteen carbon atoms. Additionally, the alkenyl, cycloalkenyl, or heteroalkenyl group may be optionally substituted.

The term "alkynyl" refers to and includes both straight and branched chain alkyne radicals. Alkynyl groups are essentially alkyl groups that include at least one carbon-carbon triple bond in the alkyl chain Preferred alkynyl groups are those containing two to fifteen carbon atoms. Additionally, the alkynyl group may be optionally substituted.

The terms "aralkyl" or "arylalkyl" are used interchangeably and refer to an alkyl group that is substituted with an aryl group. Additionally, the aralkyl group may be optionally substituted.

The term "heterocyclic group" refers to and includes aromatic and non-aromatic cyclic radicals containing at least one heteroatom. Optionally the at least one heteroatom is selected from O, S, N, P, B, Si, and Se, preferably, O, S, or N. Hetero-aromatic cyclic radicals may be used interchangeably with heteroaryl. Preferred hetero-non-aromatic cyclic groups are those containing 3 to 7 ring atoms which includes at least one hetero atom, and includes cyclic amines such as morpholino, piperidino, pyrrolidino, and the like, and cyclic ethers/thio-ethers, such as tetrahydrofuran, tetrahydropyran, tetrahydrothiophene, and the like. Additionally, the heterocyclic group may be optionally substituted.

The term "aryl" refers to and includes both single-ring aromatic hydrocarbyl groups and polycyclic aromatic ring systems. The polycyclic rings may have two or more rings in which two carbons are common to two adjoining rings (the rings are "fused") wherein at least one of the rings is an aromatic hydrocarbyl group, e.g., the other rings can be cycloalkyls, cycloalkenyls, aryl, heterocycles, and/or heteroaryls. Preferred aryl groups are those containing six to thirty carbon atoms, preferably six to twenty carbon atoms, more preferably six to twelve carbon atoms. Especially preferred is an aryl group having six carbons, ten carbons or twelve carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group may be optionally substituted.

The term "heteroaryl" refers to and includes both single-ring aromatic groups and polycyclic aromatic ring systems that include at least one heteroatom. The heteroatoms include, but are not limited to O, S, N, P, B, Si, and Se. In many instances, O, S, or N are the preferred heteroatoms. Hetero-single ring aromatic systems are preferably single rings with 5 or 6 ring atoms, and the ring can have from one to six heteroatoms. The hetero-polycyclic ring systems can have two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. The hetero-polycyclic aromatic ring systems can have from one to six heteroatoms per ring of the polycyclic aromatic ring system. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

Of the aryl and heteroaryl groups listed above, the groups of triphenylene, naphthalene, anthracene, dibenzothiophene, dibenzofuran, dibenzoselenophene, carbazole, indolocarbazole, imidazole, pyridine, pyrazine, pyrimidine, triazine, and benzimidazole, and the respective aza-analogs of each thereof are of particular interest.

The terms alkyl, cycloalkyl, heteroalkyl, heterocycloalkyl, alkenyl, cycloalkenyl, heteroalkenyl, alkynyl, aralkyl, heterocyclic group, aryl, and heteroaryl, as used herein, are independently unsubstituted, or independently substituted, with one or more general substituents.

In many instances, the general substituents are selected from the group consisting of deuterium, halogen, alkyl, cycloalkyl, heteroalkyl, heterocycloalkyl, arylalkyl, alkoxy, aryloxy, amino, silyl, germyl, alkenyl, cycloalkenyl, heteroalkenyl, alkynyl, aryl, heteroaryl, acyl, carboxylic acid, ether, ester, nitrile, isonitrile, sulfanyl, selenyl, sulfinyl, sulfonyl, phosphino, boryl, and combinations thereof.

In some instances, the preferred general substituents are selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, sulfanyl, boryl, and combinations thereof.

In some instances, the more preferred general substituents are selected from the group consisting of deuterium, fluorine, alkyl, cycloalkyl, alkoxy, aryloxy, amino, silyl, boryl, aryl, heteroaryl, sulfanyl, and combinations thereof.

In yet other instances, the most preferred general substituents are selected from the group consisting of deuterium, fluorine, alkyl, cycloalkyl, aryl, heteroaryl, and combinations thereof.

The terms "substituted" and "substitution" refer to a substituent other than H that is bonded to the relevant position, e.g., a carbon or nitrogen. For example, when $R^1$ represents mono-substitution, then one $R^1$ must be other than H (i.e., a substitution). Similarly, when $R^1$ represents di-substitution, then two of $R^1$ must be other than H. Similarly, when $R^1$ represents zero or no substitution, $R^1$, for example, can be a hydrogen for available valencies of ring atoms, as in carbon atoms for benzene and the nitrogen atom in pyrrole, or simply represents nothing for ring atoms with fully filled valencies, e.g., the nitrogen atom in pyridine. The maximum number of substitutions possible in a ring structure will depend on the total number of available valencies in the ring atoms.

As used herein, "combinations thereof" indicates that one or more members of the applicable list are combined to form a known or chemically stable arrangement that one of ordinary skill in the art can envision from the applicable list. For example, an alkyl and deuterium can be combined to form a partial or fully deuterated alkyl group; a halogen and alkyl can be combined to form a halogenated alkyl substituent; and a halogen, alkyl, and aryl can be combined to form a halogenated arylalkyl. In one instance, the term substitution includes a combination of two to four of the listed groups. In another instance, the term substitution includes a combination of two to three groups. In yet another instance, the term substitution includes a combination of two groups. Preferred combinations of substituent groups are those that contain up to fifty atoms that are not hydrogen or deuterium, or those which include up to forty atoms that are not hydrogen or deuterium, or those that include up to thirty atoms that are not hydrogen or deuterium. In many instances, a preferred combination of substituent groups will include up to twenty atoms that are not hydrogen or deuterium.

The "aza" designation in the fragments described herein, i.e. aza-dibenzofuran, aza-dibenzothiophene, etc. means that one or more of the C—H groups in the respective aromatic ring can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

As used herein, "deuterium" refers to an isotope of hydrogen. Deuterated compounds can be readily prepared using methods known in the art. For example, U.S. Pat. No. 8,557,400, Patent Pub. No. WO 2006/095951, and U.S. Pat. Application Pub. No. US 2011/0037057, which are hereby incorporated by reference in their entireties, describe the making of deuterium-substituted organometallic complexes. Further reference is made to Ming Yan, et al., *Tetrahedron* 2015, 71, 1425-30 and Atzrodt et al., *Angew. Chem. Int. Ed.* (*Reviews*) 2007, 46, 7744-65, which are incorporated by reference in their entireties, describe the deuteration of the methylene hydrogens in benzyl amines and efficient pathways to replace aromatic ring hydrogens with deuterium, respectively.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In some instance, a pair of adjacent substituents can be optionally joined or fused into a ring. The preferred ring is a five, six, or seven-membered carbocyclic or heterocyclic ring, includes both instances where the portion of the ring formed by the pair of substituents is saturated and where the portion of the ring formed by the pair of substituents is unsaturated. As used herein, "adjacent" means that the two substituents involved can be on the same ring next to each other, or on two neighboring rings having the two closest available substitutable positions, such as 2, 2' positions in a biphenyl, or 1, 8 position in a naphthalene, as long as they can form a stable fused ring system.

B. The Compounds of the Present Disclosure

In one aspect, the present disclosure provides a compound having a structure of Formula I:

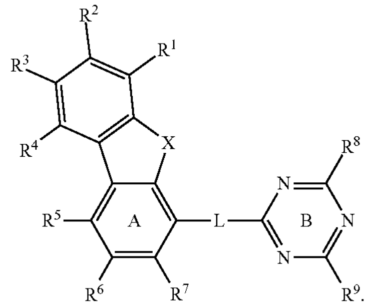

In the structure of Formula I:

each of $R^1$ to $R^7$ is independently a hydrogen or a substituent selected from the group consisting of phenyl, and a system consisting of two to ten phenyl groups connected to each other;

at least two of $R^1$ to $R^7$ are not hydrogen;

$R^8$ and $R^9$ are each independently selected from the group consisting of phenyl, and a system consisting of two to ten phenyl groups connected to each other;

X is selected from the group consisting of O, S, and Se; and

L is selected from the group consisting of direct bond and

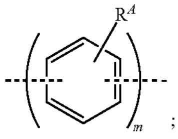

;

wherein m is an integer from 1 to 5, and $R^A$ is a hydrogen or a substituent selected from the group consisting of aromatic and heteroaromatic rings. In addition, the following structures are excluded from Formula I:

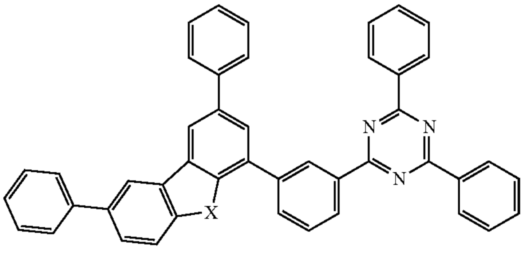

, and

-continued

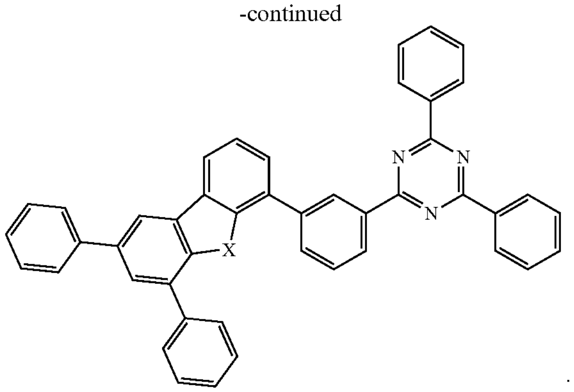

In some embodiments, m is 0. In some embodiments, m is 1 to 3. In some embodiments, m is 1 or 2.

In some embodiments, when (1) m is 1 with ring A and ring B meta to each other, and (2)(i) $R^1$ and $R^3$ are phenyl and $R^2$ and $R^4$ to $R^7$ are H, or (ii) $R^3$ and $R^6$ are phenyl and $R^1$, $R^2$, $R^4$, $R^5$, and $R^7$ are H, then $R^1$ to $R^9$ have a total of at least 5 phenyl groups. In some such embodiments, $R^1$ to $R^9$ have a total of at least 6 phenyl groups or at least 7 phenyl groups.

In some embodiments, m is 1, ring A and ring B are meta to each other, and $R^1$ to $R^9$ comprise a total of at least 6 phenyl groups. In some such embodiments, $R^1$ to $R^9$ comprise a total of at least 7 phenyl groups or a total of at least 8 phenyl groups In some embodiments, m is 1, ring A and ring B are meta to each other, and $R^1$ to $R^9$ comprise a total of at least 7 phenyl groups. In some such embodiments, $R^1$ to $R^9$ comprise a total of at least 8 phenyl groups or $R^1$ to $R^9$ comprise a total of at least 9 phenyl groups.

In some embodiments, at least two of $R^1$ to $R^4$ are not hydrogen.

In some embodiments, at least two of $R^5$ to $R^7$ are not hydrogen.

In some embodiments, at least one of $R^1$ to $R^4$ is not hydrogen and at least one of $R^5$ to $R^7$ is not hydrogen. In some embodiments, at least two of $R^1$ to $R^4$ are not hydrogen and at least one of $R^5$ to $R^7$ is not hydrogen. In some embodiments, at least one of $R^1$ to $R^4$ is not hydrogen and at least two of $R^5$ to $R^7$ are not hydrogen.

In some embodiments, at least three of $R^1$ to $R^7$ are not hydrogen.

In some embodiments, $R^8$ is phenyl and $R^9$ is phenyl. In some embodiments, $R^8$ is phenyl and $R^9$ is biphenyl. In some embodiments, $R^8$ is biphenyl and $R^9$ is biphenyl.

In some embodiments, X is O. In some embodiments, X is S. In some embodiments, X is Se.

In some embodiments, when any of $R^1$ to $R^9$ is a system consisting of two to ten phenyl groups connected to each other, each of the phenyl groups are connected in a linear, meta configuration.

In some embodiments, when any of $R^1$ to $R^9$ is a system consisting of two to ten phenyl groups connected to each other, each of the phenyl groups are connected in a linear, para configuration.

In some embodiments, when any of $R^1$ to $R^9$ is a system consisting of two to ten phenyl groups connected to each other, none of the phenyl groups are connected in an ortho configuration.

In some embodiments, $R^4$ is selected from the group consisting of hydrogen, phenyl, biphenyl, and terphenyl.

In some embodiments, L has a structure selected from the group consisting of a direct bond,

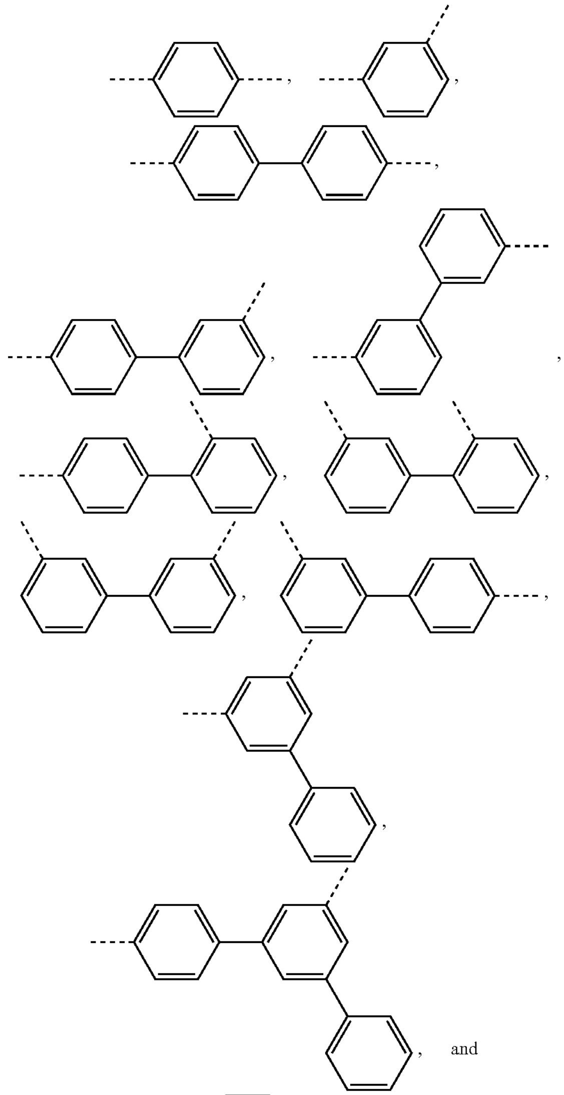

and

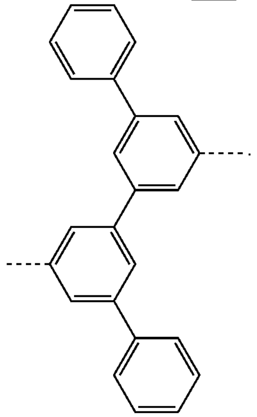

In some embodiments, $R^3$ and $R^6$ are not hydrogen. In some embodiments, $R^1$ and $R^3$ are not hydrogen.

In some embodiments, each of $R^1$ to $R^9$ that includes at least two phenyl groups has the phenyl groups connected in a linear configuration.

In some embodiments, at least one of $R^1$ to $R^9$ is a branched phenyl group. In some embodiments, at least one of $R^1$ to $R^7$ is a branched phenyl group. In some embodiments, at least one of $R^8$ and $R^9$ is a branched phenyl group.

In some embodiments, at least one of $R^1$ to $R^9$ includes at least three phenyl groups. In some embodiments, at least one of $R^1$ to $R^7$ includes at least three phenyl groups. In some embodiments, at least one of $R^8$ and $R^9$ includes at least three phenyl groups.

In some embodiments, at least one of $R^1$ to $R^9$ includes at least four phenyl groups.

In some embodiments, $R^1$ to $R^9$ includes a total of at least 6 phenyl groups. In some embodiments, $R^1$ to $R^9$ includes a total of at least 7 phenyl groups. In some embodiments, $R^1$ to $R^9$ includes a total of at least 8 phenyl groups.

In some embodiments, the compound is selected from the group consisting of:

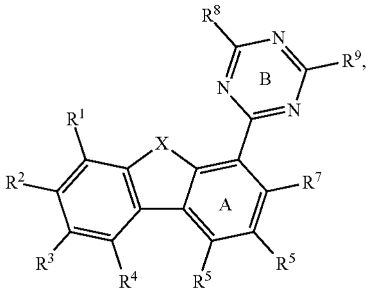

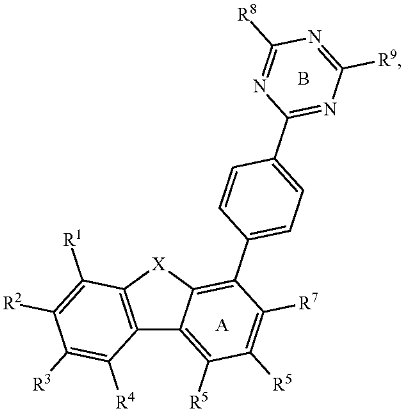

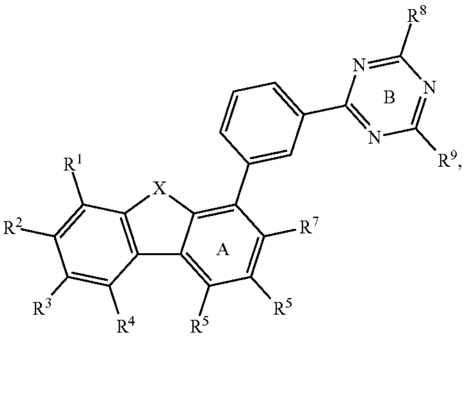

-continued

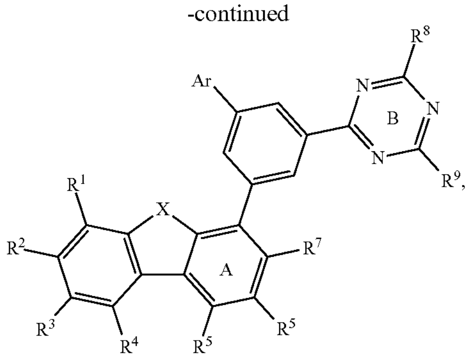

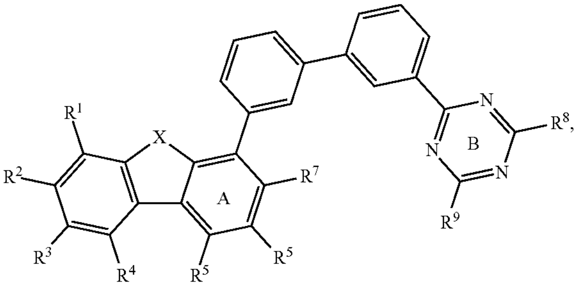

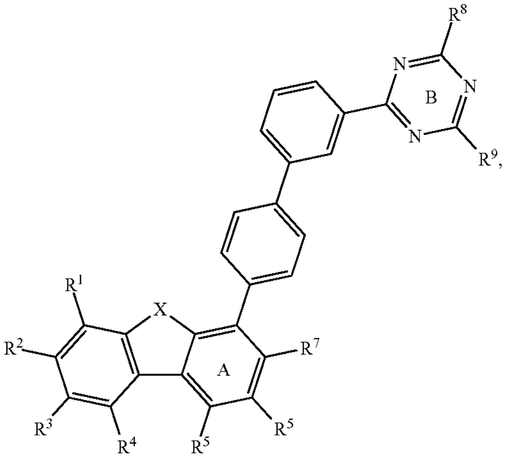

and

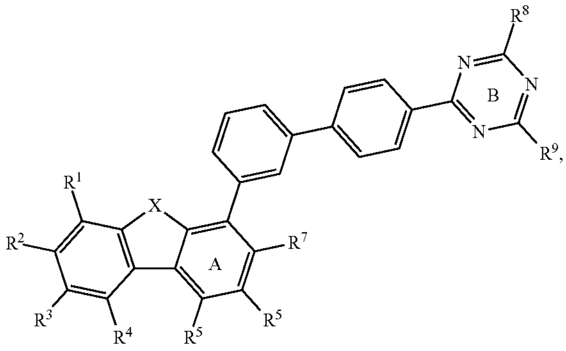

wherein Ar is an aromatic or heteroaromatic ring.

In some embodiments, the compound is selected from the group consisting of:

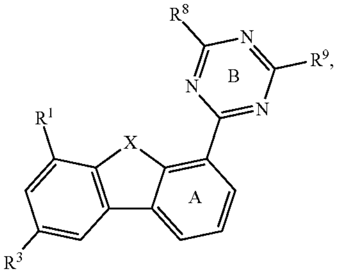
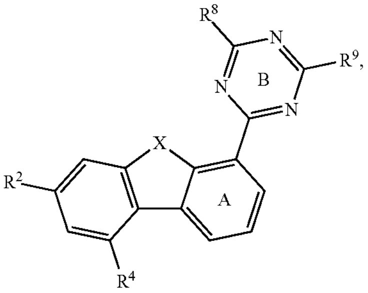
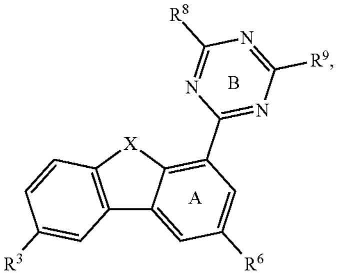
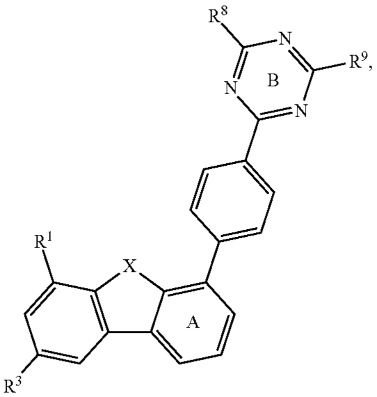
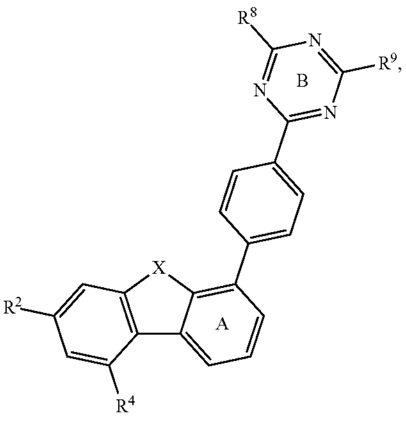
-continued
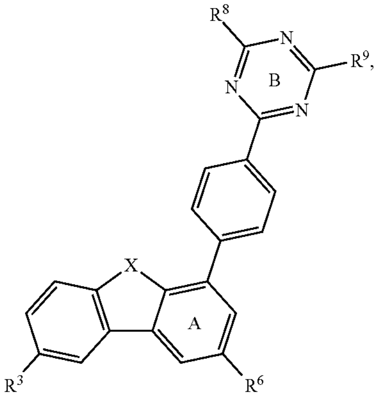
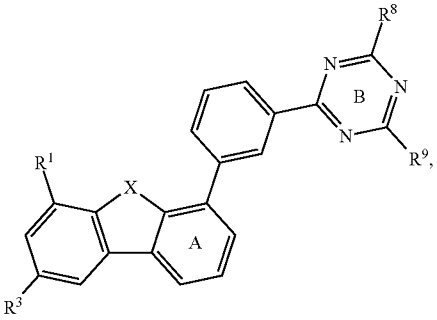
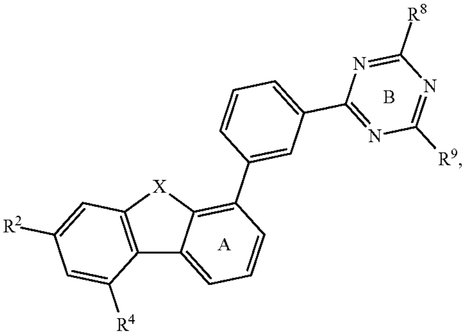
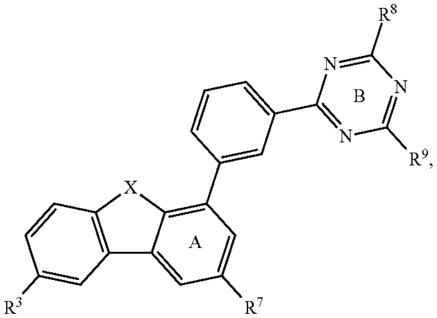
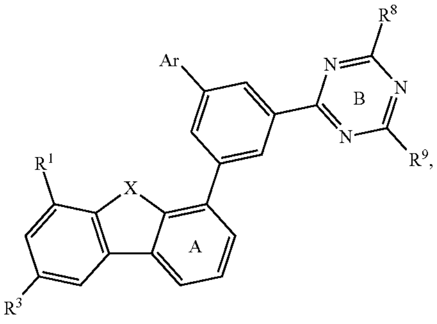

-continued
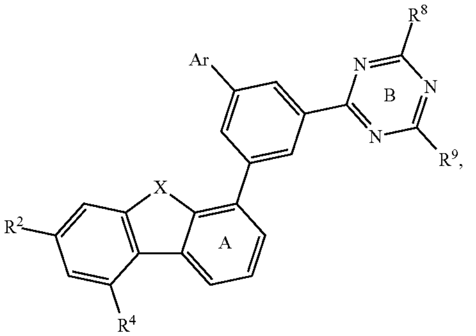
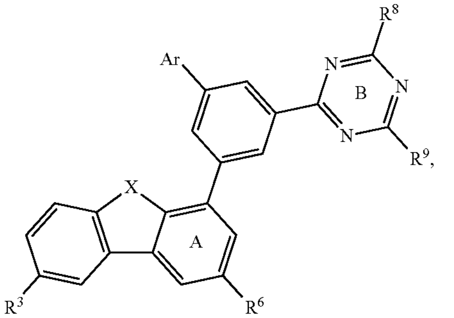
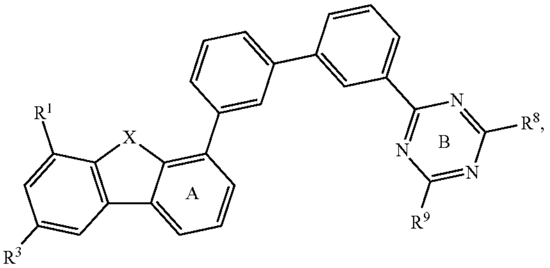
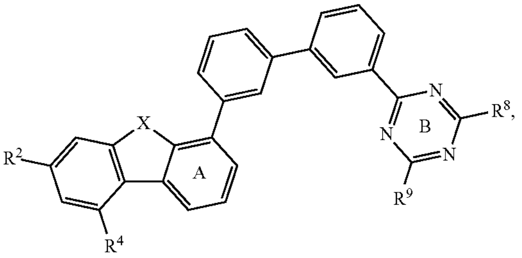
and
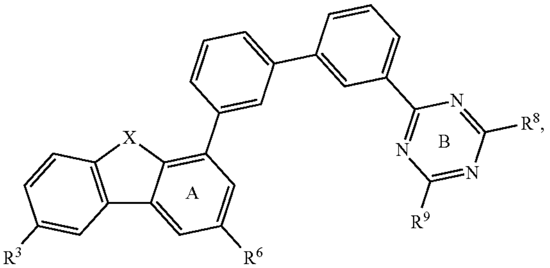
wherein Ar is an aromatic or heteroaromatic ring.
In some embodiments, the compound is selected from the group consisting of the structures in the following LIST 1:
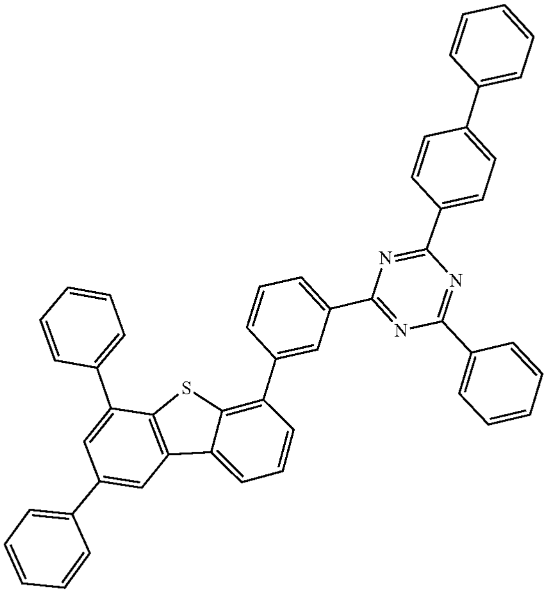
,
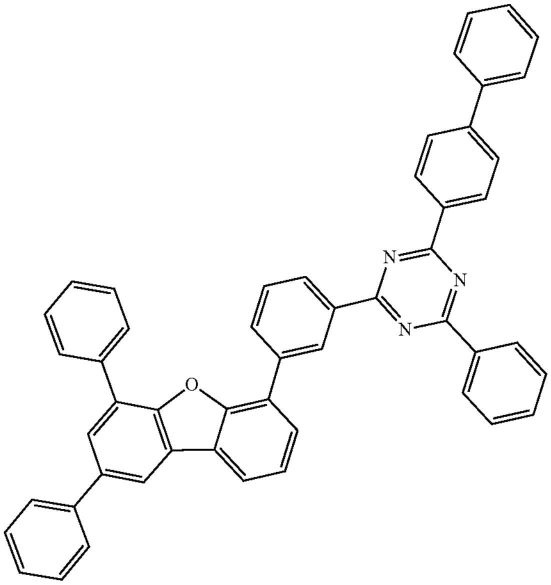
, -continued
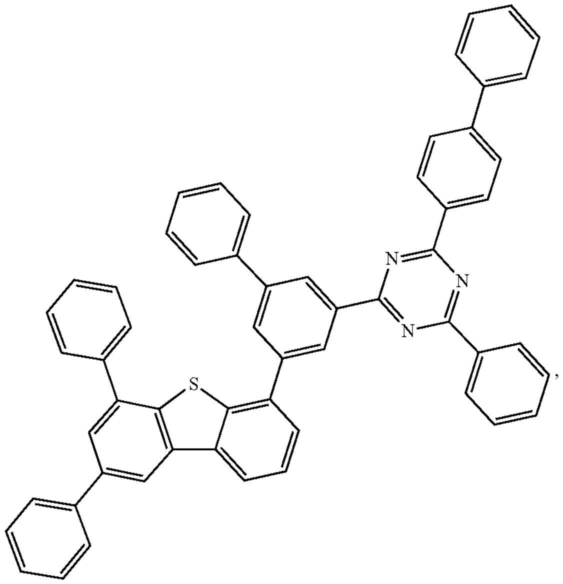
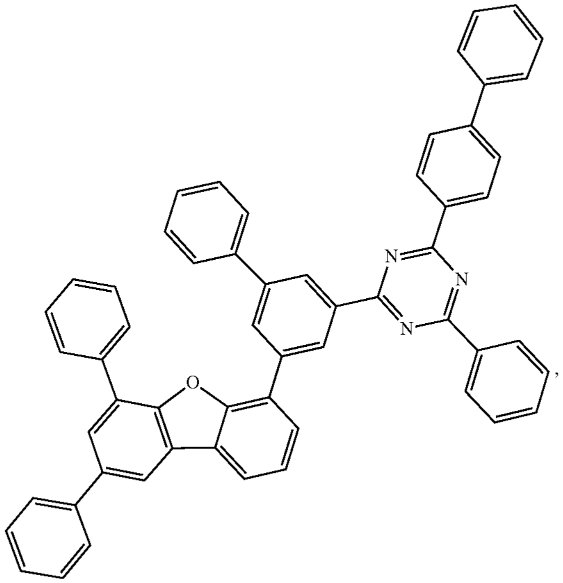
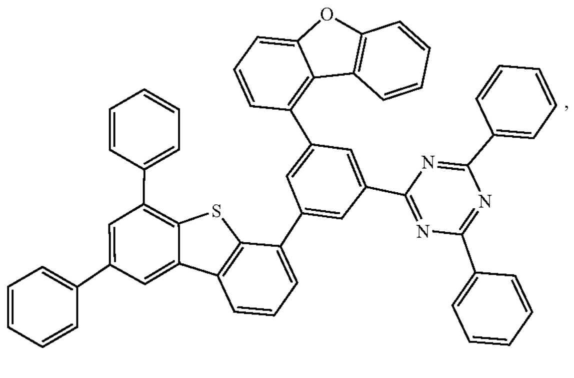
-continued
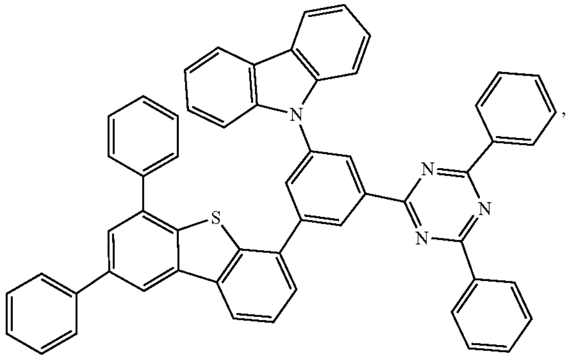
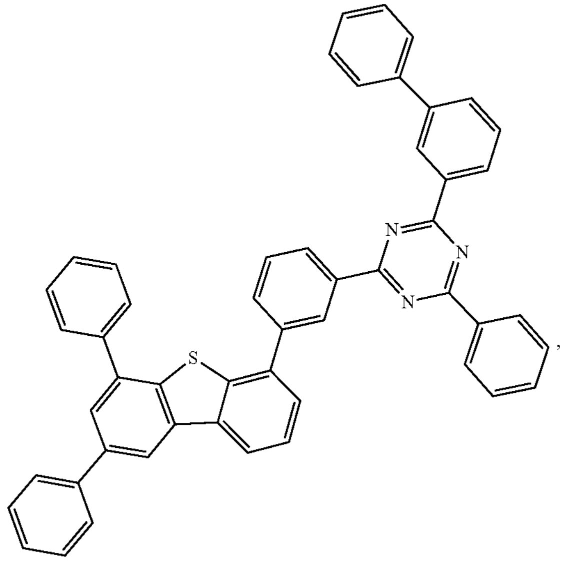
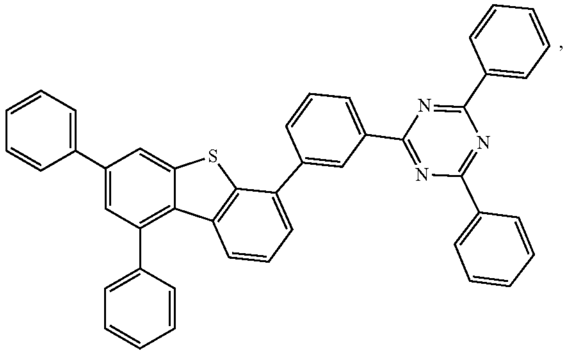
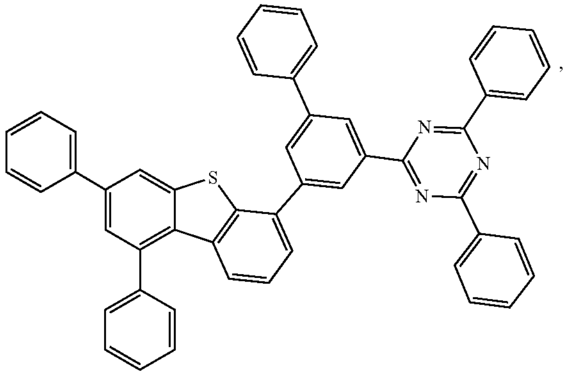

-continued
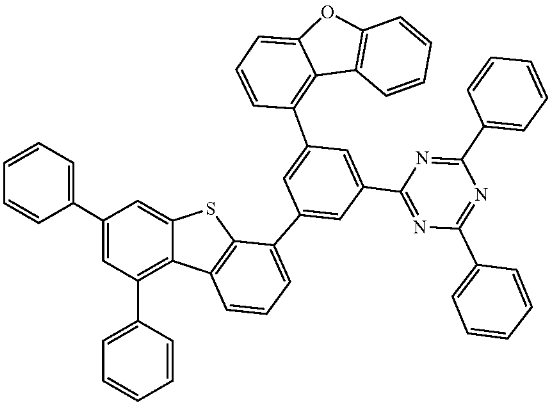,
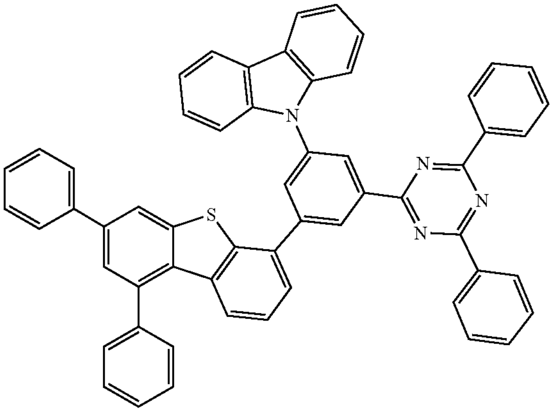,
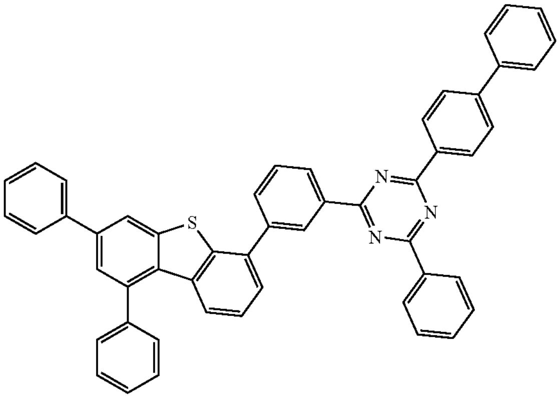,
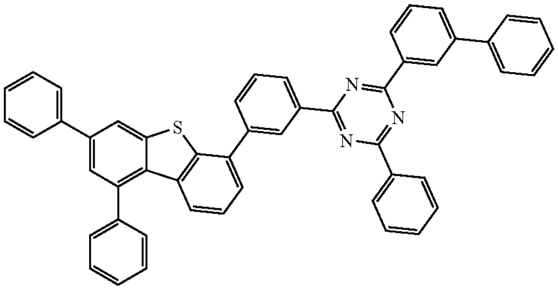,
-continued
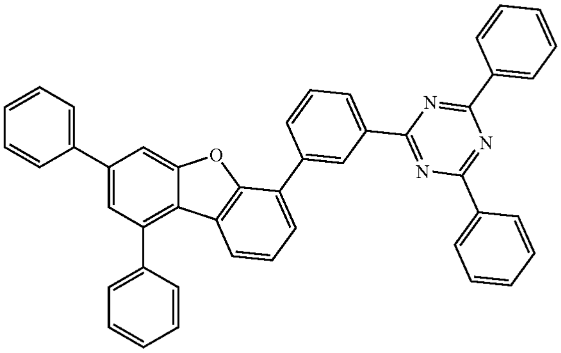,
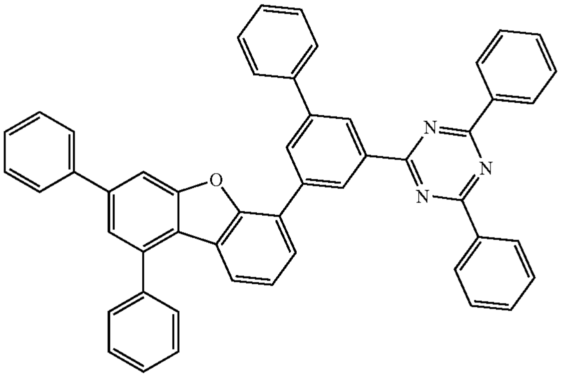,
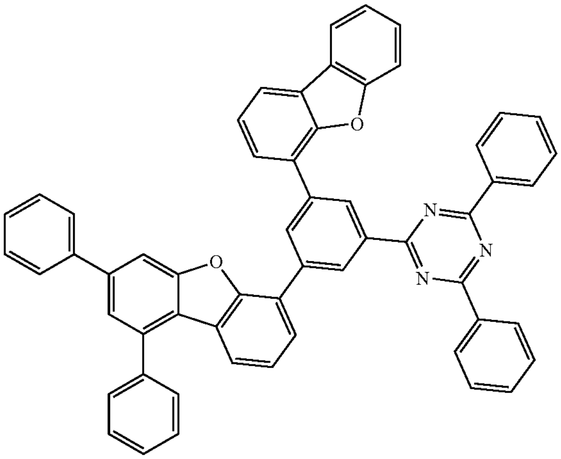,
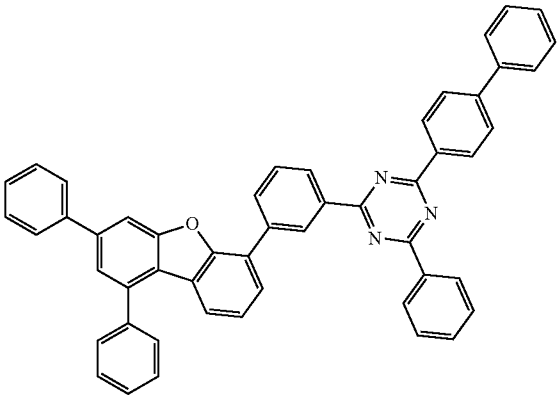, -continued
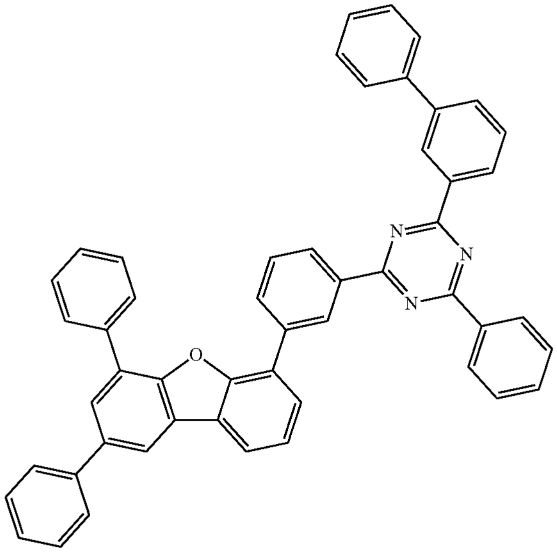
,
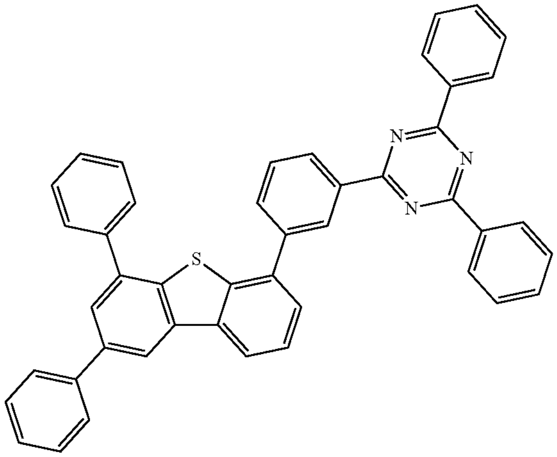
,
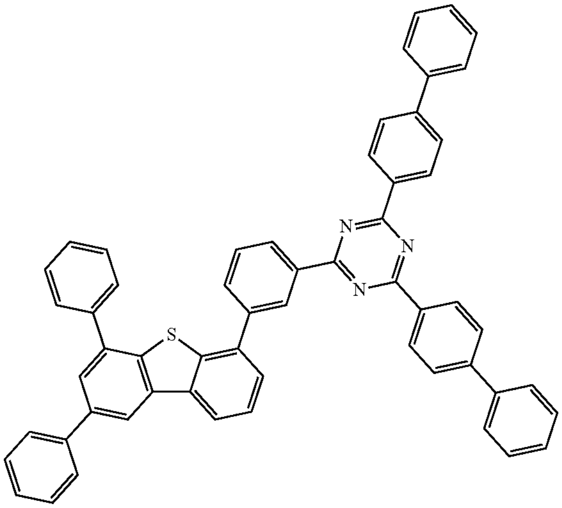
,
-continued
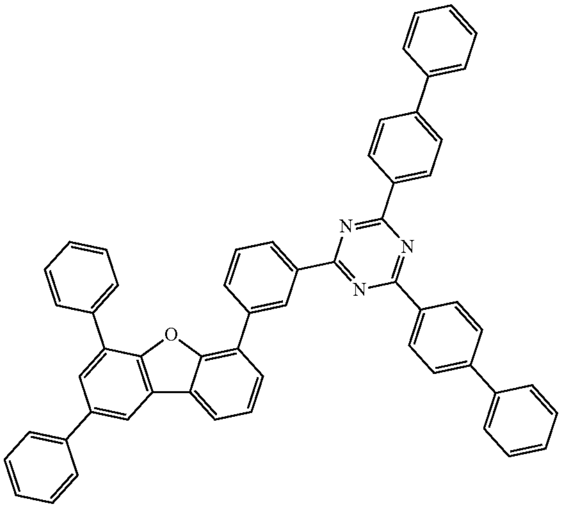
,
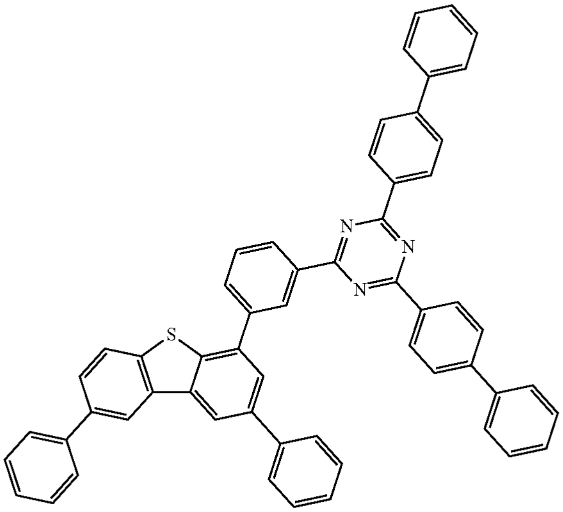
,
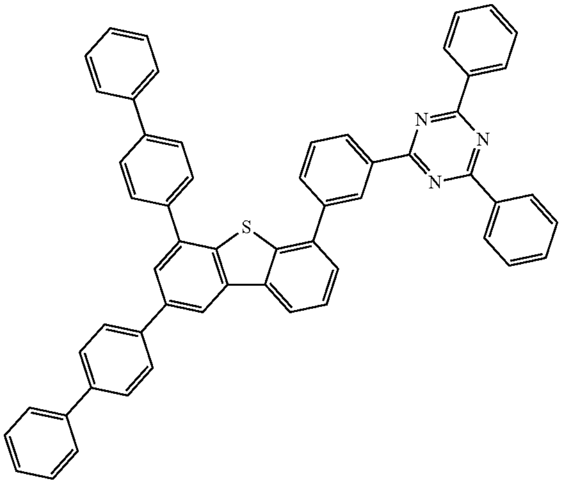
, -continued
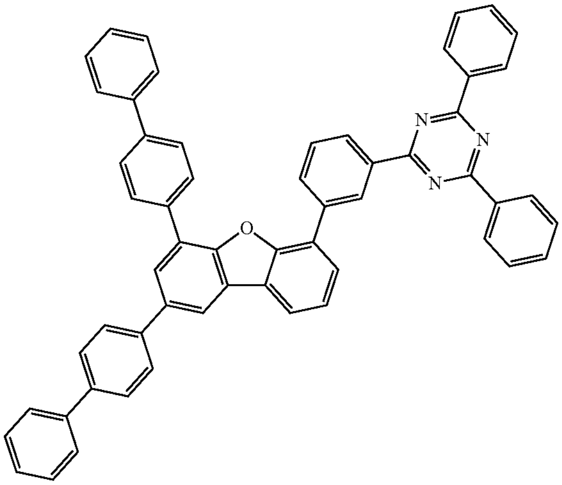
,
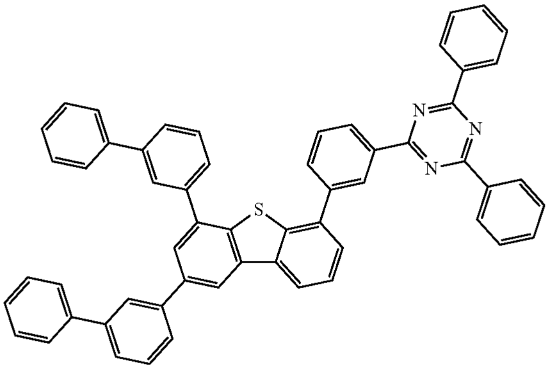
,
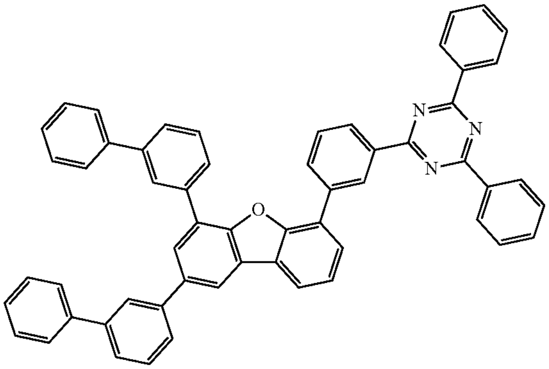
,
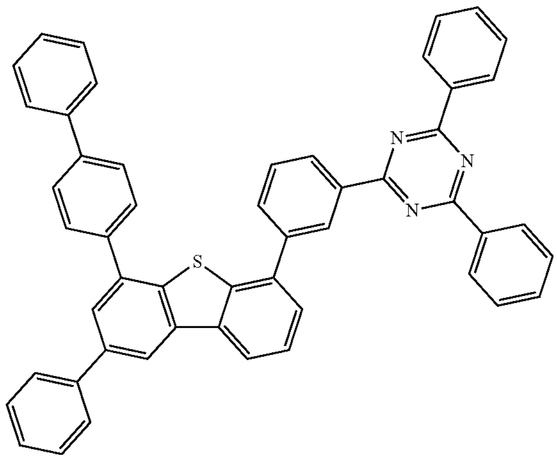
,
-continued
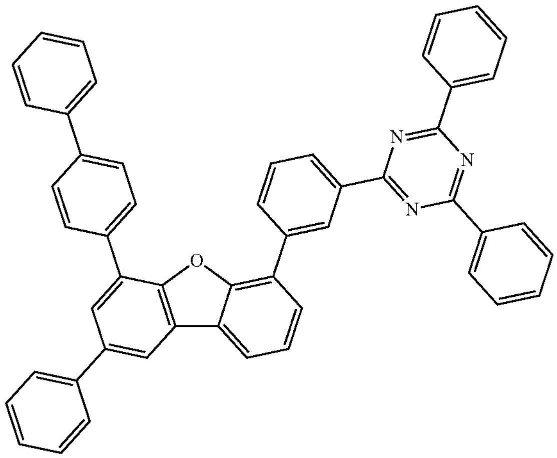
,
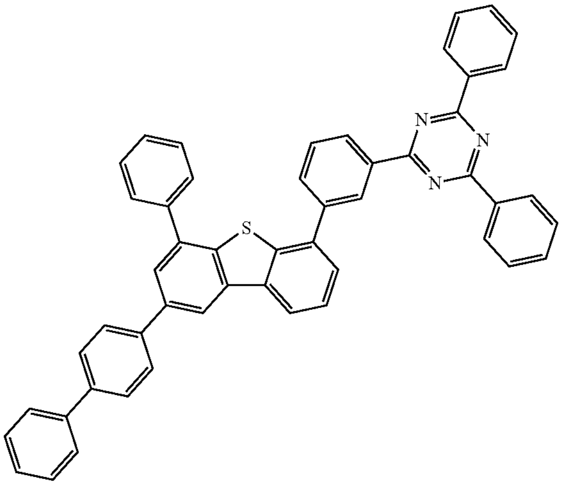
,
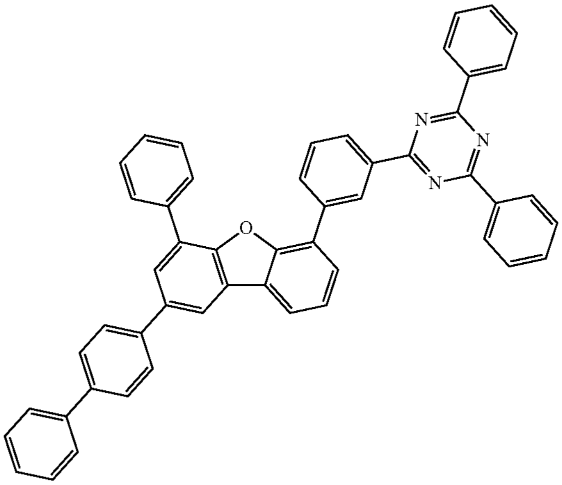
, -continued
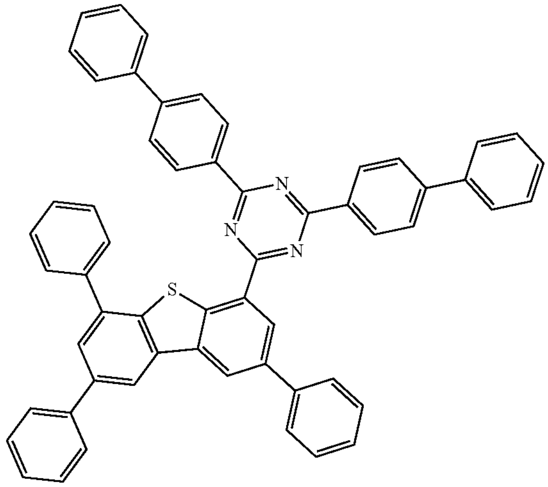
,
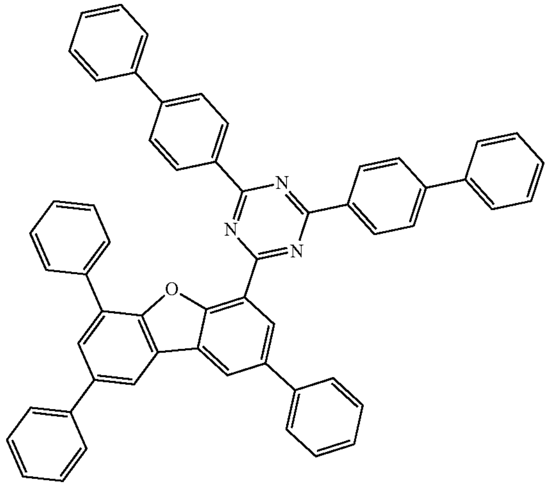
,
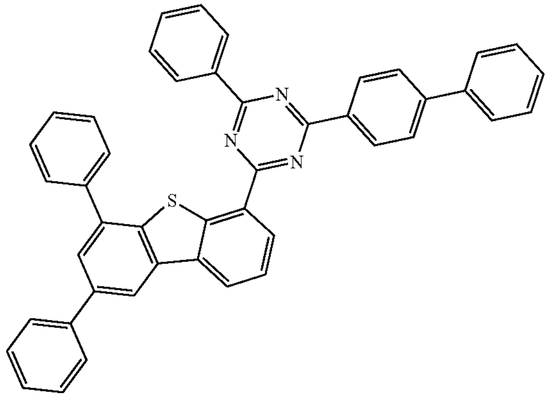
,
-continued
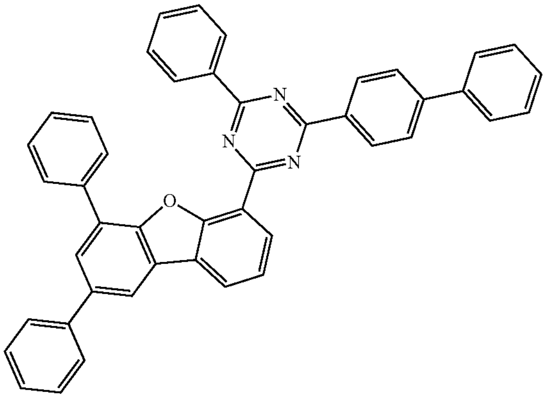
,
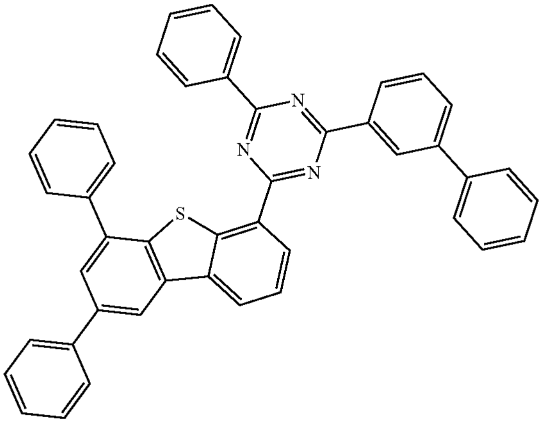
,
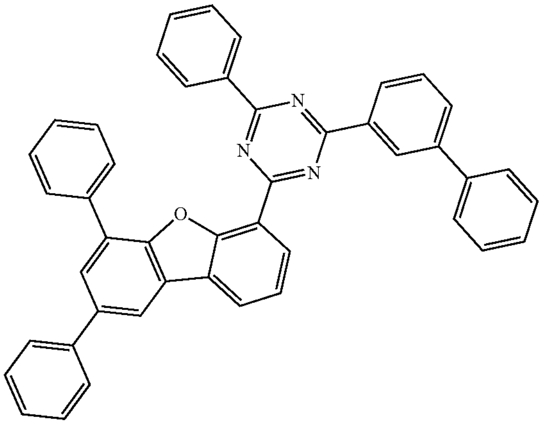
, -continued
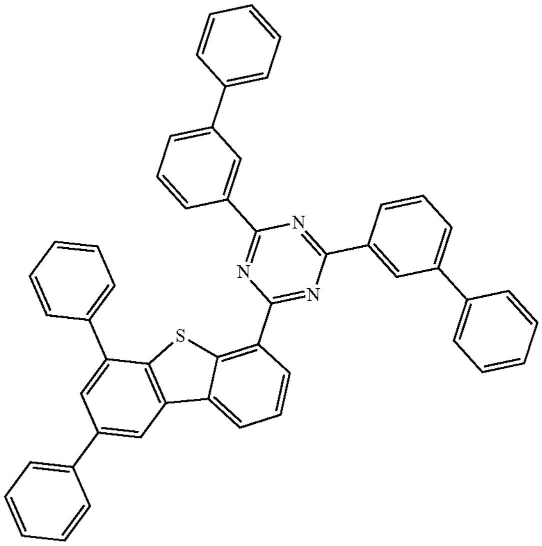
,
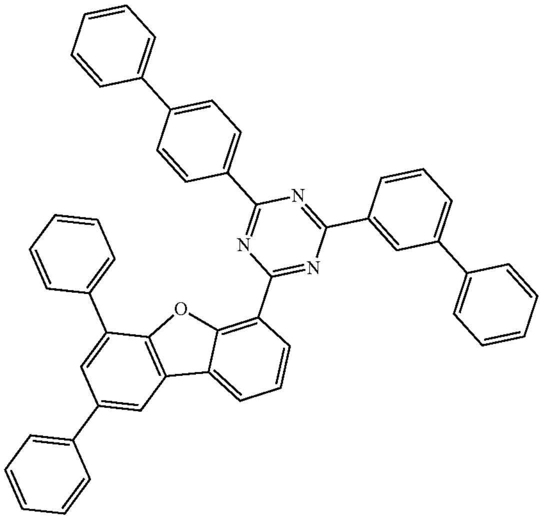
,
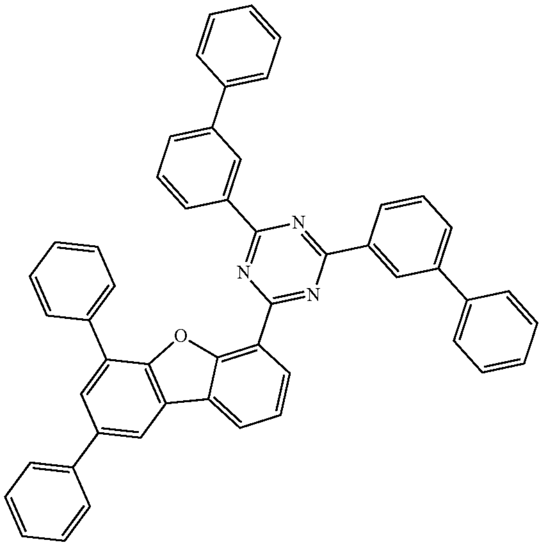
,
-continued
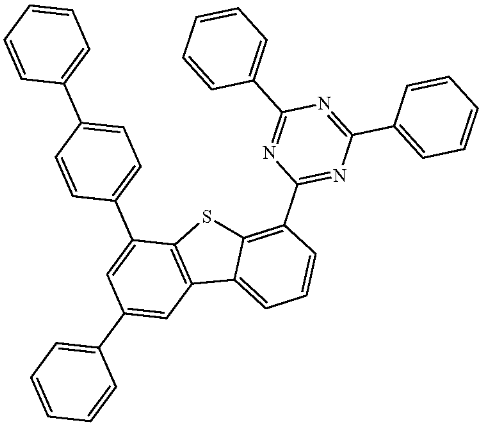
,
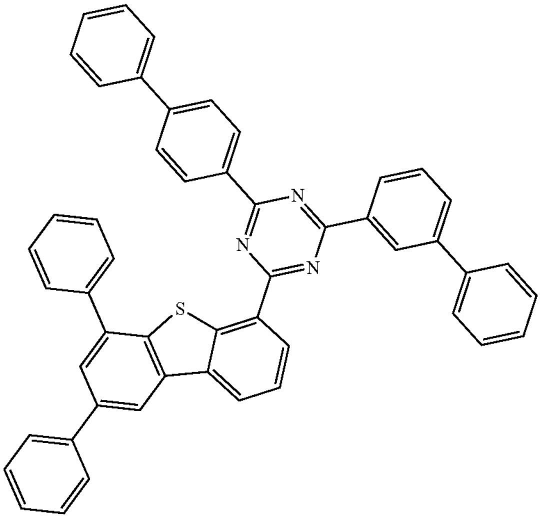
,
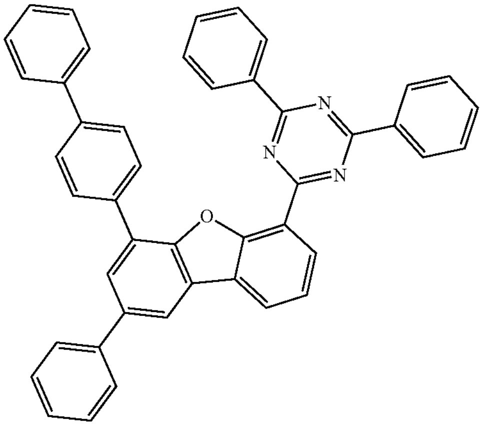
, -continued
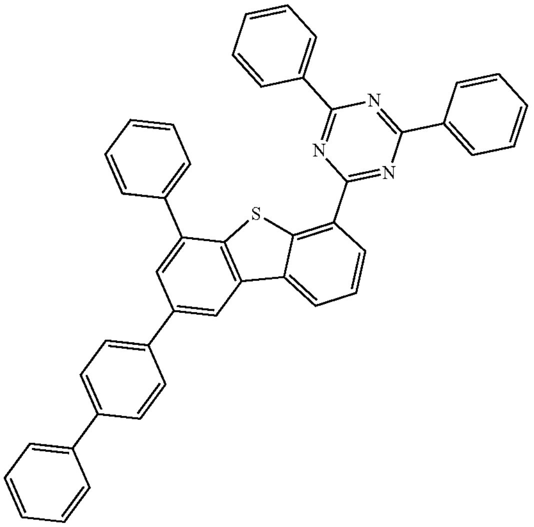
,
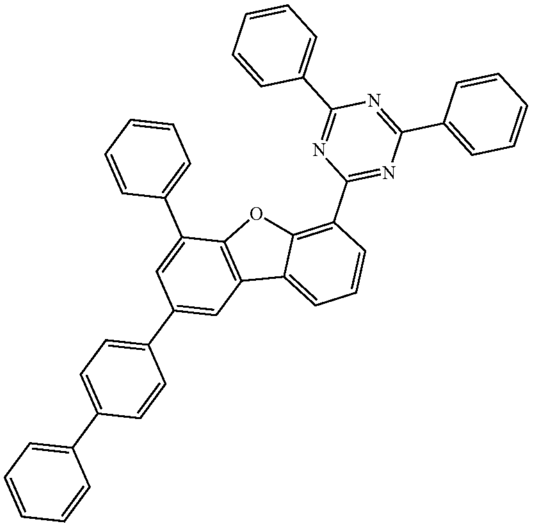
,
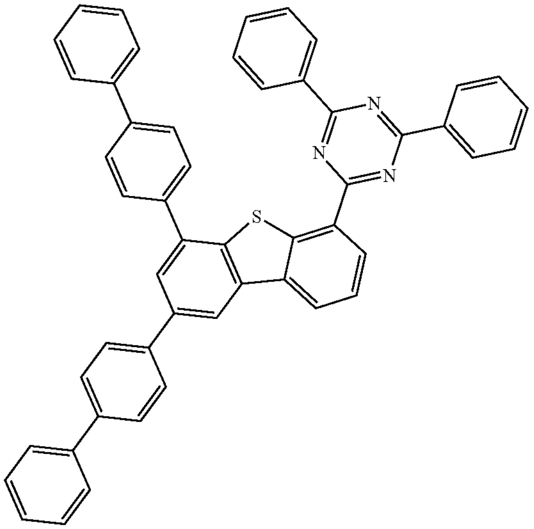
,
-continued
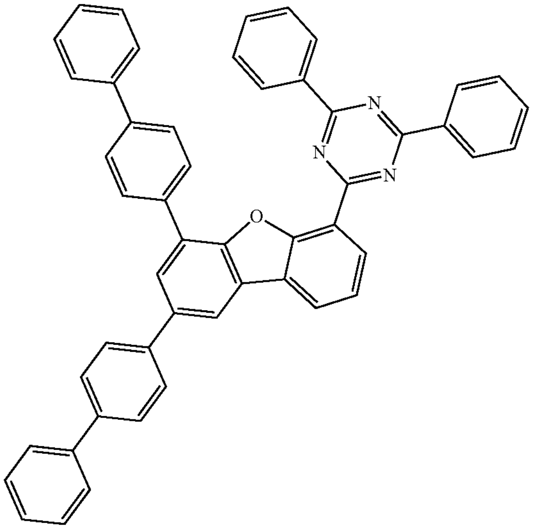
,
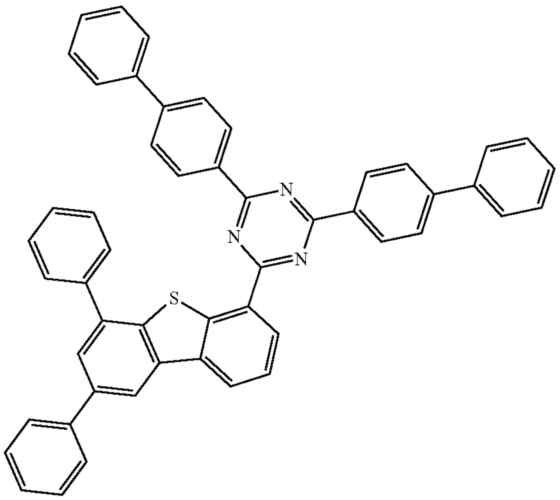
,
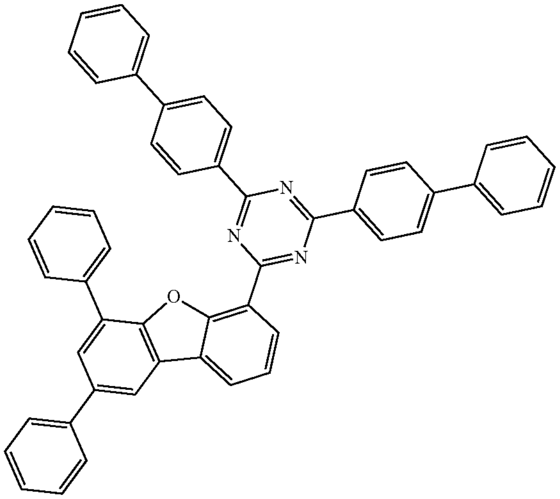
, -continued
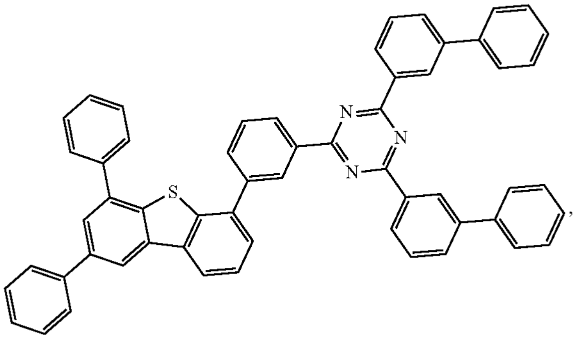
,
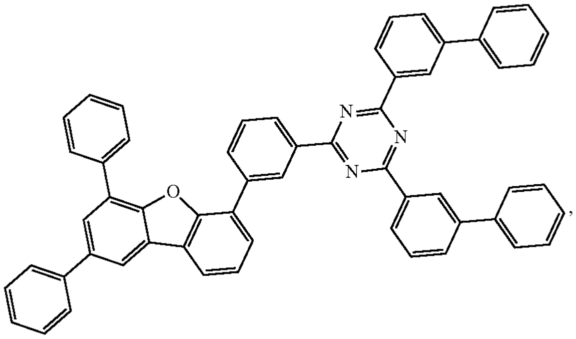
,
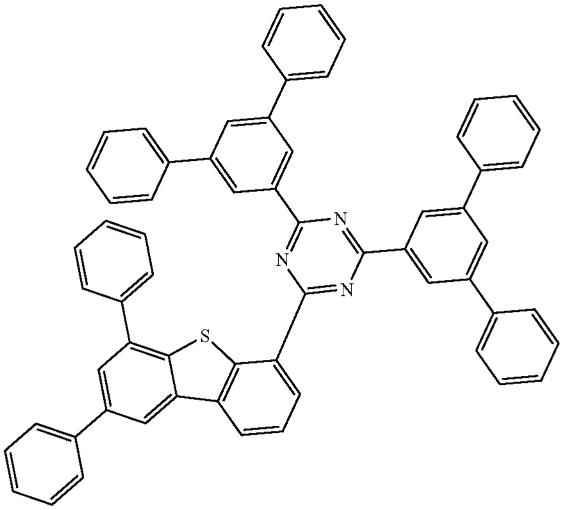
,
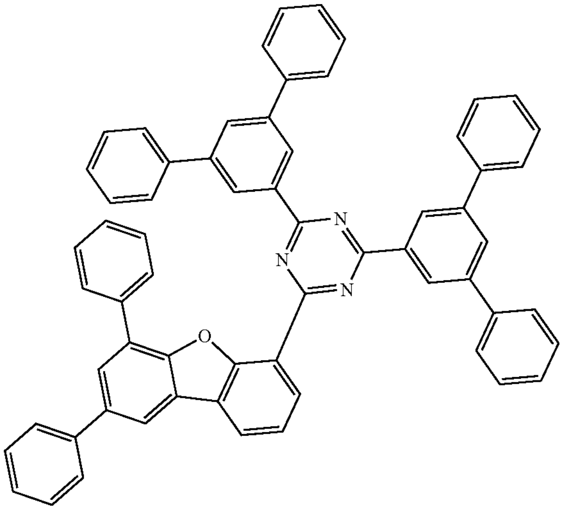
,
-continued
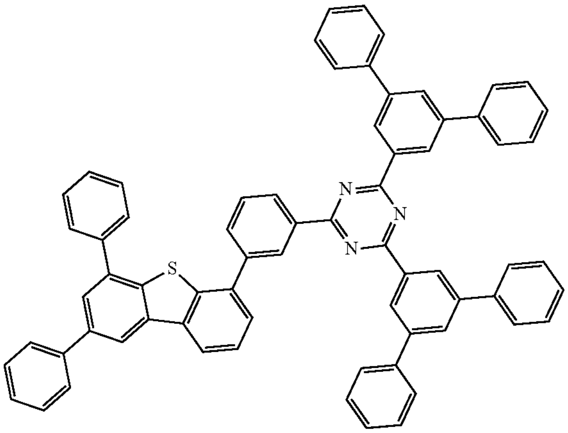
,
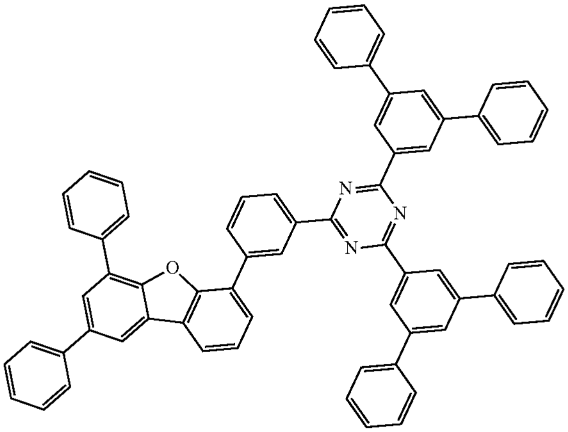
,
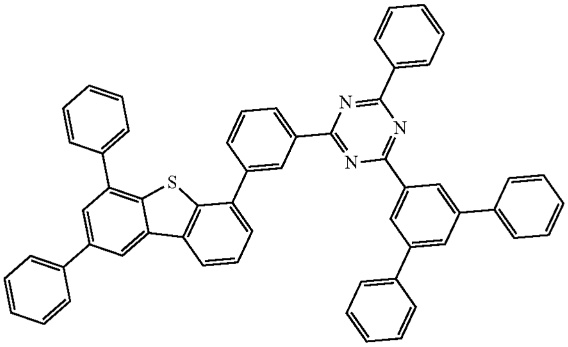
,
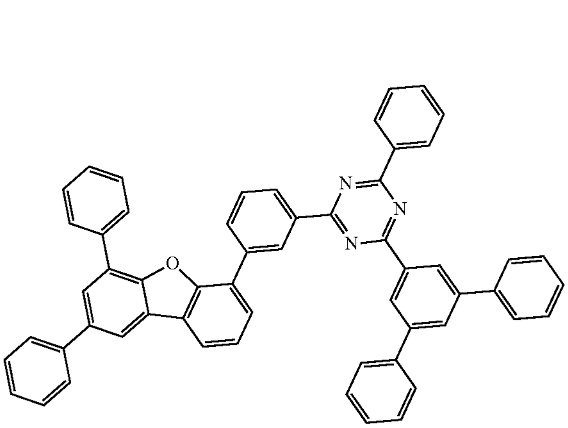
, -continued
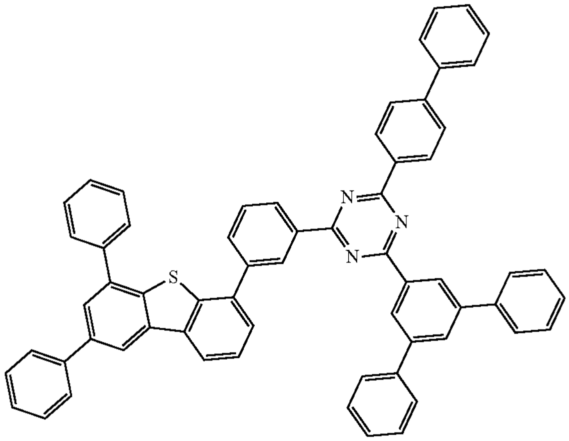
,
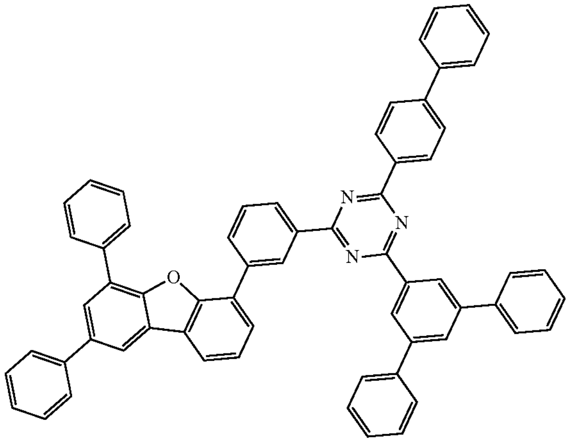
,
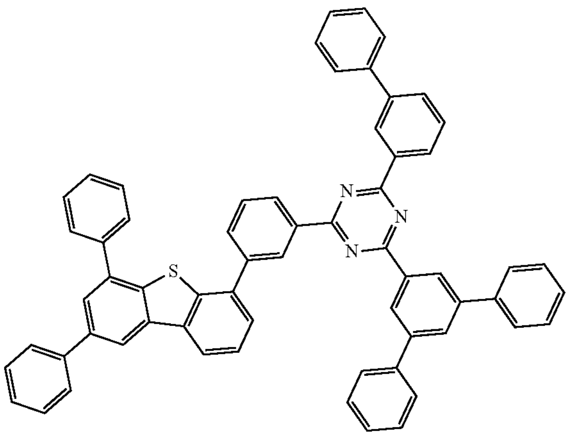
,
-continued
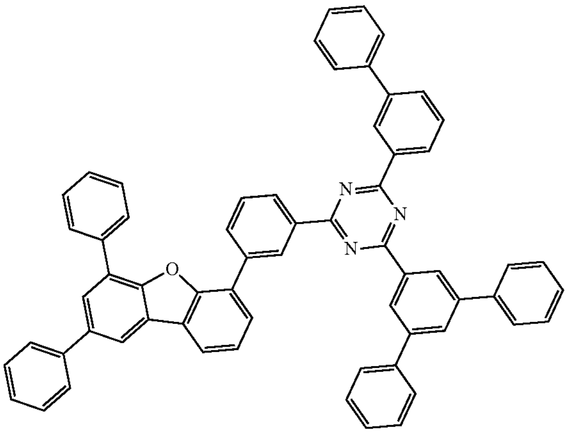
,
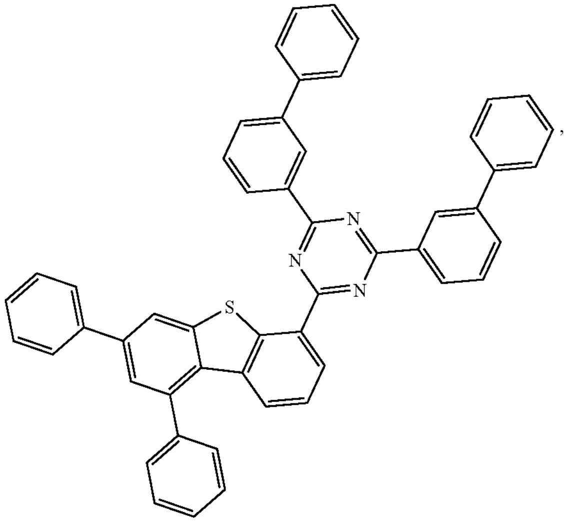
,
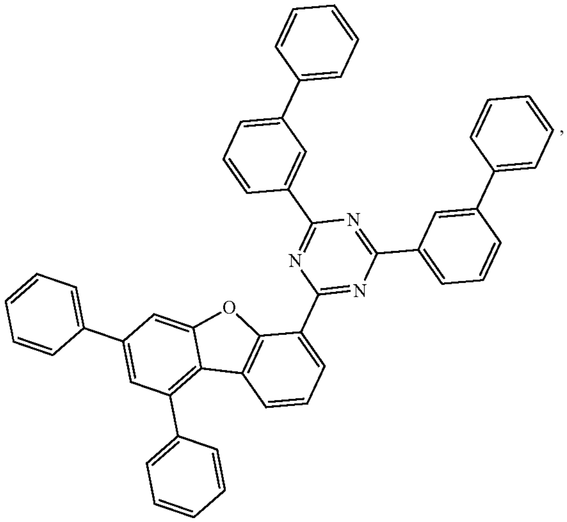
, -continued
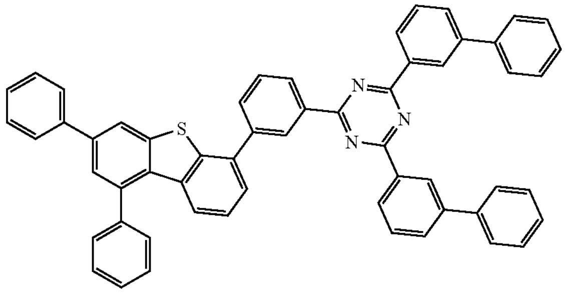
,
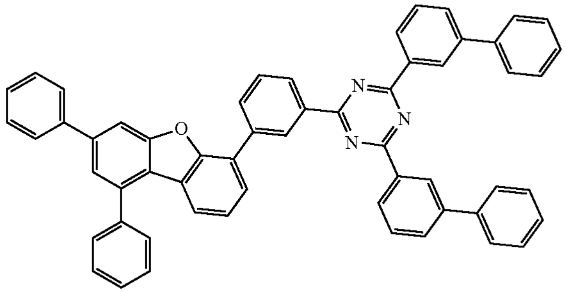
,
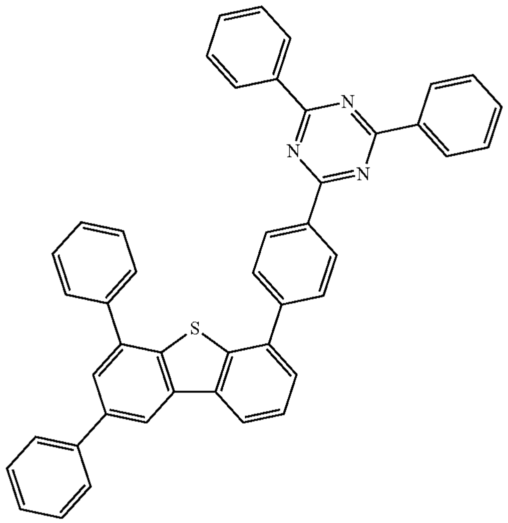
,
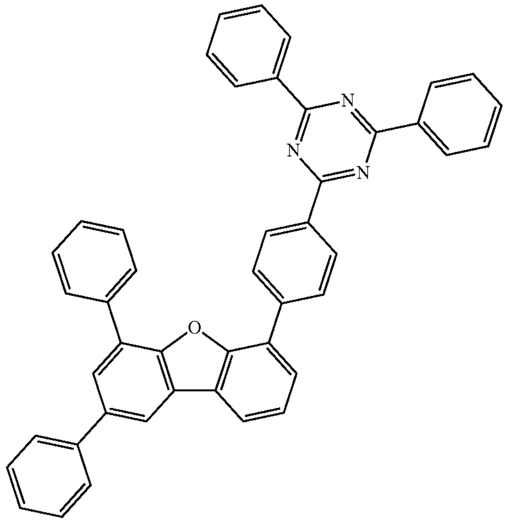
,
-continued
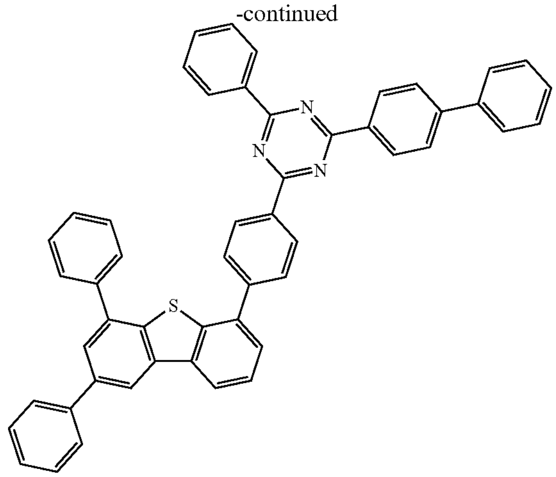
,
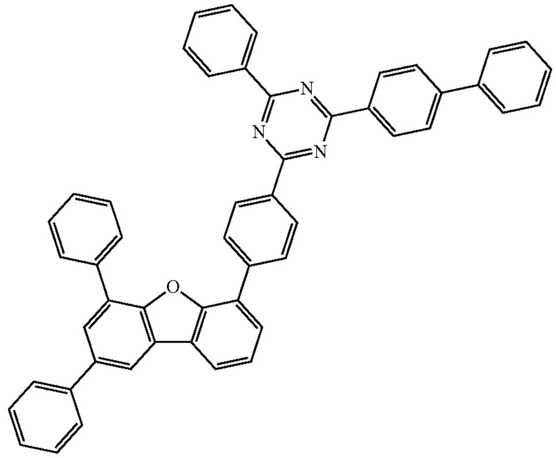
,
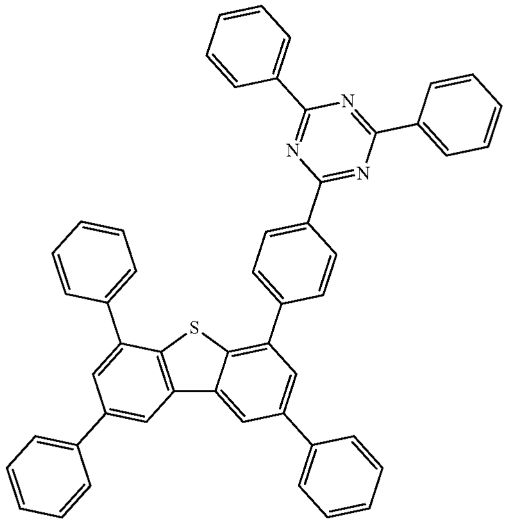
, -continued
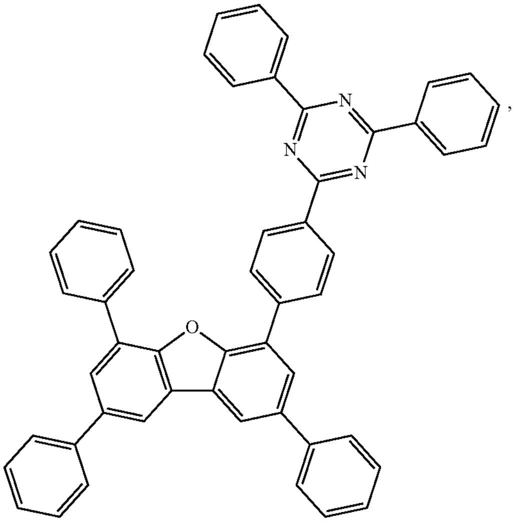
,
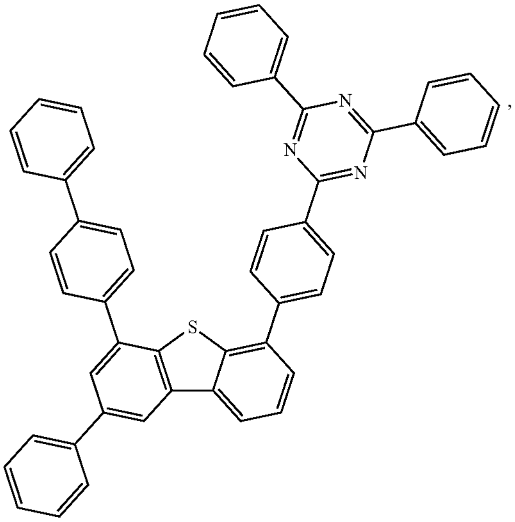
,
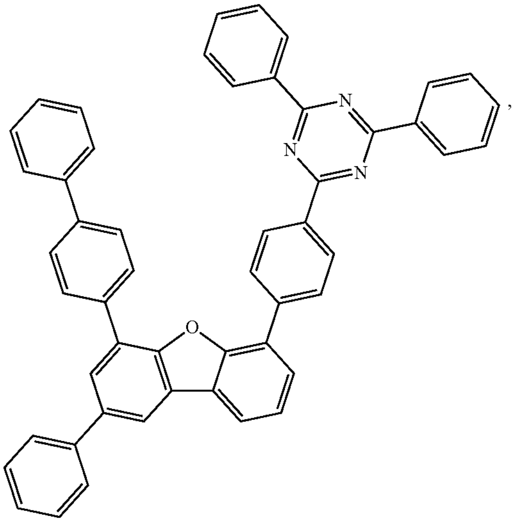
,
-continued
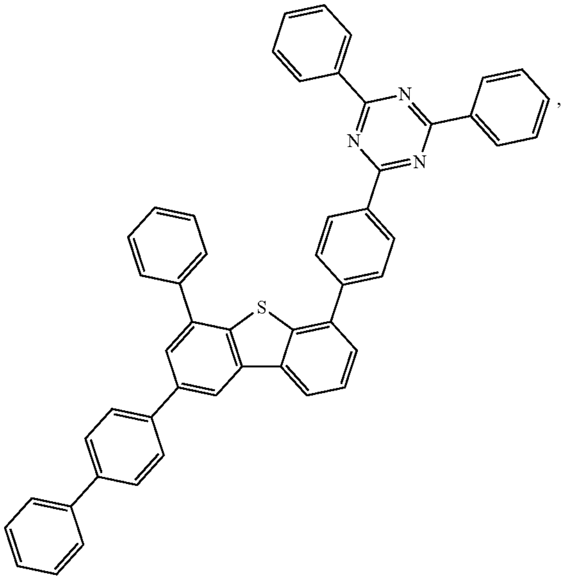
,
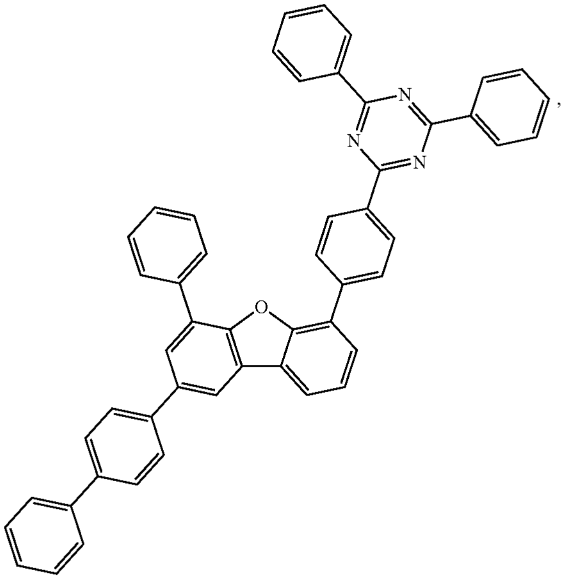
, -continued
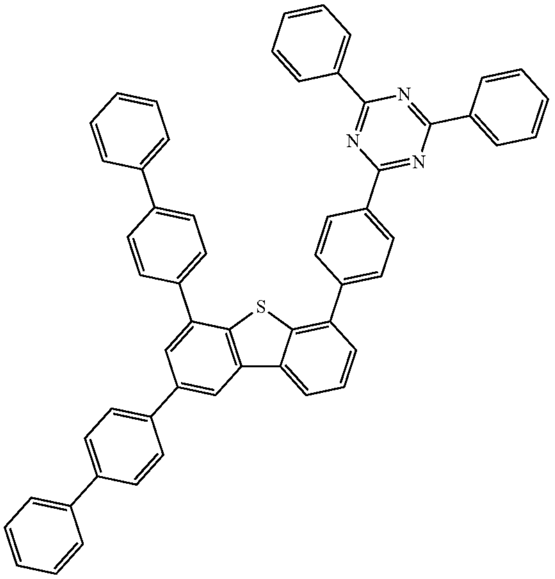
,
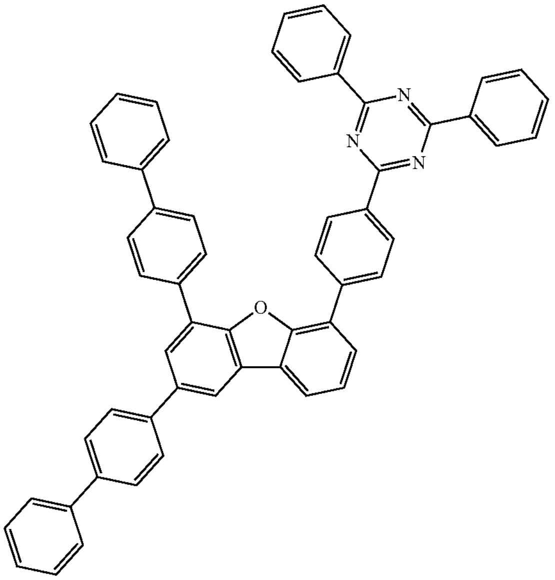
,
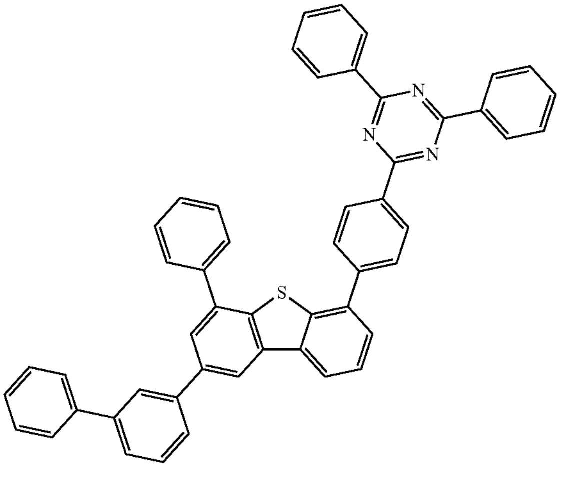
,
-continued
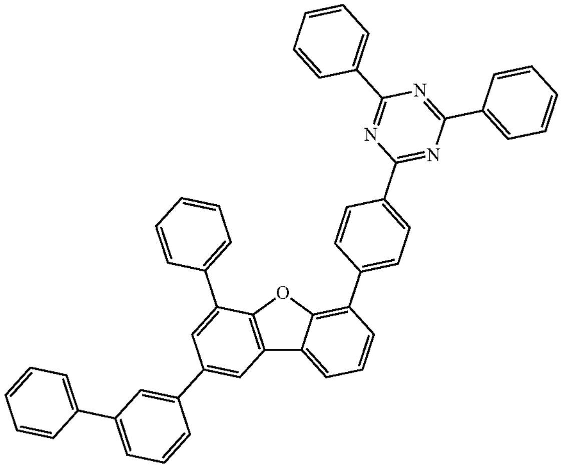
,
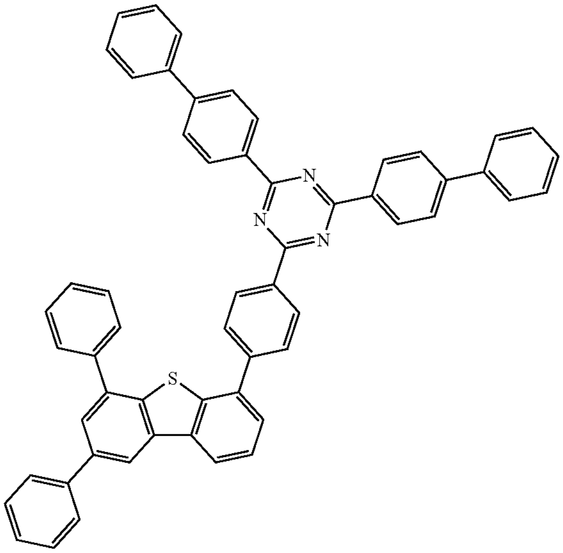
,
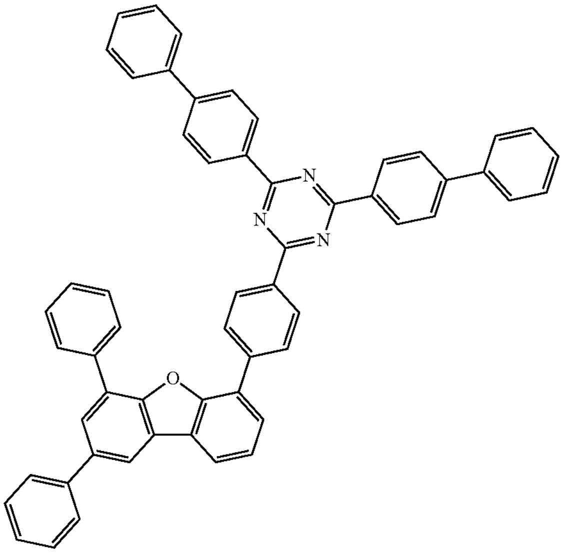
, -continued
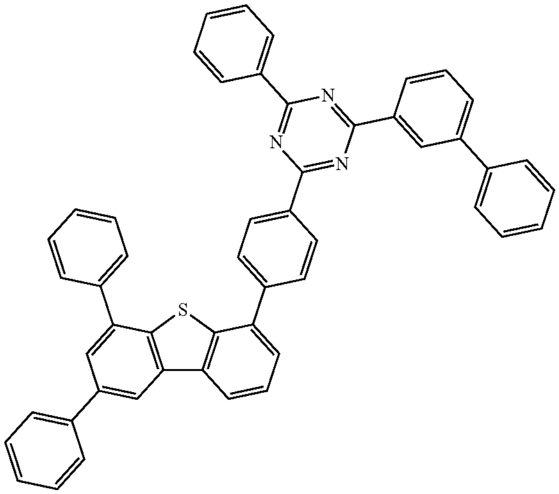
,
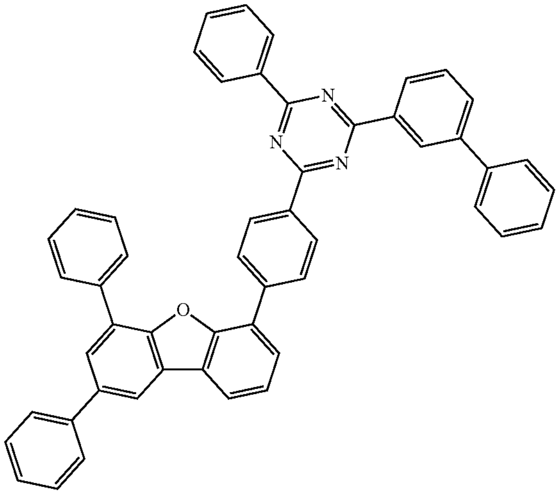
,
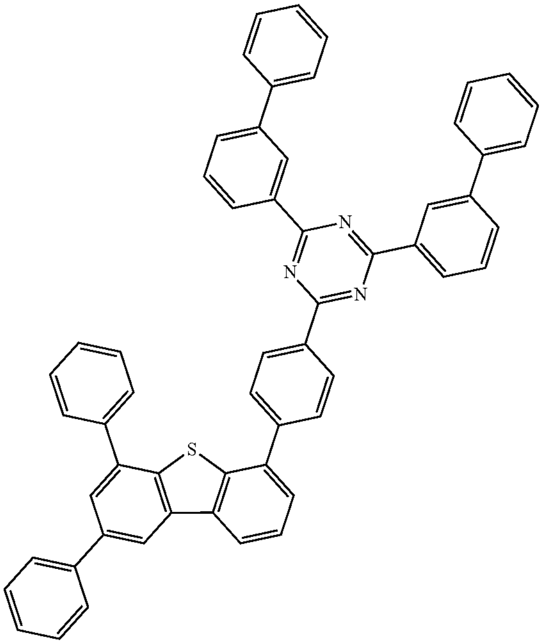
,
-continued
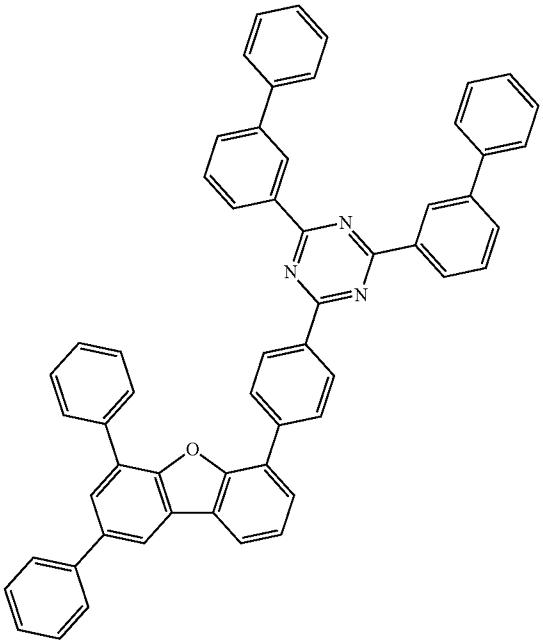
,
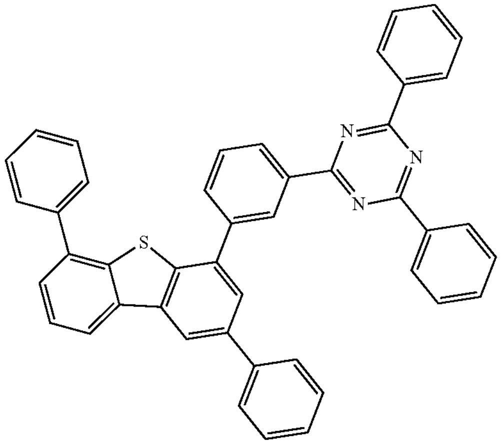
,
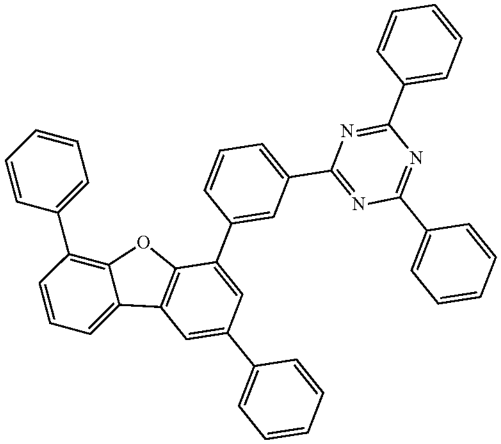
, -continued
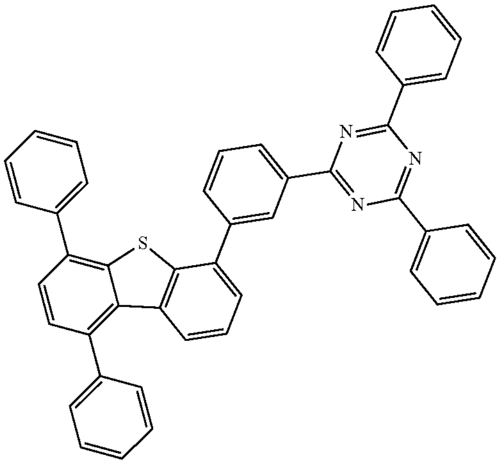,
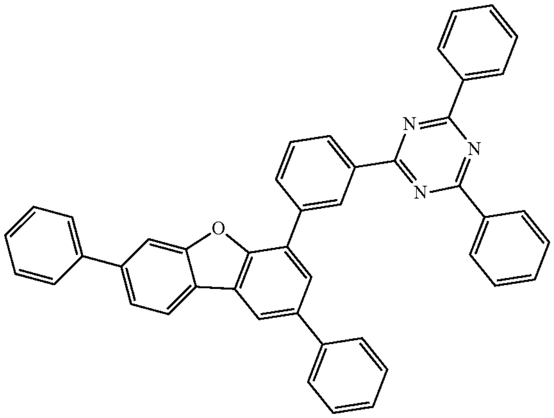,
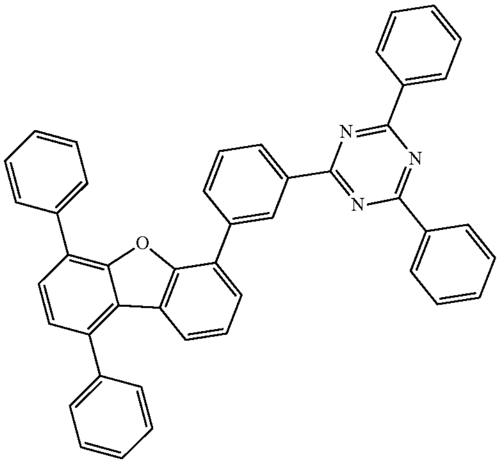,
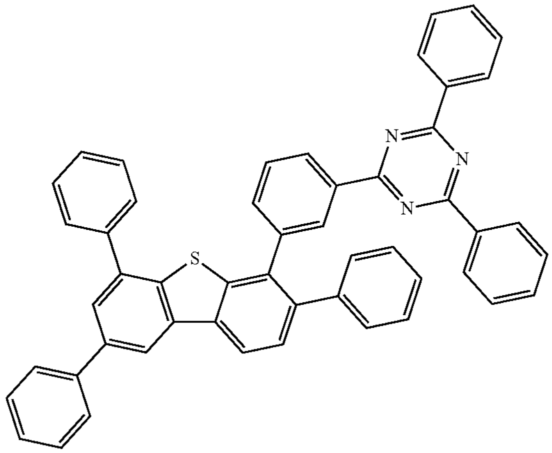,
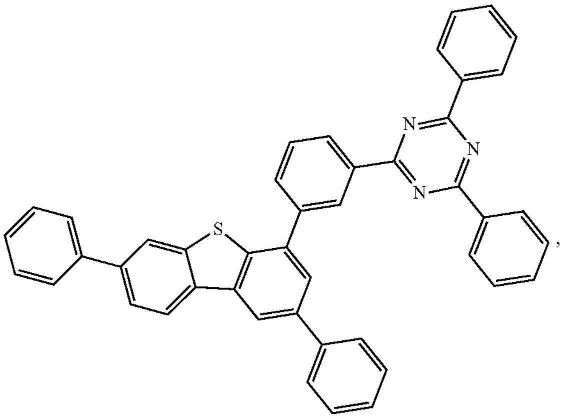,
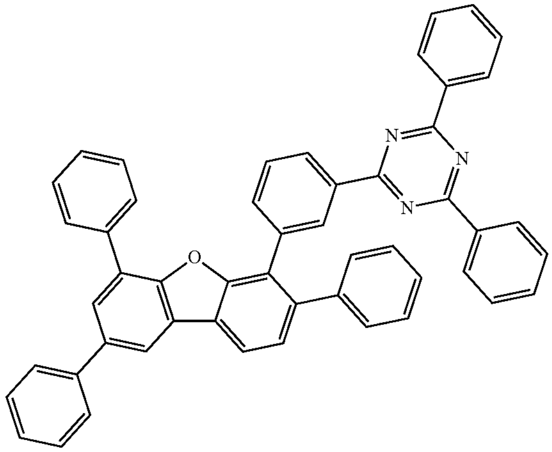, -continued
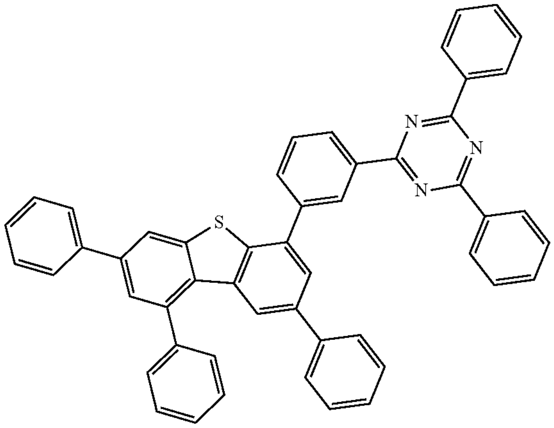
,
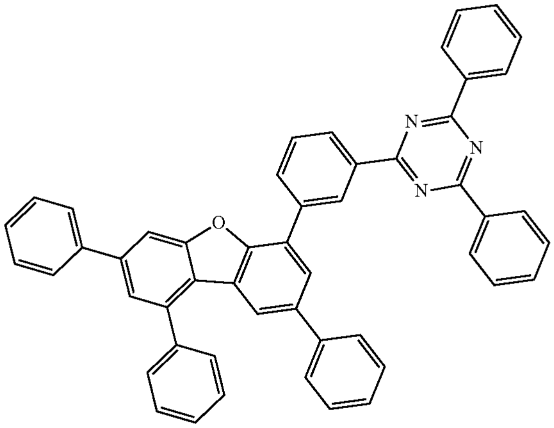
,
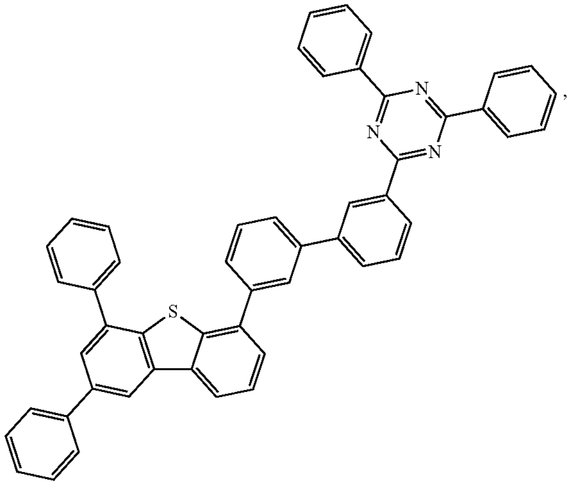
,
-continued
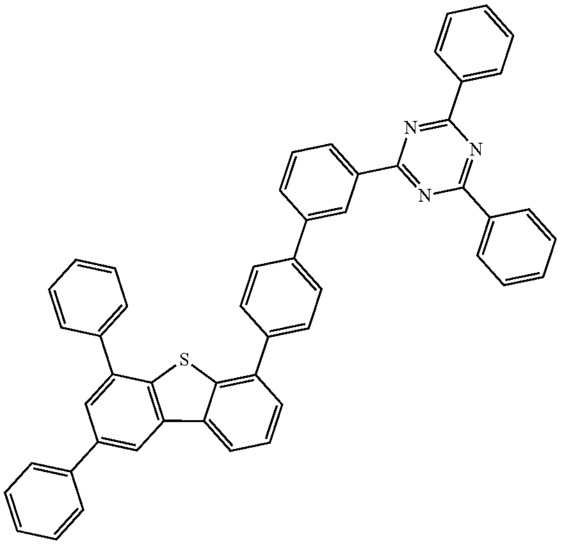
,
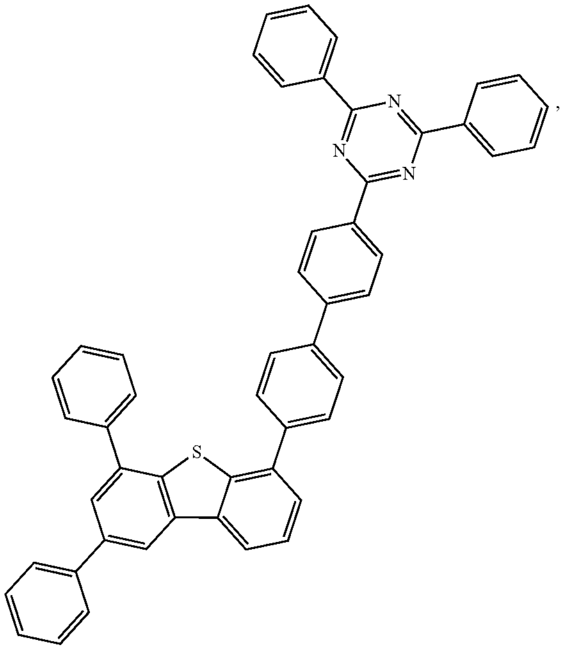
,
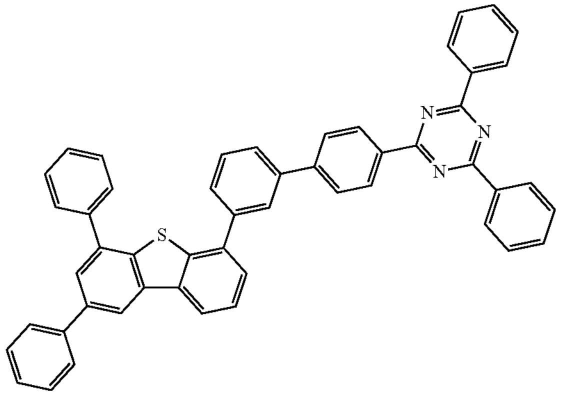
, -continued
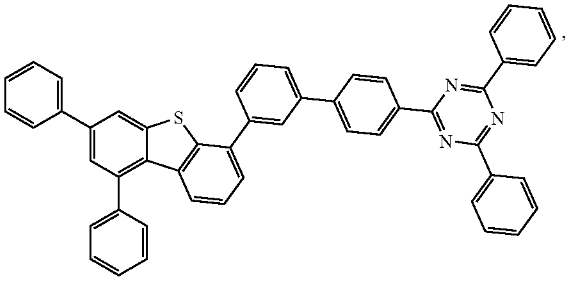
,
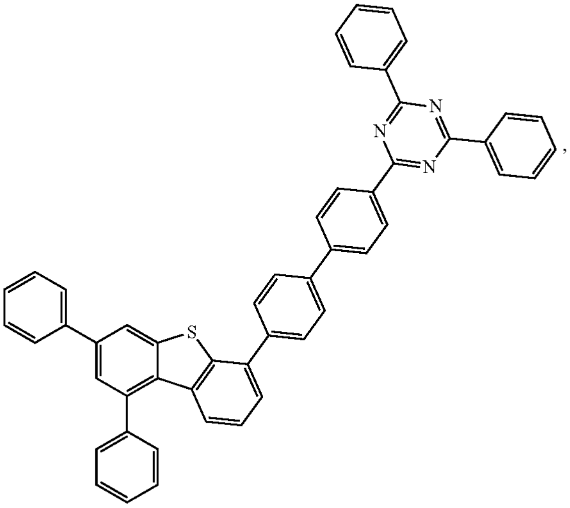
,
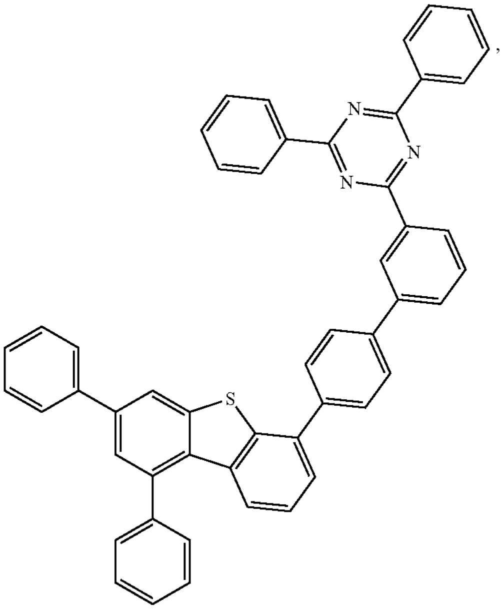
,
-continued
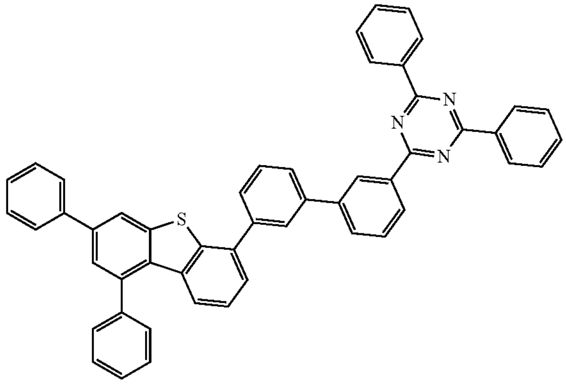
,
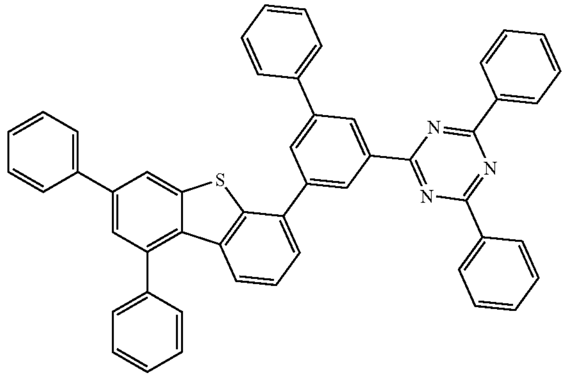
,
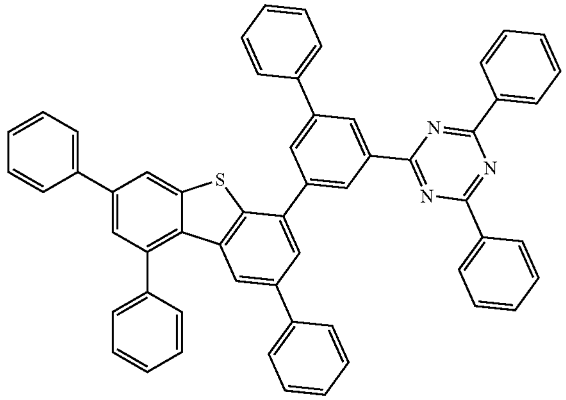
,
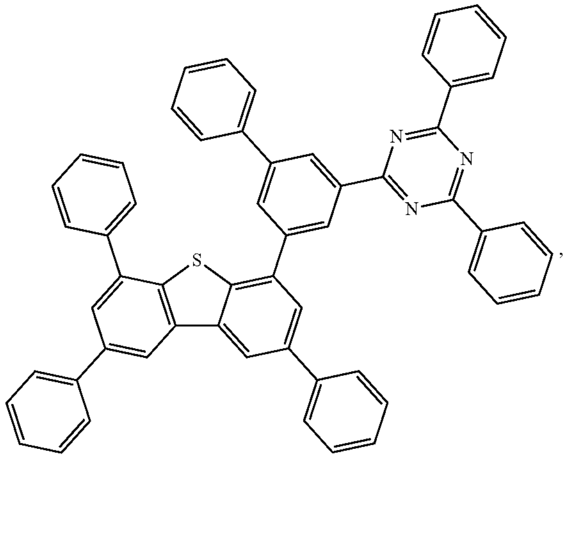
, -continued
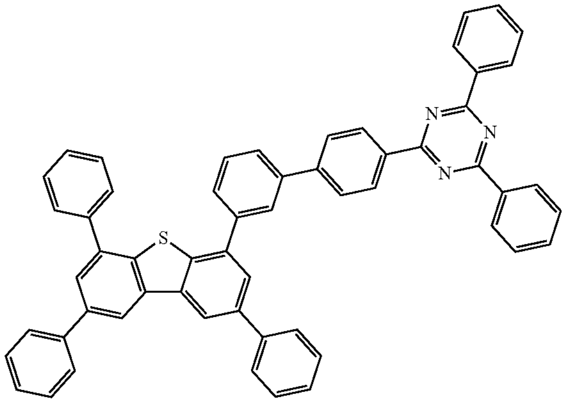
,
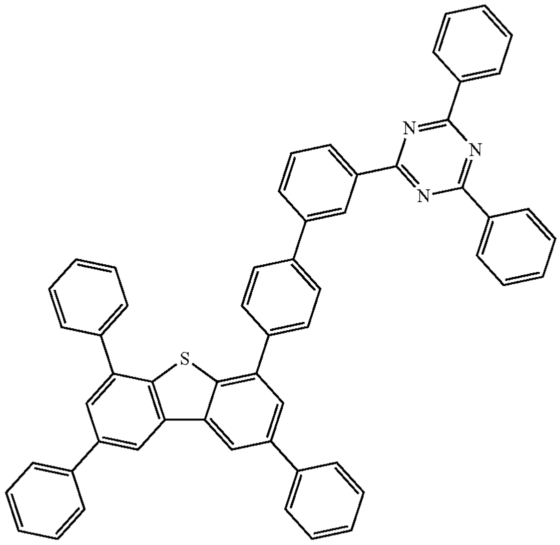
,
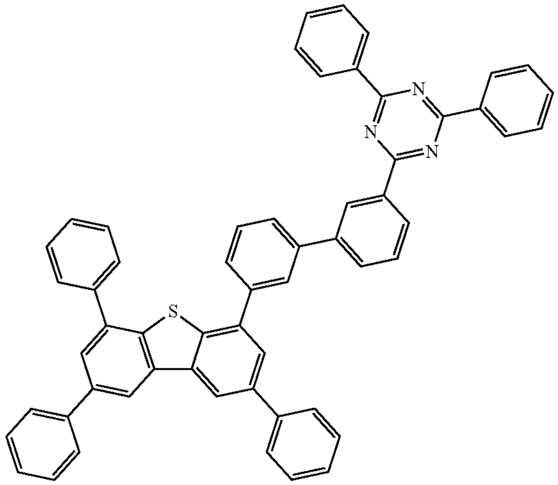
,
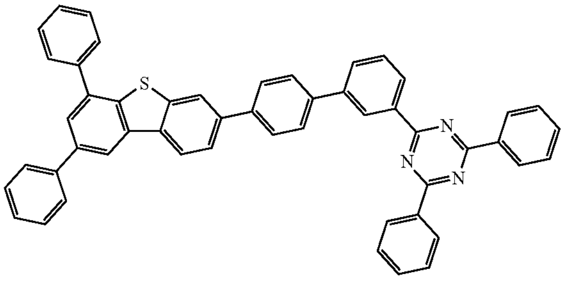
,
-continued
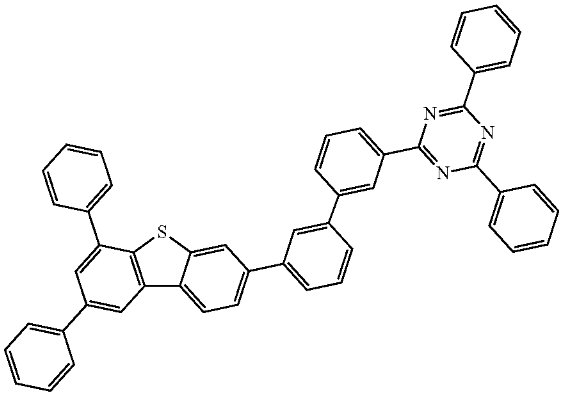
,
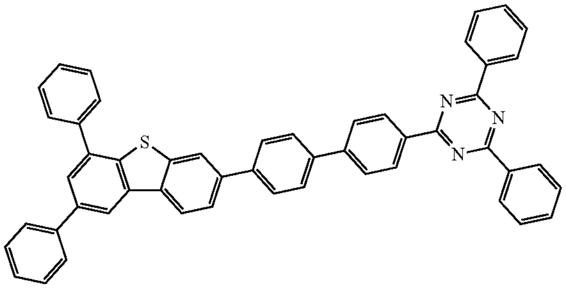
,
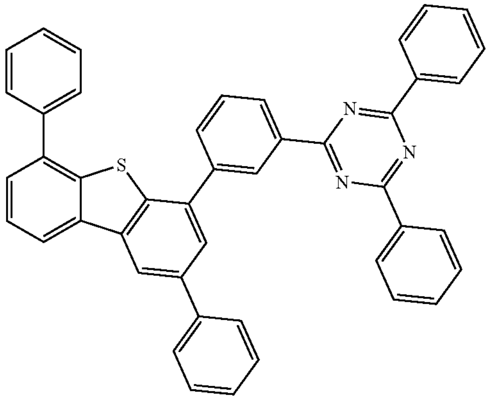
,
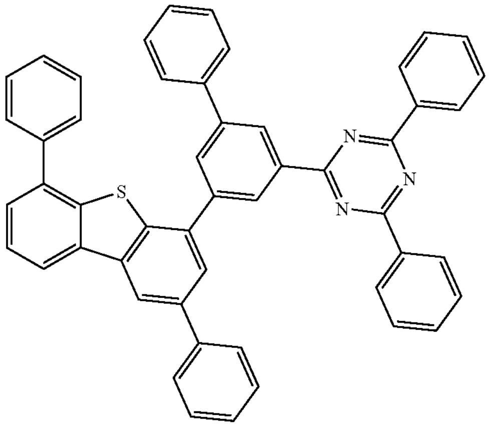
, -continued
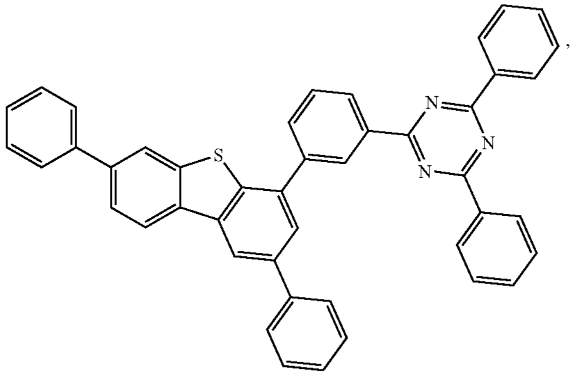,
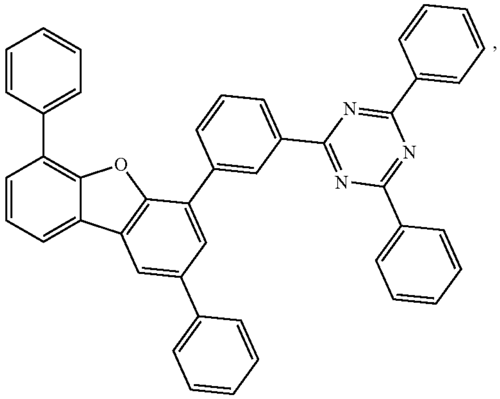,
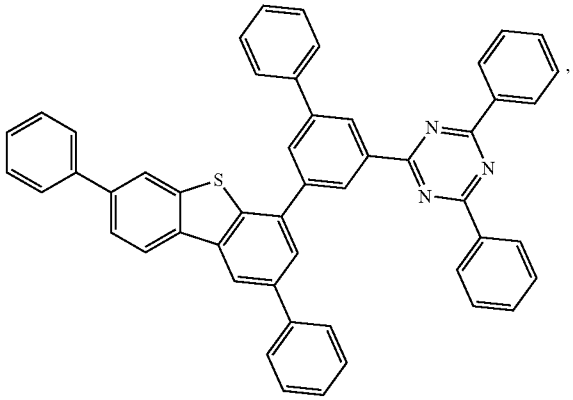,
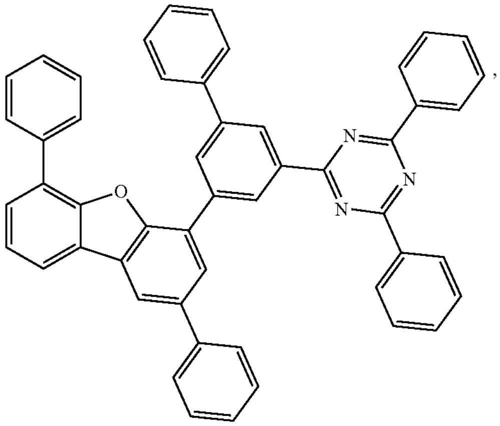,
-continued
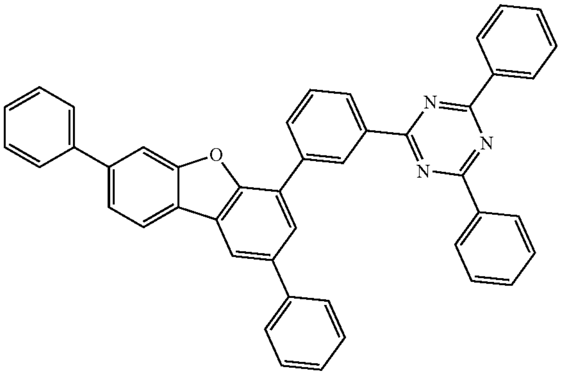,
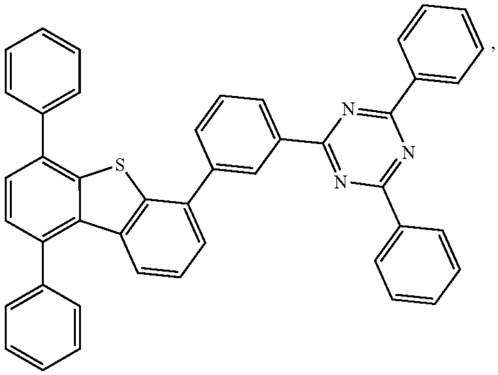,
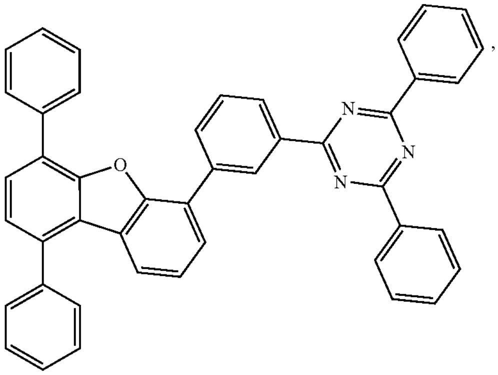,
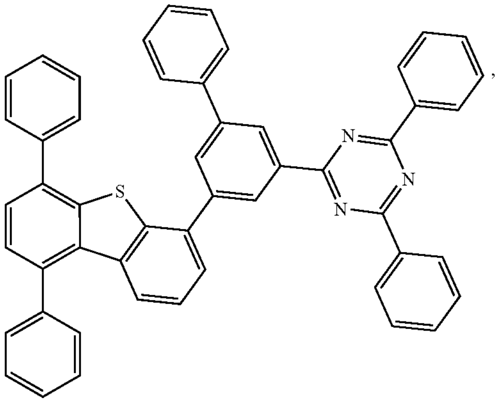, -continued
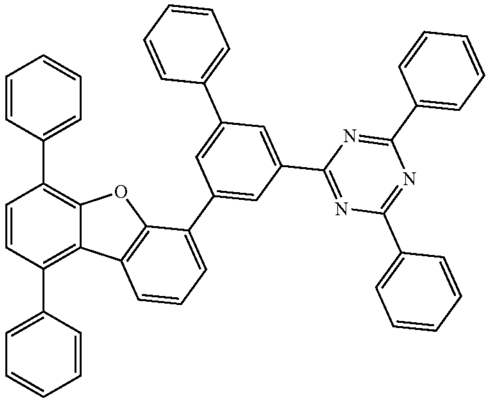
,
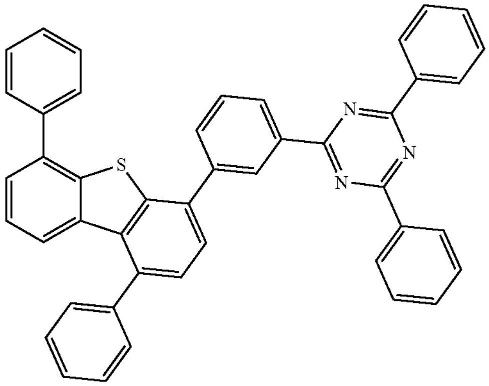
,
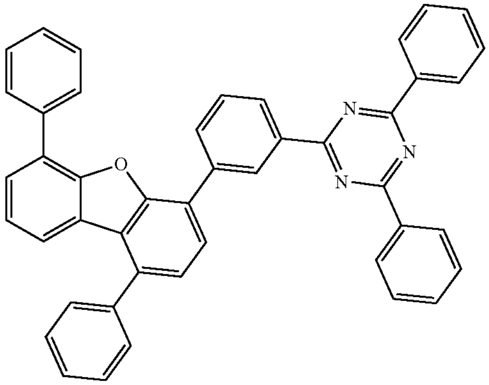
,
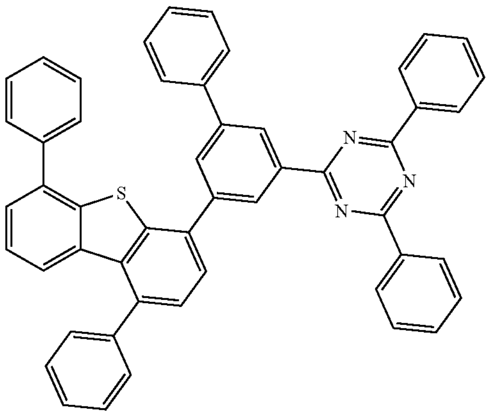
,
-continued
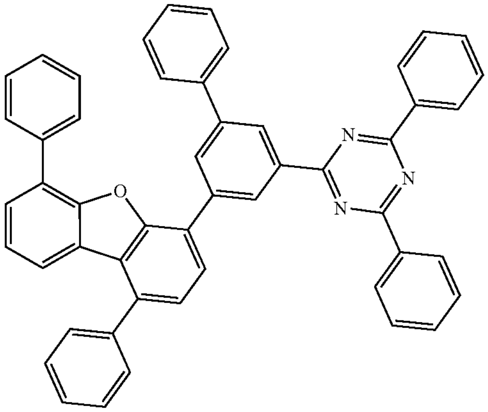
,
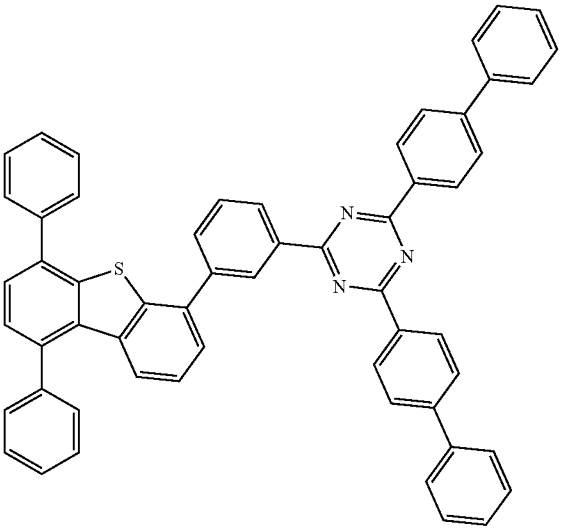
,
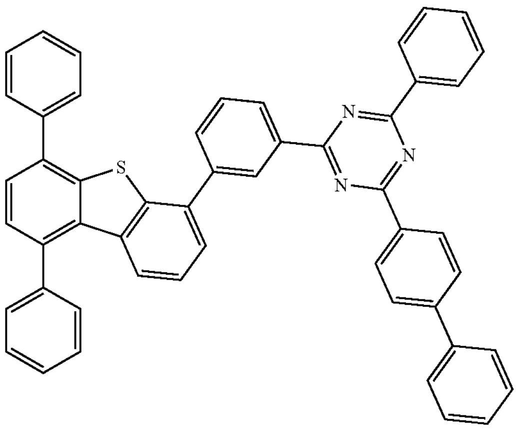
, -continued
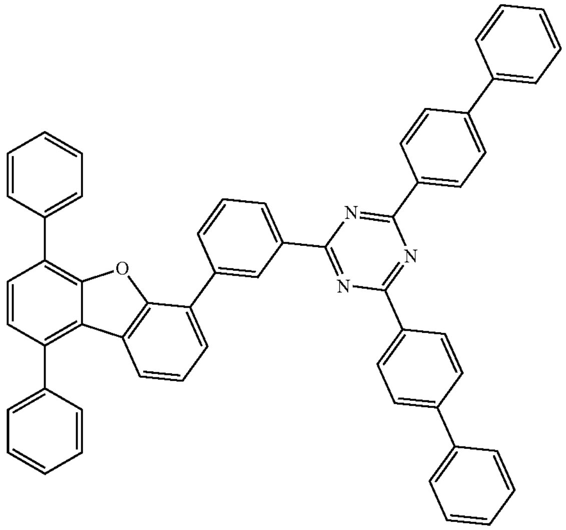
,
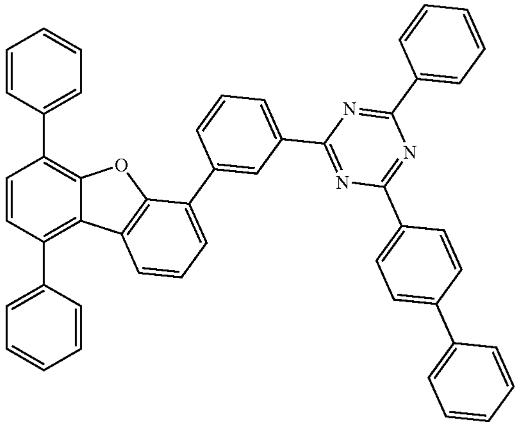
,
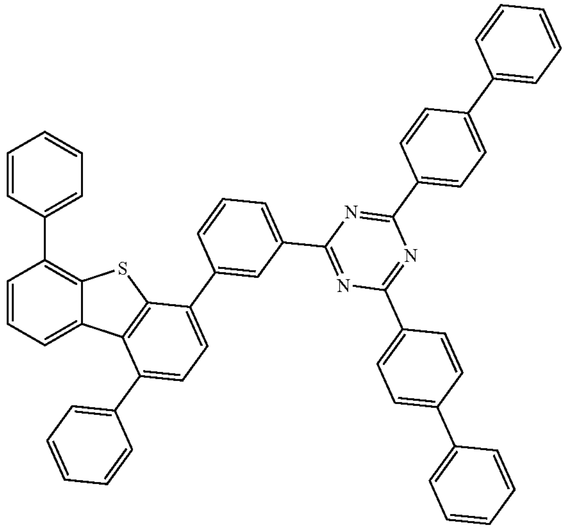
,
-continued
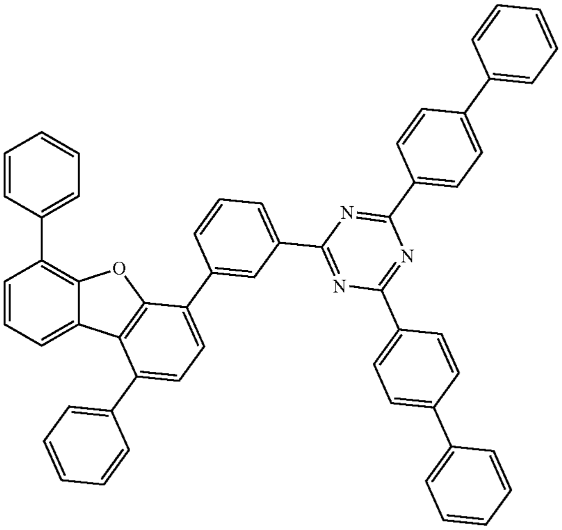
,
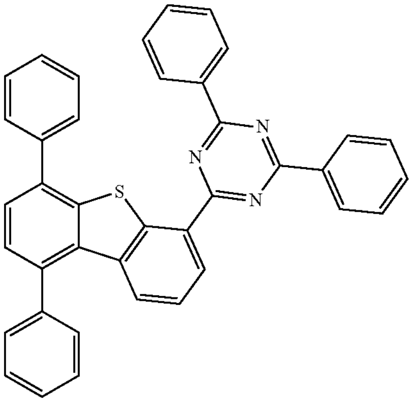
,
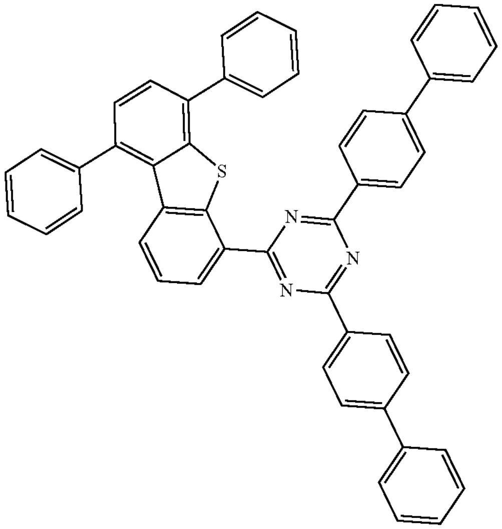
, -continued
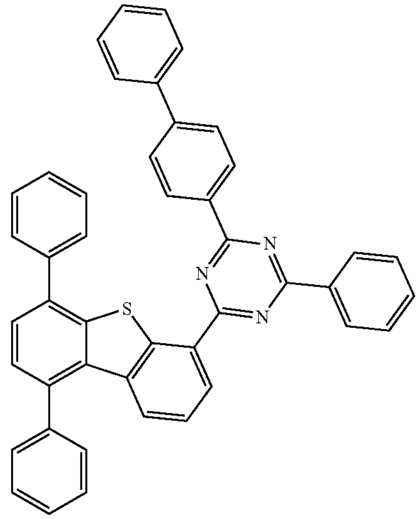
,
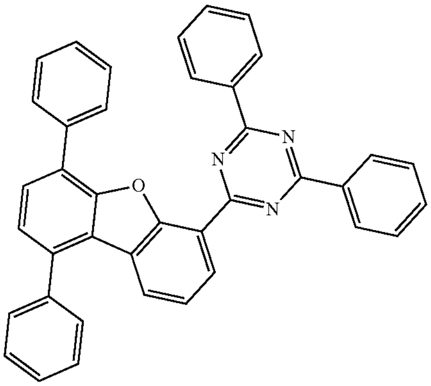
,
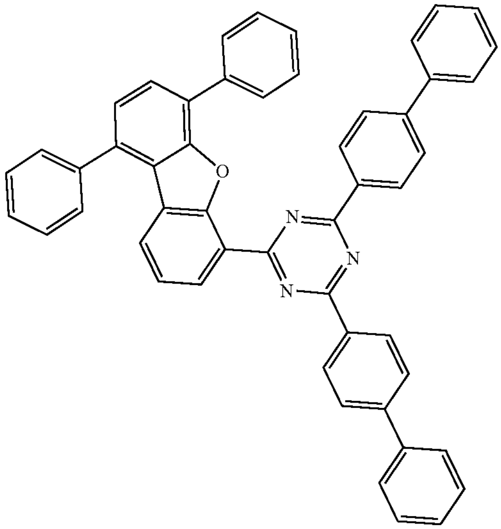
,
-continued
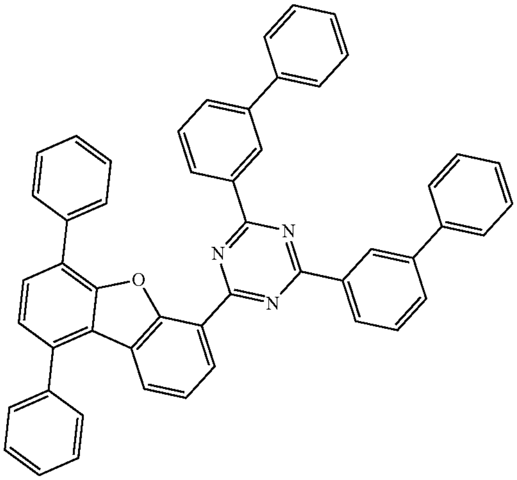
,
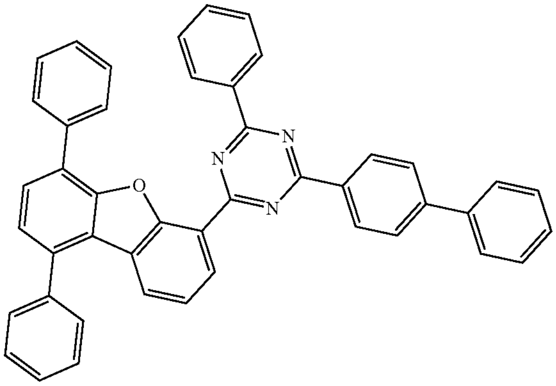
,
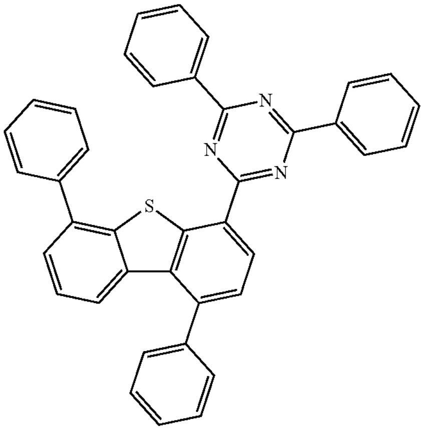
, -continued
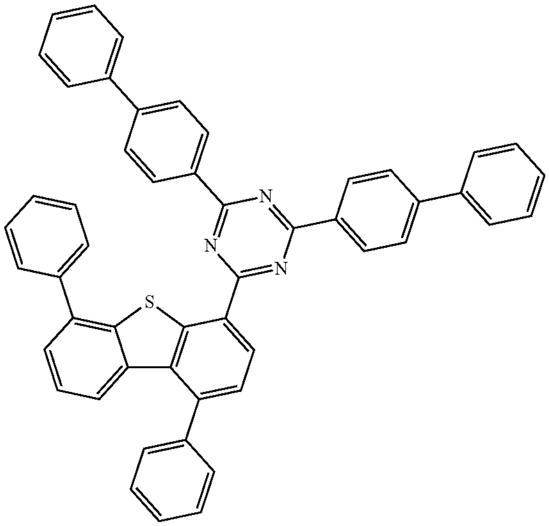
,
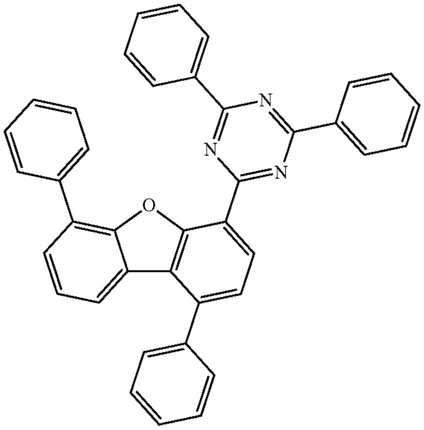
,
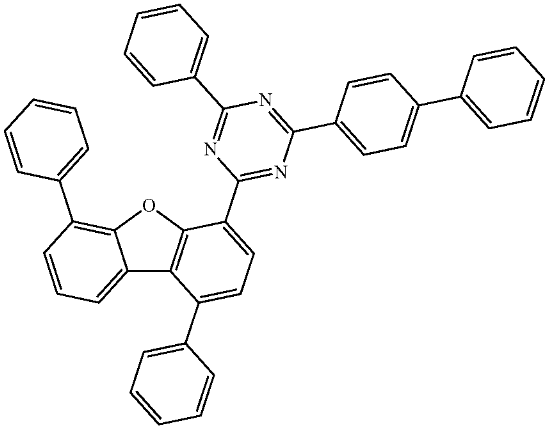
,
-continued
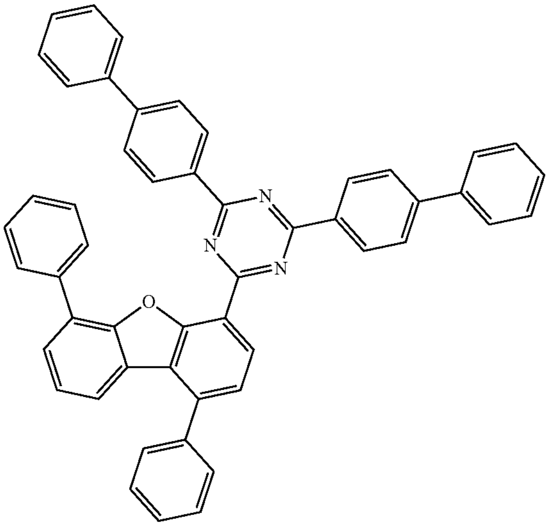
,
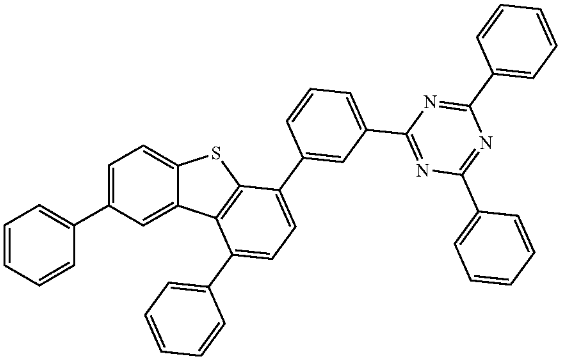
,
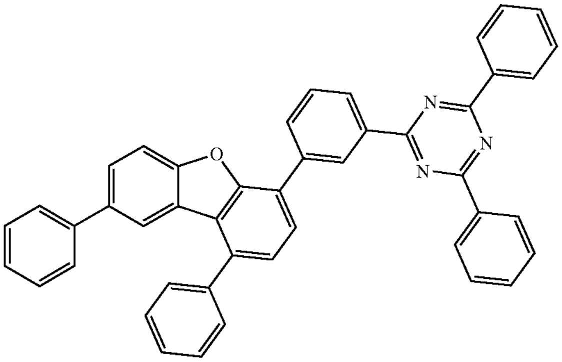
,
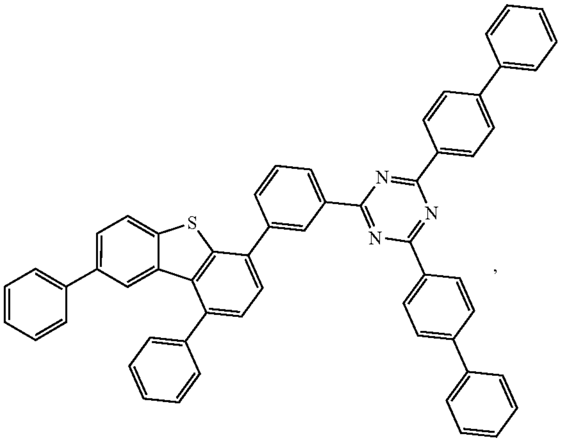
,
, -continued
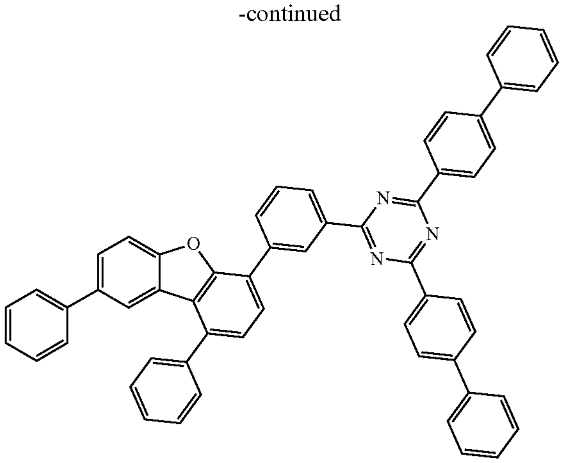
,
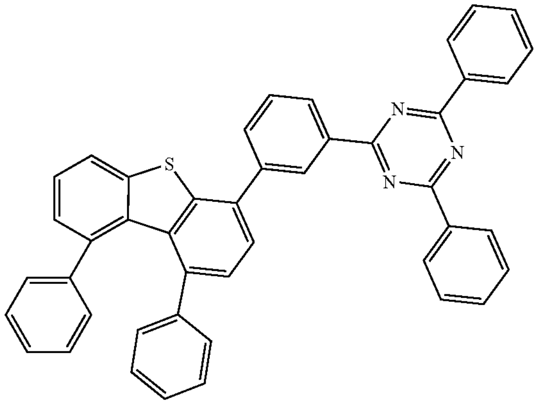
,
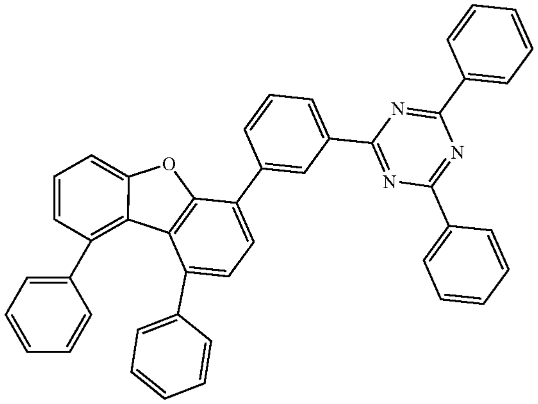
,
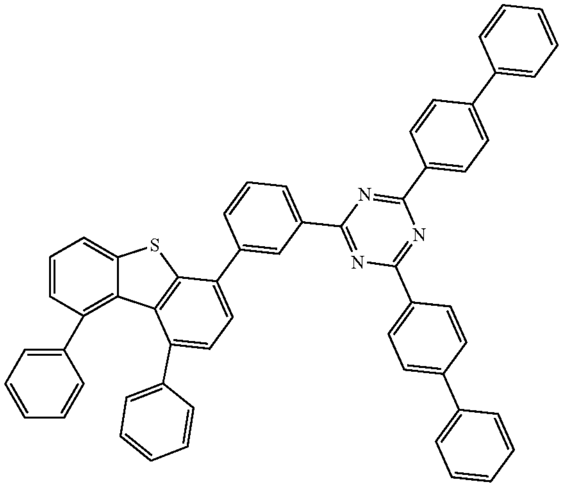
,
-continued
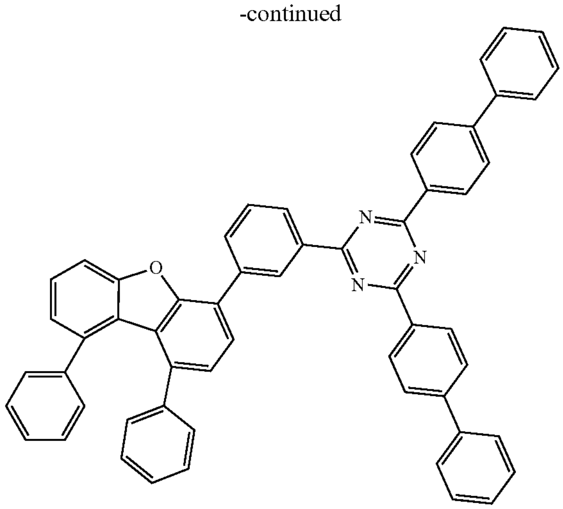
,
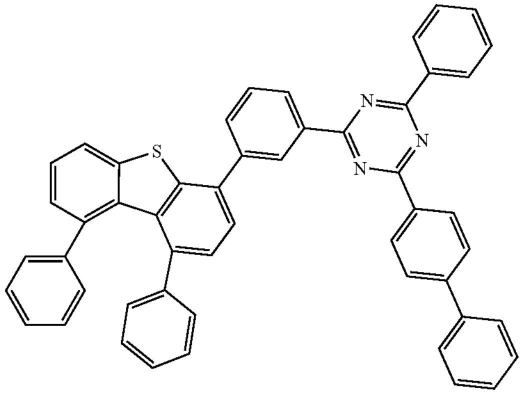
, and
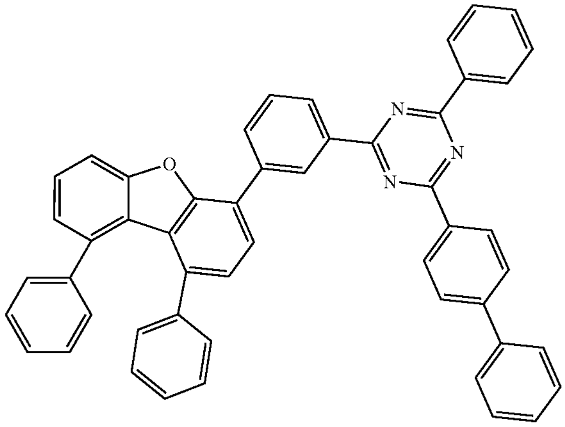
.
Also disclosed is a compound selected from the structures in the following LIST A:

-continued
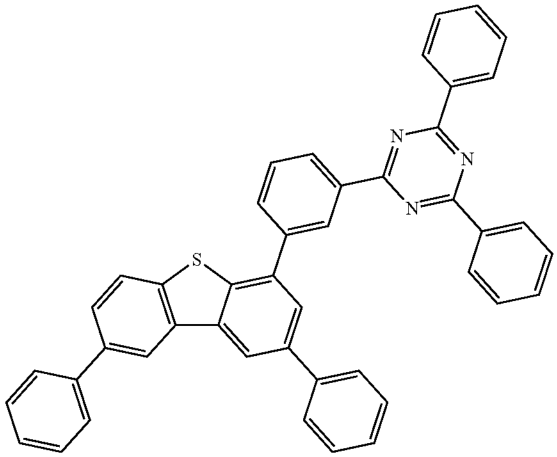
,
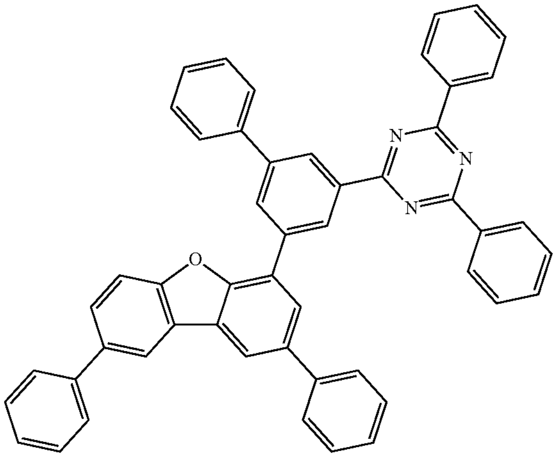
,
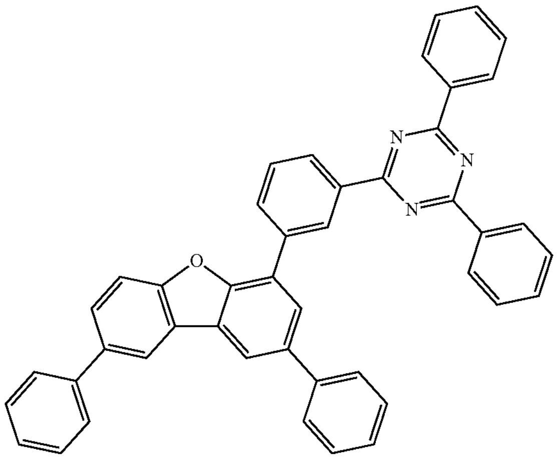
,
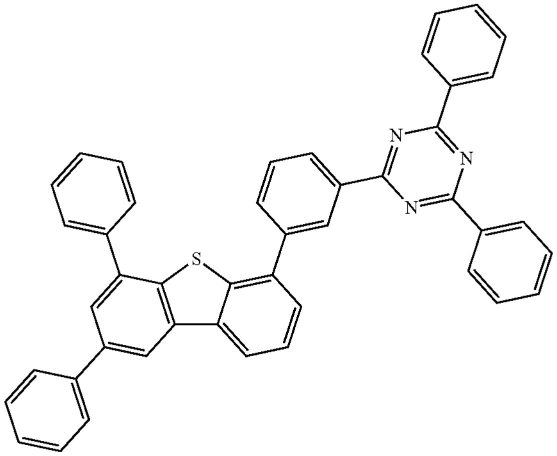
,
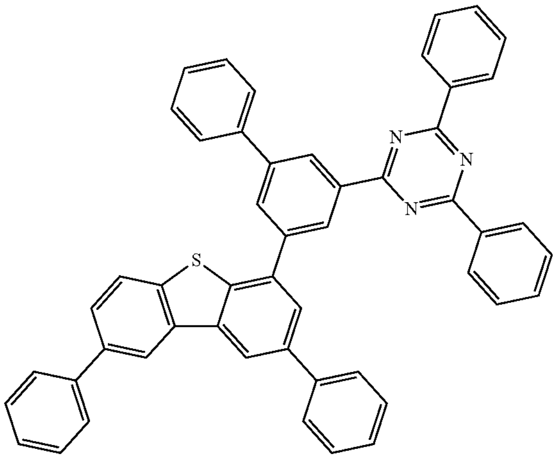
,
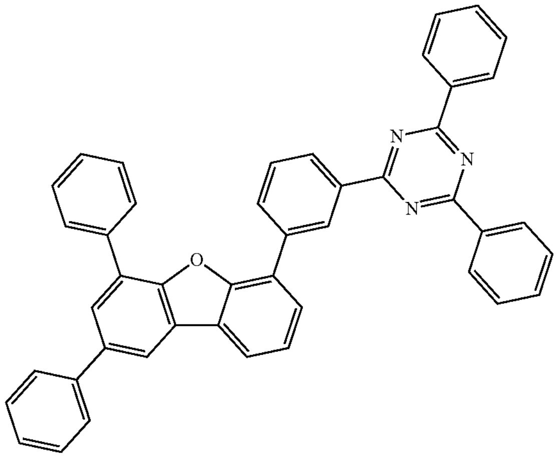
, -continued

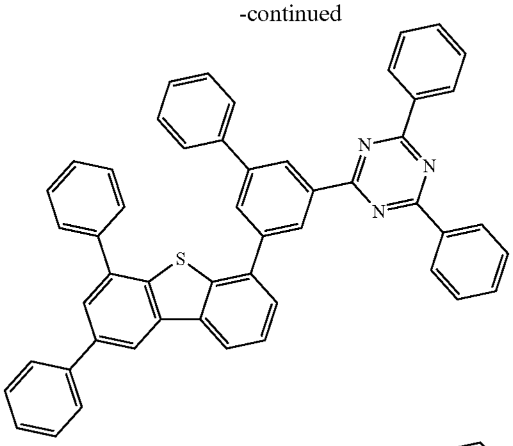

, and

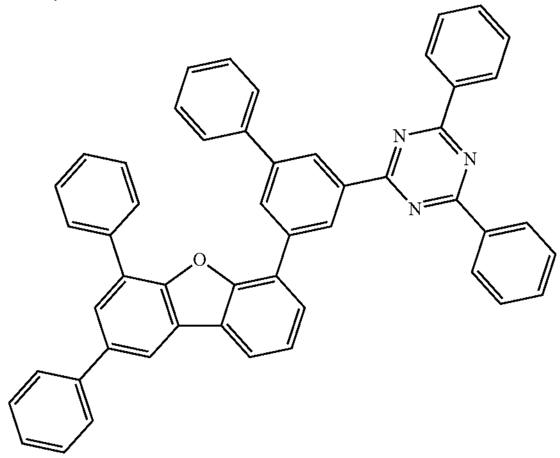

.

In some embodiments, the compound having a structure of Formula I described herein can be at least 30% deuterated, at least 40% deuterated, at least 50% deuterated, at least 60% deuterated, at least 70% deuterated, at least 80% deuterated, at least 90% deuterated, at least 95% deuterated, at least 99% deuterated, or 100% deuterated. As used herein, percent deuteration has its ordinary meaning and includes the percent of possible hydrogen atoms (e.g., positions that are hydrogen, deuterium, or halogen) that are replaced by deuterium atoms.

C. The OLEDs and the Devices of the Present Disclosure

In another aspect, the present disclosure also provides an OLED comprising a first organic layer that contains a compound as disclosed in the above compounds section of the present disclosure.

In some embodiments, the OLED comprises an anode, a cathode, and a first organic layer disposed between the anode and the cathode. The first organic layer can comprise the compounds of Formula I as described herein or the compounds of LIST A as described herein.

In some embodiments, the compound may be a host, and the first organic layer may be an emissive layer that comprises a phosphorescent emitter.

In some embodiments, the phosphorescent emitter may be a transition metal complex having at least one ligand or part of the ligand if the ligand is more than bidentate selected from the group consisting of:

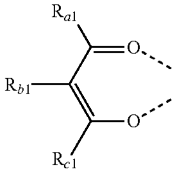

,

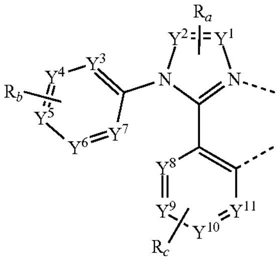

,

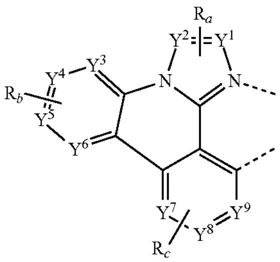

,

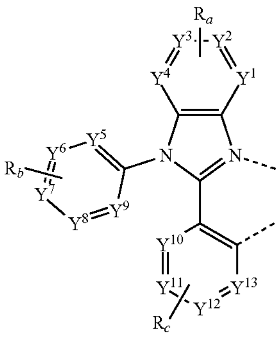

,

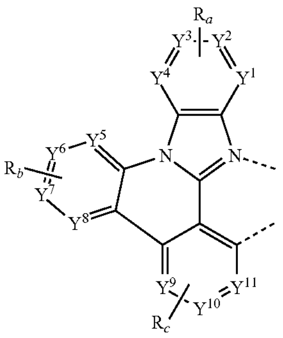

,

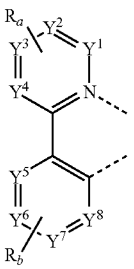

,

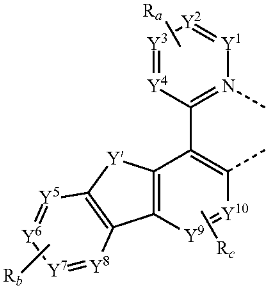

,

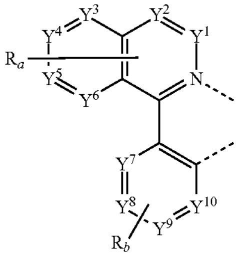

,

-continued

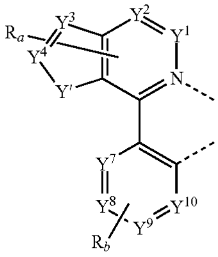

,

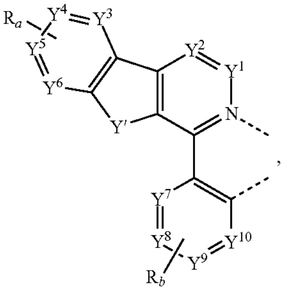

,

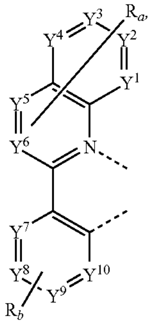

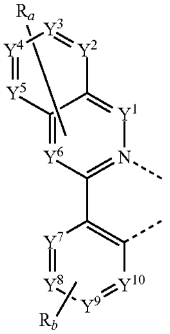

,

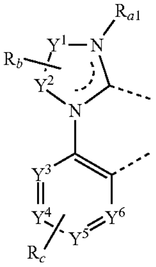

,

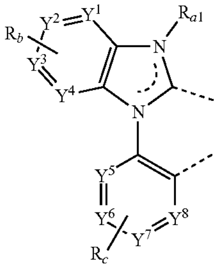

,

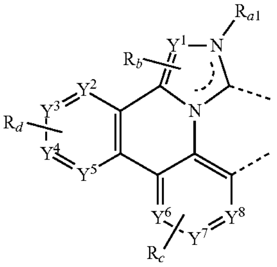

,

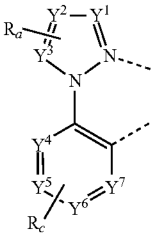

,

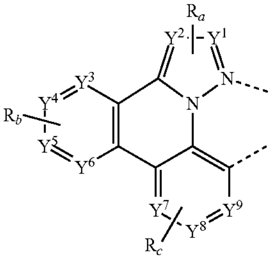

,

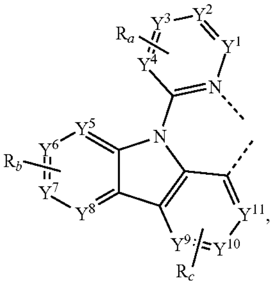

-continued

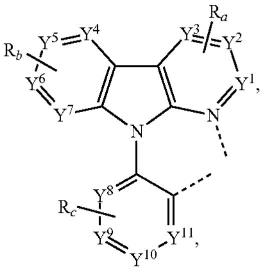

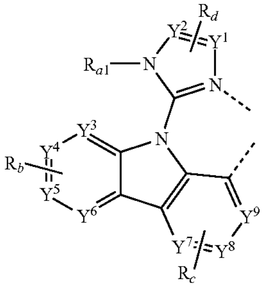

,

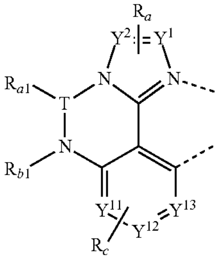

,

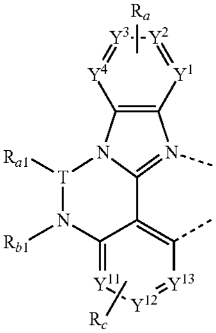

, and

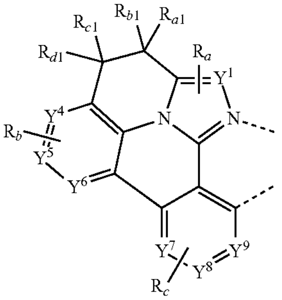

, wherein:

T is selected from the group consisting of B, Al, Ga, and In;

each of $Y^1$ to $Y^{13}$ is independently selected from the group consisting of carbon and nitrogen;

Y' is selected from the group consisting of $BR_e$, $NR_e$, $PR_e$, O, S, Se, C═O, S═O, $SO_2$, $CR_eR_f$, $SiR_eR_f$, and $GeR_eR_f$;

$R_e$ and $R_f$ can be fused or joined to form a ring;

each $R_a$, $R_b$, $R_c$, and $R_d$ independently represent zero, mono, or up to a maximum allowed number of substitutions to its associated ring;

each of $R_{a1}$, $R_{b1}$, $R_{c1}$, $R_{d1}$, $R_a$, $R_b$, $R_c$, $R_d$, $R_e$ and $R_f$ is independently a hydrogen or a substituent selected from the group consisting of deuterium, halide, alkyl, cycloalkyl, heteroalkyl, arylalkyl, alkoxy, aryloxy, amino, silyl, boryl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; the general substituents defined herein; and any two adjacent substituents of $R_a$, $R_b$, $R_c$, $R_d$, $R_e$ and $R_f$ can be fused or joined to form a ring or form a multidentate ligand.

In some embodiments, the compound may be an acceptor, and the OLED may further comprise a sensitizer selected from the group consisting of a delayed fluorescence emitter, a phosphorescent emitter, and combination thereof.

In some embodiments, the compound may be a fluorescent emitter, a delayed fluorescence emitter, or a component of an exciplex that is a fluorescent emitter or a delayed fluorescence emitter.

In some embodiments, the compound of Formula I or LIST A as described herein is an acceptor, and the OLED further comprises a sensitizer selected from the group consisting of a delayed fluorescence emitter, a phosphorescent emitter, and combination thereof.

In some embodiments, the compound of Formula I or LIST A as described herein is a fluorescent emitter, a delayed fluorescence emitter, or a component of an exciplex that is a fluorescent emitter or a delayed fluorescence emitter.

In some embodiments, the organic layer further comprises an h-host. In some embodiments, the h-host is selected from the group consisting of the structures in the following LIST 2:

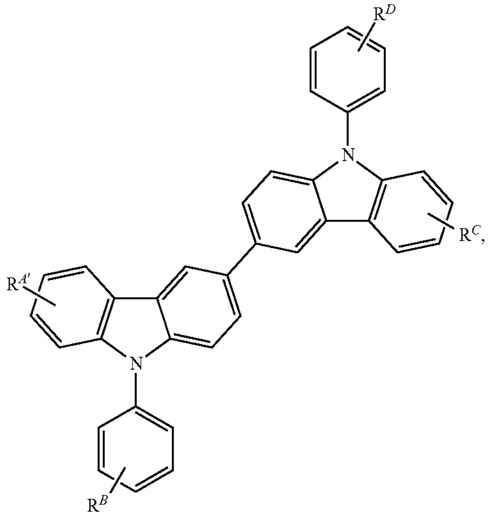

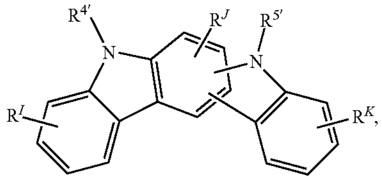

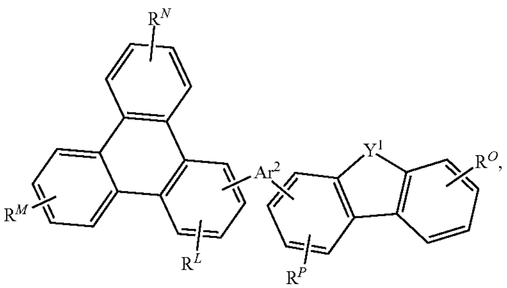

-continued

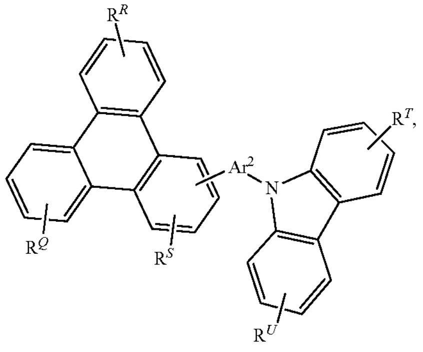

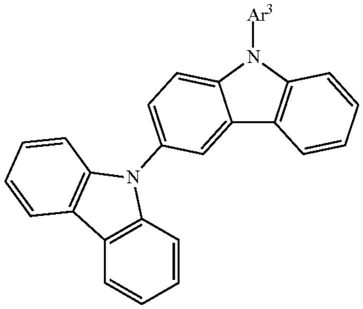

,

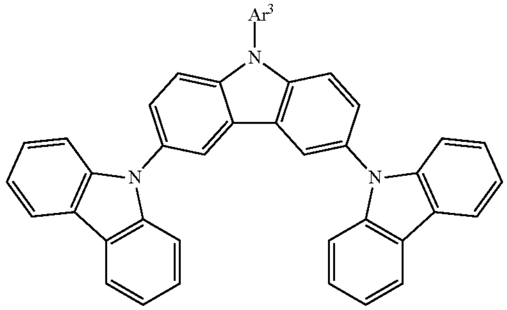

,

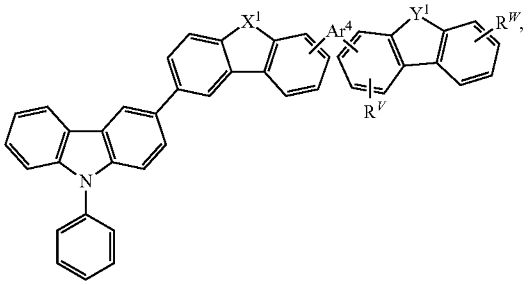

and

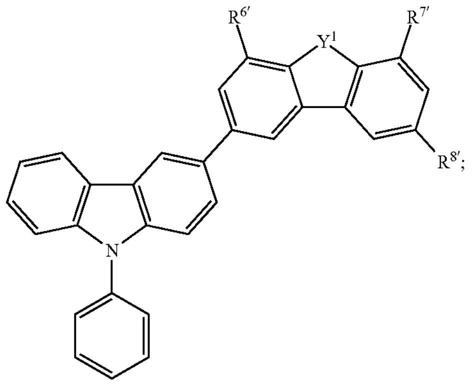

wherein:

each of $R^{A'}$, $R^B$, $R^C$, $R^D$, $R^I$, $R^J$, $R^K$, $R^L$, $R^M$, $R^N$, $R^O$, $R^P$, $R^Q$, $R^R$, $R^S$, $R^T$, $R^U$, $R^V$, and $R^W$ represent mono to the maximum allowable substitution, or no substitution;

each of $Ar^2$ and $Ar^4$ is a linker independently selected from the group consisting of a direct bond, aryl, and heteroaryl;

each of $X^1$ and $Y^1$ is independently selected from the group consisting of $BR_{e'}$, $NR_{e'}$, $PR_{e'}$, O, S, Se, C═O, S═O, $SO_2$, $CR_{e'}R_{f'}$, $SiR_{e'}R_{f'}$, and $G_{e'}R_{f'}$; and each $Ar^3$, $R^{4'}$, $R^{5'}$, $R^{6'}$, $R^{7'}$, $R^{8'}$, $R_{e'}$, $R_{f'}$, $R^{A'}$, $R^B$, $R^C$, $R^D$, $R^I$, $R^J$, $R^K$, $R^L$, $R^M$, $R^N$, $R^O$, $R^P$, $R^Q$, $R^R$, $R^s$, $R^T$, $R^U$, $R^V$, and $R^W$ is independently a hydrogen or a substituent selected from the group consisting of deuterium, halogen, alkyl, cycloalkyl, heteroalkyl, heterocycloalkyl, boryl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof.

In some embodiments, the h-host is selected from the group consisting of the structures in the following LIST 3:

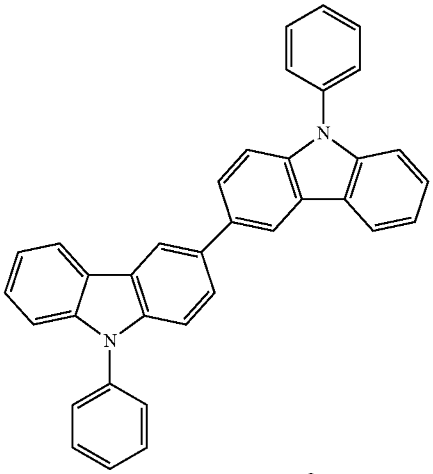
,

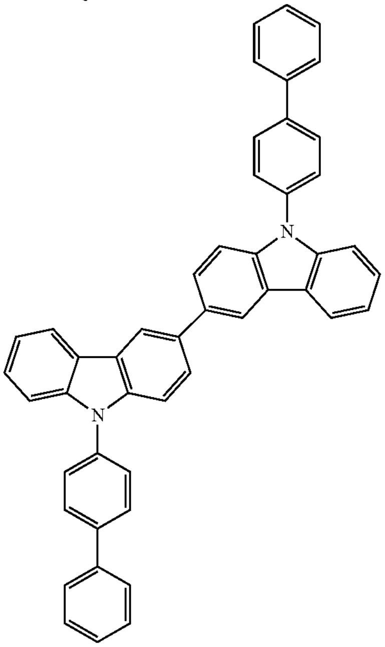
,

-continued

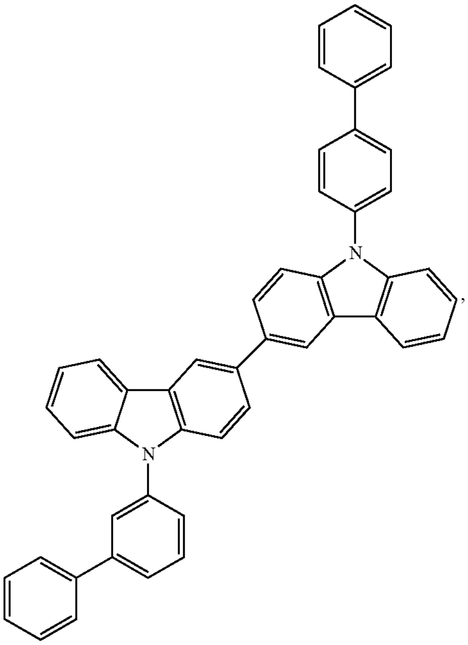
,

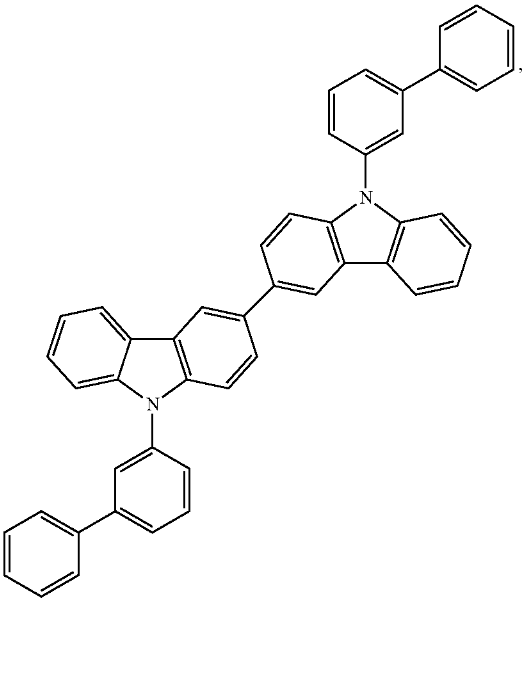
,

-continued
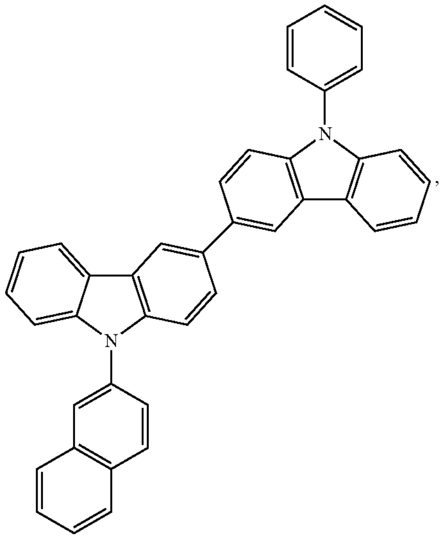
,
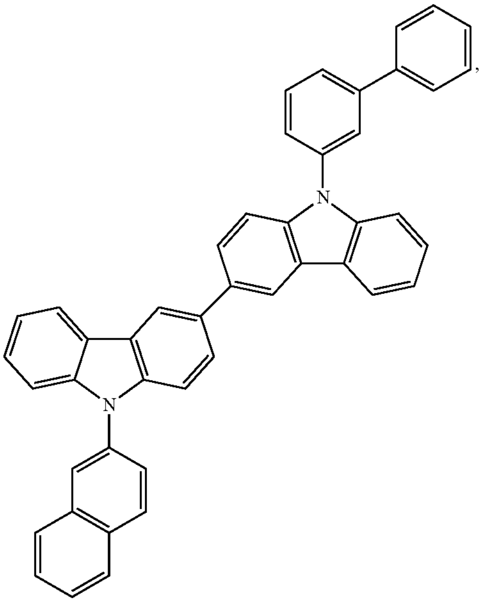
,
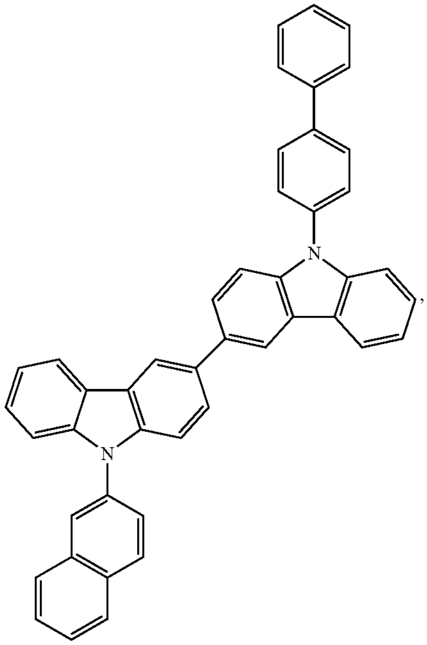
,
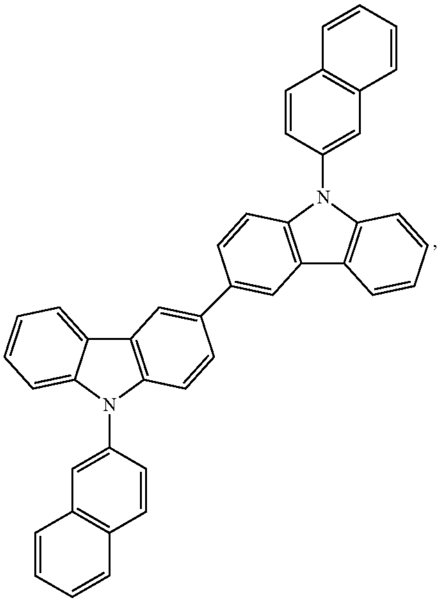
,

-continued
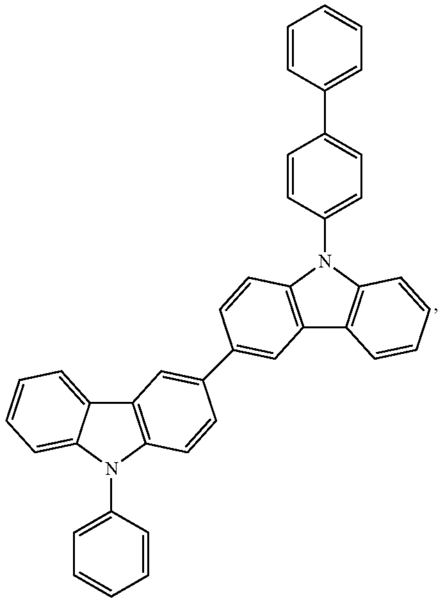
,
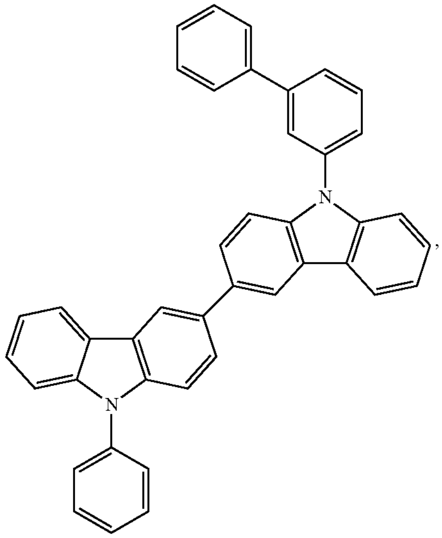
,
-continued
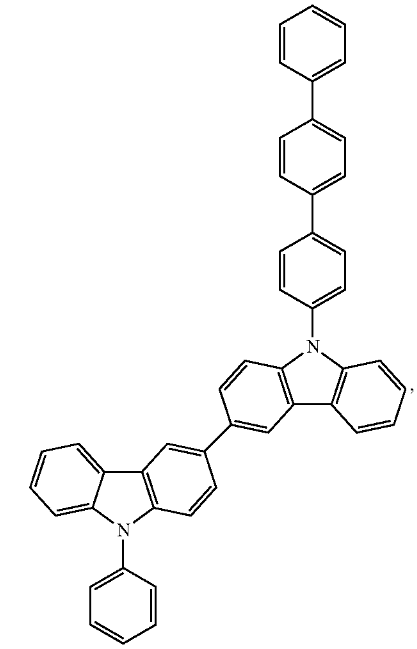
,
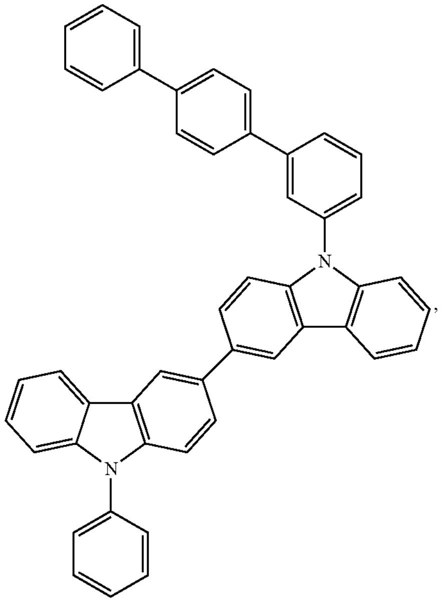
,

-continued
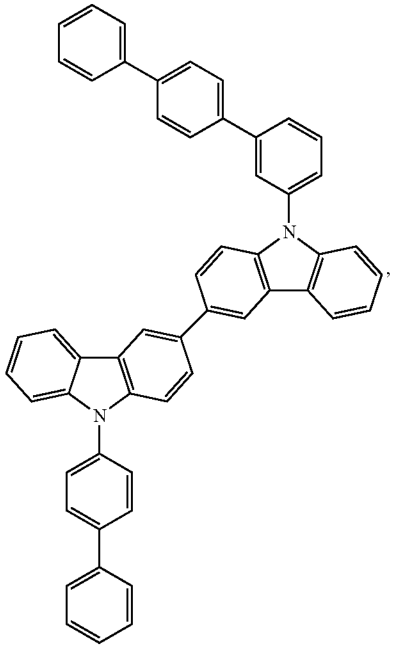,
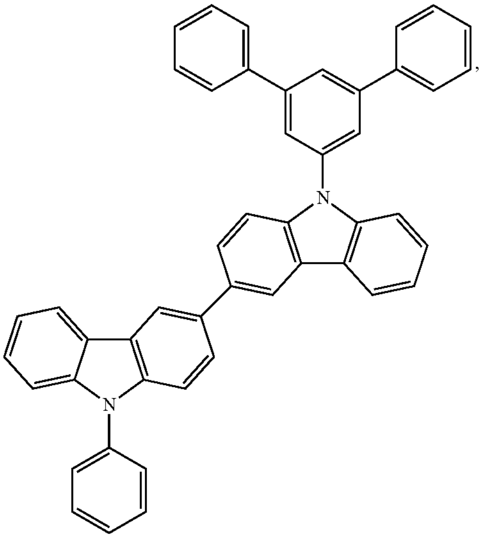,
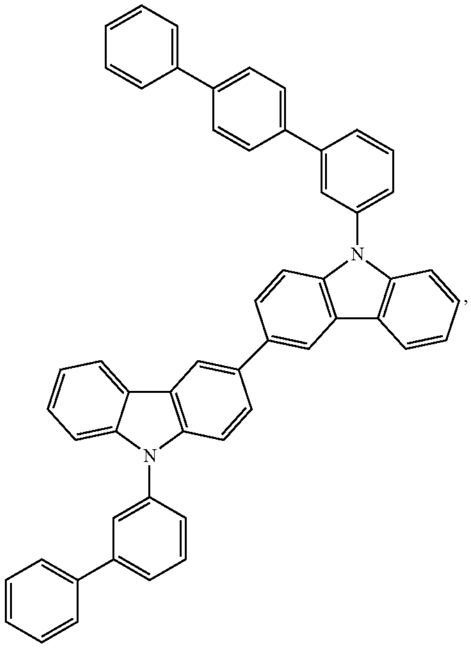,
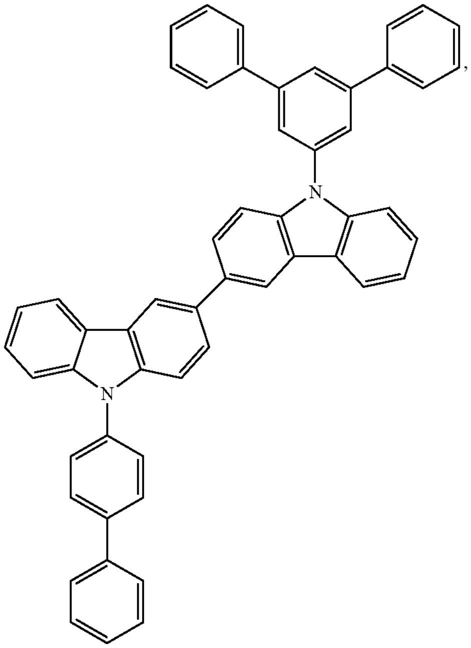,

-continued
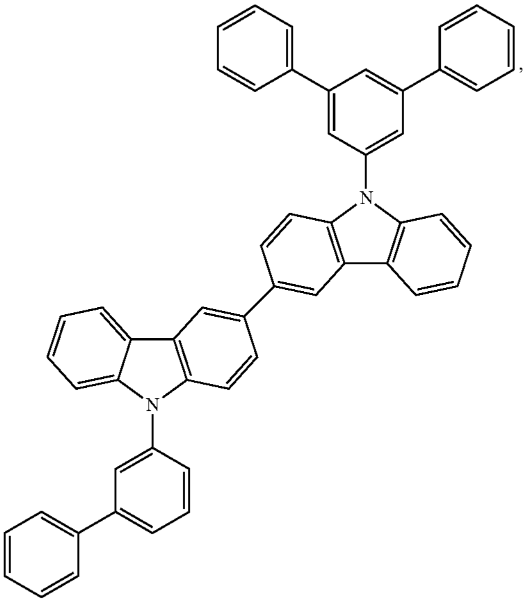
,
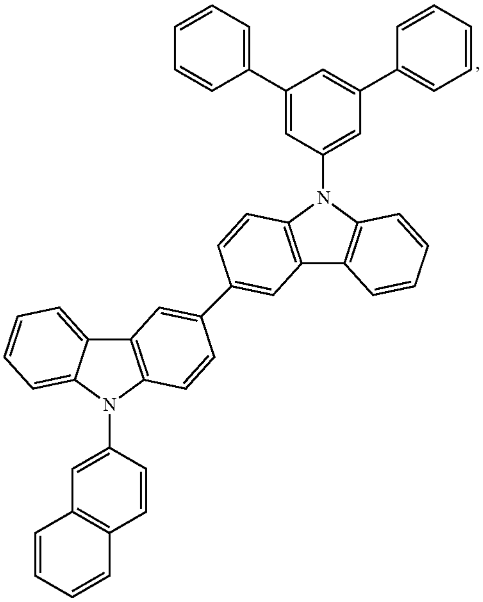
,
-continued
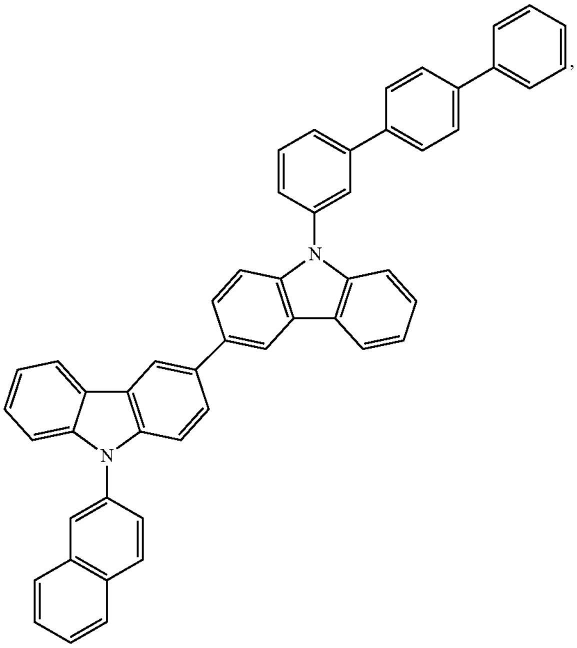
,
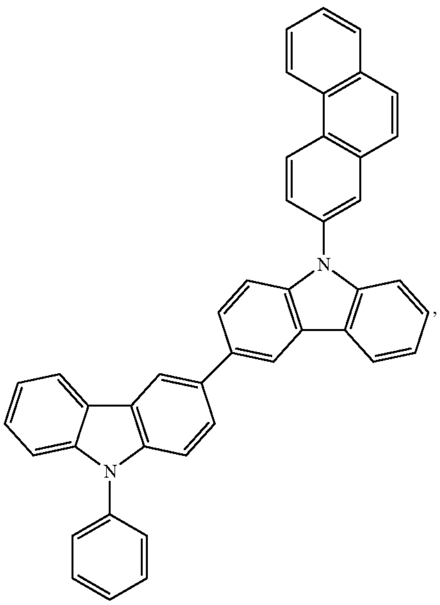
,

-continued
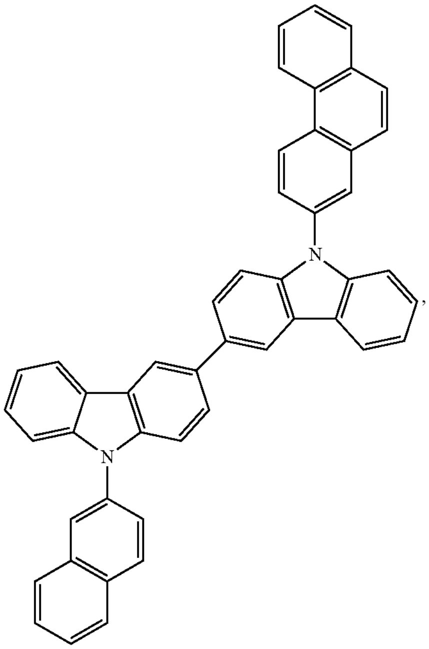
-continued
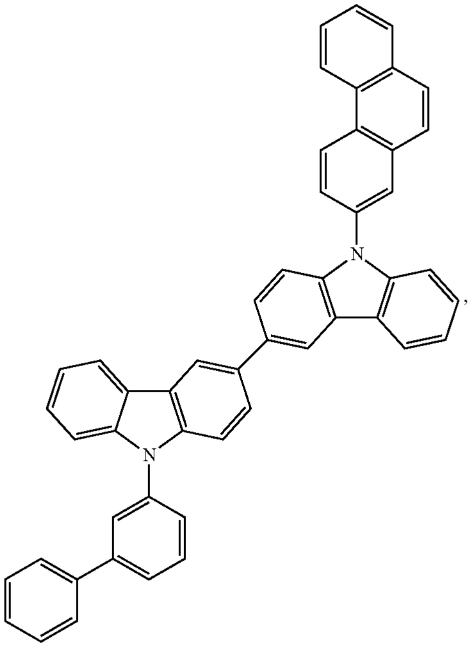
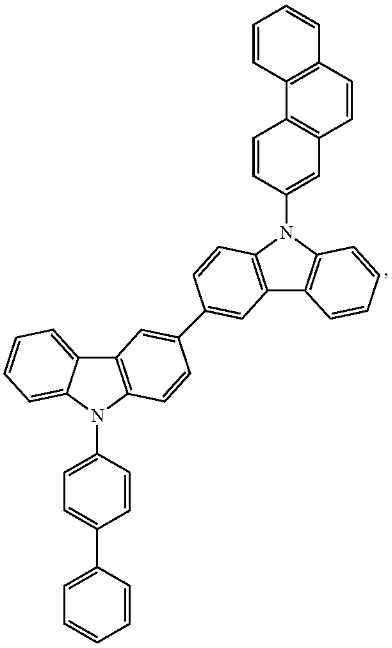 [SMILES: c1ccc(-c2ccc(-n3c4ccccc4c4cc(-c5ccc6c(c5)c5ccccc5n6-c5ccc6c(ccc7ccccc76)c5)ccc43)cc2)cc1]
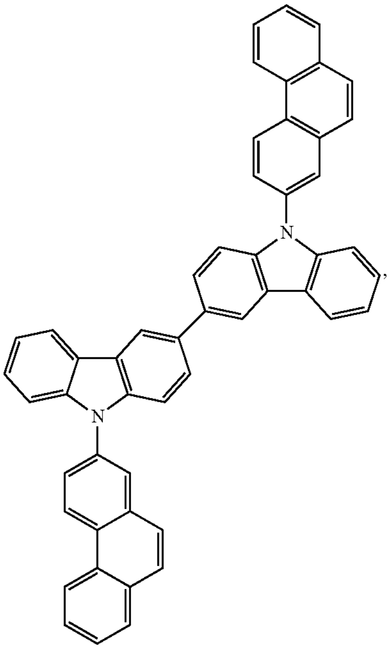

-continued
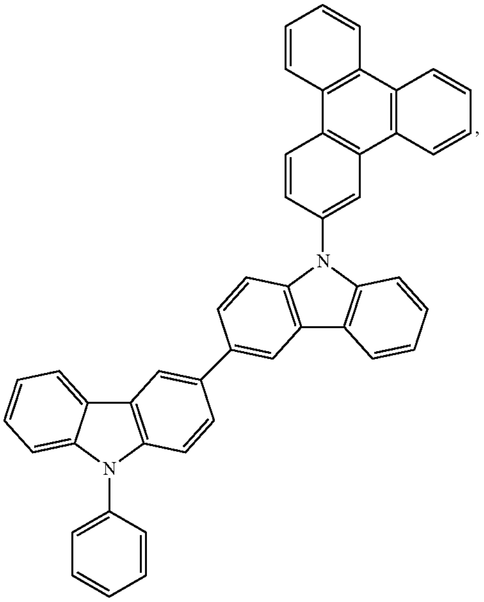
,
-continued
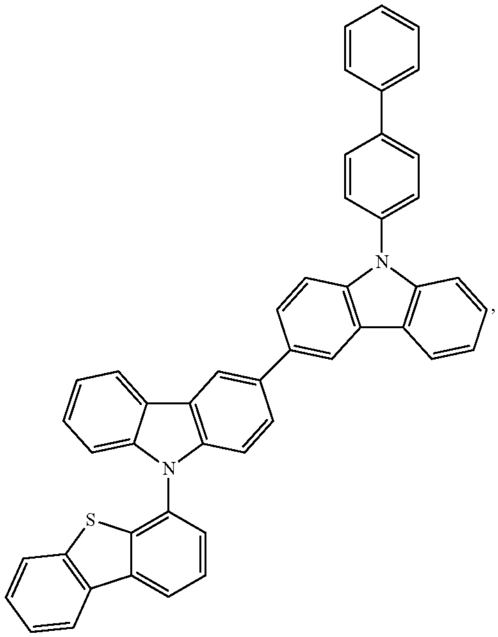
,
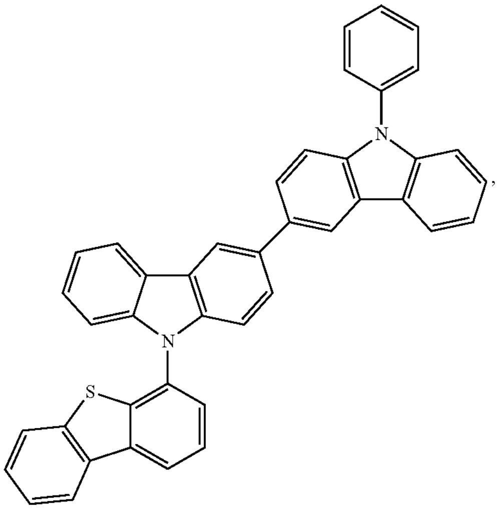
,
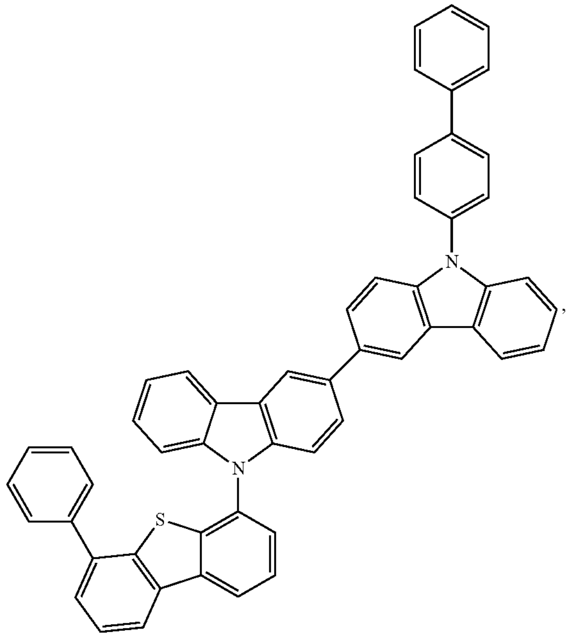
,

-continued
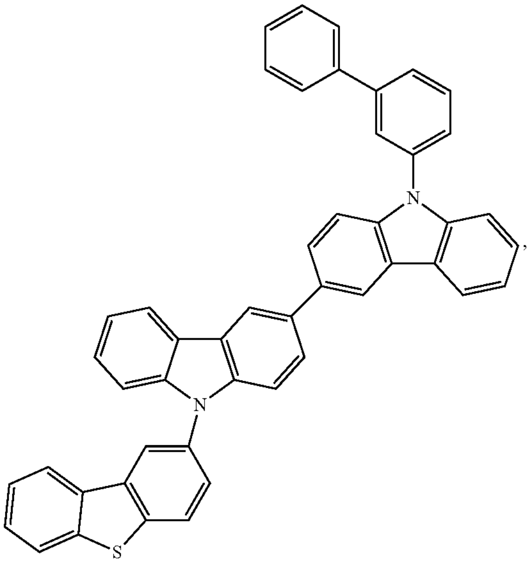
,
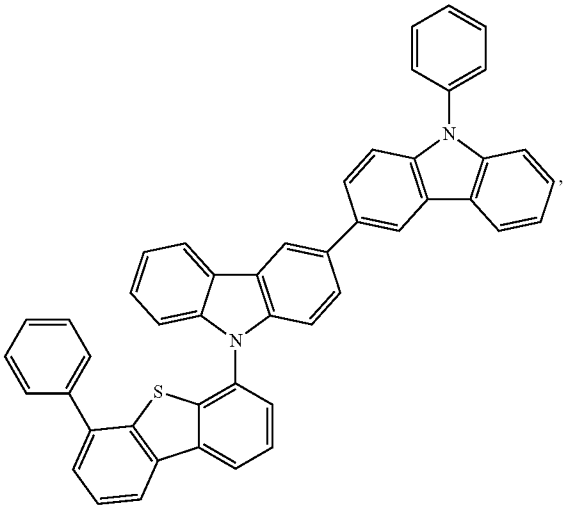
,
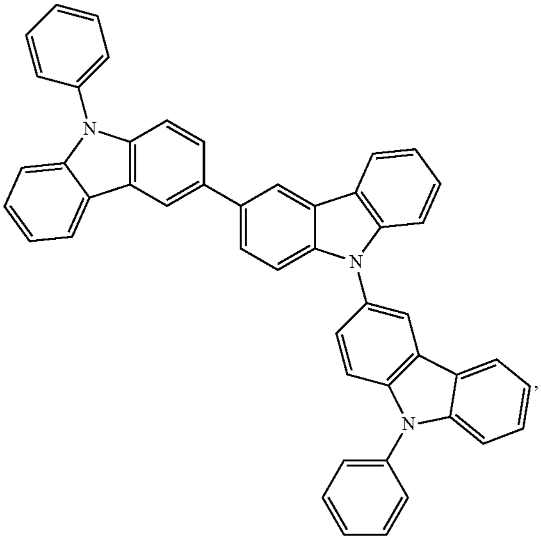
,
-continued
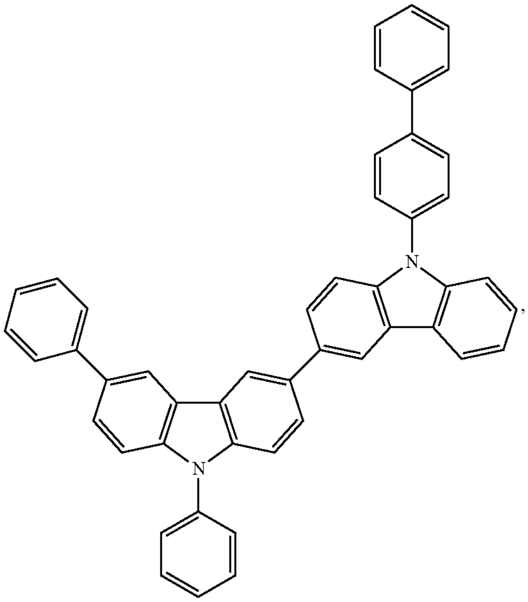
,
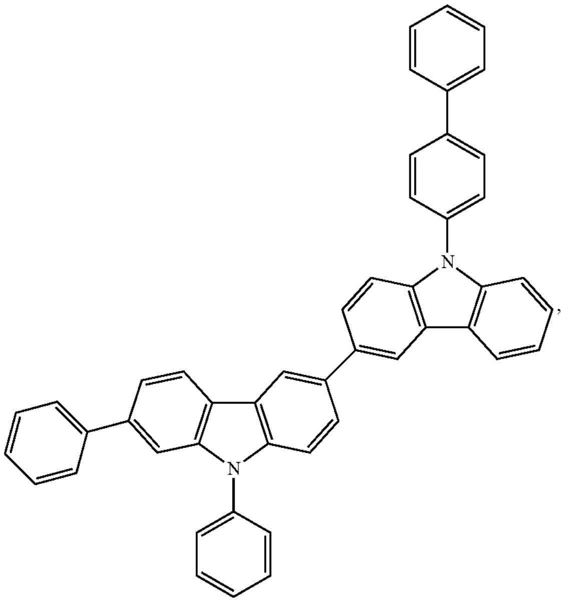
, -continued
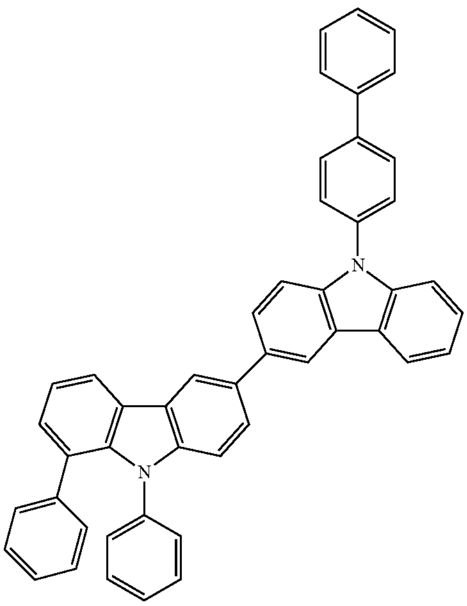
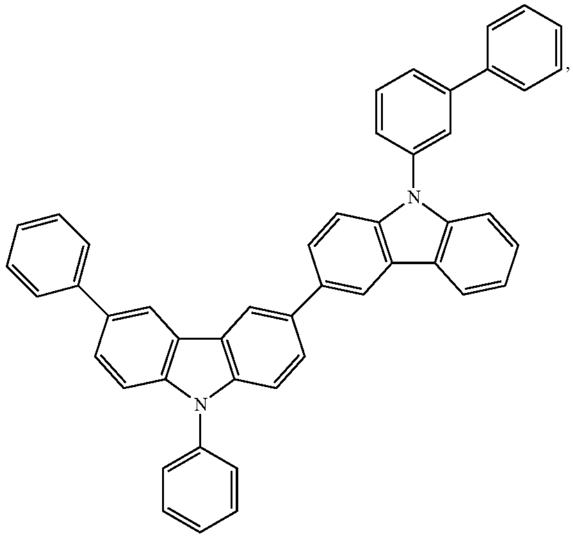
,
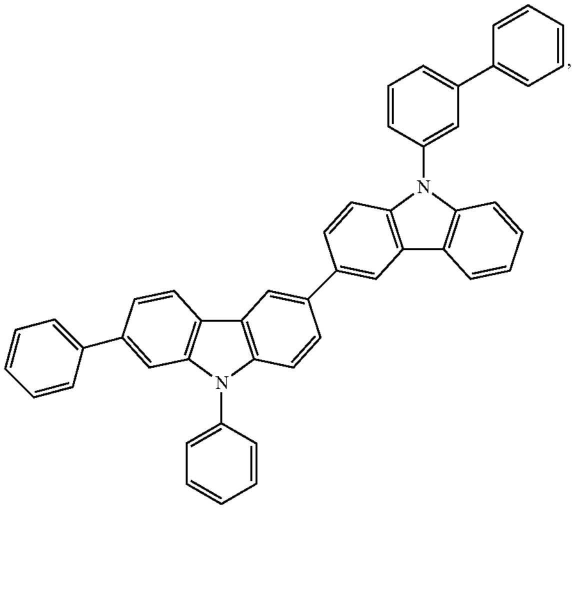
,
-continued
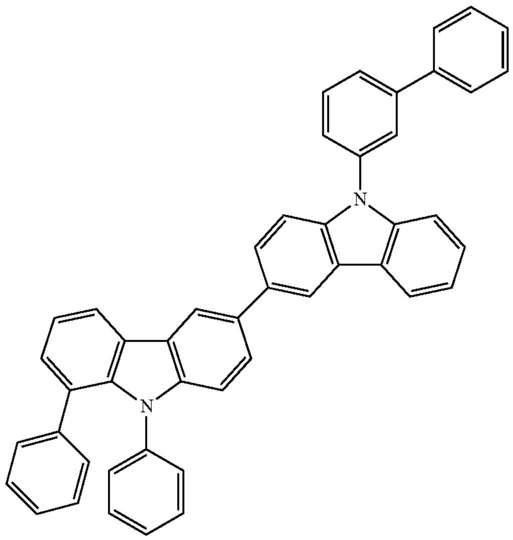
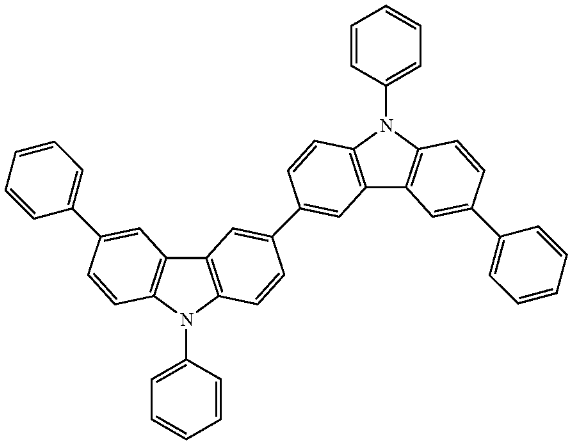
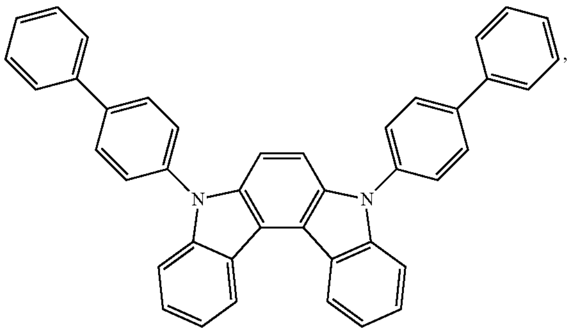
,
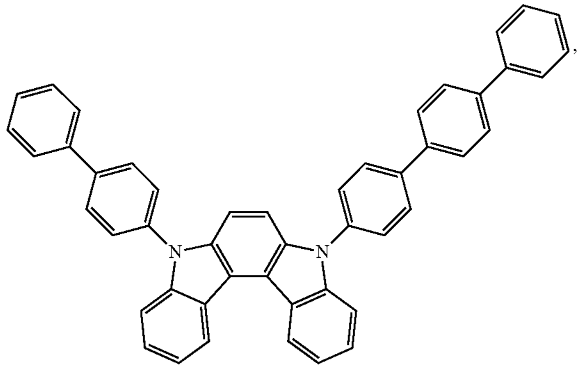
, -continued
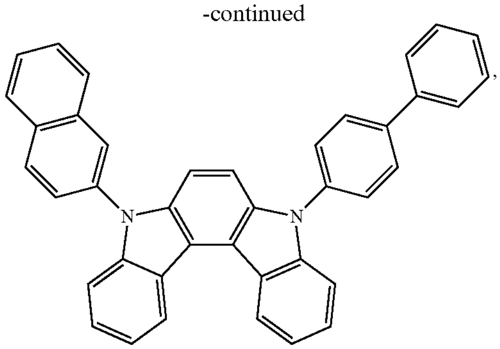
,
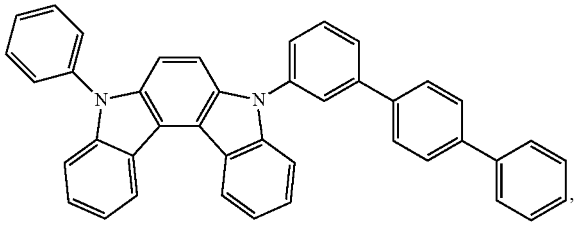
,
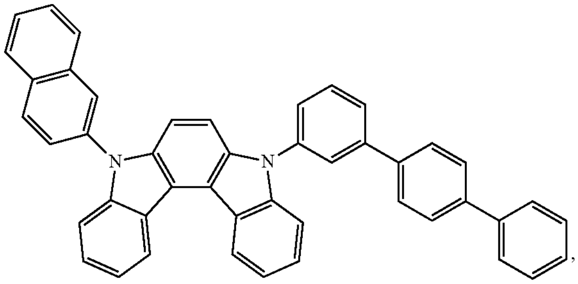
,
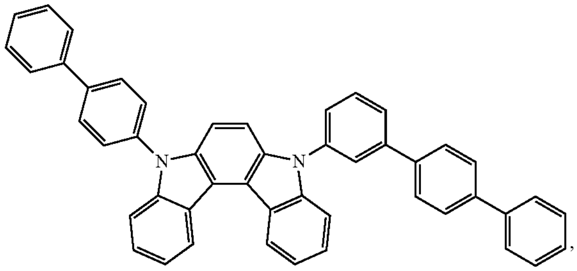
,
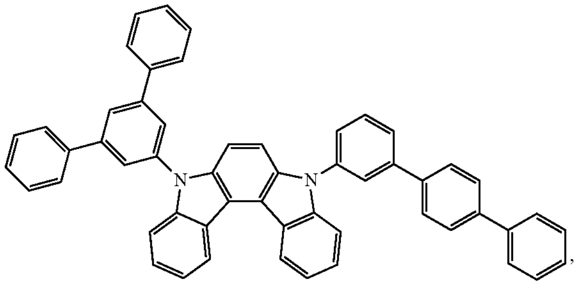
,
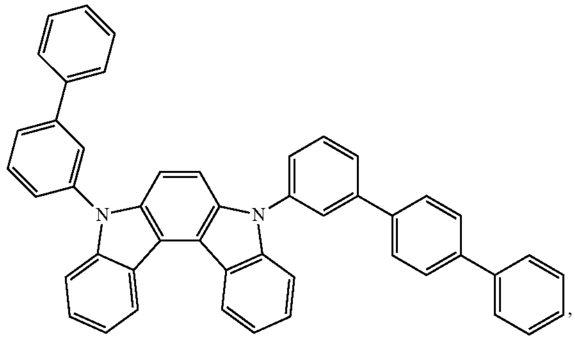
,
-continued
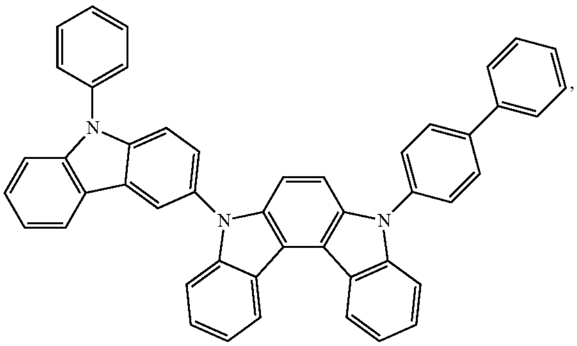
,
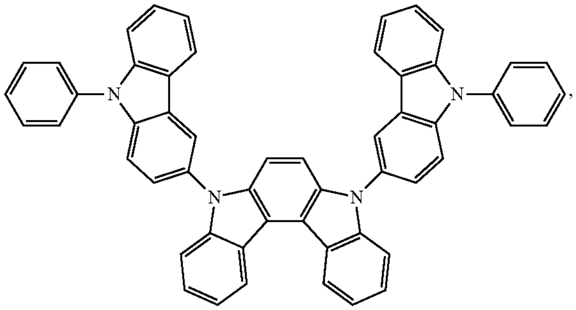
,
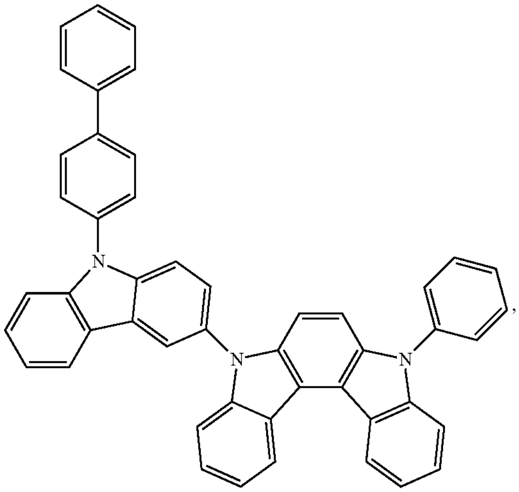
,
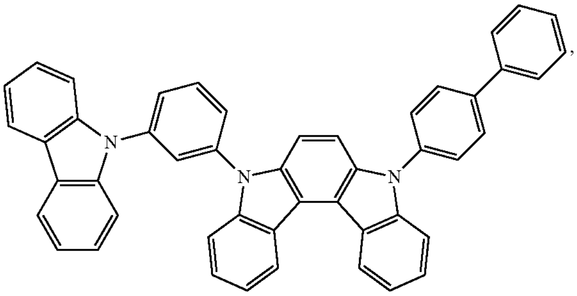
, -continued
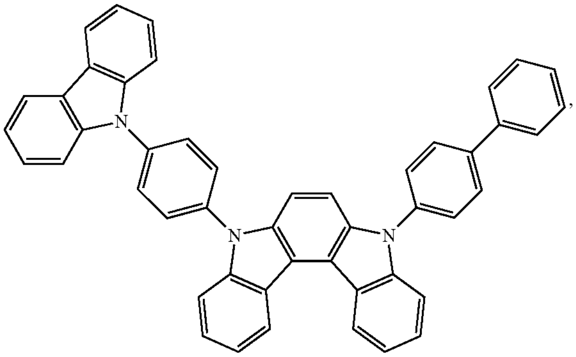,
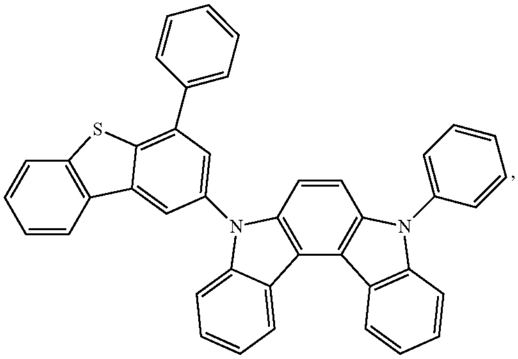,
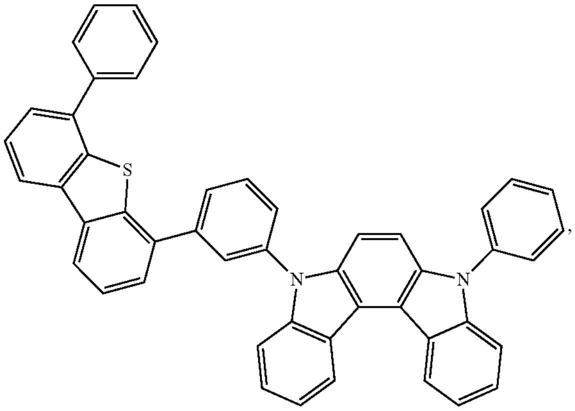,
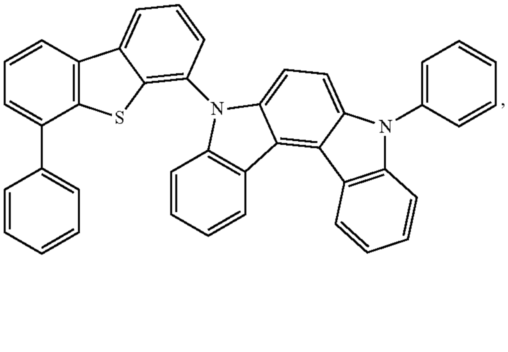,
-continued
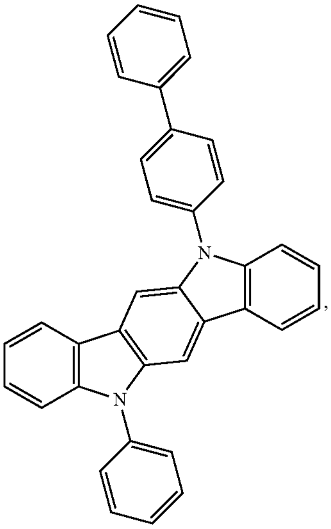,
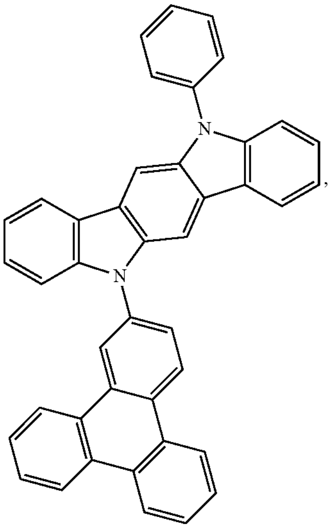,
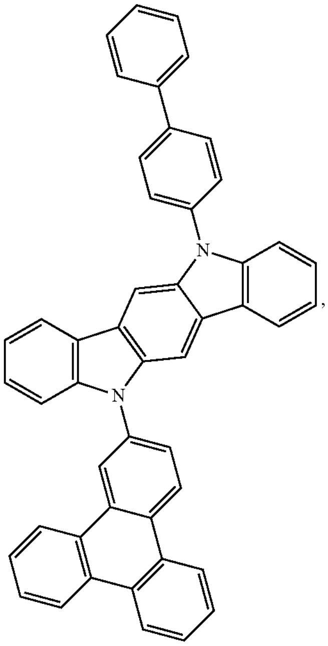, -continued
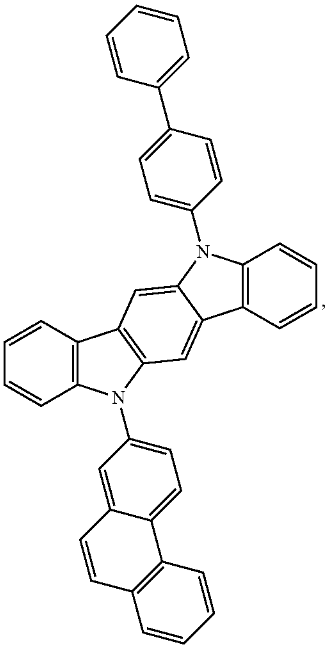
,
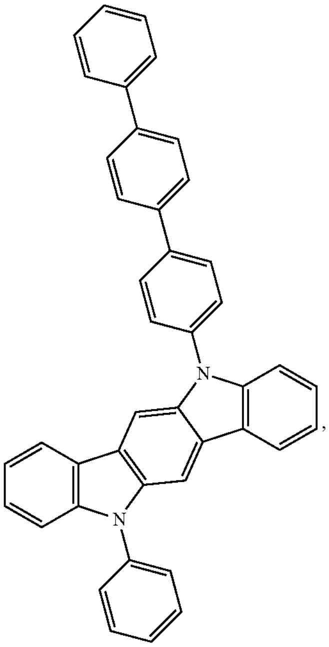
,
-continued
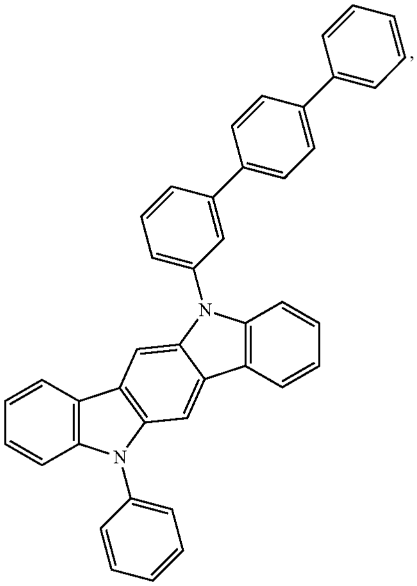
,
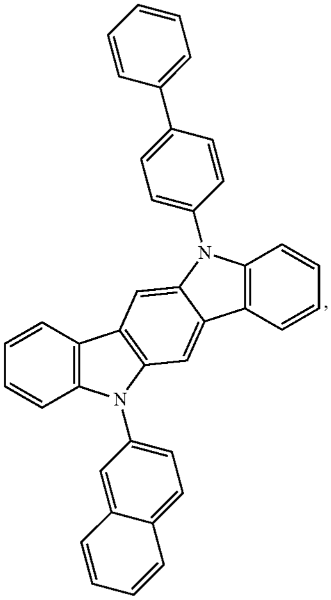
, -continued
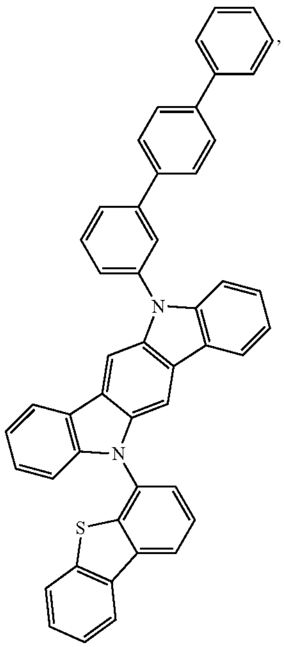
,
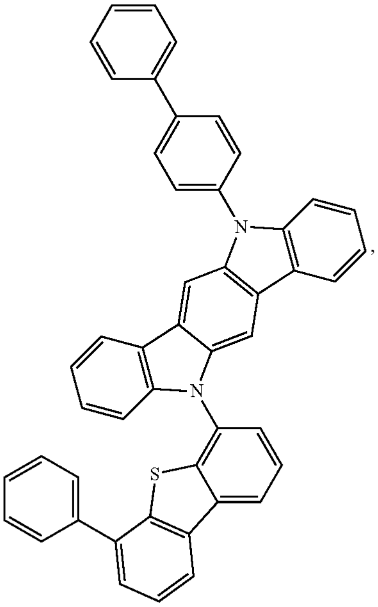
,
-continued
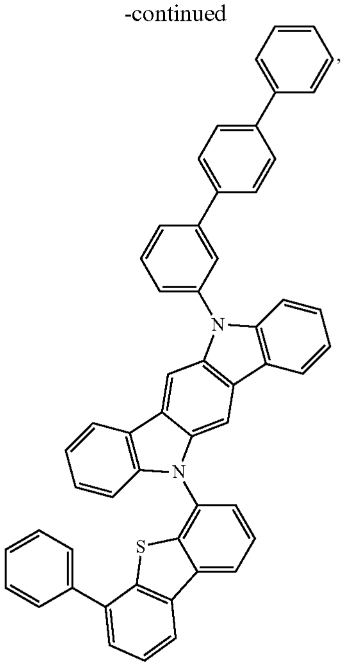
,
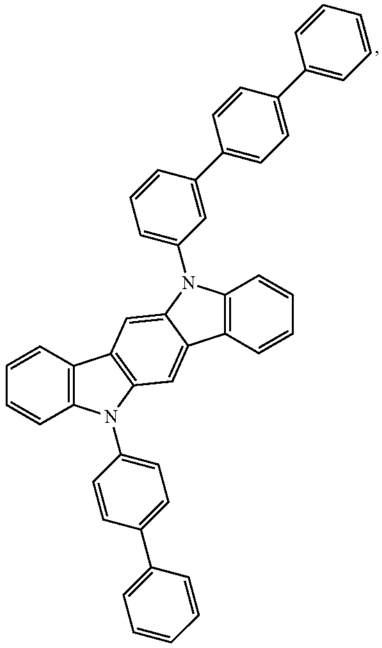
, -continued
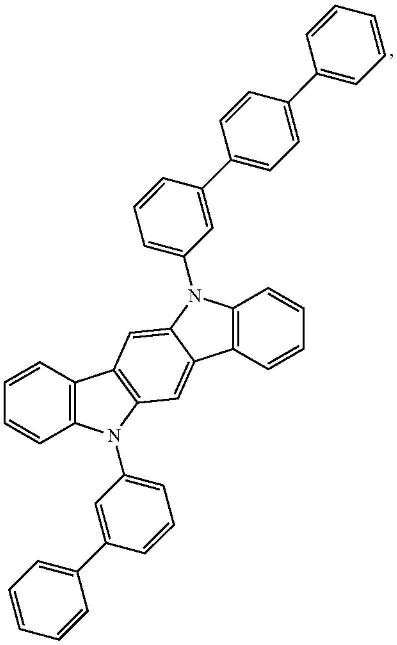
,
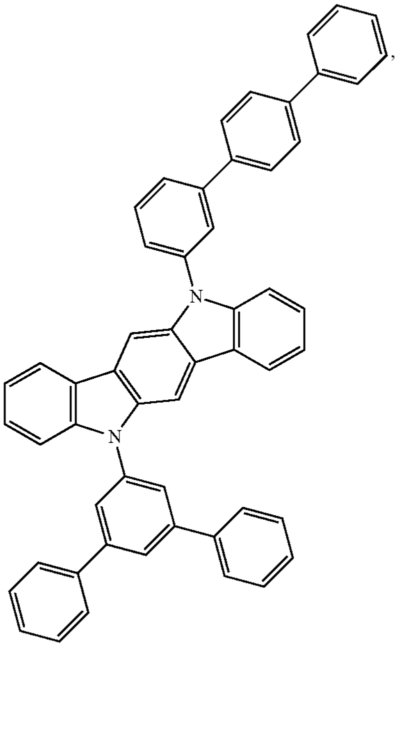
,
-continued
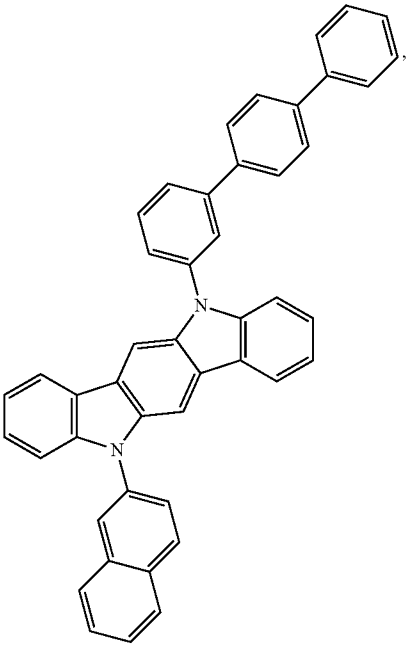
,
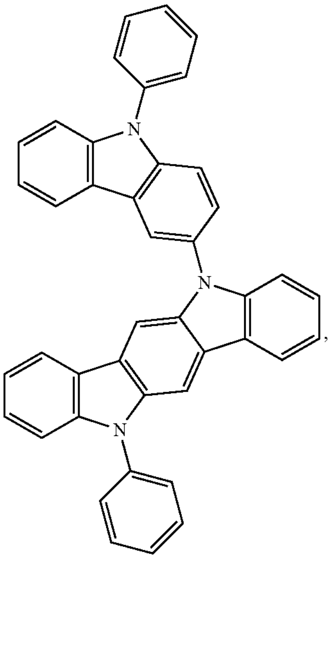
, -continued
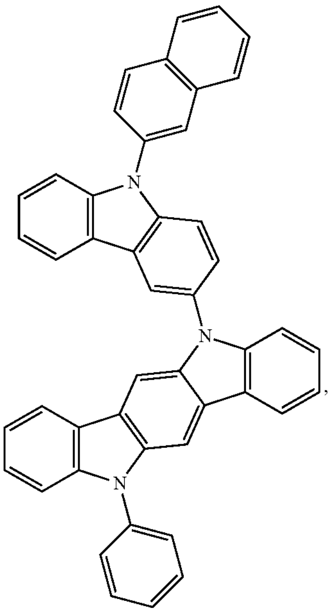
,
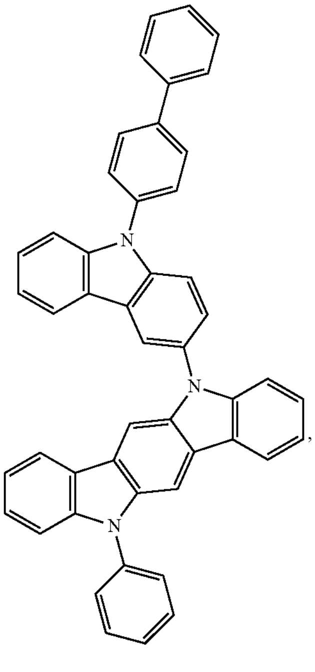
,
-continued
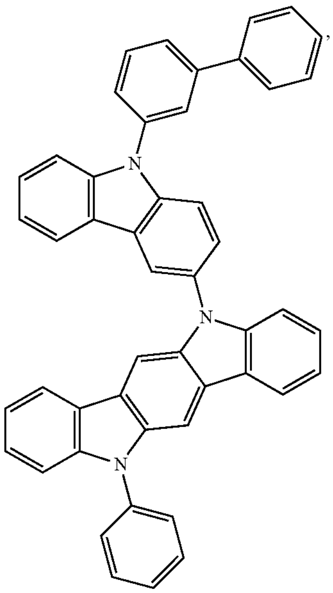
,
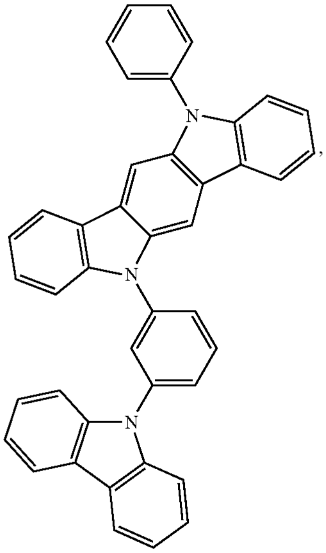
,
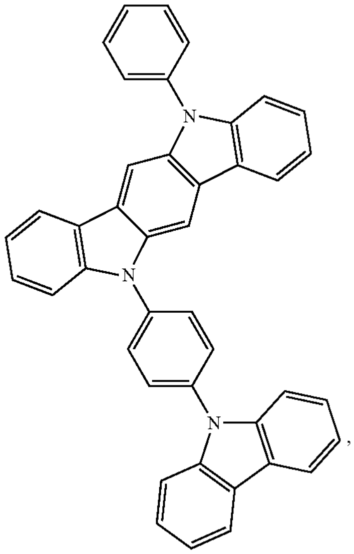
, -continued
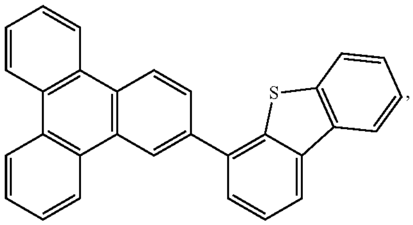
,
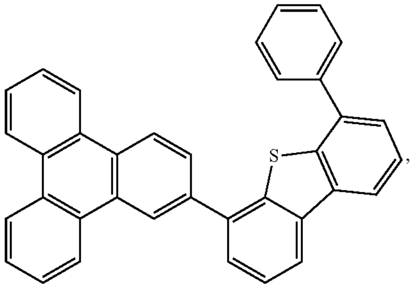
,
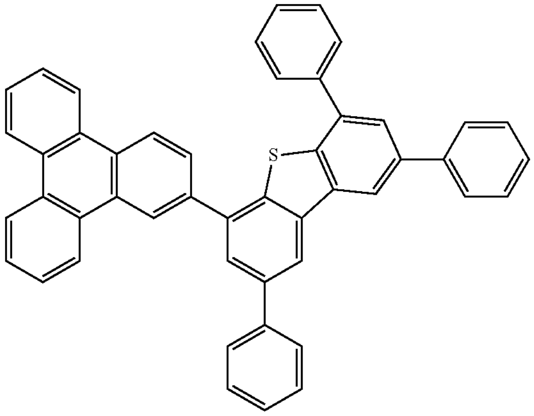
,
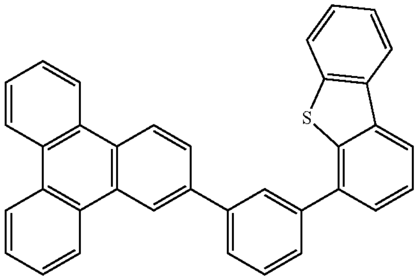
,
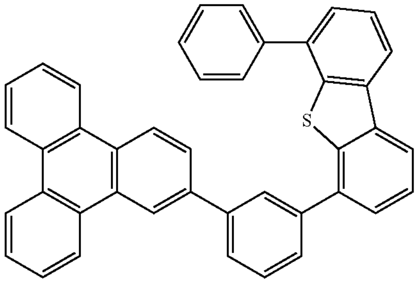
,
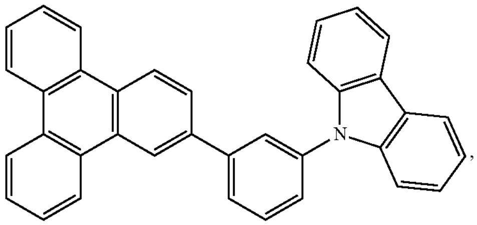
,
-continued
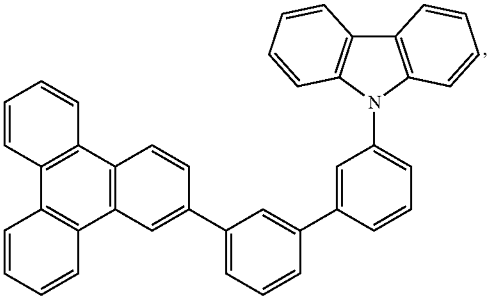
,
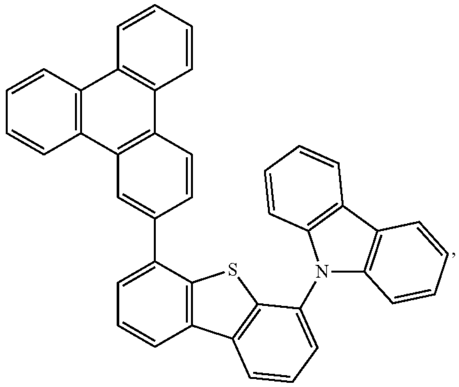
,
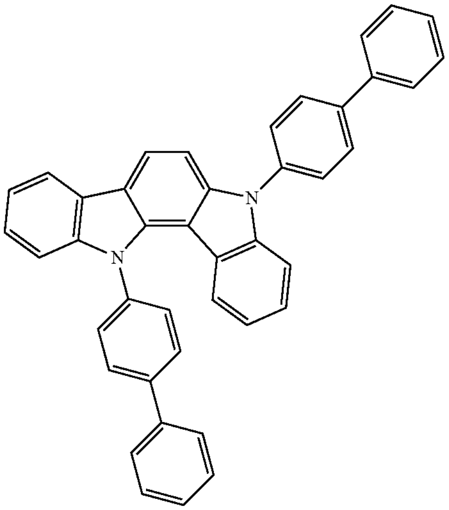
, -continued
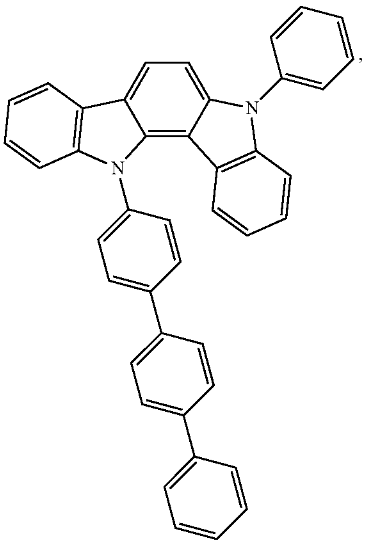
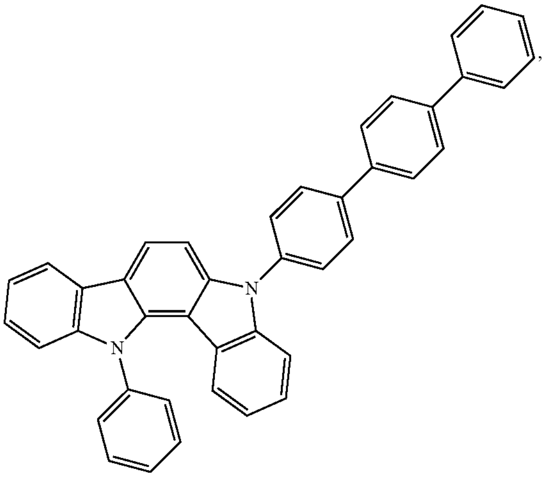
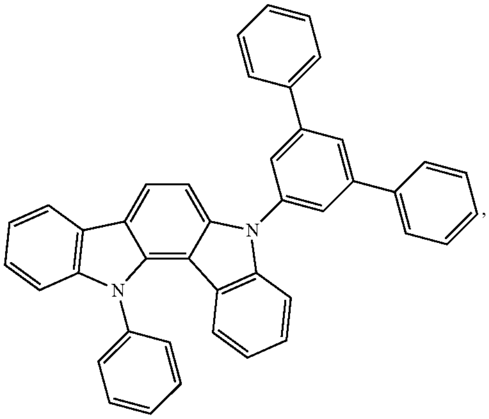
-continued
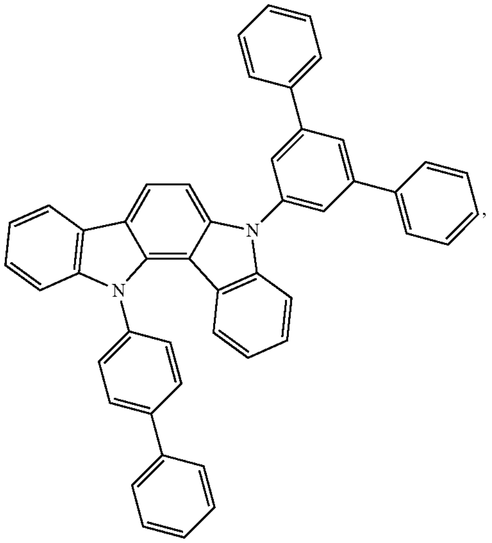
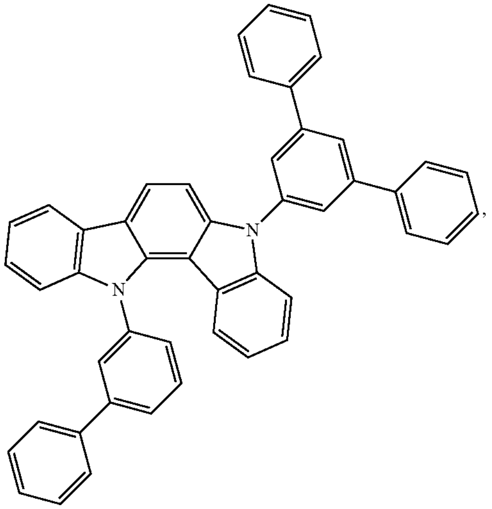
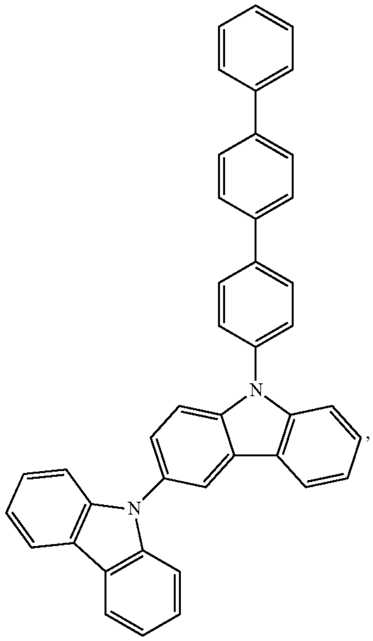

-continued
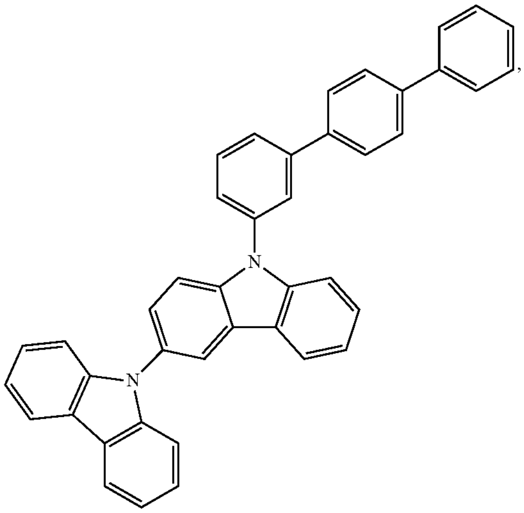
,
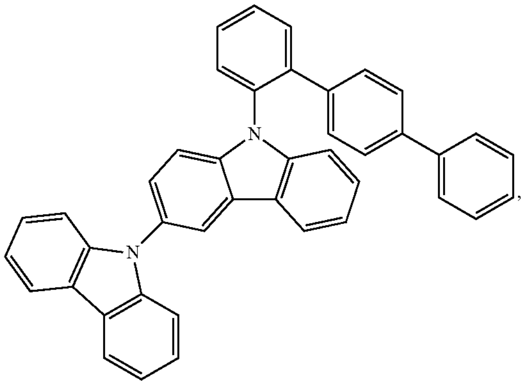
,
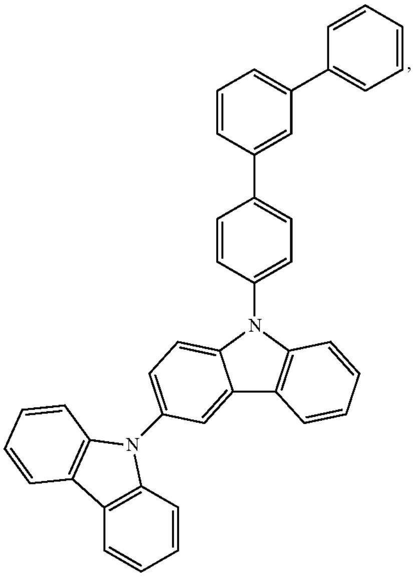
,
-continued
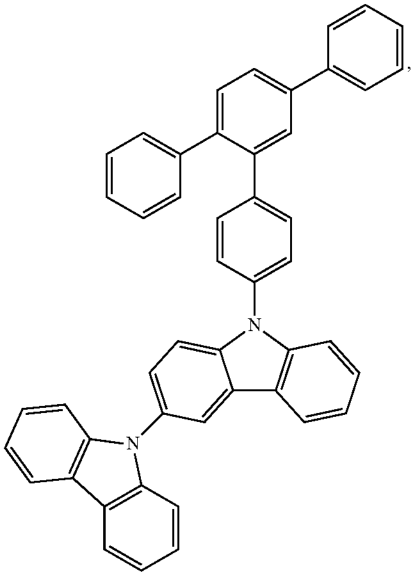
,
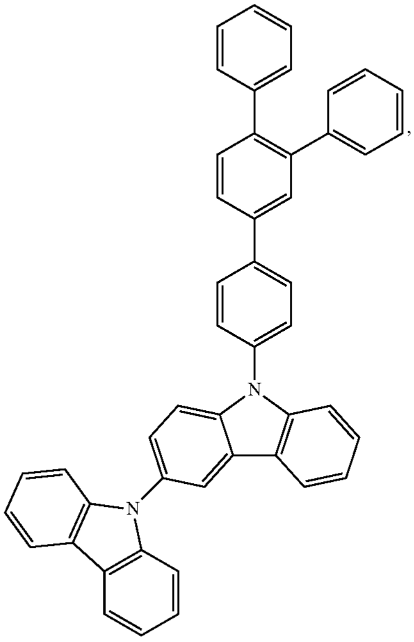
, -continued
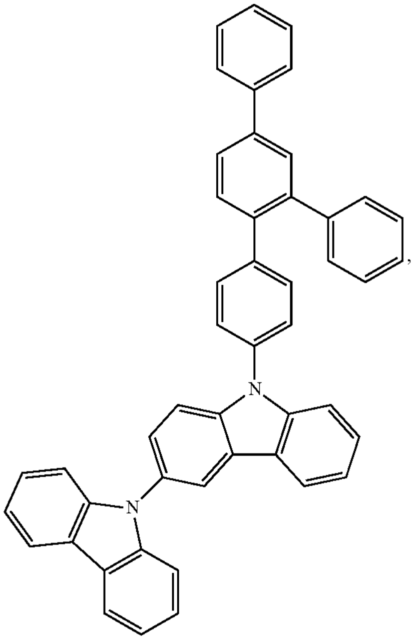
,
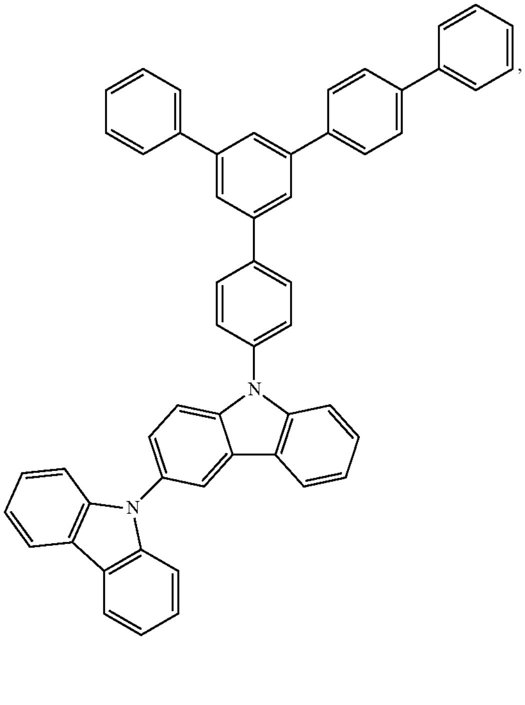
,
-continued
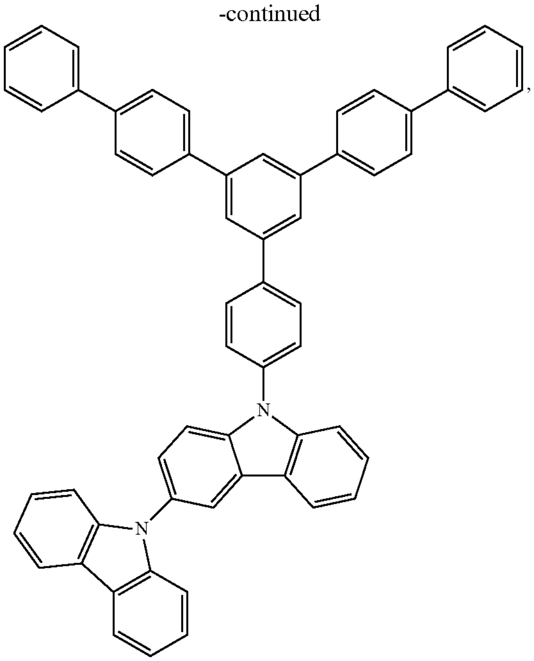
,
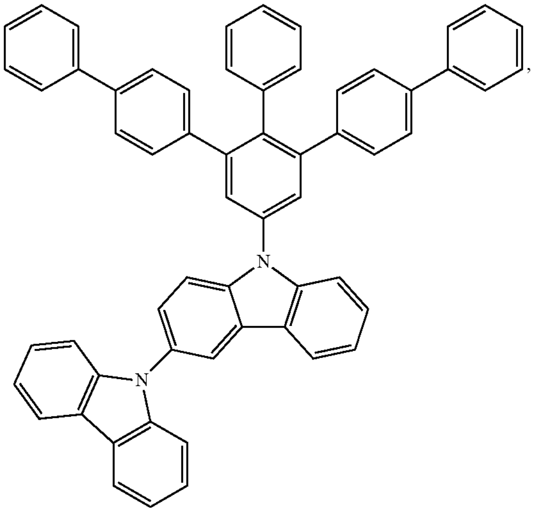
,
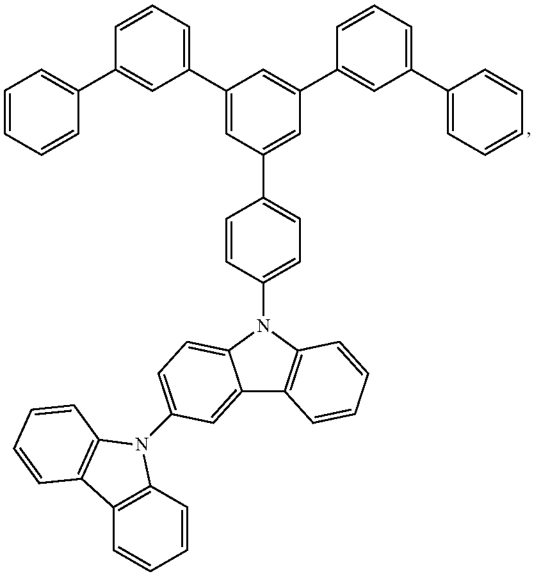
, -continued
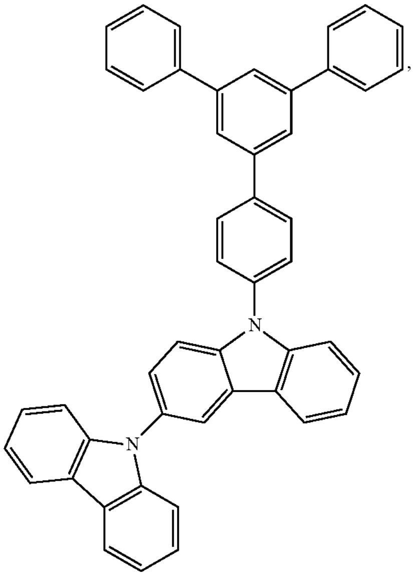
,
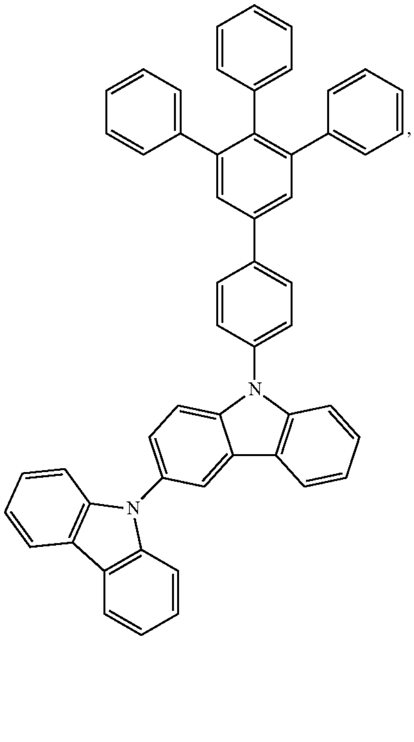
,
-continued
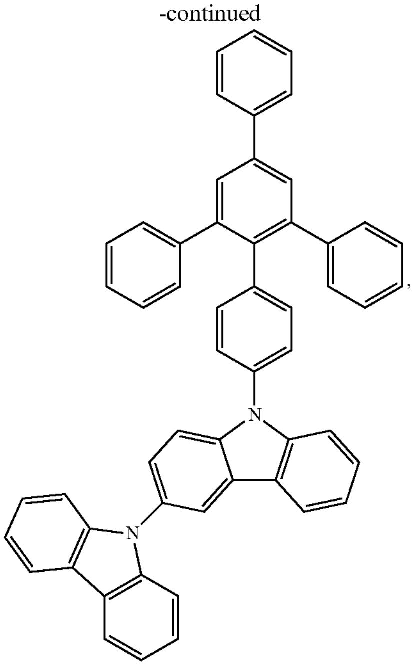
,
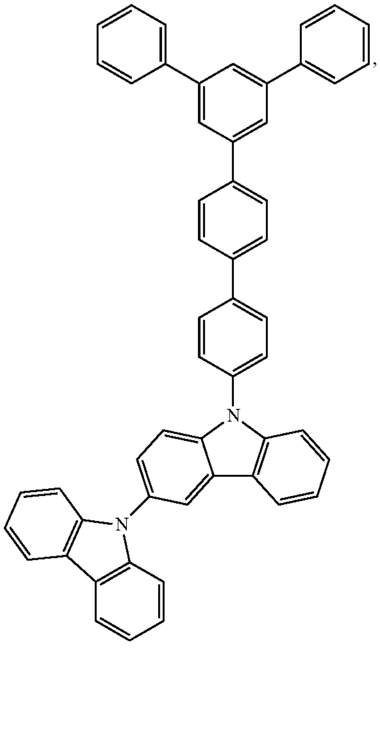
, -continued
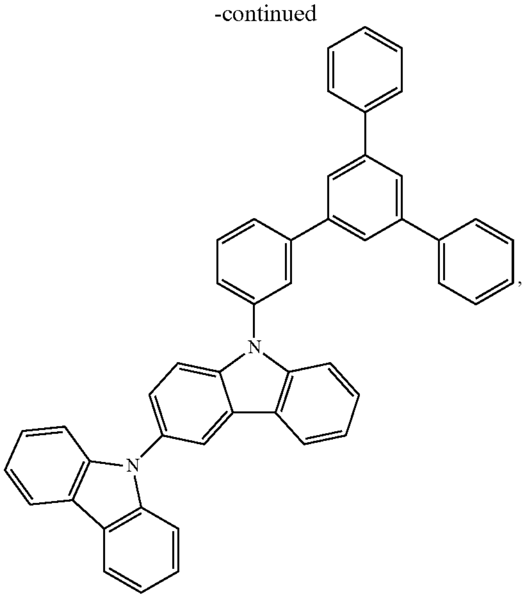
,
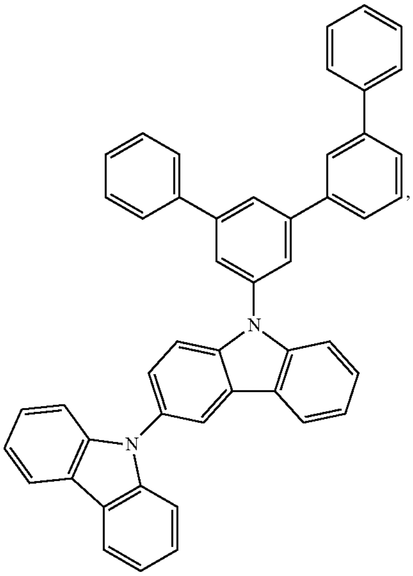
,
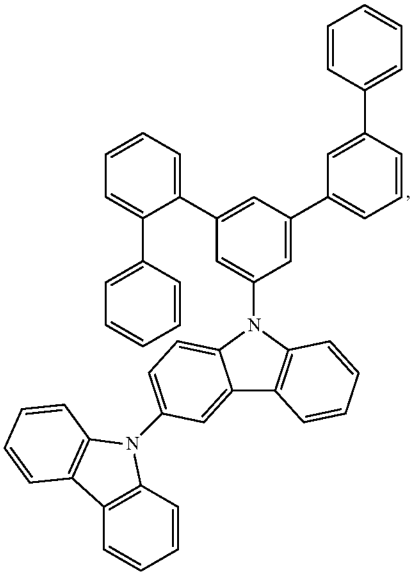
,
-continued
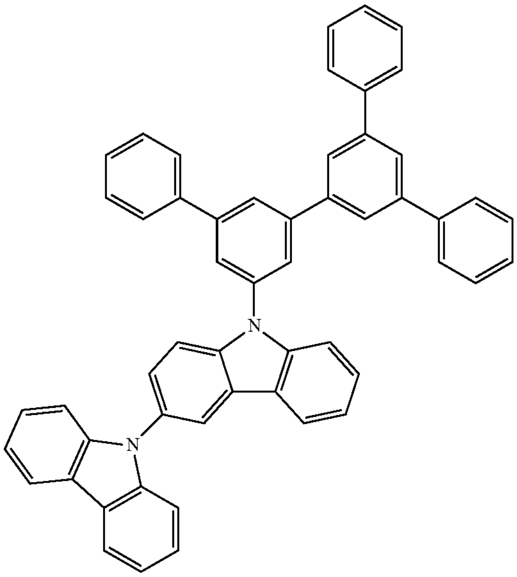
,
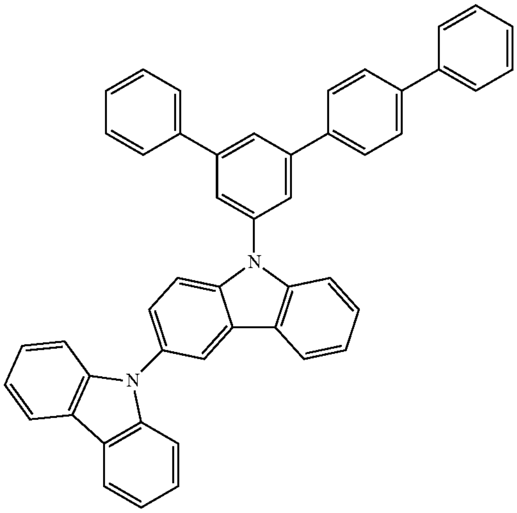
,
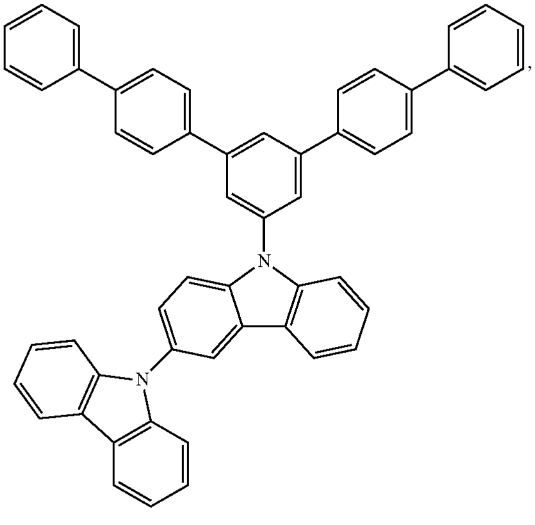
, -continued
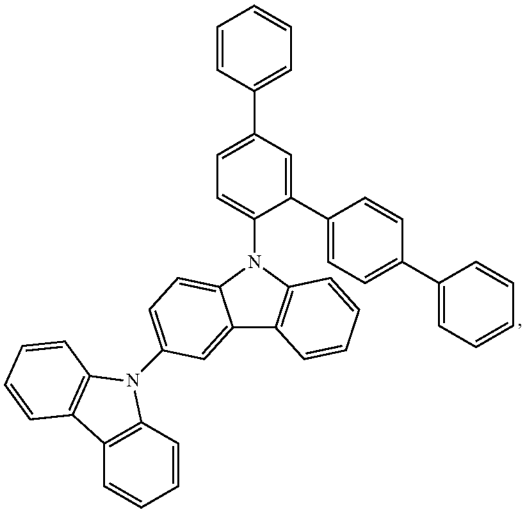
,
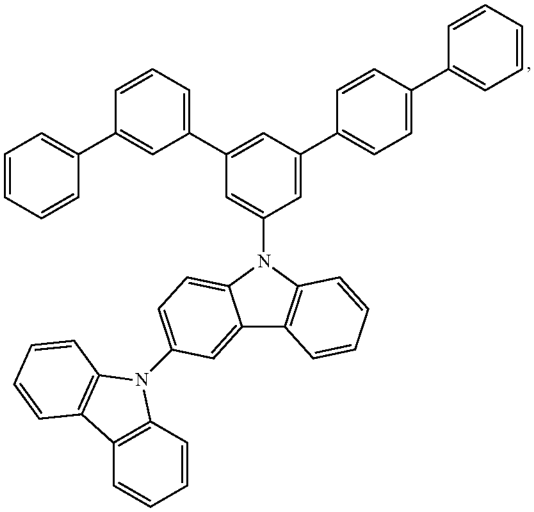
,
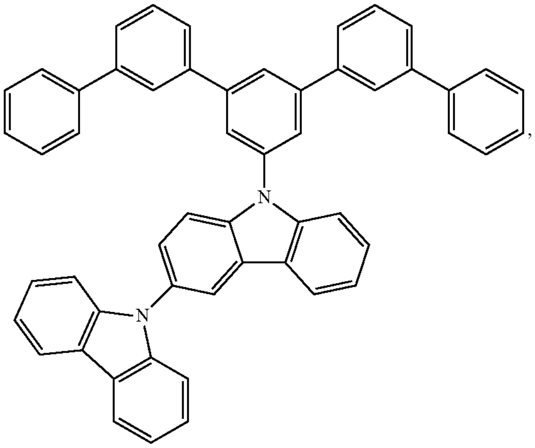
,
-continued
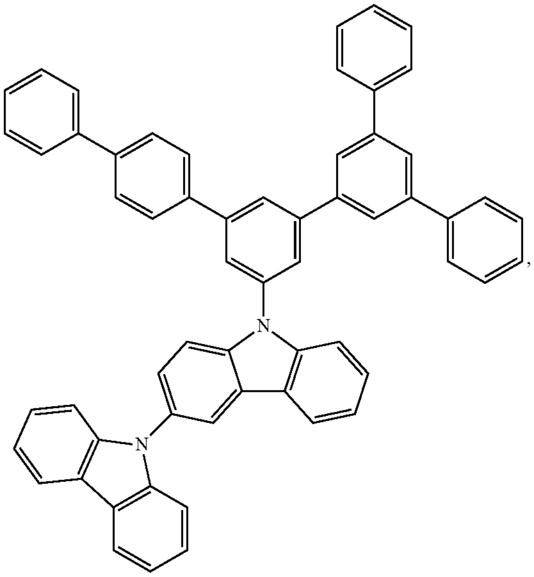
,
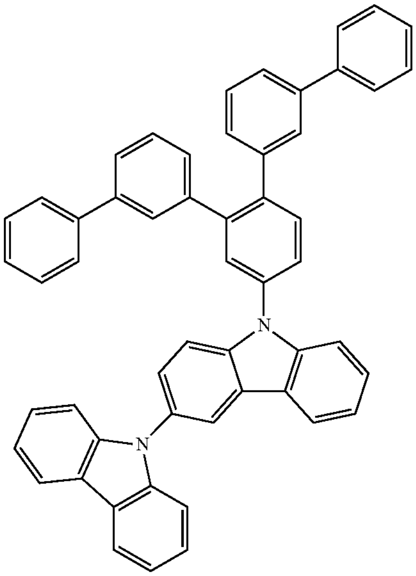
,
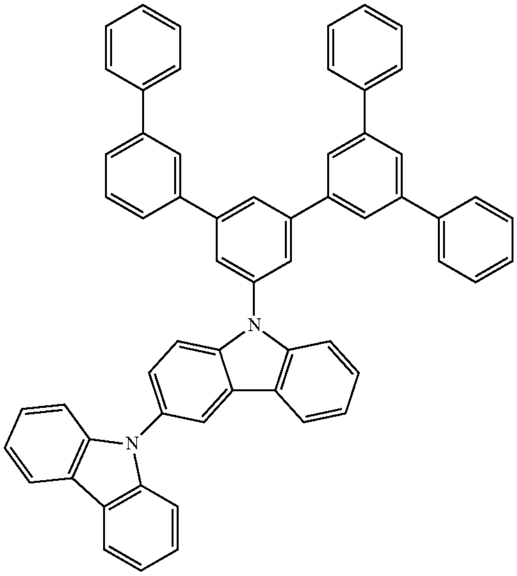
, -continued
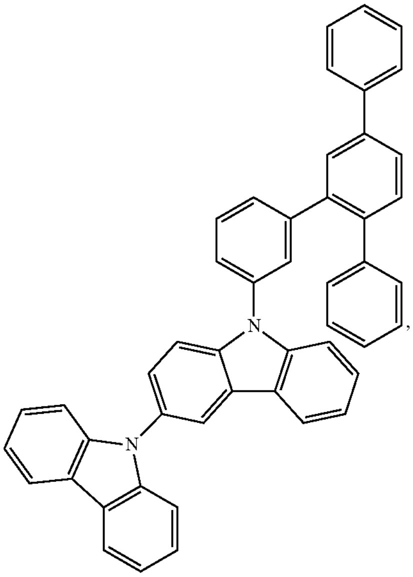
,
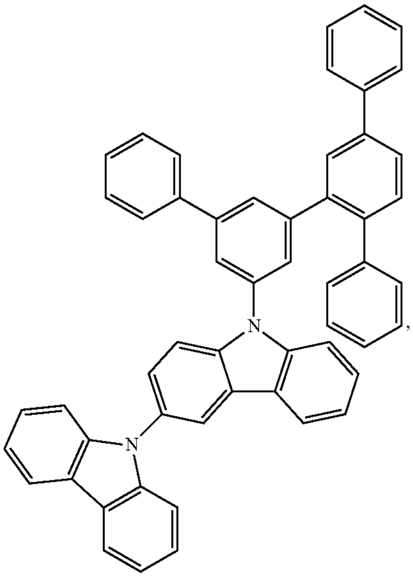
,
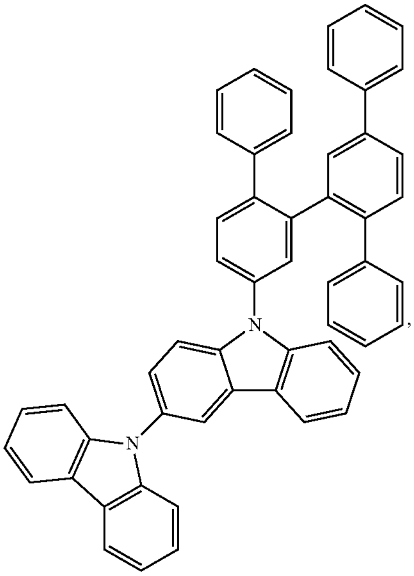
,
-continued
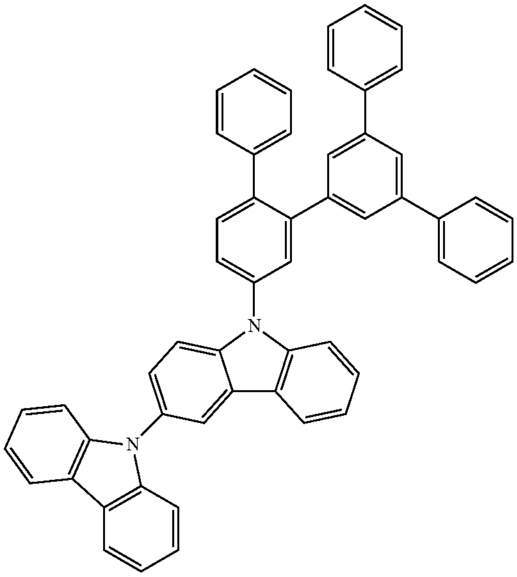
,
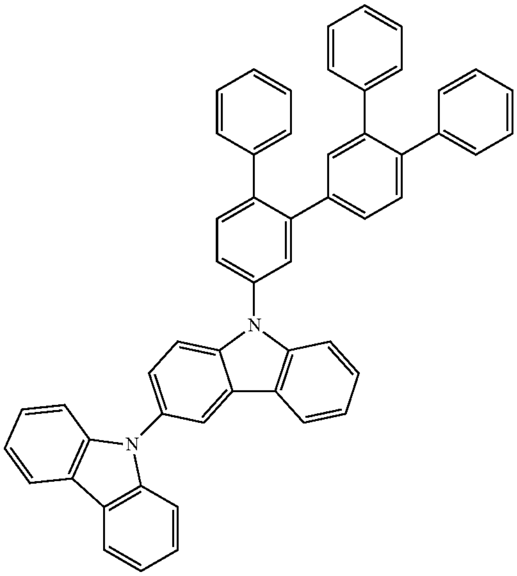
,
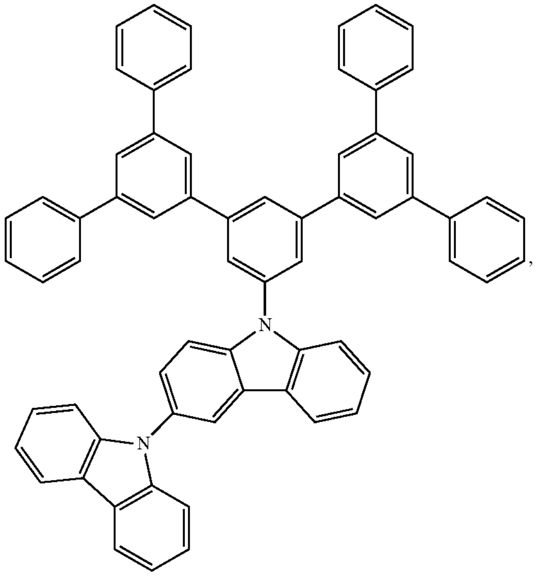
, -continued
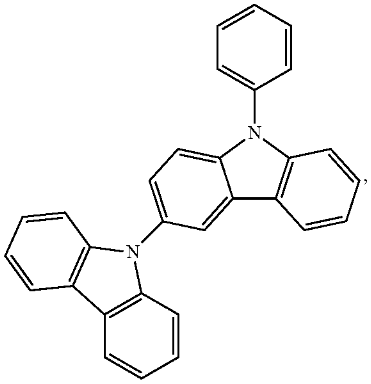,
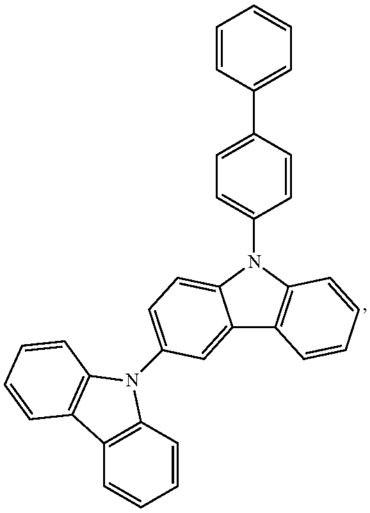,
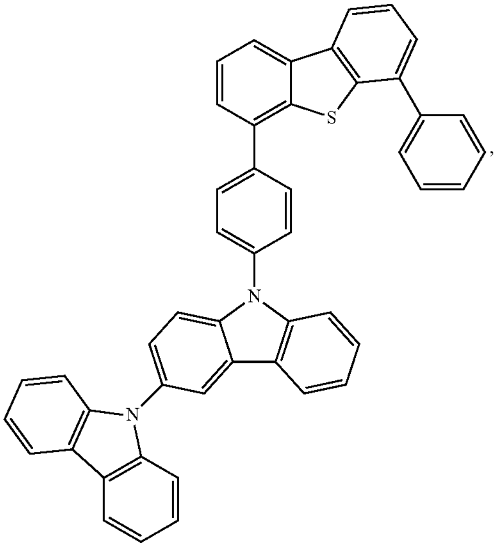,
-continued
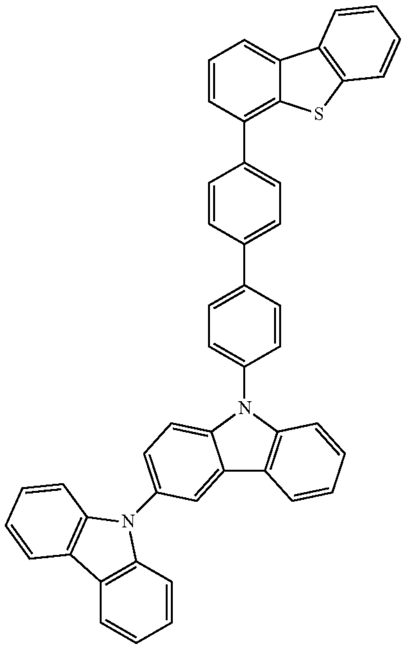,
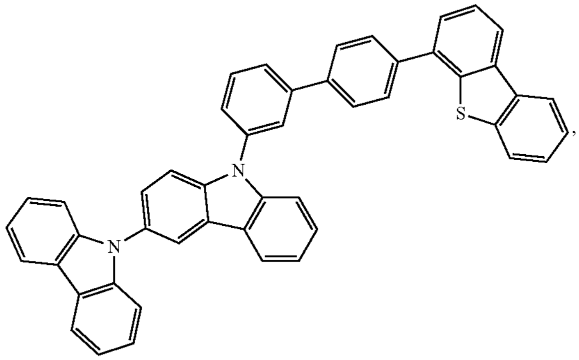,
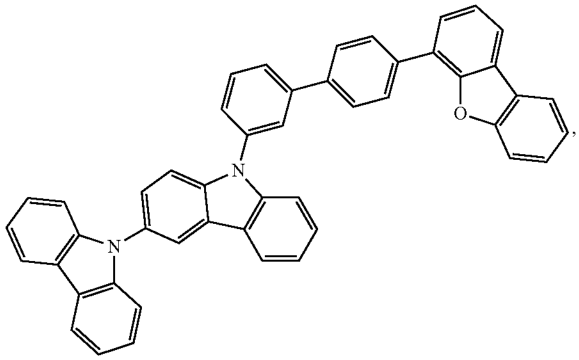, -continued
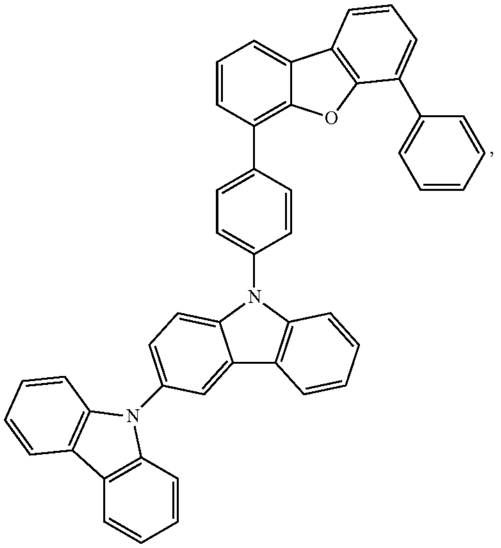
,
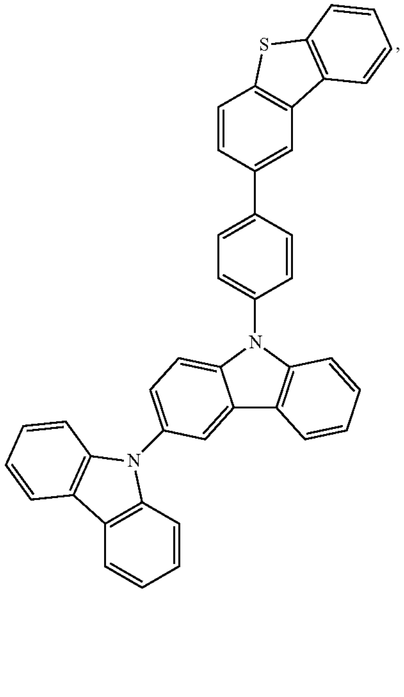
,
-continued
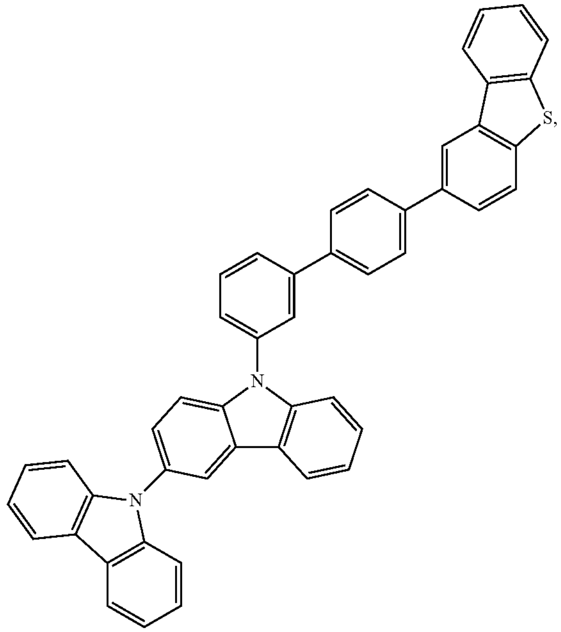
,
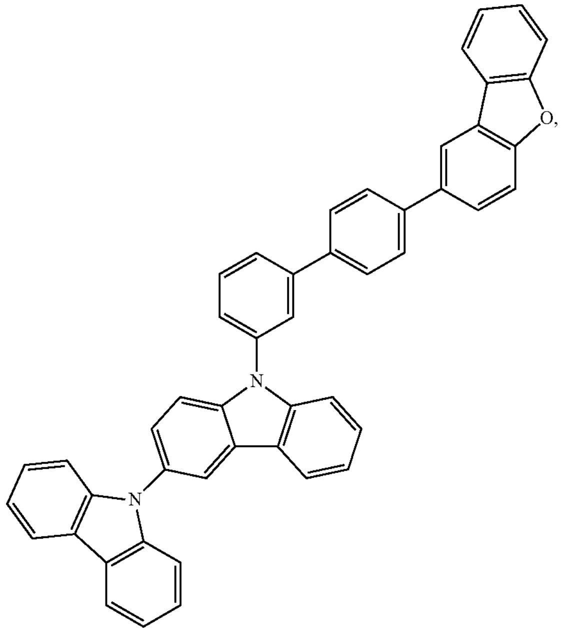
,
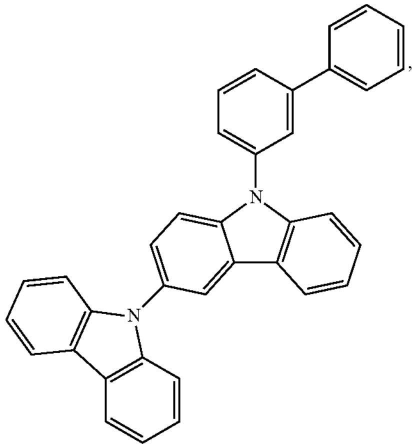
, -continued
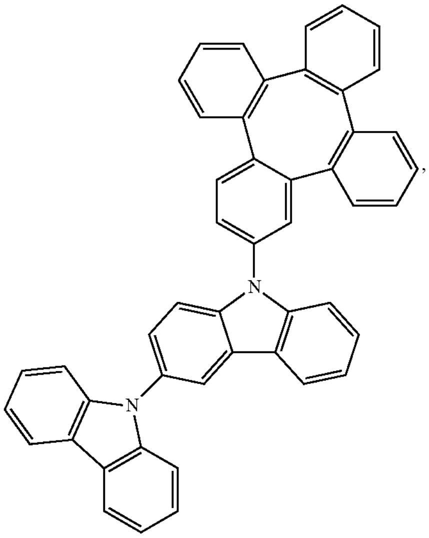
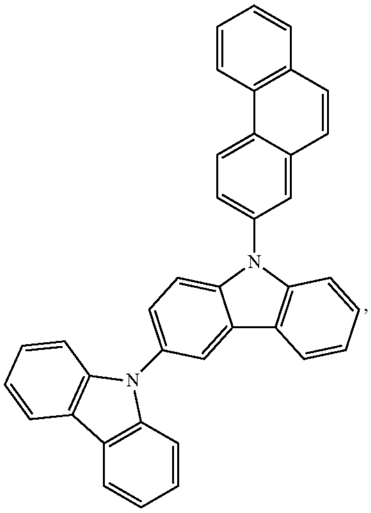
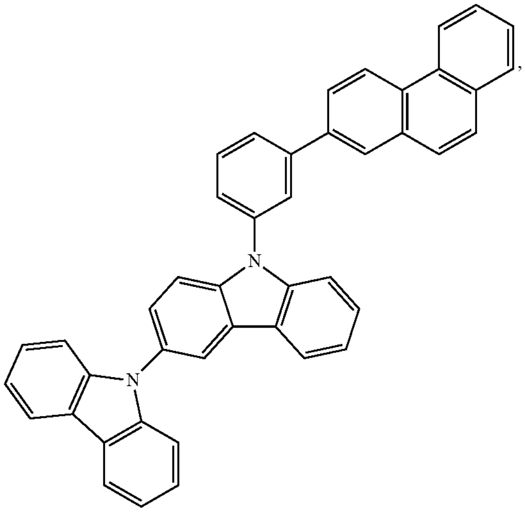
-continued
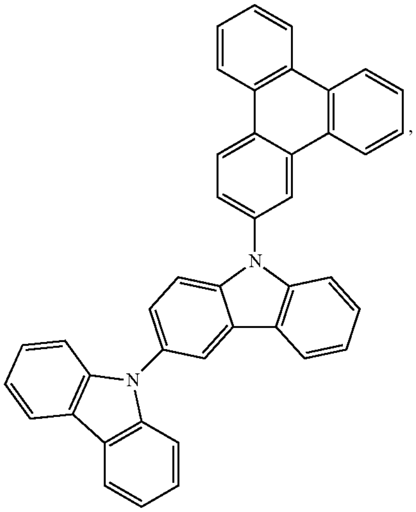
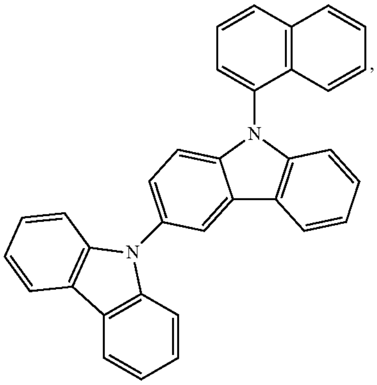
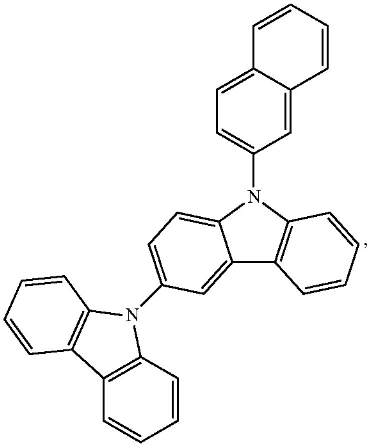

-continued
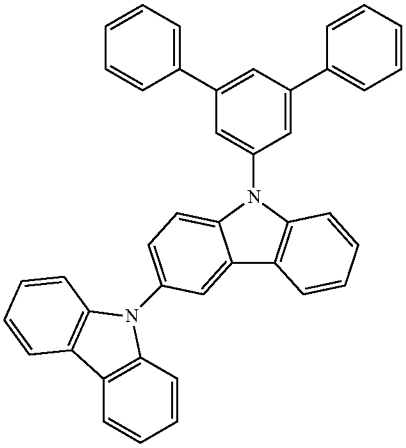
,
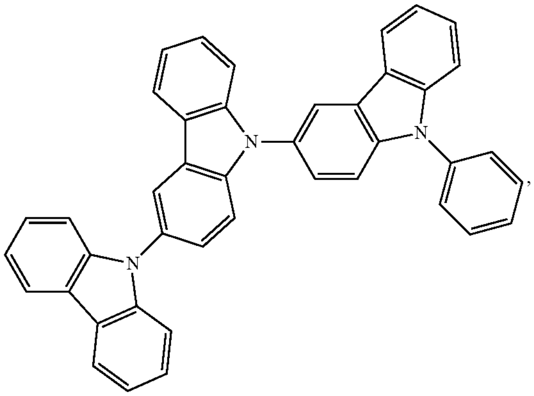
,
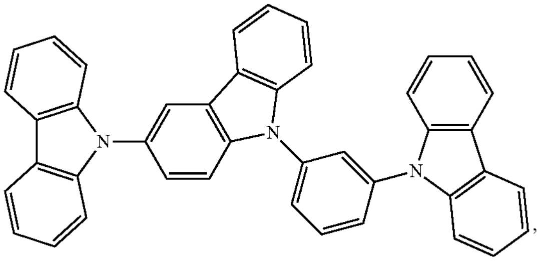
,
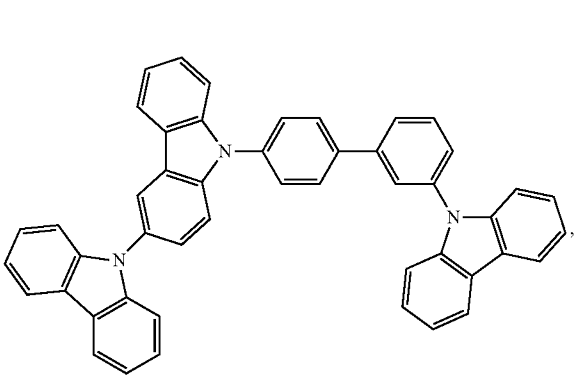
,
-continued
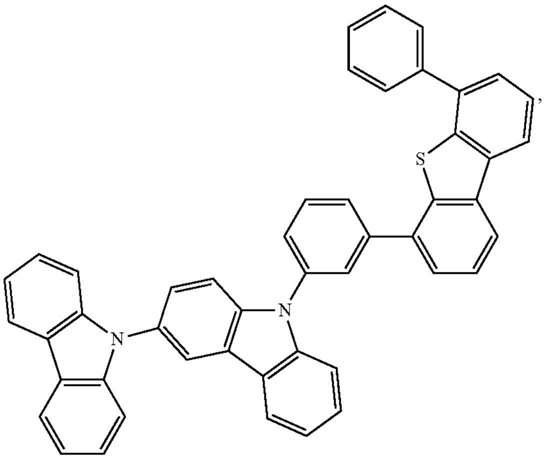
,
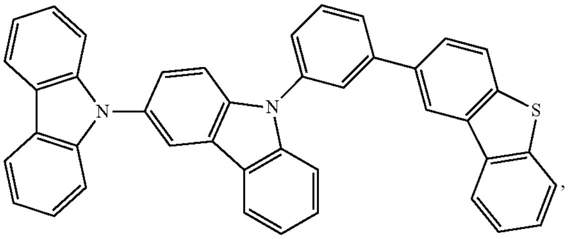
,
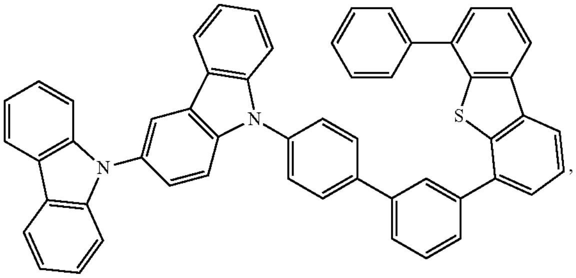
,
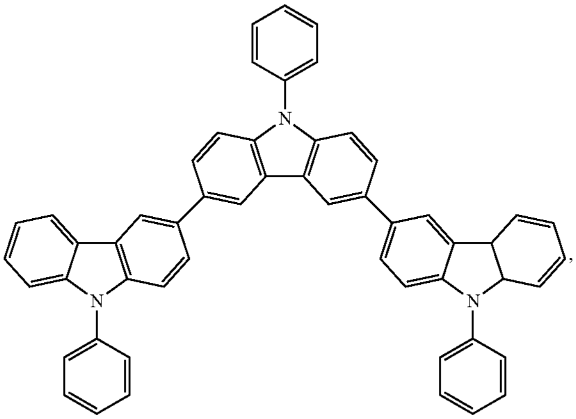
, -continued
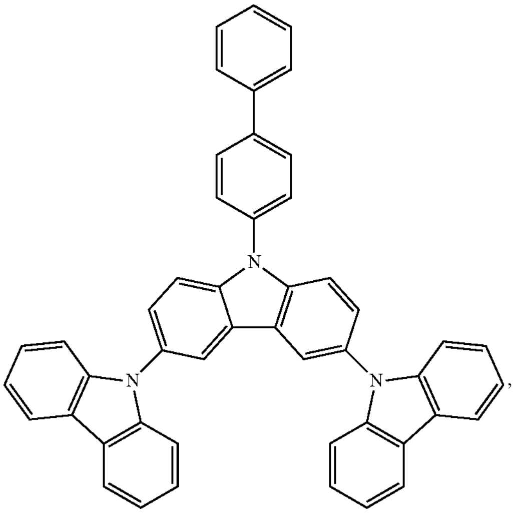
,
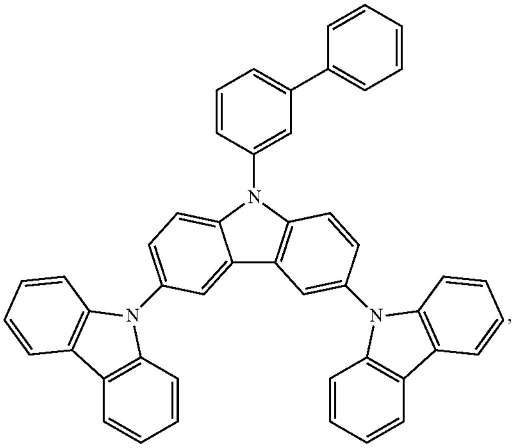
,
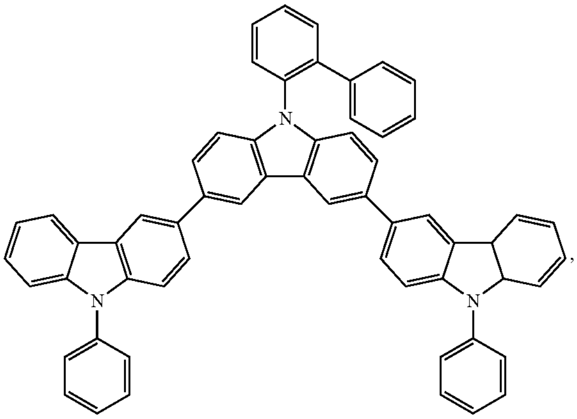
,
-continued
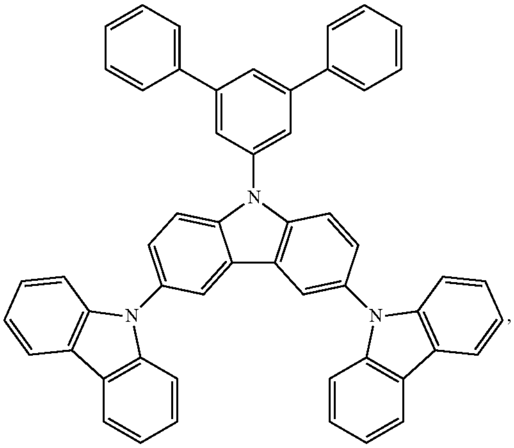
,
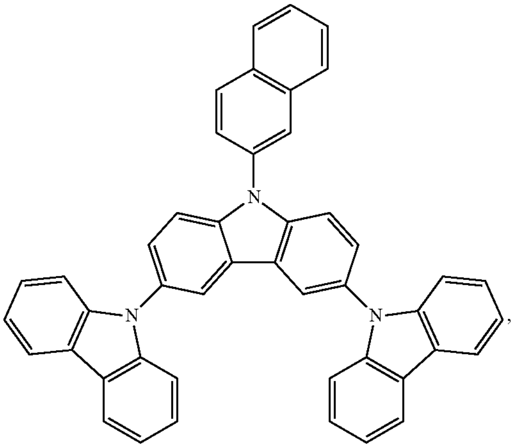
,
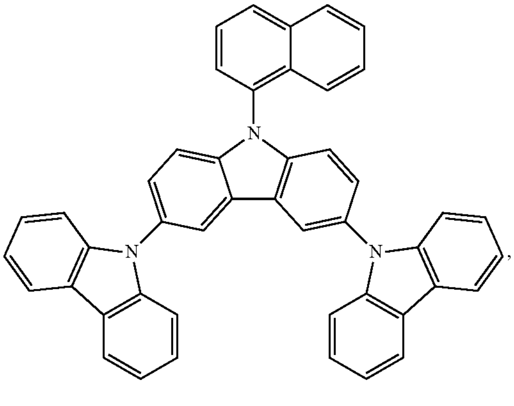
, -continued
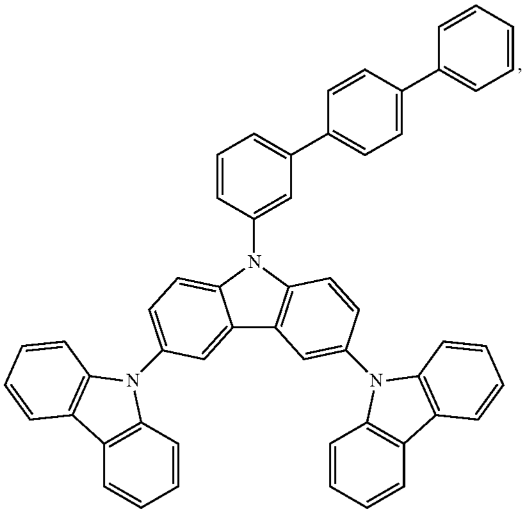,
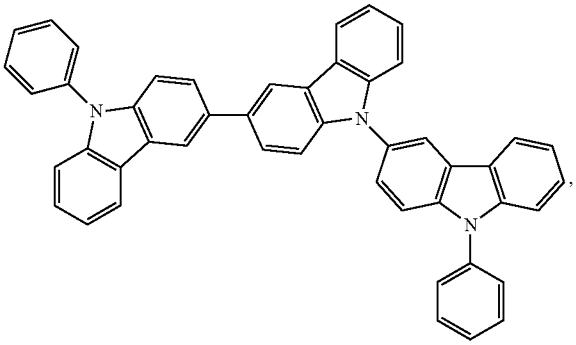,
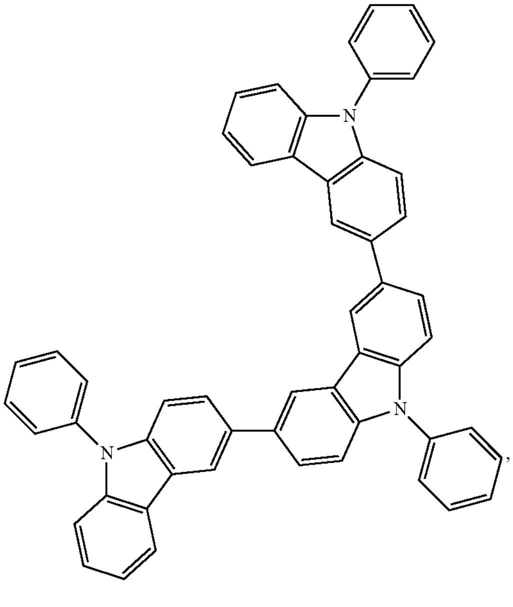,
-continued
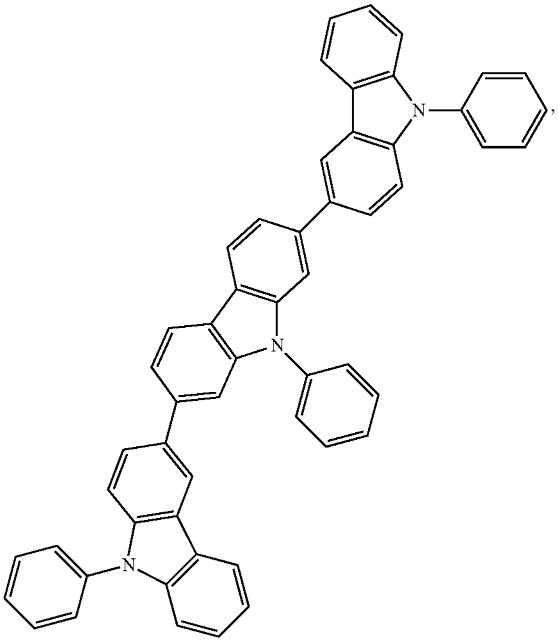,
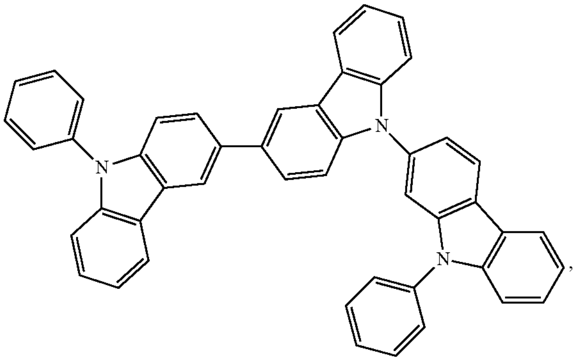,
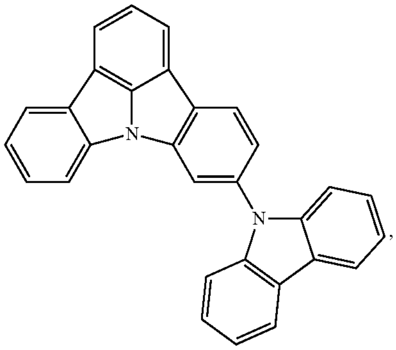,
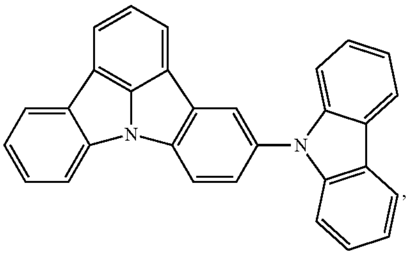, -continued
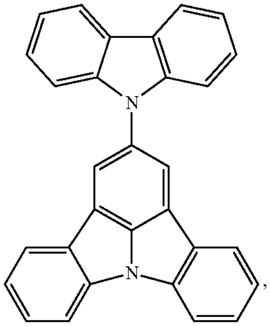
,
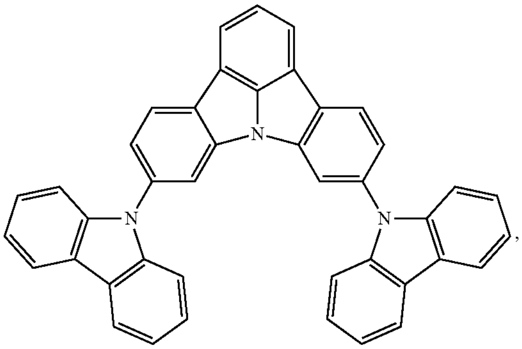
,
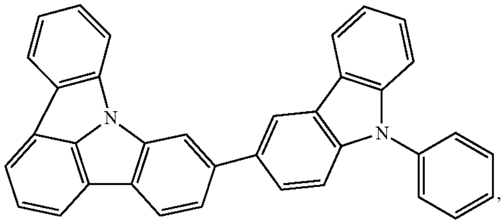
,
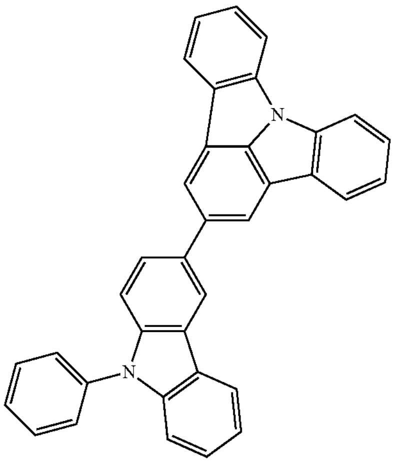
,
-continued
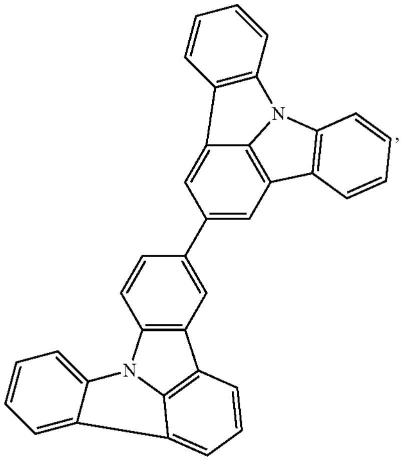
,
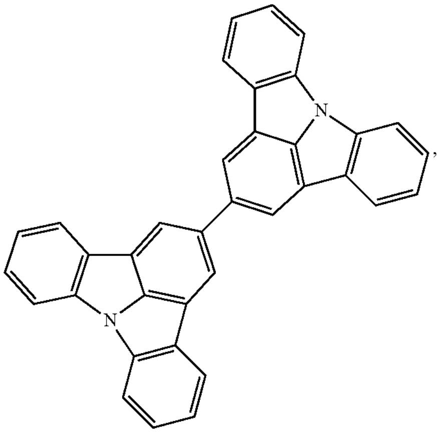
,
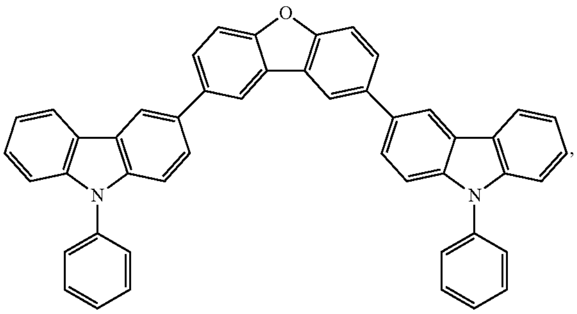
,
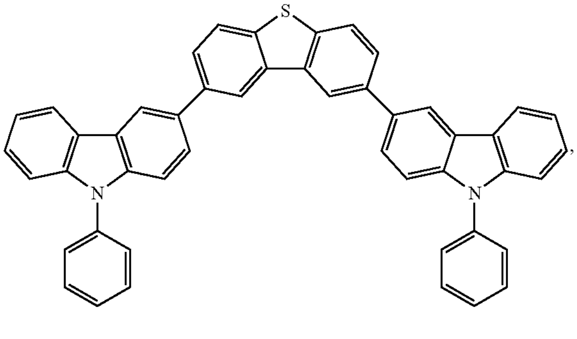
, -continued

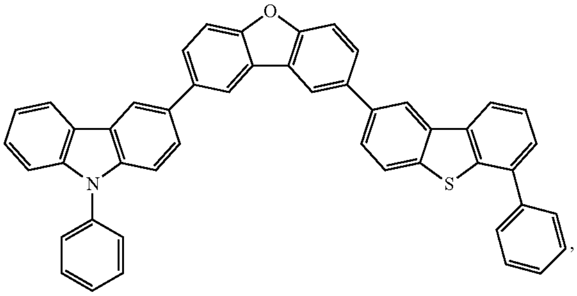

,

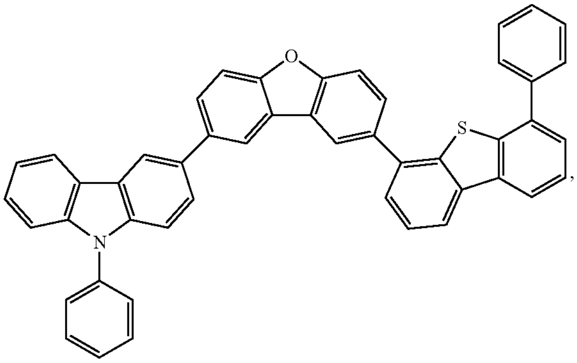

,

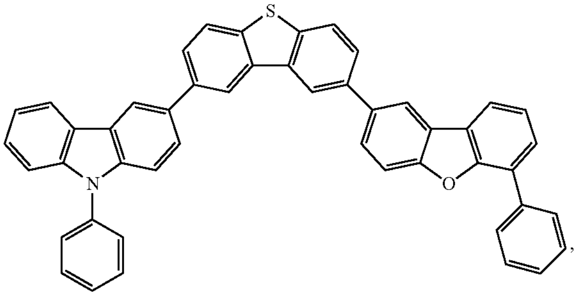

,

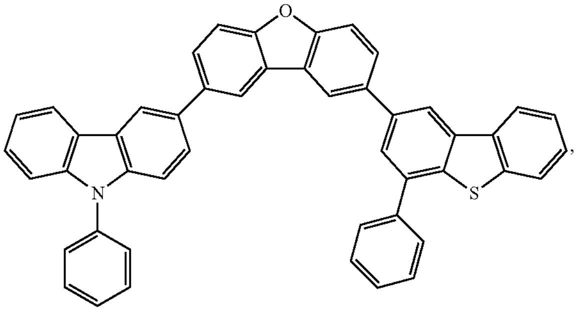

,

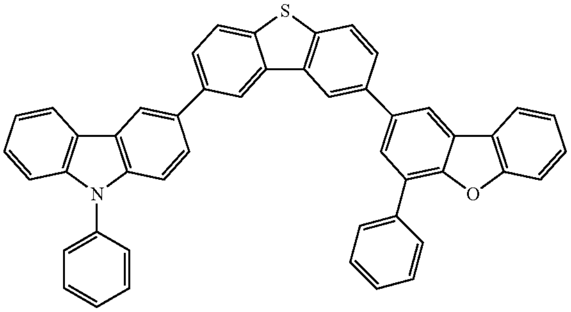

-continued

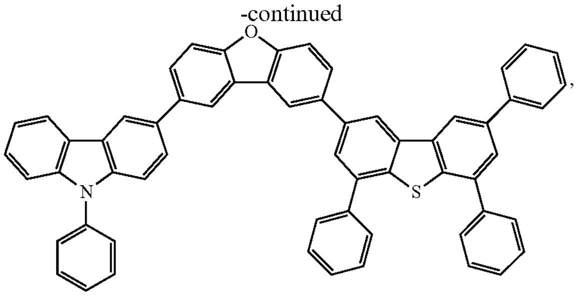

,

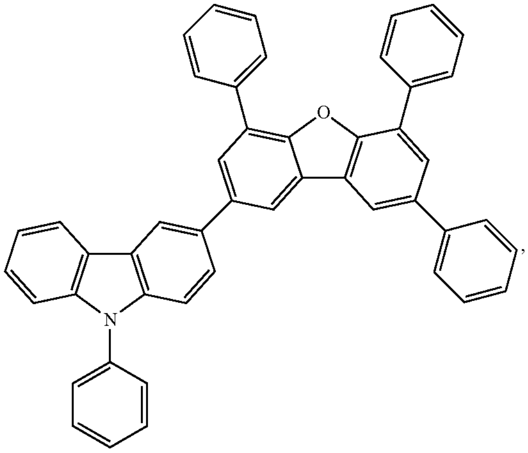

,

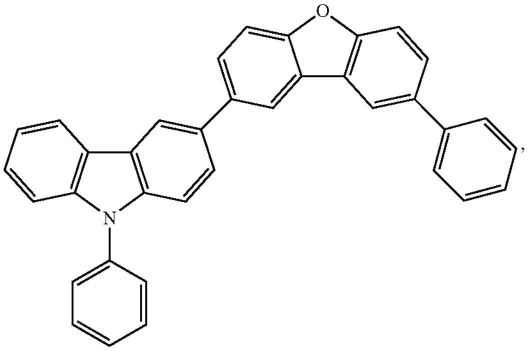

, and

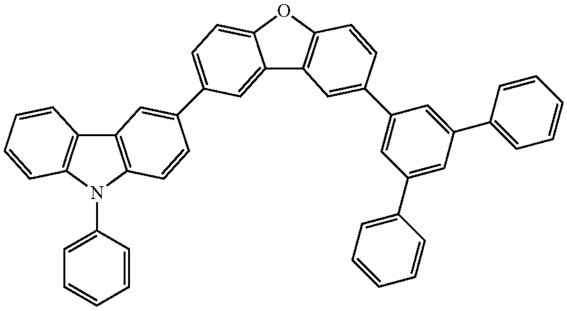

.

In yet another aspect, the OLED of the present disclosure may also comprise an emissive region containing a compound as disclosed in the above compounds section of the present disclosure.

In some embodiments, the emissive region can comprise compounds of Formula I as described herein or comprise the compounds in LIST A as described herein.

In some embodiments, at least one of the anode, the cathode, or a new layer disposed over the organic emissive layer functions as an enhancement layer. The enhancement layer comprises a plasmonic material exhibiting surface plasmon resonance that non-radiatively couples to the emitter material and transfers excited state energy from the emitter material to non-radiative mode of surface plasmon polariton. The enhancement layer is provided no more than a threshold distance away from the organic emissive layer, wherein the emitter material has a total non-radiative decay rate constant and a total radiative decay rate constant due to the presence of the enhancement layer and the threshold distance is where the total non-radiative decay rate constant is equal to the total radiative decay rate constant. In some embodiments, the OLED further comprises an outcoupling layer. In some embodiments, the outcoupling layer is disposed over the enhancement layer on the opposite side of the organic emissive layer. In some embodiments, the outcoupling layer is disposed on opposite side of the emissive layer from the enhancement layer but still outcouples energy from the surface plasmon mode of the enhancement layer. The outcoupling layer scatters the energy from the surface plasmon polaritons. In some embodiments this energy is scattered as photons to free space. In other embodiments, the energy is scattered from the surface plasmon mode into other modes of the device such as but not limited to the organic waveguide mode, the substrate mode, or another waveguiding mode. If energy is scattered to the non-free space mode of the OLED other outcoupling schemes could be incorporated to extract that energy to free space. In some embodiments, one or more intervening layer can be disposed between the enhancement layer and the outcoupling layer. The examples for interventing layer(s) can be dielectric materials, including organic, inorganic, perovskites, oxides, and may include stacks and/or mixtures of these materials.

The enhancement layer modifies the effective properties of the medium in which the emitter material resides resulting in any or all of the following: a decreased rate of emission, a modification of emission line-shape, a change in emission intensity with angle, a change in the stability of the emitter material, a change in the efficiency of the OLED, and reduced efficiency roll-off of the OLED device. Placement of the enhancement layer on the cathode side, anode side, or on both sides results in OLED devices which take advantage of any of the above-mentioned effects. In addition to the specific functional layers mentioned herein and illustrated in the various OLED examples shown in the figures, the OLEDs according to the present disclosure may include any of the other functional layers often found in OLEDs.

The enhancement layer can be comprised of plasmonic materials, optically active metamaterials, or hyperbolic metamaterials. As used herein, a plasmonic material is a material in which the real part of the dielectric constant crosses zero in the visible or ultraviolet region of the electromagnetic spectrum. In some embodiments, the plasmonic material includes at least one metal. In such embodiments the metal may include at least one of Ag, Al, Au, Ir, Pt, Ni, Cu, W, Ta, Fe, Cr, Mg, Ga, Rh, Ti, Ru, Pd, In, Bi, Ca, alloys or mixtures of these materials, and stacks of these materials. In general, a metamaterial is a medium composed of different materials where the medium as a whole acts differently than the sum of its material parts. In particular, we define optically active metamaterials as materials which have both negative permittivity and negative permeability. Hyperbolic metamaterials, on the other hand, are anisotropic media in which the permittivity or permeability are of different sign for different spatial directions. Optically active metamaterials and hyperbolic metamaterials are strictly distinguished from many other photonic structures such as Distributed Bragg Reflectors ("DBRs") in that the medium should appear uniform in the direction of propagation on the length scale of the wavelength of light. Using terminology that one skilled in the art can understand: the dielectric constant of the metamaterials in the direction of propagation can be described with the effective medium approximation. Plasmonic materials and metamaterials provide methods for controlling the propagation of light that can enhance OLED performance in a number of ways.

In some embodiments, the enhancement layer is provided as a planar layer. In other embodiments, the enhancement layer has wavelength-sized features that are arranged periodically, quasi-periodically, or randomly, or sub-wavelength-sized features that are arranged periodically, quasi-periodically, or randomly. In some embodiments, the wavelength-sized features and the sub-wavelength-sized features have sharp edges.

In some embodiments, the outcoupling layer has wavelength-sized features that are arranged periodically, quasi-periodically, or randomly, or sub-wavelength-sized features that are arranged periodically, quasi-periodically, or randomly. In some embodiments, the outcoupling layer may be composed of a plurality of nanoparticles and in other embodiments the outcoupling layer is composed of a plurality of nanoparticles disposed over a material. In these embodiments the outcoupling may be tunable by at least one of varying a size of the plurality of nanoparticles, varying a shape of the plurality of nanoparticles, changing a material of the plurality of nanoparticles, adjusting a thickness of the material, changing the refractive index of the material or an additional layer disposed on the plurality of nanoparticles, varying a thickness of the enhancement layer, and/or varying the material of the enhancement layer. The plurality of nanoparticles of the device may be formed from at least one of metal, dielectric material, semiconductor materials, an alloy of metal, a mixture of dielectric materials, a stack or layering of one or more materials, and/or a core of one type of material and that is coated with a shell of a different type of material. In some embodiments, the outcoupling layer is composed of at least metal nanoparticles wherein the metal is selected from the group consisting of Ag, Al, Au, Ir, Pt, Ni, Cu, W, Ta, Fe, Cr, Mg, Ga, Rh, Ti, Ru, Pd, In, Bi, Ca, alloys or mixtures of these materials, and stacks of these materials. The plurality of nanoparticles may have additional layer disposed over them. In some embodiments, the polarization of the emission can be tuned using the outcoupling layer. Varying the dimensionality and periodicity of the outcoupling layer can select a type of polarization that is preferentially outcoupled to air. In some embodiments the outcoupling layer also acts as an electrode of the device.

In yet another aspect, the present disclosure also provides a consumer product comprising an organic light-emitting device (OLED) having an anode; a cathode; and an organic layer disposed between the anode and the cathode, wherein the organic layer may comprise a compound as disclosed in the above compounds section of the present disclosure.

In some embodiments, the consumer product comprises an organic light-emitting device (OLED) having an anode; a cathode; and an organic layer disposed between the anode and the cathode, wherein the organic layer can comprise compounds of Formula I as described herein or the compounds of LIST A as described herein.

In some embodiments, the consumer product can be one of a flat panel display, a computer monitor, a medical monitor, a television, a billboard, a light for interior or exterior illumination and/or signaling, a heads-up display, a fully or partially transparent display, a flexible display, a laser printer, a telephone, a cell phone, tablet, a phablet, a personal digital assistant (PDA), a wearable device, a laptop computer, a digital camera, a camcorder, a viewfinder, a micro-display that is less than 2 inches diagonal, a 3-D display, a virtual reality or augmented reality display, a vehicle, a video wall comprising multiple displays tiled together, a theater or stadium screen, a light therapy device, and a sign.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

Several OLED materials and configurations are described in U.S. Pat. Nos. 5,844,363, 6,303,238, and 5,707,745, which are incorporated herein by reference in their entirety.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), are incorporated by reference in their entireties. Phosphorescence is described in more detail in U.S. Pat. No. 7,279,704 at cols. 5-6, which are incorporated by reference.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
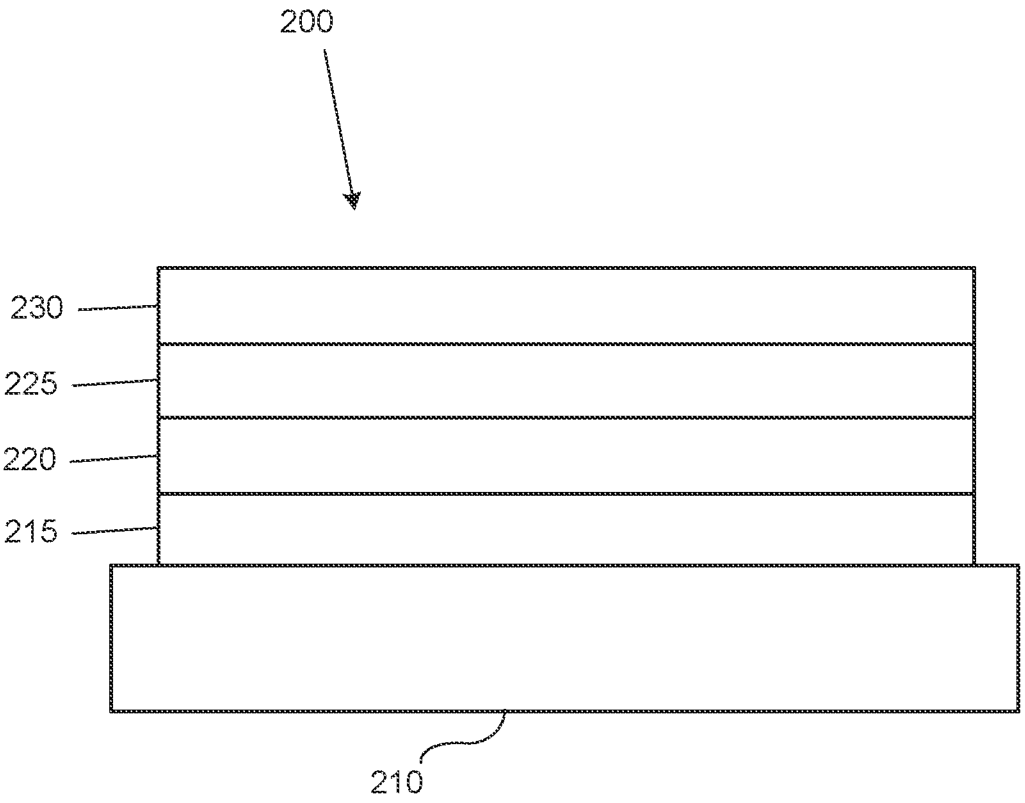
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the present disclosure may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and organic vapor jet printing (OVJP). Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons are a preferred range. Materials with asymmetric structures may have better solution processability than those having symmetric structures, because asymmetric materials may have a lower tendency to recrystallize Dendrimer substituents may be used to enhance the ability of small molecules to undergo solution processing.

Devices fabricated in accordance with embodiments of the present disclosure may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the present disclosure can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the present disclosure can be incorporated into a wide variety of consumer products that have one or more of the electronic component modules (or units) incorporated therein. A consumer product comprising an OLED that includes the compound of the present disclosure in the organic layer in the OLED is disclosed. Such consumer products would include any kind of products that include one or more light source(s) and/or one or more of some type of visual displays. Some examples of such consumer products include flat panel displays, curved displays, computer monitors, medical monitors, televisions, billboards, lights for interior or exterior illumination and/or signaling, heads-up displays, fully or partially transparent displays, flexible displays, rollable displays, foldable displays, stretchable displays, laser printers, telephones, mobile phones, tablets, phablets, personal digital assistants (PDAs), wearable devices, laptop computers, digital cameras, camcorders, viewfinders, micro-displays (displays that are less than 2 inches diagonal), 3-D displays, virtual reality or augmented reality displays, vehicles, video walls comprising multiple displays tiled together, theater or stadium screen, a light therapy device, and a sign. Various control mechanisms may be used to control devices fabricated in accordance with the present disclosure, including passive matrix and active matrix. Many of the devices are intended for use in a temperature range comfortable to humans, such as 18° C. to 30° C., and more preferably at room temperature (20-25° C.), but could be used outside this temperature range, for example, from −40° C. to +80° C.

More details on OLEDs, and the definitions described above, can be found in U.S. Pat. No. 7,279,704, which is incorporated herein by reference in its entirety.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

In some embodiments, the OLED has one or more characteristics selected from the group consisting of being flexible, being rollable, being foldable, being stretchable, and being curved. In some embodiments, the OLED is transparent or semi-transparent. In some embodiments, the OLED further comprises a layer comprising carbon nanotubes.

In some embodiments, the OLED further comprises a layer comprising a delayed fluorescent emitter. In some embodiments, the OLED comprises a RGB pixel arrangement or white plus color filter pixel arrangement. In some embodiments, the OLED is a mobile device, a hand held device, or a wearable device. In some embodiments, the OLED is a display panel having less than 10 inch diagonal or 50 square inch area. In some embodiments, the OLED is a display panel having at least 10 inch diagonal or 50 square inch area. In some embodiments, the OLED is a lighting panel.

In some embodiments, the compound can be an emissive dopant. In some embodiments, the compound can produce emissions via phosphorescence, fluorescence, thermally activated delayed fluorescence, i.e., TADF (also referred to as E-type delayed fluorescence; see, e.g., U.S. application Ser. No. 15/700,352, which is hereby incorporated by reference in its entirety), triplet-triplet annihilation, or combinations of these processes. In some embodiments, the emissive dopant can be a racemic mixture, or can be enriched in one enantiomer. In some embodiments, the compound can be homoleptic (each ligand is the same). In some embodiments, the compound can be heteroleptic (at least one ligand is different from others). When there are more than one ligand coordinated to a metal, the ligands can all be the same in some embodiments. In some other embodiments, at least one ligand is different from the other ligands. In some embodiments, every ligand can be different from each other. This is also true in embodiments where a ligand being coordinated to a metal can be linked with other ligands being coordinated to that metal to form a tridentate, tetradentate, pentadentate, or hexadentate ligands Thus, where the coordinating ligands are being linked together, all of the ligands can be the same in some embodiments, and at least one of the ligands being linked can be different from the other ligand(s) in some other embodiments.

In some embodiments, the compound can be used as one component of an exciplex to be used as a sensitizer.

In some embodiments, the sensitizer is a single component, or one of the components to form an exciplex.

According to another aspect, a formulation comprising the compound described herein is also disclosed.

According to another aspect, the presently disclosed formulation may comprise a compound having the structure of Formula I and a h-host selected from the group consisting of the structures of LIST 2 and List 3. According to another embodiments, in the formulation of the present invention, the compound of Formula I and the h-host are selected from the following combinations:

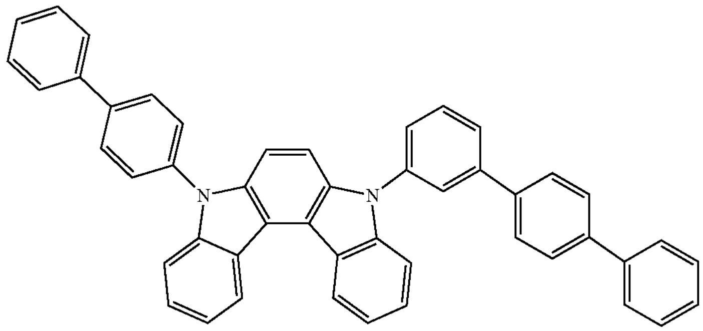

and

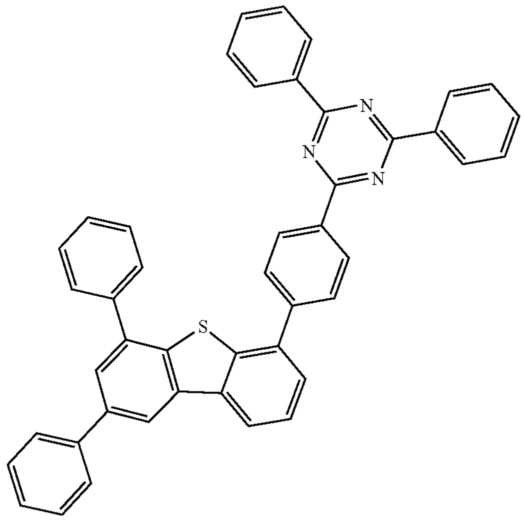

,

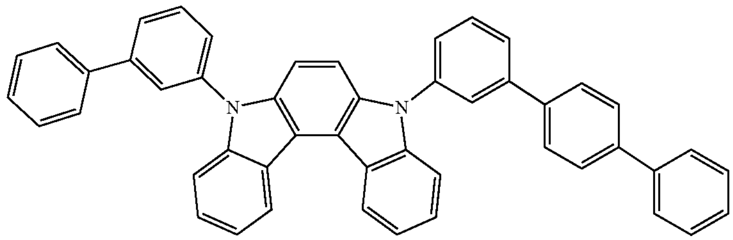

and

-continued
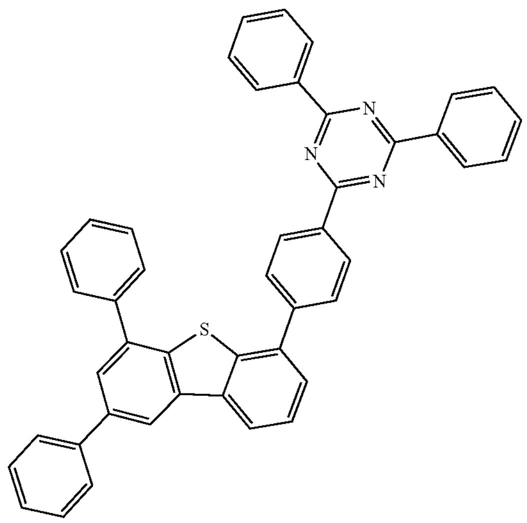
,
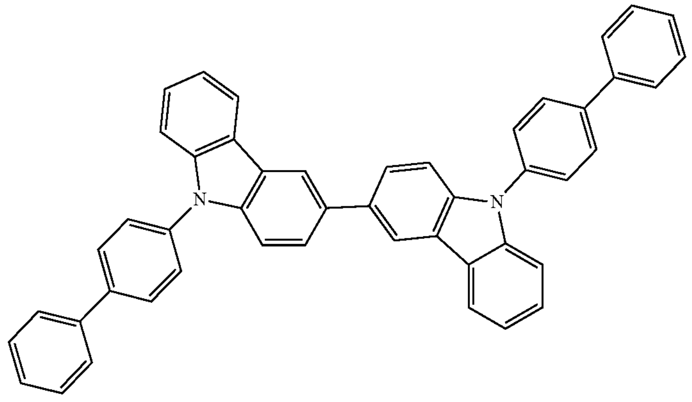
and
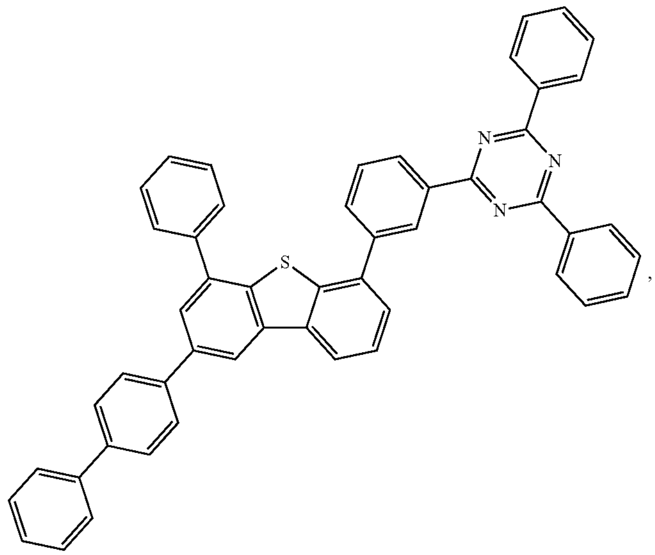
,

-continued
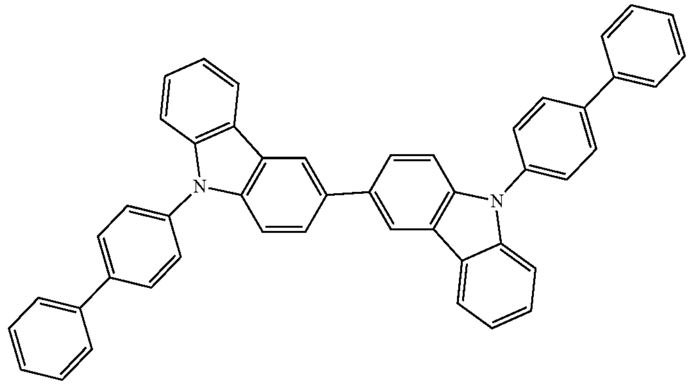
and
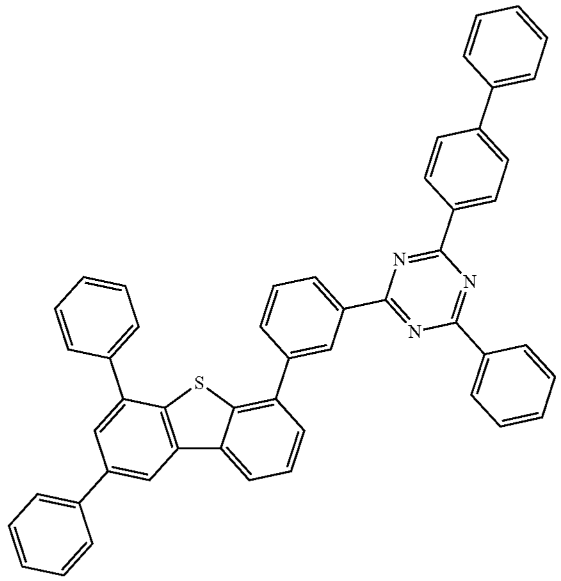
,
,
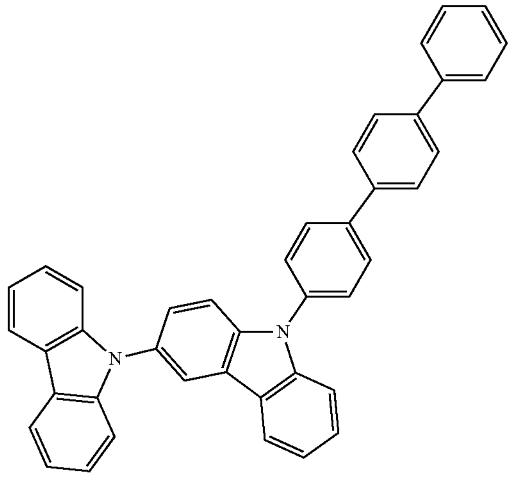
and
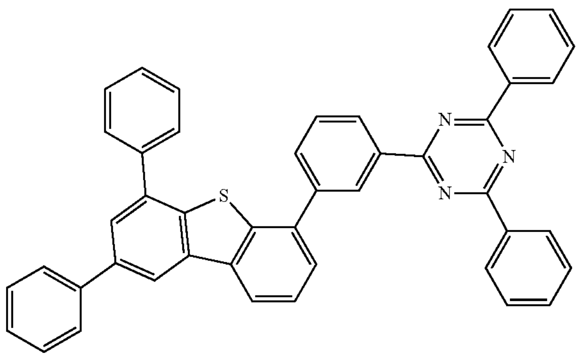
,

-continued
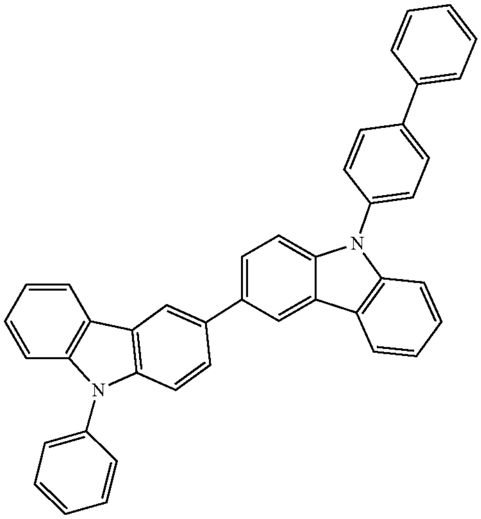
and
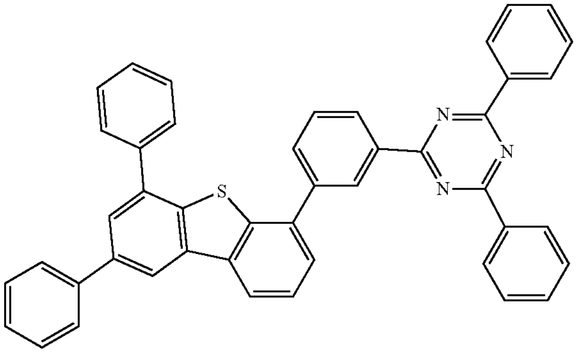
,
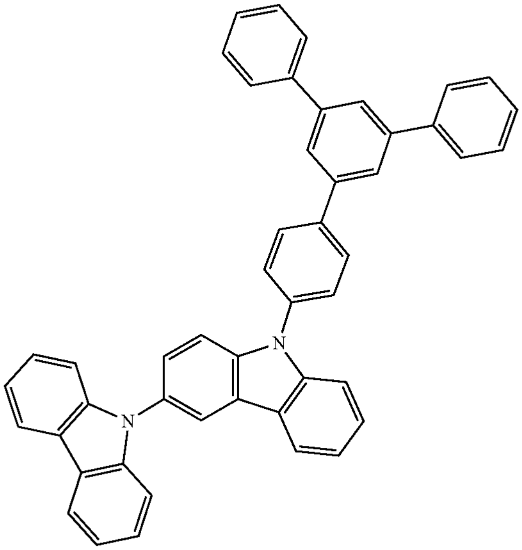
and
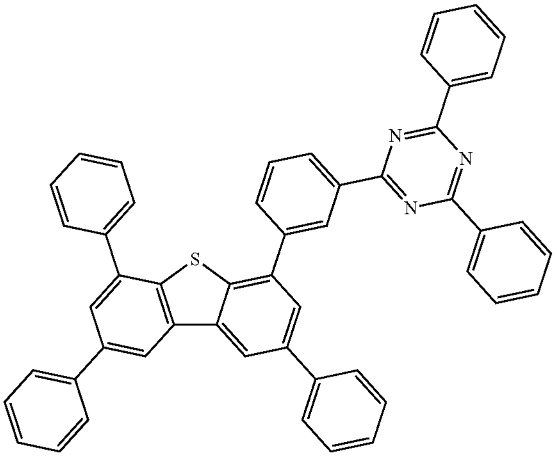
,
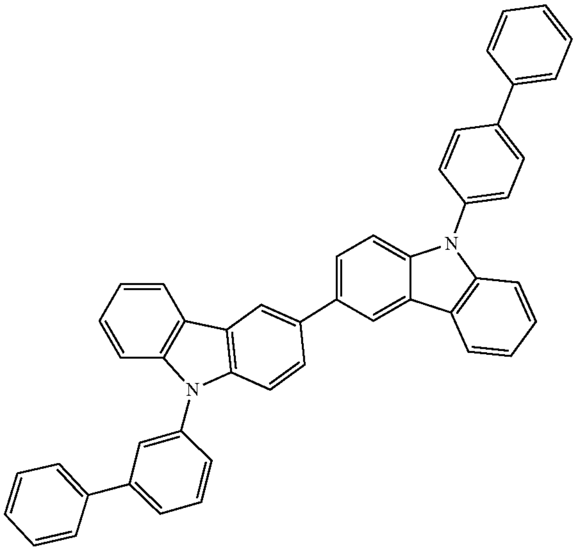
and
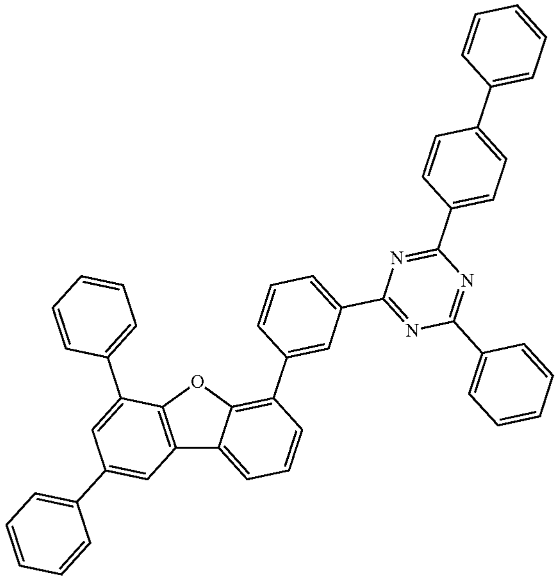
, -continued
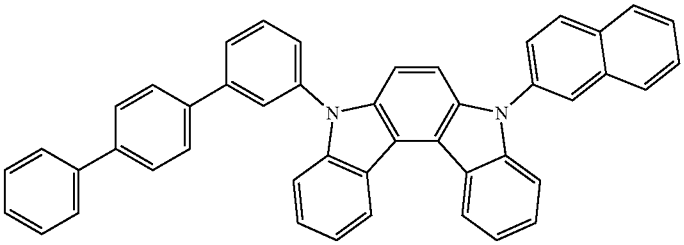
and
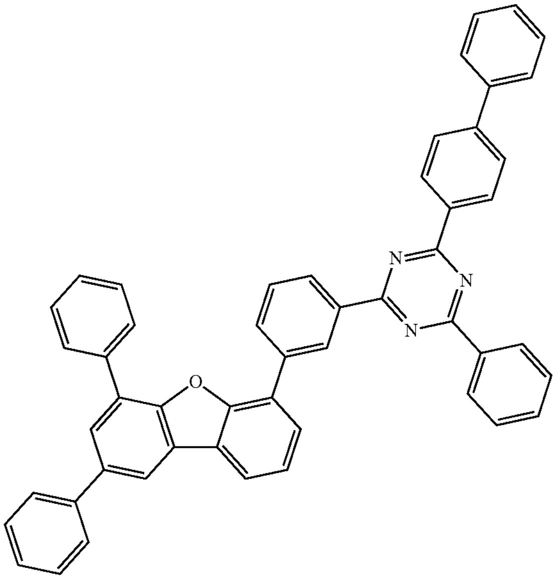
,
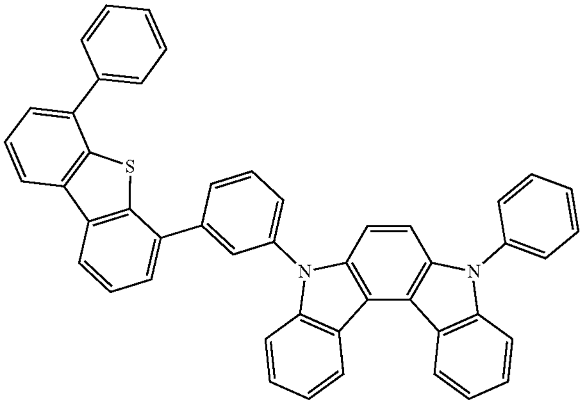
and
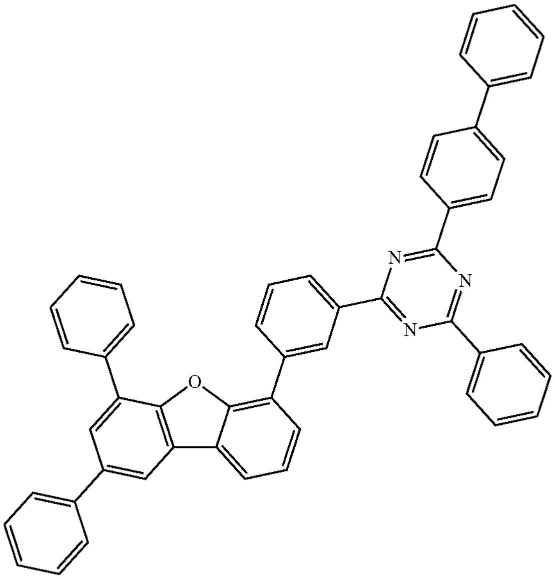
, -continued
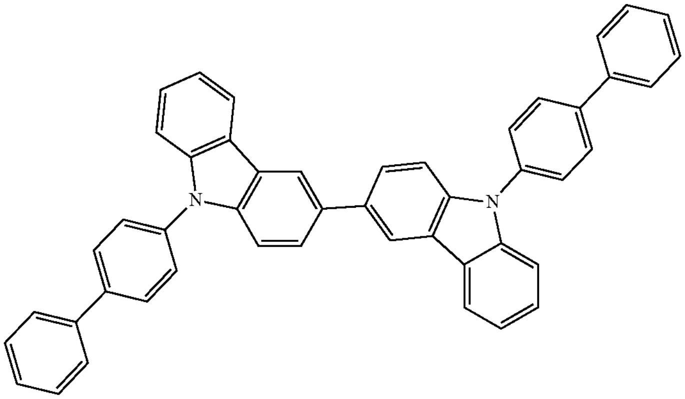
and
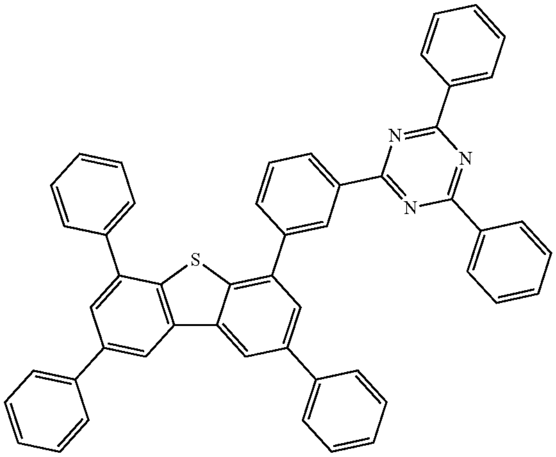
,
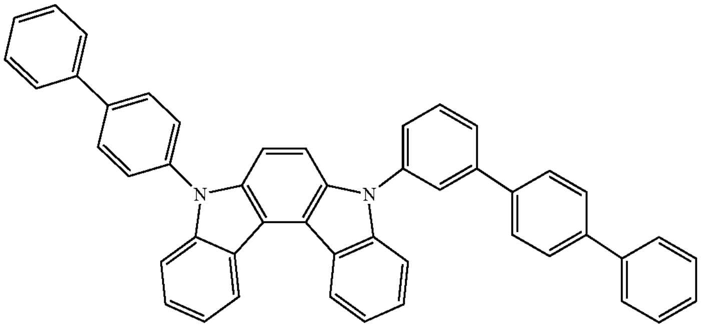
and
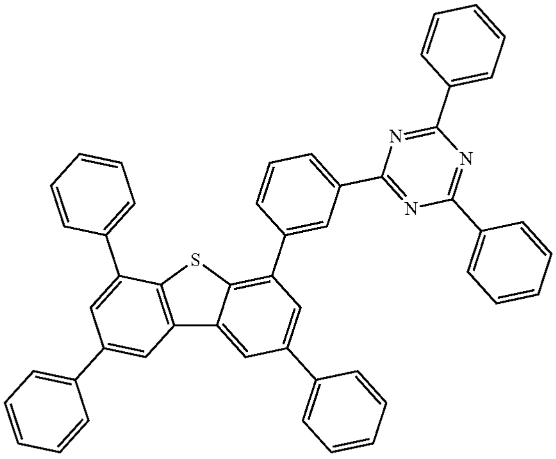
, -continued

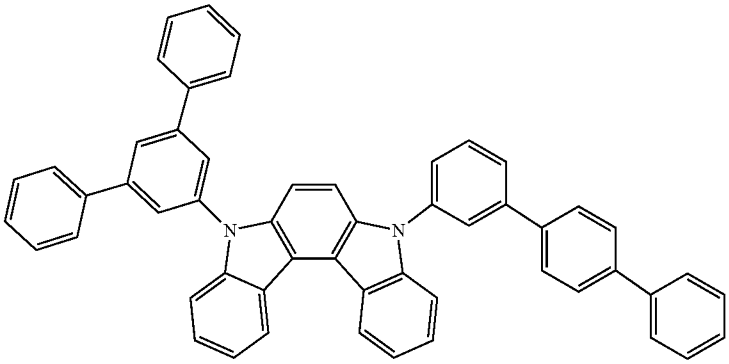

and

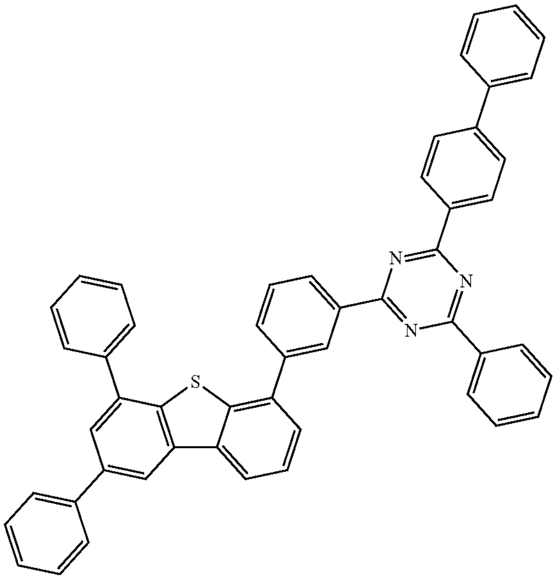

.

The OLED disclosed herein can be incorporated into one or more of a consumer product, an electronic component module, and a lighting panel. The organic layer can be an emissive layer and the compound can be an emissive dopant in some embodiments, while the compound can be a non-emissive dopant in other embodiments.

In yet another aspect of the present disclosure, a formulation that comprises the novel compound disclosed herein is described. The formulation can include one or more components selected from the group consisting of a solvent, a host, a hole injection material, hole transport material, electron blocking material, hole blocking material, and an electron transport material, disclosed herein.

The present disclosure encompasses any chemical structure comprising the novel compound of the present disclosure, or a monovalent or polyvalent variant thereof. In other words, the inventive compound, or a monovalent or polyvalent variant thereof, can be a part of a larger chemical structure. Such chemical structure can be selected from the group consisting of a monomer, a polymer, a macromolecule, and a supramolecule (also known as supermolecule). As used herein, a "monovalent variant of a compound" refers to a moiety that is identical to the compound except that one hydrogen has been removed and replaced with a bond to the rest of the chemical structure. As used herein, a "polyvalent variant of a compound" refers to a moiety that is identical to the compound except that more than one hydrogen has been removed and replaced with a bond or bonds to the rest of the chemical structure. In the instance of a supramolecule, the inventive compound can also be incorporated into the supramolecule complex without covalent bonds.

D. Combination of the Compounds of the Present Disclosure with Other Materials The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

a) Conductivity Dopants:

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved.

Hole-transporting layer can be doped by p-type conductivity dopants and n-type conductivity dopants are used in the electron-transporting layer.

Non-limiting examples of the conductivity dopants that may be used in an OLED in combination with materials disclosed herein are exemplified below together with references that disclose those materials: EP01617493, EP01968131, EP2020694, EP2684932, US20050139810, US20070160905, US20090167167, US2010288362, WO06081780, WO2009003455, WO2009008277, WO2009011327, WO2014009310, US2007252140, US2015060804, US20150123047, and US2012146012.

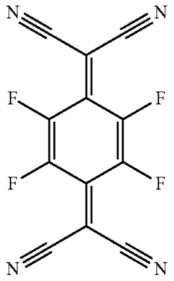

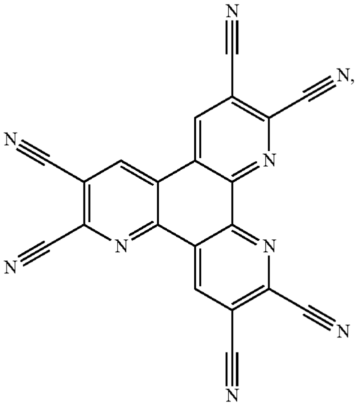

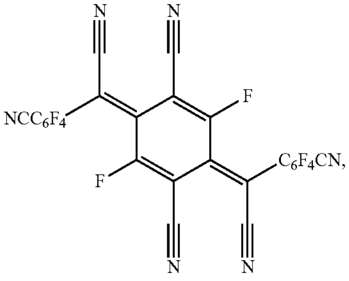

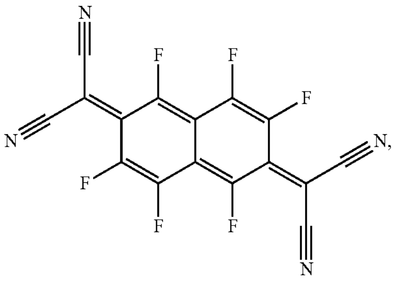

-continued

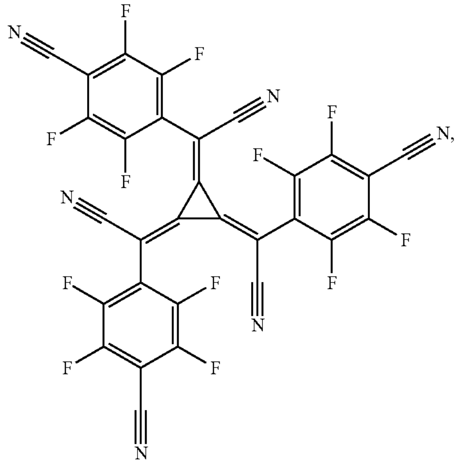

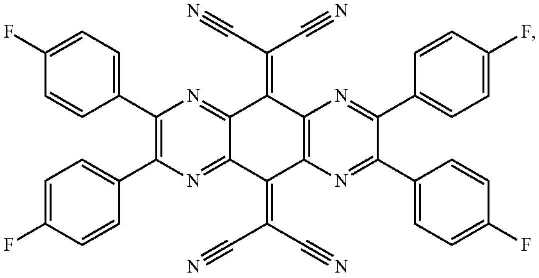

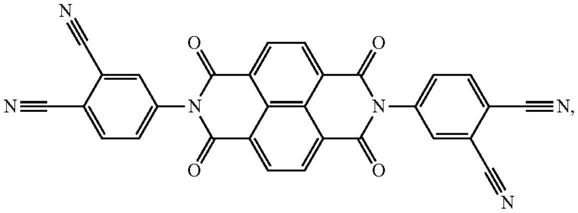

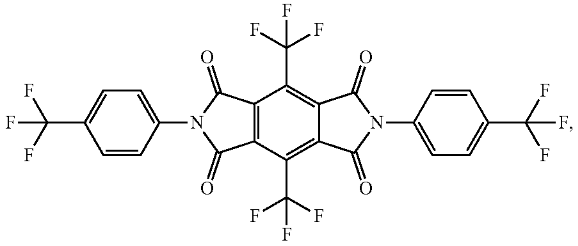

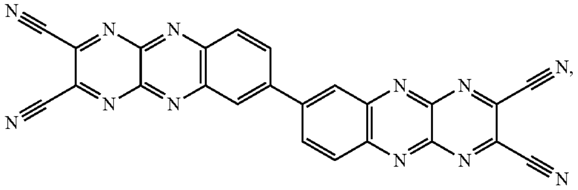

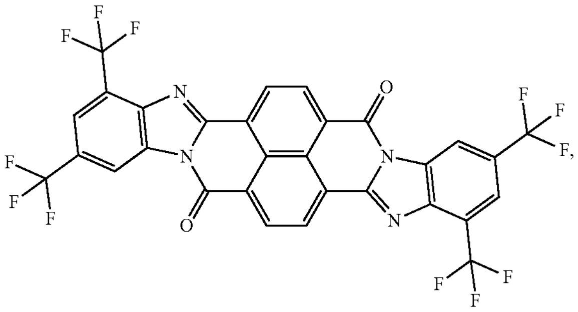

-continued

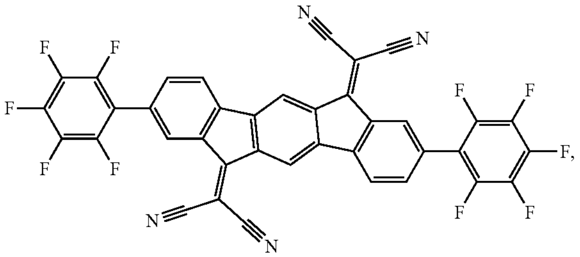

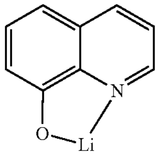, 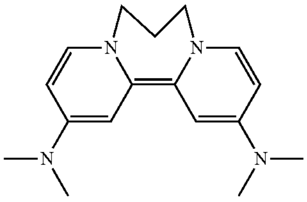 and

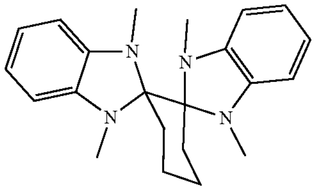.

b) HIL/HTL:

A hole injecting/transporting material to be used in the present disclosure is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphoric acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

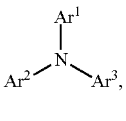, 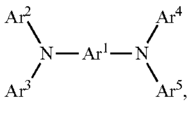, 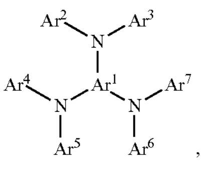,

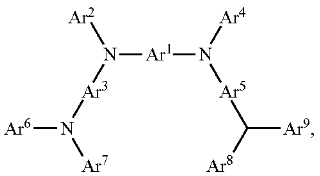, and

-continued

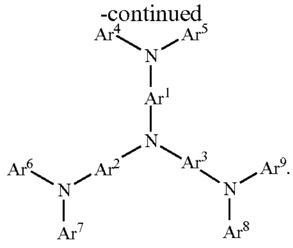.

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, $Ar^1$ to $Ar^9$ is independently selected from the group consisting of:

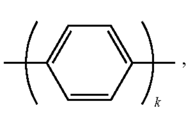, 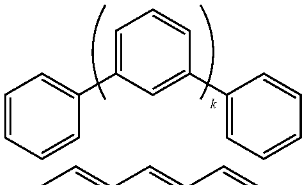,

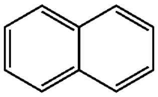, 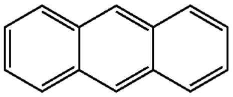,

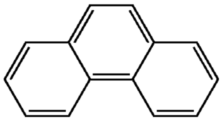, 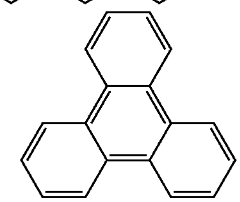,

-continued

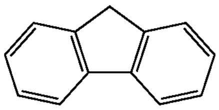

, and

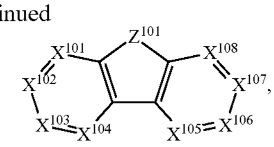

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

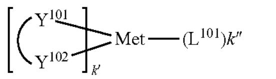

wherein Met is a metal, which can have an atomic weight greater than 40; ($Y^{101}$-$Y^{102}$) is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, ($Y^{101}$-$Y^{102}$) is a 2-phenylpyridine derivative. In another aspect, ($Y^{101}$-$Y^{102}$) is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Non-limiting examples of the HIL and HTL materials that may be used in an OLED in combination with materials disclosed herein are exemplified below together with references that disclose those materials: CN102702075, DE102012005215, EP01624500, EP01698613, EP01806334, EP01930964, EP01972613, EP01997799, EP02011790, EP02055700, EP02055701, EP1725079, EP2085382, EP2660300, EP650955, JP07-073529, JP2005112765, JP2007091719, JP2008021687, JP2014-009196, KR20110088898, KR20130077473, TW201139402, U.S. Ser. No. 06/517,957, US20020158242, US20030162053, US20050123751, US20060182993, US20060240279, US20070145888, US20070181874, US20070278938, US20080014464, US20080091025, US20080106190, US20080124572, US20080145707, US20080220265, US20080233434, US20080303417, US2008107919, US20090115320, US20090167161, US2009066235, US2011007385, US20110163302, US2011240968, US2011278551, US2012205642, US2013241401, US20140117329, US2014183517, U.S. Pat. Nos. 5,061,569, 5,639,914, WO05075451, WO07125714, WO08023550, WO08023759, WO2009145016, WO2010061824, WO2011075644, WO2012177006, WO2013018530, WO2013039073, WO2013087142, WO2013118812, WO2013120577, WO2013157367, WO2013175747, WO2014002873, WO2014015935, WO2014015937, WO2014030872, WO2014030921, WO2014034791, WO2014104514, WO2014157018.

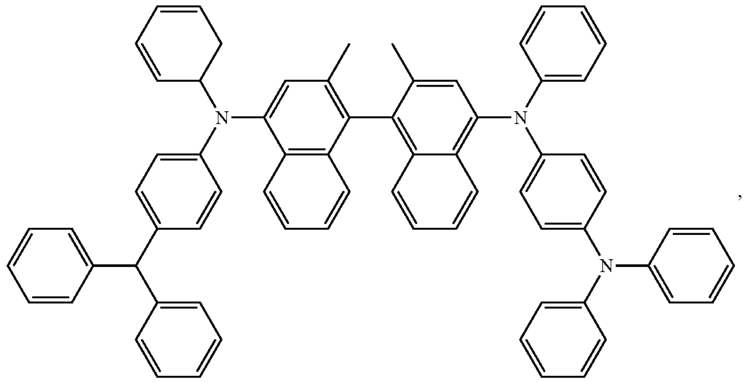

,

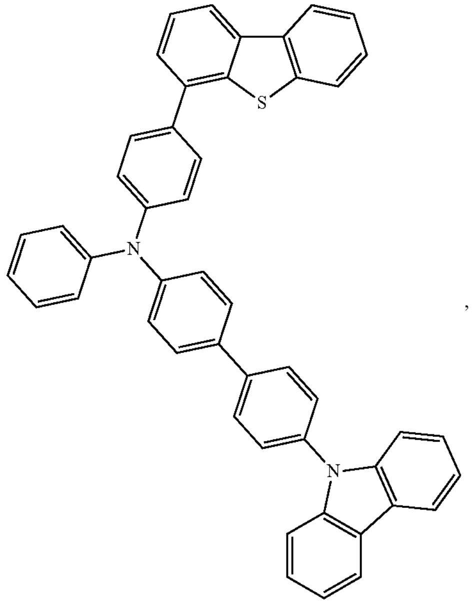

,

-continued
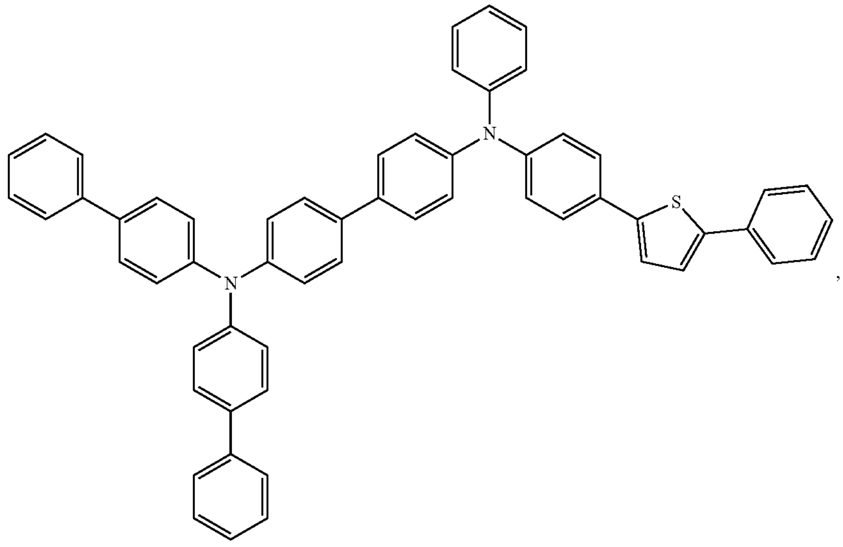
,
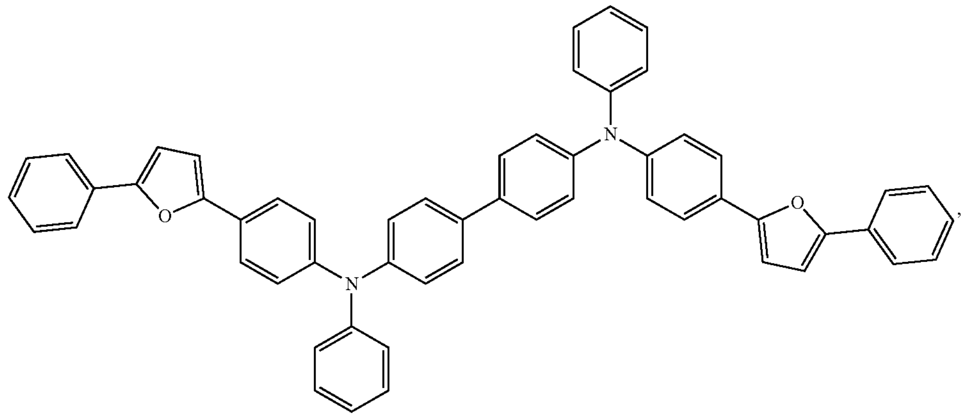
,
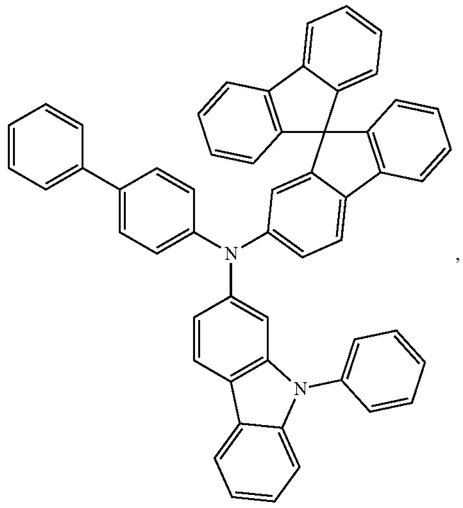
,
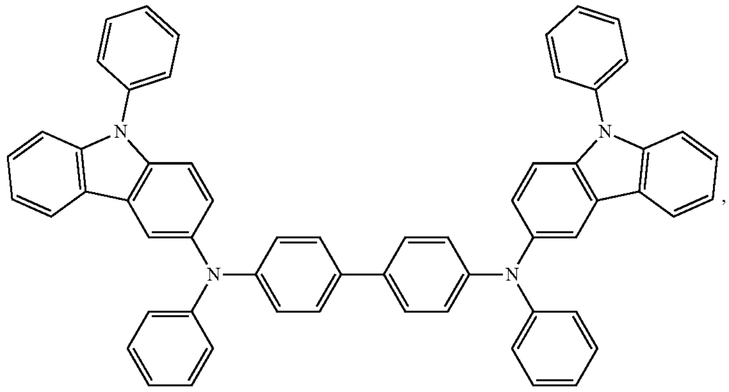
,

-continued
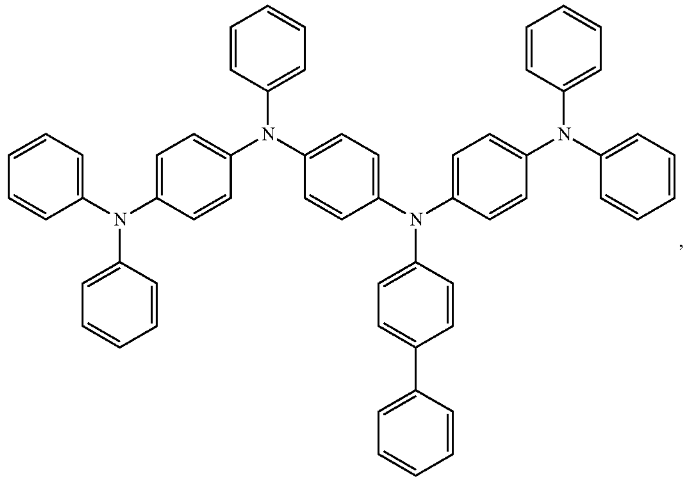
,
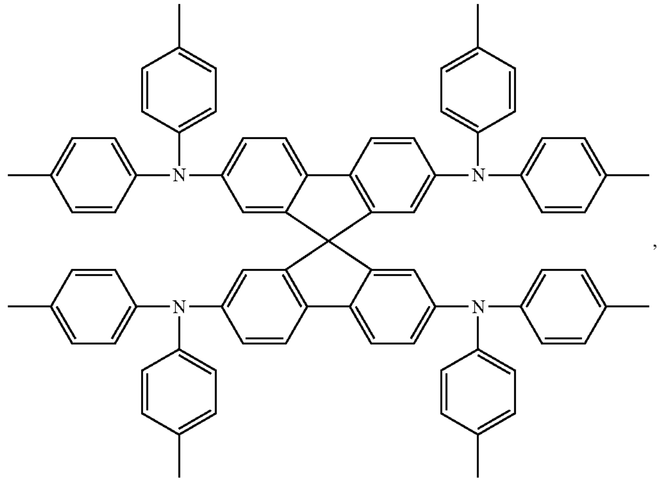
,
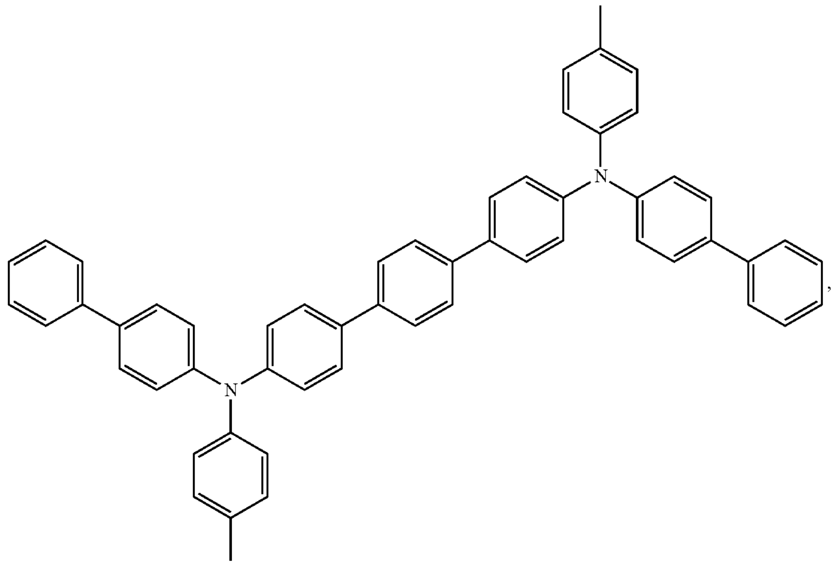
,

-continued
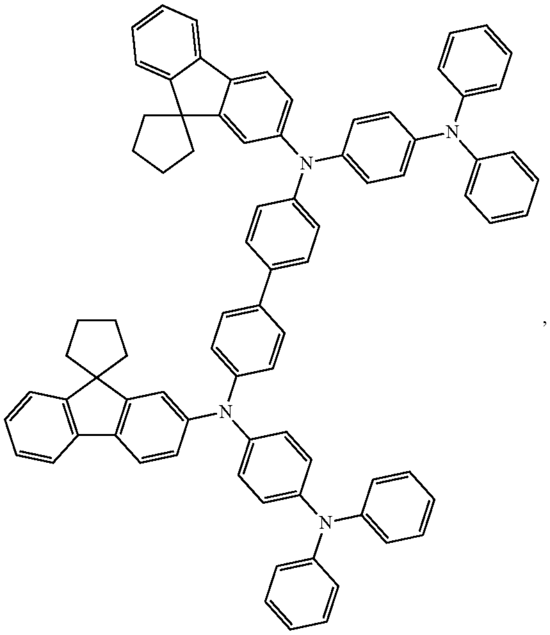
,
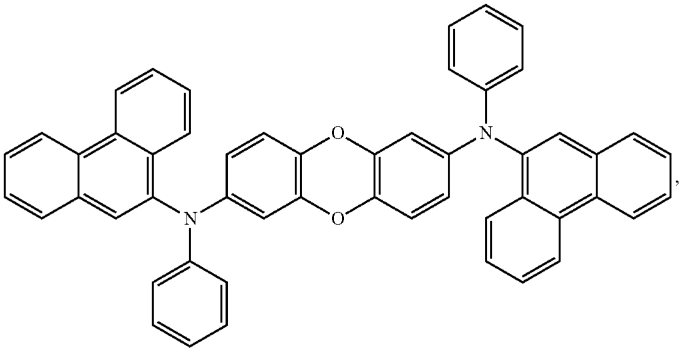
,
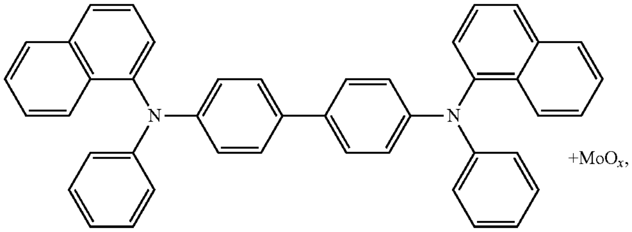
+MoO$_x$,
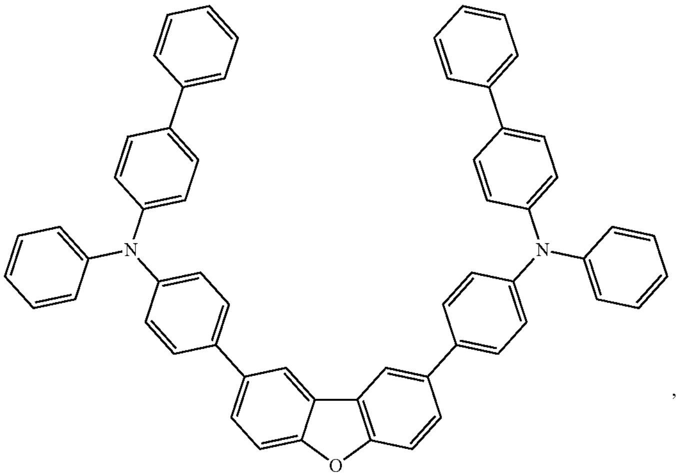
,
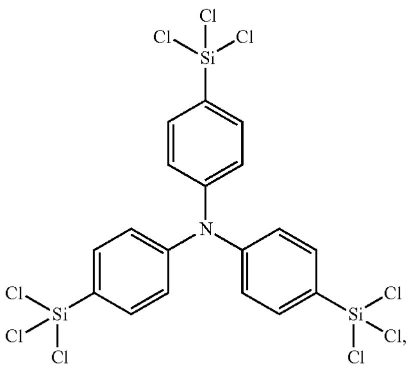

-continued
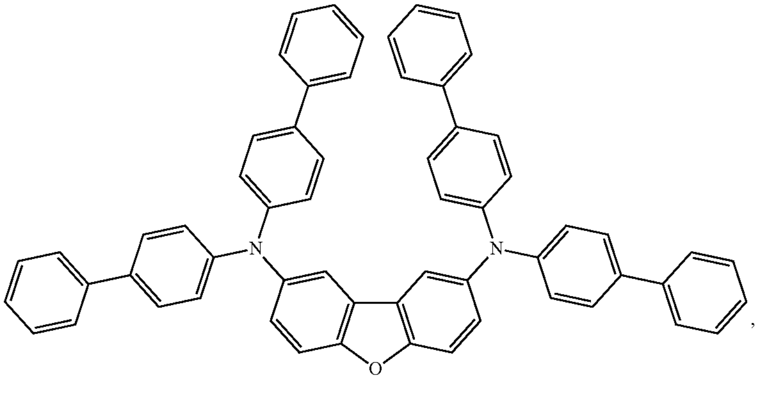
,
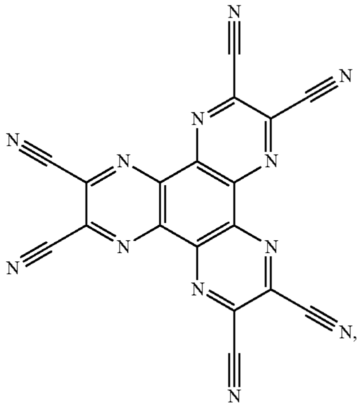
,
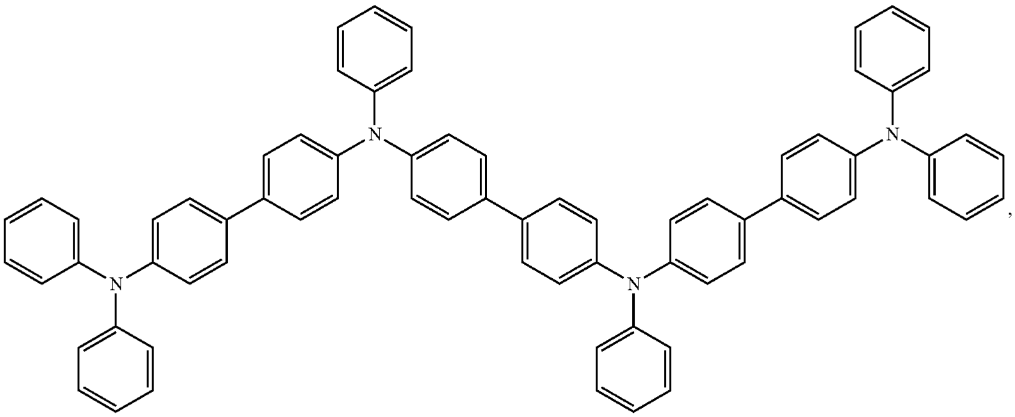
,
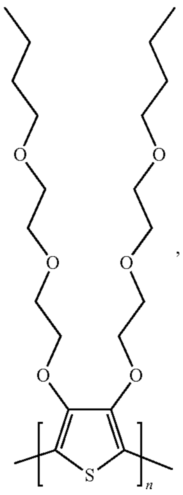
,
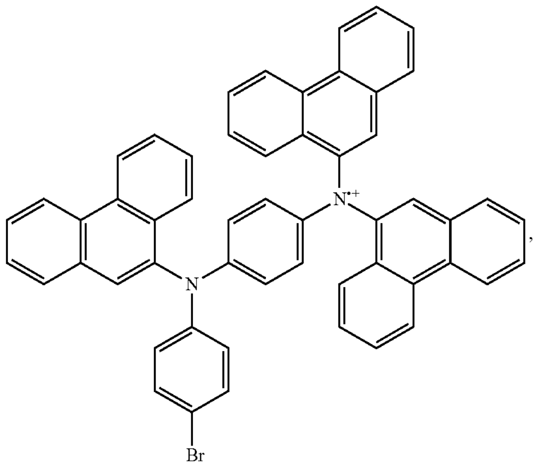
, -continued
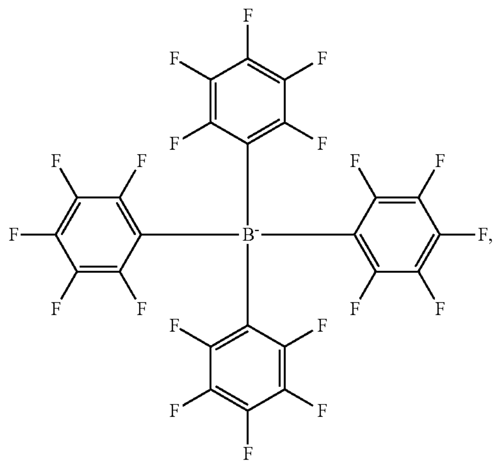
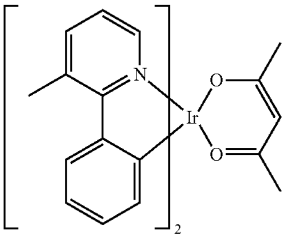
,
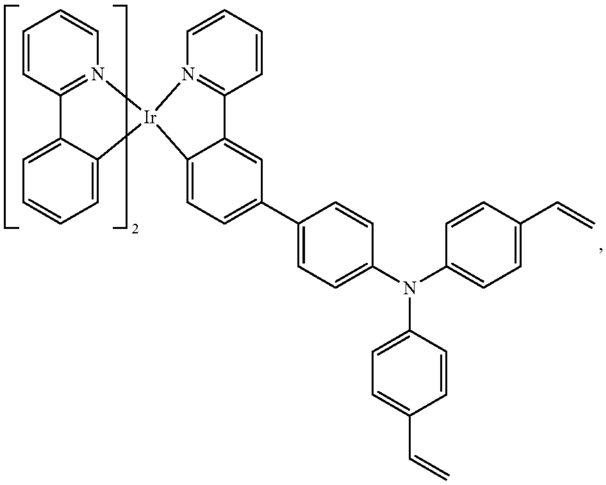
,
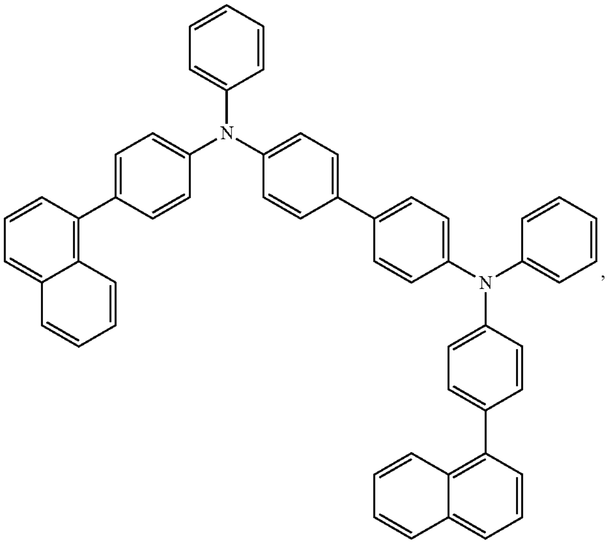
, -continued
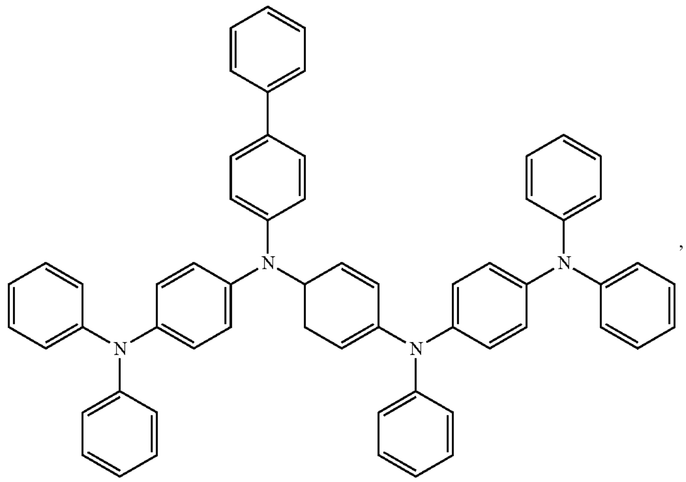
,
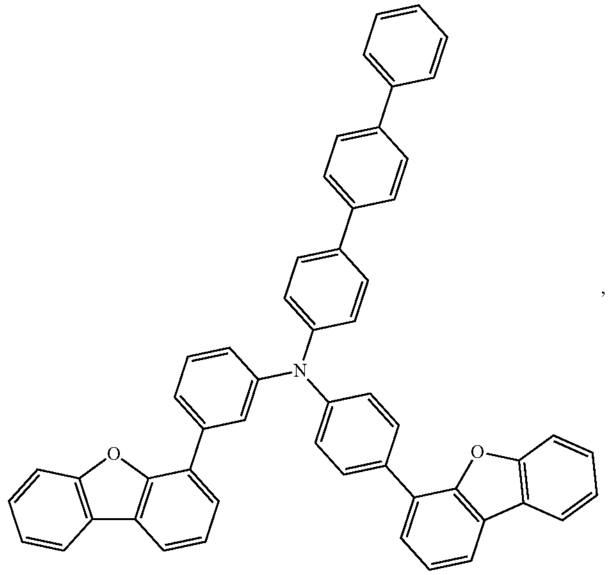
,
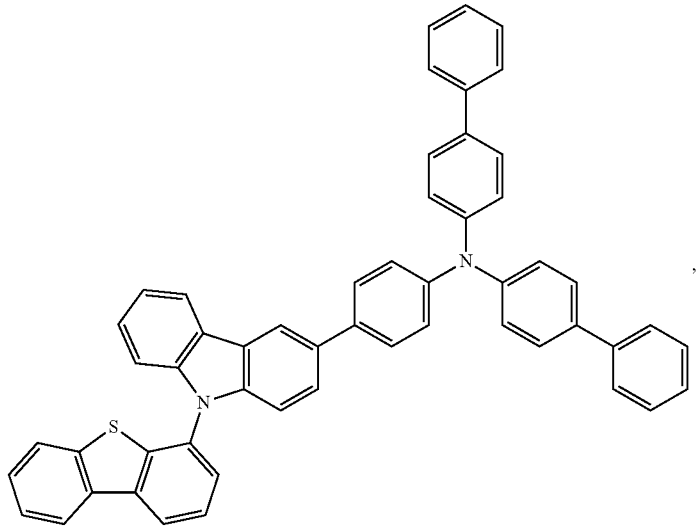
, -continued
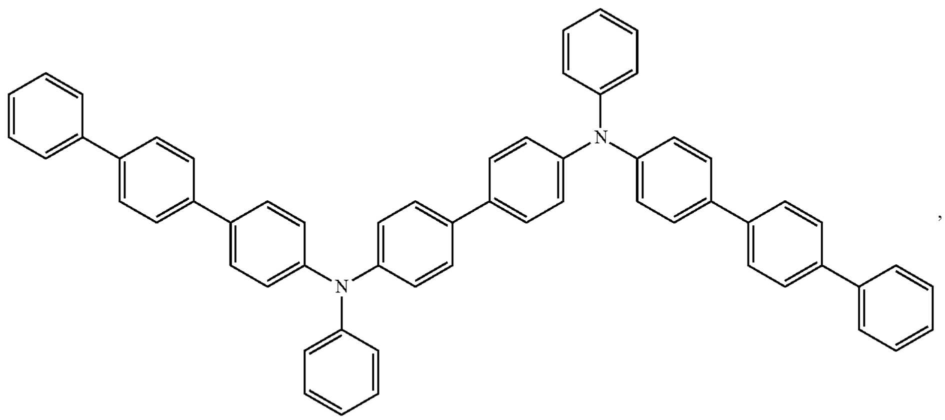
,
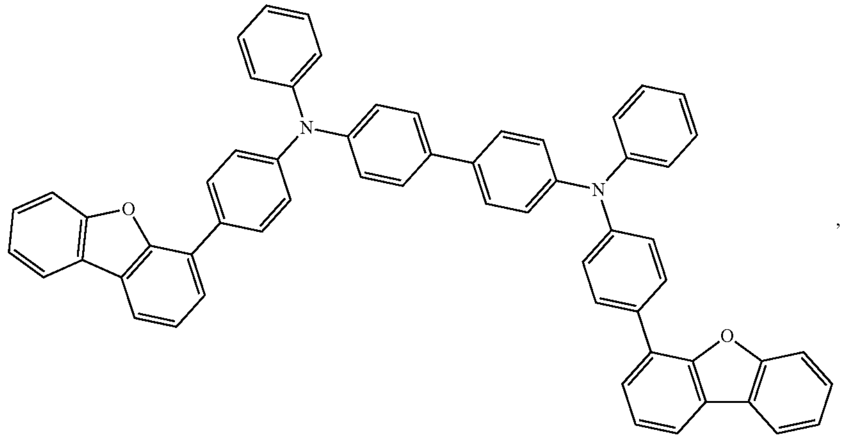
,
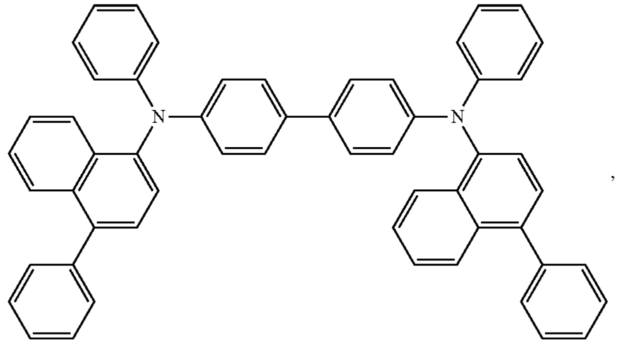
,
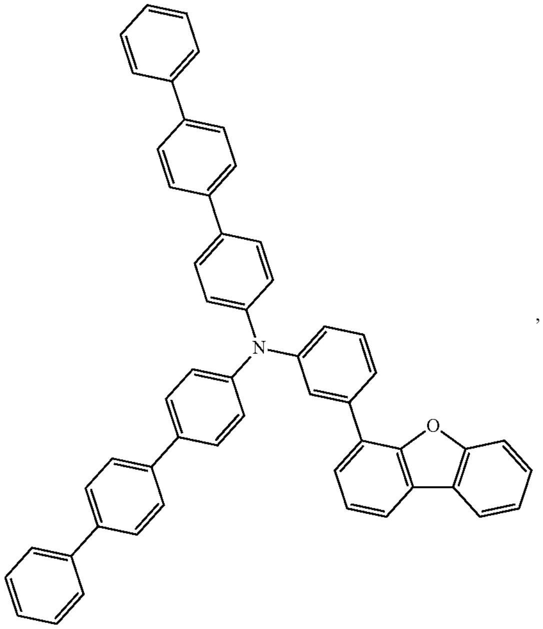
, -continued
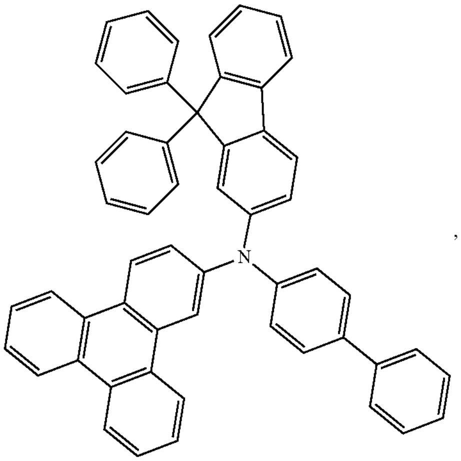
,
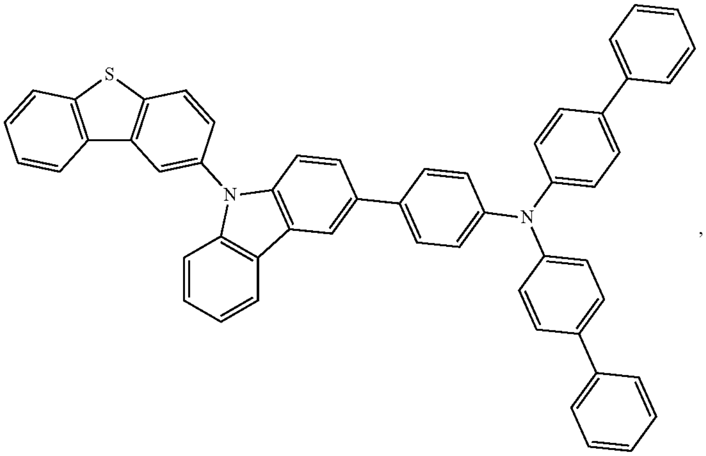
,
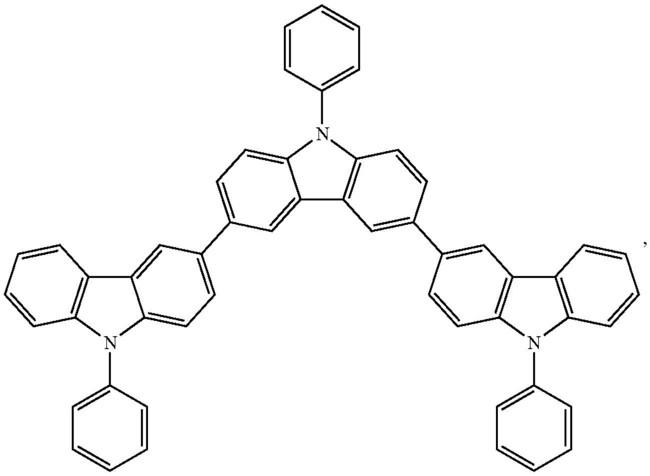
,
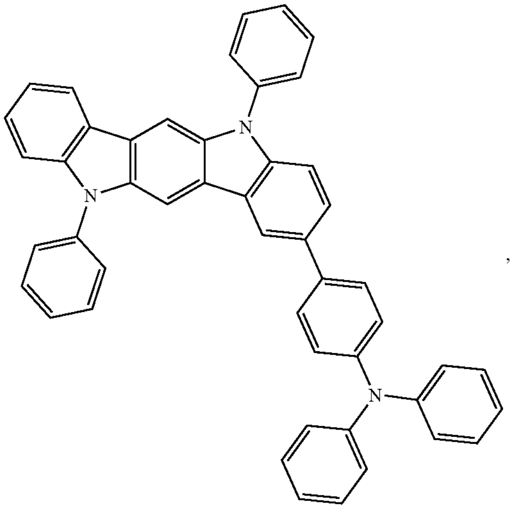
,
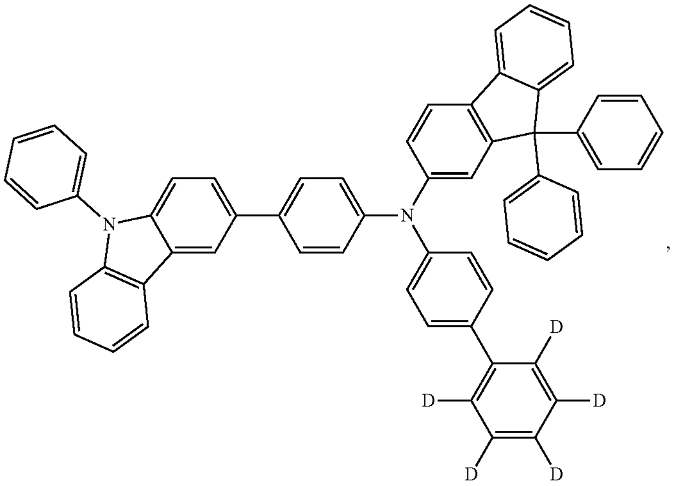
, -continued
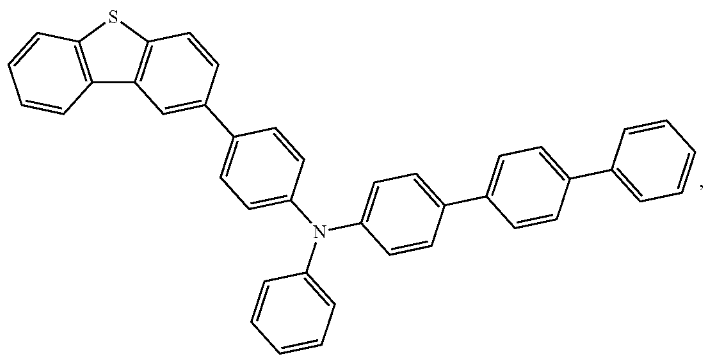
,
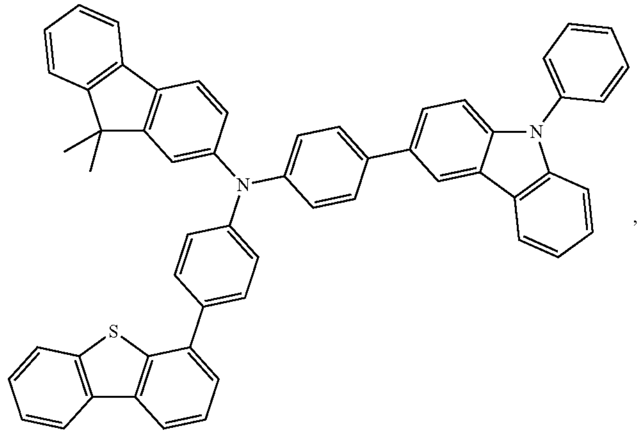
,
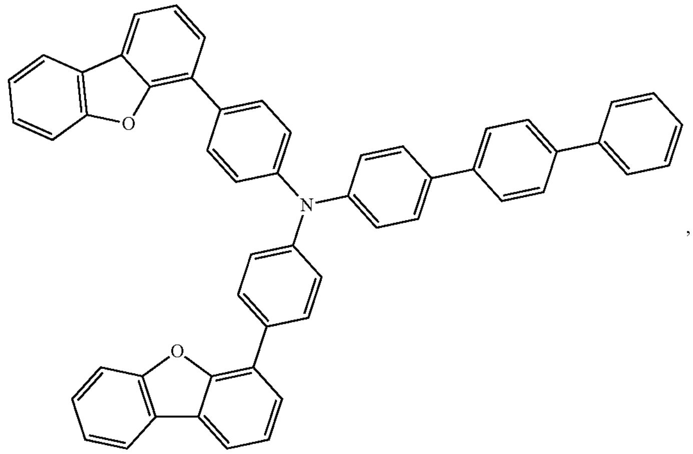
, -continued
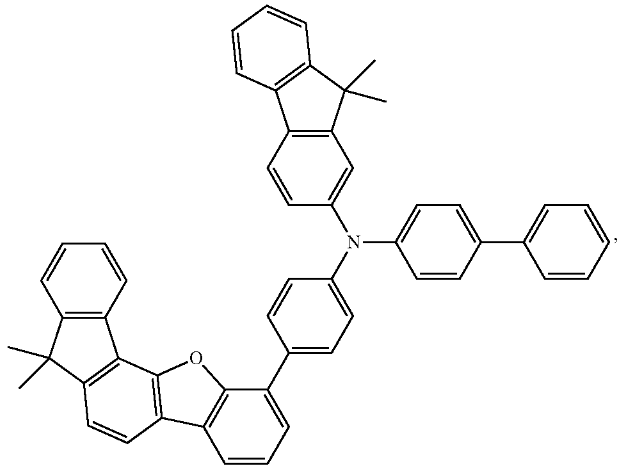
,
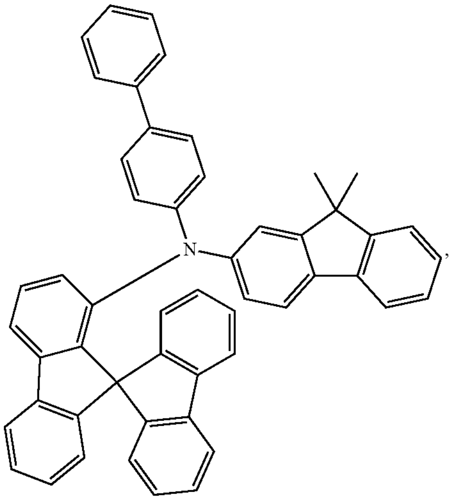
,
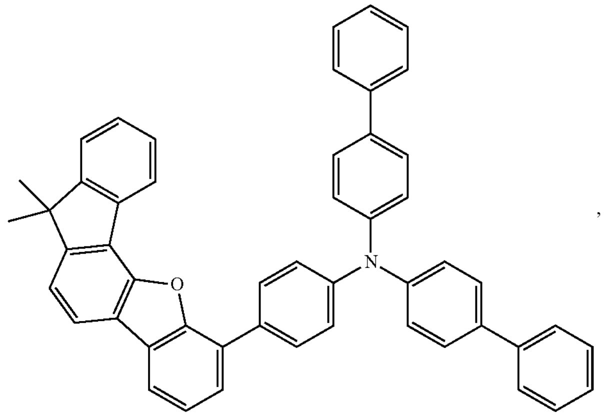
,
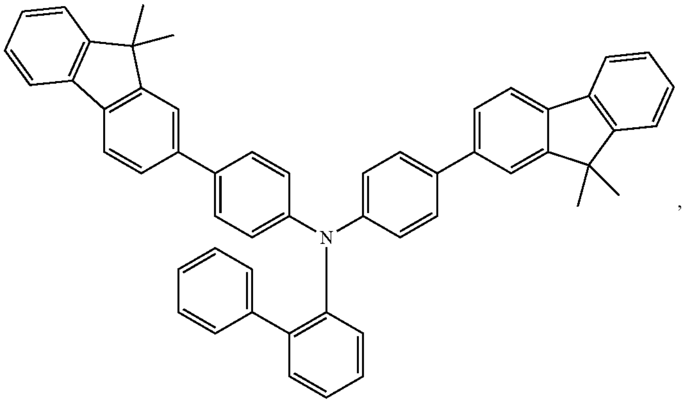
, -continued
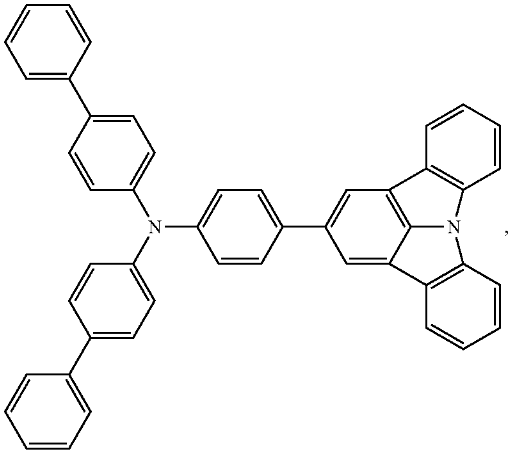
,
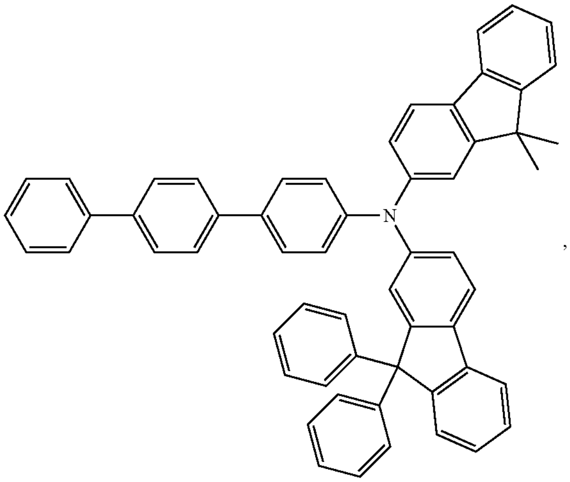
,
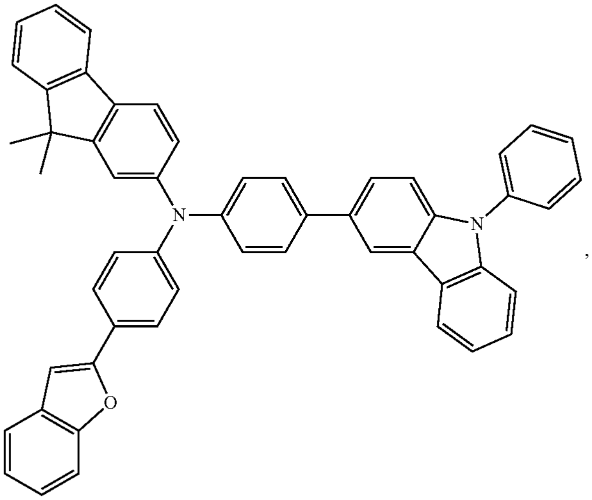
,
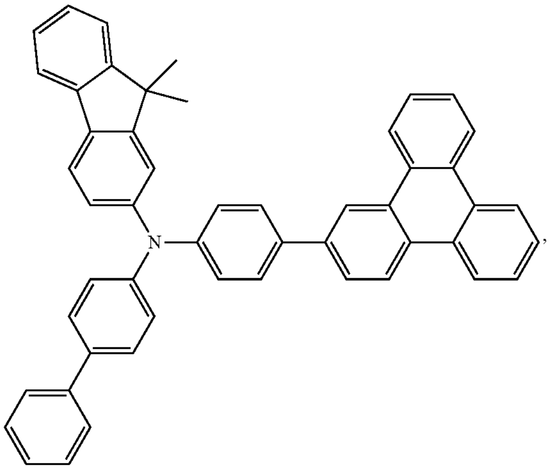
,
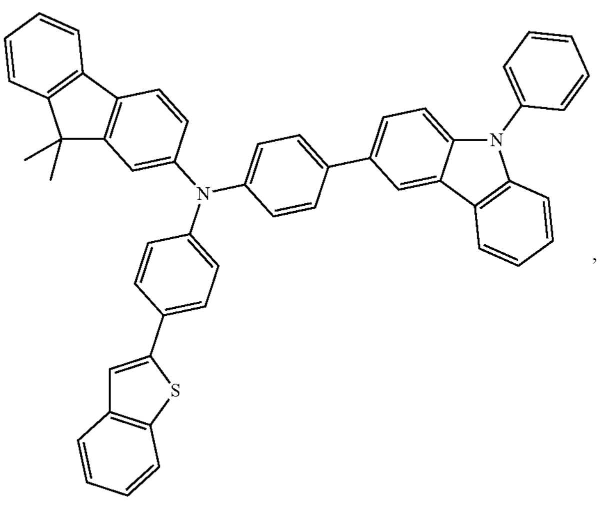
, -continued
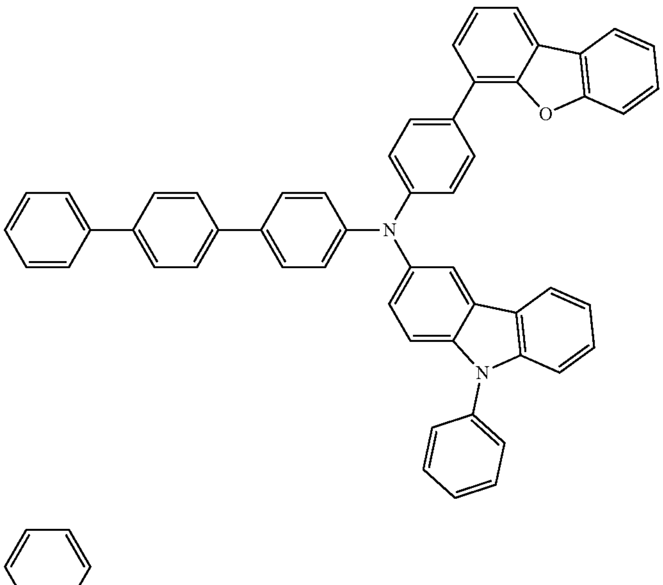
,
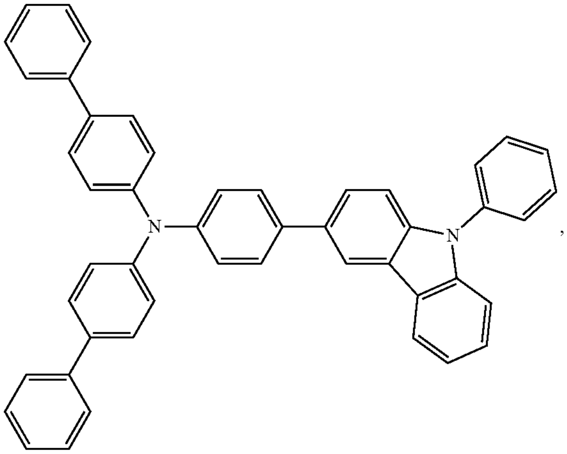
,
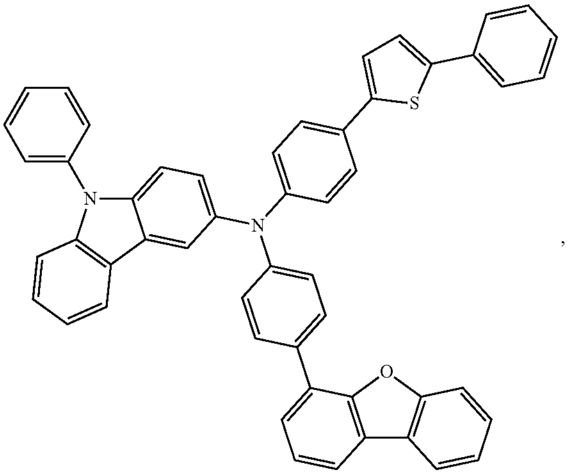
,
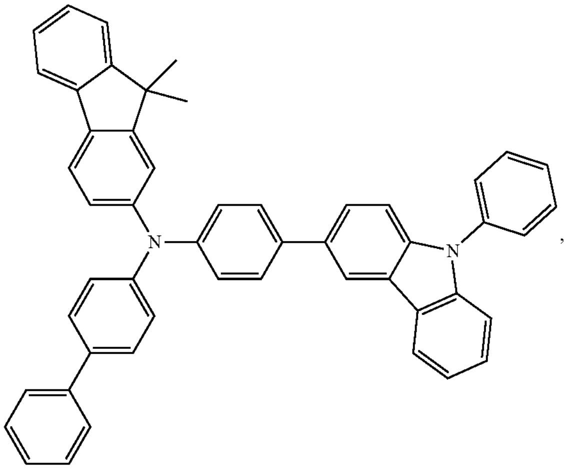
,
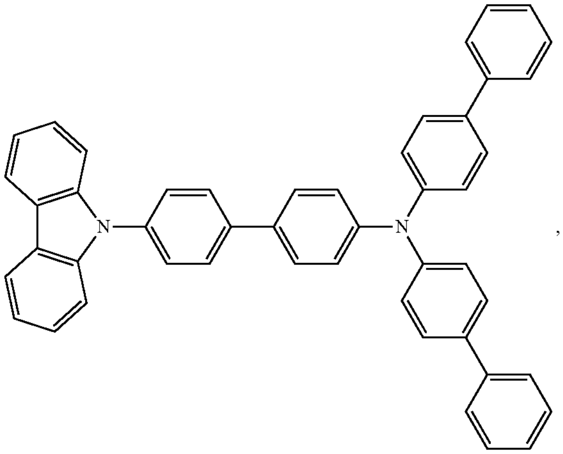
, -continued
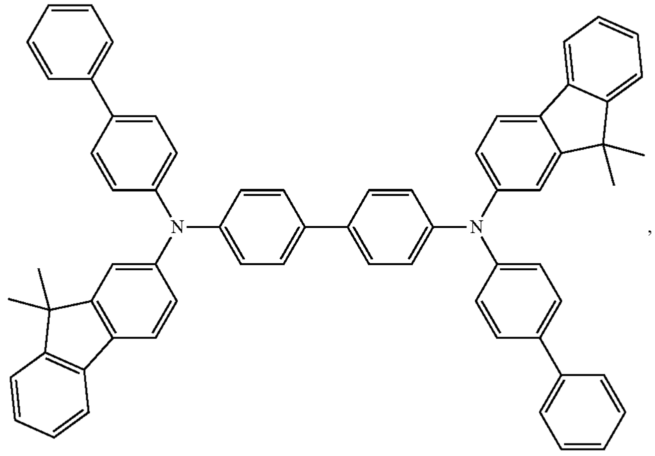
,
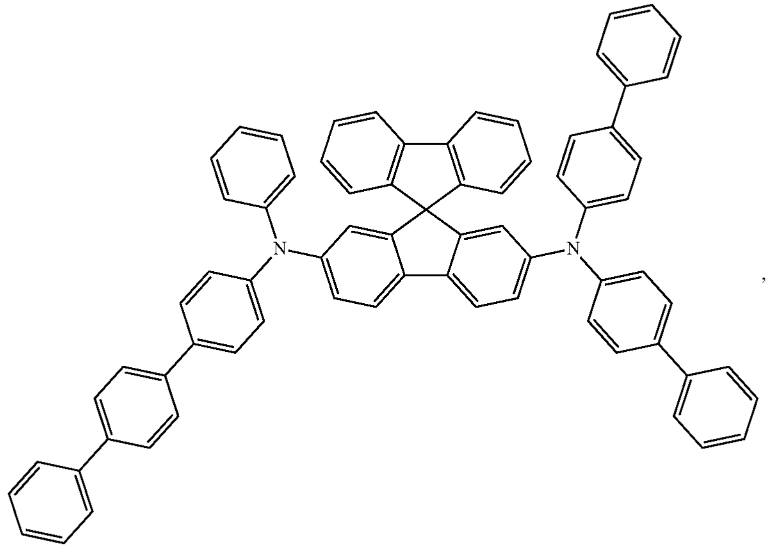
,
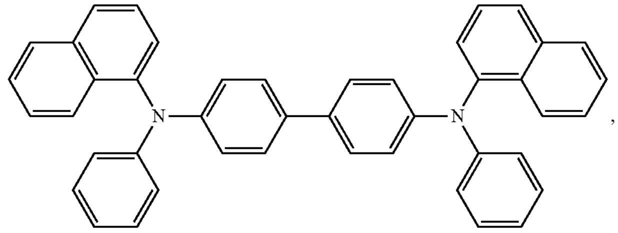
,
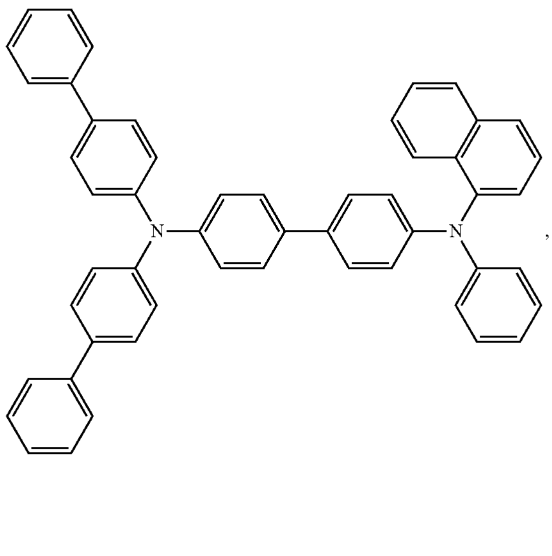
, -continued
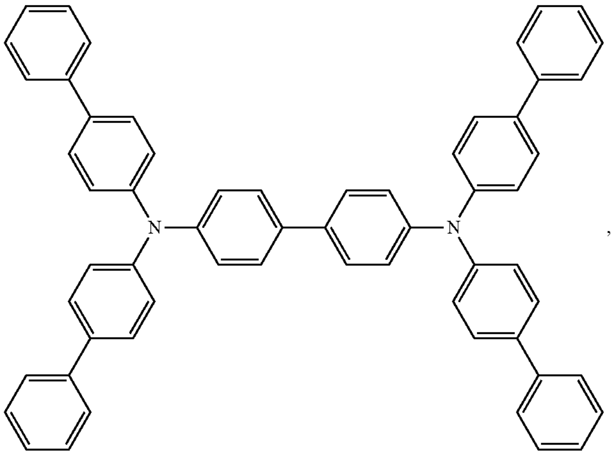
,
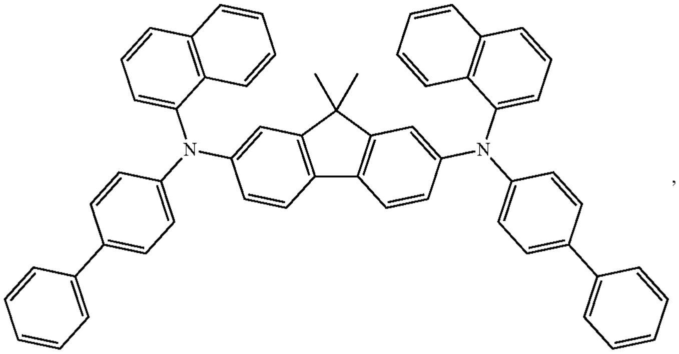
,
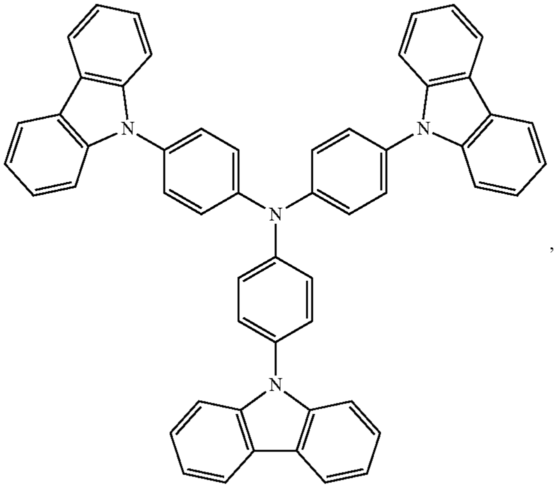
,
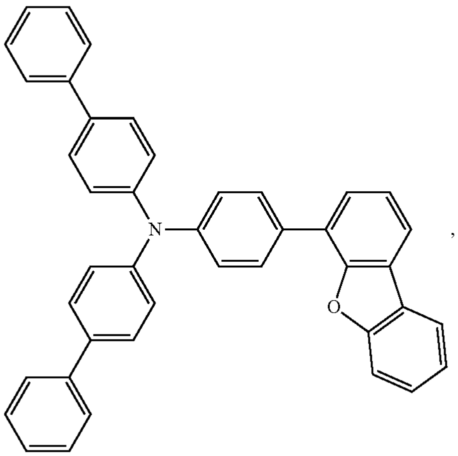
, -continued

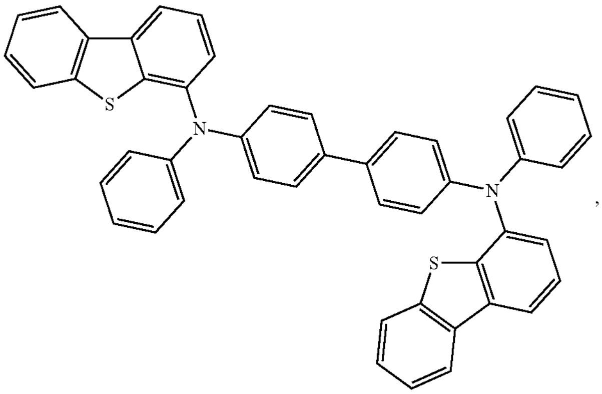

,

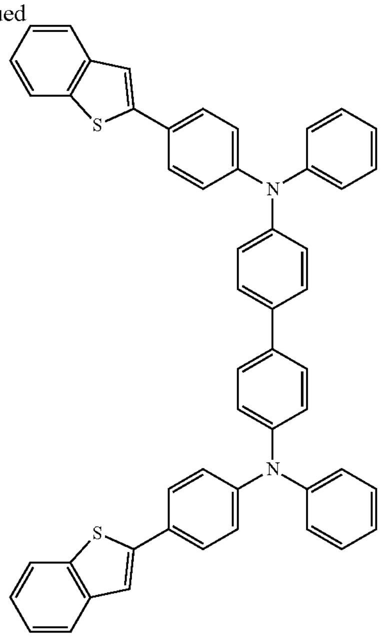

, and

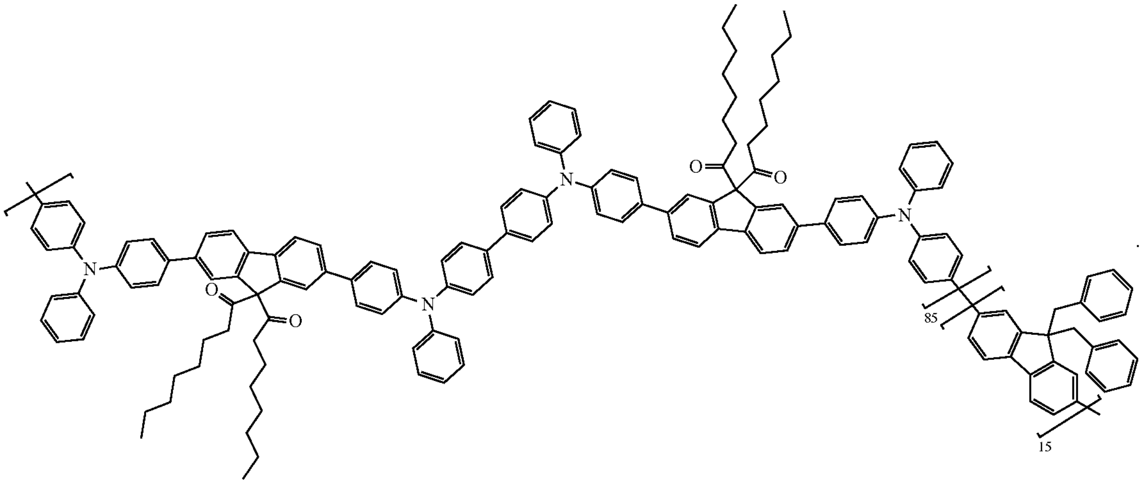

.

c) EBL:

An electron blocking layer (EBL) may be used to reduce the number of electrons and/or excitons that leave the emissive layer. The presence of such a blocking layer in a device may result in substantially higher efficiencies, and/or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and/or higher triplet energy than one or more of the hosts closest to the EBL interface. In one aspect, the compound used in EBL contains the same molecule or the same functional groups used as one of the hosts described below.

d) Hosts:

The light emitting layer of the organic EL device of the present disclosure preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. Any host material may be used with any dopant so long as the triplet criteria is satisfied.

Examples of metal complexes used as host are preferred to have the following general formula:

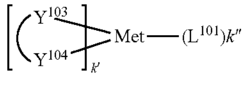

wherein Met is a metal; ($Y^{103}$-$Y^{104}$) is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

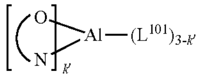

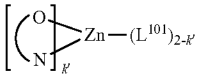

wherein (O—N) is a bidentate ligand, having metal coordinated to atoms O and N.

In another aspect, Met is selected from Ir and Pt. In a further aspect, ($Y^{103}$-$Y^{104}$) is a carbene ligand.

In one aspect, the host compound contains at least one of the following groups selected from the group consisting of aromatic hydrocarbon cyclic compounds such as benzene, biphenyl, triphenyl, triphenylene, tetraphenylene, naphthalene, anthracene, phenalene, phenanthrene, fluorene, pyrene, chlysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each option within each group may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, the host compound contains at least one of the following groups in the molecule:

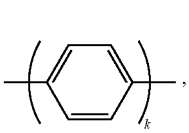

,

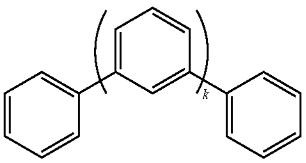

,

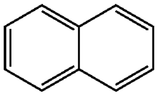

,

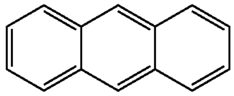

,

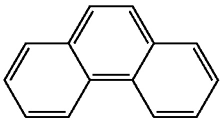

,

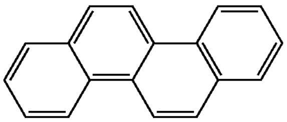

,

-continued

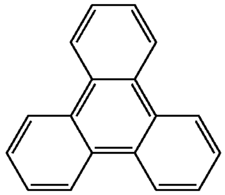

,

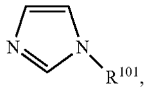

,

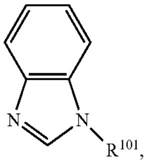

,

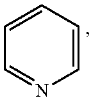

,

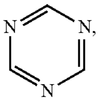

,

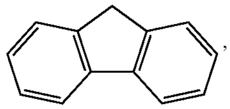

,

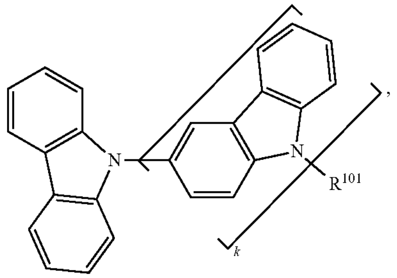

,

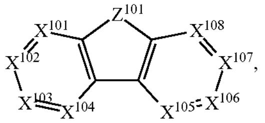

,

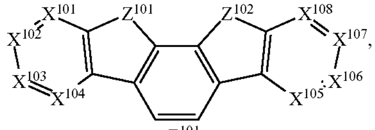

,

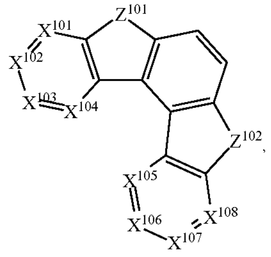

,

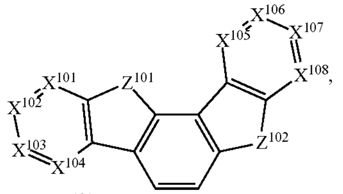

,

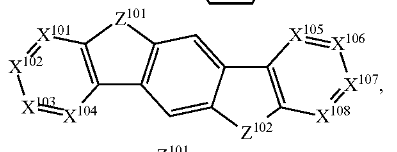

and

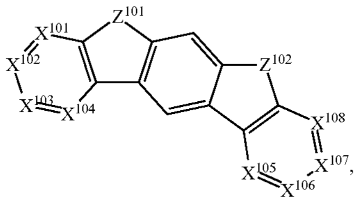

, wherein $R^{101}$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, and when it is aryl or heteroaryl, it has the similar definition as Ar's mentioned above. k is an integer from 0 to 20 or 1 to 20. $X^{101}$ to $X^{108}$ are independently selected from C (including CH) or N. $Z^{101}$ and $Z^{102}$ are independently selected from $NR^{101}$, O, or S.

Non-limiting examples of the host materials that may be used in an OLED in combination with materials disclosed herein are exemplified below together with references that disclose those materials: EP2034538, EP2034538A, EP2757608, JP2007254297, KR20100079458, KR20120088644, KR20120129733, KR20130115564, TW201329200, US20030175553, US20050238919, US20060280965, US20090017330, US20090030202, US20090167162, US20090302743, US20090309488, US20100012931, US20100084966, US20100187984, US2010187984, US2012075273, US2012126221, US2013009543, US2013105787, US2013175519, US2014001446, US20140183503, US20140225088, US2014034914, U.S. Pat. No. 7,154,114, WO2001039234, WO2004093207, WO2005014551, WO2005089025, WO2006072002, WO2006114966, WO2007063754, WO2008056746, WO2009003898, WO2009021126, WO2009063833, WO2009066778, WO2009066779, WO2009086028, WO2010056066, WO2010107244, WO2011081423, WO2011081431, WO2011086863, WO2012128298, WO2012133644, WO2012133649, WO2013024872, WO2013035275, WO2013081315, WO2013191404, WO2014142472, US20170263869, US20160163995, U.S. Pat. No. 9,466,803,

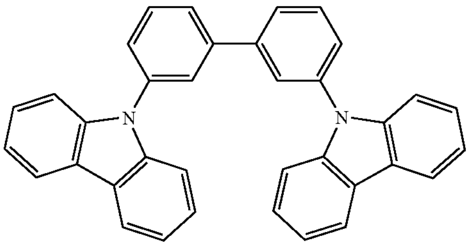

,

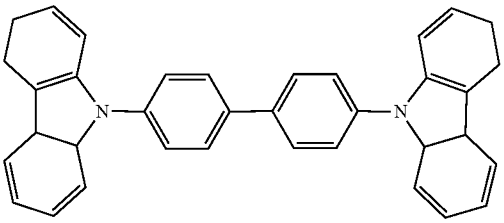

,

-continued

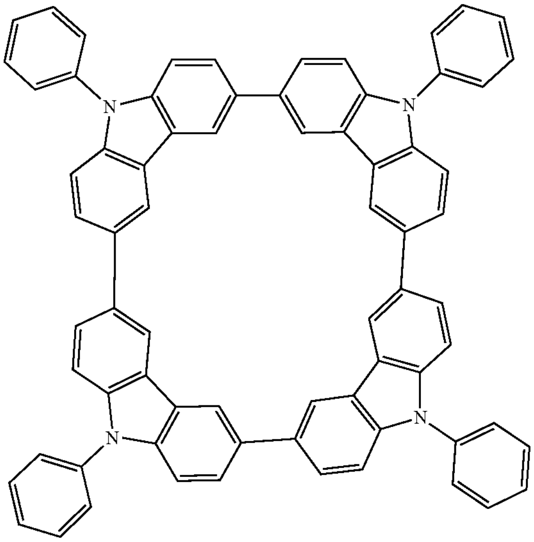

,

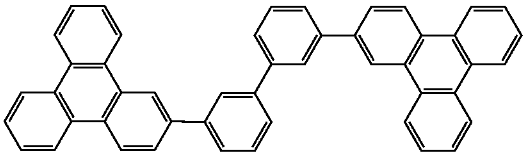

,

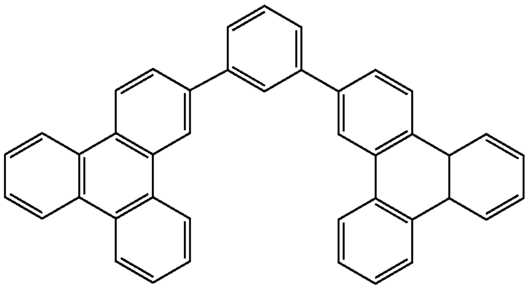

,

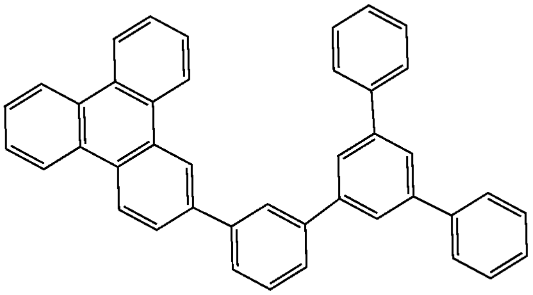

,

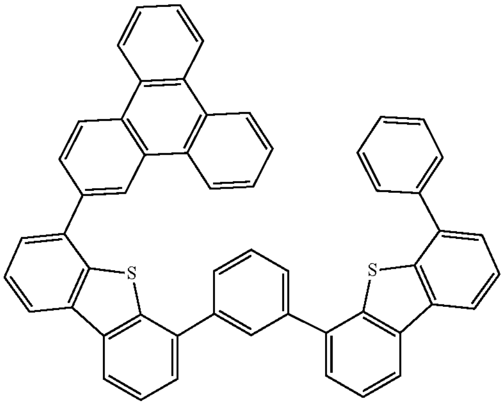

,

-continued
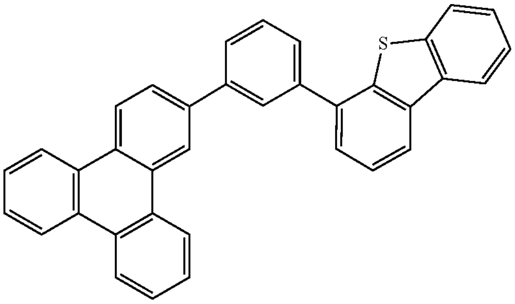
,
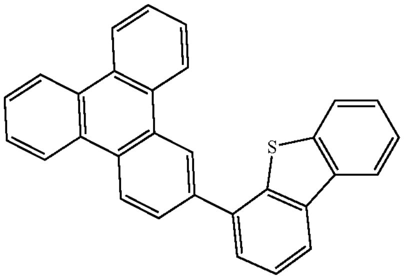
,
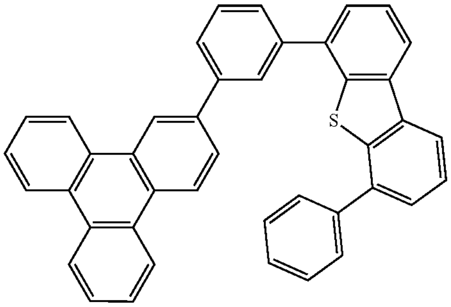
,
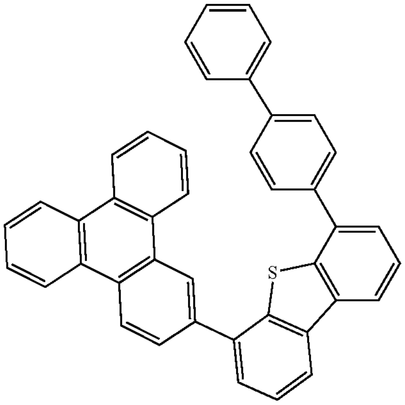
,
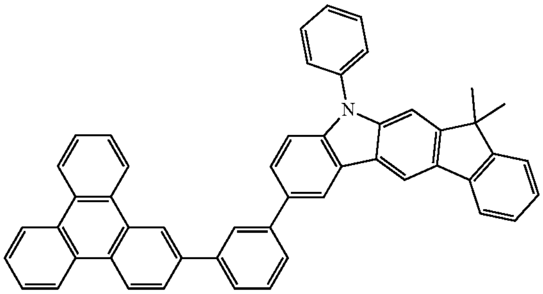
,
-continued
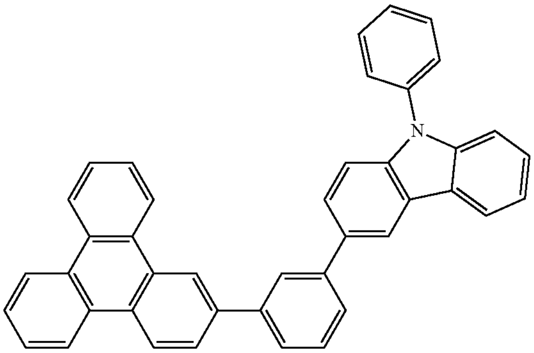
,
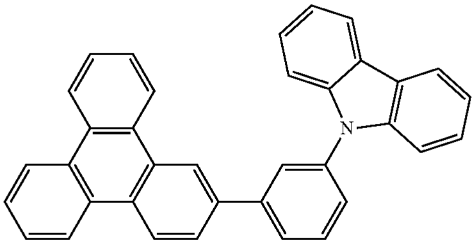
,
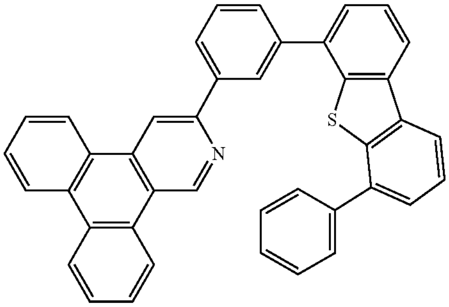
,
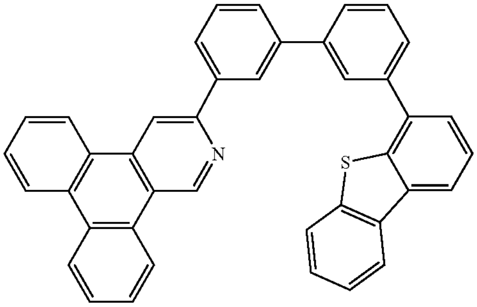
,
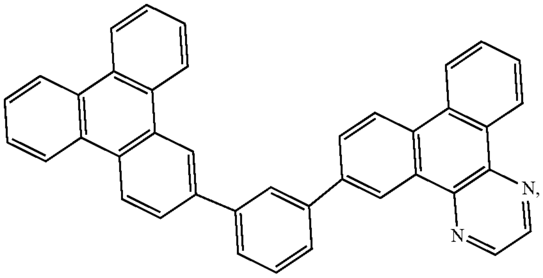
, -continued
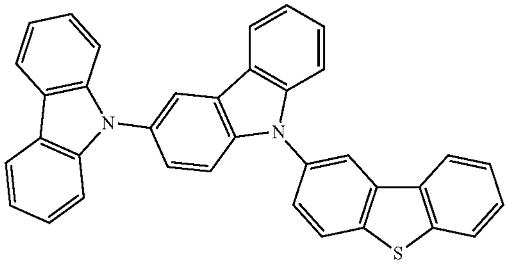
,
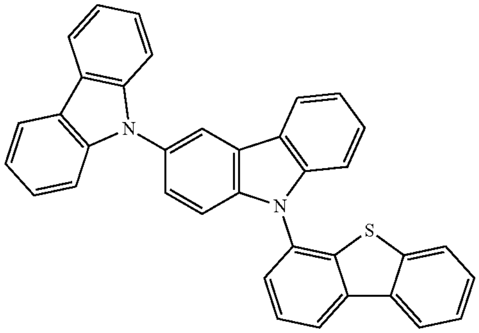
,
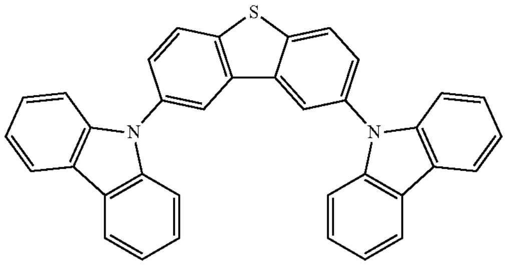
,
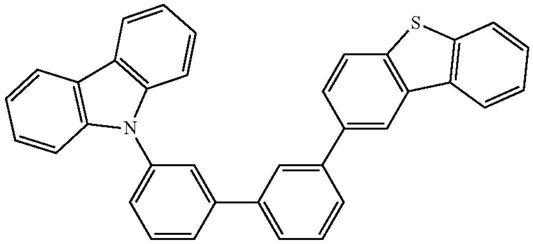
,
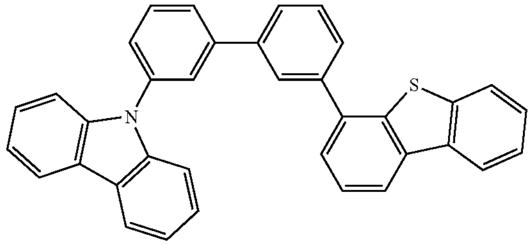
,
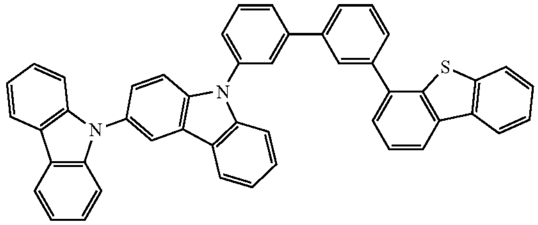
,
-continued
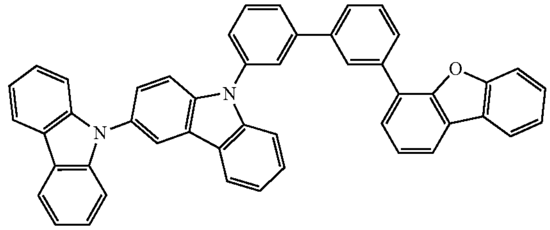
,
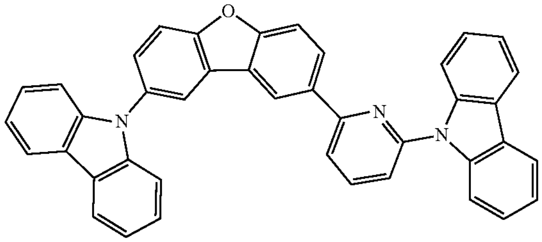
,
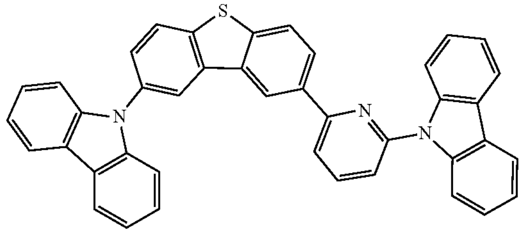
,
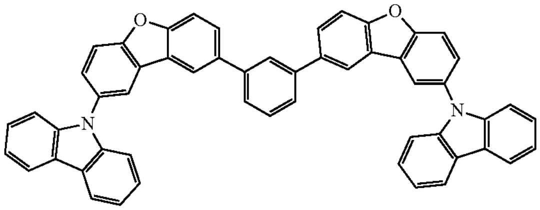
,
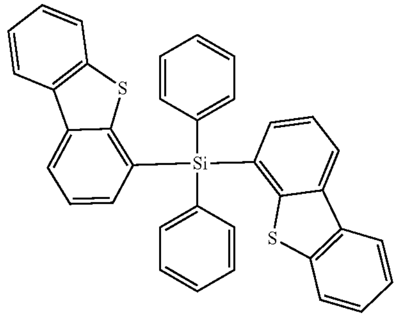
,
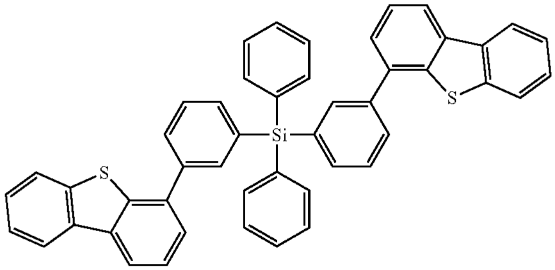
, -continued
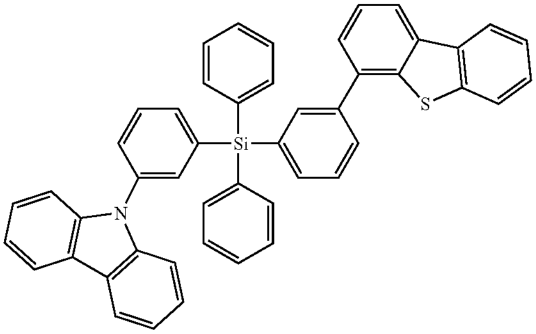
,
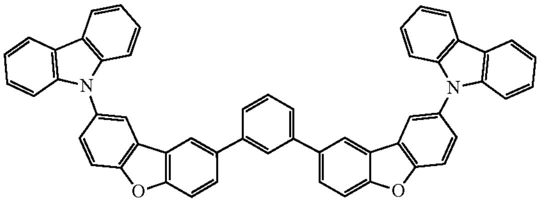
,
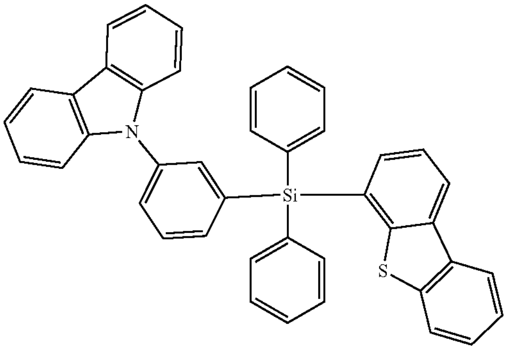
,
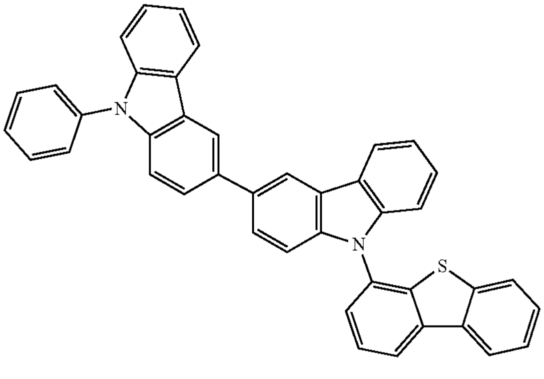
,
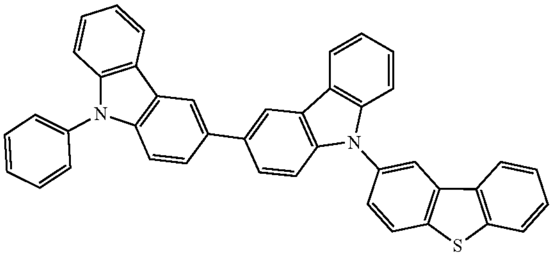
,
-continued
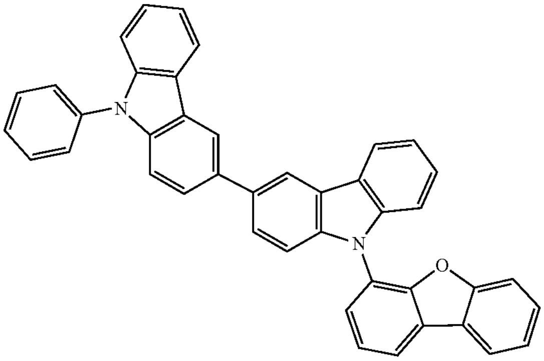
,
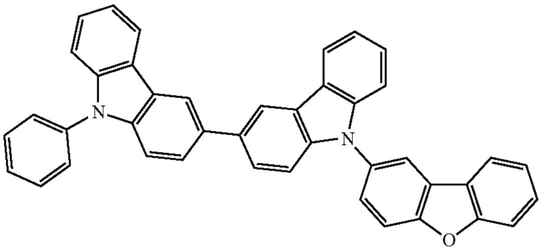
,
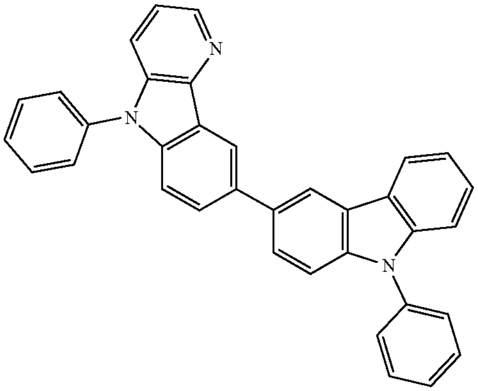
,
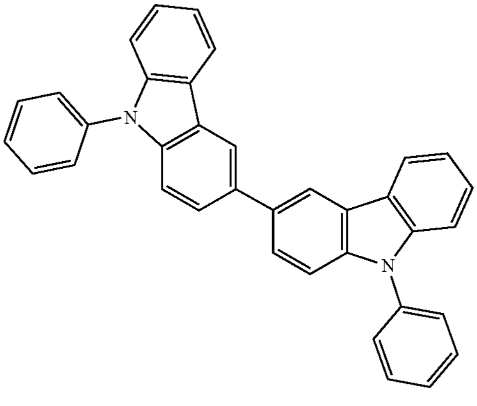
,
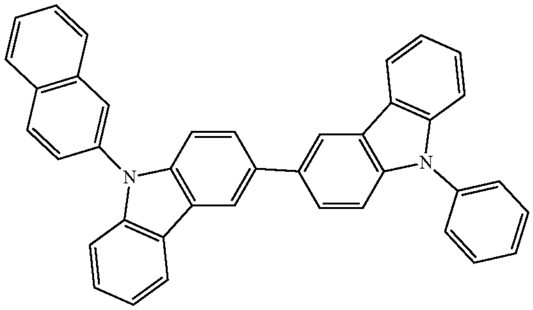
, -continued
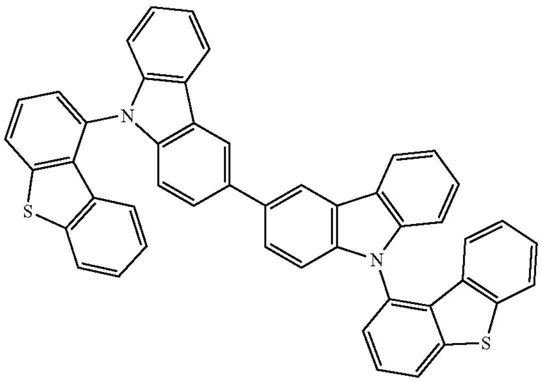
,
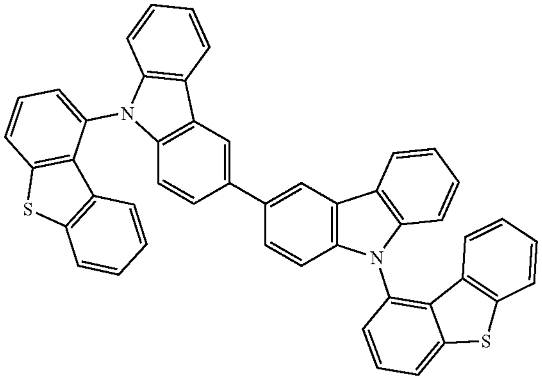
,
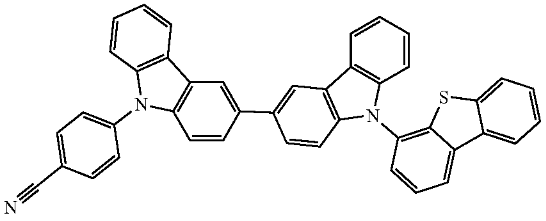
,
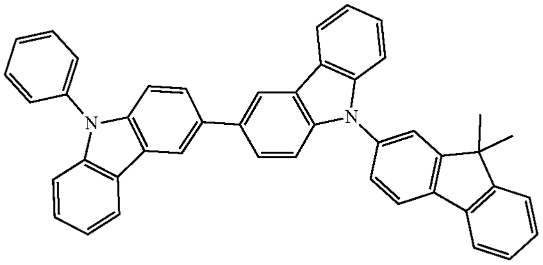
,
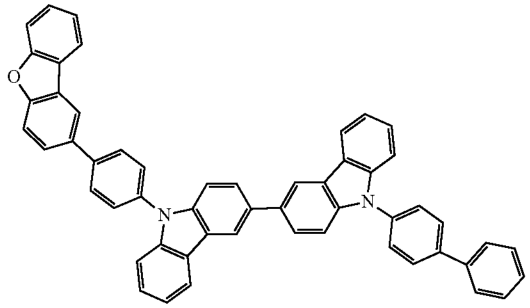
,
-continued
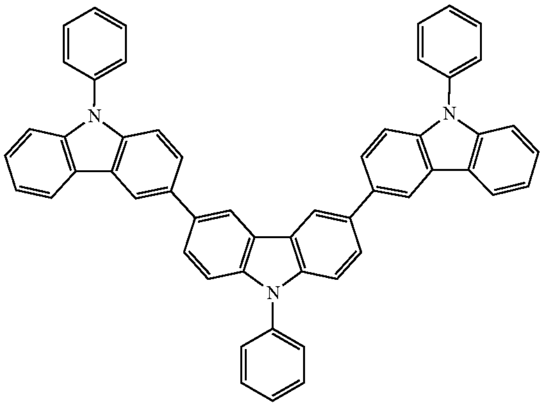
,
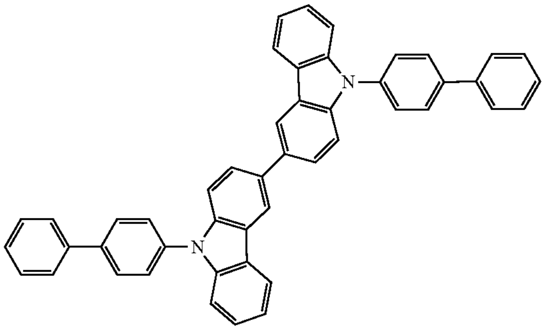
,
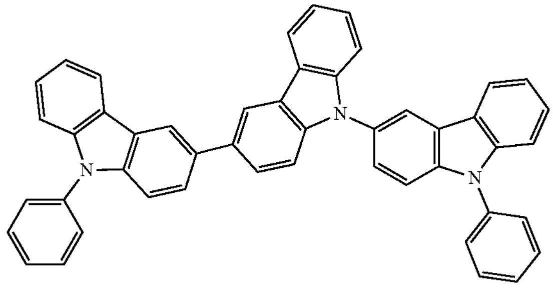
,
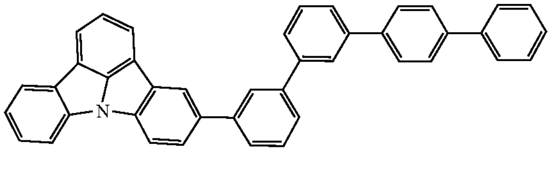
,
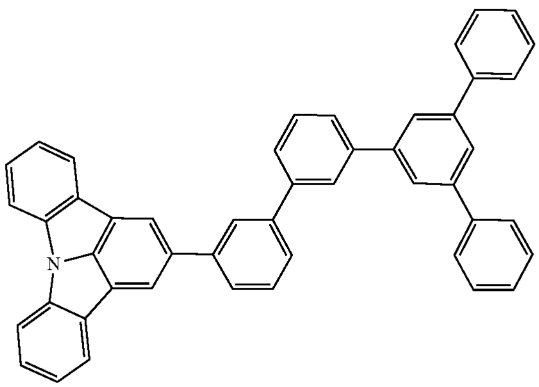
, -continued
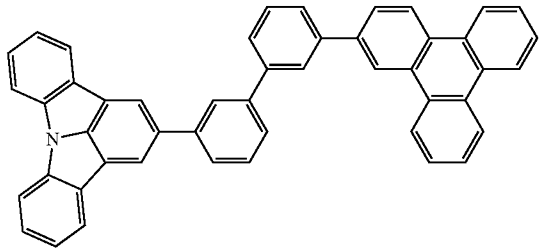
,
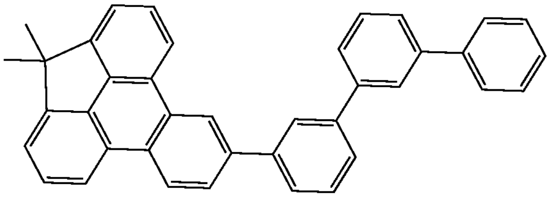
,
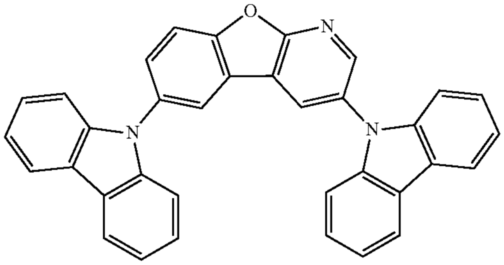
,
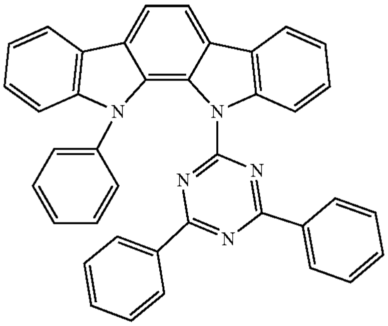
,
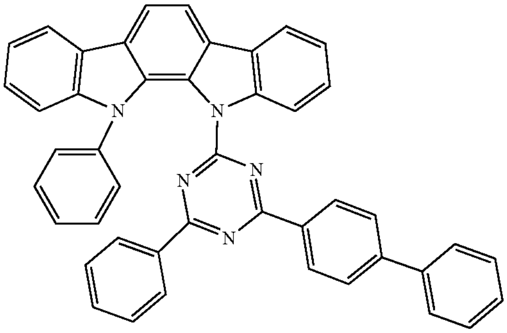
,
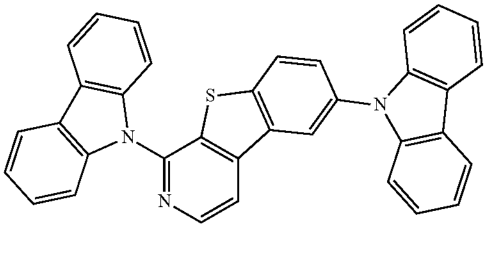
,
-continued
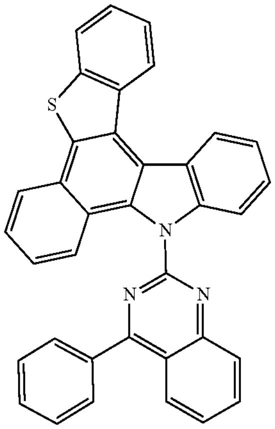
,
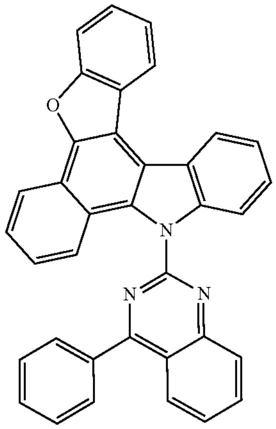
,
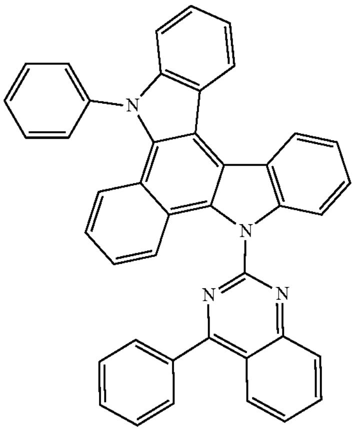
, -continued
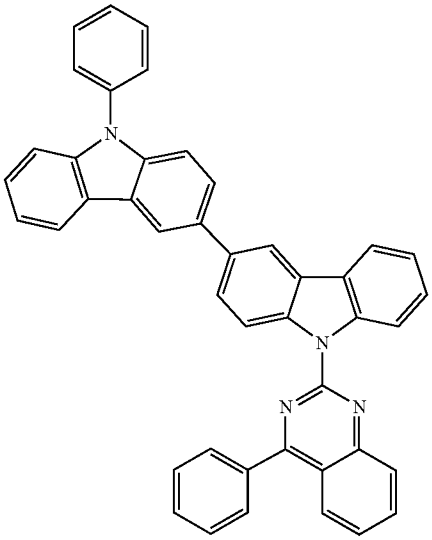
,
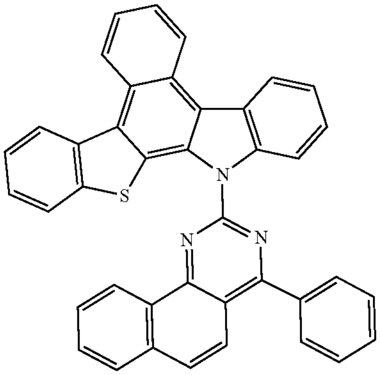
,
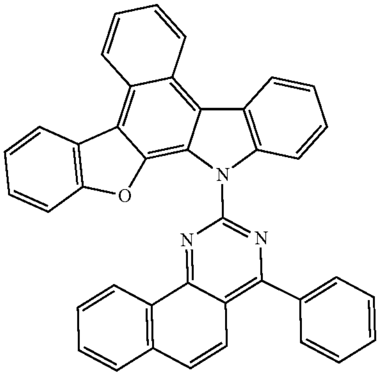
,
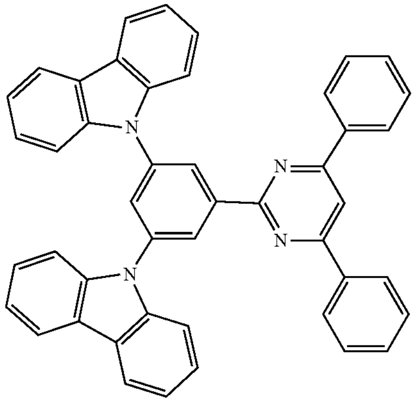
,
-continued
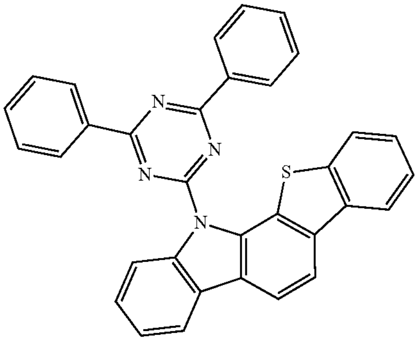
,
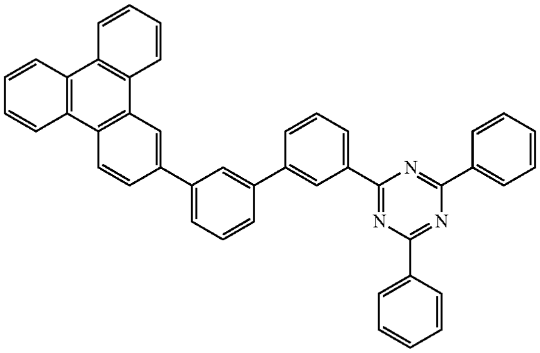
,
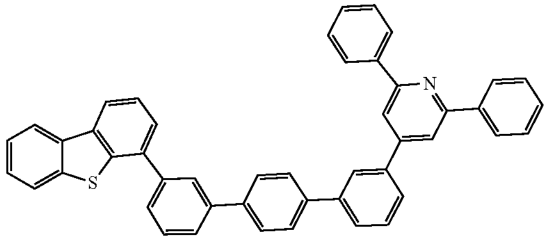
,
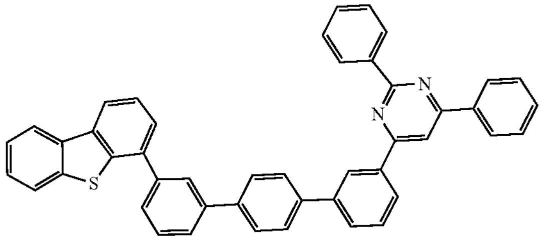
,
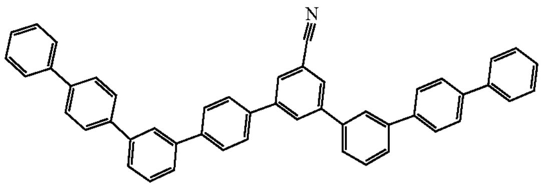
,
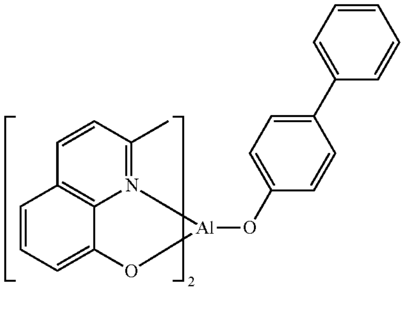
, -continued

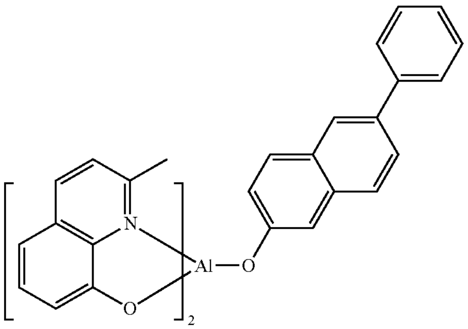

,

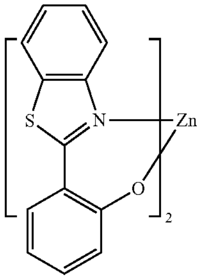

,

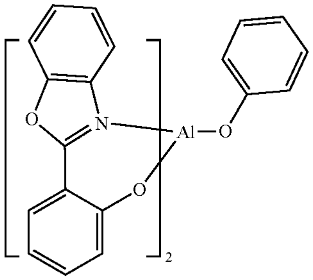

,

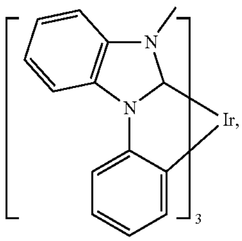

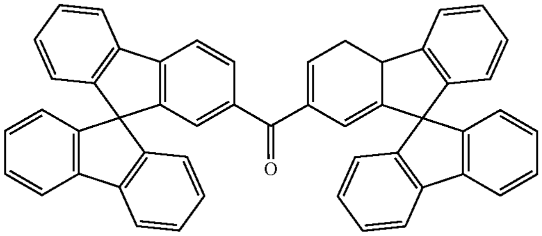

,

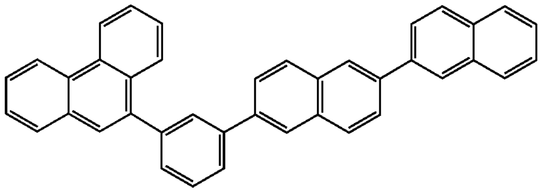

,

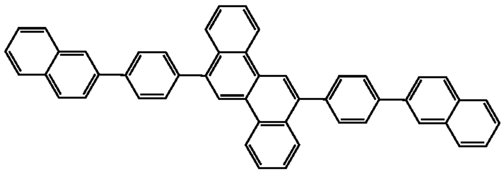

, and

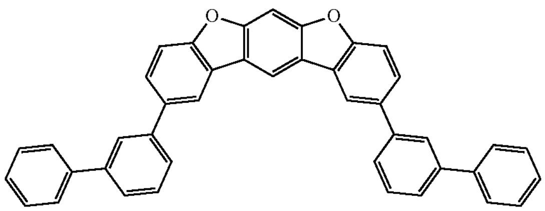

.

e) Additional Emitters:

One or more additional emitter dopants may be used in conjunction with the compound of the present disclosure. Examples of the additional emitter dopants are not particularly limited, and any compounds may be used as long as the compounds are typically used as emitter materials. Examples of suitable emitter materials include, but are not limited to, compounds which can produce emissions via phosphorescence, fluorescence, thermally activated delayed fluorescence, i.e., TADF (also referred to as E-type delayed fluorescence), triplet-triplet annihilation, or combinations of these processes.

Non-limiting examples of the emitter materials that may be used in an OLED in combination with materials disclosed herein are exemplified below together with references that disclose those materials: CN103694277, CN1696137, EB01238981, EP01239526, EP01961743, EP1239526, EP1244155, EP1642951, EP1647554, EP1841834, EP1841834B, EP2062907, EP2730583, JP2012074444, JP2013110263, JP4478555, KR1020090133652, KR20120032054, KR20130043460, TW201332980, U.S. Ser. No. 06/699,599, U.S. Ser. No. 06/916,554, US20010019782, US20020034656, US20030068526, US20030072964, US20030138657, US20050123788, US20050244673, US2005123791, US2005260449, US20060008670, US20060065890, US20060127696, US20060134459, US20060134462, US20060202194, US20060251923, US20070034863, US20070087321, US20070103060, US20070111026, US20070190359, US20070231600, US2007034863, US2007104979, US2007104980, US2007138437, US2007224450, US2007278936, US20080020237, US20080233410, US20080261076, US20080297033, US200805851, US2008161567, US2008210930, US20090039776, US20090108737, US20090115322, US20090179555, US2009085476, US2009104472, US20100090591, US20100148663, US20100244004, US20100295032, US2010102716, US2010105902, US2010244004, US2010270916, US20110057559, US20110108822, US20110204333, US2011215710, US2011227049, US2011285275, US2012292601, US20130146848, US2013033172, US2013165653, US2013181190, US2013334521, US20140246656, US2014103305, U.S. Pat. Nos. 6,303,238, 6,413,656, 6,653,654, 6,670,645, U.S. Pat. Nos. 6,687,266, 6,835,469, 6,921,915, 7,279,704, 7,332,232, 7,378,162, 7,534,505, 7,675,228, 7,728,137, 7,740,957, 7,759,489, 7,951,947, 8,067,099, 8,592,586, 8,871,361, WO06081973, WO06121811, WO07018067, WO07108362, WO07115970, WO07115981, WO08035571, WO2002015645, WO2003040257, WO2005019373, WO2006056418, WO2008054584, WO2008078800, WO2008096609, WO2008101842, WO2009000673, WO2009050281, WO2009100991, WO2010028151, WO2010054731, WO2010086089, WO2010118029, WO2011044988, WO2011051404, WO2011107491, WO2012020327, WO2012163471, WO2013094620, WO2013107487, WO2013174471, WO2014007565, WO2014008982, WO2014023377, WO2014024131, WO2014031977, WO2014038456, WO2014112450.

-continued
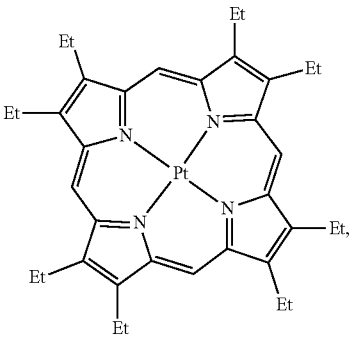
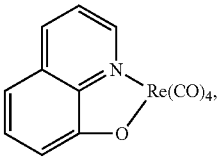
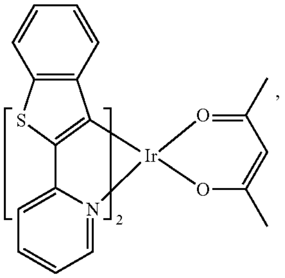
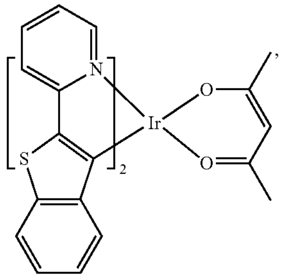
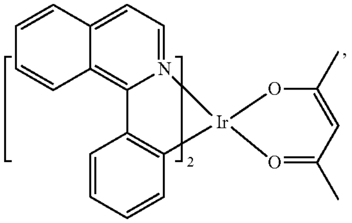
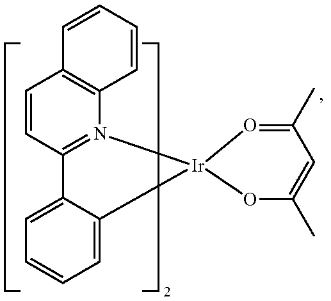
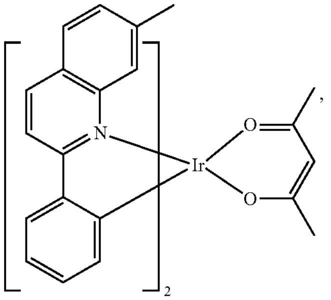
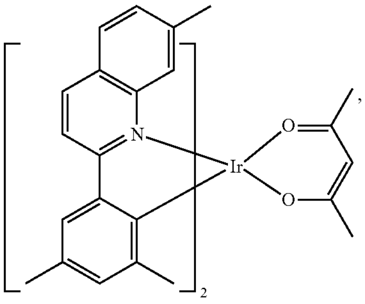
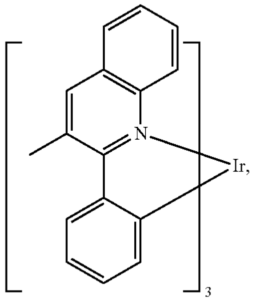
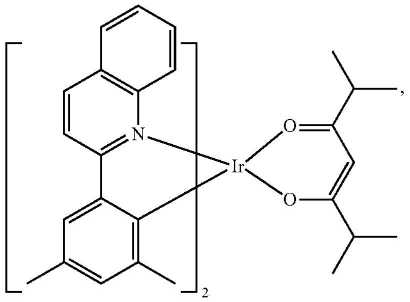
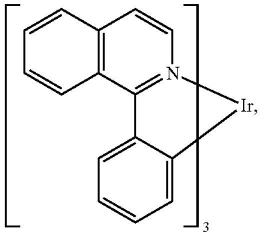
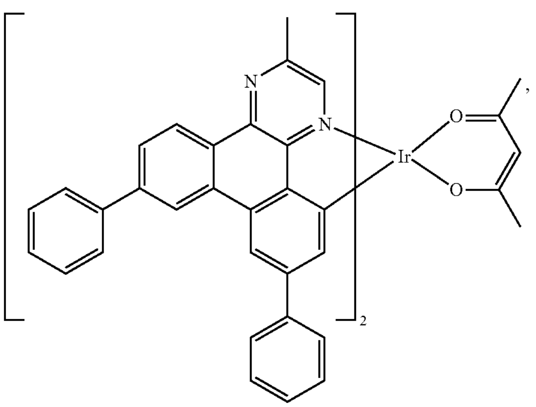

-continued
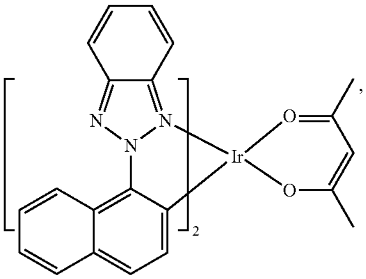
,
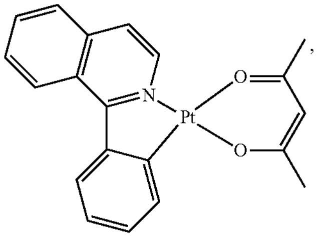
,
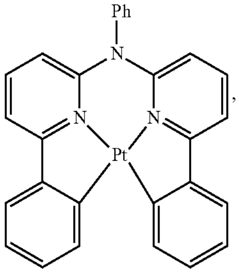
,
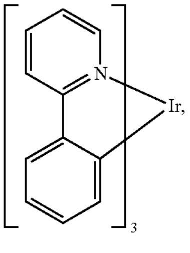
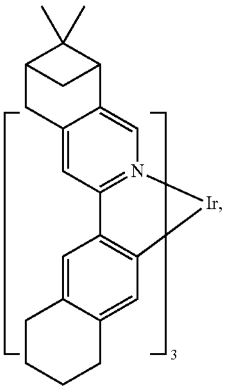
-continued
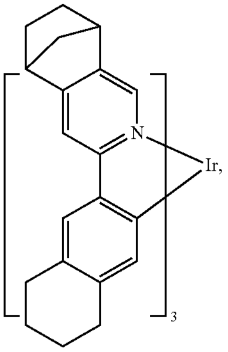
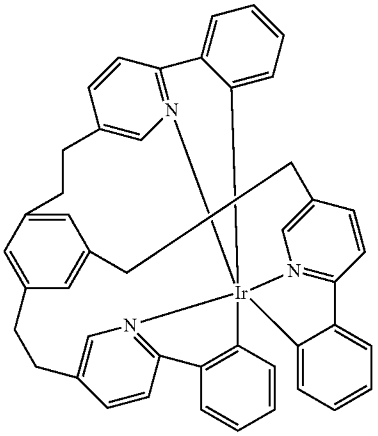
,
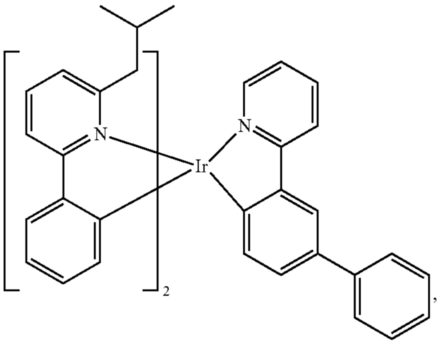
,
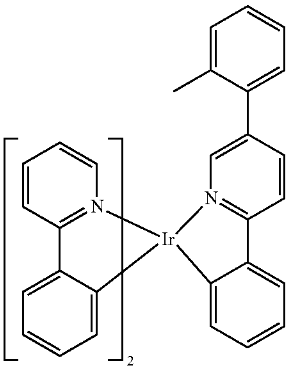
, -continued
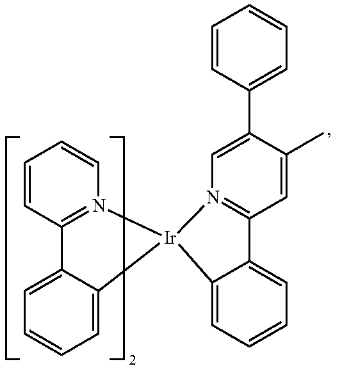
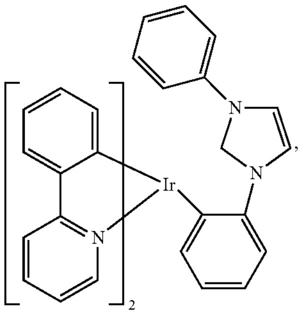
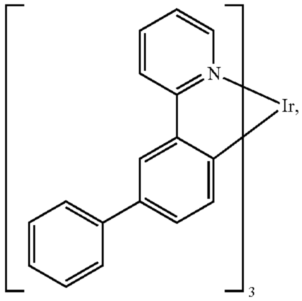
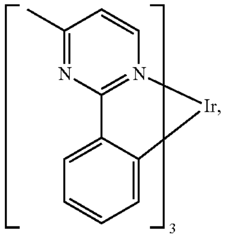
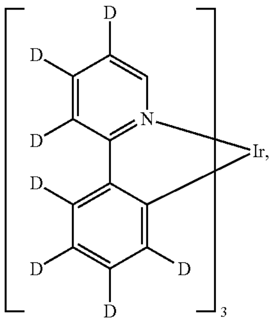
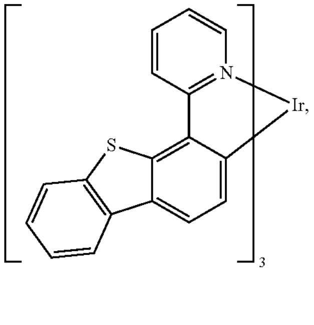
-continued
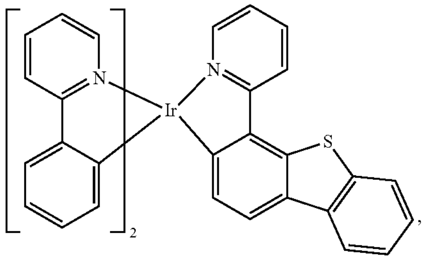
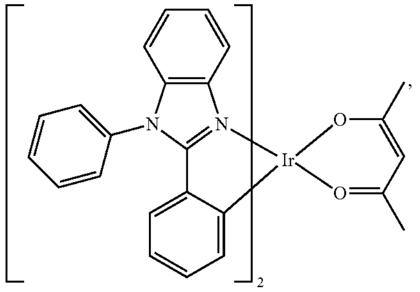
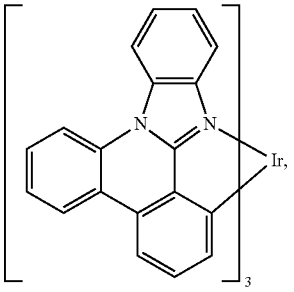
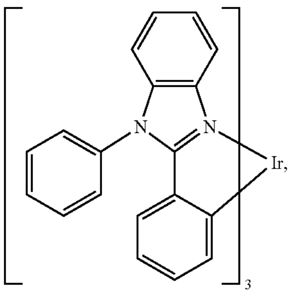
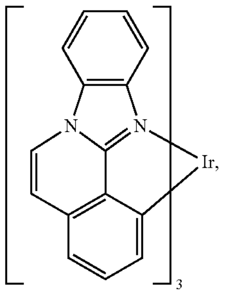
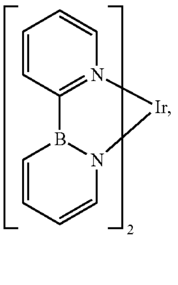
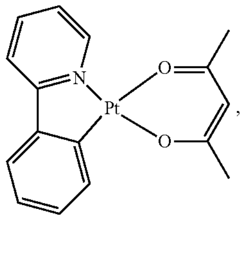

-continued
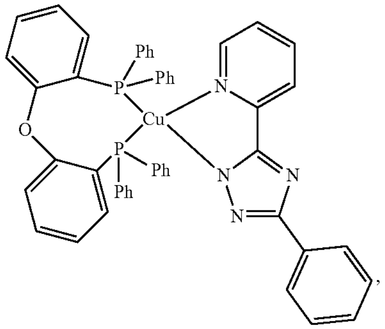
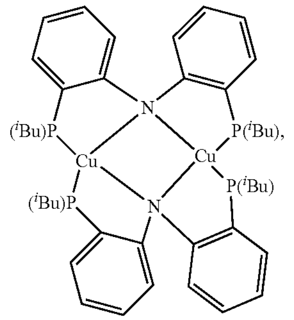
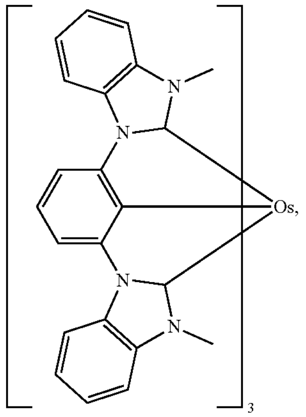
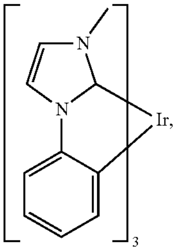
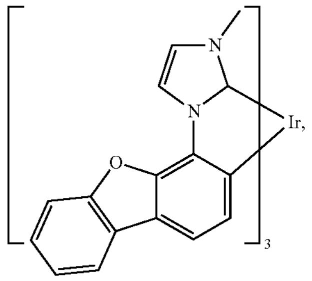
-continued
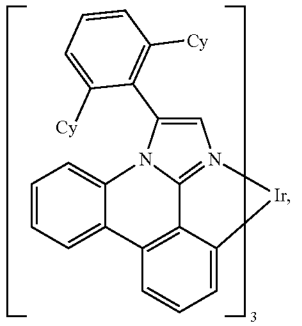
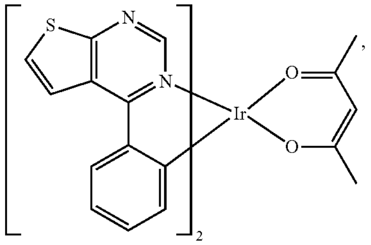
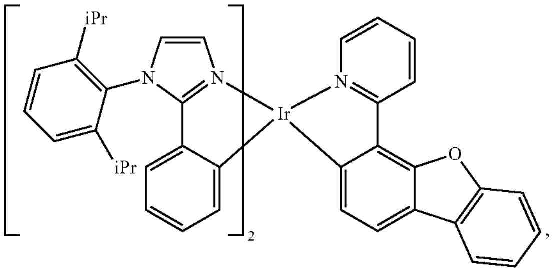
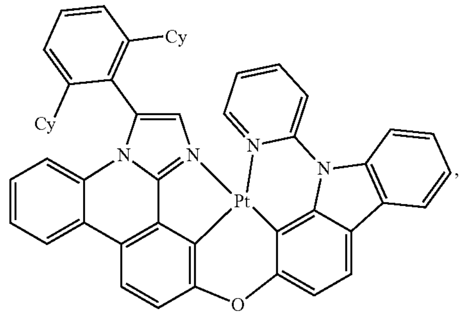
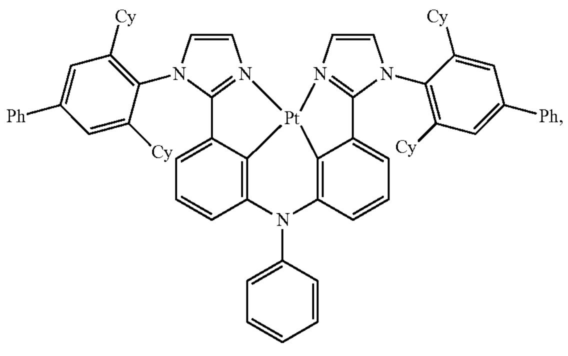

-continued
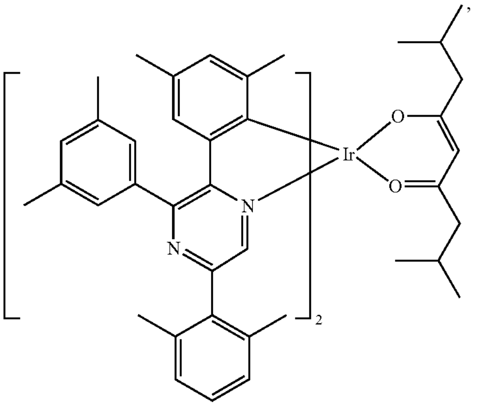
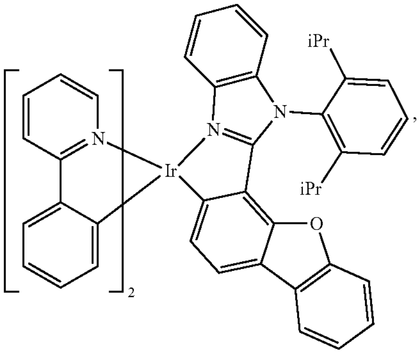
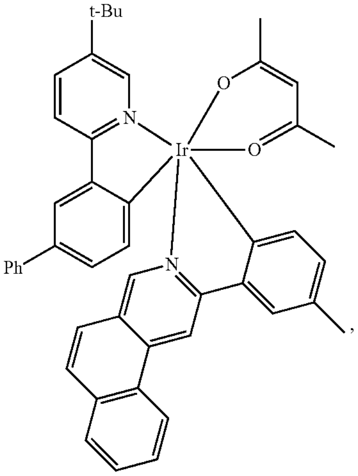
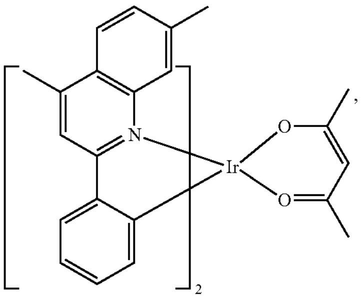
-continued
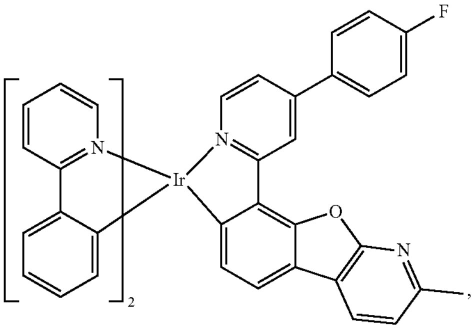
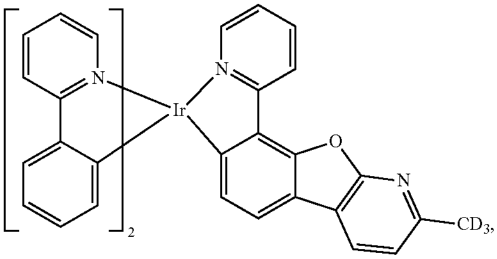
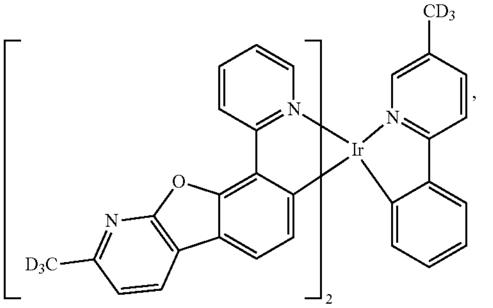
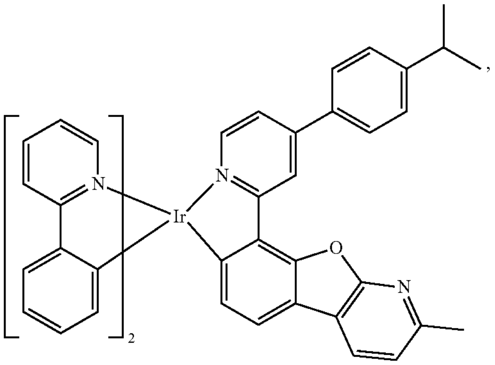
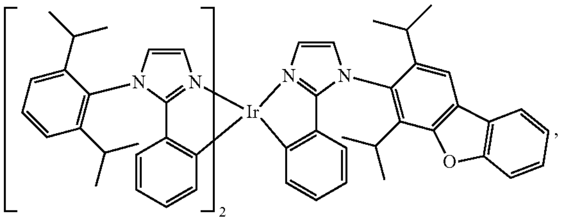

-continued
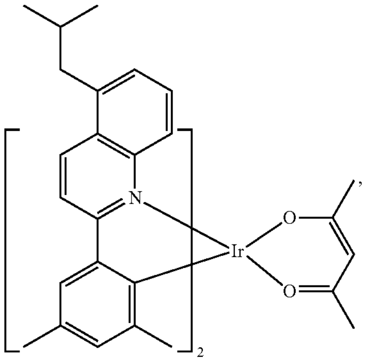
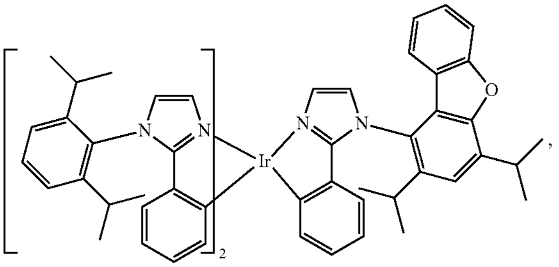
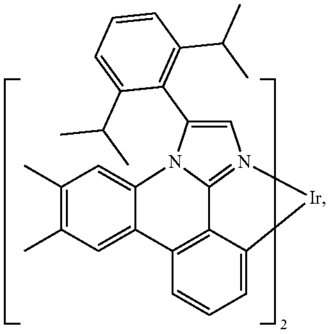
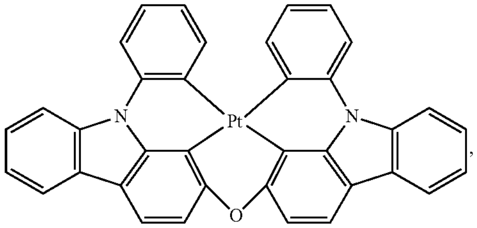
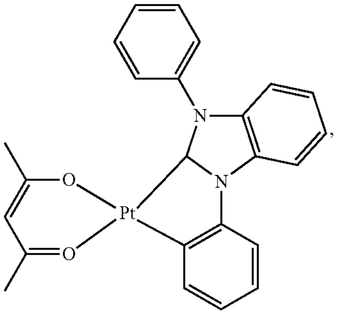
-continued
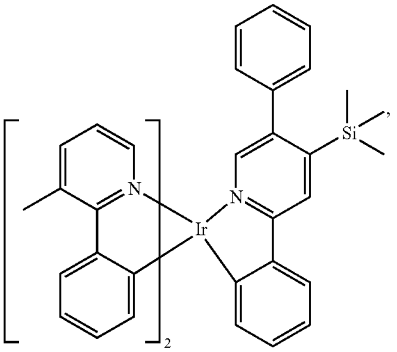
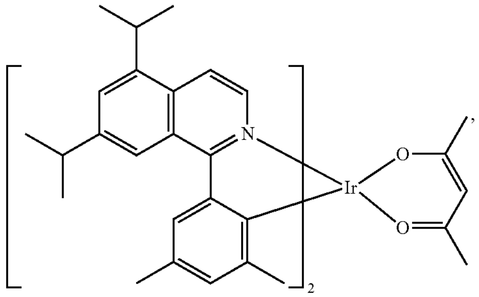
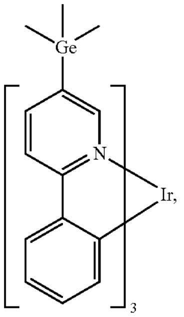
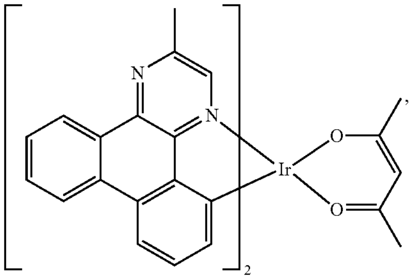
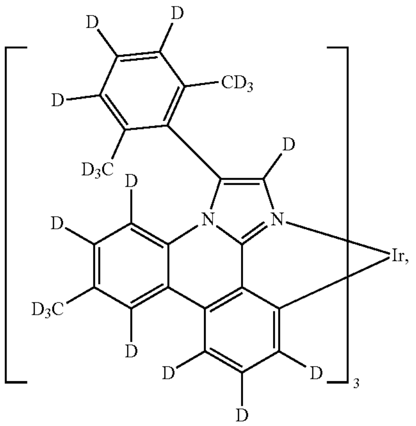

-continued
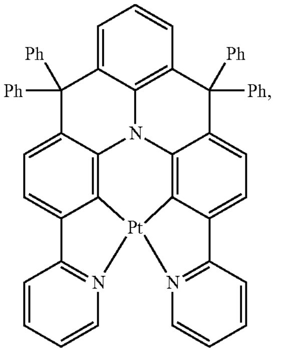
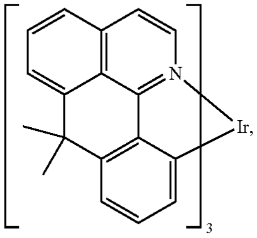
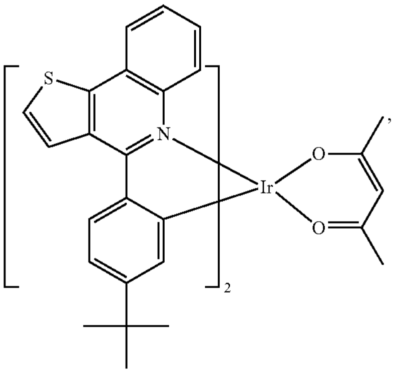
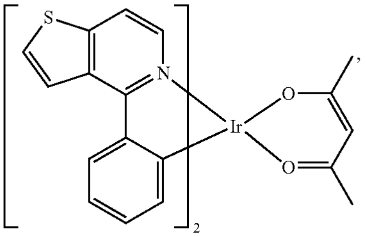
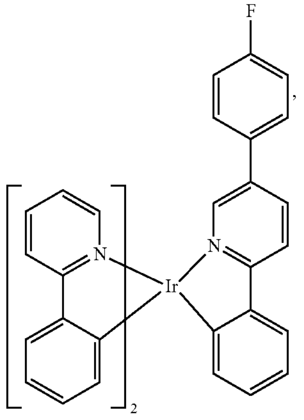
-continued
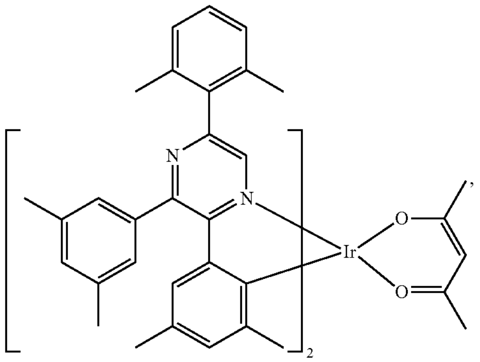
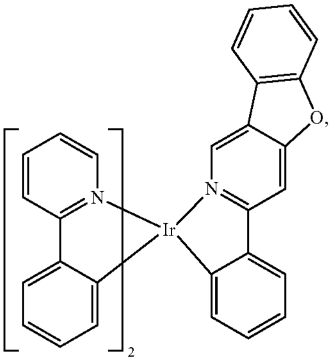
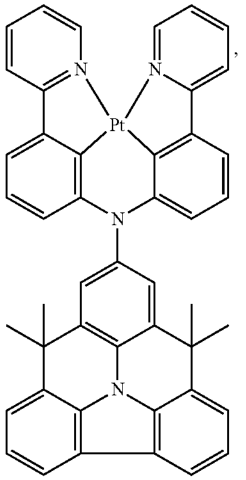
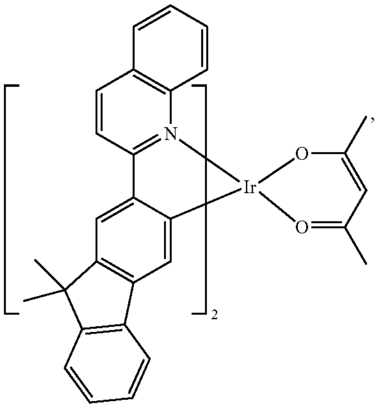

-continued
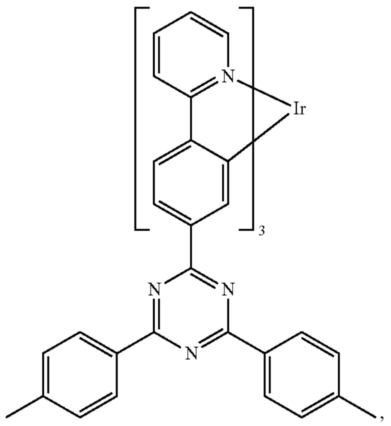
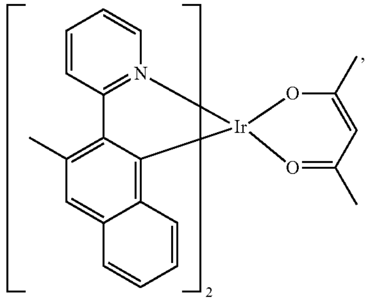
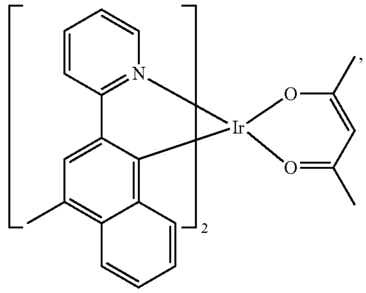
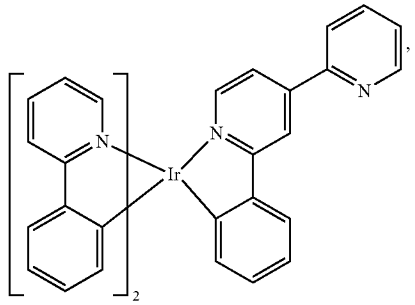
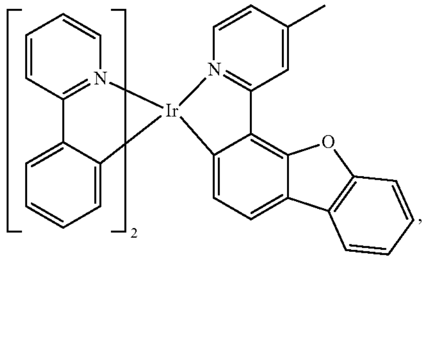
-continued
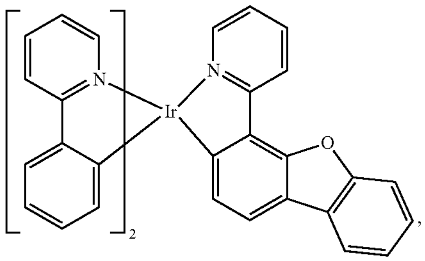
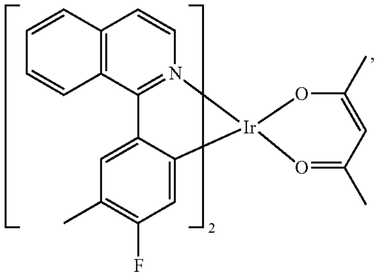
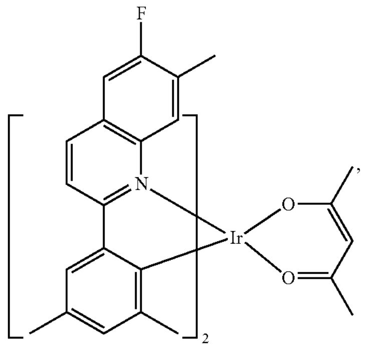
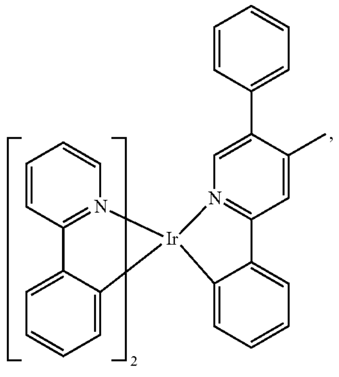
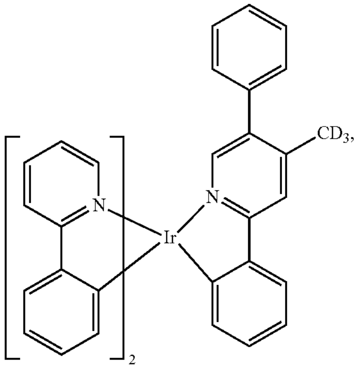

-continued
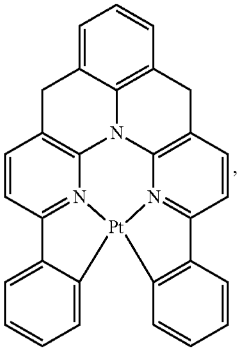
,
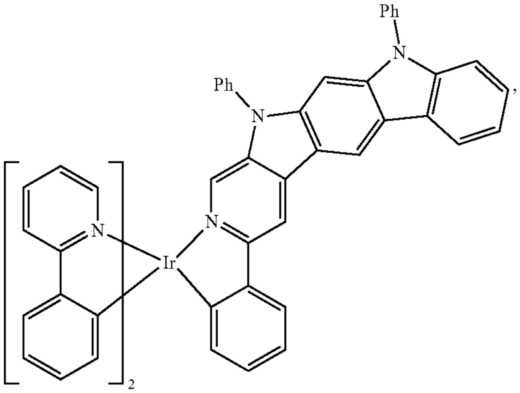
,
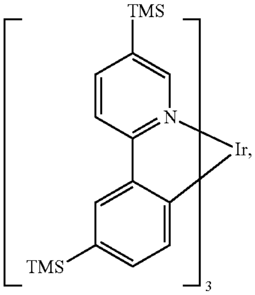
,
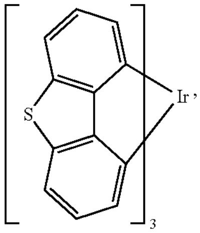
,
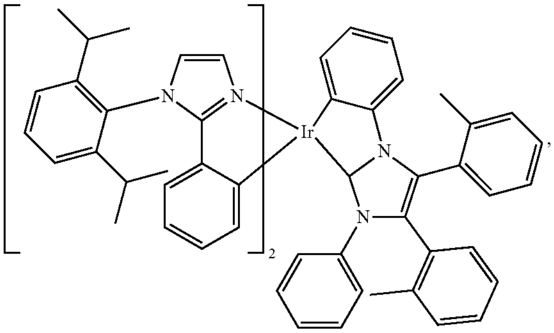
,
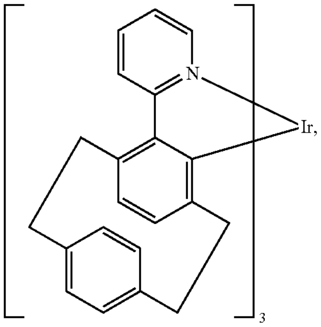
,
-continued
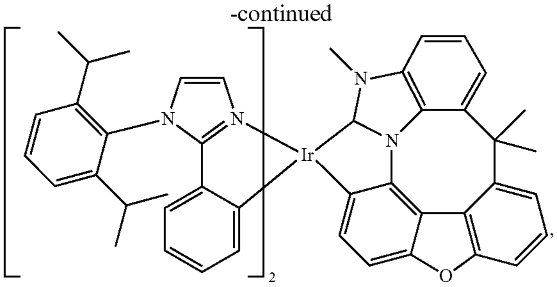
,
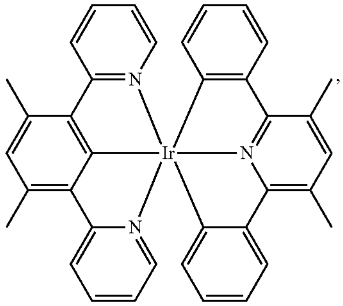
,
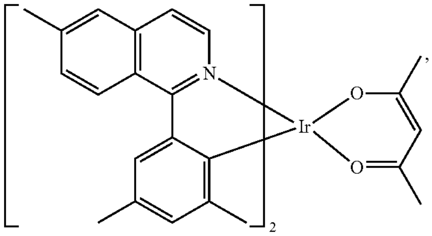
,
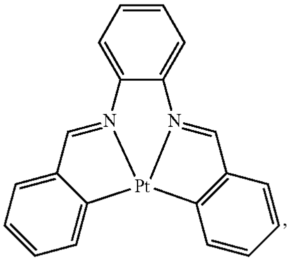
,
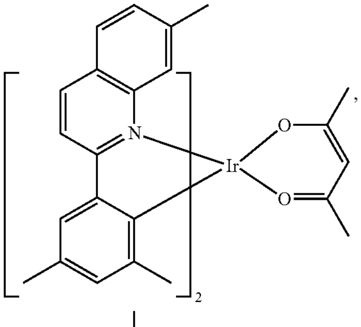
,
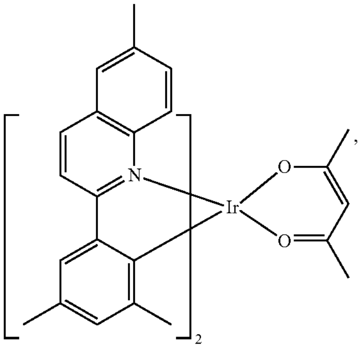
, -continued
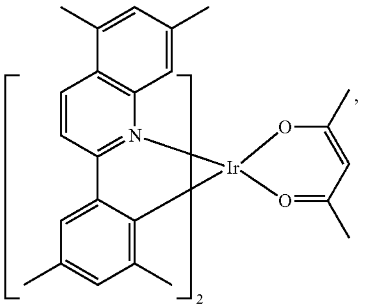
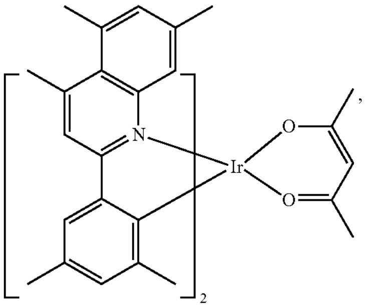
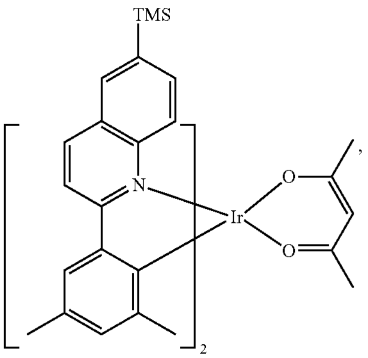
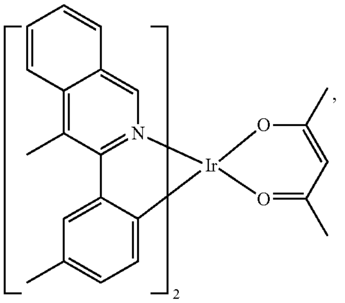
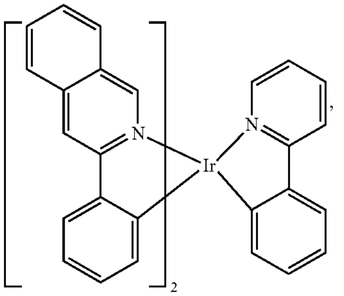
-continued
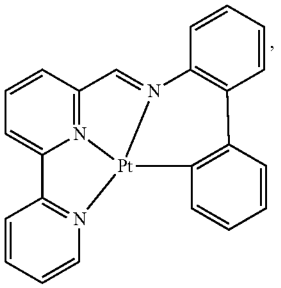
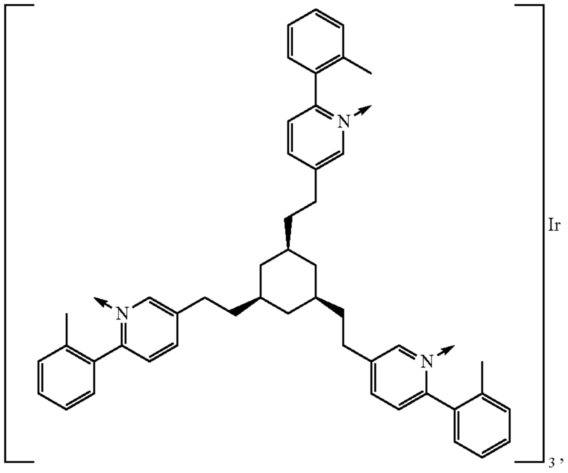
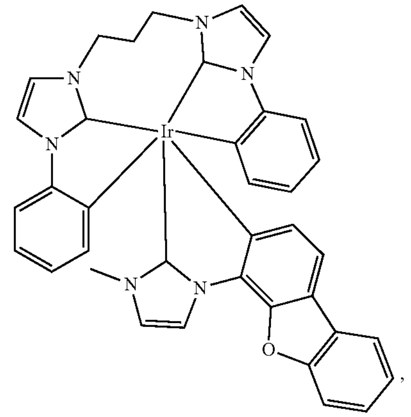
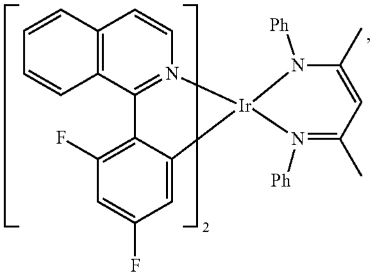

-continued
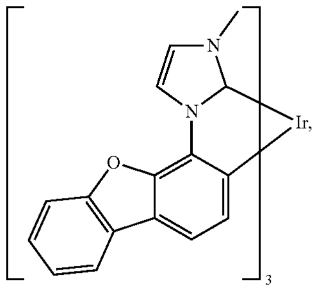
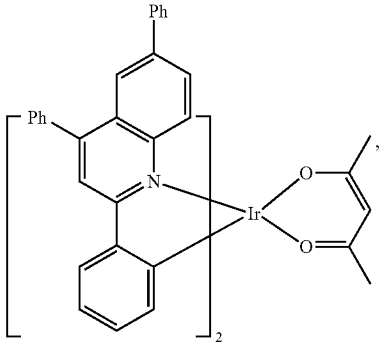
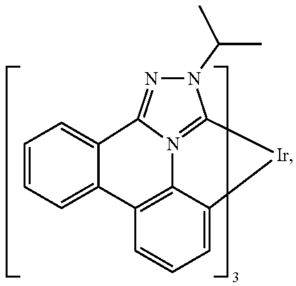
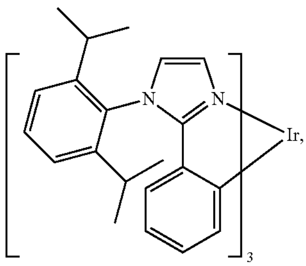
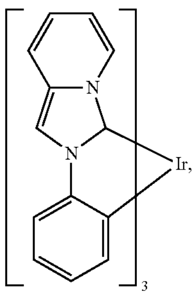
-continued
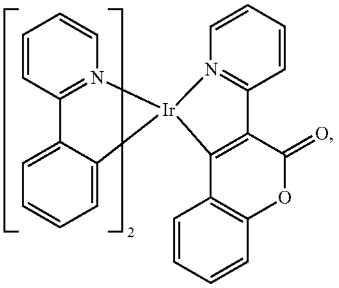
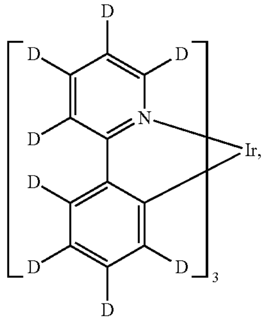
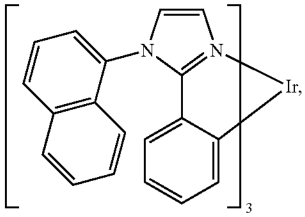
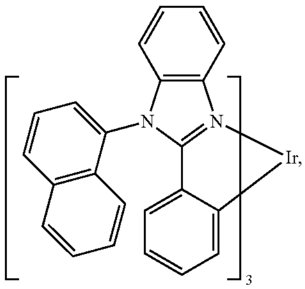
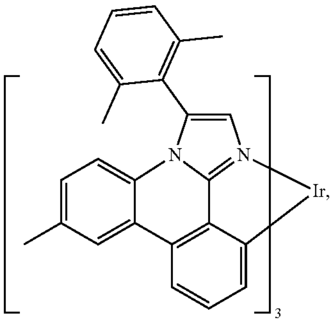
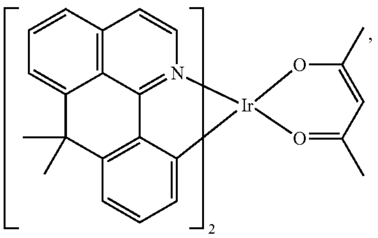

-continued

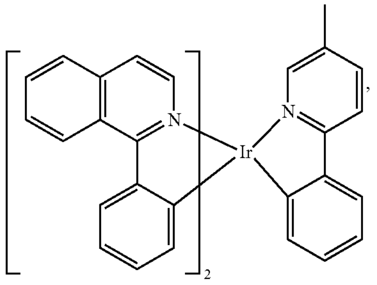

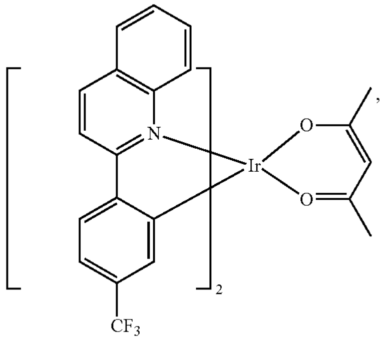

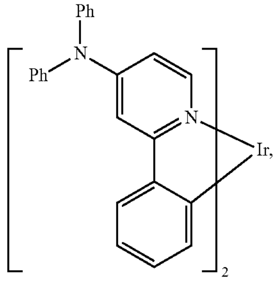

and

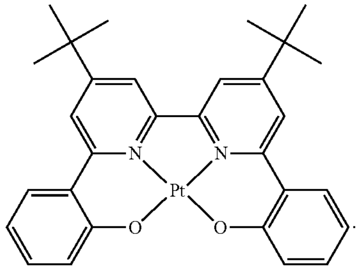

f) HBL:

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and/or higher triplet energy than the emitter closest to the HBL interface. In some embodiments, the HBL material has a lower HOMO (further from the vacuum level) and/or higher triplet energy than one or more of the hosts closest to the HBL interface.

In one aspect, compound used in HBL contains the same molecule or the same functional groups used as host described above.

In another aspect, compound used in HBL contains at least one of the following groups in the molecule:

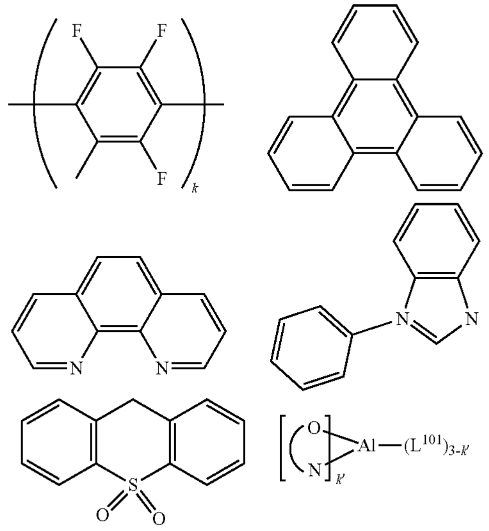

wherein k is an integer from 1 to 20; $L^{101}$ is another ligand, k' is an integer from 1 to 3.

g) ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

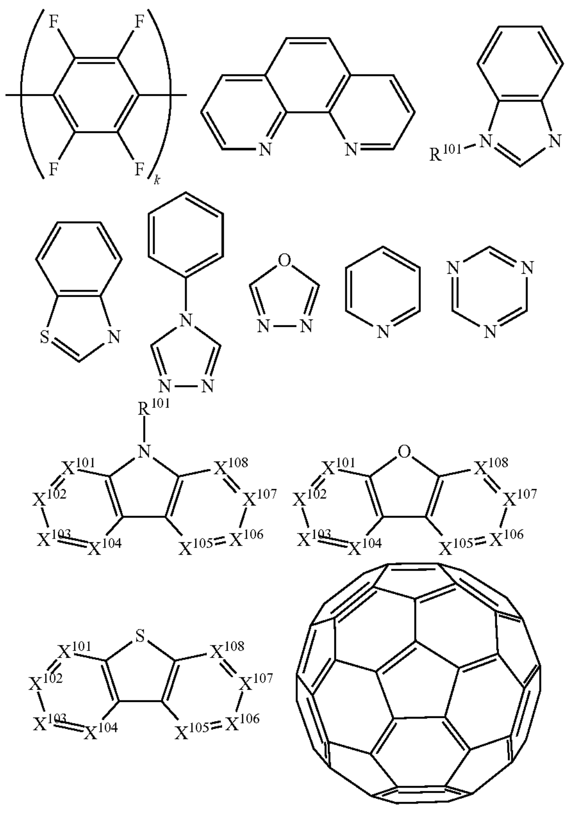

-continued

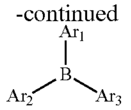

wherein $R^{101}$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

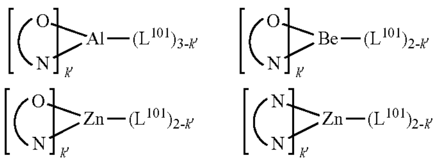

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

Non-limiting examples of the ETL materials that may be used in an OLED in combination with materials disclosed herein are exemplified below together with references that disclose those materials: CN103508940, EP01602648, EP01734038, EP01956007, JP2004-022334, JP2005149918, JP2005-268199, KR0117693, KR20130108183, US20040036077, US20070104977, US2007018155, US20090101870, US20090115316, US20090140637, US20090179554, US2009218940, US2010108990, US2011156017, US2011210320, US2012193612, US2012214993, US2014014925, US2014014927, US20140284580, U.S. Pat. Nos. 6,656,612, 8,415,031, WO2003060956, WO2007111263, WO2009148269, WO2010067894, WO2010072300, WO2011074770, WO2011105373, WO2013079217, WO2013145667, WO2013180376, WO2014104499, WO2014104535,

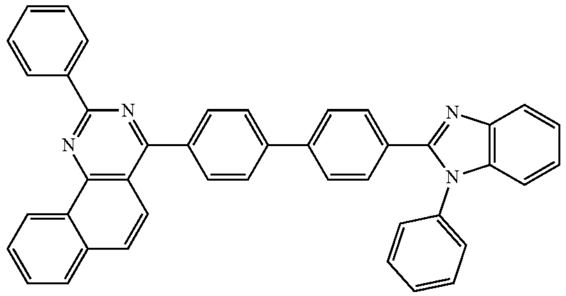

,

-continued

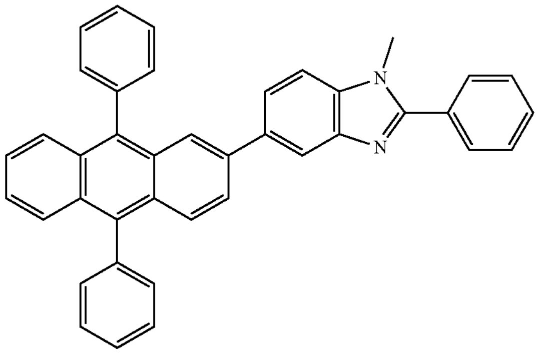

,

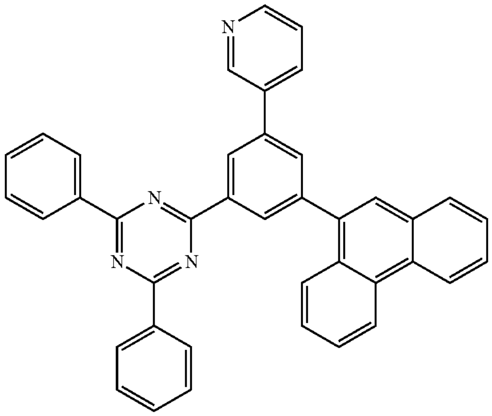

,

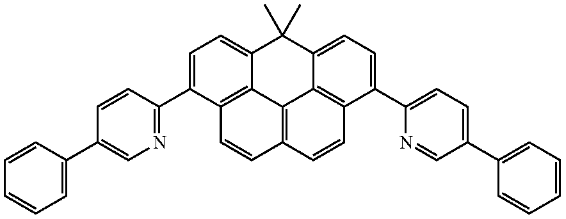

,

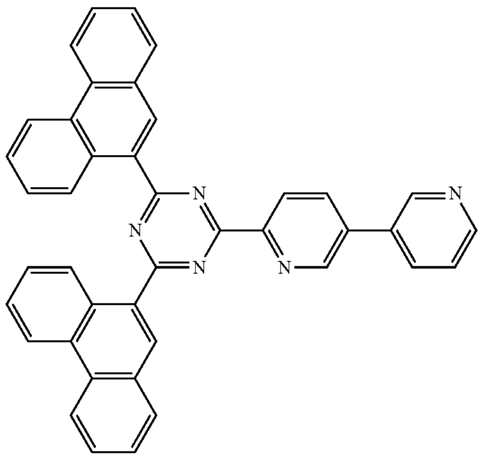

,

-continued
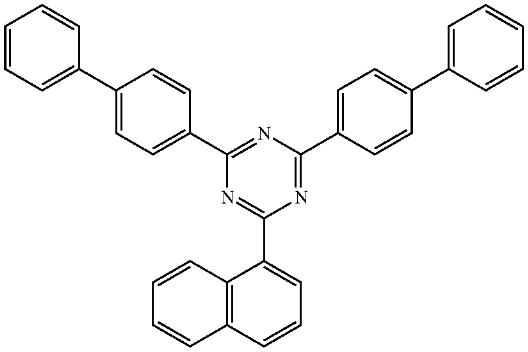
,
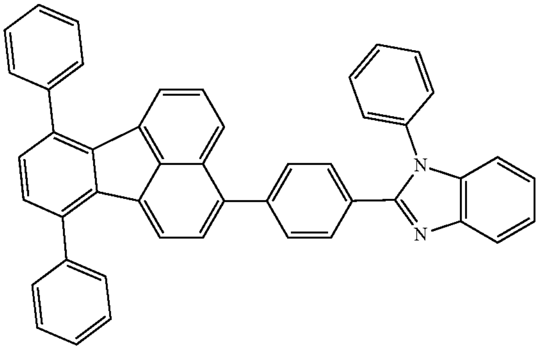
,
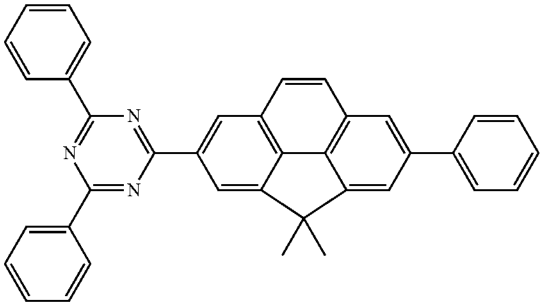
,
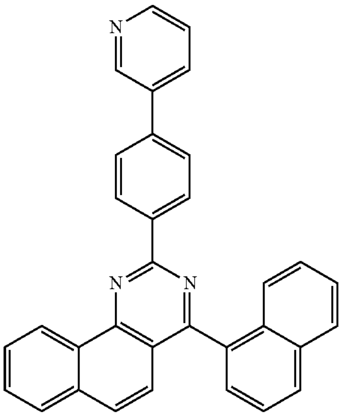
,
-continued
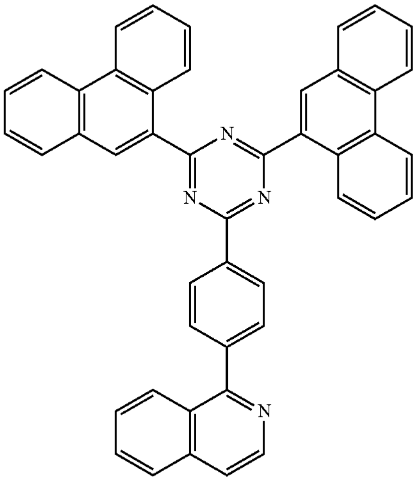
,
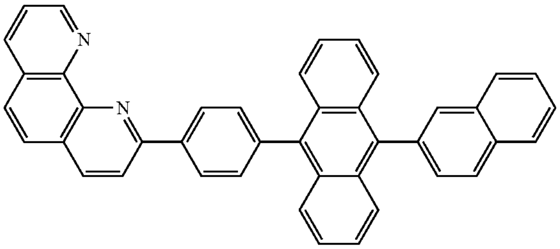
,
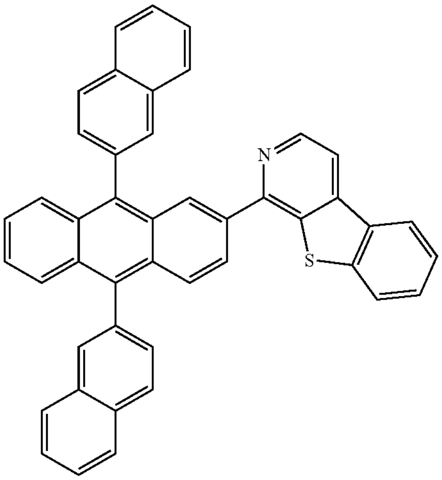
,
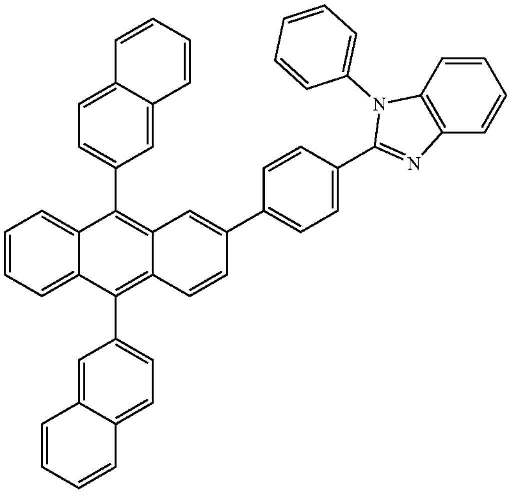
, -continued
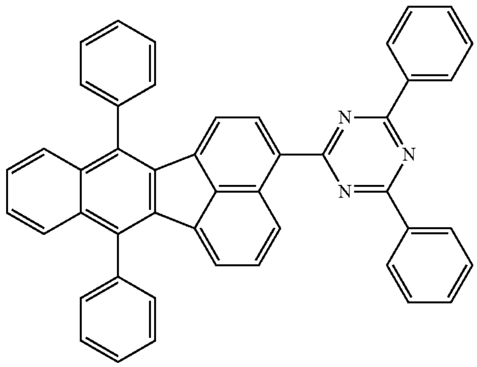
,
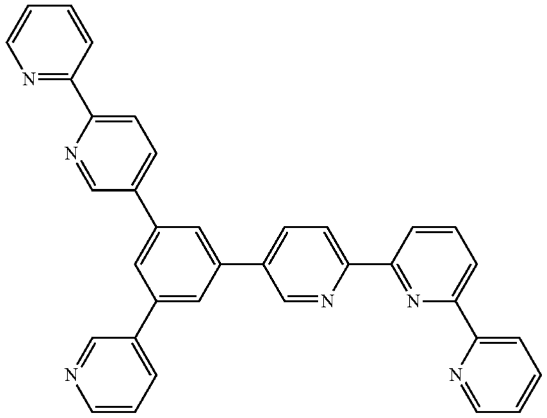
,
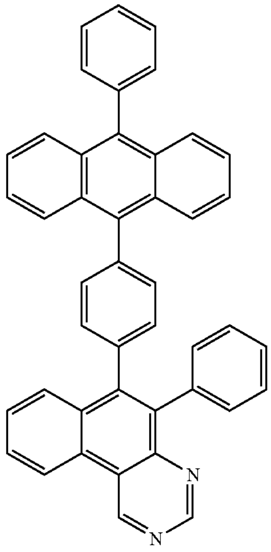
,
-continued
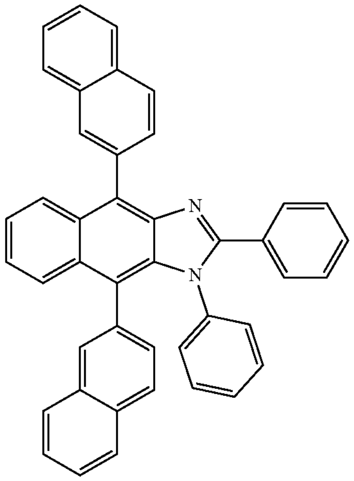
,
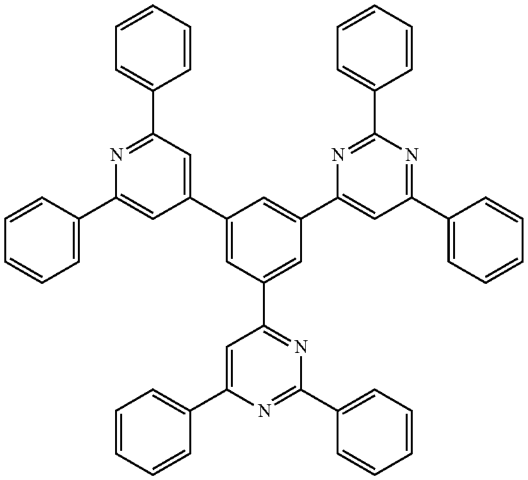
,
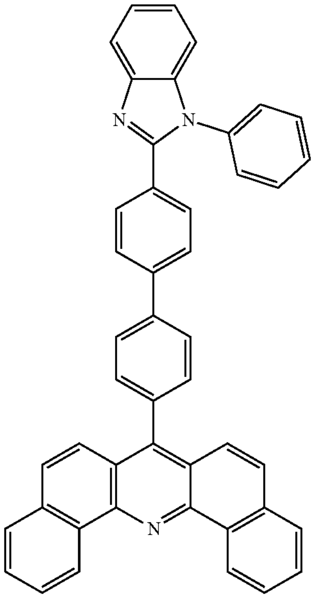
, -continued
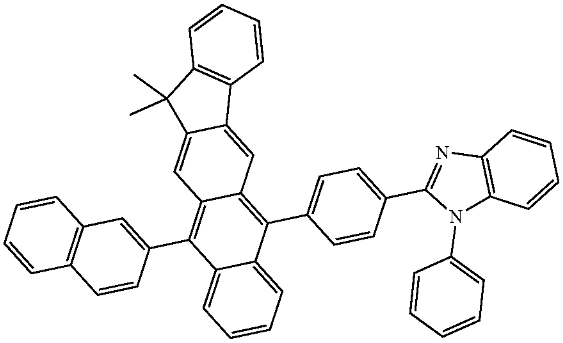
,
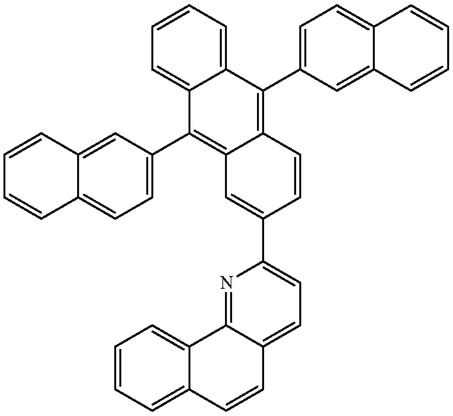
,
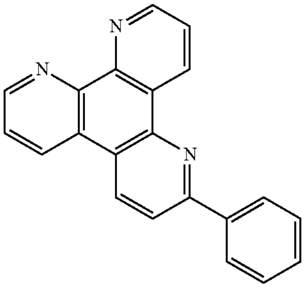
,
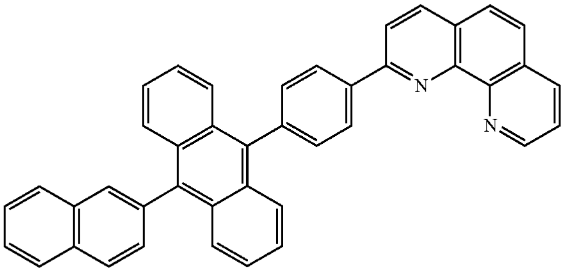
,
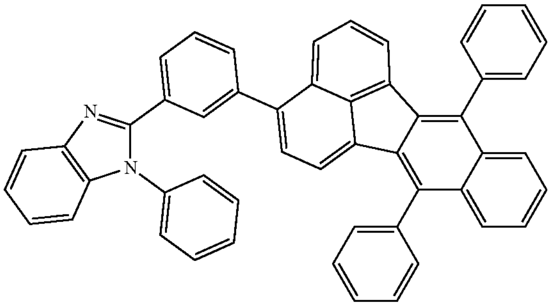
,
-continued
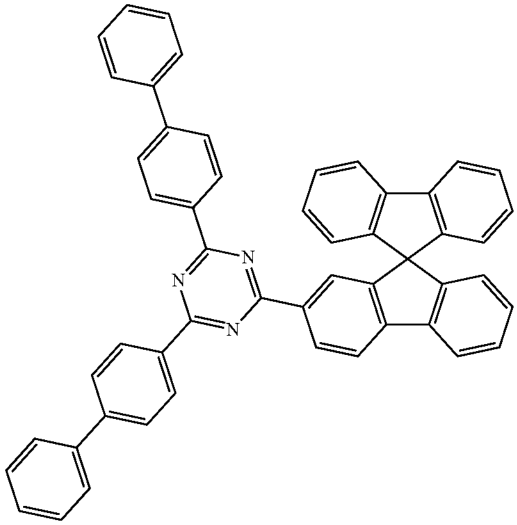
,
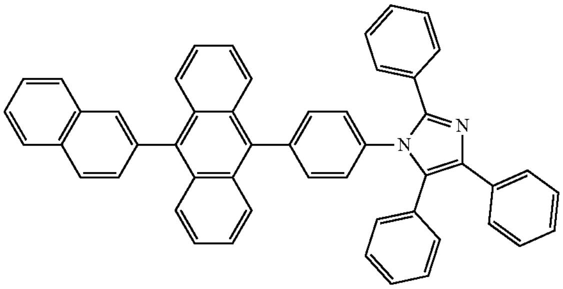
,
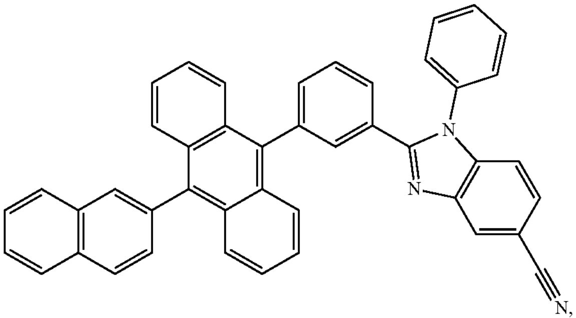
,
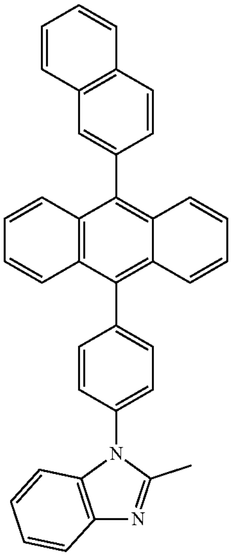
, -continued

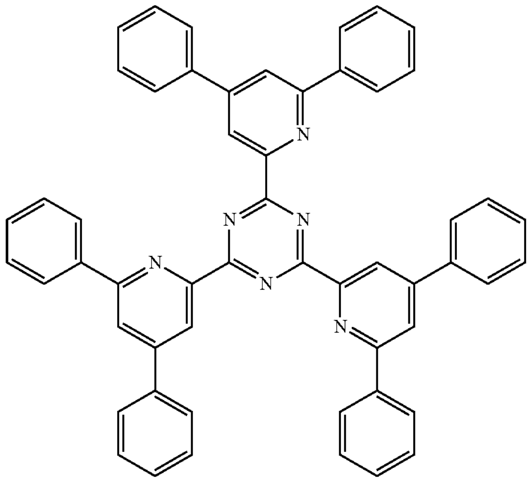

,

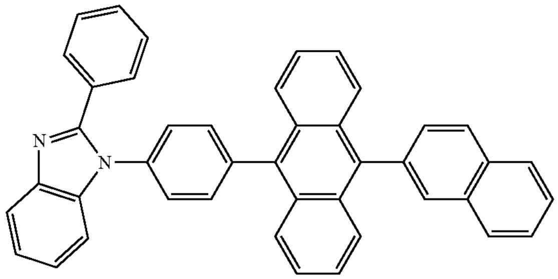

,

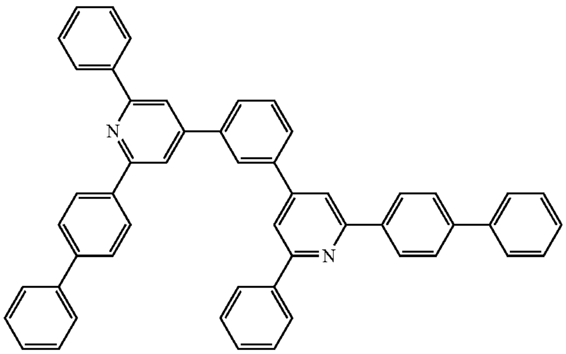

,

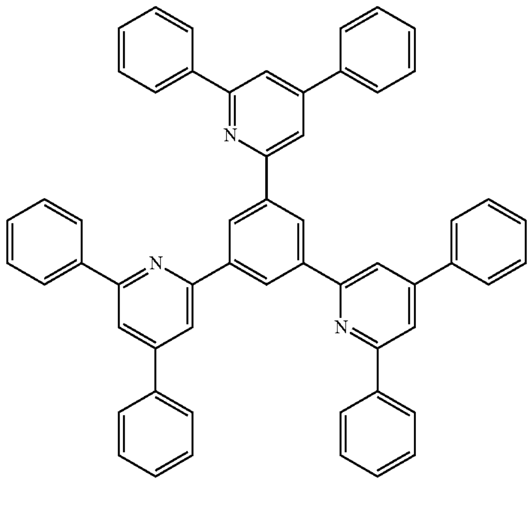

,

-continued

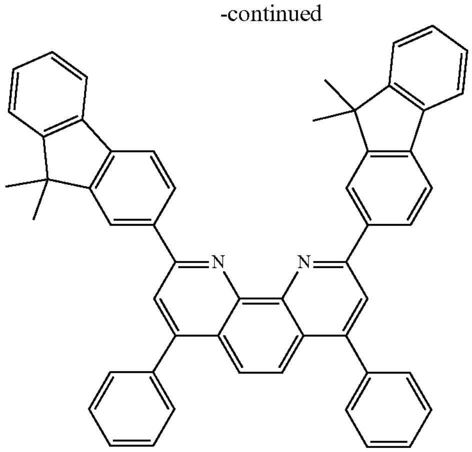

, and

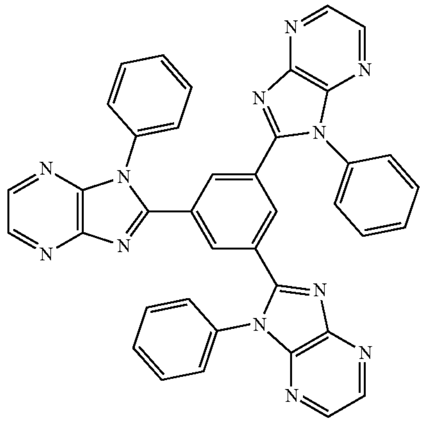

.

h) Charge Generation Layer (CGL)

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. The minimum amount of hydrogen of the compound being deuterated is selected from the group consisting of 30%, 40%, 50%, 60%, 70%, 80%, 90%, 95%, 99%, and 100%. Thus, any specifically listed substituent, such as, without limitation, methyl, phenyl, pyridyl, etc. may be undeuterated, partially deuterated, and fully deuterated versions thereof. Similarly, classes of substituents such as, without limitation, alkyl, aryl, cycloalkyl, heteroaryl, etc. also may be undeuterated, partially deuterated, and fully deuterated versions thereof.

It is understood that the various embodiments described herein are by way of example only and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

E. Experimental Data

SYNTHESIS EXAMPLES

Example 1—Synthesis of 2-([1,1'-biphenyl]-4-yl)-4-(3-(6,8-diphenyldibenzo[b,d]furan-4-yl)phenyl)-6-phenyl-1,3,5-triazine

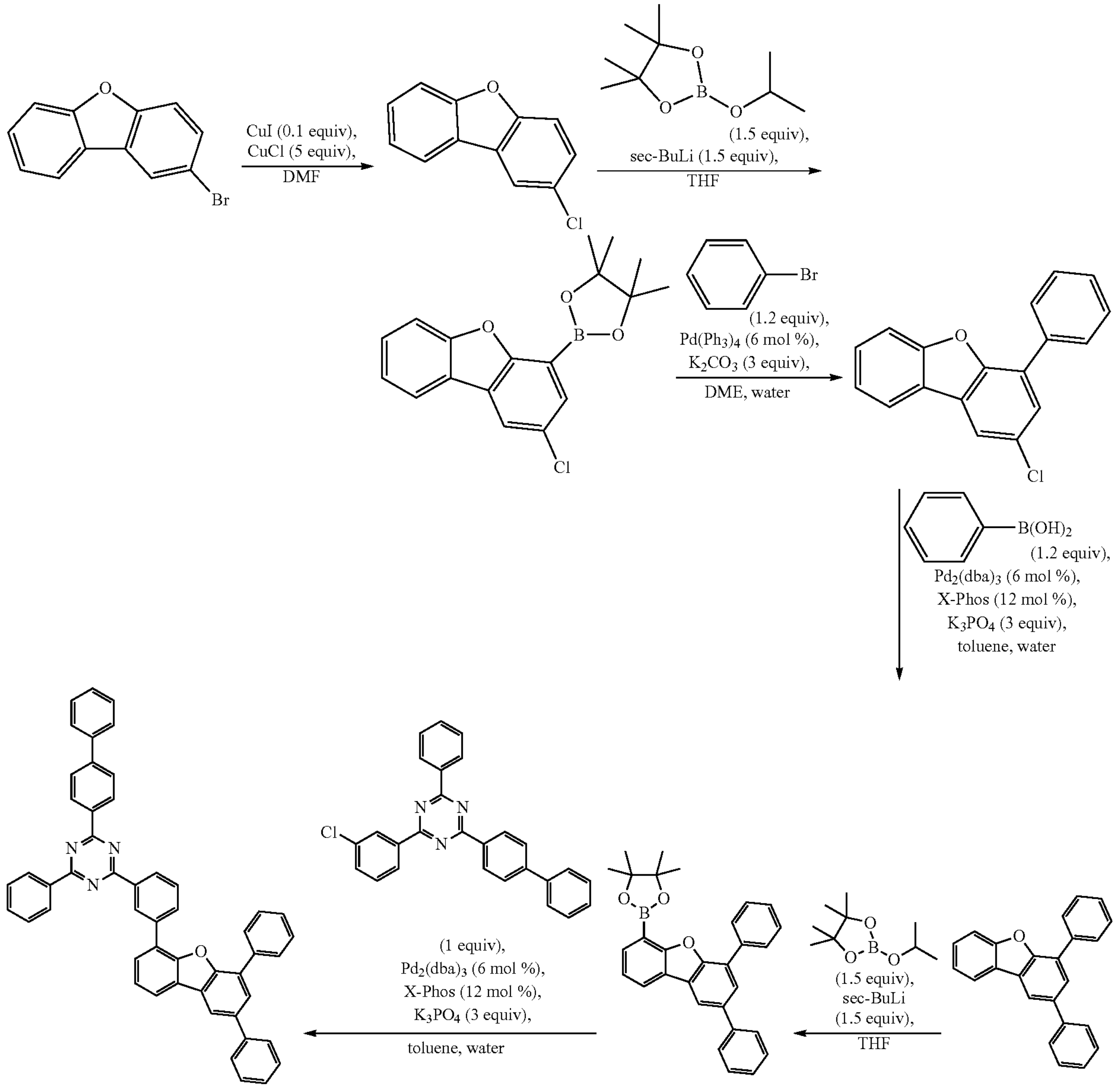

Step 1 2-chlorodibenzo[b,d]furan

A mixture of 2-bromodibenzo[b,d]furan (60 g, 243 mmol), copper(I) iodide (5.32 g, 27.9 mmol), copper(I) chloride (120 g, 1214 mmol), and DMF (971 ml) was placed in a 2 L flask equipped with a mechanical stirrer, thermowell and a water condenser with nitrogen inlet. The reaction mixture was heated to 130° C. and stirred overnight. The crude reaction mixture was cooled to room temperature and passed through a Celite (diatomaceous earth) plug (500 g) eluted with DCM (1 L). The filtrate was concentrated. The crude product was dissolved in heptane (500 ml) and filtered through a plug of silica gel eluted with heptane (16 L). Fractions containing product were combined and concentrated in vacuo to give 2-chlorodibenzo[b,d]furan (47.66 g) as a white solid.

Step 2 2-(2-chlorodibenzo[b,d]furan-4-yl)-4,4,5,5-tetramethyl-1,3,2-dioxaborolane 2-chlorodibenzo[b,d]furan (30 g, 148 mmol) in anhydrous THF (987 ml) was added to a 2 L flask equipped with a stir bar, a thermowell, a nitrogen inlet, and an addition funnel. The reaction mixture was flushed with nitrogen for 30 min and the reaction mixture was cooled to −70° C. sec-Butyllithium in cyclohexane (1.4 M, 159 ml, 222 mmol) was added dropwise, maintaining the internal temperature below −65° C. The reaction mixture was stirred for 30 min at −70° C. and a solution of 2-isopropoxy-4,4,5,5-tetramethyl-1,3,2-dioxaborolane (45.3 ml, 222 mmol) in anhydrous THF (40 ml) was added dropwise. The reaction mixture was left in the dry ice/acetone bath and slowly allowed to warm to room temperature overnight. The reaction mixture was quenched with water (1 L) and the aqueous layer was extracted with EtOAc (2×500 ml). The combined organic extract was dried over anhydrous sodium sulfate, filtered, and concentrated in vacuo. The crude material was dissolved in 20% DCM-heptane (1 L) and filtered through a plug of silica gel (1 kg) eluted with 20% DCM-heptane until all starting material was removed then eluted with 100% DCM to elute the product (total solvent used 30 L). Fractions containing the product were combined and concentrated in vacuo to give 2-(2-chlorodibenzo[b,d]furan-4-yl)-4,4,5,5-tetramethyl-1,3,2-dioxaborolane (18.51 g) as a white solid.

Step 3 2-chloro-4-phenyldibenzo[b,d]furan 2-(2-chlorodibenzo[b,d]furan-4-yl)-4,4,5,5-tetramethyl-1,3,2-dioxaborolane (18.51 g, 56.3 mmol), bromobenzene (7.08 ml, 67.6 mmol), potassium carbonate (15.57 g, 113 mmol), DME (135 ml), and water (90 ml) were added to a 500 ml flask equipped with a stir bar, a thermowell, and a water condenser with a nitrogen inlet. The reaction mixture was purged with nitrogen for 30 min and $Pd(Ph_3)_4$ (3.91 g, 3.38 mmol) was added. The reaction mixture was heated to 78° C. and stirred overnight. The reaction mixture was cooled to room temperature and extracted with DCM (3×100 ml). The combined organic extracts were dried over anhydrous sodium sulfate, filtered, and concentrated in vacuo. The crude material was dissolved in heptane (250 ml) and filtered through a silica gel (500 g) plug eluted with heptane (12 L). Fractions containing product were combined and concentrated to give 2-chloro-4-phenyldibenzo[b,d]furan (15.12 g).

Step 4 2,4-diphenyldibenzo[b,d]furan 2-chloro-4-phenyldibenzo[b,d]furan (15.12 g, 54.2 mmol), phenylboronic acid (7.94 g, 65.1 mmol), potassium phosphate (34.5 g, 163 mmol), dicyclohexyl(2',4',6'-triisopropyl-[1,1'-biphenyl]-2-yl)phosphane (3.10 g, 6.51 mmol), toluene (274 ml), and water (27.4 ml) were added to a 1 L flask equipped with a thermowell, a water condenser with a nitrogen adapter, and a stir bar. The reaction mixture was purged with nitrogen for 30 min and $Pd_2(dba)_3$ (2.98 g, 3.25 mmol) was added. The reaction mixture was heated to 91° C. and stirred overnight. The reaction mixture was cooled to room temperature and the aqueous layer was separated from the organic layer. The organic layer was concentrated in vacuo. The crude material was dissolved in cyclohexane (500 ml) and filtered through a plug of silica gel (800 g) eluted with DCM-cyclohexane (0-2% DCM, total solvent 16 L). Fractions containing product were combined and concentrated to give 2,4-diphenyldibenzo[b,d]furan (17.25 g).

Step 5 2-(6,8-diphenyldibenzo[b,d]furan-4-yl)-4,4,5,5-tetramethyl-1,3,2-dioxaborolane (Int 5)

A solution of 2,4-diphenyldibenzo[b,d]furan (9.62 g, 30.0 mmol) in anhydrous THF (200 ml) was placed in a 500 ml flask equipped with a stir bar, a thermowell, a nitrogen adapter, and an addition funnel. The reaction mixture was purged with nitrogen for 30 min and the reaction mixture was cooled to −70° C. sec-Butyllithium in cyclohexane (1.4 M, 37.5 ml, 52.5 mmol) was added dropwise (internal temp below −65° C.). The reaction mixture was stirred at −70° C. for 1 hour and a solution of 2-isopropoxy-4,4,5,5-tetramethyl-1,3,2-dioxaborolane (10.72 ml, 52.5 mmol) in anhydrous THF (12 ml) was added dropwise (internal temp below −65° C.). The reaction mixture was left in the dry ice/acetone bath and slowly allowed to warm to room temperature overnight. The crude reaction mixture was quenched with water (200 ml). The organic layer was separated and the aqueous layer was extracted with EtOAc (3×50 ml). The combined organic layers were dried over anhydrous sodium sulfate, filtered, and concentrated in vacuo to give 2-(6,8-diphenyldibenzo[b,d]furan-4-yl)-4,4,5,5-tetramethyl-1,3,2-dioxaborolane (17.32 g) as a white solid.

Step 6 2-([1,1'-biphenyl]-4-yl)-4-(3-(6,8-diphenyldibenzo[b,d]furan-4-yl)phenyl)-6-phenyl-1,3,5-triazine 2-(6,8-diphenyldibenzo[b,d]furan-4-yl)-4,4,5,5-tetramethyl-1,3,2-dioxaborolane (12.12 g, 27.1 mmol), 2-([1,1'-biphenyl]-4-yl)-4-(3-chlorophenyl)-6-phenyl-1,3,5-triazine (9.50 g, 22.62 mmol), dicyclohexyl(2',4',6'-triisopropyl-[1,1'-biphenyl]-2-yl)phosphane (1.294 g, 2.71 mmol), potassium phosphate (14.41 g, 67.9 mmol), toluene (150 ml), and water (15.00 ml) were placed in a 500 ml flask equipped with a stir bar, a thermowell, and a water condenser with nitrogen inlet. The reaction mixture was flushed with nitrogen and $Pd_2(dba)_3$ (1.243 g, 1.357 mmol) was added. The reaction mixture was heated to reflux and stirred overnight. The reaction mixture was cooled to room temperature and then placed in an ice bath to precipitate the product. The resulting solid was collected by filtration and washed with water (500 ml) and MeOH (500 ml). The solid triturated with acetone (1 L). The solid was dissolved in DCM (500 ml) and filtered through a mixed plug of silica gel and basic alumina eluted with 50% DCM-heptane (10 L). Fractions containing product were combined and concentrated in vacuo. MeOH (1 L) was added to the solid and it was triturated overnight. The solid was filtered and mixed with EtOAc (700 ml). The suspension was heated to 62° C. and stirred for 5 hours. The suspension was filtered hot. The resulting solid was dissolved in DCM (500 ml). MeOH was slowly added until the solution became murky and was stirred overnight. The solid was collected via suction filtration to give 2-([1,1'-biphenyl]-4-yl)-4-(3-(6,8-diphenyldibenzo[b,d]furan-4-yl)phenyl)-6-phenyl-1,3,5-triazine (6.58 g) as a white solid.

Example 2 Synthesis of 2-([1,1'-biphenyl]-4-yl)-4-(3-(6,8-diphenyldibenzo[b,d]thiophen-4-yl)phenyl)-6-phenyl-1,3,5-triazine

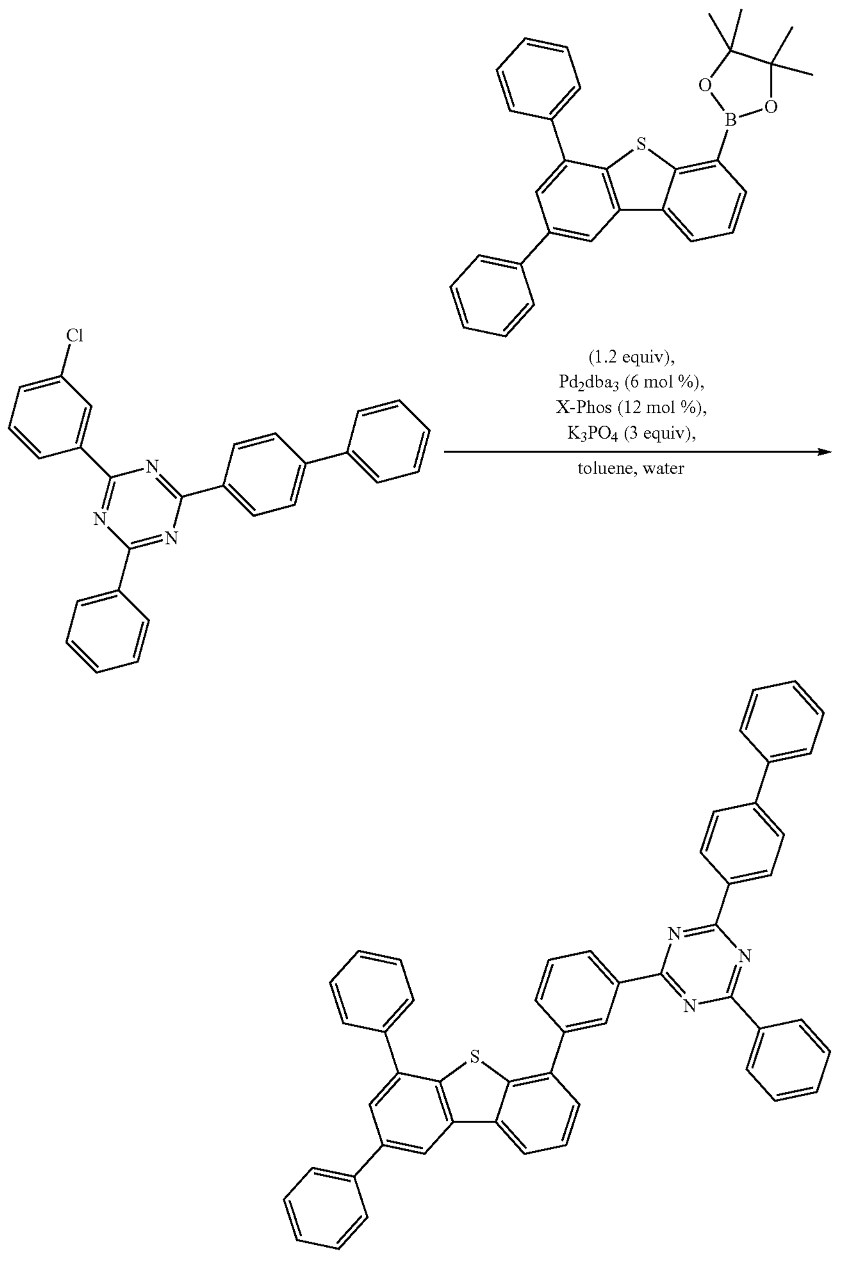 [SMILES: Clc1cccc(-c2nc(-c3ccccc3)nc(-c3ccc(-c4ccccc4)cc3)n2)c1 ; CC1(C)OB(c2cccc3c2sc2c(-c4ccccc4)cc(-c4ccccc4)cc23)OC1(C)C ; c1ccc(-c2ccc(-c3nc(-c4ccccc4)nc(-c4cccc(-c5cccc6c5sc5c(-c7ccccc7)cc(-c7ccccc7)cc56)c4)n3)cc2)cc1]

2-([1,1'-biphenyl]-4-yl)-4-(3-chlorophenyl)-6-phenyl-1,3,5-triazine (12.75 g, 30.4 mmol), diphenyldibenzo[b,d]thiophen-4-yl)-4,4,5,5-tetramethyl-1,3,2-dioxaborolane (16.85 g, 36.4 mmol), toluene (153 ml), and water (15.34 ml) were added to a 1 L flask under nitrogen, equipped with a water condenser, a magnetic stirrer, and a thermowell. The mixture was degassed by evacuating and backfilling with nitrogen 5 times. Then, dicyclohexyl(2',4',6'-triisopropyl-[1,1'-biphenyl]-2-yl)phosphane (1.737 g, 3.64 mmol) and $Pd_2dba_3$ (1.668 g, 1.822 mmol) were added. The mixture was further degassed by evacuating and backfilling with nitrogen 3 times then heated at reflux overnight. The reaction mixture was filtered, and the solids were retained. The filtrate was separated, and the aqueous phase was extracted with toluene. The organics phases were combined with the retained solids, and the mixture was heated to reflux. Additional toluene was added to dissolve the solids and the mixture was filtered through a mixed plug of silica and alumina Product was eluted with hot toluene. Pure fractions were combined based on TLC and concentrated in vacuo. Methanol was added, and the suspension was sonicated for 2 hour and filtered. The isolated solid was suspended in acetone, stirred overnight, and filtered to isolate solids. The solids were suspended in ethyl acetate and sonicated for 3 hours. The suspension was filtered to give 2-([1,1'-biphenyl]-4-yl)-4-(3-(6,8-diphenyldibenzo[b,d]thiophen-4-yl)phenyl)-6-phenyl-1,3,5-triazine (19.5 g) as a white solid.

Example 3 Synthesis of 2-(3-(7,9 dipenylidbenzo[b,d]-furan-4-yl)-4,6-diphenyl-1,3,5-triazine

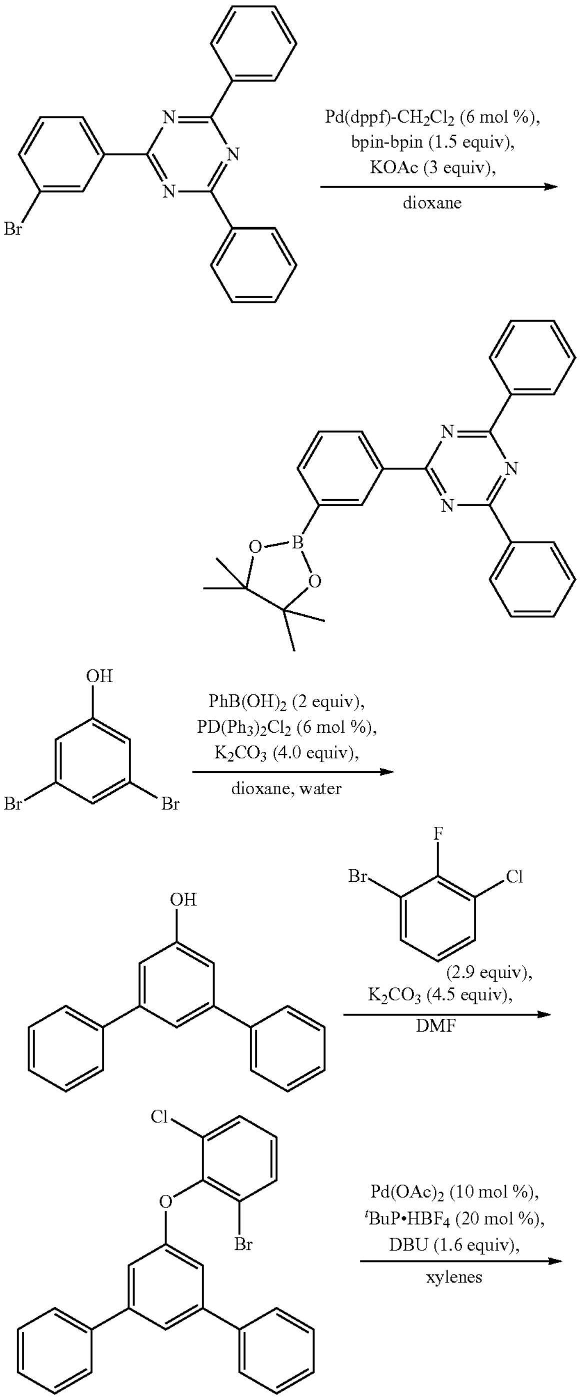

-continued

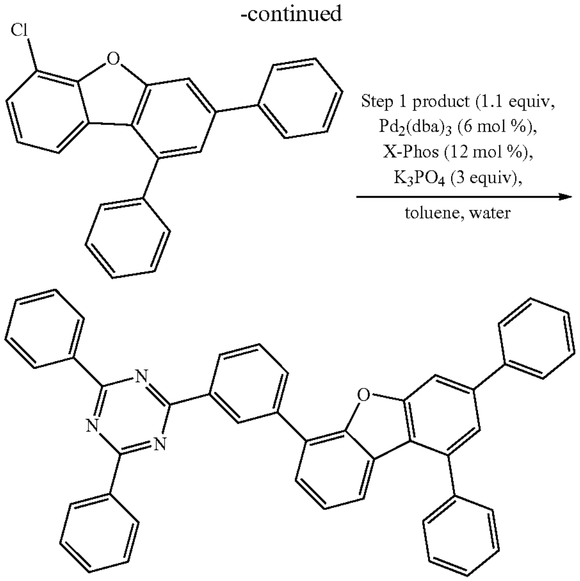

Step 1 2,4-diphenyl-6-(3-(4,4,5,5-tetramethyl-1,3,2-dioxaborolan-2-yl)phenyl)-1,3,5-triazine 2-(3-bromophenyl)-4,6-diphenyl-1,3,5-triazine (10 g, 25.8 mmol), 4,4,4',4',5,5,5',5'-octamethyl-2,2'-bi(1,3,2-dioxaborolane) (7.85 g, 30.9 mmol), potassium acetate (7.58 g, 77 mmol), and anhydrous dioxane (129 ml) were placed in a 500 ml flask equipped with a stir bar, a thermowell, and a water condenser with a nitrogen inlet. The reaction mixture was purged with nitrogen for 30 min and $PdCl_2(dppf)-CH_2Cl_2$ adduct (1.262 g, 1.545 mmol) was added. The reaction mixture was heated to 90° C. and stirred overnight. The reaction mixture was cooled to ambient temperature and filtered through a Celite plug. The plug was eluted with DCM. The filtrate was combined and concentrated in vacuo. The crude reaction mixture was dissolved in 30% DCM-heptane (200 ml) and filtered through a plug of silica gel (500 g). The plug was eluted with 30-50% DCM in heptane. The fractions containing product were combine and concentrated in vacuo to give 2,4-diphenyl-6-(3-(4,4,5,5-tetramethyl-1,3,2-dioxaborolan-2-yl)phenyl)-1,3,5-triazine (6.14 g) as a white solid.

Step 2 3,5-diphenylphenol 3,5-dibromophenol (50 g, 198 mmol), potassium carbonate (110 g, 794 mmol), phenylboronic acid (72.6 g, 595 mmol), dioxane (794 ml), and water (198 ml) were placed in a 3 L flask equipped with a stir bar, a thermowell, and a water condenser with a nitrogen inlet. The reaction mixture was purged with nitrogen for 30 min and $Pd(Ph_3)_2Cl_2$ (7.62 g, 11.91 mmol) was added. The reaction mixture was heated to 80° C. and stirred for 2 hours. After 2 hours, the reaction mixture was slowly allowed to cool to ambient overnight. The reaction mixture was passed through a celite plug eluted with DCM. The filtrate was concentrated in vacuo. The crude material was dissolved in 40% DCM-heptane (500 ml) and filtered through a silica gel plug eluted with 40% DCM-heptane. Fractions containing product were combined and concentrated in vacuo to give 3,5-diphenylphenol (36.71 g) as a white solid.

Step 3 5'-(2-bromo-6-chlorophenoxy)-1,1':3',1"-terphenyl[

1,1':3',1"-terphenyl]-5'-ol (29.66 g, 120 mmol), 1-bromo-3-chloro-2-fluorobenzene (50.4 g, 241 mmol), potassium carbonate (49.9 g, 361 mmol), and DMF (602 ml) were placed in a 2 L flask equipped with a stir bar, a thermowell, and a water condenser with a nitrogen inlet. The solution was purged with nitrogen for 30 minutes. The solution was heated to 110° C. and stirred overnight. The reaction mixture was cooled to ambient temperature and additional 1-bromo-3-chloro-2-fluorobenzene (25 g, 103 mmol) and potassium carbonate (25 g, 181 mmol) were added. The reaction mixture was heated to 110° C. and stirred overnight. The reaction mixture was cooled to ambient temperature and poured into water (500 ml). The aqueous layer was extracted with EtOAc (3×500 ml). The combined organic extract was washed with water (500 ml), brine (500 ml), dried over anhydrous sodium sulfate, filtered, and concentrated in vacuo. The crude material was dissolved in heptane (500 ml) and filtered through a plug of silica gel (1.1 kg). The plug was eluted with 7% DCM-heptane. Fractions containing product were combined and concentrated in vacuo to give 5'-(2-bromo-6-chlorophenoxy)-1,1':3',1"-terphenyl (44.06 g) as a white solid.

Step 4 6-chloro-1,3-diphenyldibenzo[b,d]furan

5'-(2-bromo-6-chlorophenoxy)-1,1': 3',1"-terphenyl (15 g, 34.4 mmol), xylene (172 ml), 2,3,4,6,7,8,9,10-octahydropyrimido[1,2-a]azepine (8.30 ml, 55.1 mmol), tri-tert-butyl (tetrafluoro-15-boranyl)-15-phosphane (1.997 g, 6.88 mmol), and diacetoxypalladium (0.773 g, 3.44 mmol) were placed in a 500 ml flask equipped with a stir bar, a thermowell, and a water condenser with a nitrogen inlet. The reaction mixture was flushed with nitrogen for 30 minutes and it was heated to 140° C. The reaction mixture was left to stir overnight. The reaction was allowed to cool to ambient temperature. It was poured into water (200 ml) and the aqueous layer was extracted with EtOAc (3×100 ml). The combined organic extract was dried over anhydrous sodium sulfate, filtered, and concentrated in vacuo. The crude material was dissolved in 2% DCM-heptane (200 ml) and filtered through a plug of silica gel (700 g) eluted with 2% DCM-heptane. Fractions containing product were combined and concentrated in vacuo to give 6-chloro-1,3-diphenyldibenzo[b,d]furan (6.48 g) as a white solid.

Step 5 2-(3-(7,9 dipenylidbenzo[b,d]furan-4-yl)-4,6-diphenyl-1,3,5-triazine 6-chloro-1,3-diphenyldibenzo[b,d]furan (3.75 g, 10.57 mmol), 2,4-diphenyl-6-(3-(4,4,5,5-tetramethyl-1,3,2-dioxaborolan-2-yl)phenyl)-1,3,5-triazine (4.83 g, 11.10 mmol), potassium phosphate (6.73 g, 31.7 mmol), dicyclohexyl(2',4',6'-triisopropyl-[1,1'-biphenyl]-2-yl)phosphane (0.605 g, 1.268 mmol), toluene (53.4 ml), and water (5.34 ml) were placed in a 250 ml flask equipped with a stir bar, a thermowell, and a water condenser with a nitrogen inlet. The reaction mixture was purged with nitrogen for 30 minutes and $Pd_2(dba)_3$ (0.581 g, 0.634 mmol) was added. The reaction mixture was heated to 91° C. and stirred overnight. The reaction mixture was cooled to ambient temperature. The solid was collected by filtration. The solid was dissolved in hot toluene (1 L) and filtered through a mixed plug of silica gel (300 g) and basic alumina (500 g) eluted with boiling toluene (8 L). Fractions containing product were combined and concentrated in vacuo. The solid was triturated in MeOH (500 ml) for 5 hours, the solid was filtered, and it was triturated in acetone (500 ml) overnight. The solid was collected by filtration. The solid (~4 g) was triturated in DCM (600 ml)/MeOH (250 ml) for 80 hours. The solid was collected by filtration. The solid was placed in a 500 ml flask and EtOAc (350 ml) was added. The flask was heated to 65° C. and the mixture was filtered hot. The solid was triturated in EtOAc (700 ml) overnight. The solid was collected by filtration. The solid was triturated in $CHCl_3$ overnight. The solid was collected by filtration. The solid was dissolved in 70% DCM-heptane (1 L). and filtered through a mixed plug of silica gel (300 g) and basic alumina (500 g) eluted with DCM. The fractions containing product were concentrated to half volume and the resulting suspension was stirred for 48 h. The solid was collected by filtration. The solid was triturated overnight in DCM. The solid was filtered. The solid was recrystallized from toluene. The solid was triturated in THF and the solid collected by filtration to give 2-(3-(7,9 dipenylidbenzo[b,d]-furan-4-yl)-4,6-diphenyl-1,3,5-triazine (2.14 g) as a white solid.

Example 4 Synthesis of 2-(3-(7,9-diphenyldibenzo[b,d]thiophen-4-yl)phenyl)-4,6-diphenyl-1,3,5-triazine

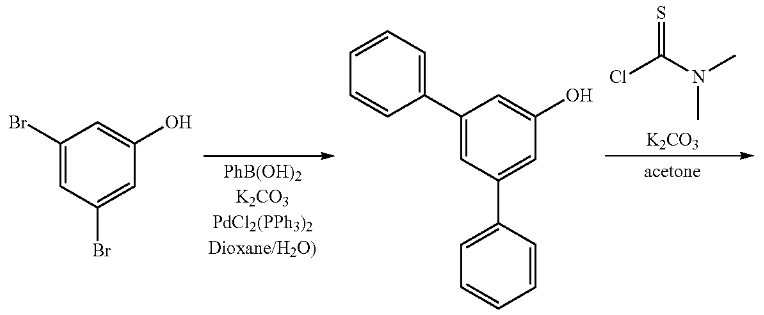

-continued

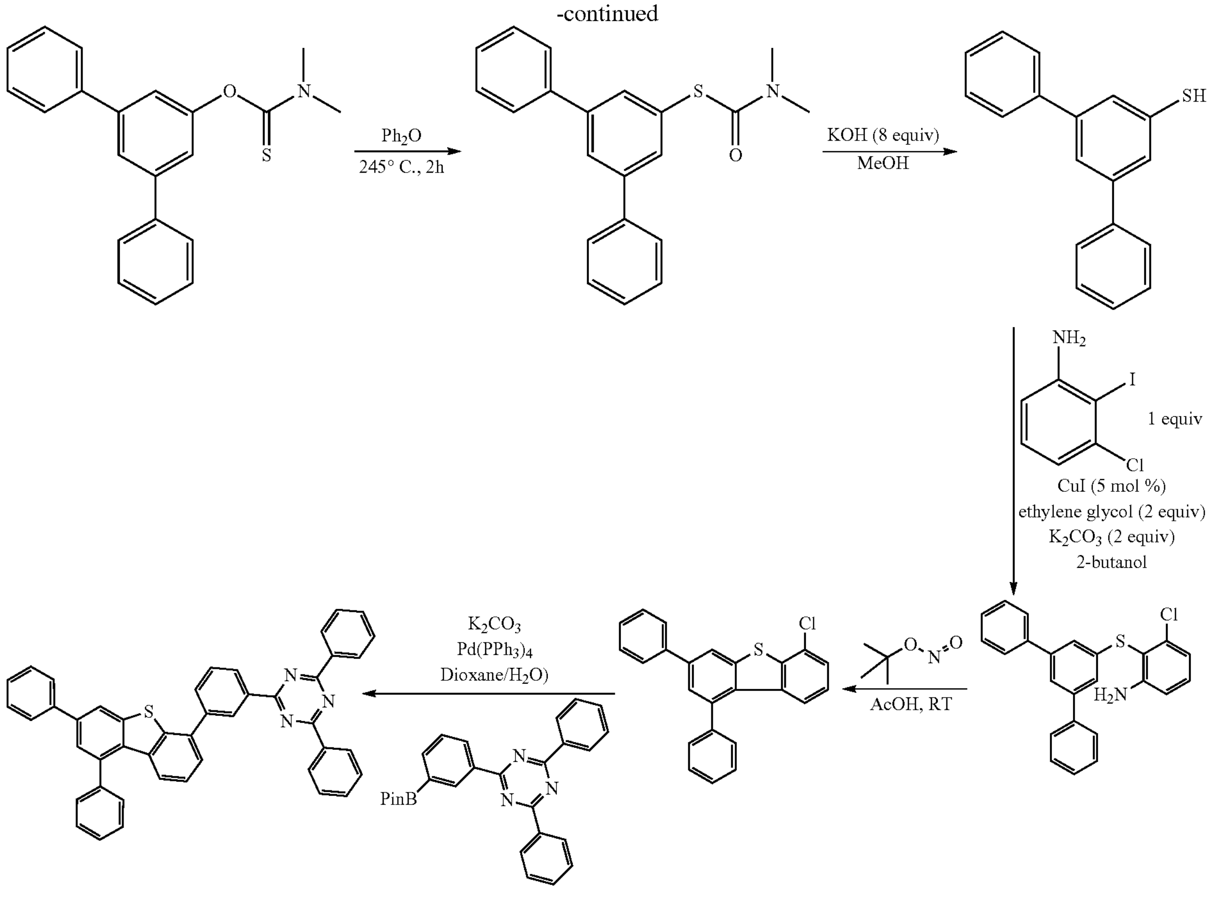

Step 1 [1,1:3',1"-terphenyl]-5'-ol 3,5-dibromophenol (50 g, 198 mmol), phenylboronic acid (97 g, 796 mmol), potassium carbonate (137 g, 991 mmol), dioxane (1000 mL), water (250 mL), and $PdCl_2(PPh_3)_2$ (7.73 g, 11 mmol) were placed in a 3 L flask under nitrogen equipped with a water condenser, a magnetic stirrer, and a heating mantle. The reaction was heated to reflux and stirred for 2 hours. Water was added and the reaction mixture was extracted with diethyl ether, dried over sodium sulfate, and concentrated. The residue was purified by silica gel chromatography eluted with EtOAc/heptane (3-10%) to give [1,1':3',1"-terphenyl]-5'-ol (37 g, 76%).

Step 2 O-([1,1':3',1"-terphenyl]-5'-yl)dimethylcarbamothioate

Acetone (1194 mL), potassium carbonate (140 g, 1.02 mol) and [1,1':3',1"-terphenyl]-5'-ol (50 g, 203 mmol) were placed in a 2 L flask under nitrogen, equipped with a water condenser, a magnetic stirrer and a heating mantle. The mixture was stirred for 1 hour at room temperature. Then dimethylcarbamothioic chloride (50.2 g, 406 mmol) was added and the mixture was heated to reflux (56° C.) overnight. The mixture was allowed to cool to room temperature. Water (2 L) was added and the mixture was extracted with ethyl acetate. The organic layer was dried with sodium sulfate, concentrated and the solid was purified by vacuum chromatography on silica gel and eluted with 0-8% EtOAc/heptane to give O-([1,1':3',1"-terphenyl]-5'-yl)dimethylcarbamothioate (53 g, 78%).

Step 3 S-([1,1':3',1"-terphenyl]-5'-yl)dimethylcarbamothioate

O-([1,1':3',1"-terphenyl]-5'-yl) dimethylcarbamothioate (29.3 g, 88 mmol) and diphenyl ether (125 mL) were placed in a 500 mL flask equipped with a condenser. The reaction was stirred at 245° C. overnight. The mixture was poured onto a silica gel column and flushed with 100% heptane until all the diphenyl ether was eluted and then 5% EtOAc/heptane to elute product. The fractions were concentrated to give S-([1,1':3',1"-terphenyl]-5'-yl)dimethylcarbamothioate (29 g, 99%) as a white solid.

Step 4 [1,1:3',1"-terphenyl]-5'-thiol

S-([1,1':3',1"-terphenyl]-5'-yl) dimethylcarbamothioate (29.3 g, 88 mmol) and MeOH (2 L) were placed in a 3 L flask equipped with a reflux condenser and flushed with nitrogen and nitrogen was bubbled through for 1 hour. KOH (39.4 g, 703 mmol) was added and the reaction was stirred at 62° C. overnight under nitrogen. After completion, the reaction was cooled to room temperature and 1 M HCl (1.5 L) was added slowly under nitrogen. The white solid was filtered off and washed with water. The mixture was suspended in methanol and stirred for 15 minutes, filtered and dried under high vacuum to give [1,1':3',1"-terphenyl]-5'-thiol (22.8 g, 99%).

Step 5 2-([1,1':3',1"-terphenyl]-5'-ylthio)-3-chloroaniline 2-butanol (225 mL), [1,1':3',1"-terphenyl]-5'-thiol (28.85 g, 110 mmol), 3-chloro-2-iodoaniline (25 g, 99 mmol), potassium carbonate (31.6 g, 229 mmol) and ethylene glycol (12.75 mL) were placed in a 500 mL flask. Nitrogen was bubbled for 20 minutes and Cud (1.09 g, 5.72 mmol) was added. The reaction was stirred for 3 hours at 90° C. and 85° C. for 9 hours. The thick solution was poured into water (2.7 L) and extracted with ethyl acetate (2 L×2). The ethyl acetate layer was concentrated and purified by silica gel column, eluting with 5-20% EtOAc/heptane to give 2-([1,1':3',1"-terphenyl]-5'-ylthio)-3-chloroaniline (22.78 g, 60%) as a white solid.

Step 6 6-chloro-1,3-diphenyldibenzo[b,d]thiophene 2-([1,1':3',1"-terphenyl]-5'-ylthio)-3-chloroaniline (22.78 g, 58.7 mmol) and acetic acid (540 mL). tert-Butyl nitrite (6.07 g, 58.9 mmol) was added dropwise over 40 minutes to a 3 L flask equipped with an addition funnel under nitrogen. The reaction mixture was stirred at room temperature for 40 hours. Water (1 L) and sodium thiosulphate (0.055 eq, 0.512 g) were added and the mixture was stirred for 1 hour. The orange precipitate was filtered and washed with water. The solid was triturated in methanol for 2 hours and then filtered and dried. The solid was further purified by silica gel vacuum column chromatography eluted with 100% heptane to give 6-chloro-1,3-diphenyldibenzo[b,d]thiophene (16 g, 74%) as a white solid.

Step 7 2-(3-(7,9-diphenyldibenzo[b,d]thiophen-4-yl)phenyl)-4,6-diphenyl-1,3,5-triazine To a 500 mL flask equipped with a water condenser, a magnetic stirrer, an oil bath and thermowell containing 2,4-diphenyl-6-(3-(4,4,5,5-tetramethyl-1,3,2-dioxaborolan-2-yl)phenyl)-1,3,5-triazine, 6-chloro-1,3-diphenyldibenzo[b,d]thiophene (15 g, 40.4 mmol), potassium carbonate (11.18 g, 81 mmol), water 35 mL were added and the mixture was degassed (nitrogen backfill) and $Pd(PPh_3)_4$ (2.8 g, 2.43 mmol) were added and the mixture was degassed. The reaction was heated to reflux and stirred for 16 hours. The reaction was allowed to cool to room temperature and concentrated. The solid was dissolved in hot toluene and filtered through a plug of silica gel. The fractions were concentrated and the solid was triturated in methanol. the mixture was filtered to give 2-(3-(7,9-diphenyldibenzo[b,d]thiophen-4-yl)phenyl)-4,6-diphenyl-1,3,5-triazine (19 g, 73%) as a white solid.

Example 5 Synthesis of 2-(3-(6,8-diphenyldibenzo[b,d]thiophen-4-yl)phenyl)-4,6-diphenyl-1,3,5-triazine

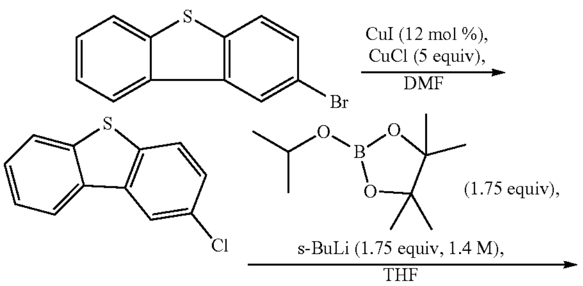

-continued

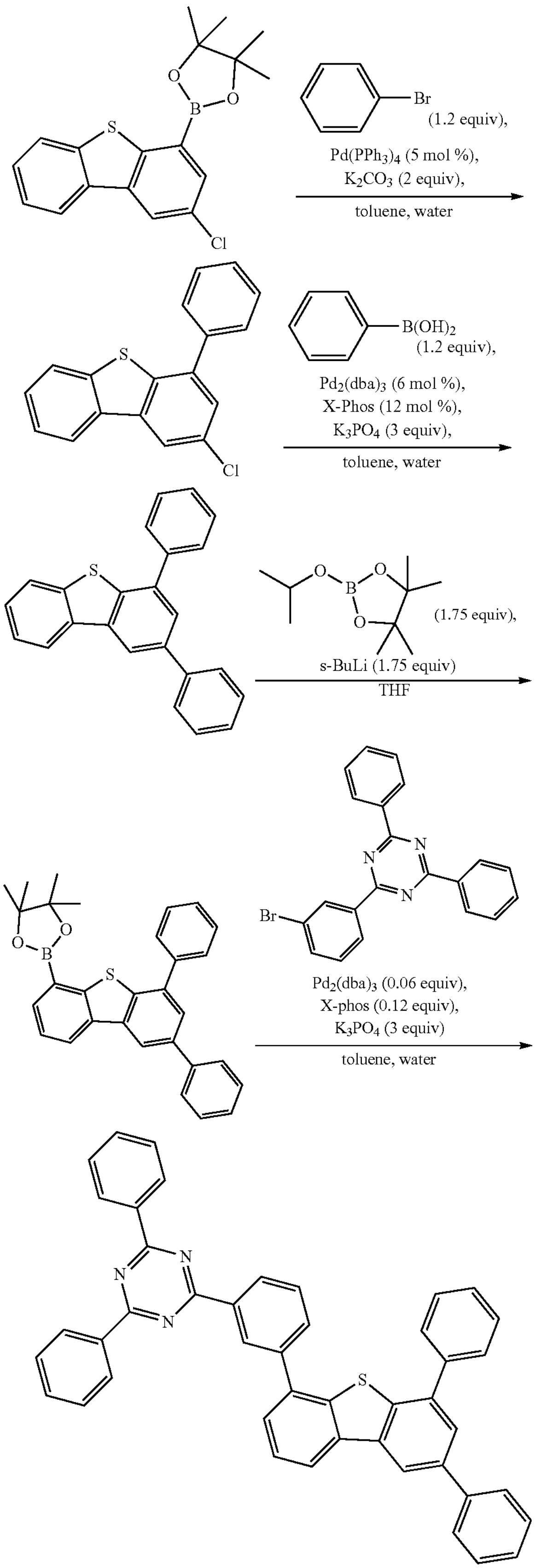

Step 1 2-chlorodibenzo[b,d]thiophene 2-bromodibenzo[b,d]thiophene (50 g, 190 mmol), copper (I) iodide (4.16 g, 21.85 mmol), copper(I) chloride (94 g, 950 mmol), and DMF (760 ml) were placed in a dry 2 L flask under nitrogen, equipped with a mechanical stirrer, a reflux condenser and a thermowell. The reaction mixture was heated to 130° C. After 18 hours, the reaction was cooled down to room temperature, filtered through celite and washed with DCM (2 L). The crude material was concentrated to dryness. The material was purified by vacuum chromatography on silica gel eluted with DCM/Heptane to obtain 2-chlorodibenzo[b,d]thiophene (38 g) as an off-white solid.

Step 2 2-(2-chlorodibenzo[b,d]thiophen-4-yl)-4,4,5,5-tetramethyl-1,3,2-dioxaborolane 2-chlorodibenzo[b,d]thiophene (20 g, 91 mmol) and anhydrous THF (540 ml) were placed in a dry 2 L flask under nitrogen, equipped with a magnetic stirrer and a thermowell. The solution was cooled to −75° C. sec-Butyllithium in cyclohexane (1.4 M, 114 ml, 160 mmol) was added dropwise using an addition funnel. The mixture was allowed to warm to −40° C. over 90 minutes. The mixture was cooled to −68° C. and 2-isopropoxy-4,4,5,5-tetramethyl-1,3,2-dioxaborolane (32.6 ml, 160 mmol) was added dropwise. The reaction mixture was slowly warmed to room temperature overnight. After overnight stirring, the reaction mixture was cooled in an ice bath and half saturated ammonium chloride aqueous solution was added and stirred for 10 minutes. The organic layer was separated and the aqueous layer was extracted with dichloromethane. The organic layers were combined, dried over sodium sulfate, filtered, concentrated, and triturated with heptane to afford 2-(2-chlorodibenzo[b,d]thiophen-4-yl)-4,4,5,5-tetramethyl-1,3,2-dioxaborolane (20 g) as an off-white solid.

Step 3 2-chloro-4-phenyldibenzo[b,d]thiophene 2-chloro-4-phenyldibenzo[b,d]thiophene (17 g, 57.7 mmol, 99% yield), bromobenzene (7.29 ml, 69.6 mmol), potassium carbonate (16.04 g, 116 mmol), toluene (174 ml), water (116 ml) were placed in a 1 L flask equipped with a magnetic stirrer, a reflux condensor and a thermowell. The mixture was degassed by purging with nitrogen gas. $Pd(Ph_3P)_4$ (3.35 g, 2.90 mmol) was added and the reaction mixture was heated to reflux and stirred overnight. After 18 h the reaction mixture was cooled to rt and the desired compound was extracted with toluene, concentrated, and purified by vacuum chromatography on silica gel eluting with DCM in heptane. Fractions containing product were combined and concentrated to give 2-chloro-4-phenyldibenzo[b,d]thiophene (17 g) as a white solid.

Step 4 2,4-diphenyldibenzo[b,d]thiophene 2-chloro-4-phenyldibenzo[b,d]thiophene (17 g, 57.7 mmol), phenylboronic acid (8.44 g, 69.2 mmol), toluene (290 ml), and water (29 ml), dicyclohexyl(2',4',6'-triisopropyl-[1,1'-biphenyl]-2-yl)phosphane (3.30 g, 6.92 mmol), and $Pd_2dba_3$ (3.17 g, 3.46 mmol) were placed in a dry 1 L flask under nitrogen, equipped with a water condenser, a magnetic stirrer, and a thermowell. The reaction mixture was heated to reflux. After 16 hours the reaction mixture was cooled to room temperature and water (100 mL) was added. The organic layer separated and filtered over a pad of silica gel eluted with toluene. The fractions containing product were combined and concentrated to afford 2,4-diphenyldibenzo[b,d]thiophene (16 g) as an off-white solid.

Step 5 2-(6,8-diphenyldibenzo[b,d]thiophen-4-yl)-4,4,5,5-tetramethyl-1,3,2-dioxaborolane 2,4-diphenyldibenzo[b,d]thiophene (16 g, 47.6 mmol), and anhydrous THF (238 ml) were placed in a dry 1 L flask under nitrogen, equipped with a magnetic stirrer and a thermowell. The solution was cooled to −72° C. sec-Butyllithium (1.4 M, 59.4 ml, 83 mmol) was added dropwise using an addition funnel. The mixture was allowed to warm to −40° C. over 60 minutes. The mixture was cooled to −68° C. and 2-isopropoxy-4,4,5,5-tetramethyl-1,3,2-dioxaborolane (16.98 ml, 83 mmol) was added dropwise. The reaction mixture was slowly warmed to room temperature and stirred for 1 hour. The reaction mixture was cooled in an ice bath and half-saturated ammonium chloride aqueous solution (200 mL) was added and stirred for 10 minutes. The organic layer was separated and the aqueous layer was extracted with dichloromethane. The organic layers combined, dried over sodium sulfate, filtered, concentrated, and triturated in heptane to give 2-(6,8-diphenyldibenzo[b,d]thiophen-4-yl)-4,4,5,5-tetramethyl-1,3,2-dioxaborolane (17 g) as an off-white solid.

Step 6 2-(3-(6,8-diphenyldibenzo[b,d]thiophen-4-yl)phenyl)-4,6-diphenyl-1,3,5-triazine 2-(3-bromophenyl)-4,6-diphenyl-1,3,5-triazine (12.5 g, 32.2 mmol), 2-(6,8-diphenyldibenzo[b,d]thiophen-4-yl)-4,4,5,5-tetramethyl-1,3,2-dioxaborolane (18.61 g, 40.2 mmol), toluene (90 ml), water (9 ml), dicyclohexyl(2',4',6'-triisopropyl-[1,1'-biphenyl]-2-yl)phosphane (1.842 g, 3.86 mmol), and $Pd_2dba_3$ (1.769 g, 1.932 mmol) were placed in a 500 mL flask under nitrogen, equipped with a water condenser, a magnetic stirrer, and a thermowell. The reaction mixture was heated to reflux. After 16 hours, the reaction mixture was cooled to room temperature and the precipitated solid was filtered off and the organic layer in the filtrate was separated. The aqueous layer was extracted with dichloromethane. The organic layers were combined with the previously filtered solid. The mixture was concentrated to obtain a brown solid which was dissolved in boiling toluene (3.5 L). The hot solution was filtered through a mixed plug of silica gel and basic alumina. The compound was eluted with hot toluene and fractions containing the compound were combined and concentrated. Methanol (2 L) was added and the suspension was stirred overnight. After filtration, the solid obtained was suspended in acetone and triturated overnight. The suspension was filtered and the solid obtained was suspended in EtOAc (1 L) and triturated for 3 h. The suspension was filtered to give 2-(3-(6,8-diphenyldibenzo[b,d]thiophen-4-yl)phenyl)-4,6-diphenyl-1,3,5-triazine (19 g) as a white solid.

Example 6 Synthesis of 2-([1,1'-biphenyl]-4-yl)-4-(3-(7,9-diphenyldibenzo[b,d]thiophen-4-yl)phenyl)-6-phenyl-1,3,5-triazine

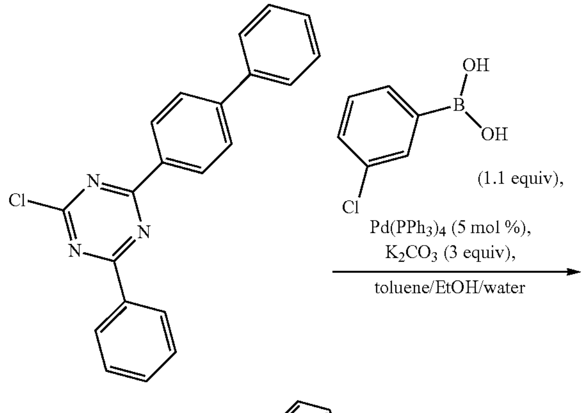

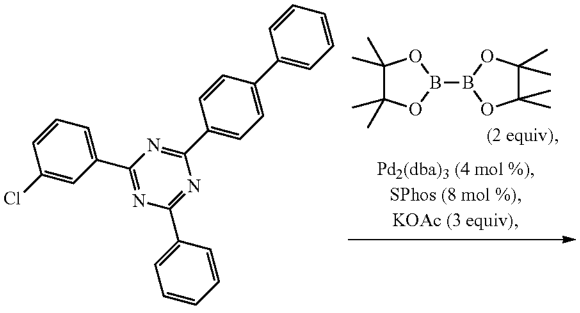

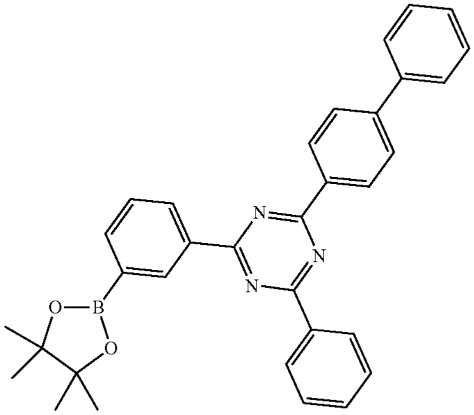

Int B

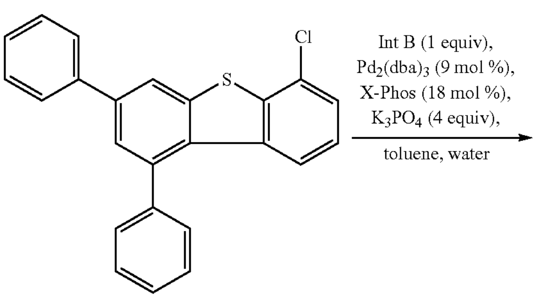

-continued

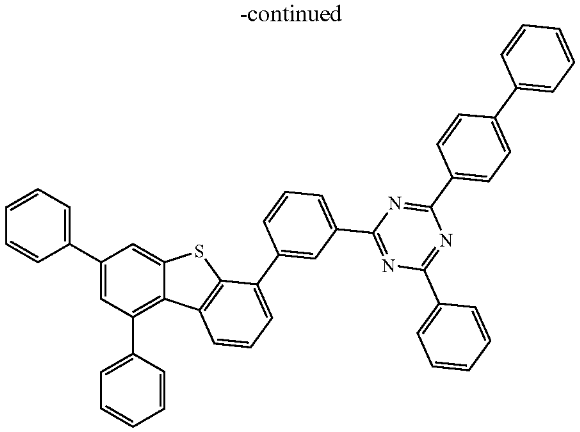

Step 1 2-([1,1'-biphenyl]-4-yl)-4-(3-chlorophenyl)-6-phenyl-1,3,5-triazine

In a 500 mL flask equipped with a water condenser with a nitrogen inlet, a thermowell, and a mechanical stirrer was placed 2-([1,1'-biphenyl]-4-yl)-4-chloro-6-phenyl-1,3,5-triazine (15 g, 43.6 mmol), (3-chlorophenyl) boronic acid (7.50 g, 48.0 mmol), $K_2CO_3$ (18.09 g, 131 mmol), and $Pd(PPh_3)_4$ (2.52 g, 2.181 mmol). A solution of toluene (92 ml), ethanol (45.8 ml), and water (45.8 ml) (purged with N2 for 45 min) was cannulated to the flask. The reaction mixture was heated to reflux (73° C.) overnight. The reaction mixture was cooled to room temperature. The solid was filtered and washed with water, methanol, and acetone. The filtrate was extracted with heptane (3×400 mL). The combined organic extract was washed with brine, dried over anhydrous sodium sulfate, filtered, and concentrated in vacuo. Both sets of solids were combined and suspended in acetone (250 mL) and triturated for 2 h. The solid was filtered and washed with acetone. 2-([1,1'-Biphenyl]-4-yl)-4-(3-chlorophenyl)-6-phenyl-1,3,5-triazine (14.72 g) was obtained as a white solid. HPLC purity 99.1%.

Step 2 2-([1,1'-biphenyl]-4-yl)-4-phenyl-6-(3-(4,4,5,5-tetramethyl-1,3,2-dioxaborolan-2-yl)phenyl)-1,3,5-triazine $Pd_2(dba)_3$ (1.308 g, 1.429 mmol), dicyclohexyl(2',6'-dimethoxy-[1,1'-biphenyl]-2-yl)phosphane (1.173 g, 2.86 mmol), 4,4,4',4',5,5,5',5'-octamethyl-2,2'-bi(1,3,2-dioxaborolane) (18.14 g, 71.4 mmol), potassium acetate (10.52 g, 107 mmol), 2-([1,1'-biphenyl]-4-yl)-4-(3-chlorophenyl)-6-phenyl-1,3,5-triazine (15 g, 35.7 mmol), and dioxane (200 ml) were placed in a 500 mL flask under nitrogen. The reaction mixture was heated to 90° C. for 8 hours. After cooling to room temperature, the solution was filtered through a pad of celite and concentrated. 2-([1,1'-biphenyl]-4-yl)-4-phenyl-6-(3-(4,4,5,5-tetramethyl-1,3,2-dioxaborolan-2-yl)phenyl)-1,3,5-triazine was used in the next step without further purification.

Step 3 2-([1,1'-biphenyl]-4-yl)-4-(3-(7,9-diphenyldibenzo[b,d]thiophen-4-yl)phenyl)-6-phenyl-1,3,5-triazine Dicyclohexyl(2',4',6'-triisopropyl-[1,1'-biphenyl]-2-yl) phosphane (2.60 g, 5.46 mmol), potassium phosphate tribasic (25.7 g, 121 mmol), $Pd_2(dba)_3$ (2.498 g, 2.73 mmol), 6-chloro-1,3-diphenyldibenzo[b,d]thiophene (11.24 g, 30.3 mmol), 2-([1,1'-biphenyl]-4-yl)-4-phenyl-6-(3-(4,4,5,5-tetramethyl-1,3,2-dioxaborolan-2-yl)phenyl)-1,3,5-triazine (15.5 g, 30.3 mmol), toluene (135 ml), and water (13.50 ml) were placed in a 500 mL flask under nitrogen. The reaction mixture was heated to 90° C. and stirred for 40 hours. The organic layer was separated and filtered through a plug of silica gel and basic alumina. The plug was eluted with toluene and the fractions containing product were concentrated. The resulting brown oil was diluted with acetone, warmed, stirred and then cooled. Gray-white powder precipitated over an hour and was collected via vacuum filtration. The solid was triturated with 15% DCM/Acetone for 18 hours. The grey ppt (9.5 g) was dissolved in hot toluene (450 mL) and then cooled slowly, about 500 mL MeOH added over a 30 min period to induce crystallization the mixture was stirred for 40 hours. The solid was collected via vacuum filtration and was then triturated with EtOAc for 24 h. Flash chromatography on silica gel eluted with 0-50% $CHCl_3$ in heptane the purest fractions were combined and concentrated. The solid was triturated with DCM/heptane to give 2-([1,1'-biphenyl]-4-yl)-4-(3-(7,9-diphenyldibenzo[b,d]thiophen-4-yl)phenyl)-6-phenyl-1,3,5-triazine (2.9 g) as white solid. HPLC purity 99.93%.

Example 7 Synthesis of 2,4-diphenyl-6-(3-(2,6,8-triphenyldibenzo[b,d]thiophen-4-yl)phenyl)-1,3,5-triazine

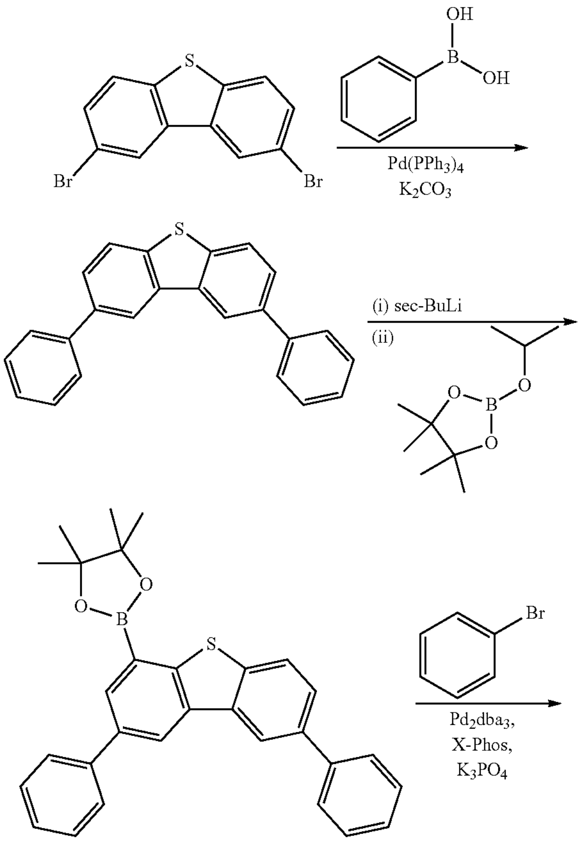

-continued

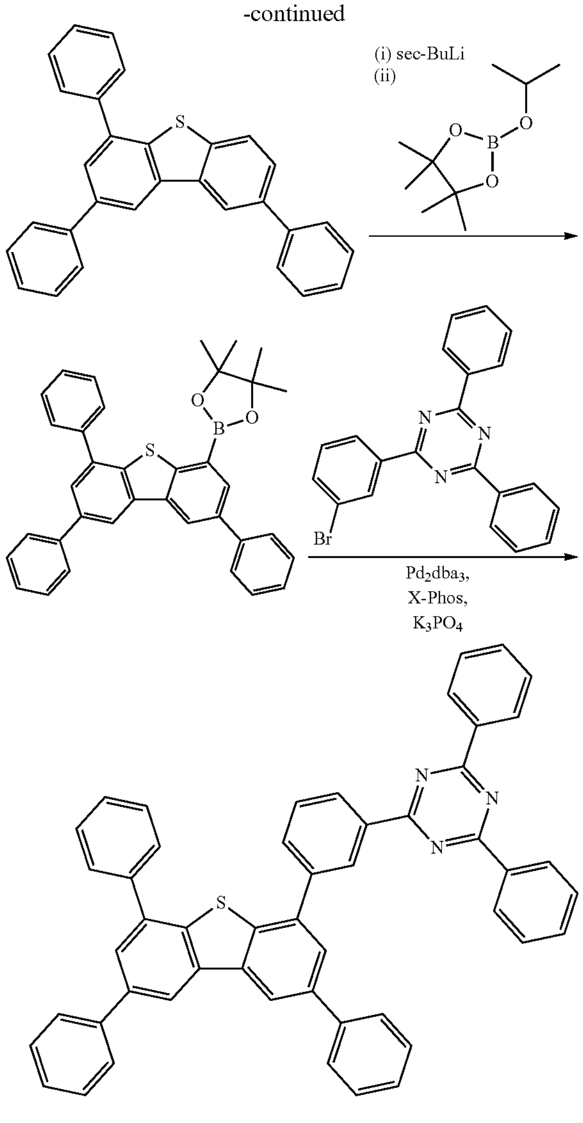

Step 1 2,8-diphenyldibenzo[b,d]thiophene 2,8-dibromodibenzo[b,d]thiophene (20 g, 58.5 mmol), phenylboronic acid (17.82 g, 146 mmol), DME (402 ml), and water (120 ml) were placed in a 1 L flask under nitrogen, equipped with a water condenser, a magnetic stirrer, and a thermowell. The mixture was degassed (vacuum-nitrogen backfilled 5 times). $Pd(PPh_3)_4$ (3.38 g, 2.92 mmol) was added and the resulting mixture was heated to reflux. After 16 hours, TLC indicated complete consumption of 2,8-dibromodibenzo[b,d]thiophene. The reaction mixture was cooled and the organic layer was separated, concentrated and then purified by vacuum chromatography on silica gel eluting with DCM in heptane to give 2,8-diphenyldibenzo[b,d]thiophene (16.6 g, 84%).

Step 2 2-(2,8-diphenyldibenzo[b,d]thiophen-4-yl)-4,4,5,5-tetramethyl-1,3,2-dioxaborolane 2,8-diphenyldibenzo[b,d]thiophene (16 g, 47.6 mmol) was added. Anhydrous THF (238 ml), was added via cannulation to a dry 1 L flask under nitrogen, equipped with a magnetic stirrer and a thermowell, and the solution was cooled to −72° C. A solution of 1.4 M sec-butyllithium in cyclohexane (59.4 ml, 83 mmol) was added dropwise using an addition funnel. The mixture was allowed to warm to −40° C. over 60 minutes. The mixture was cooled down to −68° C. and 2-isopropoxy-4,4,5,5-tetramethyl-1,3,2-dioxaborolane (16.98 ml, 83 mmol) was added dropwise. The reaction mixture was slowly warmed to room temperature and stirred for 1 hour. TLC indicated complete consumption of starting material. The reaction mixture was cooled in an ice bath and half-saturated ammonium chloride aqueous solution (200 mL) was added and stirred for 10 minutes. The organic layer was separated, and the aqueous layer was extracted with dichloromethane. The organic layers were pooled and dried over sodium sulfate, filtered and the filtrate was evaporated to dryness to afford 2-(2,8-diphenyldibenzo[b,d]thiophen-4-yl)-4,4,5,5-tetramethyl-1,3,2-dioxaborolane (22 g, 100%) as an off-white solid.

Step 3 2,4,8-triphenyldibenzo[b,d]thiophene 2-(2,8-diphenyldibenzo[b,d]thiophen-4-yl)-4,4,5,5-tetramethyl-1,3,2-dioxaborolane (22 g, 47.6 mmol), bromobenzene (9.96 ml, 95 mmol), potassium carbonate (13.15 g, 95 mmol), toluene (143 ml), and water (95 ml) were placed in a 500 mL flask equipped with a magnetic stirrer, a reflux condenser, and a thermowell, and the mixture was degassed by purging with nitrogen gas. $Pd(PPh_3)_4$ (2.75 g, 2.379 mmol) was added and the reaction mixture was heated to reflux and stirred overnight. After 18 hours, TLC showed complete consumption of starting material. The reaction mixture was cooled and the desired compound was extracted using toluene, concentrated, and purified by vacuum chromatography on silica gel using DCM in heptane to give 2,4,8-triphenyldibenzo[b,d]thiophene (16 g, 82%).

Step 4 4,4,5,5-tetramethyl-2-(2,6,8-triphenyldibenzo[b,d]thiophen-4-yl)-1,3,2-dioxaborolane 2,4,8-triphenyldibenzo[b,d]thiophene (11.5 g, 27.9 mmol) were placed in a dry 500 mL flask under nitrogen, equipped with a magnetic stirrer and a thermowell. Anhydrous THF (140 ml) was added and the solution was cooled to −72° C. A solution of 1.4 M sec-butyllithium in cyclohexane (34.8 ml, 48.8 mmol) was added dropwise using an addition funnel. The mixture was allowed to warm to −40° C. over 60 minutes. The mixture was cooled to −68° C. and 2-isopropoxy-4,4,5,5-tetramethyl-1,3,2-dioxaborolane (9.95 ml, 48.8 mmol) was added dropwise. The reaction mixture was slowly warmed to room temperature and stirred for 1 hour. TLC indicated complete consumption of starting material. The reaction mixture was cooled in an ice bath and half-saturated ammonium chloride aqueous solution (100 mL) was added and stirred for 10 minutes. The organic layer was separated, and the aqueous layer was extracted with dichloromethane. The organic layers were pooled and dried over sodium sulfate, filtered and the filtrate was evaporated to dryness to afford 4,4,5,5-tetramethyl-2-(2,6,8-triphenyldibenzo[b,d]thiophen-4-yl)-1,3,2-dioxaborolane (14.3 g, 95%) as an off-white solid.

Step 5 2,4-diphenyl-6-(3-(2,6,8-triphenyldibenzo[b,d]thiophen-4-yl)phenyl)-1,3,5-triazine To a 500 mL flask under nitrogen, equipped with a water condenser, magnetic stirrer, and thermowell, 2-(3-bromophenyl)-4,6-diphenyl-1,3,5-triazine (8.5 g, 21.89 mmol), 4,4,5,5-tetramethyl-2-(2,6,8-triphenyldibenzo[b,d]thiophen-4-yl)-1,3,2-dioxaborolane (14.15 g, 26.3 mmol), toluene (111 ml), and water (11.06 ml) were added and the mixture was degassed. Dicyclohexyl(2',4',6'-triisopropyl-[1,1'-biphenyl]-2-yl)phosphane (1.252 g, 2.63 mmol) and $Pd_2(dba)_3$ (1.203 g, 1.314 mmol) were added and the resulting mixture was heated to reflux. After 16 h, TLC indicated complete consumption of starting material. The precipitated solid was collected via suction filtration. The filtered solid was dissolved in boiling toluene (3.5 L) and passed through a plug of silica gel and basic alumina. The compound was eluted with hot toluene and fractions containing the compound were pooled and concentrated. Methanol (2 L) was added, and the suspension was stirred for 2 hours. After filtration, the solid obtained was suspended in acetone and triturated. The suspension was filtered and the solid obtained was suspended in ethyl acetate (1 L) and triturated overnight. The suspension was filtered to give 2,4-diphenyl-6-(3-(2,6,8-triphenyldibenzo[b,d]thiophen-4-yl)phenyl)-1,3,5-triazine (13.1 g, 83%) as a white solid.

Example 8 Synthesis of 2-(3-(6,8-di([1,1'-biphenyl]-4-yl)dibenzo[b,d]thiophen-4-yl)phenyl)-4,6-diphenyl-1,3,5-triazine

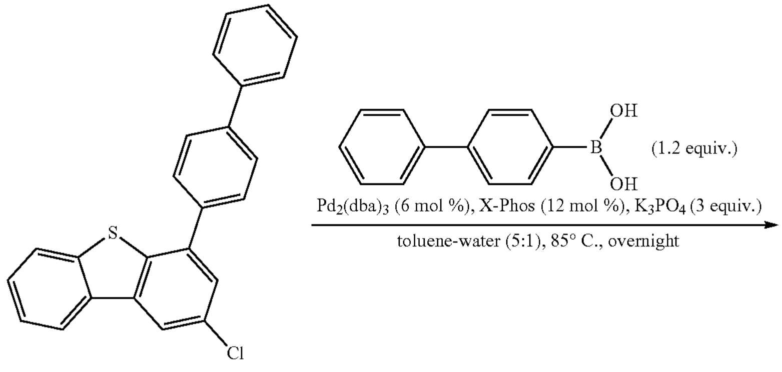

-continued
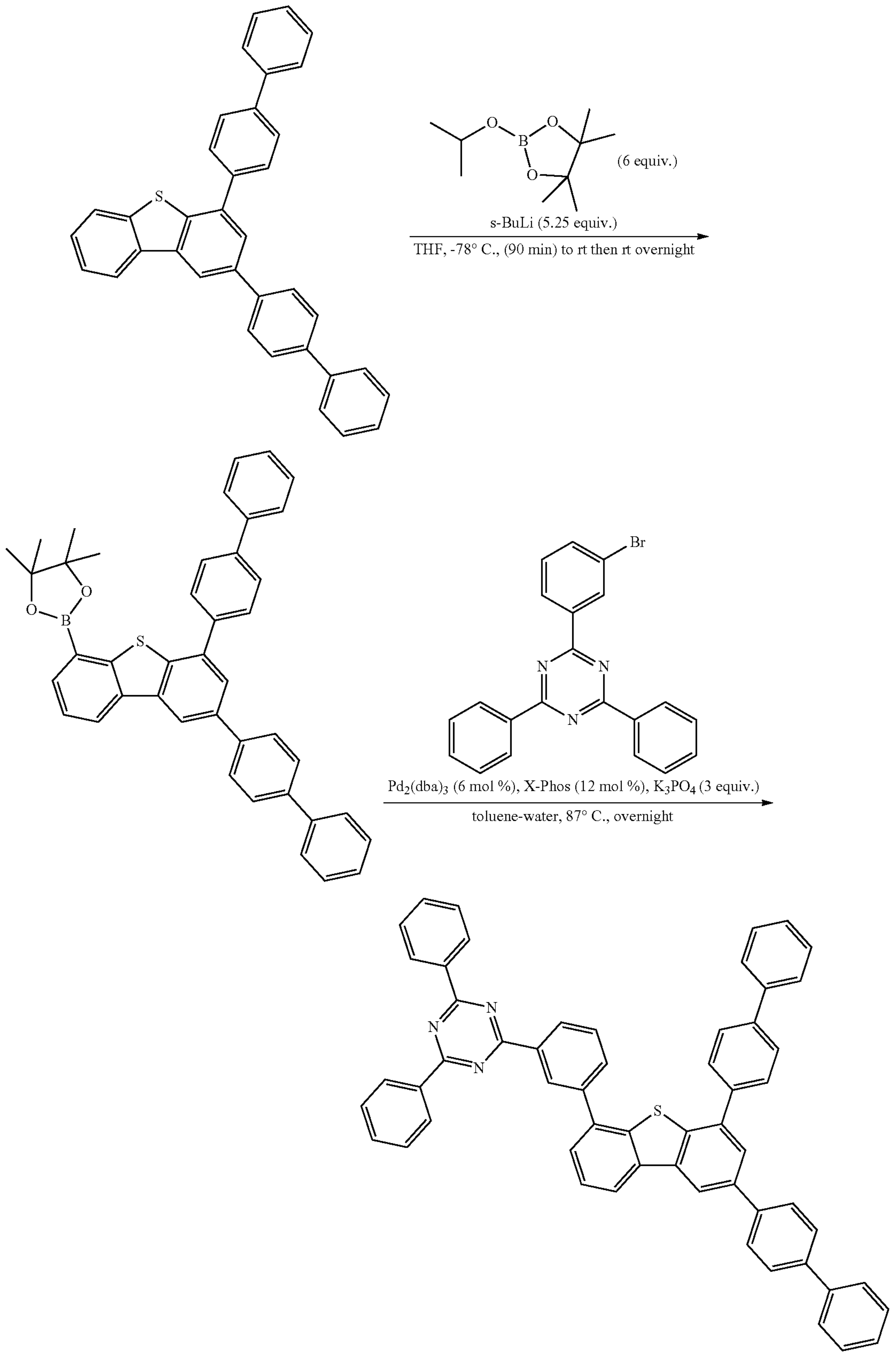

Step 1 2,4-di([1,1'-biphenyl]-4-yl)dibenzo[b,d]thiophene

In an oven-dried 500 mL 3-neck round bottomed flask under nitrogen, equipped with a reflux condenser, a magnetic stir bar, and a thermowell, 4-([1,1'-biphenyl]-4-yl)-2-chlorodibenzo[b,d]thiophene (12 g, 32.4 mmol), [1,1'-biphenyl]-4-ylboronic acid (7.69 g, 38.8 mmol, 1.2 equiv.), toluene (150 ml), and water (30.0 ml) were added and the mixture was purged with nitrogen for 15 minutes. After that, X-Phos (1.851 g, 3.88 mmol, 12 mol %) and $Pd_2dba_3$ (1.778 g, 1.941 mmol, 6 mol %) were added and the resulting mixture was further purged with nitrogen for another 15 minutes and then reaction mixture was heated to reflux at 85° C. overnight. After 16 hours, TLC indicated the complete consumption of starting material and heating was removed at that point. The reaction mixture was cooled to room temperature and 100 mL water was added. The organic layer was separated and was filtered over a pad of silica and the solid residue was washed with toluene until no UV active material eluted further. All the fractions were collected and was concentrated in vacuo. The solid material was then dissolved in THF (100 mL) and the THF solution was poured into stirring heptane (900 mL). The precipitated material was collected through filtration to give 2,4-di([1,1'-biphenyl]-4-yl)dibenzo[b,d]thiophene (14.63 g, 93%).

Step 2 2-(6,8-di([1,1'-biphenyl]-4-yl)dibenzo[b,d]thiophen-4-yl)-4,4,5,5-tetramethyl-1,3,2-dioxaborolane In an oven-dried 2 L 3-neck flask under nitrogen, equipped with a magnetic stirrer, 125 mL addition funnel, and thermowell, were added 2,4-di([1,1'-biphenyl]-4-yl)dibenzo[b,d]thiophene (11.3 g, 23.13 mmol) and anhydrous THF (650 ml) sequentially and then the solution was cooled to −78° C. followed by the slow addition of 1.4 M sec-butyllithium in cyclohexane (87 ml, 121 mmol, 5.25 equiv.) dropwise over 1 hour. The reaction mixture was stirred at the same temperature for 90 min and then 2-isopropoxy-4,4,5,5-tetramethyl-1,3,2-dioxaborolane (28.3 ml, 139 mmol, 6 equiv.) was added portion wise 5 mL every 3 minutes. After completion of the addition, reaction mixture was slowly warmed to room temperature and was stirred overnight. After 16 hours, the reaction mixture was cooled in an ice bath and saturated aqueous ammonium chloride solution was added and stirred for 10 minutes. The organic layer was separated, and the aqueous layer was extracted with dichloromethane (2×200 mL). The organic layers were combined and dried over sodium sulfate, filtered, and the filtrate was evaporated to dryness to afford 2-(6,8-di([1,1'-biphenyl]-4-yl)dibenzo[b,d]thiophen-4-yl)-4,4,5,5-tetramethyl-1,3,2-dioxaborolane (20.3 g, 99%) as a white solid.

Step 3 2-(3-(6,8-di([1,1'-biphenyl]-4-yl)dibenzo[b,d]thiophen-4-yl)phenyl)-4,6-diphenyl-1,3,5-triazine 2-(6,8-di([1,1'-biphenyl]-4-yl)dibenzo[b,d]thiophen-4-yl)-4,4,5,5-tetramethyl-1,3,2-dioxaborolane (20.3 g, 23.12 mmol), 2-(3-bromophenyl)-4,6-diphenyl-1,3,5-triazine (9.87 g, 25.4 mmol, 1.1 equiv.), toluene (193 ml), and water (38.5 ml) were placed in an oven-dried 500 mL 3-neck flask under nitrogen, equipped with a reflux condenser, a stir bar, and a thermowell, and the mixture was purged with nitrogen gas for 15 minutes. After that, dicyclohexyl(2',4',6'-triisopropyl-[1,1'-biphenyl]-2-yl)phosphane (1.323 g, 2.77 mmol, 12 mol %) and $Pd_2dba_3$ (1.270 g, 1.387 mmol, 6 mol %) were added and the resulting mixture was further purged with nitrogen gas for another 15 minutes. The reaction mixture was then heated to reflux at 89° C. for 3 days. The reaction mixture was then cooled to room temperature and water (200 mL) was added, the solid was filtered off and the filtrate was separated in a separatory funnel. The organic layer was separated and was combined with the solid collected previously and concentrated under reduced pressure. The combined solid was dissolved in hot toluene and was passed through a mixed pad of silica gel and basic alumina and washed with near-boiling toluene (8 L) until no UV active material eluted further. All fractions containing product were combined and concentrated in vacuo. The white solid was sonicated for 1 h in 300 ml toluene and poured into stirring MeOH (1 L). The white solid (25.6 g) was collected through filtration and was dried under vacuum. The white solid was triturated with acetone (800 mL) and the white solid (16.28 g) collected through filtration and was dried under vacuum. The white solid material was dissolved in hot THF (400 mL) and poured into stirring heptane (1.2 L). MeOH (200 mL) was added slowly to the stirring. Precipitation occurred and the material was stirred overnight. The white solid (15.5 g) was collected through filtration and was dried under vacuum. This white material was then dissolved in 1 L of boiling DCM and 500 mL of MeOH was added slowly with stirring. The precipitation gradually occurred and the mixture was stirred overnight. The solid was collected via suction filtration to give 2-(3-(6,8-di([1,1'-biphenyl]-4-yl)dibenzo[b,d]thiophen-4-yl)phenyl)-4,6-diphenyl-1,3,5-triazine (14.3 g) as a white solid with HPLC purity of 99.99% (254 nm).

Example 9 Synthesis of 2-(3-(6-([1,1'-biphenyl]-4-yl)-8-phenyldibenzo[b,d]thiophen-4-yl)phenyl)-4,6-diphenyl-1,3,5-triazine

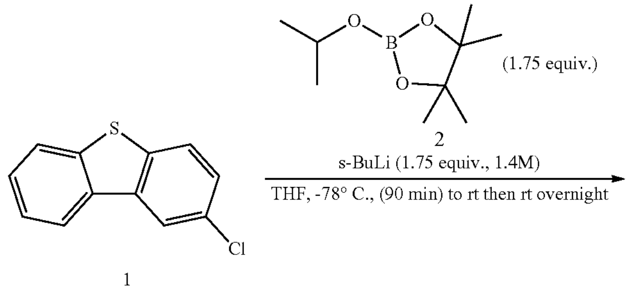

-continued
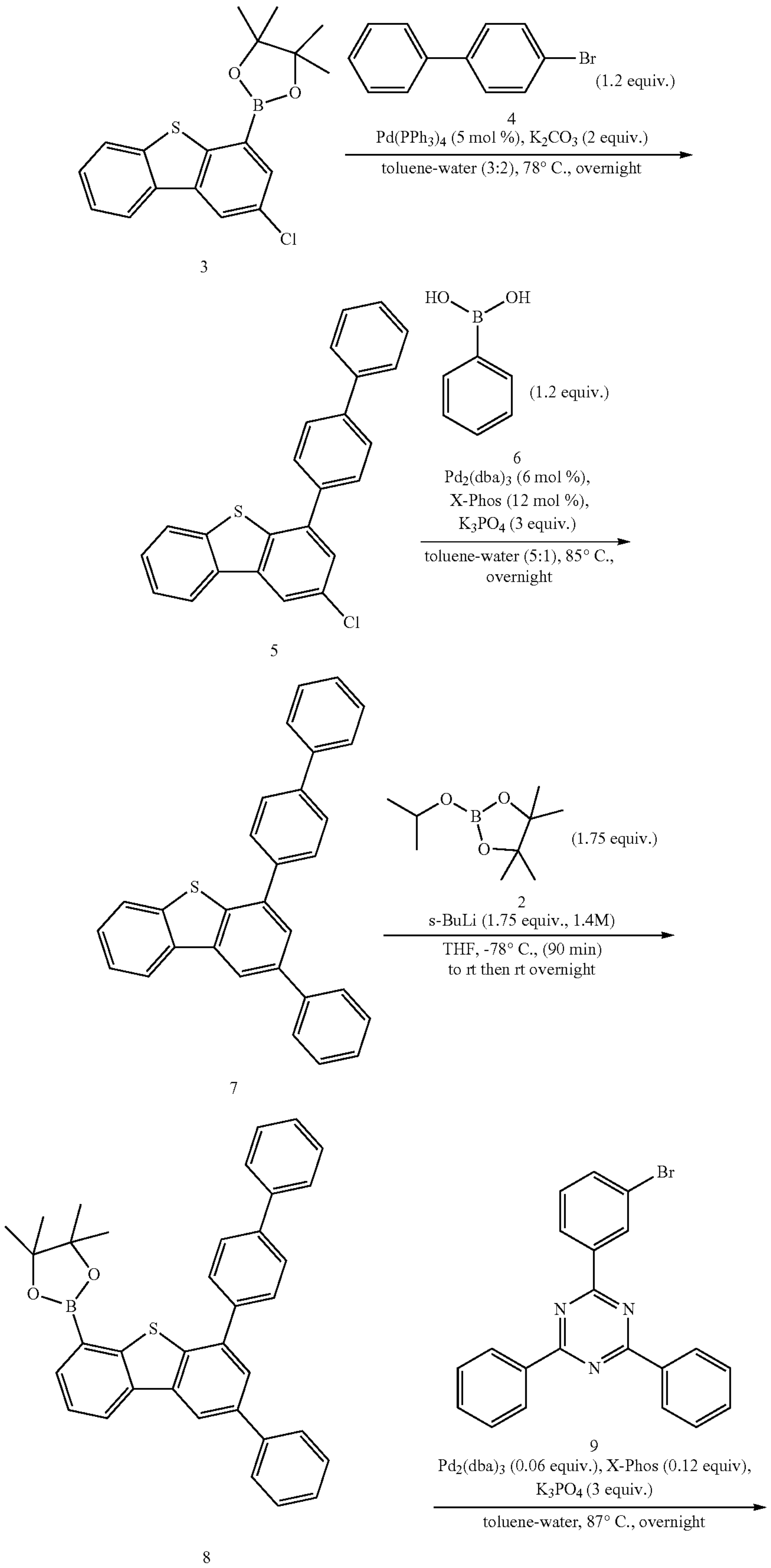

-continued

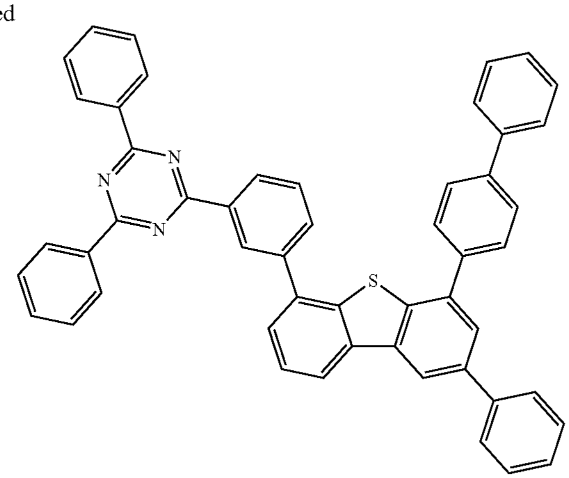

PA20180

Step 1 2-(2-chlorodibenzo[b,d]thiophen-4-yl)-4,4,5,5-tetramethyl-1,3,2-dioxaborolane 2-chlorodibenzo[b,d]thiophene (60 g, 274 mmol) and anhydrous THF (1372 ml) were placed in an oven-dried 5 L 3-neck flask under nitrogen, equipped with a magnetic stirrer, 500 mL addition funnel, and a thermowell, and then the solution was cooled to −78° C. 1.4 M sec-butyllithium in cyclohexane (343 ml, 480 mmol, 1.75 equiv.) was added dropwise from an addition funnel over an hour. The mixture was stirred for 90 minutes at the same temperature and then 2-isopropoxy-4,4,5,5-tetramethyl-1,3,2-dioxaborolane (98 ml, 480 mmol, 1.75 equiv.) was added dropwise at such a rate that the temperature didn't go above −70° C. After the completion of the addition, the reaction mixture was slowly warmed to room temperature and was stirred overnight. The reaction mixture was then cooled in an ice bath and a saturated aqueous ammonium chloride solution was added and was stirred for 10 minutes. The organic layer was separated, and the aqueous layer was extracted with dichloromethane. The organic layers were combined and was dried over sodium sulfate, filtered and the filtrate was evaporated to dryness to afford an off-white solid. The solid was triturated with heptane (500 mL) and was filtered. 2-(2-Chlorodibenzo[b,d]thiophen-4-yl)-4,4,5,5-tetramethyl-1,3,2-dioxaborolane (31.56 g, 33%) was isolated as an off-white solid.

Step 2 4-([1,1'-biphenyl]-4-yl)-2-chlorodibenzo[b,d]thiophene

In an oven-dried 1-L 3-neck flask equipped with a magnetic stirrer, a thermowell, and a reflux condenser, 4-([1,1'-biphenyl]-4-yl)-2-chlorodibenzo[b,d]thiophene (24.29 g, 65.5 mmol), 4-bromo-1,1'-biphenyl (24.19 g, 104 mmol, 1.2 equiv.), potassium carbonate (23.90 g, 173 mmol, 2 equiv.), toluene (259 ml), and water (173 ml) were added under nitrogen and the mixture was purged with nitrogen for 15 minutes. $Pd(Ph_3P)_4$ (5.00 g, 4.32 mmol, 2 mol %) was added and the mixture was again purged with nitrogen for another 15 minute and the reaction mixture was then heated to 78° C. and was stirred at the same temperature overnight. The hot reaction mixture was filtered, and the solid precipitates were suspended in 500 mL heptane and the heterogeneous mixture was sonicated for 90 min and was filtered over a Buchner funnel. The pure white solid (18.43 g) was dried under vacuum. The remaining mother liquor was concentrated to dryness and redissolved in 100 mL of hot toluene and was precipitated in 500 mL heptane resulting in another 5.86 g of pure product. Combined yield: 24.29 g (76%).

Step 3 4-([1,1'-biphenyl]-4-yl)-2-phenyldibenzo[b,d]thiophene

To a 500 mL 3-neck flask under nitrogen, equipped with a reflux condenser, a magnetic stir bar, and a thermowell, 4-([1,1'-biphenyl]-4-yl)-2-chlorodibenzo[b,d]thiophene (12 g, 32.4 mmol), phenylboronic acid (4.73 g, 38.8 mmol, 1.2 equiv.), toluene (150 ml), and water (30.0 ml) were added and the mixture was purged with nitrogen for 15 minutes. After initial degassing, X-Phos (1.851 g, 3.88 mmol, 12 mol %) and $Pd_2dba_3$ (1.778 g, 1.941 mmol, 6 mol %) were added and the resulting mixture was again purged with nitrogen for another 15 minutes and then the reaction mixture was heated to reflux at 85° C. overnight. After 16 hours, TLC indicated complete consumption of starting material. At that point, the reaction mixture was cooled to room temperature and 100 mL water was added. The organic layer was separated and was filtered over a pad of silica and washed with toluene until no UV active material eluted. Concentration of the filtered material resulted in a white solid, which was then dissolved in 100 mL of THF, and the solution was poured into stirring heptane (900 mL) to remove minor impurity. The precipitated material was collected affording pure 4-([1,1'-biphenyl]-4-yl)-2-phenyldibenzo[b,d]thiophene as a white solid (10.96 g, 82% yield).

Step 4 2-(6-([1,1'-biphenyl]-4-yl)-8-phenyldibenzo[b,d]thiophen-4-yl)-4,4,5,5-tetramethyl-1,3,2-dioxaborolane To a dry 250 mL 4-neck flask under nitrogen, equipped with a magnetic stirrer, 60 mL addition funnel, and thermowell, was weighed 4-([1,1'-biphenyl]-4-yl)-2-phenyldibenzo[b,d]thiophene (10.9 g, 26.4 mmol). Anhydrous tetrahydrofuran (132 ml) was added via cannulation and the solution was cooled to −78° C. 1.4 M sec-butyllithium in cyclohexane (33.0 ml, 46.2 mmol, 1.75 equiv.) was added dropwise from an addition funnel over 25 min. The mixture was then stirred for 90 minutes and then 2-isopropoxy-4,4,5,5-tetramethyl-1,3,2-dioxaborolane (10.78 ml, 52.8 mmol, 1.75 equiv.) was added dropwise. The reaction mixture was slowly warmed to room temperature and was stirred overnight. After overnight stirring, the reaction mixture was cooled in an ice bath and saturated aqueous ammonium chloride solution was added and was stirred for 10 minutes. The organic layer was separated, and the aqueous layer was extracted with dichloromethane (100 mL) twice. The organic layers were combined and dried over sodium sulfate, filtered, and concentrated in vacuo to afford an opaque oil. The oil was dissolved in 20 mL dichloromethane, and the solution was poured into 900 mL of stirring heptane and was stirred for 1 hour. Precipitates were formed and filtered off. The mother-liquor was concentrated to dryness to afford 14.6 g of 2-(6-([1,1'-biphenyl]-4-yl)-8-phenyldibenzo[b,d]thiophen-4-yl)-4,4,5,5-tetramethyl-1,3,2-dioxaborolane. The solid was used in the next step without further purification.

Step 5 2-(3-(6-([1,1'-biphenyl]-4-yl)-8-phenyldibenzo[b,d]thiophen-4-yl)phenyl)-4,6-diphenyl-1,3,5-triazine To a 500 mL 3-neck flask under nitrogen, equipped with a reflux condenser, magnetic stir bar, and thermowell, 2-(6-([1,1'-biphenyl]-4-yl)-8-phenyldibenzo[b,d]thiophen-4-yl)-4,4,5,5-tetramethyl-1,3,2-dioxaborolane (14 g, 26.0 mmol), 2-(3-bromophenyl)-4,6-diphenyl-1,3,5-triazine (11.10 g, 28.6 mmol), toluene (120 ml), and water (24.07 ml) were added and the mixture was purged with nitrogen for 15 minutes. After that, dicyclohexyl(2',4',6'-triisopropyl-[1,1'-biphenyl]-2-yl)phosphane (1.487 g, 3.12 mmol) and $Pd_2dba_3$ (1.428 g, 1.560 mmol) were added and the reaction mixture was heated to reflux at 85° C. under stirring overnight. After 16 hours, TLC indicated complete consumption of starting material. The reaction mixture was cooled to room temperature and 100 mL water was added. The organic layer separated and filtered over a mixed pad of silica gel and basic alumina and washed with hot toluene (12 L) until no UV active material eluted further. All the pure fractions collected were combined and concentrated. Dichloromethane (100 ml) was added to the solid and the mixture was sonicated for 1 hour and the mixture was poured into stirring MeOH (1 L). This mixture was then stirred for another 1 hour and the solid was filtered to afford a white solid 17.08 g. The white solid was triturated with acetone (300 mL) for 48 hours. The solid was triturated with EtOAc (300 mL) for 16 hours. The material was then triturated in THF (400 mL) for 16 hours. The white solid (15.9 g) was then dissolved in boiling $CHCl_3$ (800 mL) and added to stirring MeOH (350 mL) and the mixture was stirred for 3 hours. The white solid was collected to give 2-(3-(6-([1,1'-biphenyl]-4-yl)-8-phenyldibenzo[b,d]thiophen-4-yl)phenyl)-4,6-diphenyl-1,3,5-triazine (8.62 g) [HPLC=>99.99% (315 nm), 99.91% (254 nm)].

Example 9 Synthesis of 2-(3-(8-([1,1'-biphenyl]-4-yl)-6-phenyldibenzo[b,d]thiophen-4-yl)-4,6-diphenyl-1,3,5-triazine

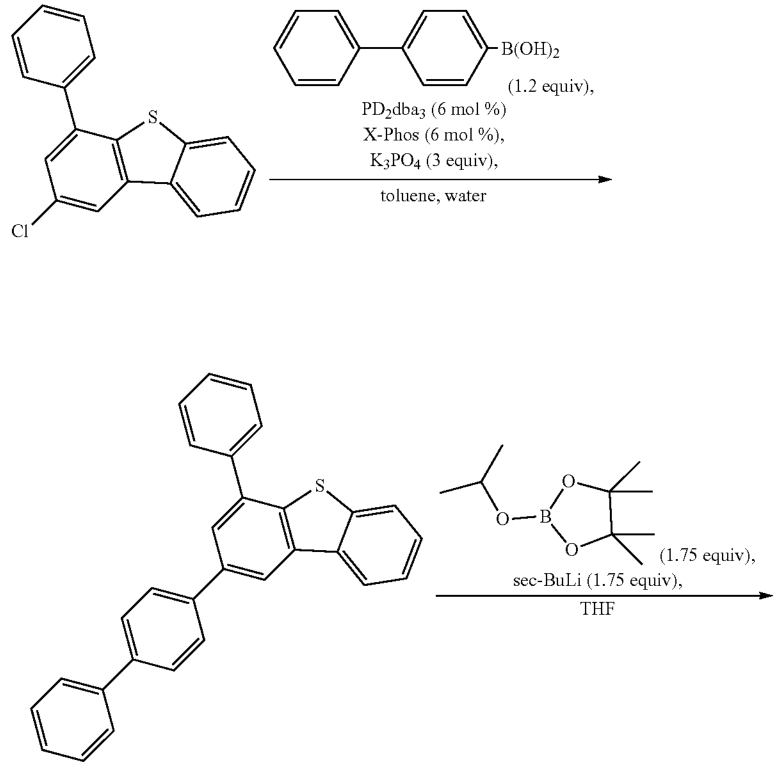

-continued

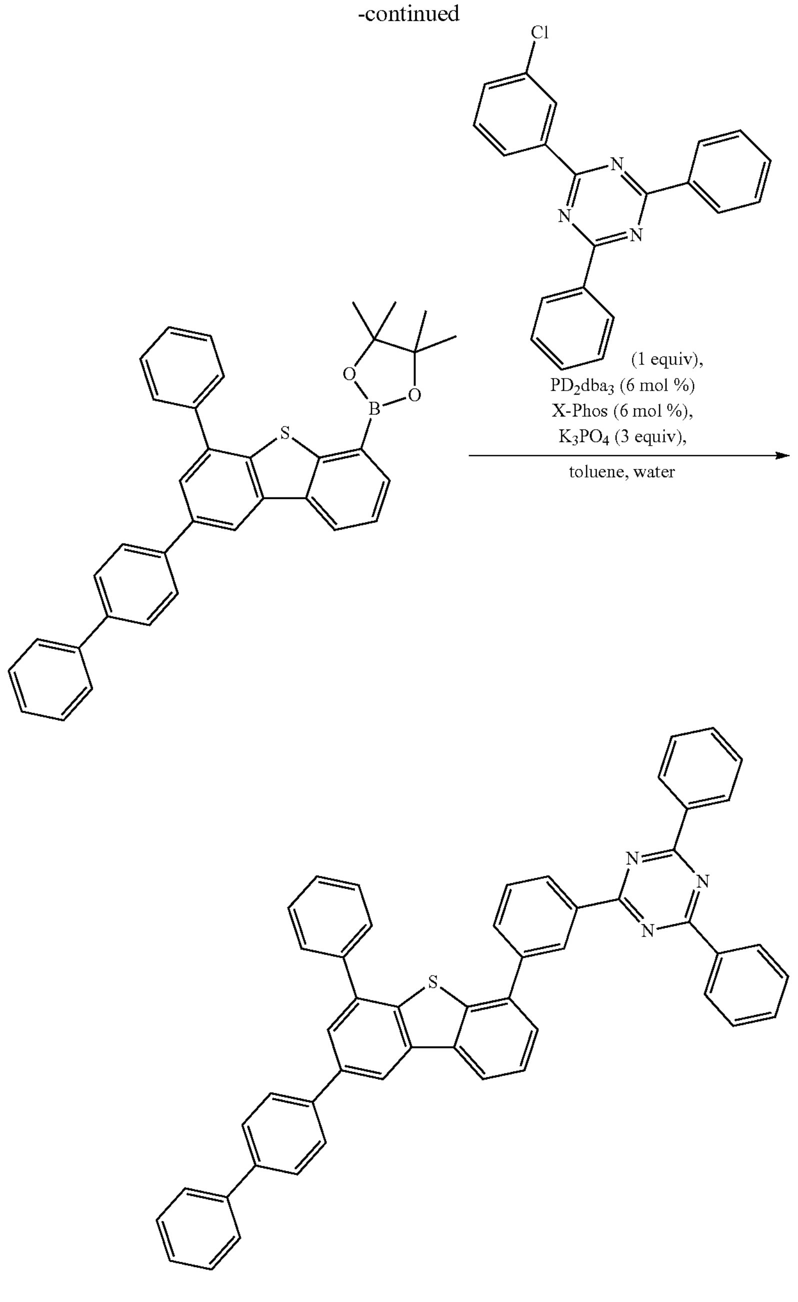

Step 1 2-([1,1'-biphenyl]-4-yl)-4-phenyldibenzo[b,d] thiophene

To a 1 L flask under nitrogen, equipped with a water condenser, magnetic stirrer and thermowell was added 2-chloro-4-phenyldibenzo[b,d]thiophene (20 g, 67.8 mmol)), [1,1'-biphenyl]-4-ylboronic acid (16.12 g, 81 mmol), potassium phosphate (3 equiv), toluene (308 ml) and water (30.8 ml) The mixture was degassed (vacuum-nitrogen backfill for 5 times). $Pd_2(dba)_3$ (3.73 g, 4.07 mmol) and dicyclohexyl(2',4',6'-triisopropyl-[1,1'-biphenyl]-2-yl)-phosphane (1.941 g, 4.07 mmol) were added and the resulting mixture was further degassed (vacuum-nitrogen backfill for 3 times). The reaction mixture was heated to reflux overnight. After 16 hours, the reaction mixture was cooled to room temperature and water (100 mL) was added. The organic layer separated and filtered over a pad of silica gel eluted with toluene. The fractions were combined and concentrated. The crude material was then dissolved in toluene and filtered through a plug of silica gel eluted with toluene. The fractions were concentrated to give 2-([1,1'-biphenyl]-4-yl)-4-phenyldibenzo[b,d]thiophene (24 g) as an off-white solid.

Step 2
2-(3-bromophenyl)-4,6-diphenyl-1,3,5-triazine

To a dry 1 L 3-neck flask under nitrogen, equipped with a magnetic stirrer and thermowell was added 2-([1,1'-biphenyl]-4-yl)-4-phenyldibenzo[b,d]thiophene (24 g, 58.2 mmol). Anhydrous THF (291 ml), was added via cannulation and the solution was cooled to −68° C. sec-butyllithium in cyclohexane (1.4 M, 72.7 ml, 102 mmol) was added dropwise using an addition funnel. The mixture was allowed to warm to −40° C. over 90 minutes. The mixture was cooled down to −68° C. and 2-isopropoxy-4,4,5,5-tetramethyl-1,3,2-dioxaborolane (20.77 ml, 102 mmol) was added dropwise. The reaction mixture was slowly warmed to room temperature overnight. The reaction mixture was cooled in an ice bath and half saturated ammonium chloride aqueous solution was added and stirred for 10 minutes. The organic layer was separated, and the aqueous layer was extracted with dichloromethane. The organic layers were combined, dried over sodium sulfate, filtered and concentrated to afford an off-white solid. The solid was triturated in heptane and filtered to give 2-(3-bromophenyl)-4,6-diphenyl-1,3,5-triazine (20 g).

Step 3 2-(3-(8-([1,1'-biphenyl]-4-yl)-6-phenyldibenzo[b,d]thiophen-4-yl)-4,6-diphenyl-1,3,5-triazine To a 1 L flask under nitrogen, equipped with a condenser, magnetic stirrer and thermowell was added 2-(3-bromophenyl)-4,6-diphenyl-1,3,5-triazine (12.98 g, 33.4 mmol), 2-(8-([1,1'-biphenyl]-4-yl)-6-phenyldibenzo[b,d]thiophen-4-yl)-4,4,5,5-tetramethyl-1,3,2-dioxaborolane (20 g, 37.1 mmol), potassium phosphate (23.65 g, 111 mmol) toluene (188 ml), and water (18.76 ml). The mixture was degassed (vacuum-nitrogen backfill for 5 times). $Pd_2dba_3$ (2.041 g, 2.228 mmol) and dicyclohexyl(2',4',6'-triisopropyl-[1,1'-biphenyl]-2-yl)-phosphane (2.125 g, 4.46 mmol) were added and the resulting mixture was further degassed (vacuum-nitrogen backfill for 3 times). The reaction mixture was heated to reflux overnight. After cooling to room temperature, the precipitated solid was filtered off and the organic layer in the filtrate was separated. The aqueous layer was extracted with toluene. The organic layers were combined and the previously filtered solid was added and heated. Additional boiling toluene was added to dissolve the solid. The mixture was filtered through a mixed plug of silica gel and basic alumina and eluted with hot toluene. Methanol (1 L) was added and the suspension was sonicated for 2 h and filtered. After filtration, the solid obtained was suspended in acetone and stirred overnight. The solid was suspended in ethyl acetate and sonicated for 3 h. The suspension was filtered to give 2-(3-(8-([1,1'-biphenyl]-4-yl)-6-phenyldibenzo[b,d]thiophen-4-yl)-4,6-diphenyl-1,3,5-triazine (15 g).

Example 10 Synthesis of 2,4-di([1,1'-biphenyl]-4-yl)-6-(3-(6,8-diphenyldibenzo[b,d]furan-4-yl)phenyl)-1,3,5-triazine

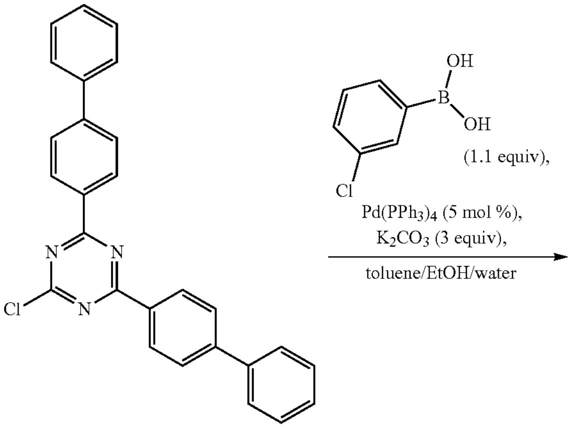

-continued

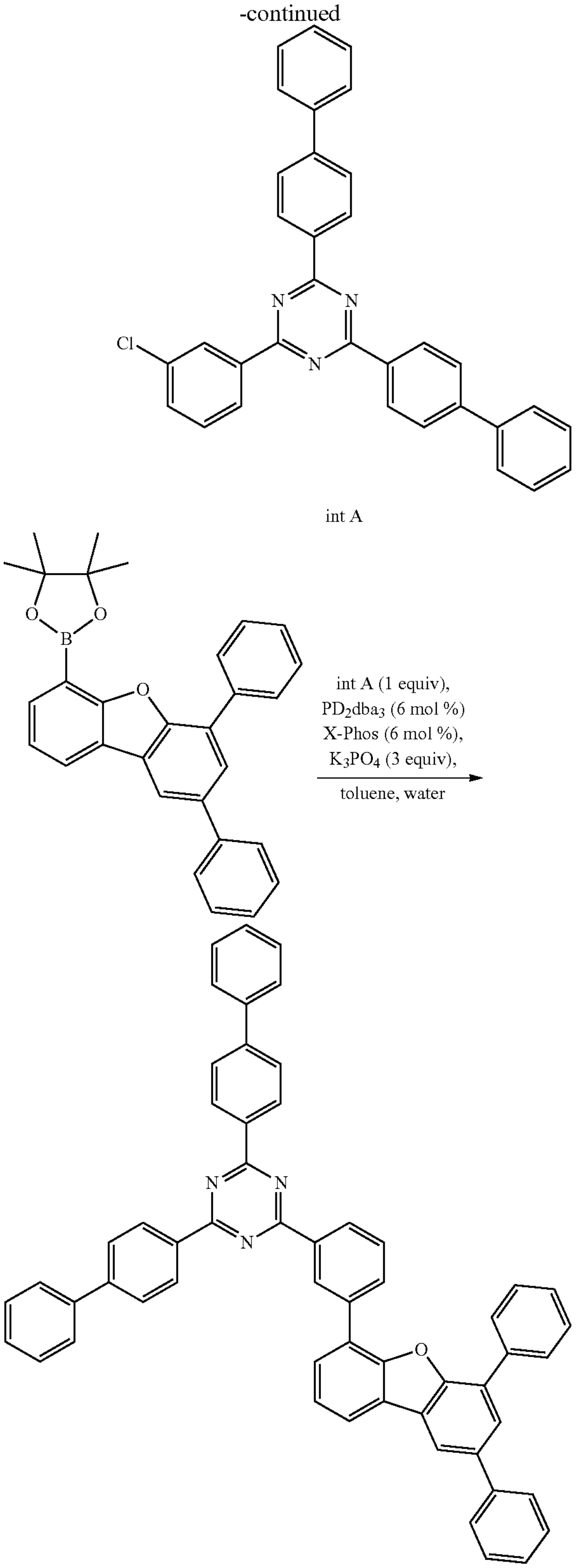

Step 1 2,4-di([1,1'-biphenyl]-4-yl)-6-(3-chlorophenyl)-1,3,5-triazine

In a nitrogen flushed 500 mL flask, 2,4-di([1,1'-biphenyl]-4-yl)-6-chloro-1,3,5-triazine (150 g, 357 mmol), (3-chlorophenyl) boronic acid (61.4 g, 393 mmol), potassium carbonate (148 g, 1072 mmol), $Pd(PPh_3)_4$ (20.64 g, 17.86 mmol), toluene (1 L), ethanol (500 ml), and water (500 ml) were added. The reaction mixture was heated to 73° C. After overnight stirring the reaction mixture was cooled to room temperature. The solid was filtered and washed with acetone. The solid was triturated with MeOH/DCM and filtered. The solid was then dissolved in hot $CHCl_3$ and filtered through a plug of silica gel eluted with hot $CHCl_3$. Fractions containing product were combined and concentrated to give 2,4-di([1,1'-biphenyl]-4-yl)-6-(3-chlorophenyl)-1,3,5-triazine (120 g) as a white solid.

Step 2 2,4-di([1,1'-biphenyl]-4-yl)-6-(3-(6,8-diphenyldibenzo[b,d]furan-4-yl)phenyl)-1,3,5-triazine To a 250 ml flask equipped with a stir bar, thermowell, and water condenser with nitrogen inlet was added 2-(6,8-diphenyldibenzo[b,d]furan-4-yl)-4,4,5,5-tetramethyl-1,3,2-dioxaborolane (7.03 g, 15.75 mmol), 2,4-di([1,1'-biphenyl]-4-yl)-6-(3-chlorophenyl)-1,3,5-triazine (7.10 g, 14.31 mmol), potassium phosphate (9.12 g, 42.9 mmol), toluene (72.3 ml), and water (7.23 ml). The reaction mixture was purged with nitrogen for 30 min and dicyclohexyl(2',4',6'-triisopropyl-[1,1'-biphenyl]-2-yl)phosphane (0.819 g, 1.718 mmol) was added followed by $Pd_2(dba)_3$ (0.786 g, 0.859 mmol). The reaction mixture was heated to reflux and stirred overnight. The reaction mixture was cooled to rt and the solid was filtered. The solid was washed with water (250 ml), MeOH (250 ml), and acetone (250 ml) to remove salts and residual color. The gray solid was dissolved in boiling toluene (1.5 L) and filtered through a mixed plug of silica gel (300 g) and basic alumina (500 g) eluted with hot toluene (8 L). The fractions containing product were combined and concentrated to ⅕ the volume. MeOH (300 ml) was added and the mixture was stirred overnight. The solid was collected via suction filtration. The solid was then triturated with acetone (700 mL) to give 2,4-di([1,1'-biphenyl]-4-yl)-6-(3-(6,8-diphenyldibenzo[b,d]furan-4-yl)phenyl)-1,3,5-triazine (8.06 g) as a white solid.

Example 11 Synthesis of 2,4-di([1,1'-biphenyl]-4-yl)-6-(3-(2,8-diphenyldibenzo[b,d]thiophen-4-yl)phenyl)-1,3,5-triazine

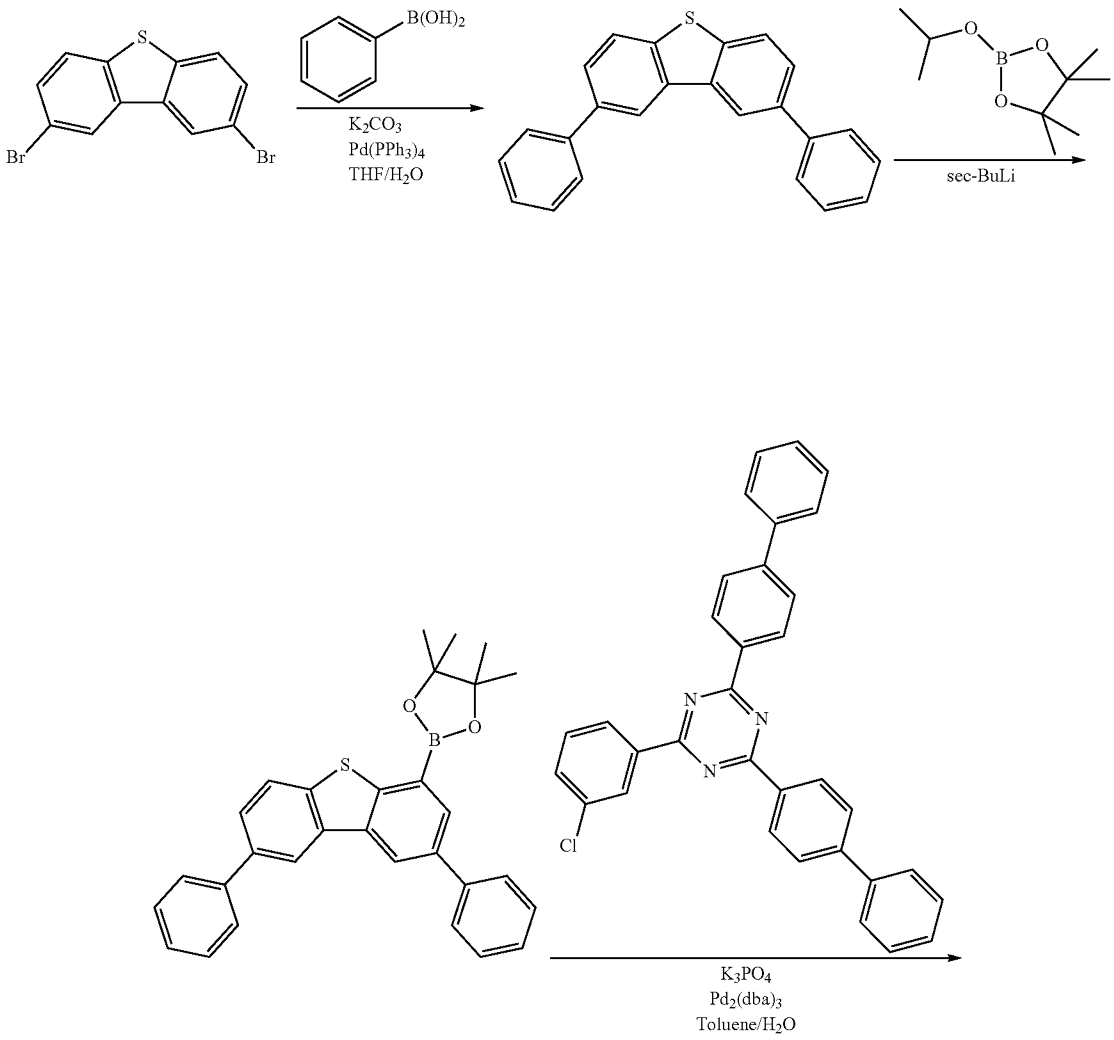

-continued

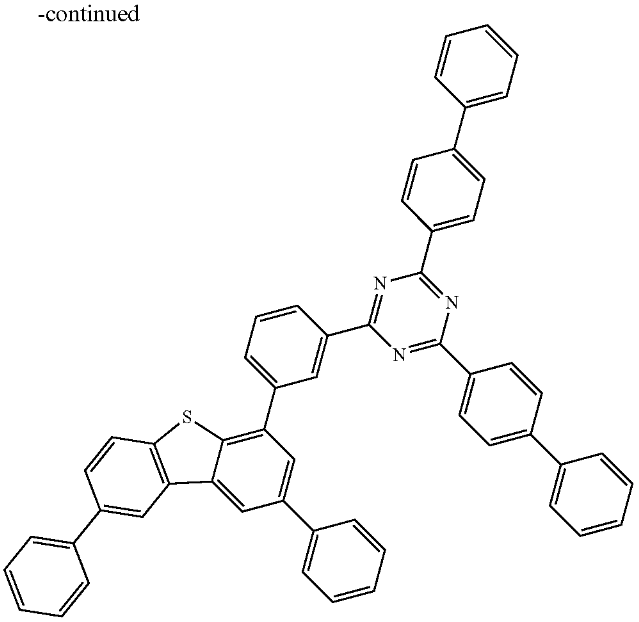

Step 1 2,8-diphenyldibenzo[b,d]thiophene

To a 1 L flask equipped with a water condenser, magnetic stirrer, and thermowell 2,8-dibromodibenzo[b,d]thiophene (30 g, 88 mmol), phenylboronic acid (26.7 g, 219 mmol), potassium carbonate (60.6 g, 439 mmol), water (202 mL) and DME (472 mL) were added. The mixture was degassed (nitrogen bubbling). $Pd(PPh_3)_4$ (5.07 g, 4.39 mmol) was added and the reaction was heated to reflux and stirred for 16 hours. The reaction was allowed to cool to room temperature and the solid was filtered. The solid was dissolved in toluene and filtered through a silica gel plug. The fractions were concentrated and the solid was triturated in methanol to give 2,8-diphenyldibenzo[b,d]thiophene (22 g, 75%) as a white solid.

Step 2 2-(2,8-diphenyldibenzo[b,d]thiophen-4-yl)-4,4,5,5-tetramethyl-1,3,2-dioxaborolane To a dry 1 L flask under nitrogen was added 2,8-diphenyldibenzo[b,d]thiophene (22 g, 65.4 mmol) and THF (327 ml). The solution was cooled to −78° C. A solution of 1.4 M sec-butyllithium in cyclohexane (82 ml, 114 mmol) was added slowly to the solution keeping the internal temperature below −68° C. The solution was stirred at this temperature for 1 h. 2-isopropoxy-4,4,5,5-tetramethyl-1,3,2-dioxaborolane (21.29 g, 114 mmol) was then added dropwise to the solution and the reaction was allowed to slowly warm to room temperature overnight. Saturated $NH_4Cl$ (aq) and water (100 mL each) were added and the THF layer was separated. The aqueous layer was extracted with DCM (3x100 mL) and the combined organic layers were washed with brine, dried over $Na_2SO_4$ and concentrated. The residue was suspended in heptane and sonicated for 30 minutes. The white solid was filtered off and dried under high vacuum to give 2-(2,8-diphenyldibenzo[b,d]thiophen-4-yl)-4,4,5,5-tetramethyl-1,3,2-dioxaborolane (27.3 g, 90%).

Step 3 2,4-di([1,1'-biphenyl]-4-yl)-6-(3-(2,8-diphenyldibenzo[b,d]thiophen-4-yl)phenyl)-1,3,5-triazine To a 500 mL flask equipped with a water condenser, magnetic stirrer and thermowell, diphenyldibenzo[b,d]thiophen-4-yl)-4,4,5,5-tetramethyl-1,3,2-dioxaborolane (15 g, 32.4 mmol), 2,4-di([1,1'-biphenyl]-4-yl)-6-(3-chlorophenyl)-1,3,5-triazine (16.09 g, 32.4 mmol), potassium phosphate, tribasic (20.66 g, 97 mmol), toluene (147 mL) and water (15 mL) were added and the mixture was degassed (nitrogen bubbling). $Pd_2(dba)_3$ (1.78 g, 1.946 mmol) and dicyclohexyl(2',4',6'-triisopropyl-[1,1'-biphenyl]-2-yl)phosphane (1.856 g, 3.89 mmol) were added and the reaction mixture was heated to reflux and stirred for 16 hours. The reaction mixture was allowed to cool to room temperature and the solid was filtered. The white solid was dissolved in boiling toluene and passed through a silica gel/basic alumina plug. A white solid precipitated after fractions cooled to room temperature. The solid was filtered off and triturated in MeOH. The solid was resuspended in DCM/MeOH solution and triturated overnight. The solid was further triturated in ethyl acetate and DCM/acetone to give 2,4-di([1,1'-biphenyl]-4-yl)-6-(3-(2,8-diphenyldibenzo[b,d]thiophen-4-yl)phenyl)-1,3,5-triazine (9.35 g, 36%) as a white solid.

Example 12 Synthesis of 2-(3-(2,6-diphenyldibenzo[b,d]thiophen-4-yl)phenyl)-4,6-diphenyl-1,3,5-triazine

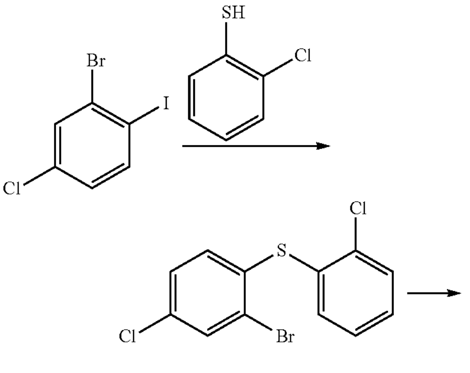

-continued

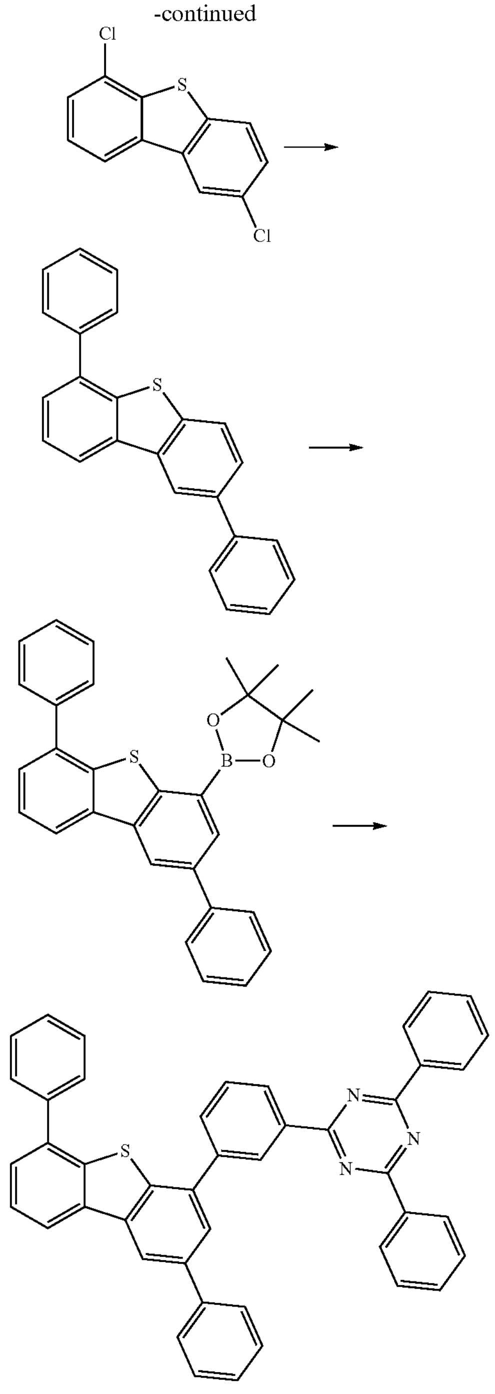

Step 1 (2-bromo-4-chlorophenyl)(2-chlorophenyl)sulfane

In a 1 L round bottom flask was introduced $Pd_2dba_3$ (0.931 g, 1.016 mmol), (oxybis(2,1-phenylene))bis(diphenylphosphane) (1.129 g, 2.033 mmol) and dry toluene (825 mL). The reaction mixture was purged with nitrogen for 20 minutes while stirring vigorously. Then, 2-bromo-4-chloro-1-iodobenzene (32.9 g, 102 mmol), 2-chlorobenzenethiol (11.76 ml, 102 mmol), and potassium 2-methylpropan-2-olate (12.67 g, 112 mmol) were added and the mixture was stirred at 115° C. for 4 hours (oil bath temp.). LC-MS showed no starting material left and 98.2% of a new product, no mass detected. TLC (100% heptanes) showed a brown spot with an Rf of 0.5. Brine (500 mL) was added and the 2 layers were separated. The aqueous layer was extracted with ethyl acetate (3×250 mL). The combined organic layers were dried over $MgSO_4$, filtered and concentrated under vacuum at 45° C. to give a brown oil. This oil was directly loaded with the aid of heptanes into a 3 inches wide column containing 790 g of silica gel (17 inches length). The product was eluted using heptanes (6 L). The fractions containing the product were collected and concentrated under vacuum to give the product (2-bromo-4-chlorophenyl)(2-chlorophenyl) sulfane as a colorless oil, 32.89 g, 96%. LC-MS showed the purity of 99% at 254 nm Step 2 2,6-dichlorodibenzo[b,d]thiophene In a 2 L round bottom flask was added dichlorobis (triphenylphosphine)palladium(II) (2.144 g, 2.99 mmol) to a deaerated solution of (2-bromo-4-chlorophenyl)(2-chlorophenyl)sulfane (20 g, 59.9 mmol), potassium pivalate (17.13 g, 120 mmol) in dimethylacetamide (550 mL) and the headspace was purged with nitrogen for 30 minutes. The reaction mixture was stirred for 14 hours at 140° C. under nitrogen (oil bath temp.). The reaction mixture was analyzed by TLC and LC-MS. LC-MS showed no starting material left and 95.8% of a new product, no mass detected. TLC (100% heptanes) showed a major spot with an Rf of 0.5, brown spot. Brine (4 L) was added as well as ethyl acetate (1 L) and the 2 layers were separated. The organic layer was washed with brine (4×1 L), dried over $MgSO_4$, filtered and concentrated under vacuum at 45° C. to give a brown solid. 40 g of silica gel and 350 mL of dichloromethane were added and then concentrated under vacuum at 45° C. to give a fine powder. The obtained material was loaded into a 3 inches wide column containing 650 g of silica (13 inches length) and was eluted using 100% heptanes (10 L). The fractions containing the product were collected and concentrated under vacuum at 45° C. to give a slightly yellow product. This solid was suspended in heptanes (100 mL) and stirred overnight. The solid was filtered and washed with heptanes (2×25 mL) to give the product 2,6-dichlorodibenzo [b,d]thiophene as a white solid, 10.5 g, 69%. LC-MS showed the purity of 99% at 254 nm.

Step 3 2,6-diphenyldibenzo[b,d]thiophene

In a 1 L round bottom flask was introduced 2,6-dichlorodibenzo[b,d]thiophene (10 g, 38.7 mmol), phenylboronic acid (19.07 g, 155 mmol), SPhosPdG2 (1.423 g, 1.936 mmol), tetrahydrofuran (350 mL) and a freshly prepared aqueous solution of potassium phosphate (240 mL, 120 mmol, 0.5 M). The reaction mixture was purged with nitrogen for 20 minutes and then stirred at 60° C. (oil bath temp.) for 3.5 hours under nitrogen. LC-MS showed no starting material left and 95% of the product, no mass detected. The reaction was cooled down to room temperature. Water (350 mL) was added and the 2 layers were separated. The aqueous layer was extracted with ethyl acetate (2×200 mL). The combined organic layers were dried over $MgSO_4$, filtered and concentrated under vacuum at 45° C. to give a brown solid. To the crude was added 25 g of silica gel, 150 mL of dichloromethane, and concentrated under vacuum to give a fine powder. The obtained material was loaded into a 2.5 inches wide column containing 300 g of silica gel (9 inches length) and was eluted using 100% heptanes (3 L) and finally 50% heptanes/dichloromethane (4

L). The fractions containing the product were collected and concentrated under vacuum at 45° C. to give the product 2,6-diphenyldibenzo[b,d]thiophene as a white solid, 13.1 g, 99%. LC-MS showed the purity of 98.7% at 254 nm.

Step 4 2-(2,6-diphenyldibenzo[b,d]thiophen-4-yl)-4,4,5,5-tetramethyl-1,3,2-dioxaborolane In a 1 L 3-neck round-bottom flask, 2,6-diphenyldibenzo[b,d]thiophene (13 g, 38.1 mmol) and tetrahydrofuran (400 mL) were introduced under nitrogen and then the reaction mixture was cooled down to an internal temperature of −78° C. using a dry ice-acetone bath. Then sec-butyllithium (60 ml, 84 mmol) was added dropwise over 60 minutes. The reaction quickly became brown during the addition. The reaction mixture was stirred at the same temperature for 2 hours. Then, 2-isopropoxy-4,4,5,5-tetramethyl-1,3,2-dioxaborolane (16.38 ml, 76 mmol) was added dropwise over 15 minutes at −78° C. The reaction mixture became ink blue just after finishing the addition. The mixture was allowed to warm up to room temperature very slowly, keeping the dry-ice/acetone bath. Around 0° C., the mixture became colorless but turbid. The mixture was stirred for 18 hours at room temperature. After 18 hours, the reaction was studied by LC-MS which showed a major peak, 95.8% area at 254 nm, no mass detected. The reaction mixture was diluted with ethyl acetate (100 mL), followed by the addition of a saturated aqueous solution of ammonium chloride (500 mL). The 2 layers were separated, the aqueous layer was additionally extracted with ethyl acetate (2×250 ml). The combined organic layers were dried over $MgSO_4$, filtered and concentrated under vacuum at 45° C. TLC (30% ethyl acetate/heptanes) showed a major spot with an Rf of 0.6, brown in UV. To the crude was added 30 g of silica gel, 250 mL of dichloromethane, and concentrated under vacuum to give a fine powder. The obtained material was loaded into a 2.5 inches wide column containing 320 g of silica gel (9 inches length) and was eluted using heptanes (3 L), dichloromethane (2 L) and finally ethyl acetate (2 L). The fractions containing the product were collected and concentrated under vacuum at 45° C. to give the product 2-(2,6-diphenyldibenzo[b,d]thiophen-4-yl)-4,4,5,5-tetramethyl-1,3,2-dioxaborolane as a white solid, 17.42 g, 98%. LC-MS showed the purity of 99% at 254 nm.

Step 5 2-(3-(2,6-diphenyldibenzo[b,d]thiophen-4-yl)phenyl)-4,6-diphenyl-1,3,5-triazine To a mixture of 2-(3-bromophenyl)-4,6-diphenyl-1,3,5-triazine (13.98 g, 34.9 mmol), diphenyldibenzo[b,d]thiophen-4-yl)-4,4,5,5-tetramethyl-1,3,2-dioxaborolane (17.42 g, 36.9 mmol) SPhos PdG2 (1.352 g, 1.838 mmol), and tetrahydrofuran (400 ml), was added a freshly prepared aqueous solution of tripotassium phosphate (450 mL, 113 mmol, 0.25M in water). The headspace was purged with nitrogen for 30 minutes and the reaction mixture was stirred at 63° C. for 5 hours under nitrogen (oil bath temp.). The mixture was colorless while warming up, then became brown after 1 hour of reflux and a gray solid was formed that wasn't soluble in THF or water after 2 hours of refluxing. LC-MS showed no starting material left. The reaction mixture was cooled down to room temperature. The obtained suspension was filtered and the solid was washed with water (2×100 mL) and tetrahydrofuran (4×100 mL) and dried overnight to give 21.38 g of the product as an off-white solid, which was confirmed by $^1H$ NMR.

Device Examples

All example devices were fabricated by high vacuum ($<10^{-7}$ Torr) thermal evaporation. The anode electrode was 750 Å of indium tin oxide (ITO). The cathode consisted of 10 Å of Liq (8-hydroxyquinoline lithium) followed by 1,000 Å of Al. All devices were encapsulated with a glass lid sealed with an epoxy resin in a nitrogen glove box (<1 ppm of $H_2O$ and $O_2$) immediately after fabrication with a moisture getter incorporated inside the package. The organic stack of the device examples consisted of sequentially, from the ITO Surface: 100 Å of HAT-CN as the hole injection layer (HIL); 450 Å of HTM as a hole transporting layer (HTL); emissive layer (EML) with thickness 400 Å. Emissive layer containing H-host (HH): E-host 40 weight % and 10 weight % of green emitter GD1. EML was followed by 350 Å of Liq (8-hydroxyquinoline lithium) doped with 40% of ETM as the electron transporting layer (ETL). E-host EH1 was used as inventive Example 1, E-host EH2 was used a comparative example CE1. Device structure is shown in the table yyy The chemical structures of the device materials are shown below.

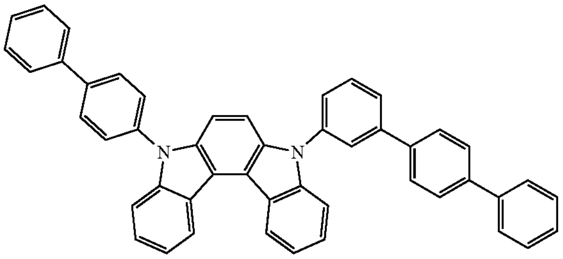

HH

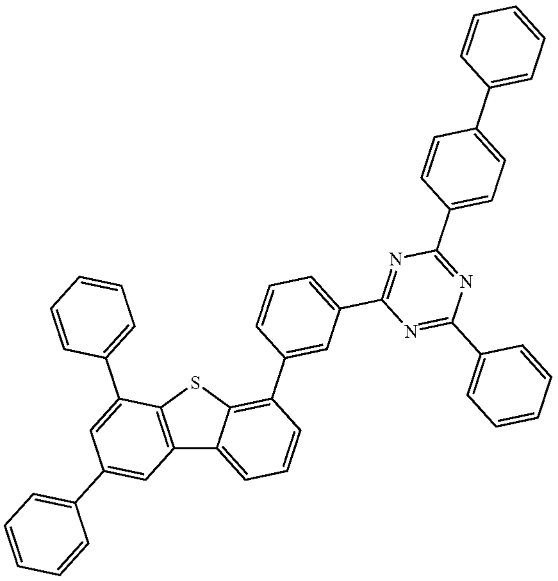

EH1

-continued

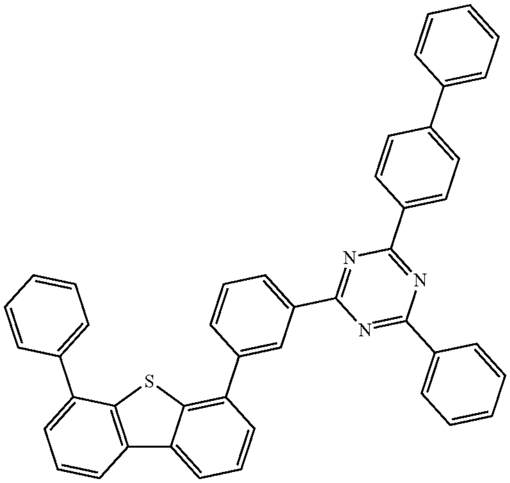

EH2

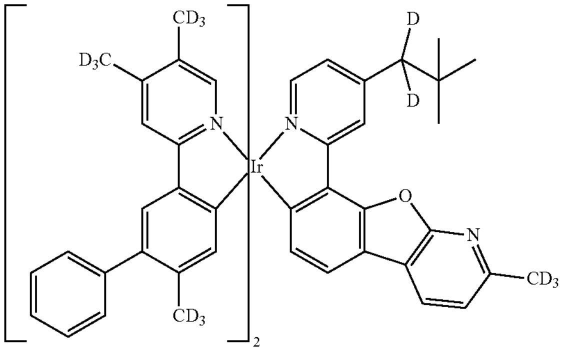

GD1

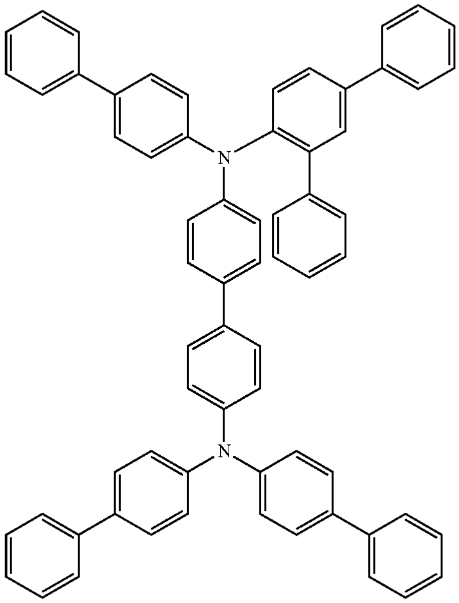

HTM

-continued

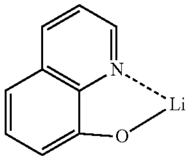

Liq

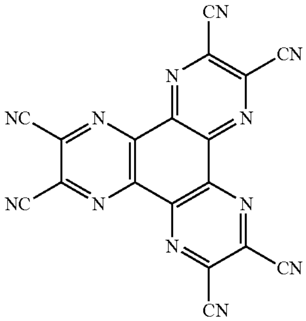

HATCN

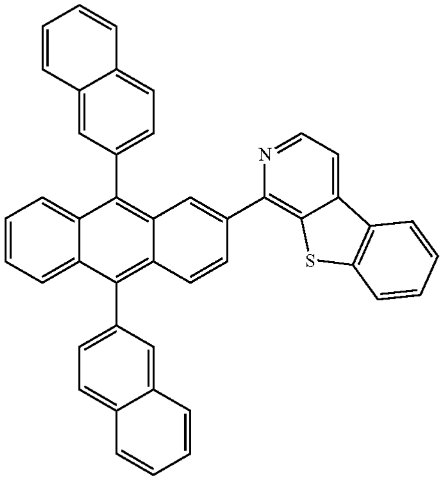

ETM

Upon fabrication the devices EL and JVL performance have been measured. All device examples emitted green emission with maximum wavelength 527 nm defined by green emitter GD1. The devices stability (lifetime) was tested at very high luminance accelerated conditions at DC current density of 80 mA/cm$^2$. The lifetime value at 1,000 nits was calculated assuming acceleration factor 1.8 from accelerated lifetime data. Device performance is shown in Table 2 below.

TABLE 1

| Device example layer structure | | |
|---|---|---|
| Layer | Material | Thickness [Å] |
| Anode | ITO | 750 |
| HIL | HAT-CN | 100 |
| HTL | HTM | 450 |
| Green EML | HH:EH 40%:GD1 10% | 400 |
| ETL | Liq: ETM 40% | 350 |
| EIL | Liq | 10 |
| Cathode | Al | 1,000 |

TABLE 2

| Device Performance of Examples 1 and CE1 | | | | | | |
|---|---|---|---|---|---|---|
| | | | Maximum | At 1,000 nits | | |
| Example | E-Host | Color | emission wavelength [nm] | Voltage [V] | LE [%] | $LT_{95\%}$ [%] |
| Example 1 | EH1 | green | 527 | 2.8 | 100% | 130% |
| CE 1 | EH2 | green | 527 | 2.8 | 100% | 100% |

It can be seen here that the inventive compound EH1 (Example 1) has 30% longer LT vs. comparative compound EH2 while maintaining all other properties. This improvement is above any value that could be attributed to experimental error and the observed improvement is significant. Based on the fact that the Inventive Compound has a similar structure as the Comparative Compound with the only difference being the additional phenyl ring, the significant performance improvement observed in the above data was unexpected.

Premixture PM-1: Compound A1 and Compound B1 were provided at a weight ratio of 1:1, physically mixed, grinded and loaded into an evaporation source. The premixed compositions were thermally co-evaporated at a rate of 2 Å/s in a vacuum chamber under a pressure less than $10^{-7}$ Torr, and deposited onto glass substrates. The substrates were replaced continuously after deposition of 500 Å of film without stopping the deposition and cooling the source. The compositions of films were analyzed by high-performance liquid chromatography (HPLC) and the results are shown in Table 3.

TABLE 3

HPLC composition (%) of sequentially deposited films form a premixture (PM-1) comprising Compound A1 and Compound B1 with weight ratio 1:1. HPLC Conditions: C18 reverse column, 100% acetonitrile as mobile phase, detection wavelength 254 nm. Due to different absorption coefficients, the HPLC composition may or may not agree with the weight ratio.

| | A1 | B1 |
|---|---|---|
| Plate1 | 50.0 | 50.0 |
| Plate2 | 48.3 | 51.7 |
| Plate3 | 48.1 | 51.9 |
| Plate4 | 47.8 | 52.2 |
| Plate5 | 48.1 | 51.9 |
| Plate6 | 48.1 | 51.9 |
| Plate7 | 48.6 | 51.4 |
| Plate8 | 49.0 | 51.0 |
| Plate9 | 49.7 | 50.3 |

A1

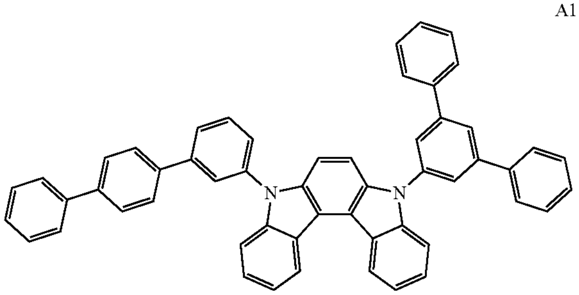

-continued

B1

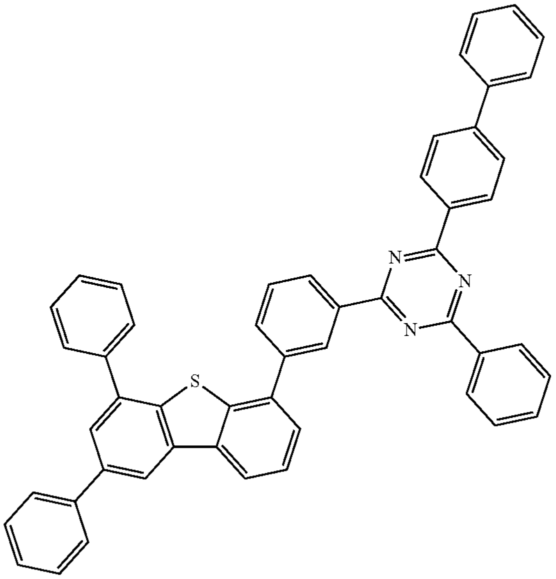

What is claimed is:

1. A compound having a structure of Formula I:

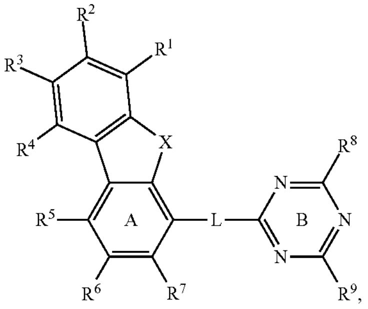

wherein:

each of $R^1$ to $R^7$ is independently a hydrogen or a substituent selected from the group consisting of phenyl, and a system consisting of two to ten phenyl groups connected to each other;

at least two of $R^1$ to $R^7$ are not hydrogen;

if $R^1$ and $R^3$ are not hydrogen, then at least one of the following is true: 1) $R^1$ and $R^3$ are different from each other; or 2) at least one of $R^1$ or $R^3$ is an unsubstituted phenyl;

if one of the at least two $R^1$ to $R^7$ that is not hydrogen is the system consisting of two to ten phenyl groups connected to each other, then the phenyl group directly bonded to the structure of Formula I having X bonds to exactly one phenyl group;

$R^8$ and $R^9$ are each independently selected from the group consisting of phenyl, and a system consisting of two to ten phenyl groups connected to each other;

X is selected from the group consisting of O, S, and Se; and

L is selected from the group consisting of direct bond and

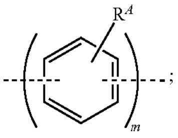

wherein m is an integer from 1 to 5, and $R^A$ is a hydrogen or a substituent selected from the group consisting of aromatic and heteroaromatic rings; and subject to the following provisos i) to iv):

i) if L is biphenyl, one phenyl of the biphenyl bonds to ring A and the other phenyl bonds to ring B;

ii) if X is O, then least one of $R^1$, $R^3$, or $R^5$ is H;

iii) if X is S, then at least one of $R^1$ or $R^6$ is H but if $R^6$ is H and $R^1$ is not H, then at least one of $R^3$ or $R^5$ is H; and iv) the following structures are excluded

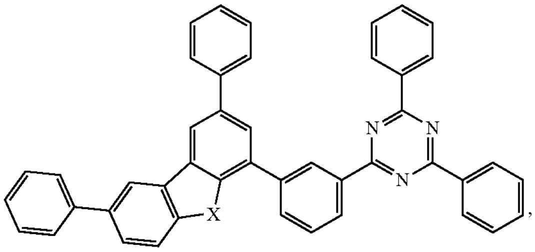

, and

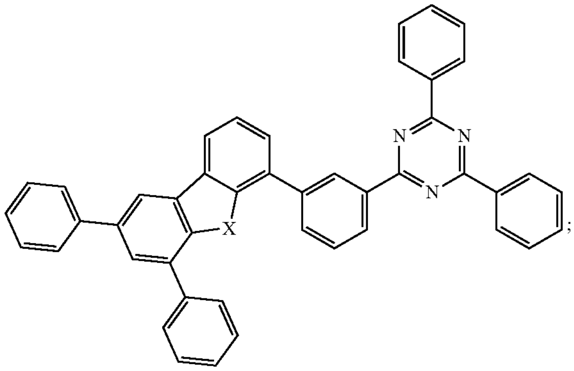

;

and wherein at least one of the following conditions 1) to 4) is true:

1) M is 1, ring A and ring B are meta to each other, and $R^1$ to $R^9$ comprise a total of at least 6 phenyl groups;

2) at least one of $R^1$ to $R^4$ is not hydrogen and at least one of $R^5$ to $R^7$ is not hydrogen;

3) $R^8$ is phenyl and $R^9$ is biphenyl; or

4) X is S.

2. The compound of claim 1, wherein m is 1, ring A and ring B are meta to each other, and $R^1$ to $R^9$ comprise a total of at least 6 phenyl groups.

3. The compound of claim 1, wherein at least one of $R^1$ to $R^4$ is not hydrogen and at least one of $R^5$ to $R^7$ is not hydrogen.

4. The compound of claim 1, wherein $R^8$ is phenyl and $R^9$ is phenyl.

5. The compound of claim 1, wherein $R^8$ is phenyl and $R^9$ is biphenyl.

6. The compound of claim 1, wherein X is O.

7. The compound of claim 1, wherein X is S.

8. The compound of claim 1, wherein $R^A$ is selected from the group consisting of hydrogen, phenyl, biphenyl, and terphenyl.

9. The compound of claim 1, wherein L has a structure selected from the group consisting of a direct bond.

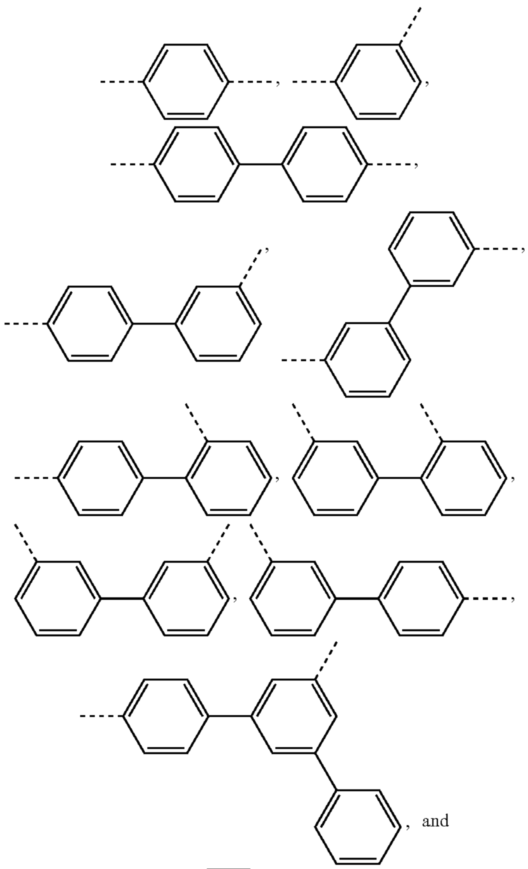

, and

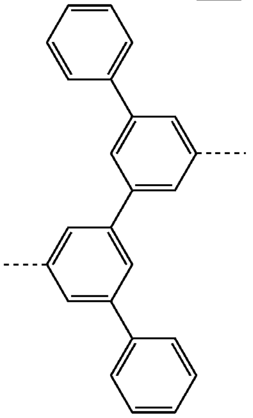

10. The compound of claim 1, wherein at least one of $R^1$ to $R^9$ comprises at least 3 phenyl groups wherein a first phenyl group bonds to the moiety containing atom X or bonds to ring B and the other two phenyl groups are bonded to the first phenyl at a meta position to each other.

11. The compound of claim 1, wherein at least one of $R^1$ to $R^9$ includes at least three phenyl groups.

12. The compound of claim 1, wherein the compound is selected from the group consisting of:

-continued
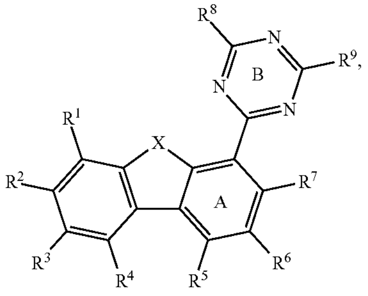
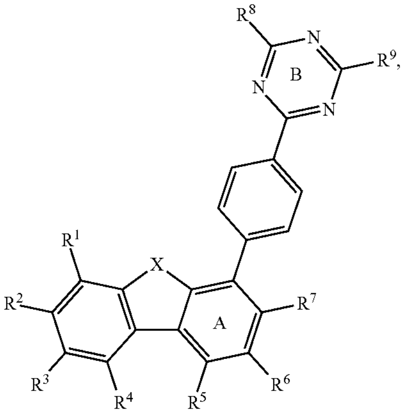
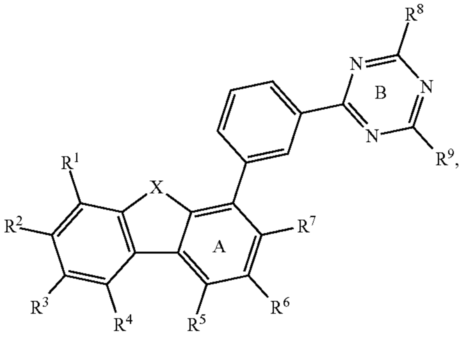
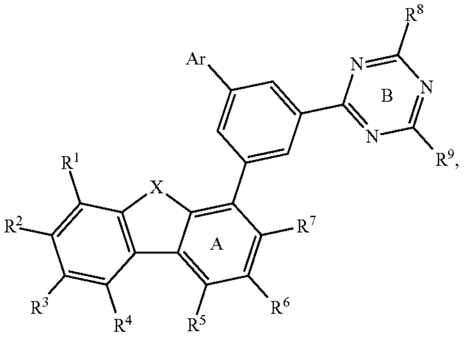
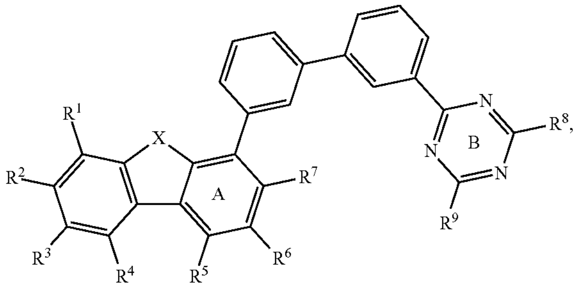
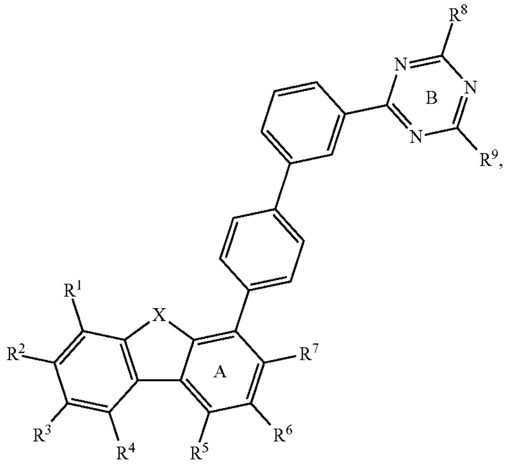
and
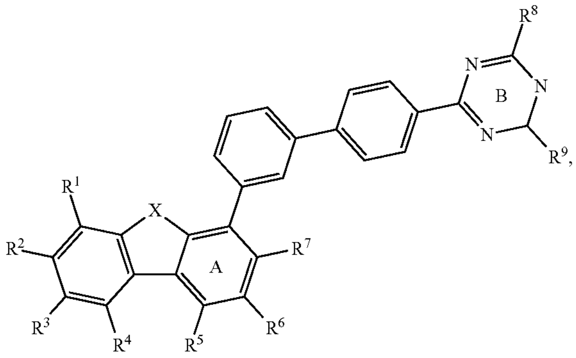
wherein Ar is an aromatic or heteroaromatic ring.
13. The compound of claim 1, wherein the compound is selected from the group consisting of:
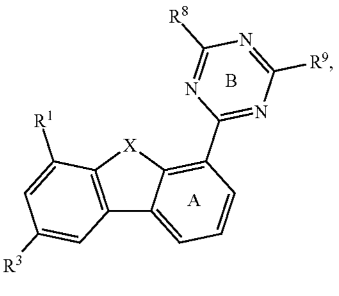
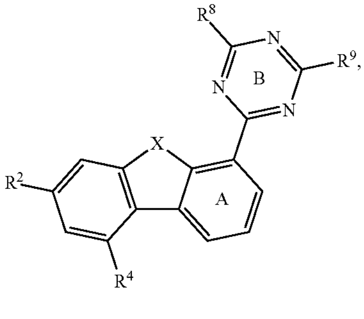

-continued
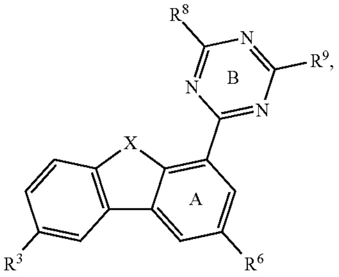
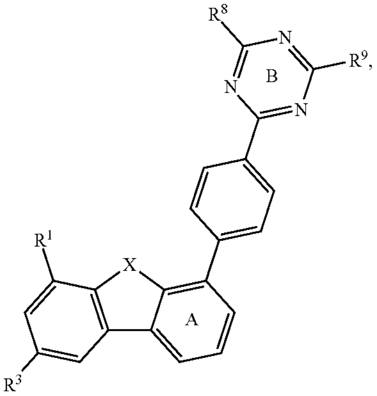
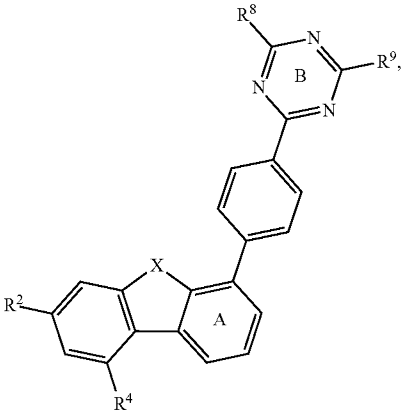
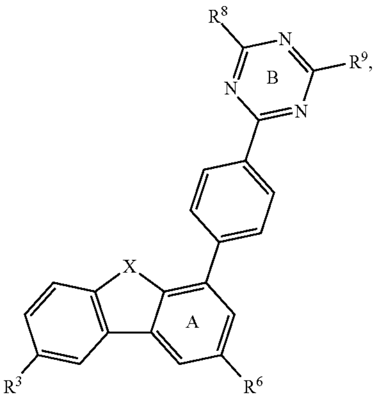
-continued
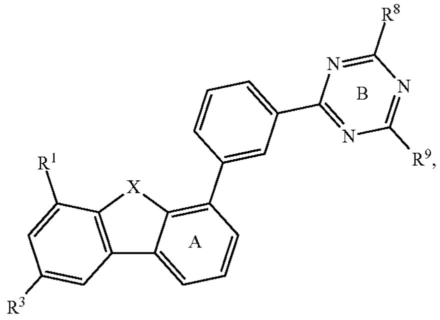
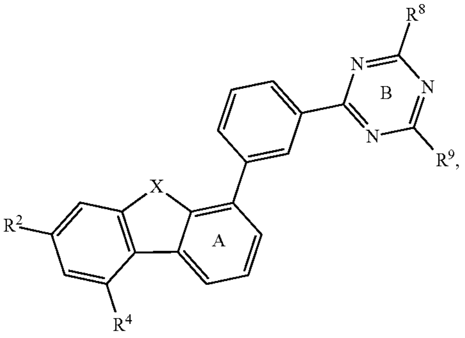
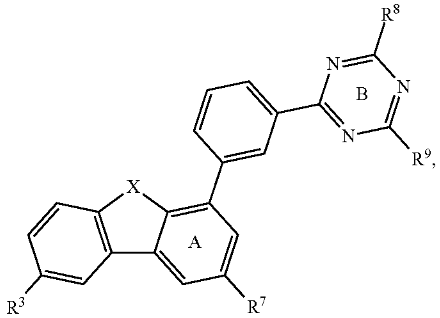
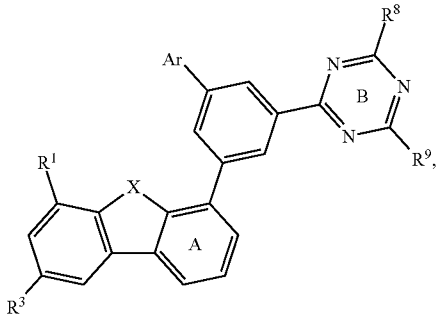
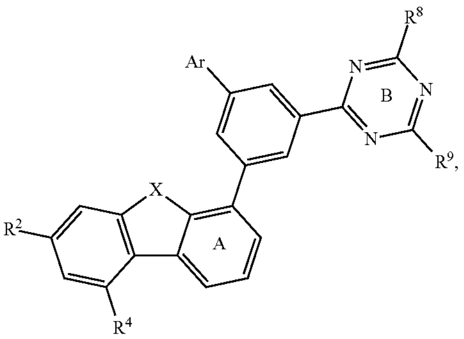

-continued
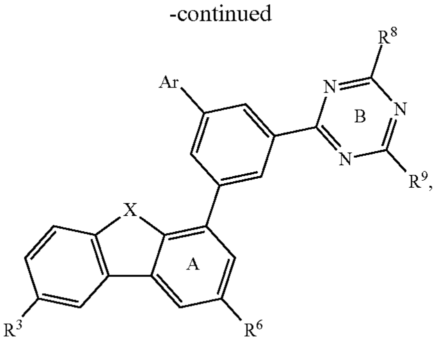
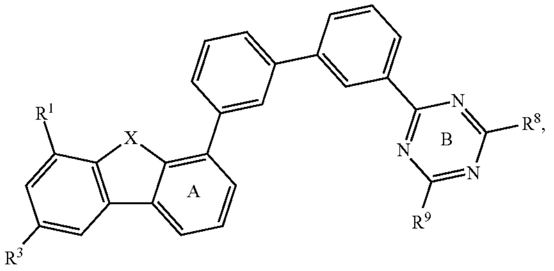
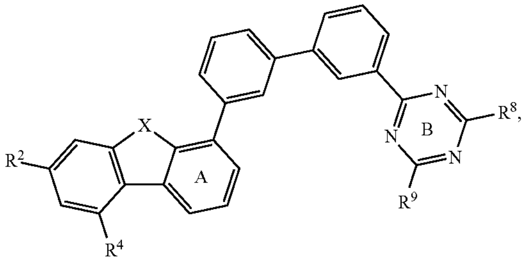
and
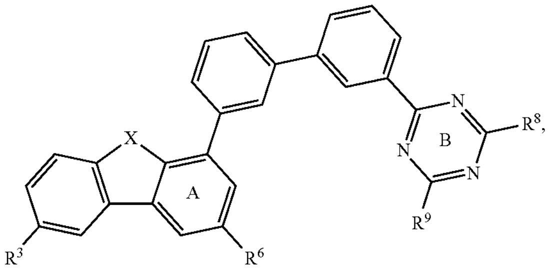
wherein Ar is an aromatic or heteroaromatic ring.
14. The compound of claim 1, wherein the compound is selected from the group consisting of:
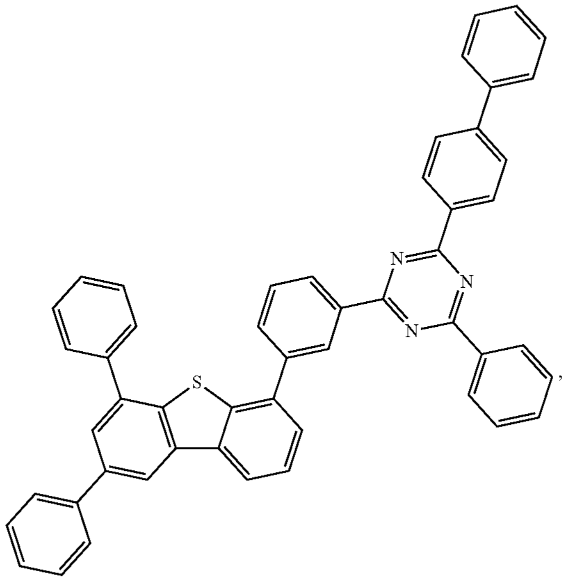
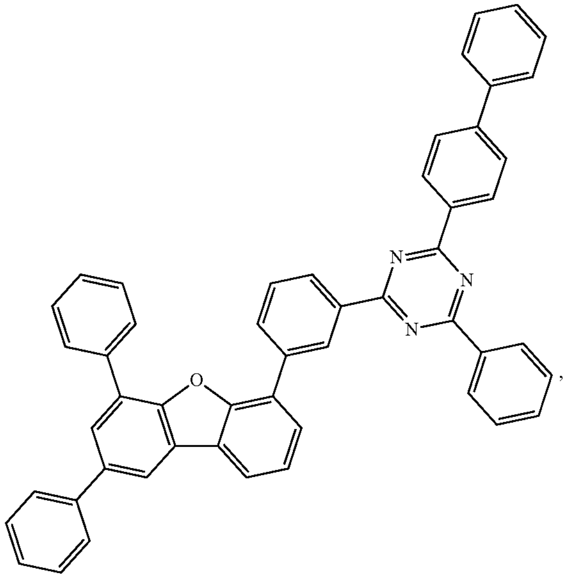
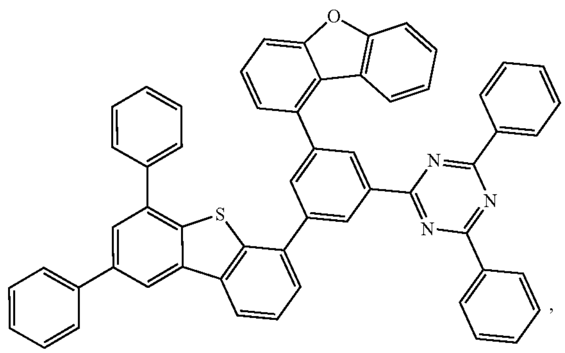

-continued
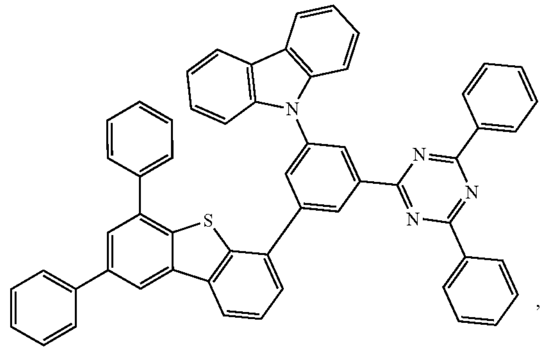
,
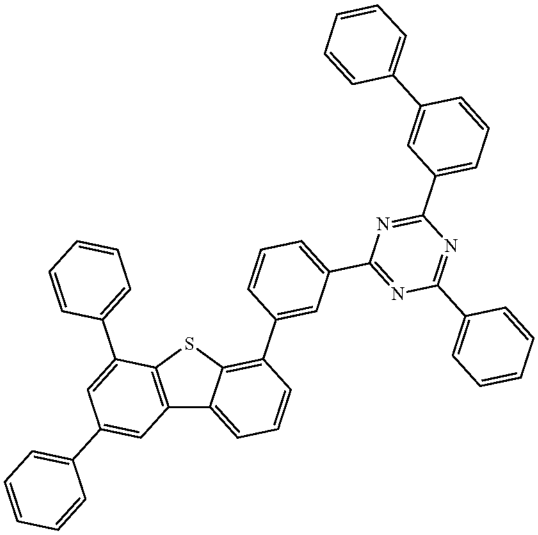
,
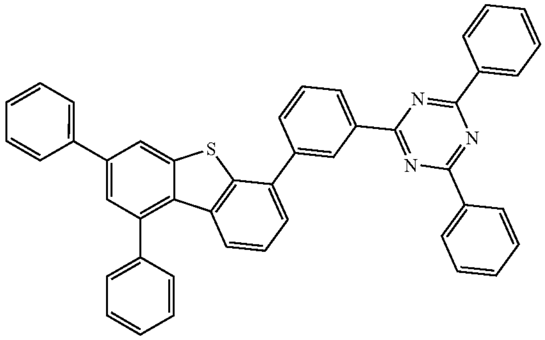
,
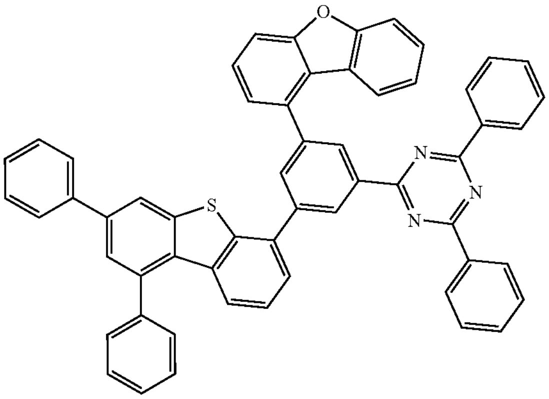
,
-continued
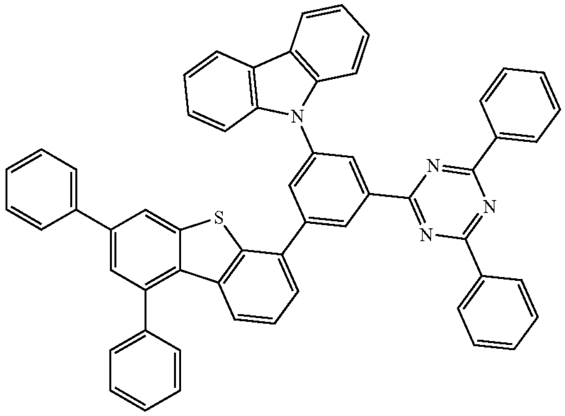
,
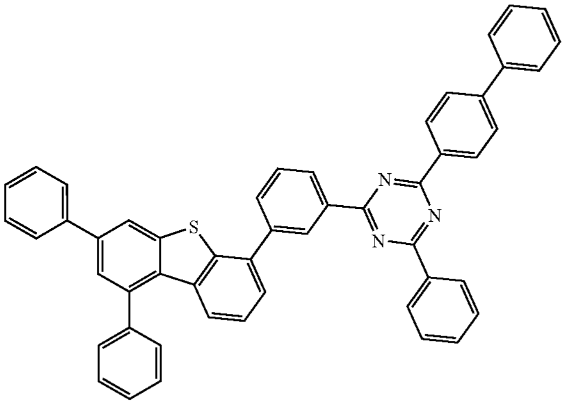
,
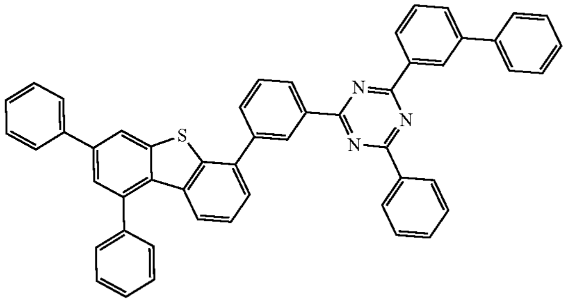
,
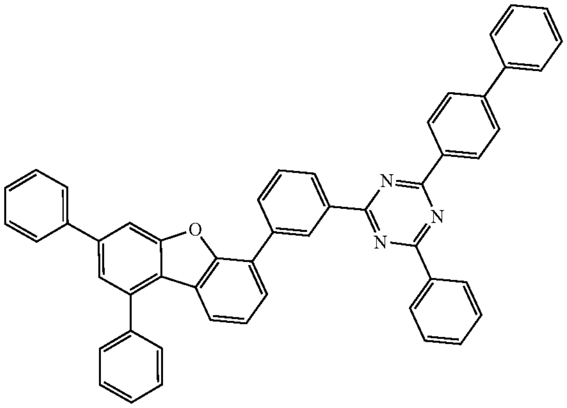
, -continued
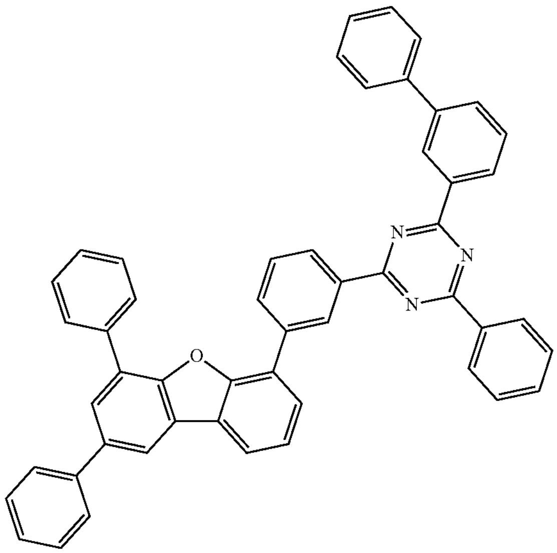
,
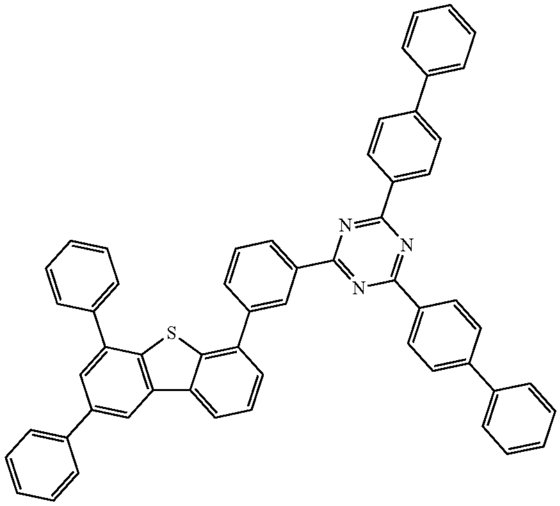
,
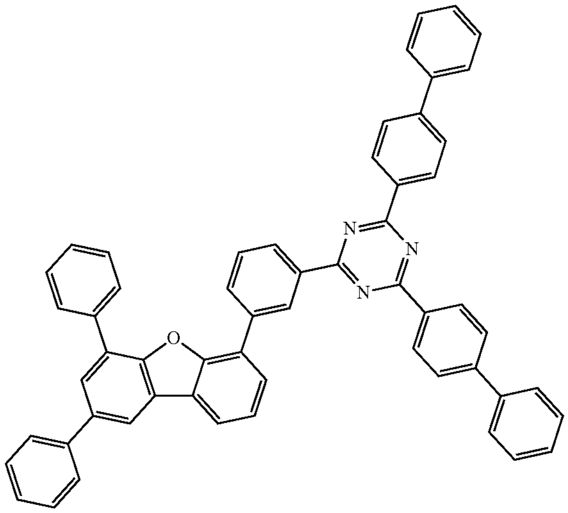
,
-continued
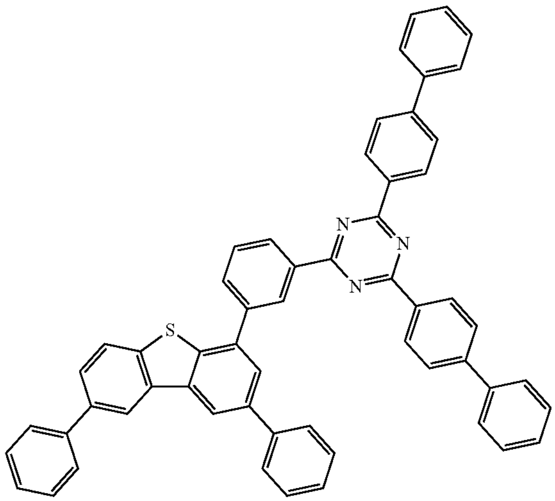
,
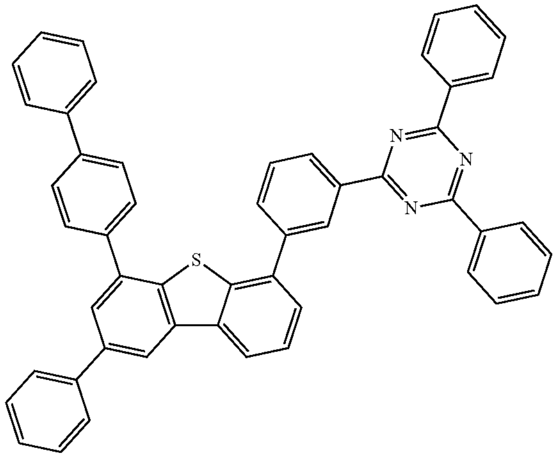
,
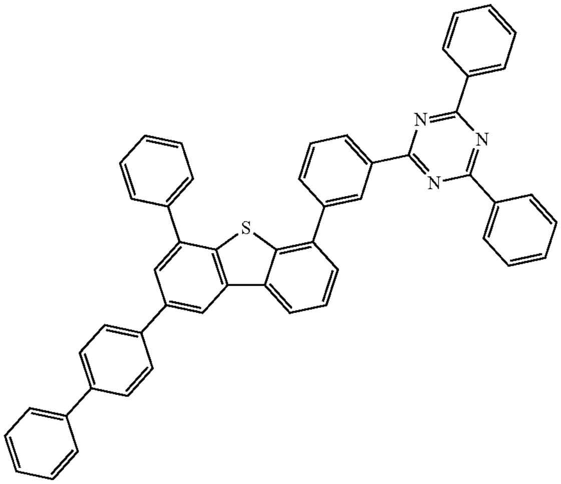
, -continued
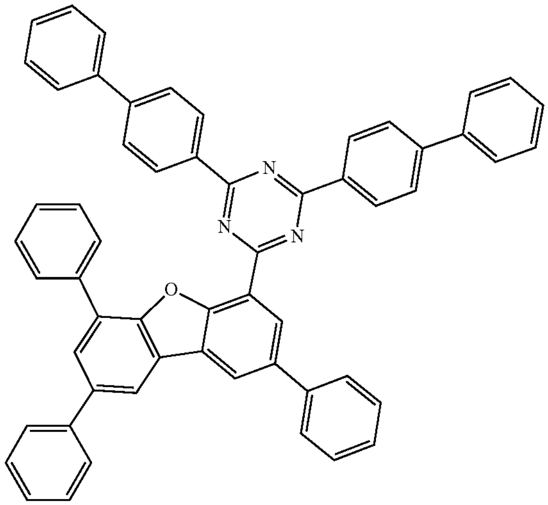
,
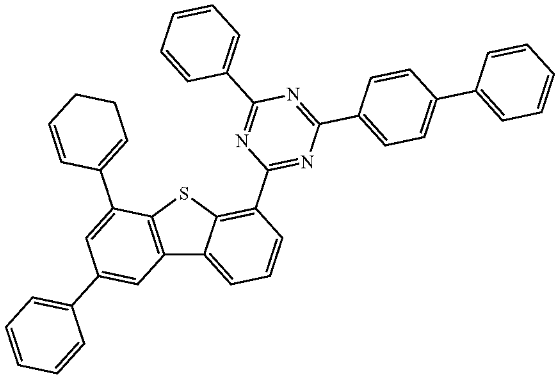
,
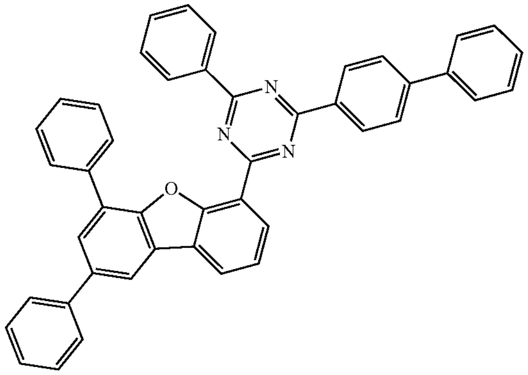
,
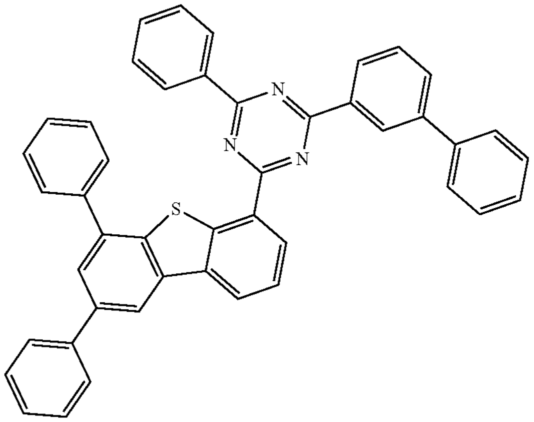
,
-continued
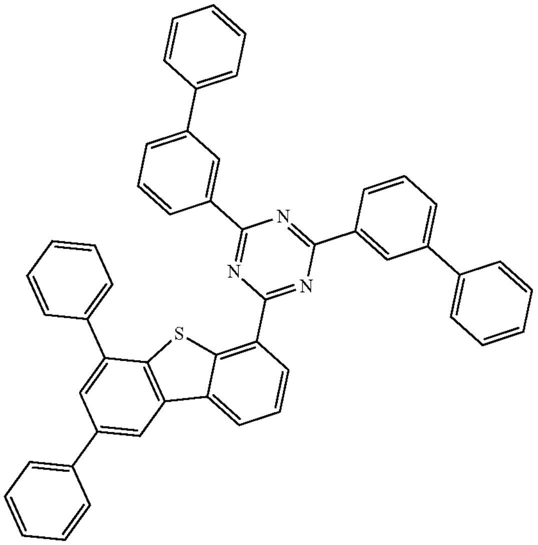
,
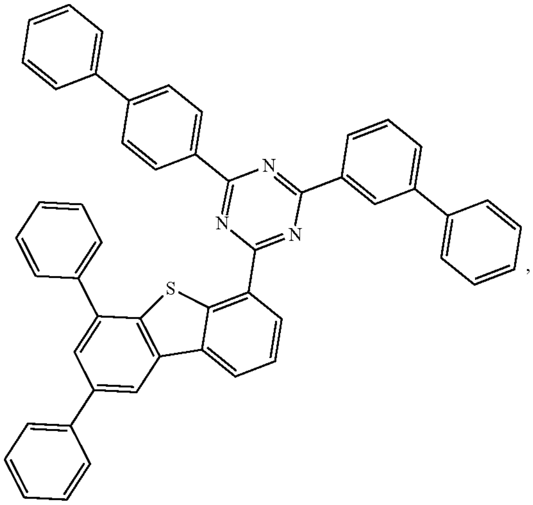
,
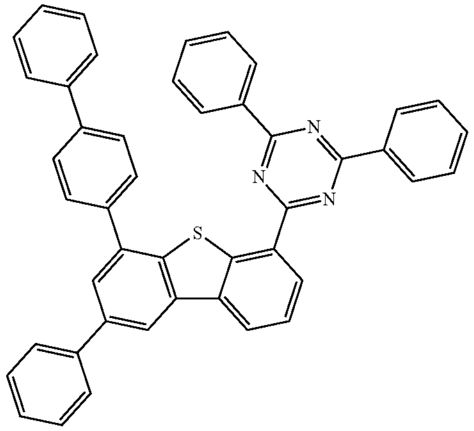
, -continued
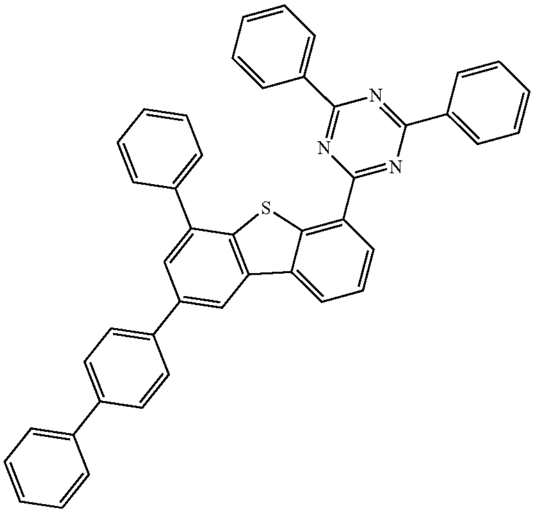
,
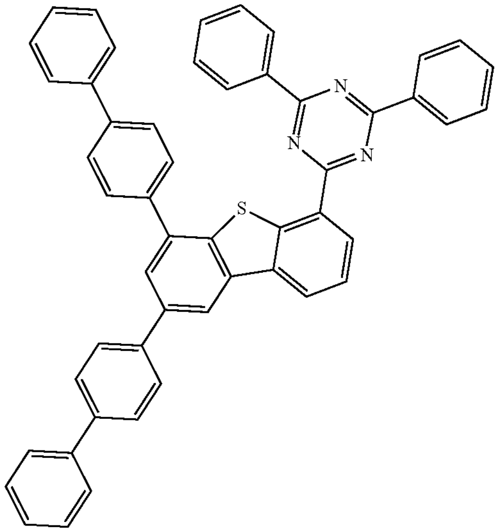
,
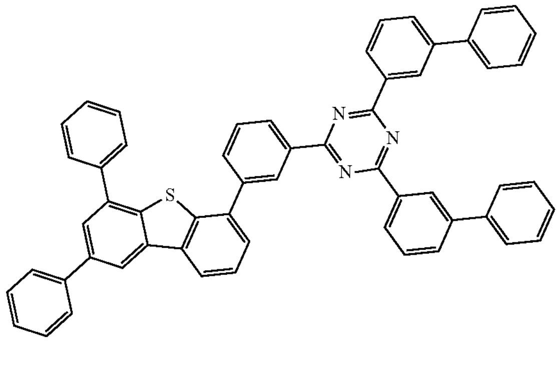
,
-continued
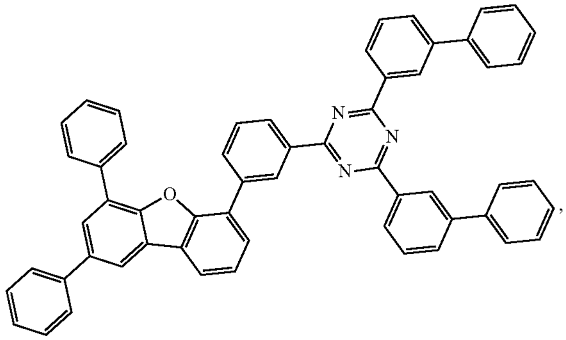
,
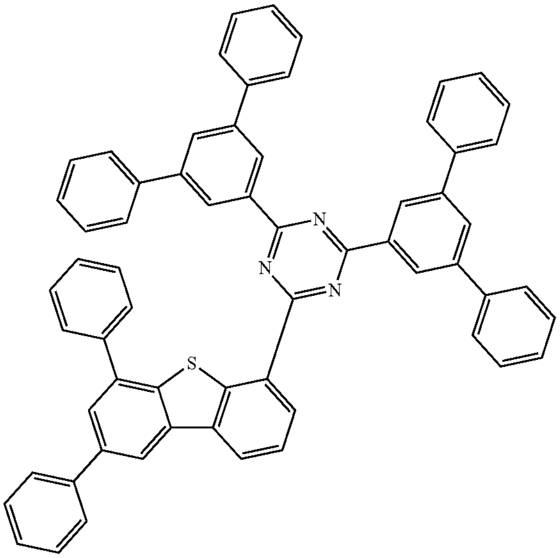
,
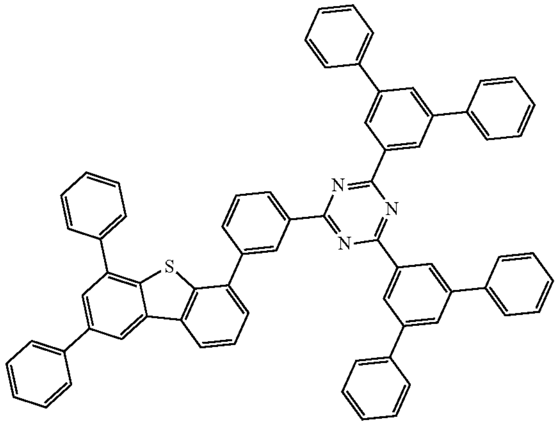
, -continued
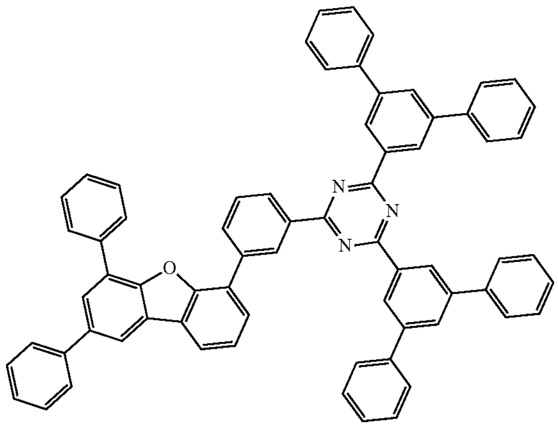
,
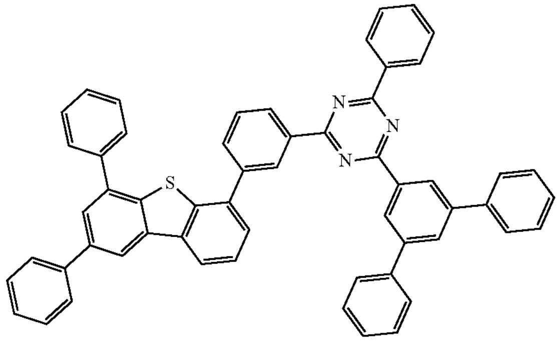
,
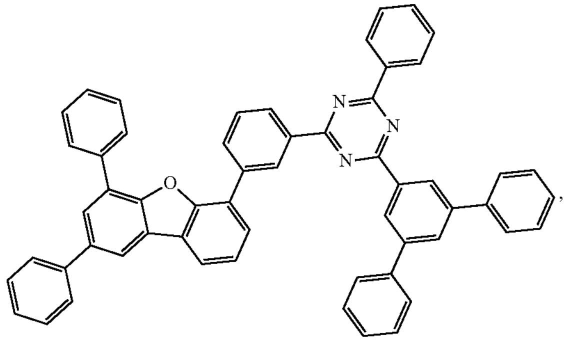
,
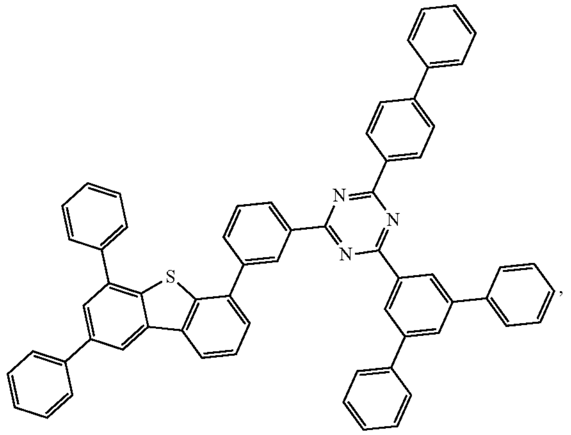
,
-continued
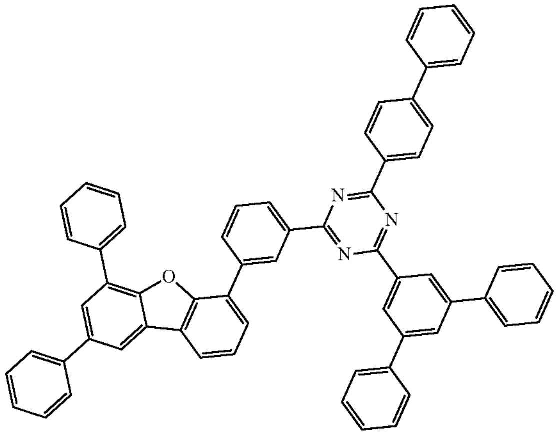
,
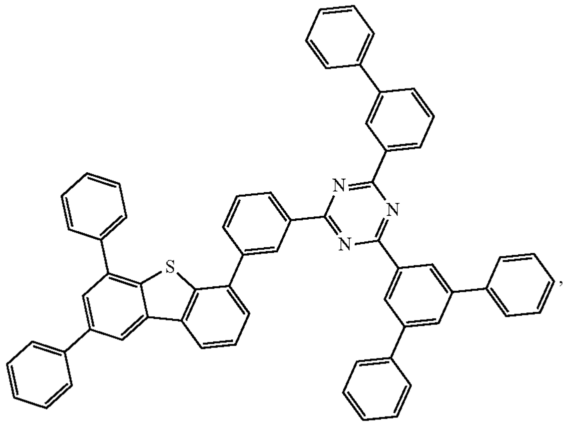
,
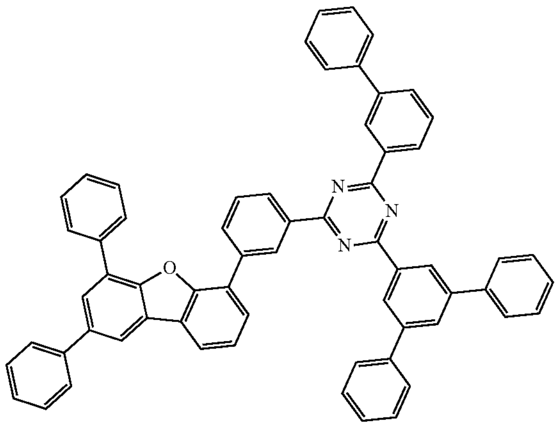
, -continued
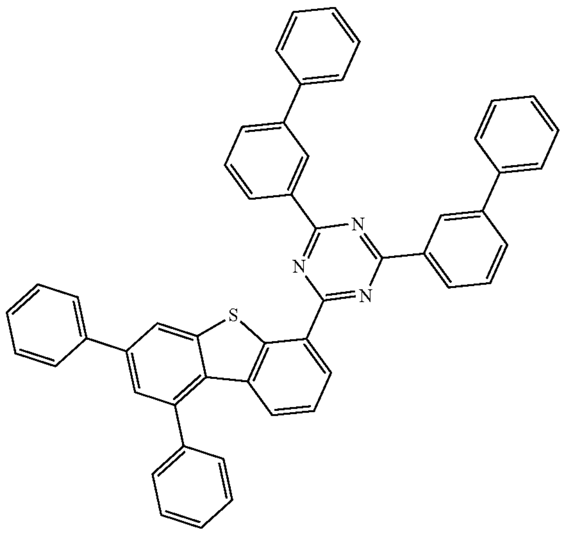
,
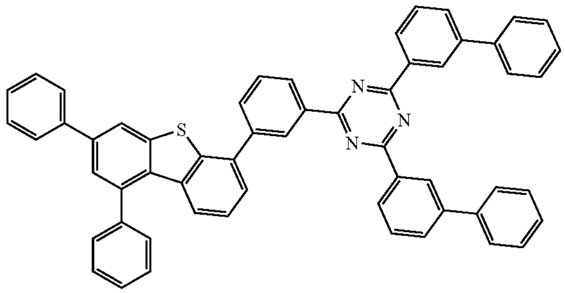
,
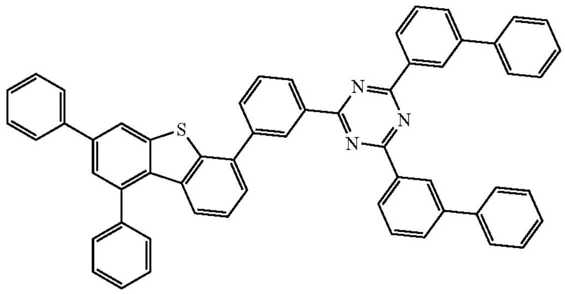
,
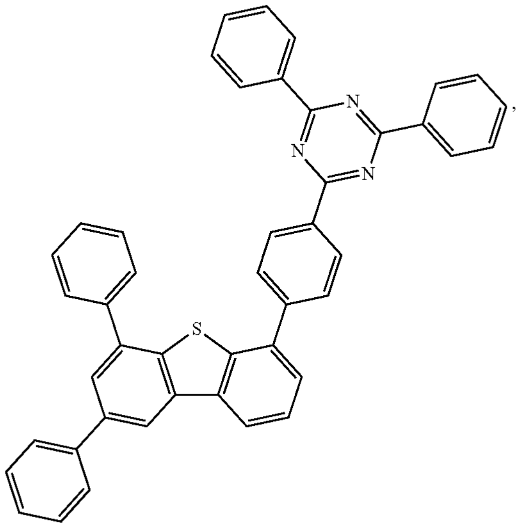
,
-continued
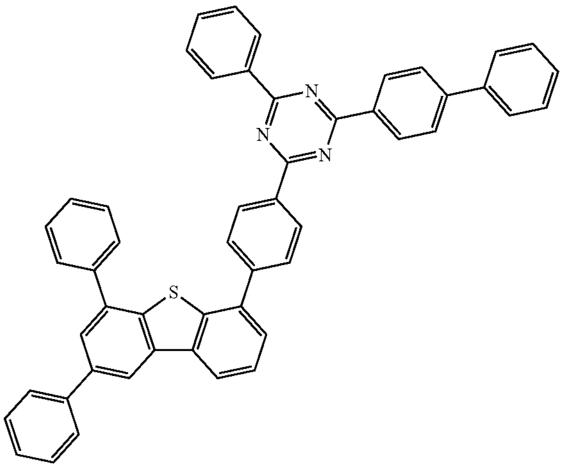
,
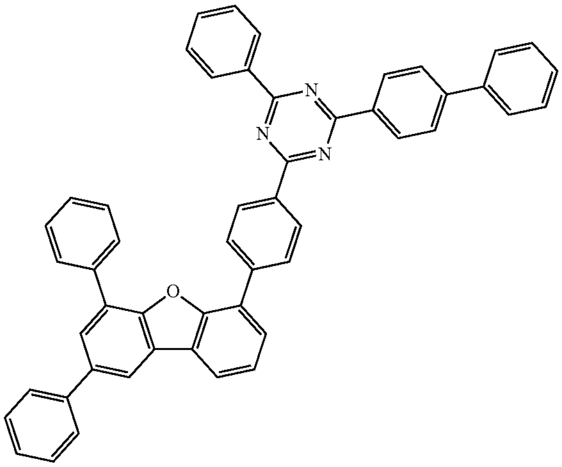
,
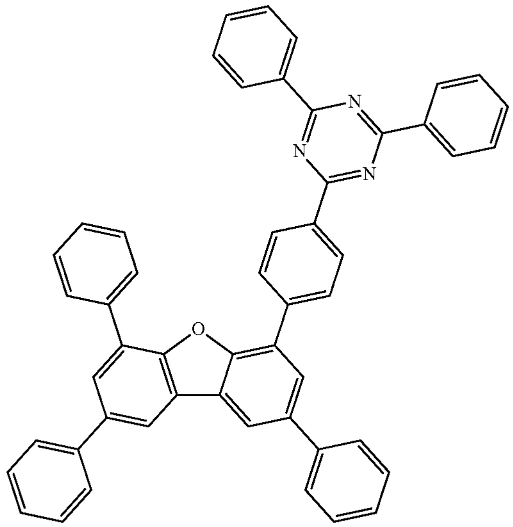
, -continued
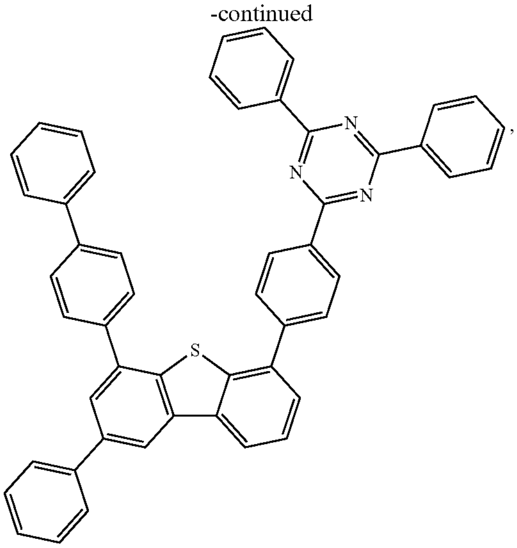
,
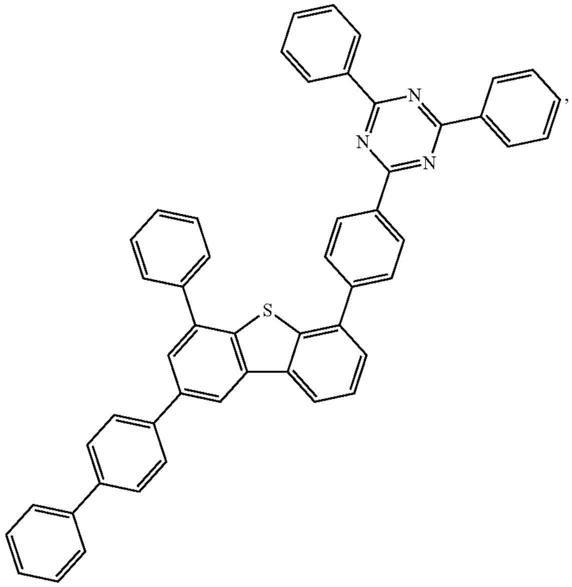
,
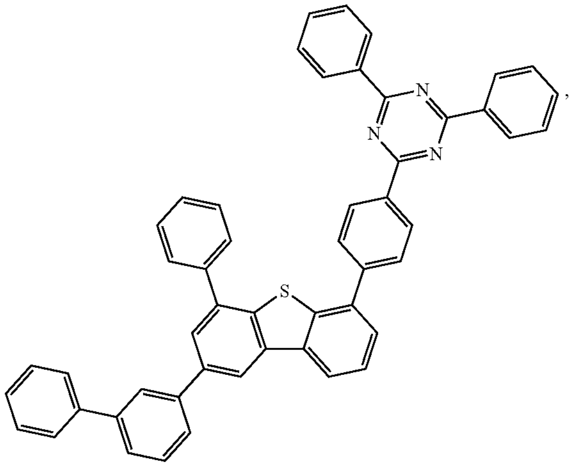
,
-continued
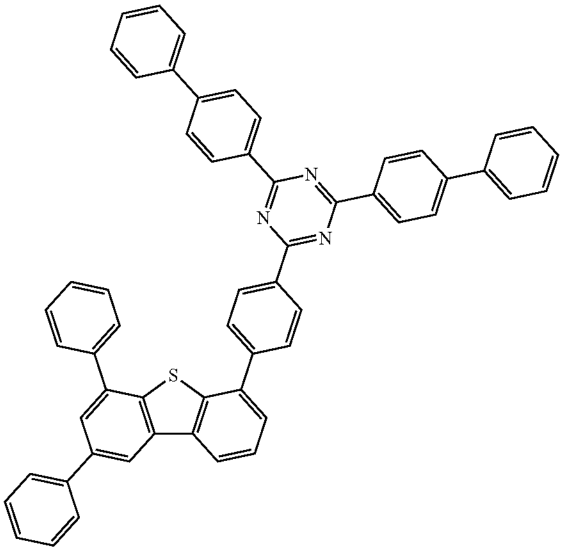
,
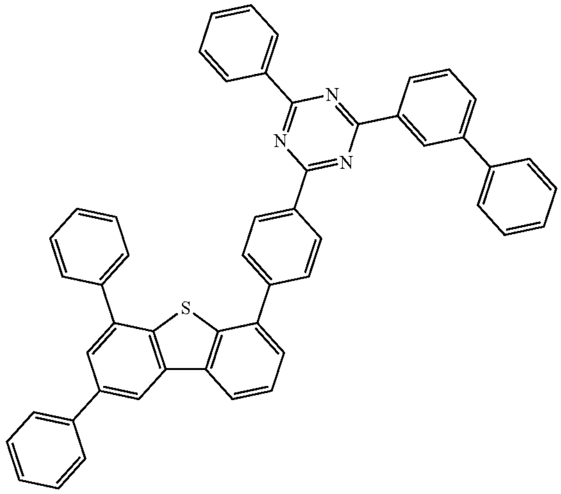
,
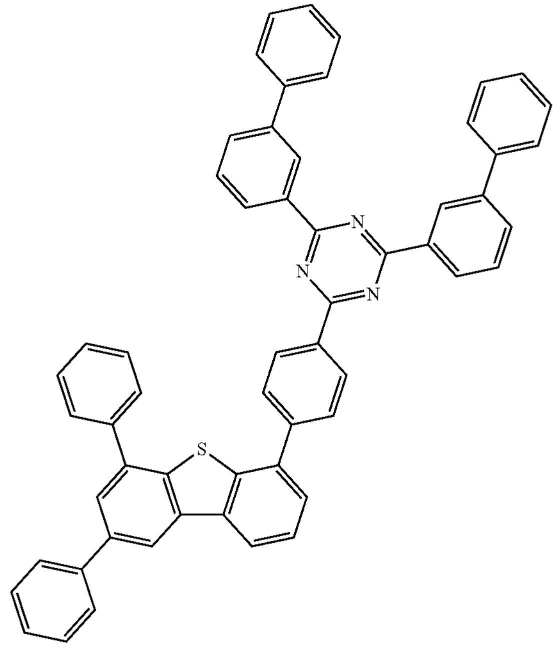
,

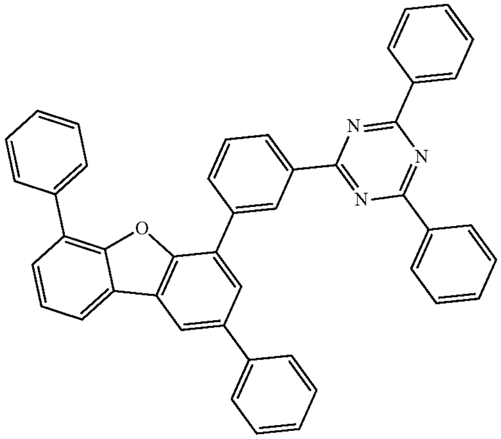
,
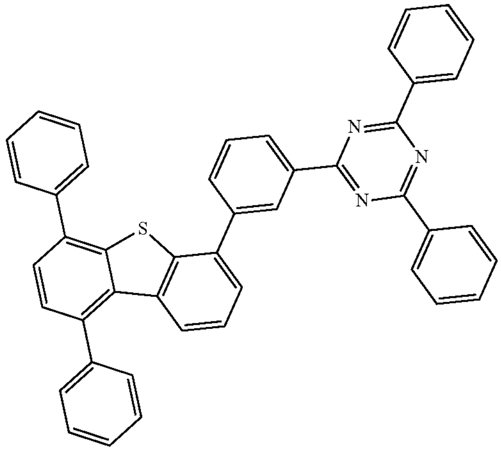
,
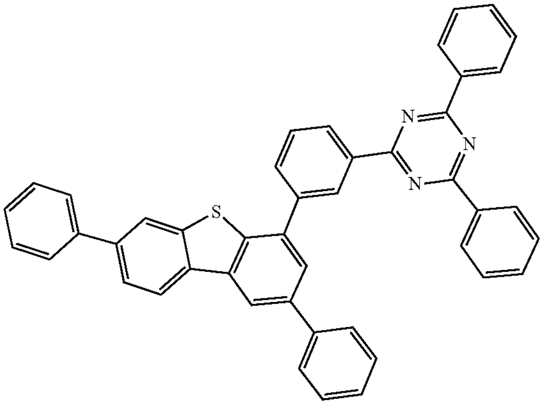
,
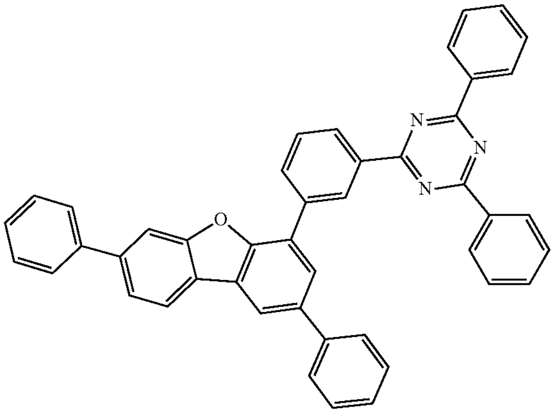
,
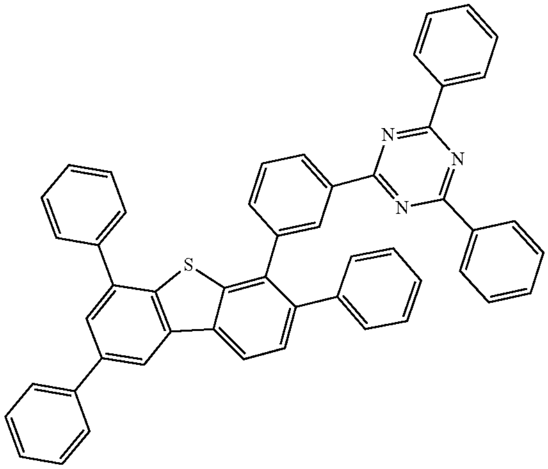
,
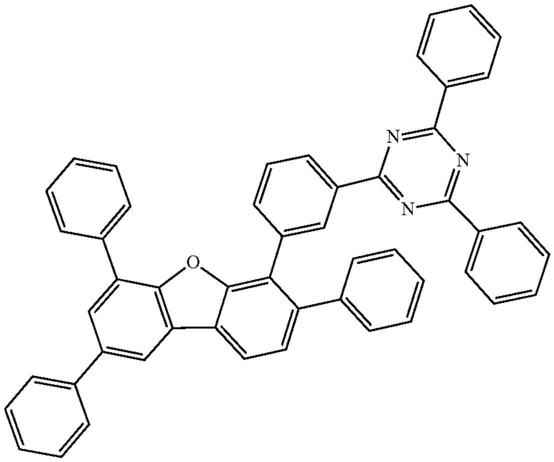
, -continued
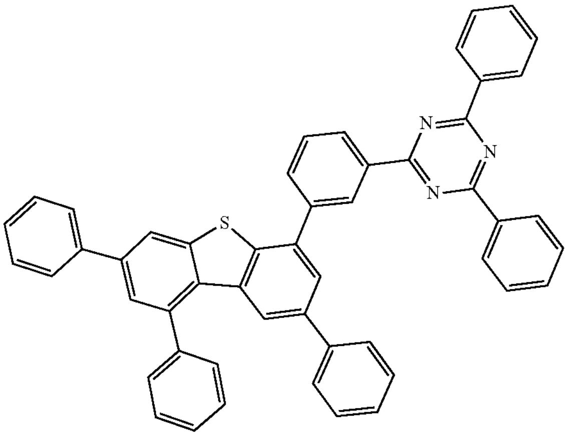
,
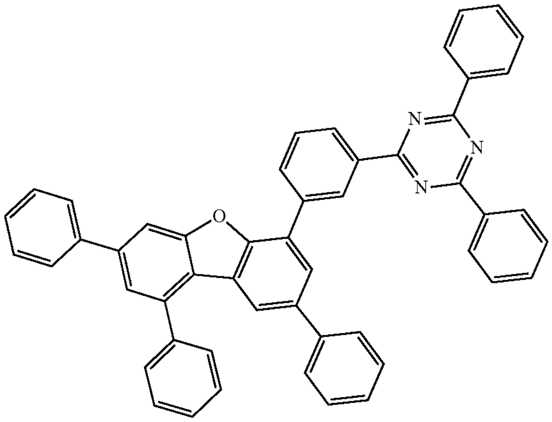
,
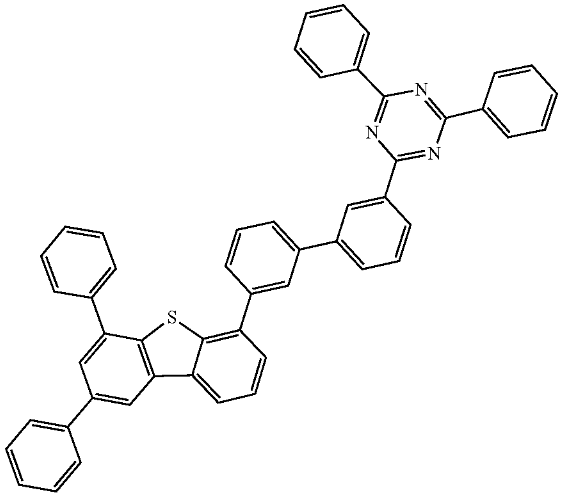
,
-continued
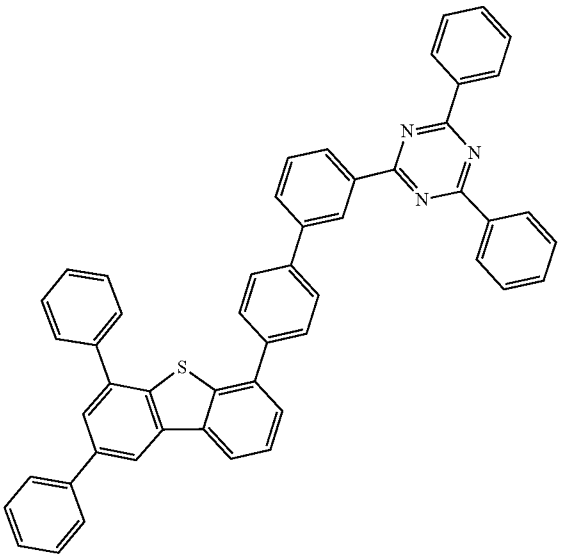
,
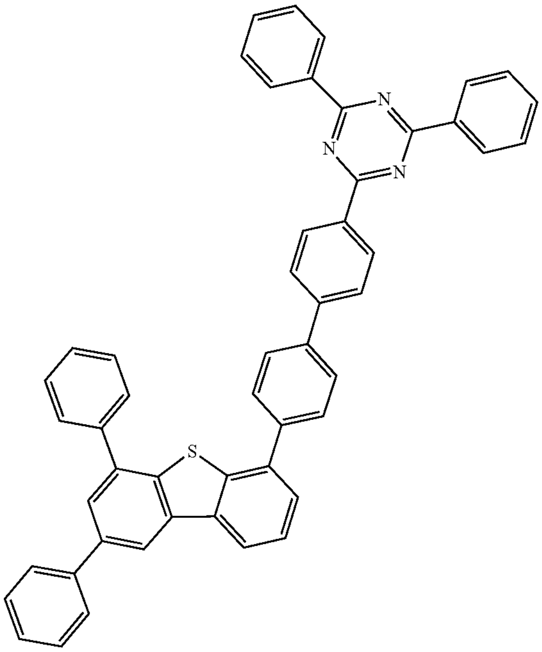
,
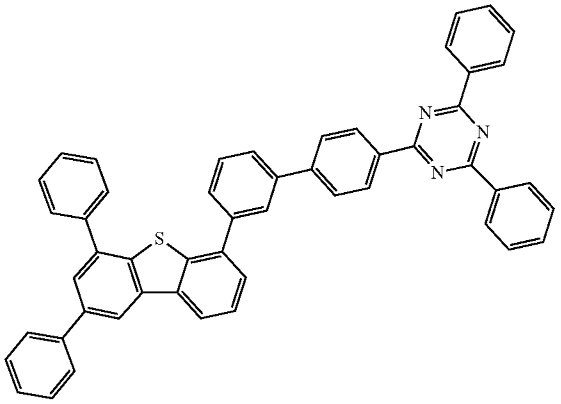
, -continued
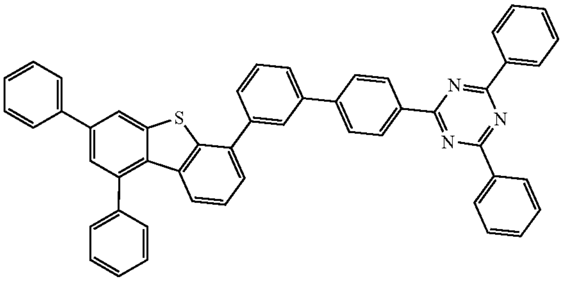
,
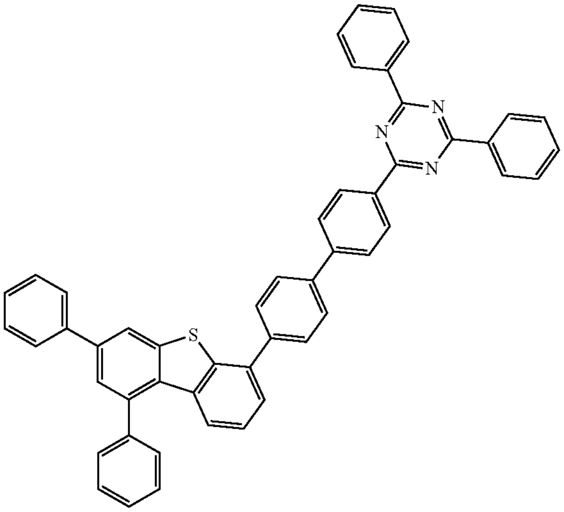
,
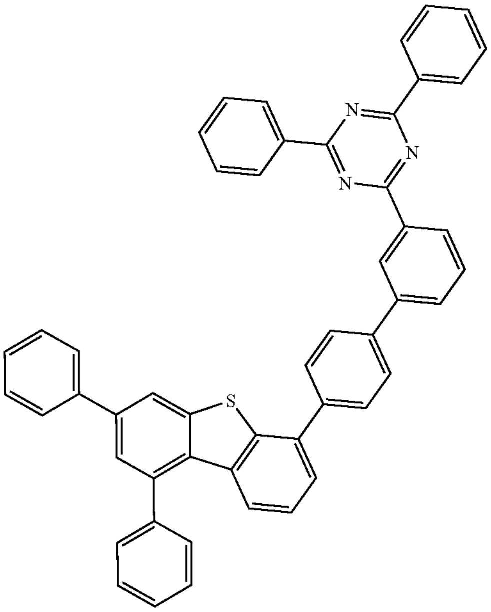
,
-continued
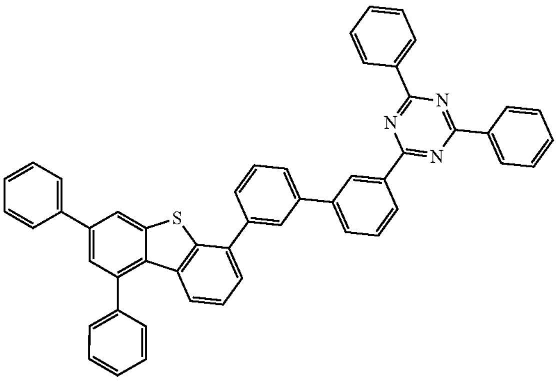
,
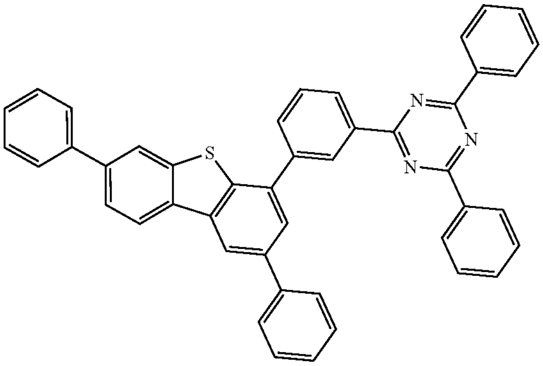
,
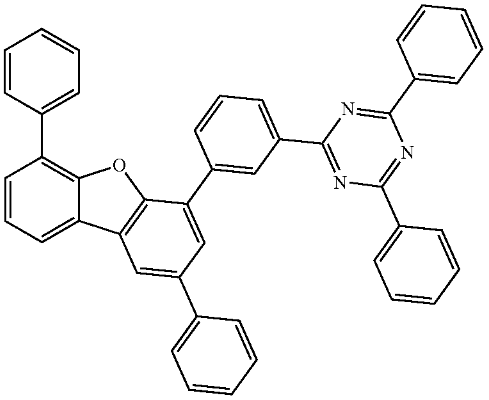
,
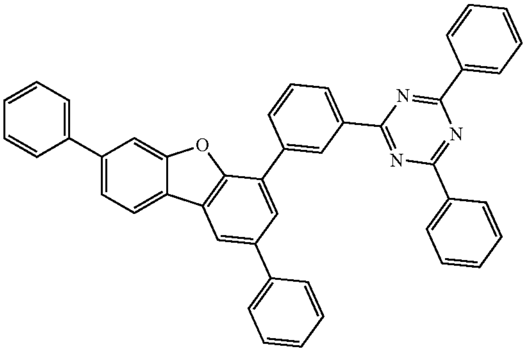
, -continued
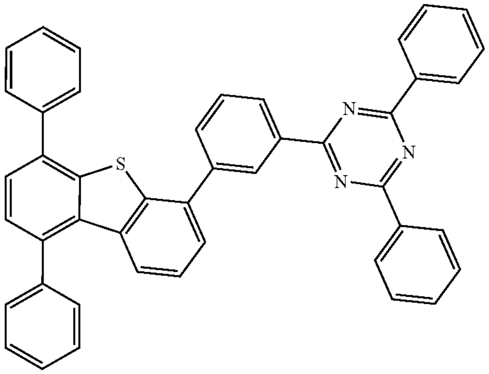
,
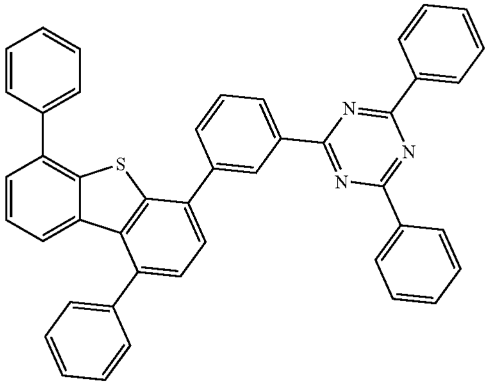
,
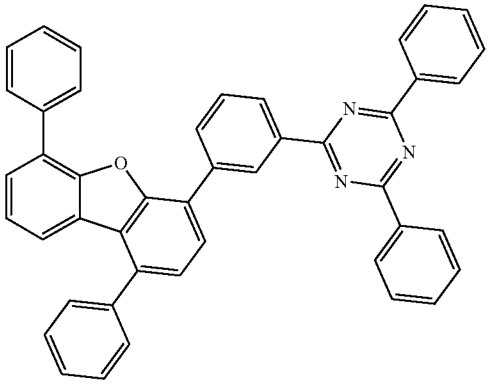
,
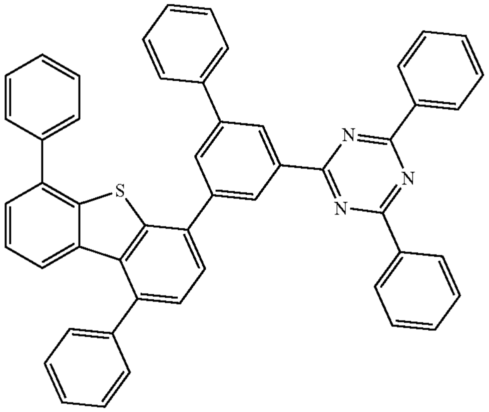
,
-continued
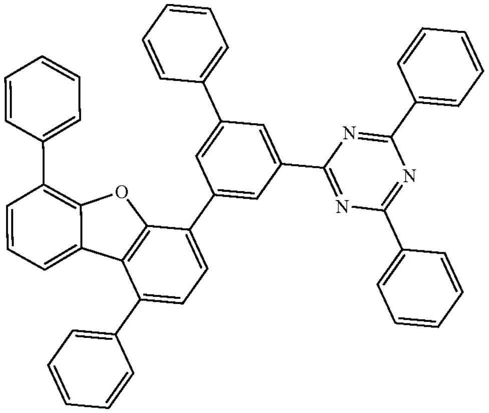
,
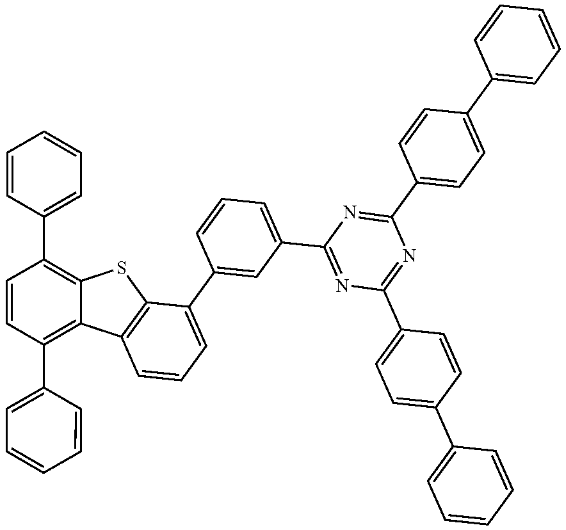
,
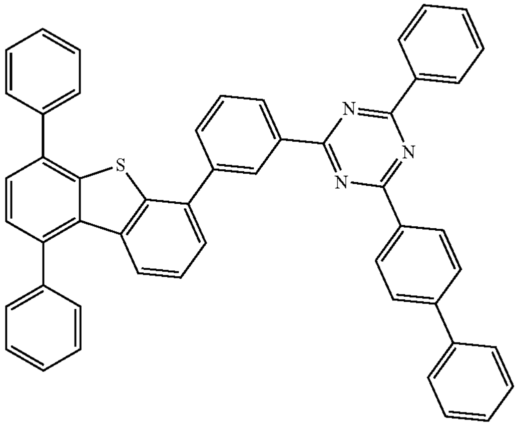
, -continued
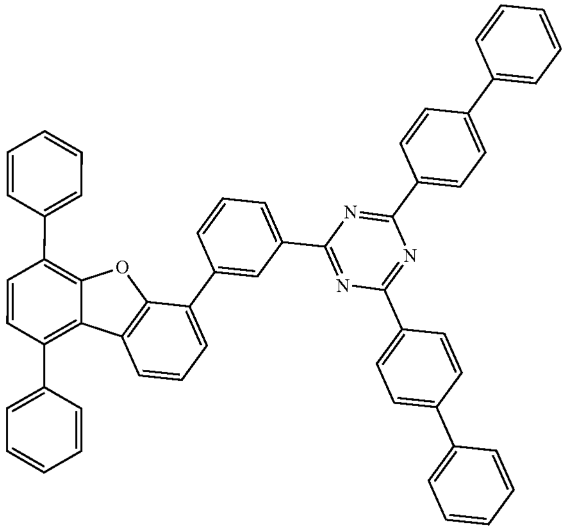
,
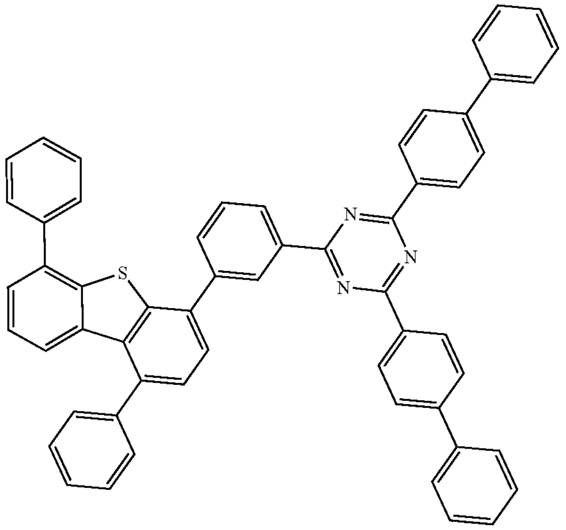
,
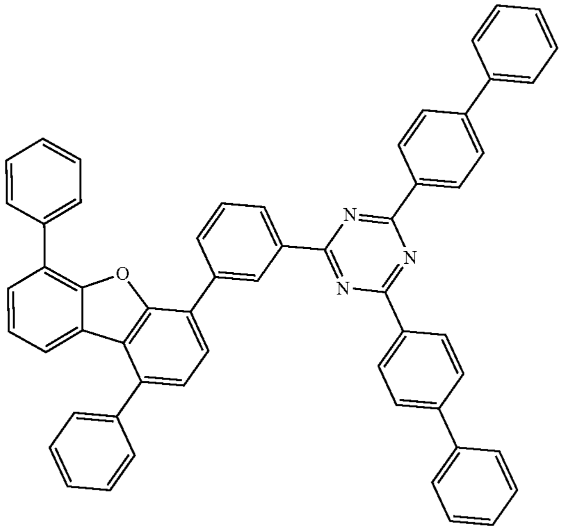
,
-continued
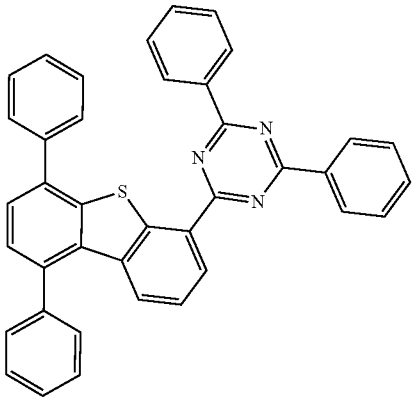
,
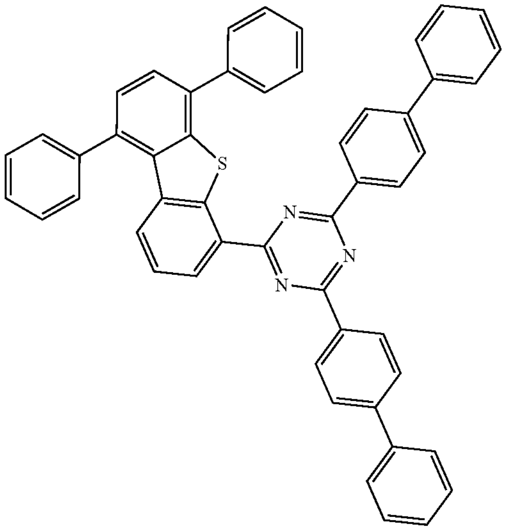
,
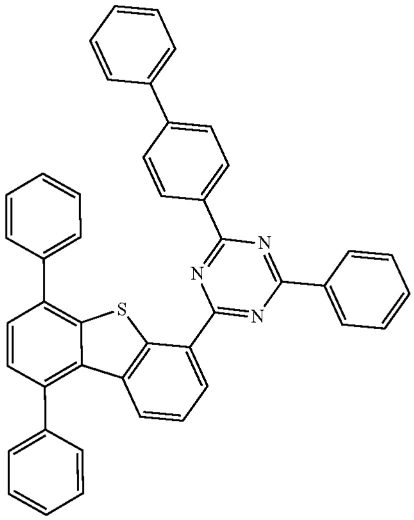
, -continued
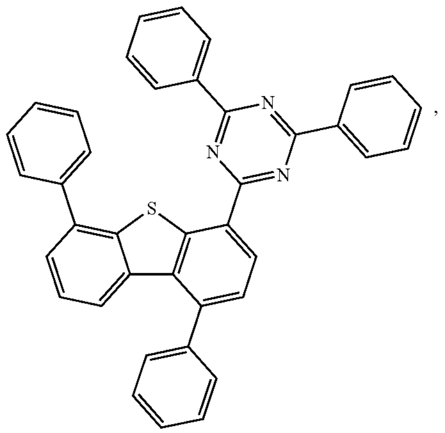
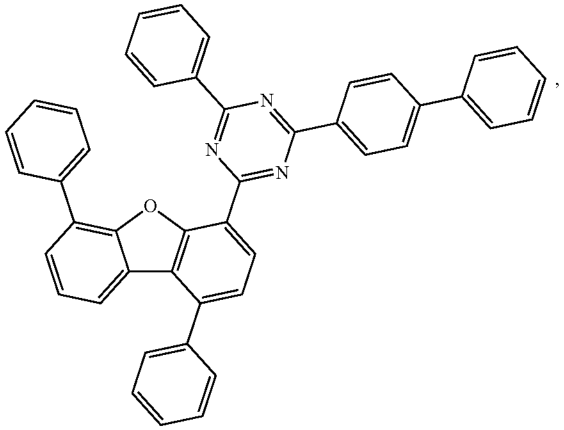
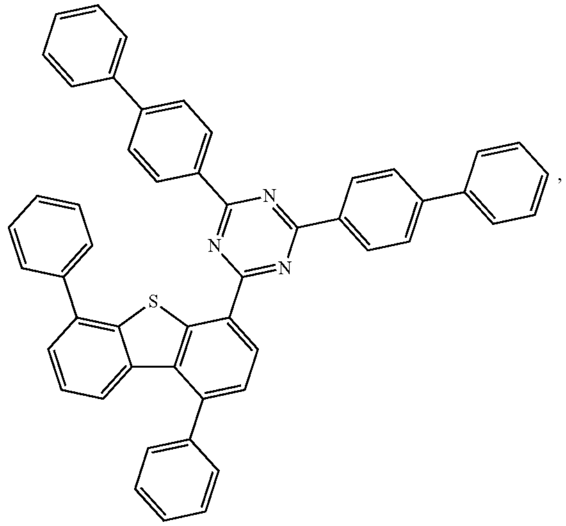
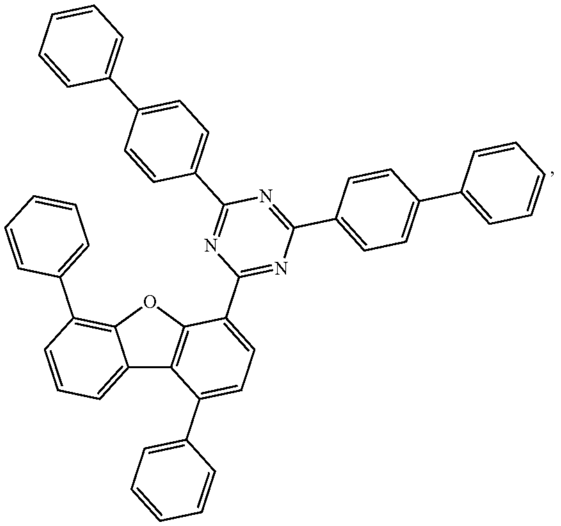
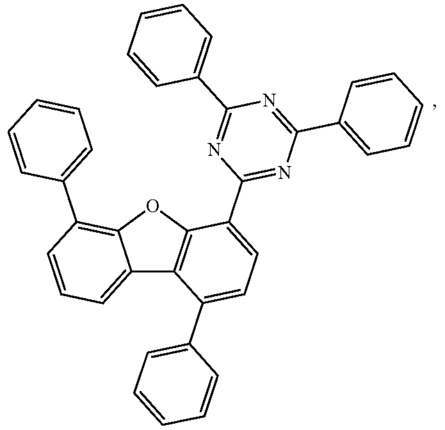
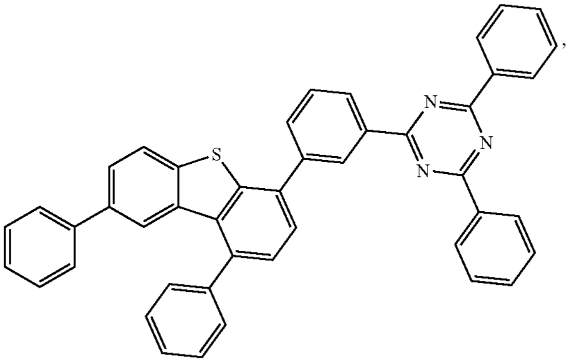
-continued -continued
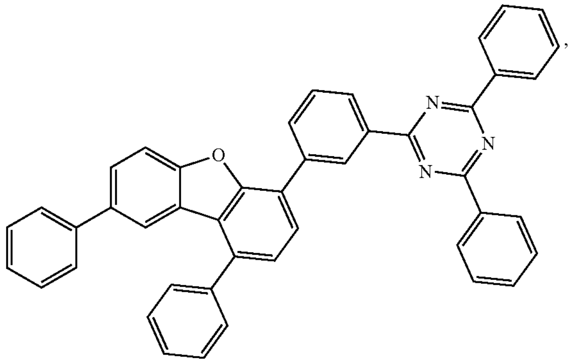
,
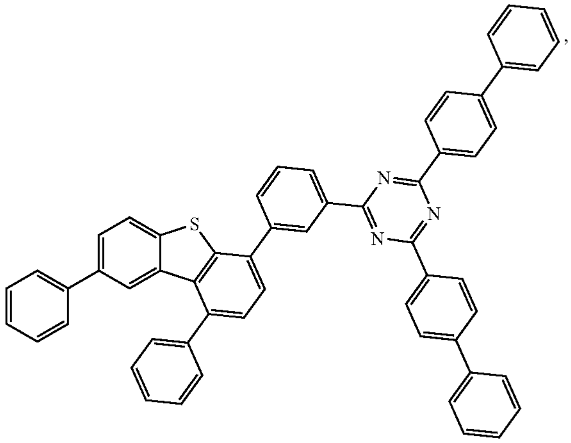
,
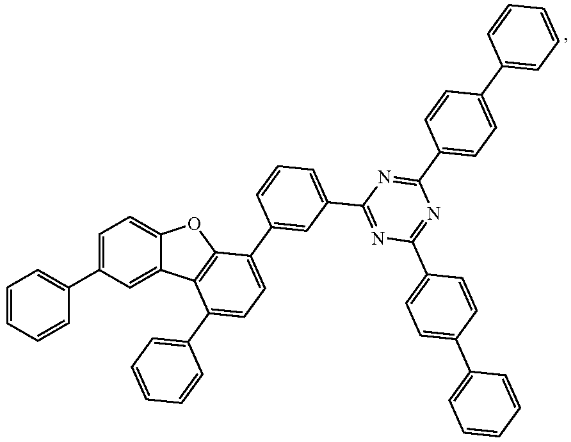
,
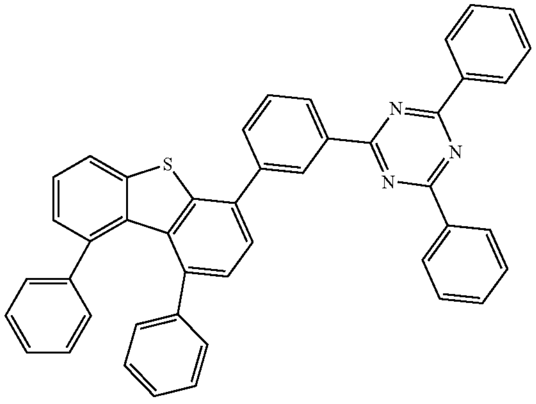
,
-continued
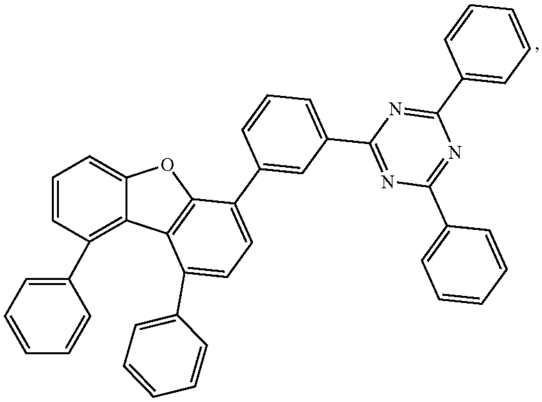
,
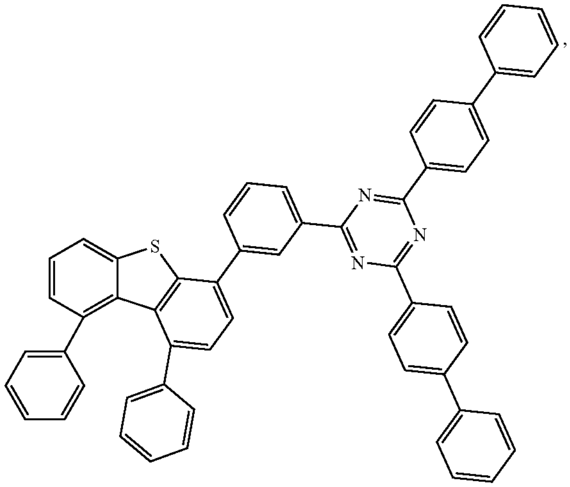
,
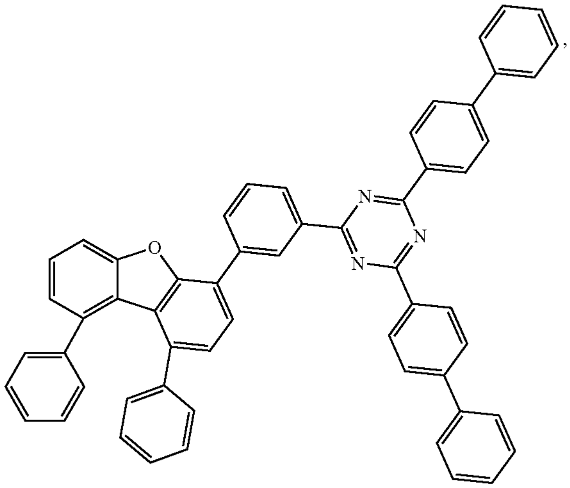
, -continued

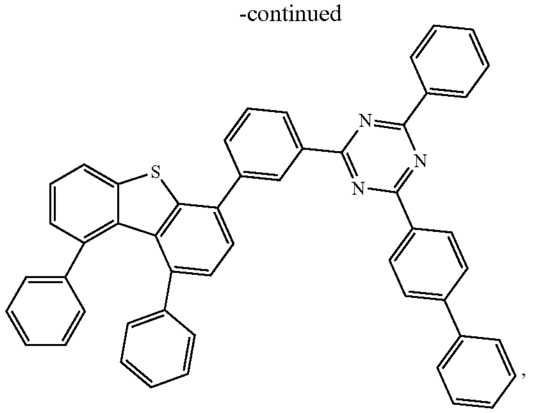

, and

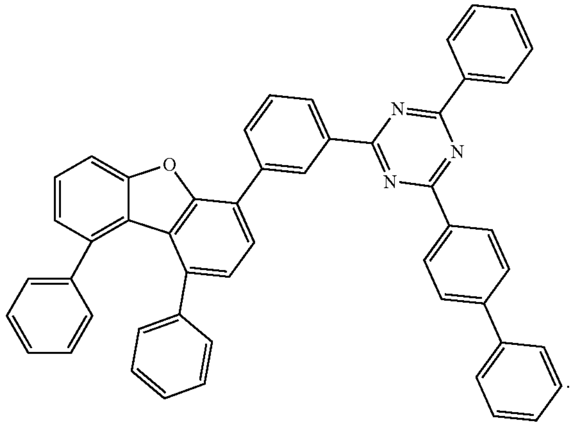

.

15. The compound of claim 1, wherein $R^1$ and $R^3$ are not hydrogen and $R^1$ and $R^3$ are different from each other.

16. The compound of claim 1, wherein $R^1$ and $R^3$ are not hydrogen and at least one of $R^1$ or $R^3$ is an unsubstituted phenyl.

17. An organic light emitting device (OLED) comprising:

an anode;

a cathode; and an organic layer disposed between the anode and the cathode, wherein the organic layer comprises a compound having a structure of Formula I:

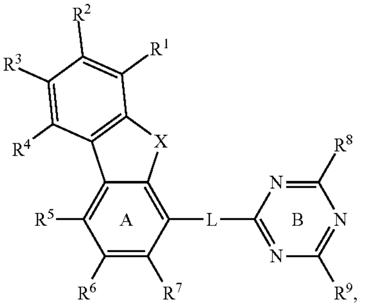

wherein:

each of $R^1$ to $R^7$ is independently a hydrogen or a substituent selected from the group consisting of phenyl, and a system consisting of two to ten phenyl groups connected to each other;

at least two of $R^1$ to $R^7$ are not hydrogen;

if $R^1$ and $R^3$ are not hydrogen, then at least one of the following is true: 1) $R^1$ and $R^3$ are different from each other; or 2) at least one of $R^1$ or $R^3$ is an unsubstituted phenyl;

if one of the at least two $R^1$ to $R^7$ that is not hydrogen is the system consisting of two to ten phenyl groups connected to each other, then the phenyl group directly bonded to the structure of Formula I having X bonds to exactly one phenyl group;

$R^8$ and $R^9$ are each independently selected from the group consisting of phenyl, and a system consisting of two to ten phenyl groups connected to each other;

X is selected from the group consisting of O, S, and Se; and

L is selected from the group consisting of direct bond and

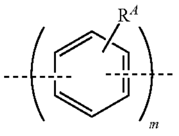

;

wherein m is an integer from 1 to 5, and $R^A$ is a hydrogen or a substituent selected from the group consisting of aromatic and heteroaromatic rings; and subject to the following provisos i) to iv):

i) if L is biphenyl, one phenyl of the biphenyl bonds to ring A and the other phenyl bonds to ring B;

ii) if X is O, then least one of $R^1$, $R^3$, or $R^5$ is H;

iii) if X is S, then at least one of $R^1$ or $R^6$ is H but if $R^6$ is H and $R^1$ is not H, then at least one of $R^3$ or $R^5$ is H; and iv) the following structures are excluded

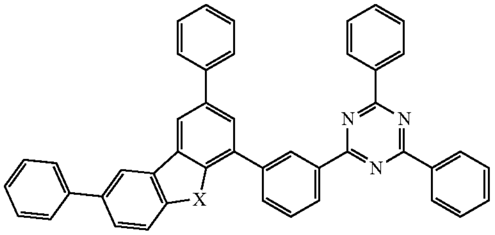

, and

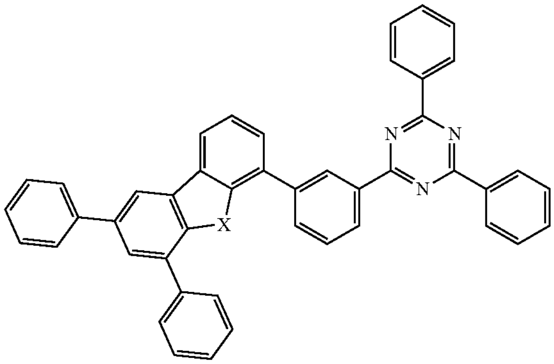

;

and wherein at least one of the following conditions 1) to 4) is true:

1) M is 1, ring A and ring B are meta to each other, and $R^1$ to $R^9$ comprise a total of at least 6 phenyl groups;

2) at least one of $R^1$ to $R^4$ is not hydrogen and at least one of $R^5$ to $R^7$ is not hydrogen;

3) $R^8$ is phenyl and $R^9$ is biphenyl; or

4) X is S.

18. The OLED of claim 17, wherein the organic layer further comprises an h-host selected from the group consisting of:

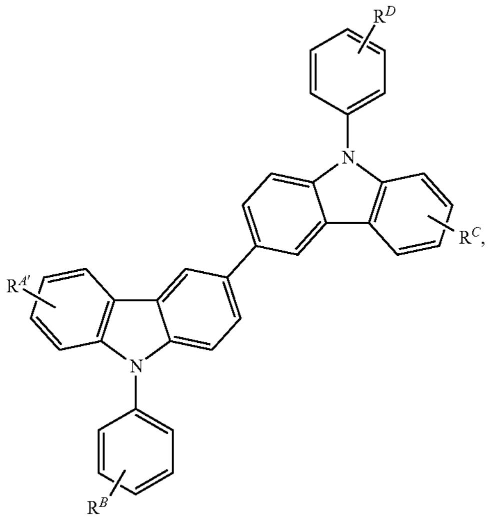

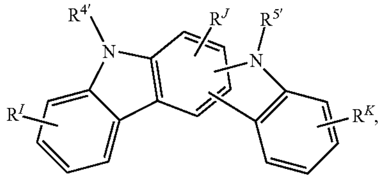

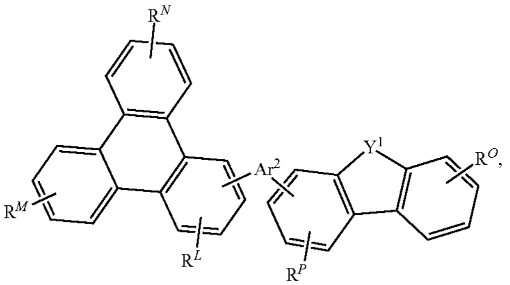

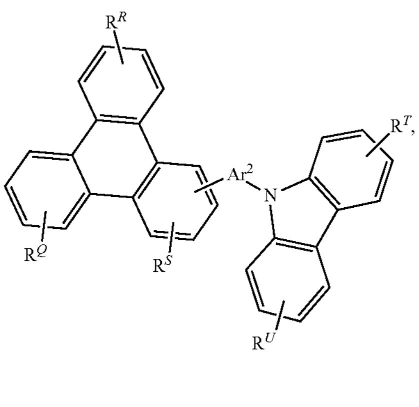

-continued

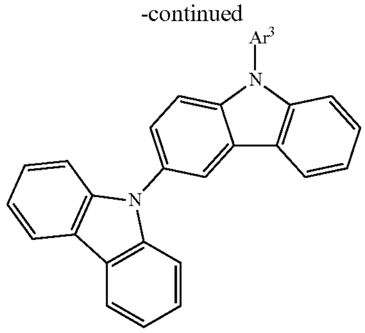

,

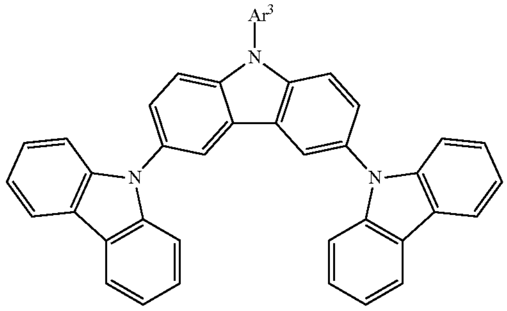

,

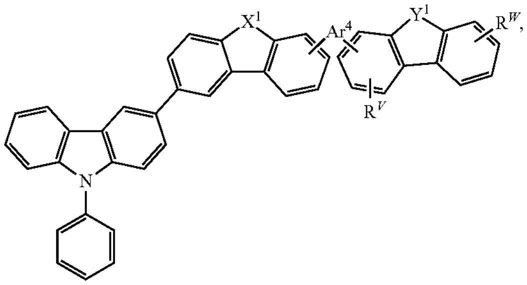

and

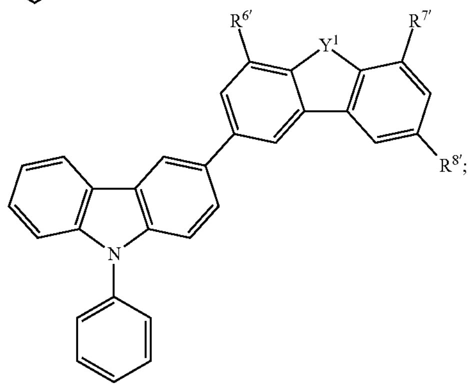

wherein:

each of $R^{A'}$, $R^B$, $R^C$, $R^D$, $R^I$, $R^J$, $R^K$, $R^L$, $R^M$, $R^N$, $R^O$, $R^P$, $R^Q$, $R^R$, $R^S$, $R^T$, $R^U$, $R^V$, and $R^W$ represent mono to the maximum allowable substitution, or no substitution;

each of $Ar^2$ and $Ar^4$ is a linker independently selected from the group consisting of a direct bond, aryl, and heteroaryl;

each of $X^1$ and $Y^1$ is independently selected from the group consisting of $BR_{e'}$, $NR_{e'}$, $PR_{e'}$, O, S, Se, C═O, S═O, $SO_2$, $CR_{e'}R_{f'}$, $SiR_{e'}R_{f'}$, and $GeR_{e'}R_{f'}$; and each $Ar^3$, $R^{4'}$, $R^{5'}$, $R^{6'}$, $R^{7'}$, $R^{8'}$, $R_{e'}$, $R_{f'}$, $R^{A'}$, $R^B$, $R^C$, $R^D$, $R^I$, $R^J$, $R^K$, $R^L$, $R^M$, $R^N$, $R^O$, $R^P$, $R^Q$, $R^R$, $R^S$, $R^T$, $R^U$, $R^V$, and $R^W$ is independently a hydrogen or a substituent selected from the group consisting of deuterium, halogen, alkyl, cycloalkyl, heteroalkyl, heterocycloalkyl, boryl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof.
19. The OLED of claim 17, wherein the h-host is selected from the group consisting of:
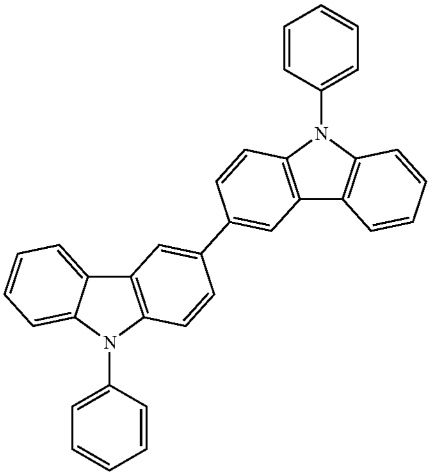
,
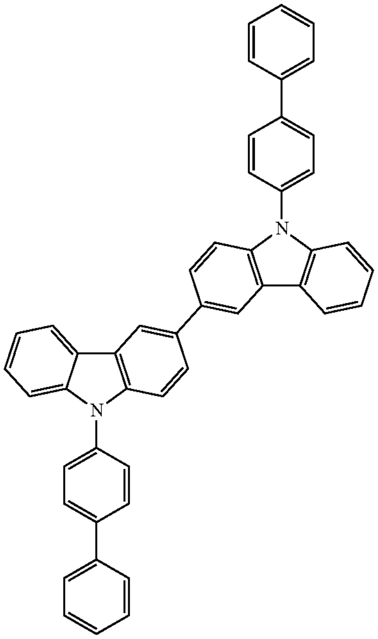
,
-continued
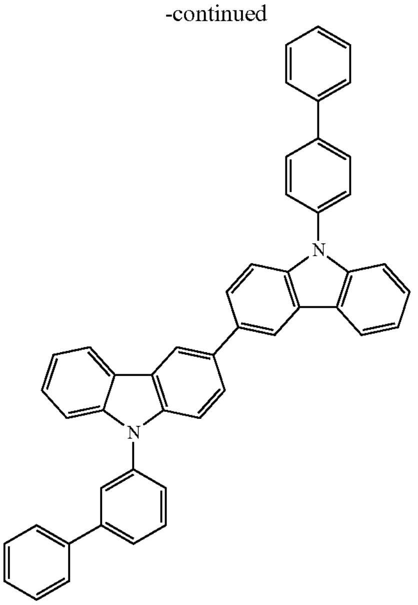
,
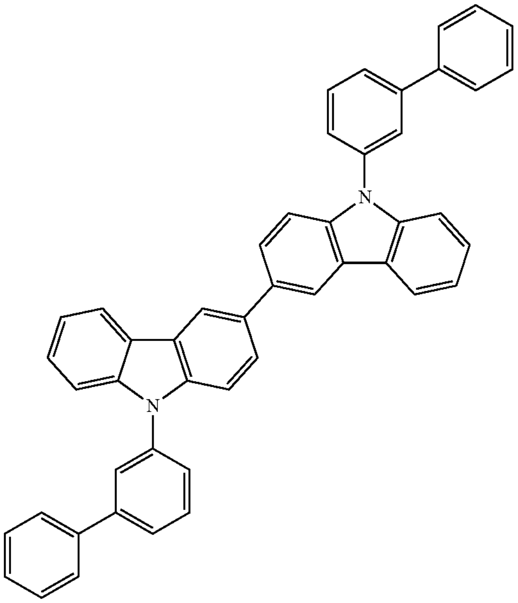
,
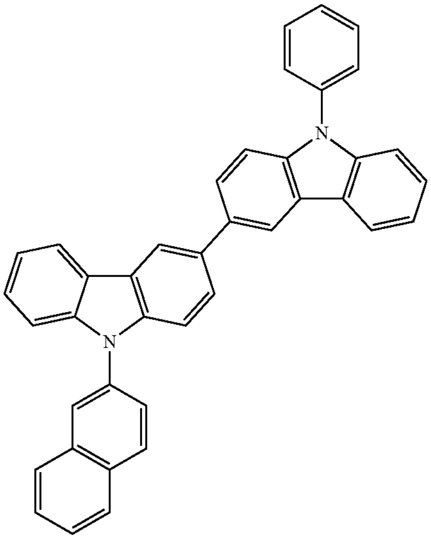
, -continued
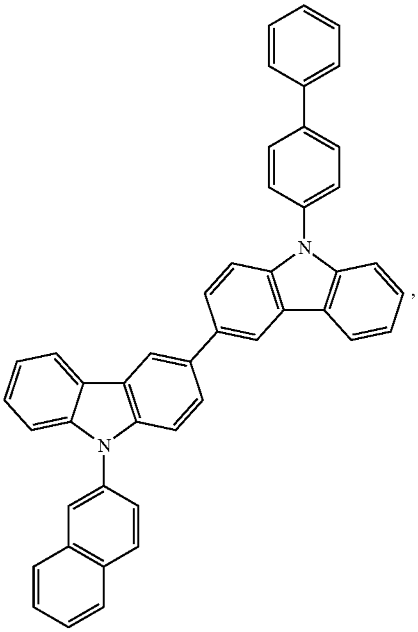
,
-continued
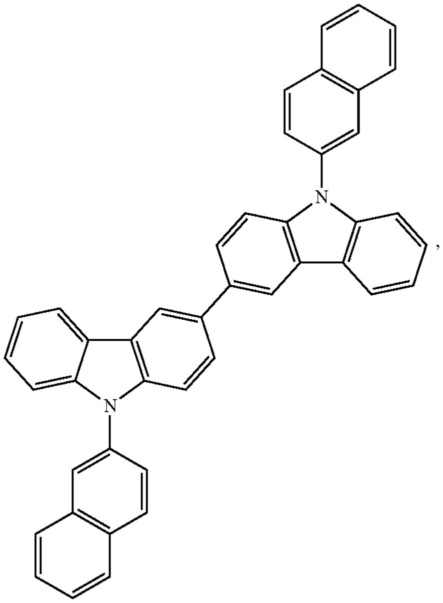
,
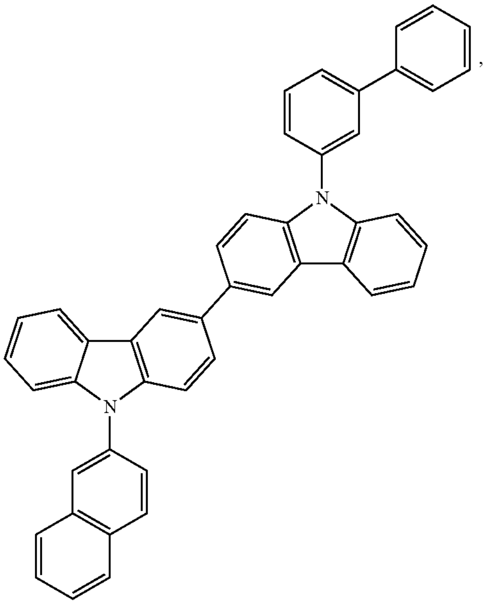
,
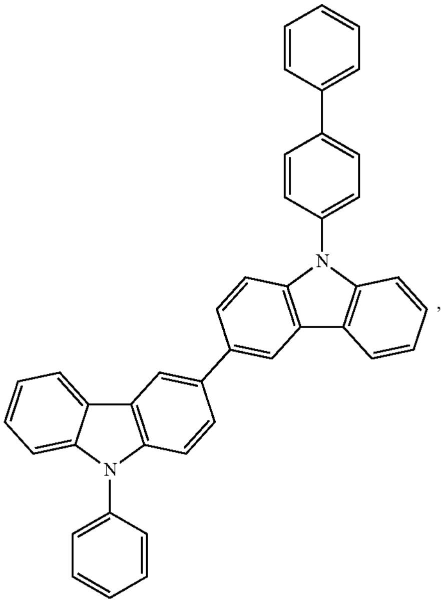
, -continued
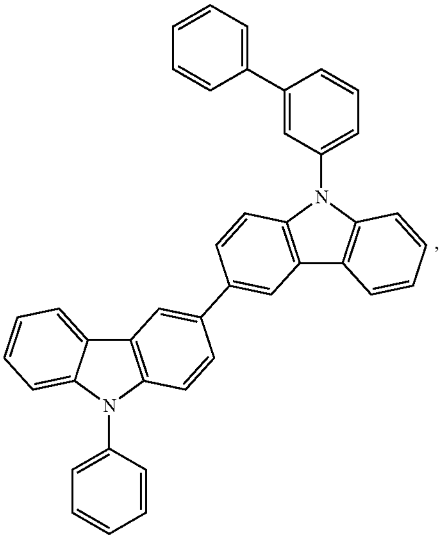
,
-continued
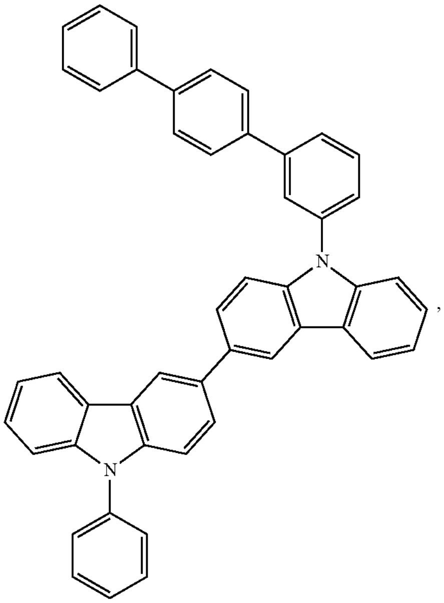
,
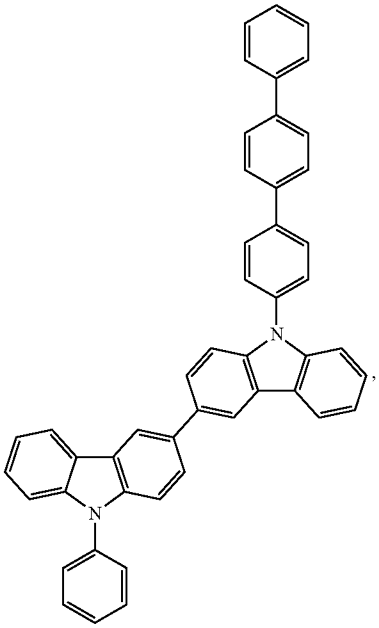
,
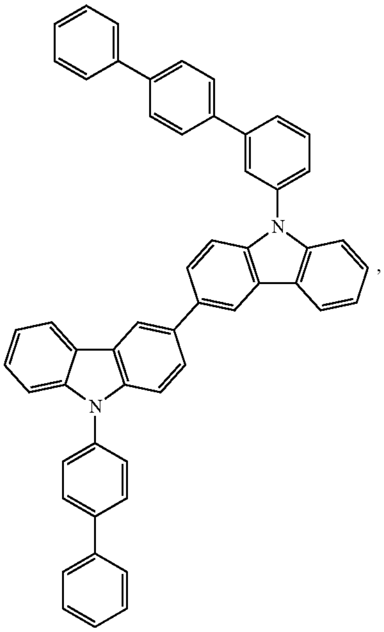
, -continued
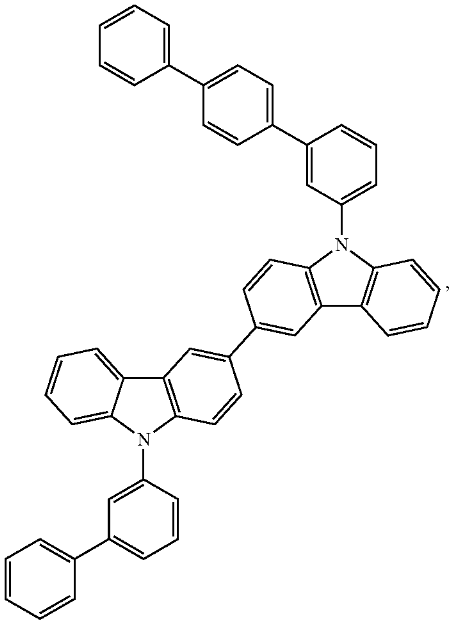
,
-continued
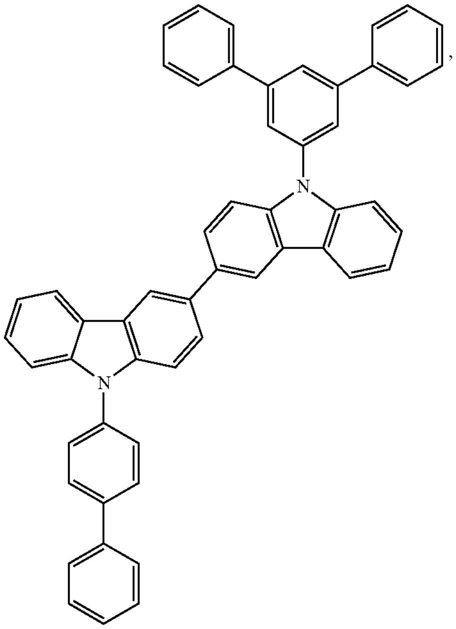
,
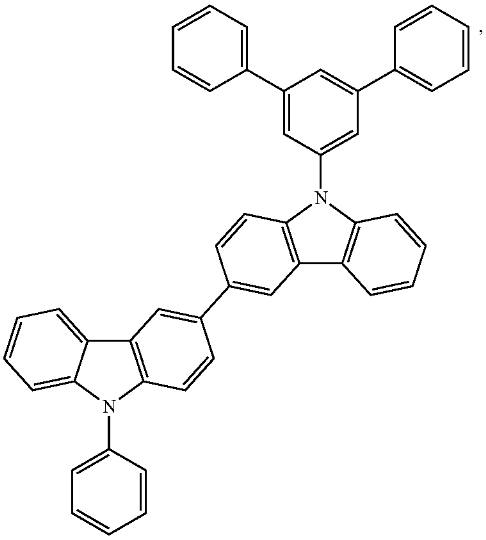
,
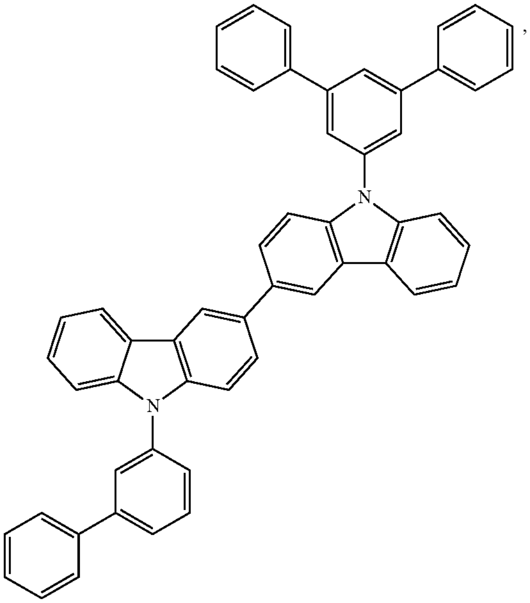
, -continued
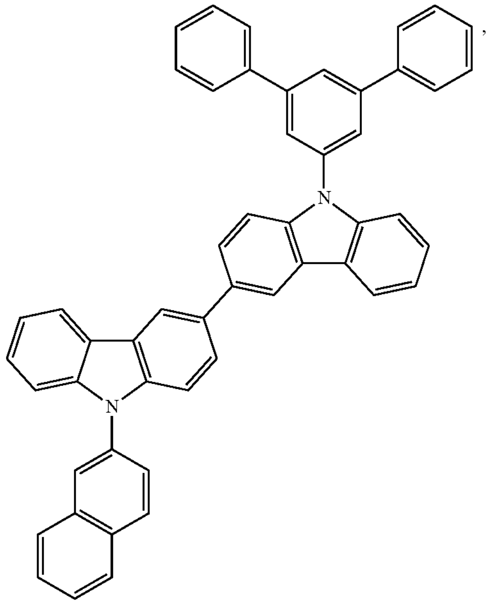
,
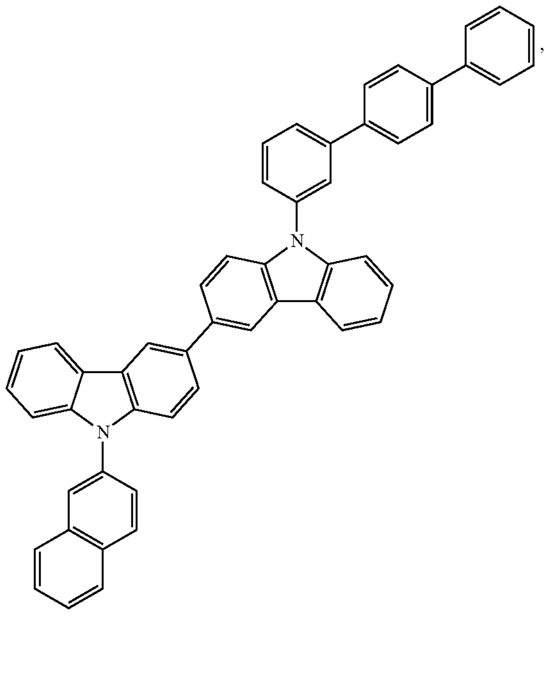
,
-continued
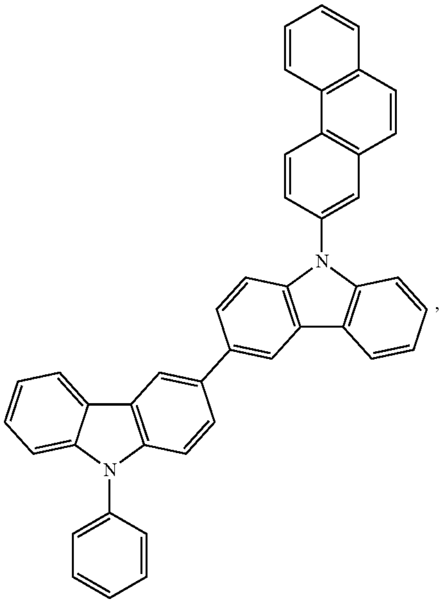
,
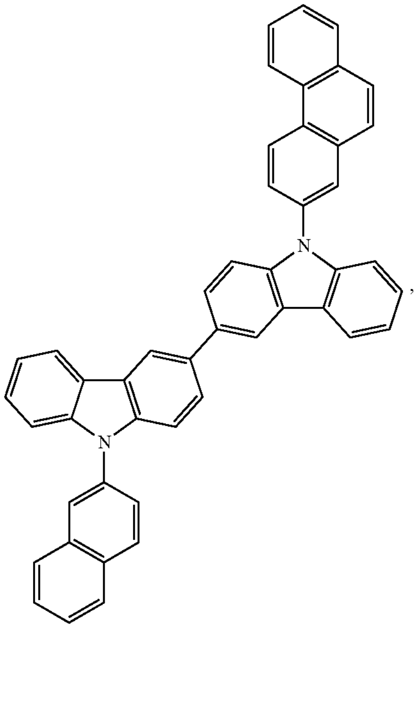
, -continued
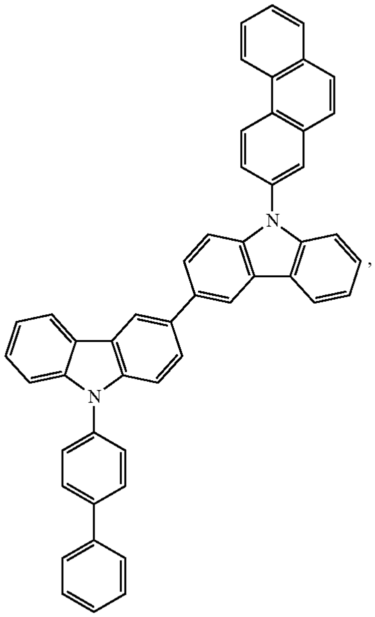,
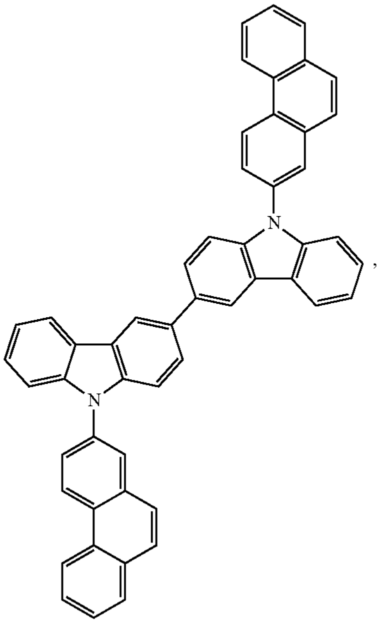,
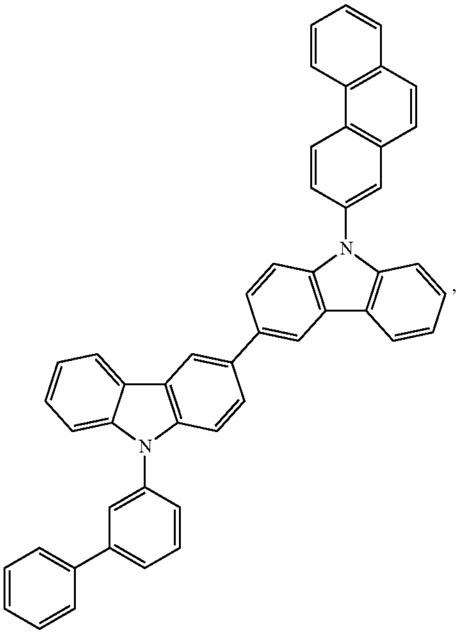,
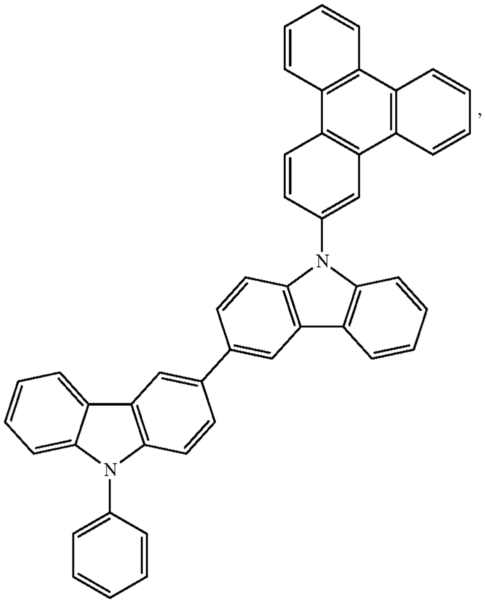, -continued
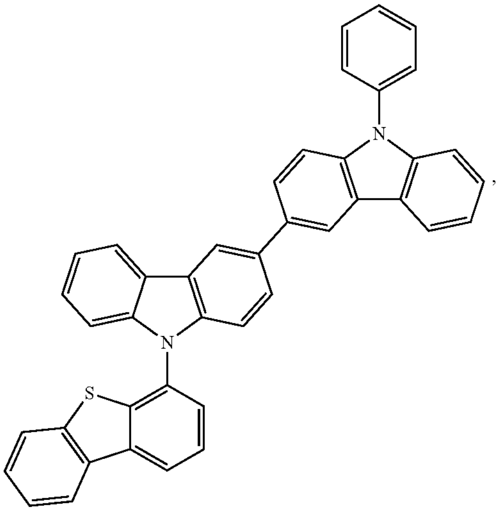
,
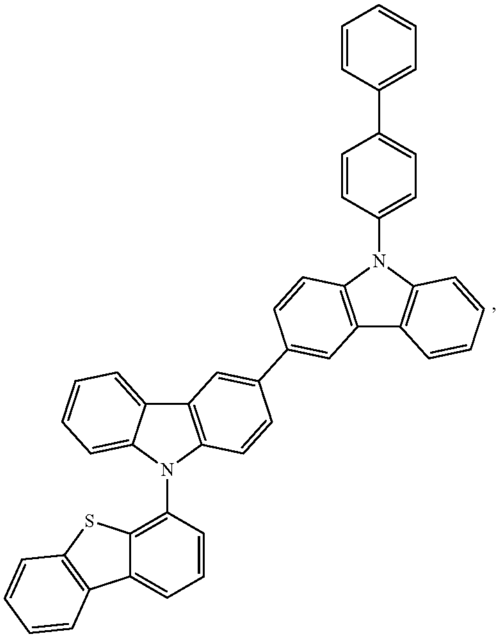
,
-continued
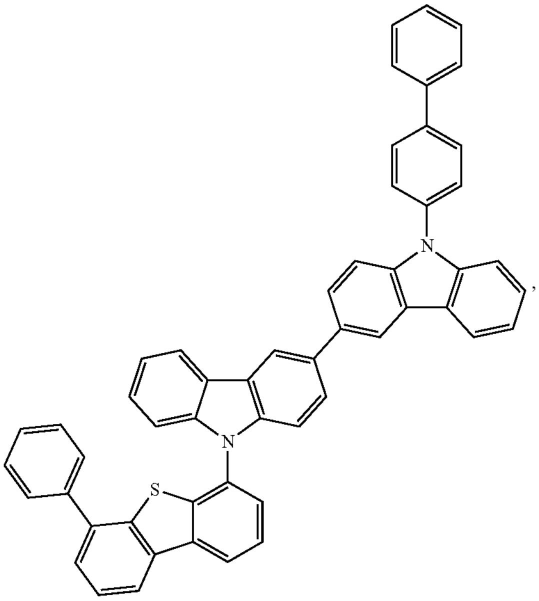
,
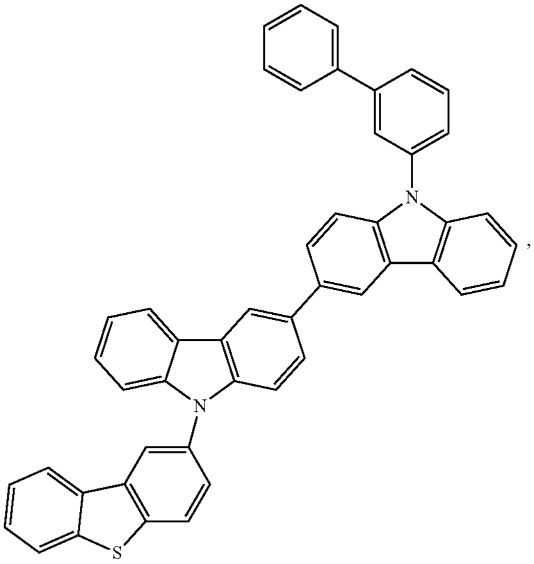
,
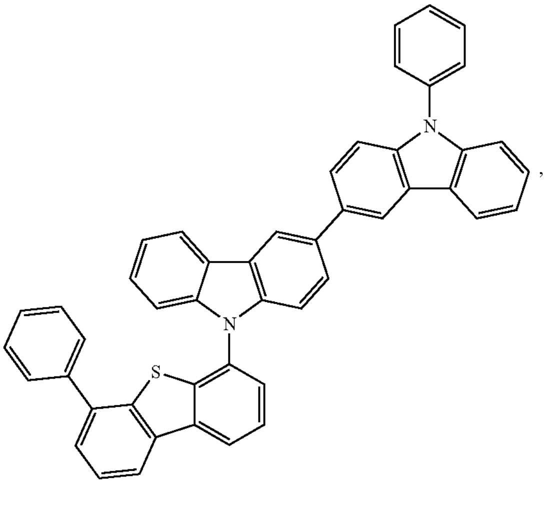
, -continued
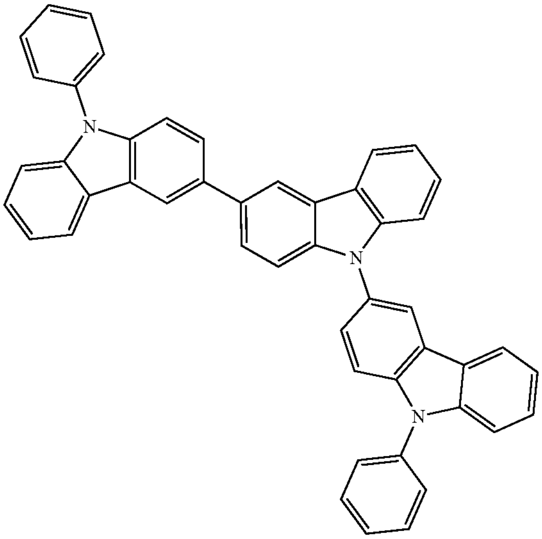
,
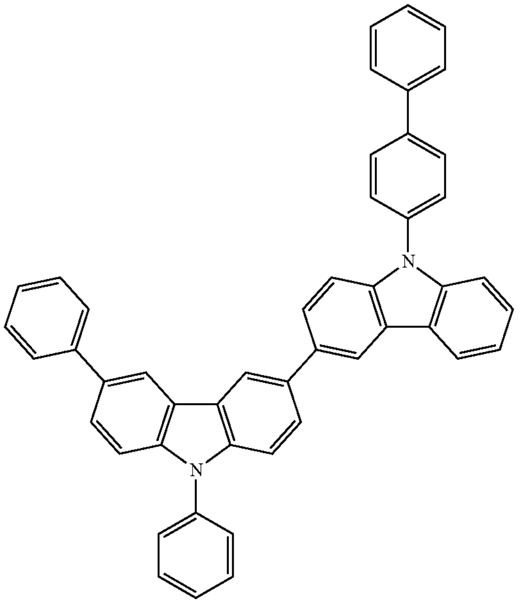
,
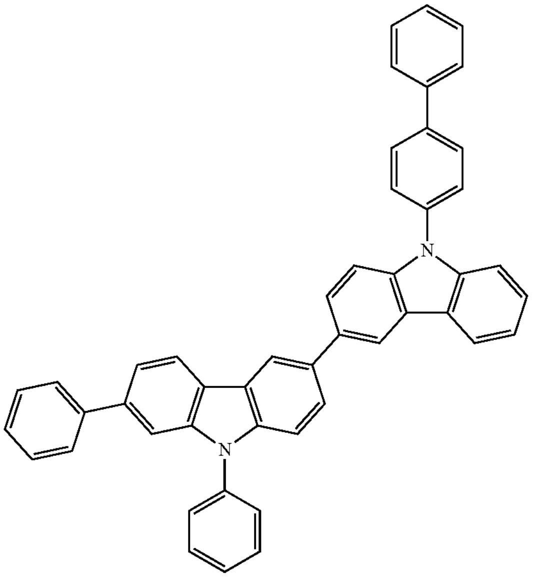
,
-continued
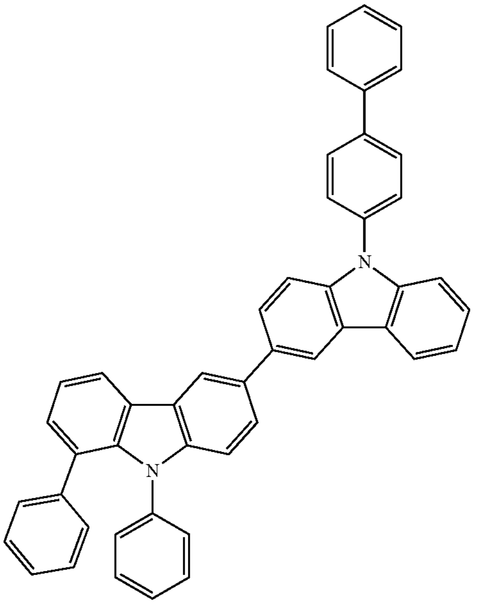
,
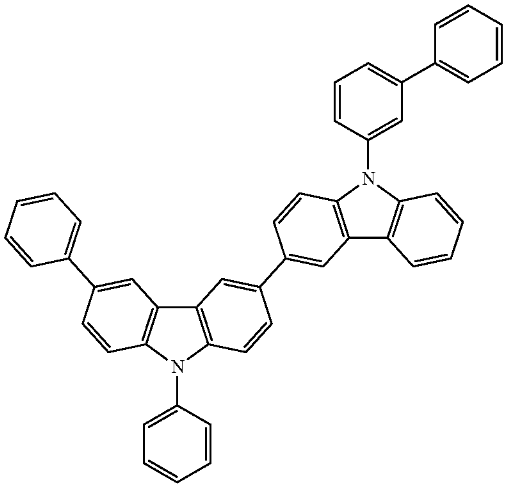
,
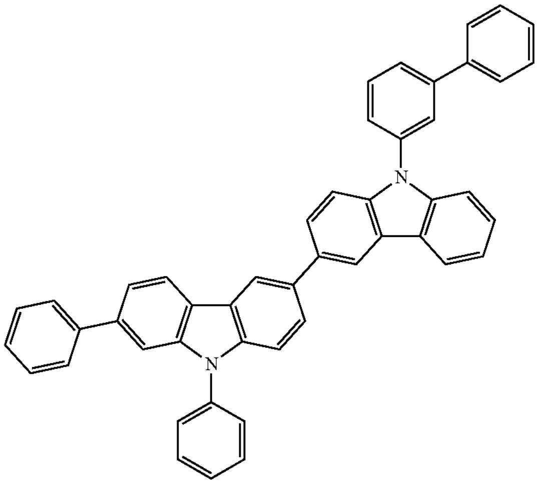
, -continued
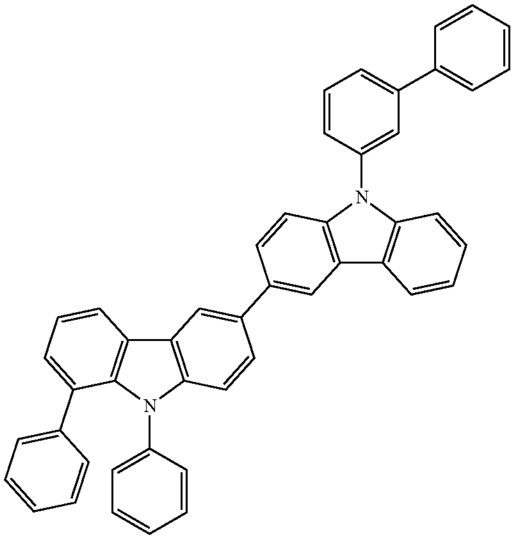
,
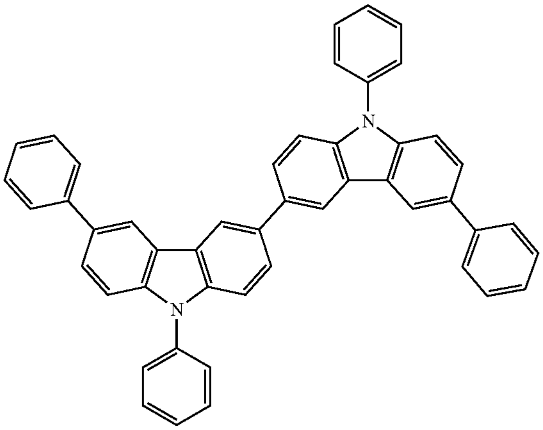
,
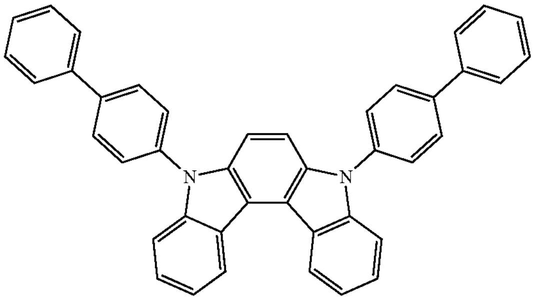
,
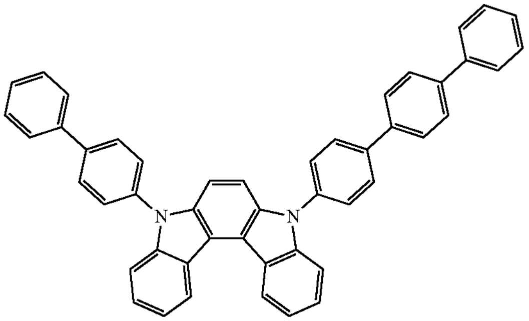
,
-continued
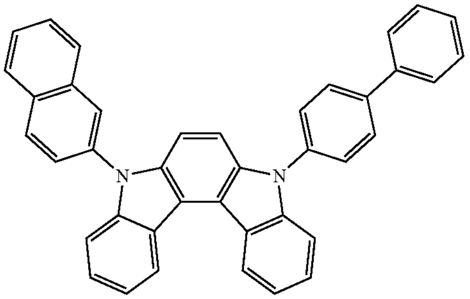
,
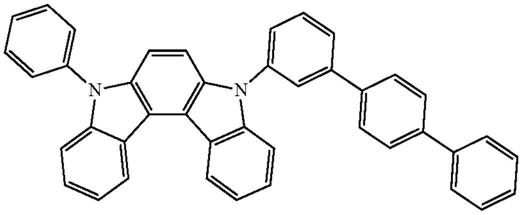
,
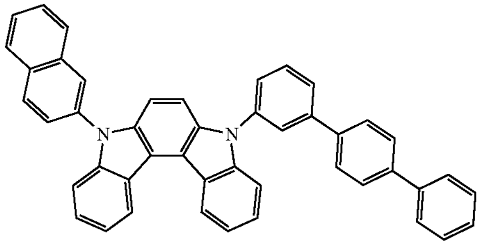
,
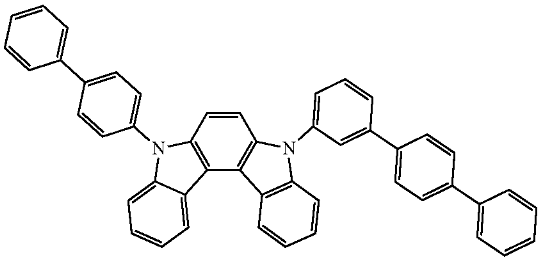
,
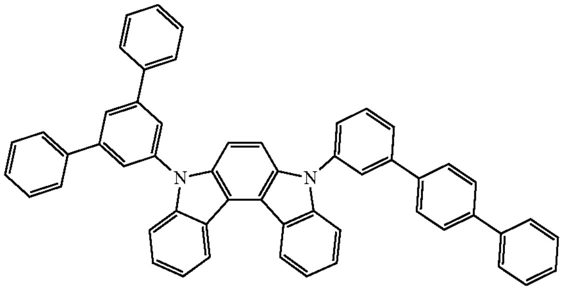
,
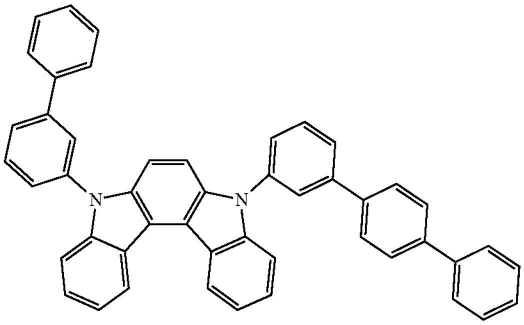
,

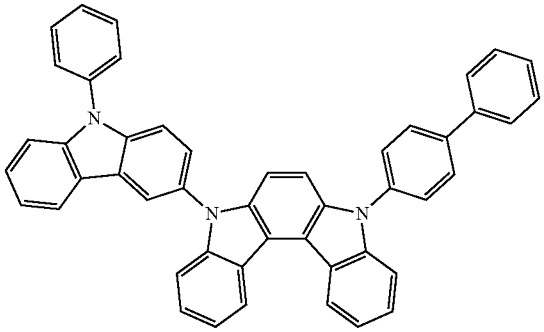
,
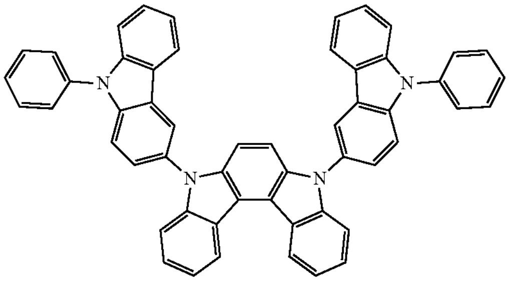
,
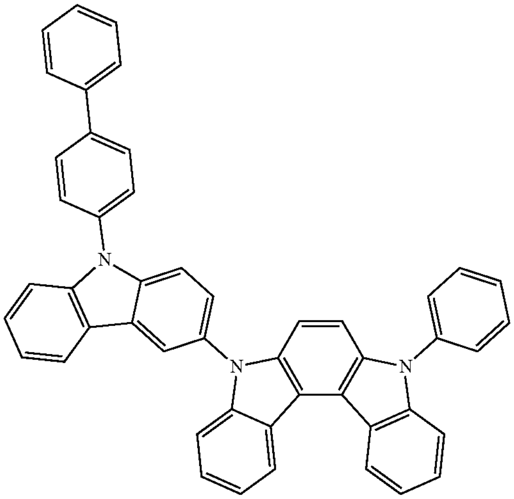
,
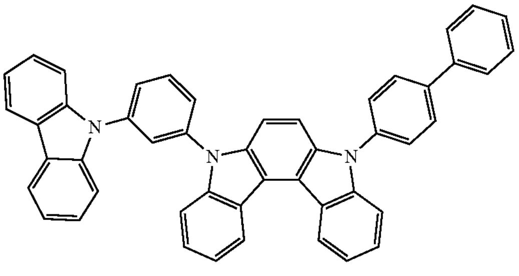
,
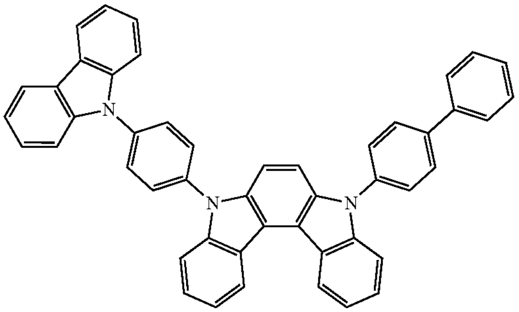
,
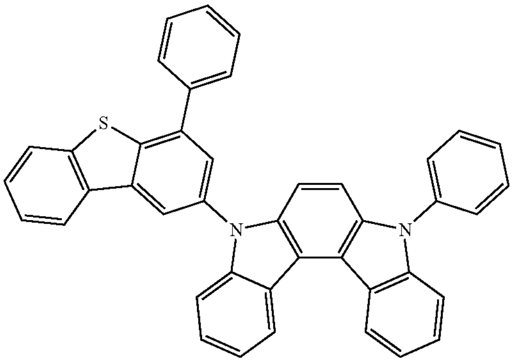
,
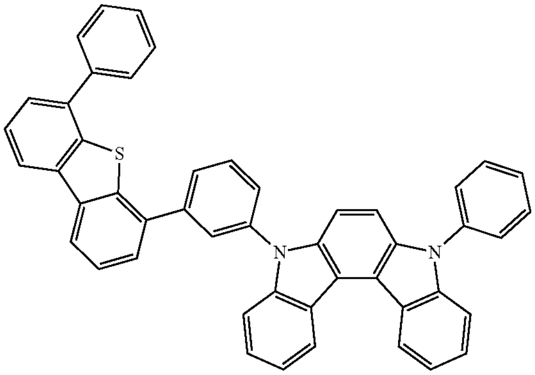
,
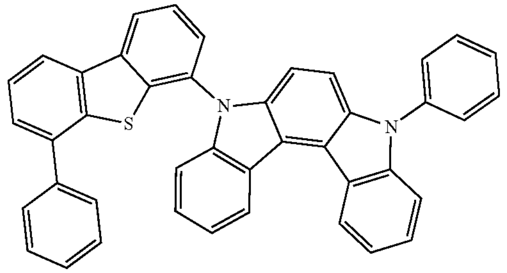
,
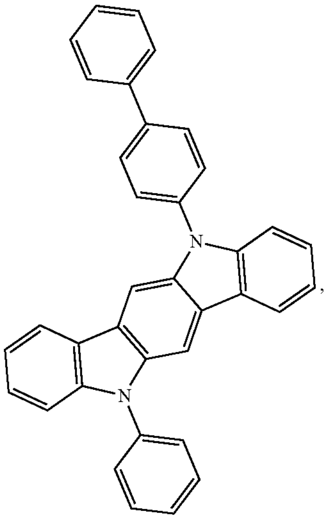
, -continued
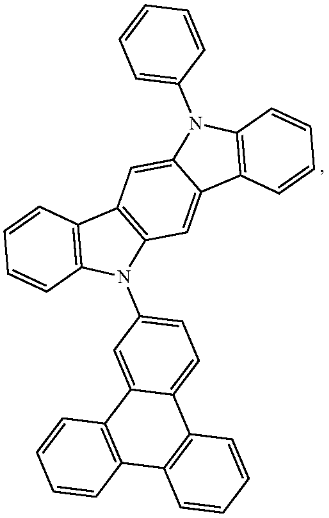
-continued
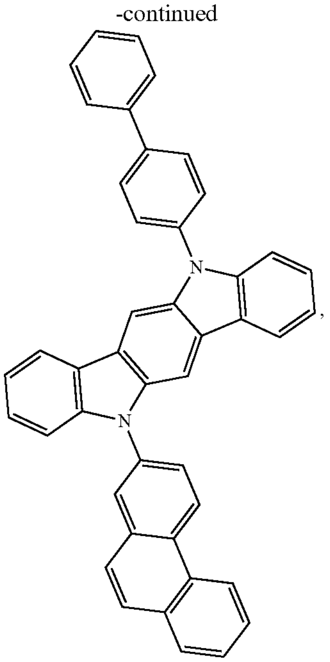
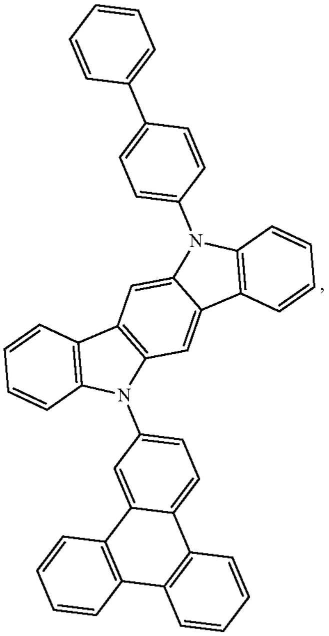
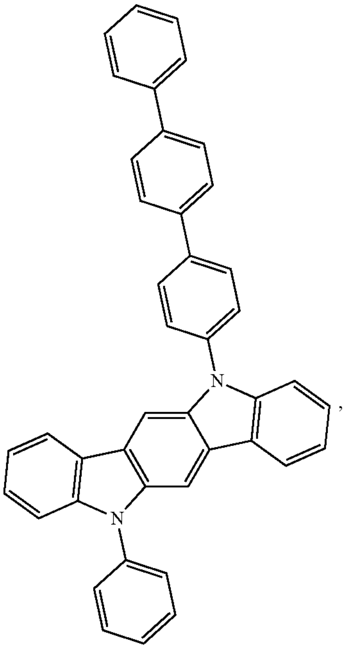

-continued
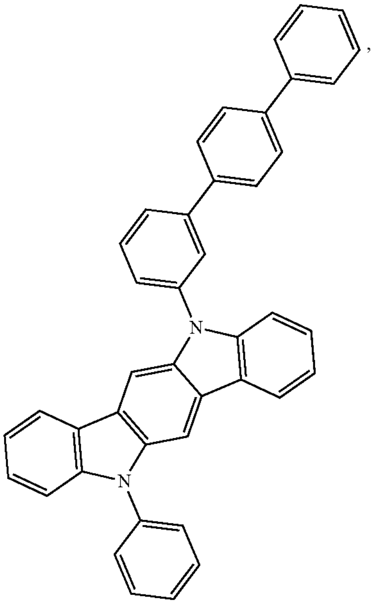
,
-continued
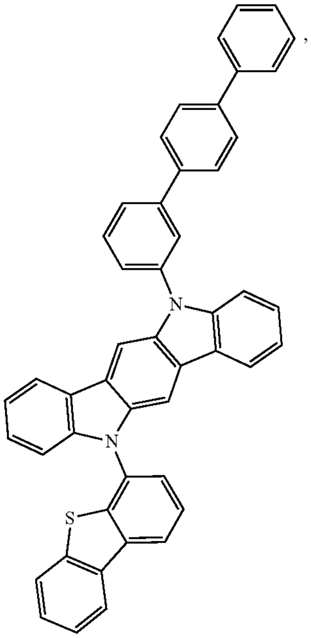
,
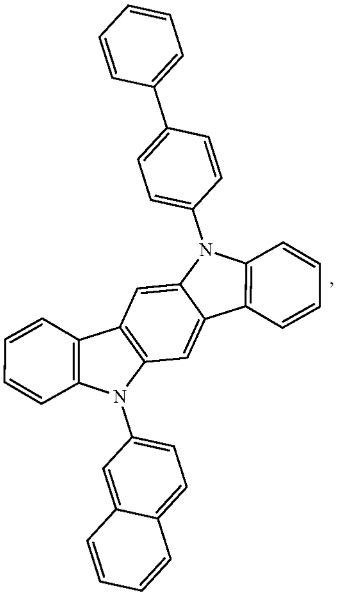
,
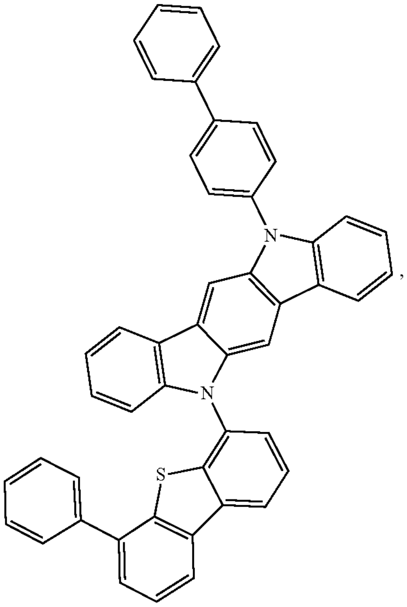
, -continued
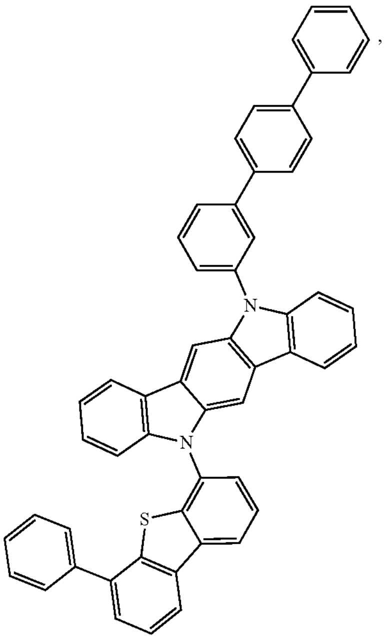
,
-continued
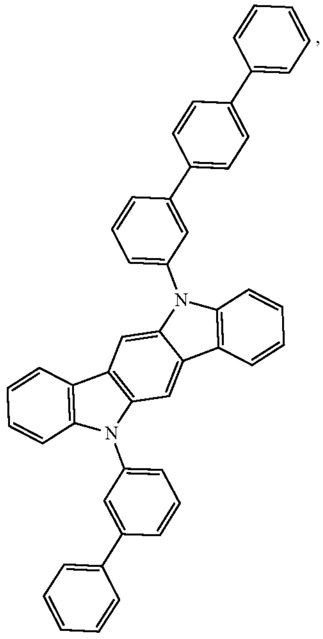
,
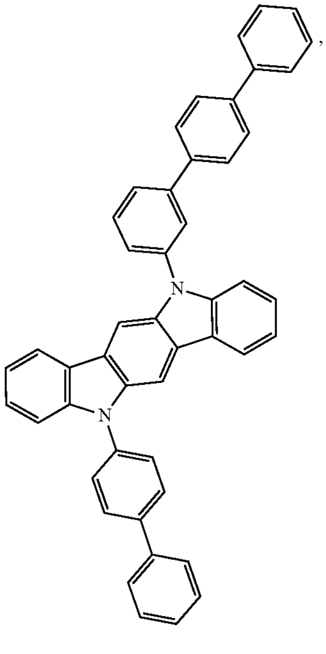
,
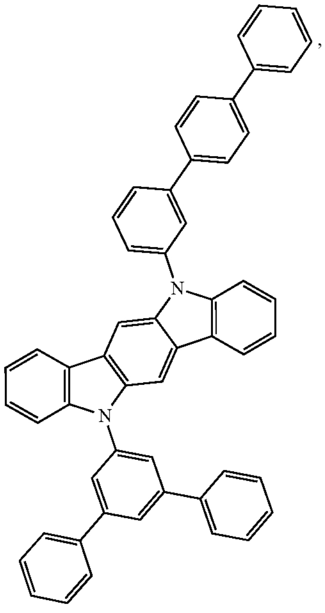
, -continued
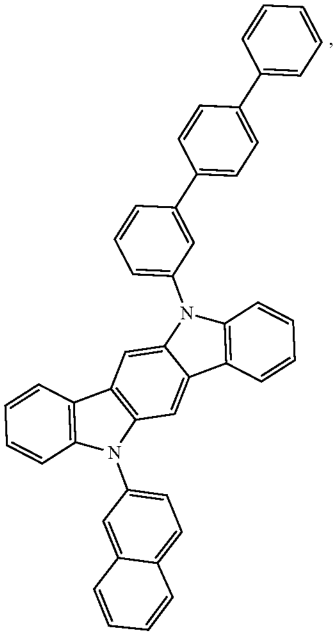
,
-continued
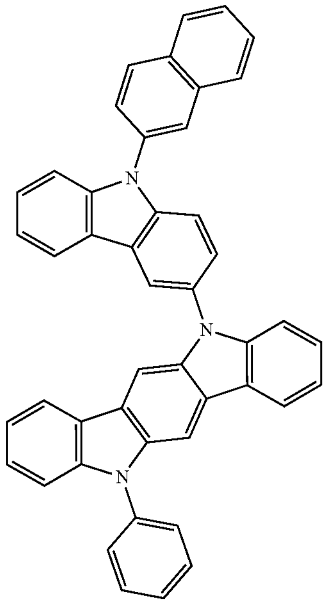
,
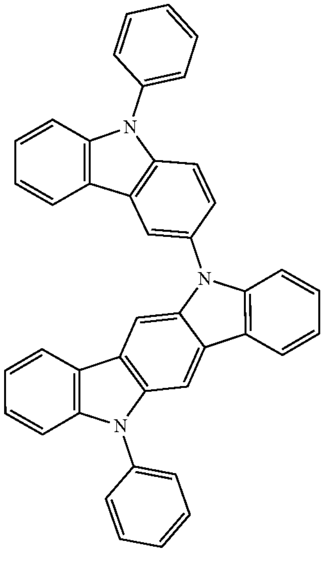
,
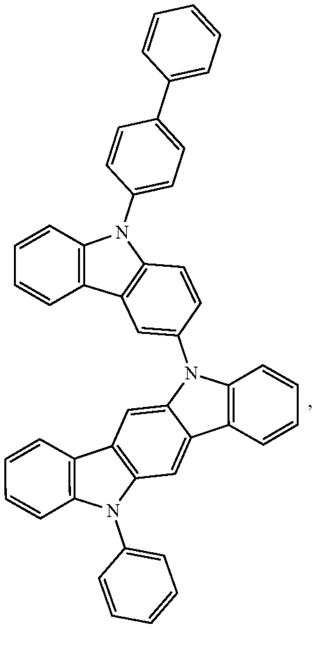
, -continued
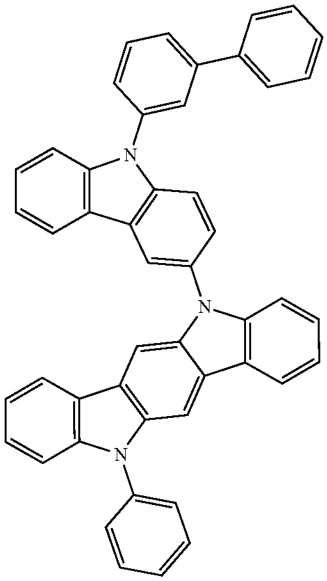
,
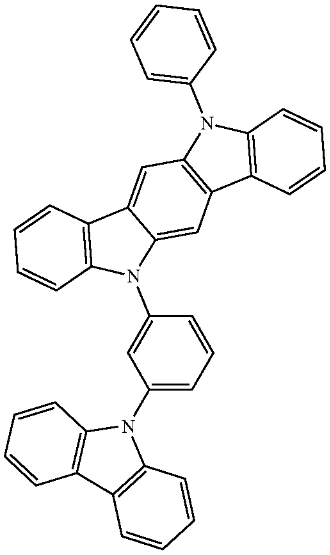
,
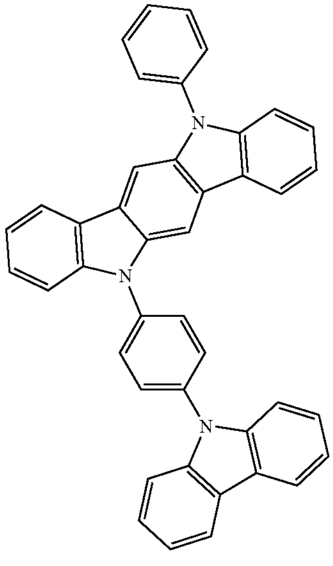
,
-continued
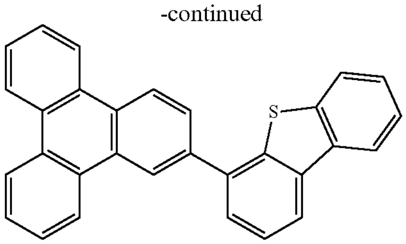
,
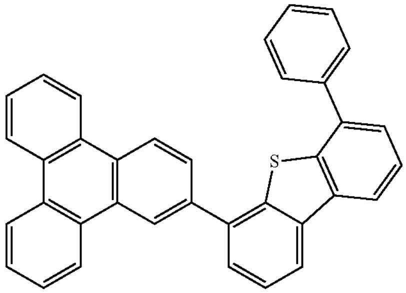
,
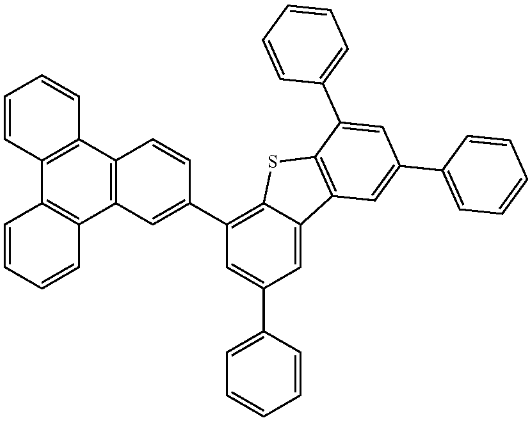
,
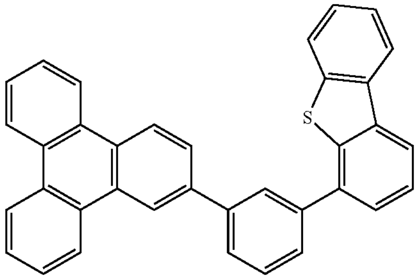
,
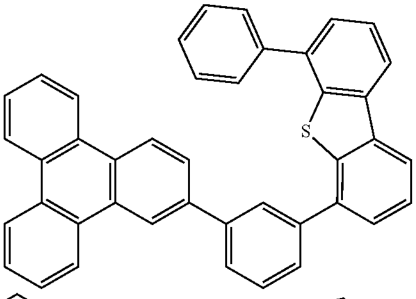
,
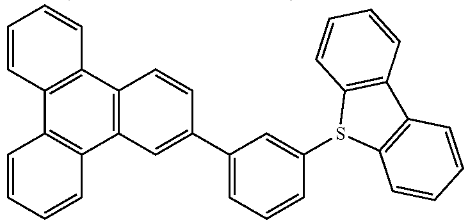
, -continued
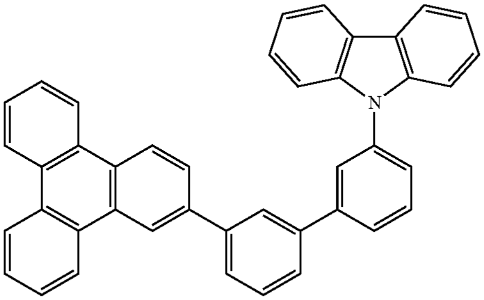
,
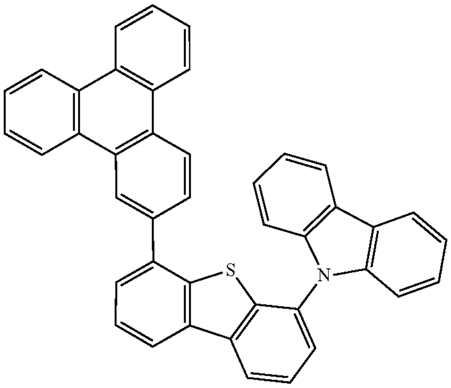
,
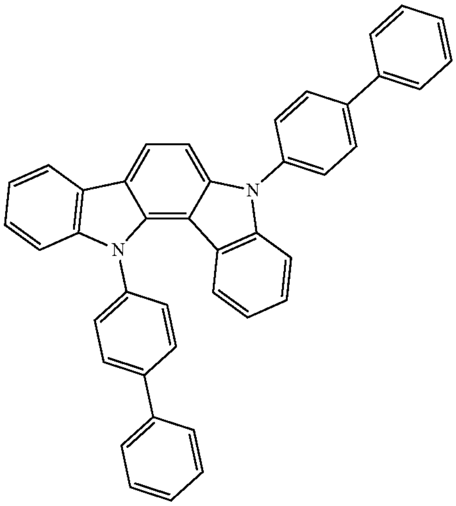
,
-continued
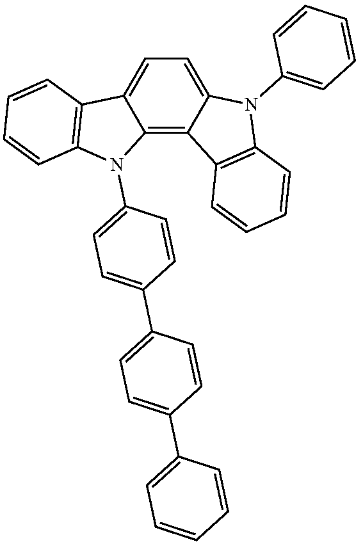
,
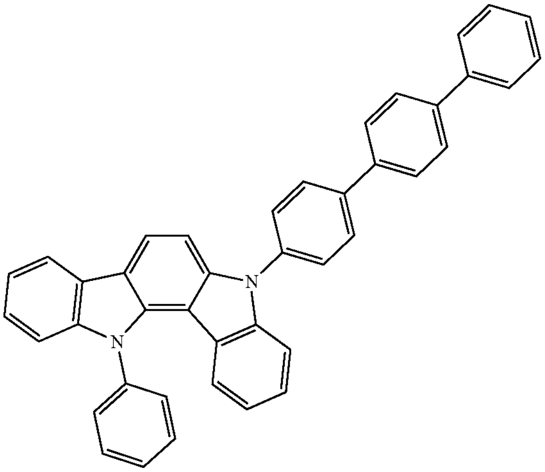
,
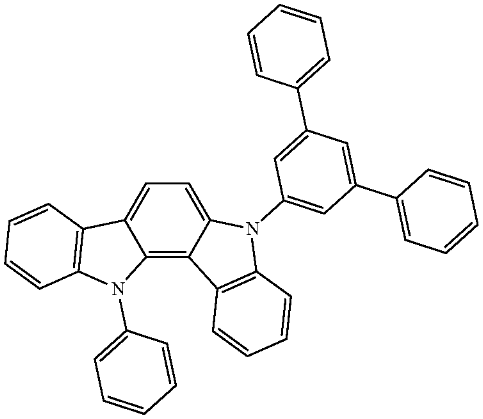
, -continued
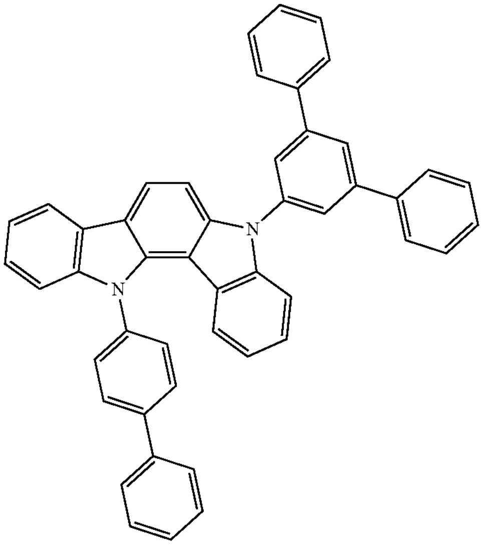
,
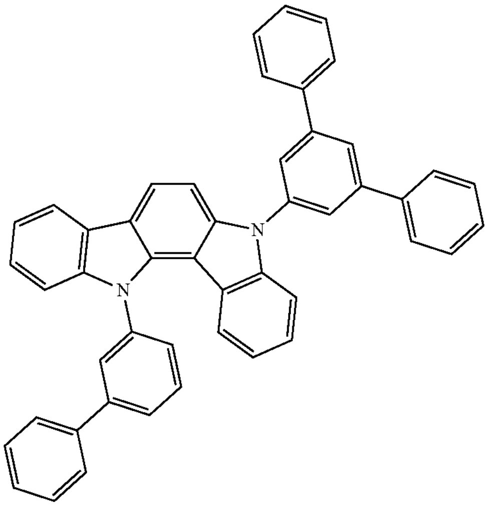
,
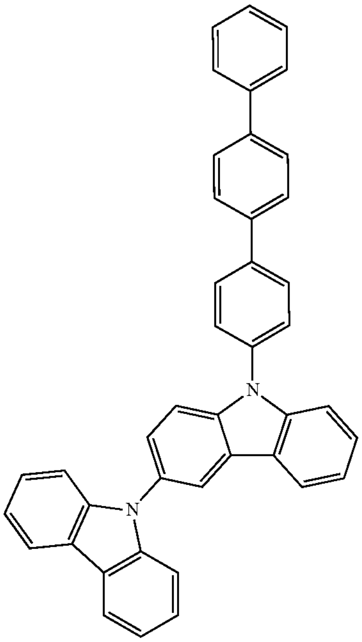
,
-continued
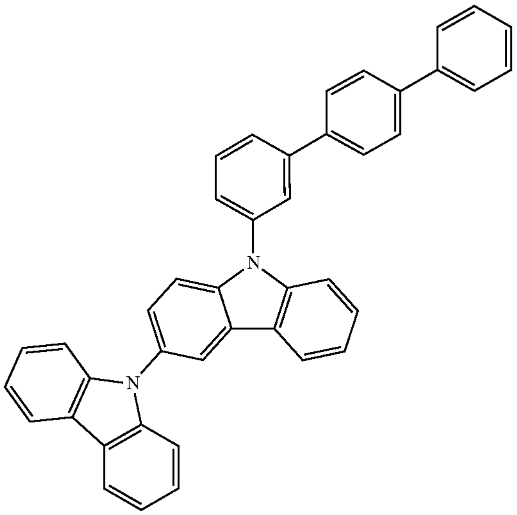
,
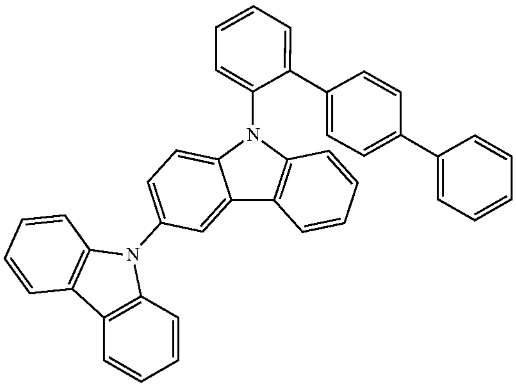
,
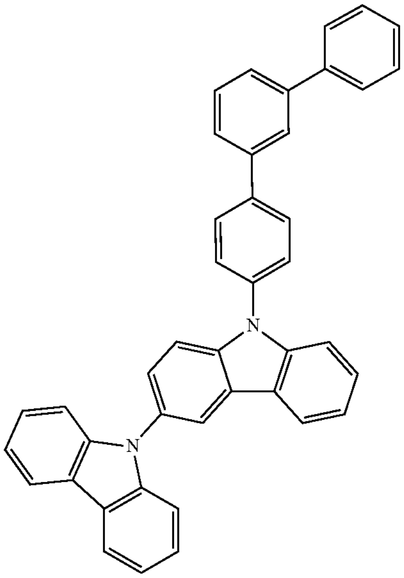
, -continued
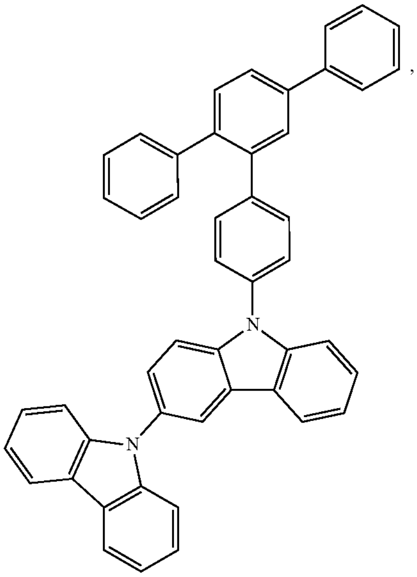,
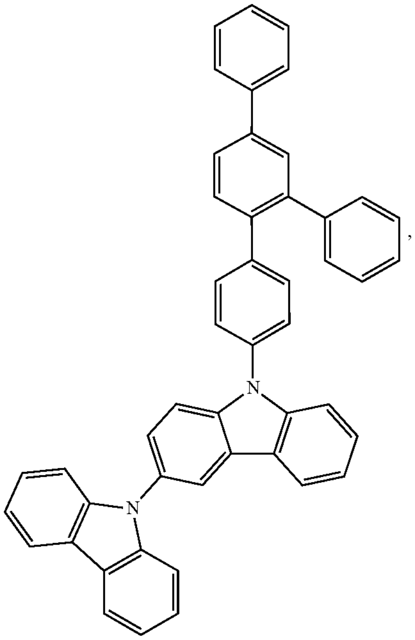,
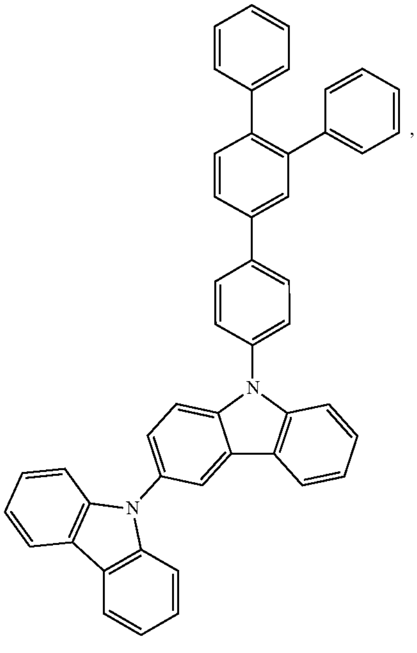,
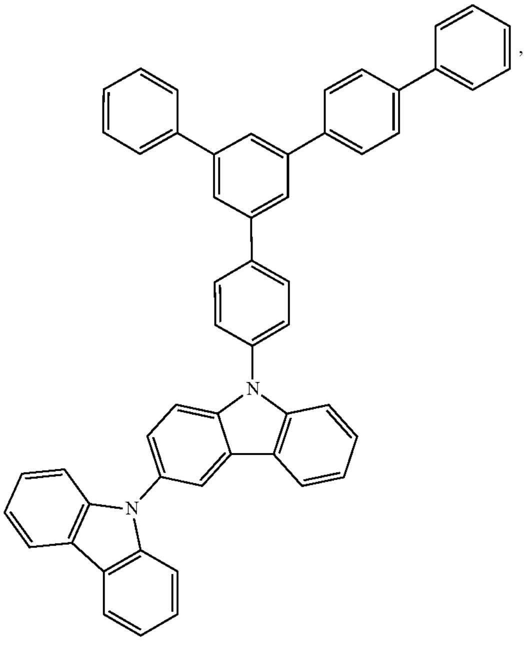, -continued
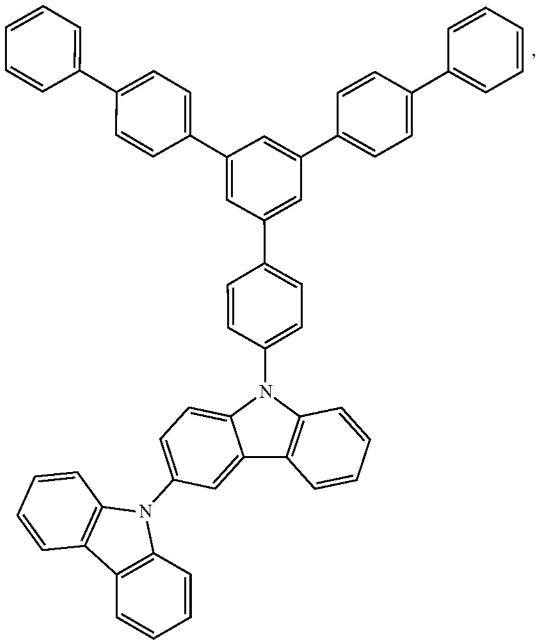
,
-continued
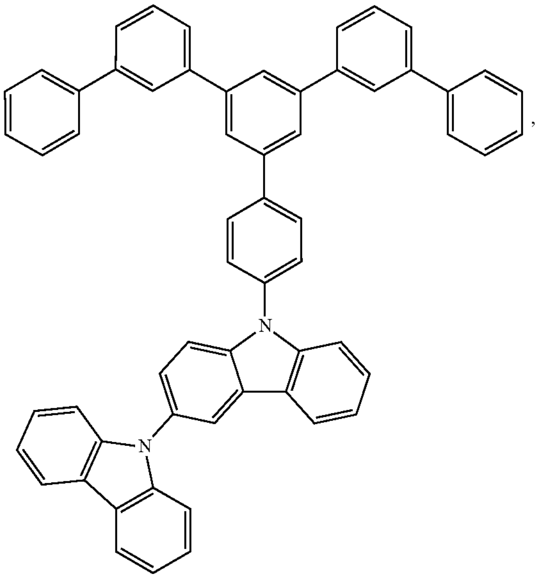
,
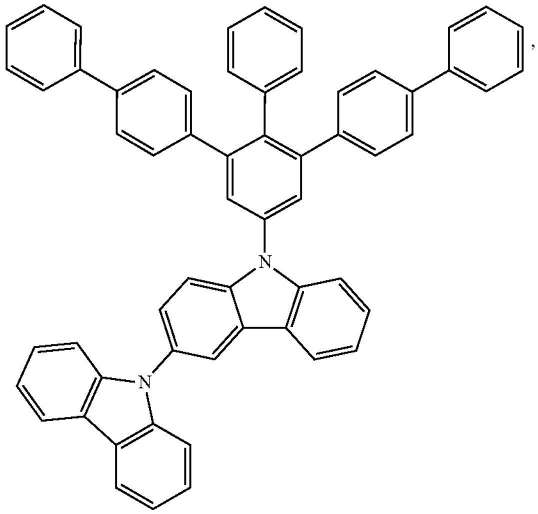
,
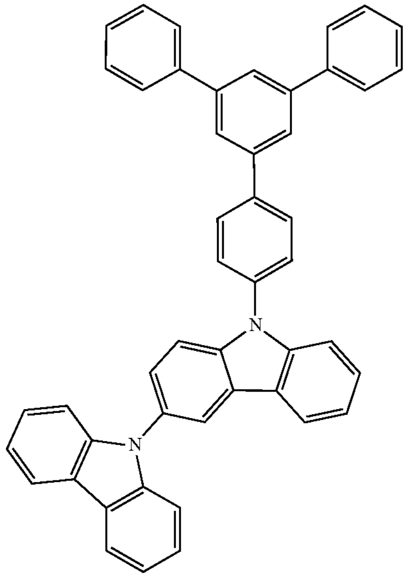
, -continued
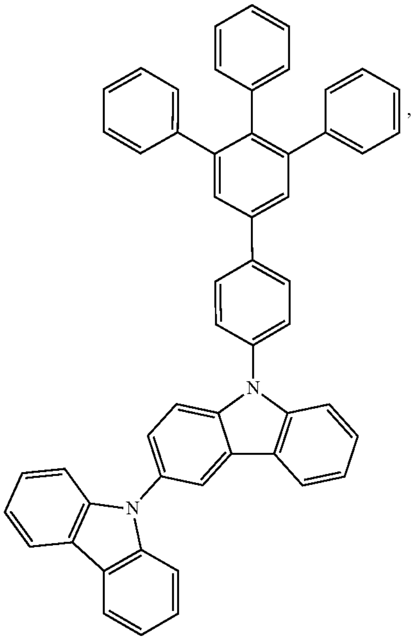
,
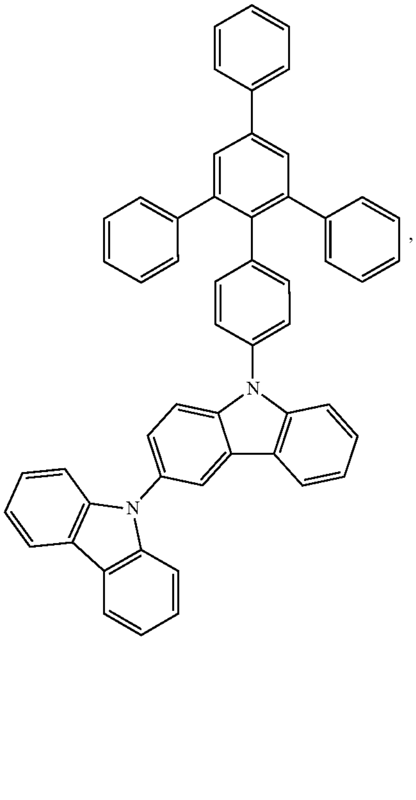
,
-continued
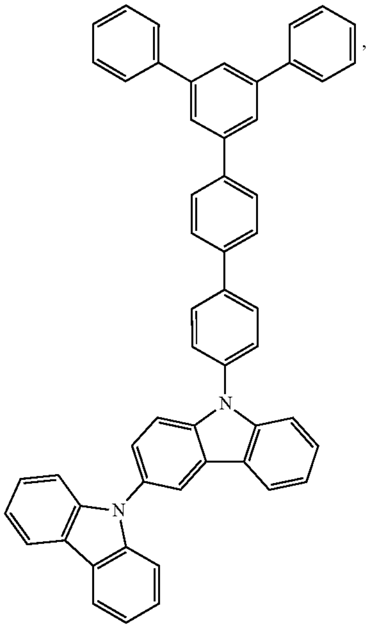
,
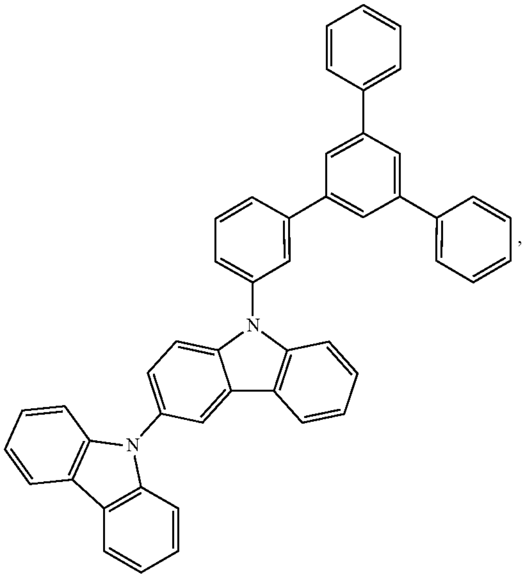
, -continued
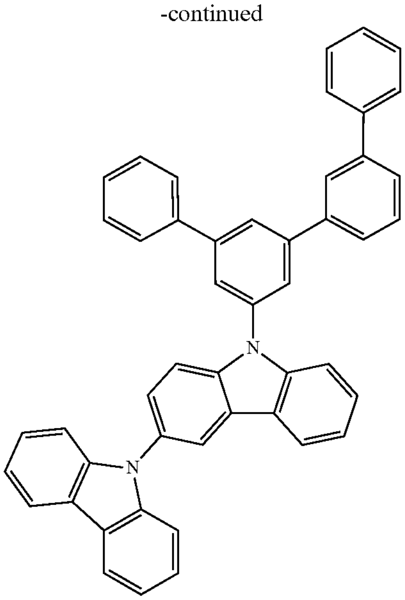
,
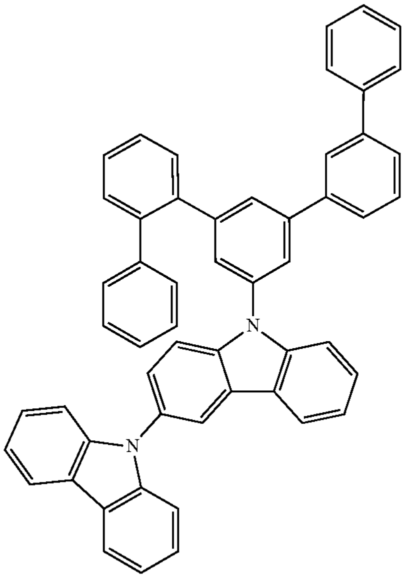
,
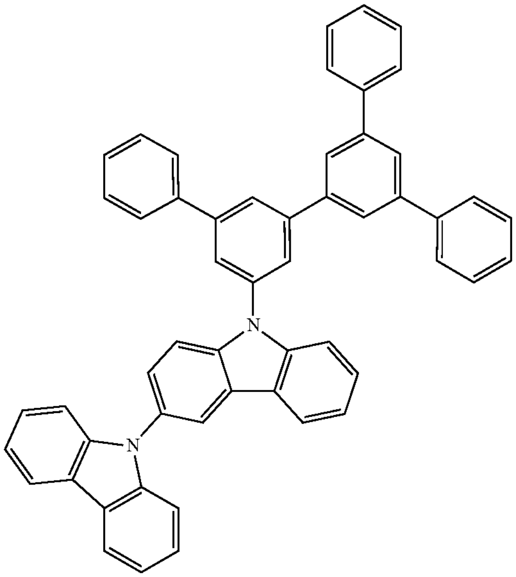
,
-continued
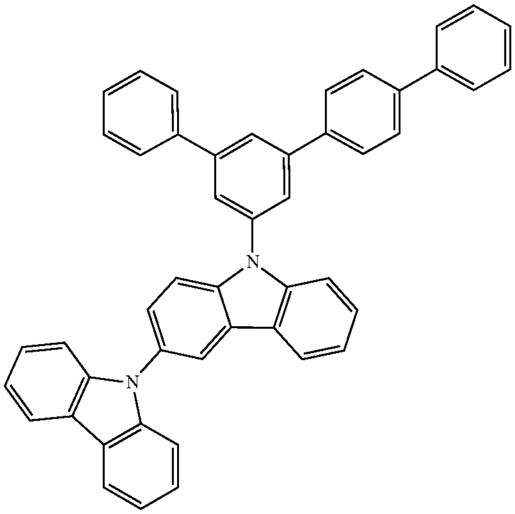
,
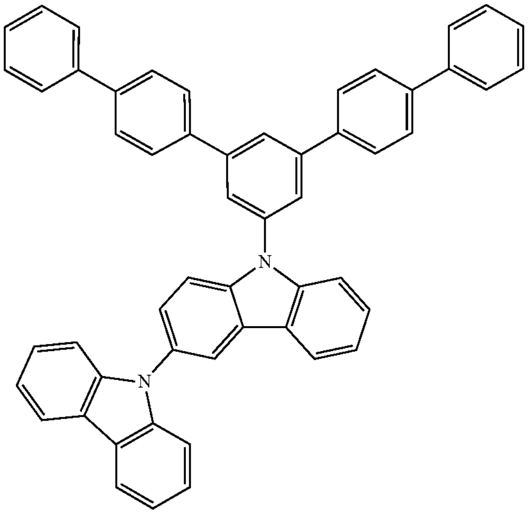
,
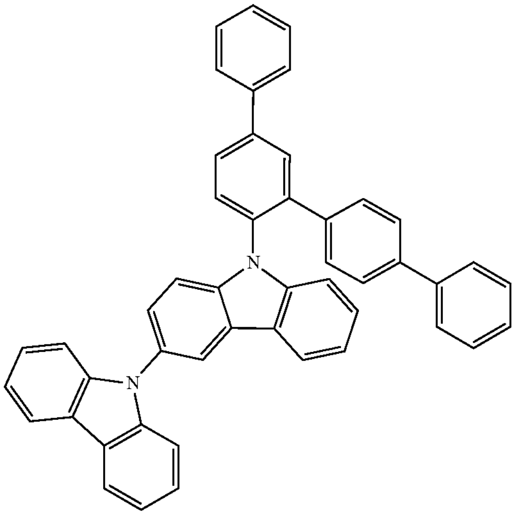
, -continued
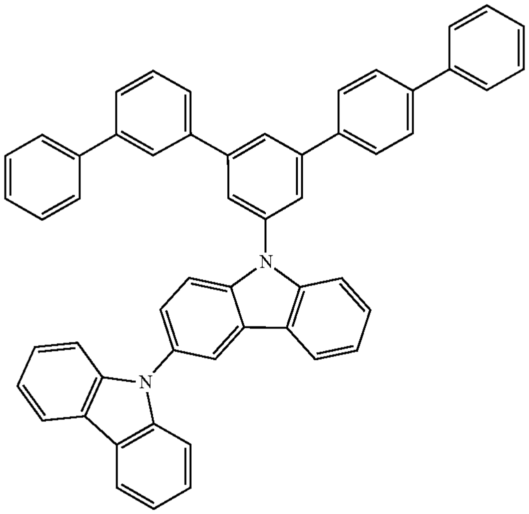
,
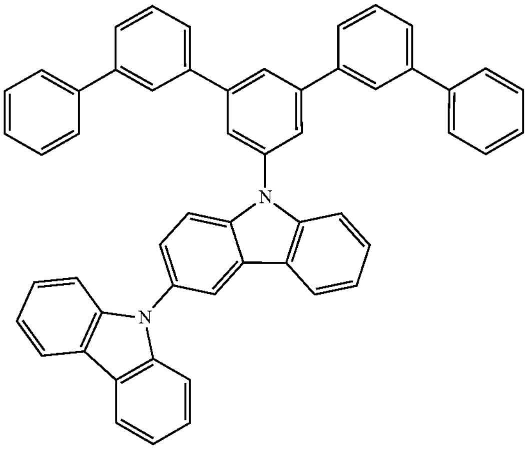
,
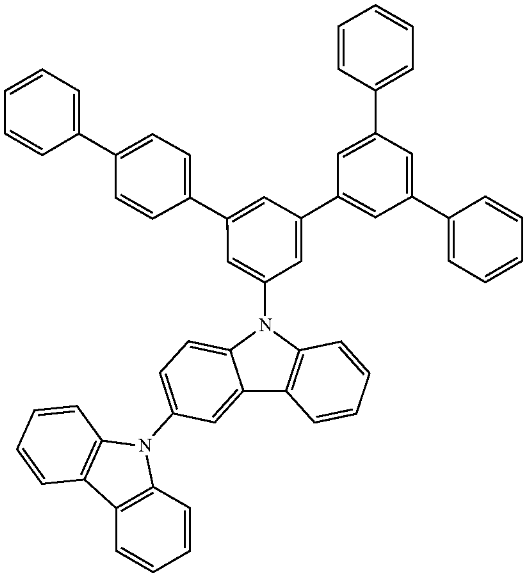
,
-continued
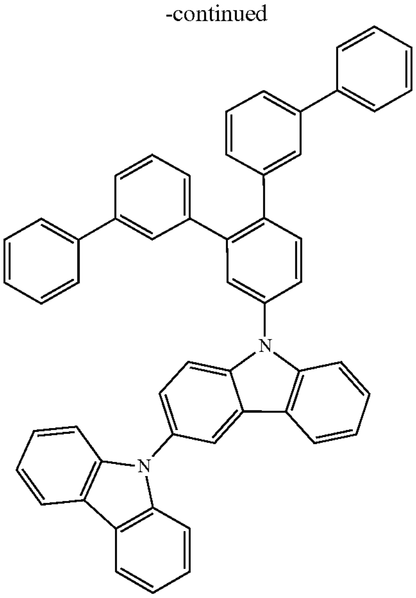
,
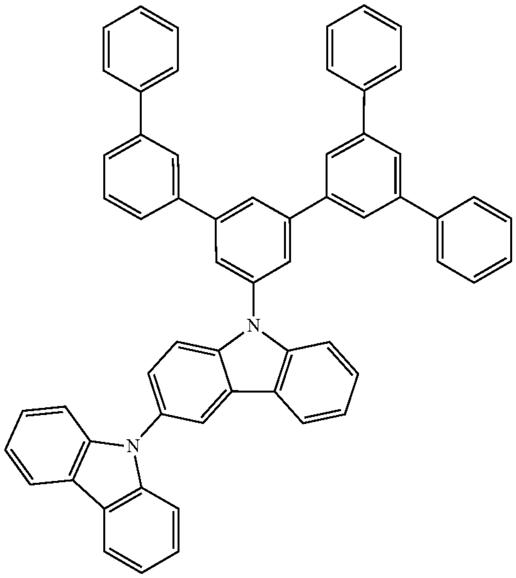
,
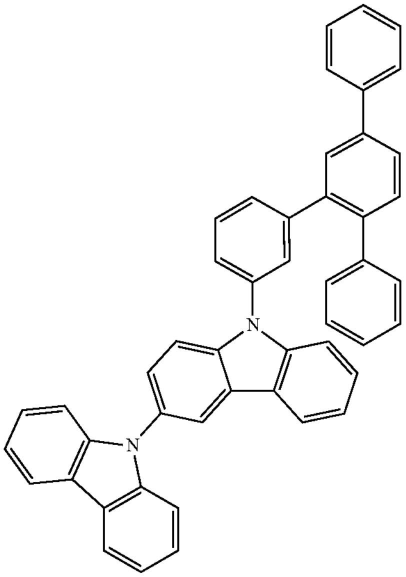
, -continued
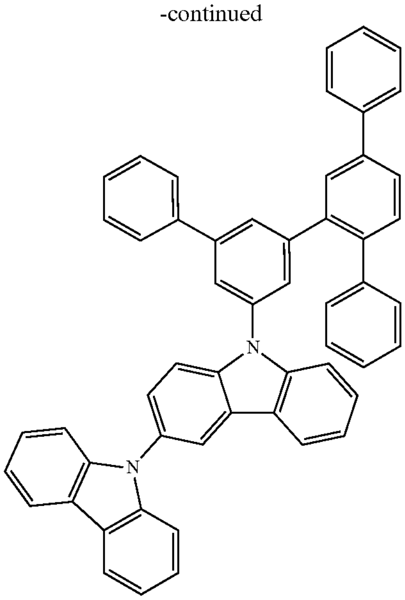
,
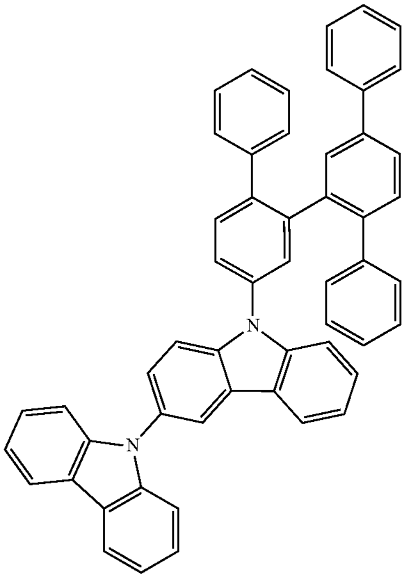
,
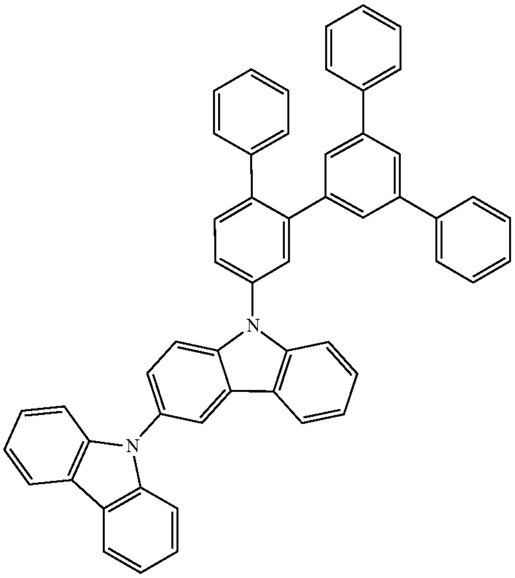
,
-continued
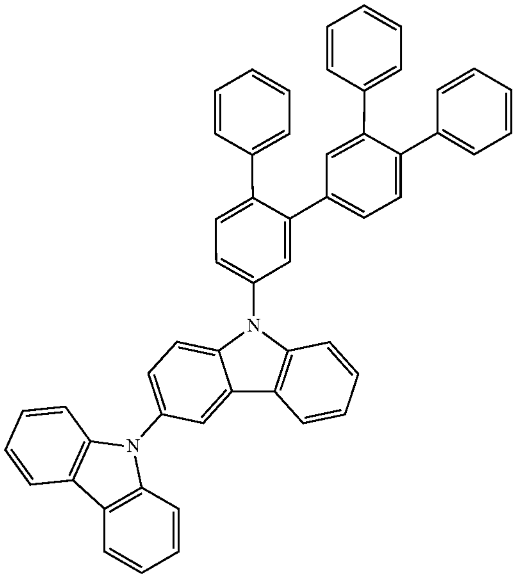
,
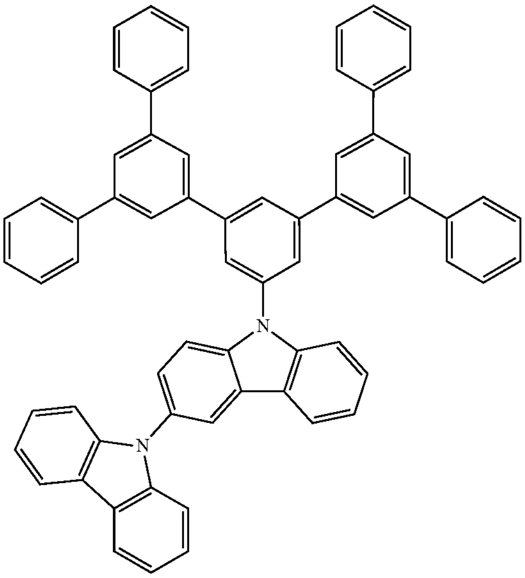
,
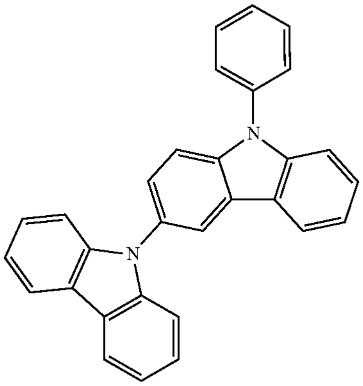
, -continued
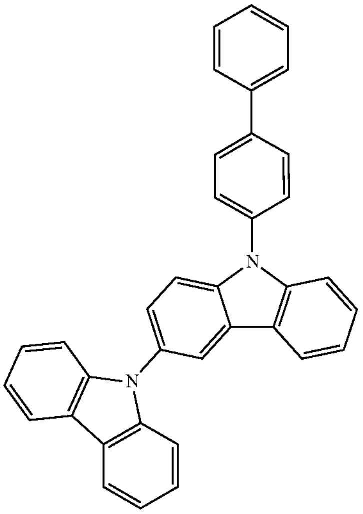
,
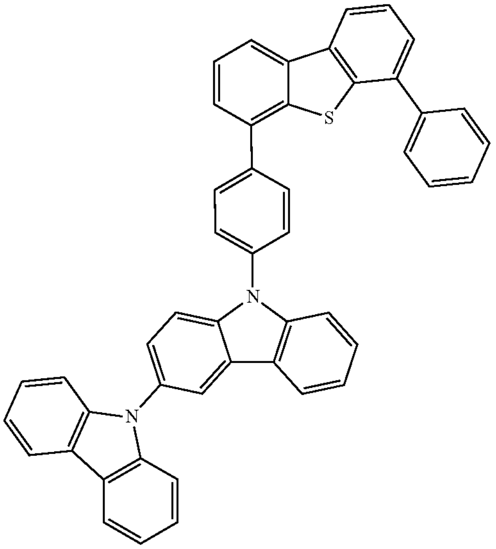
,
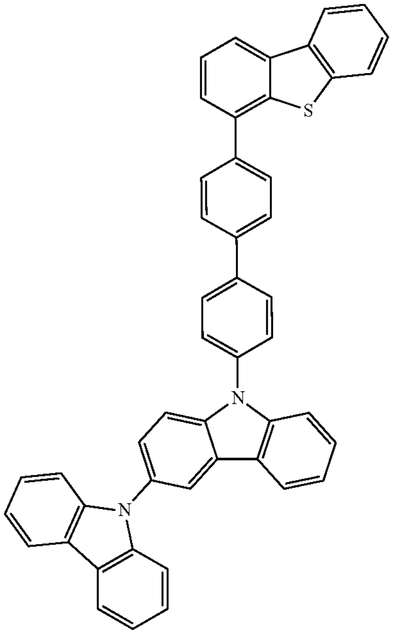
,
-continued
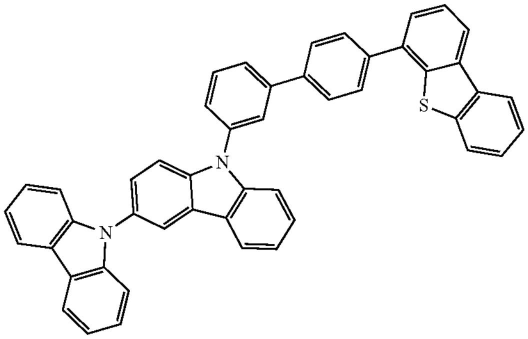
,
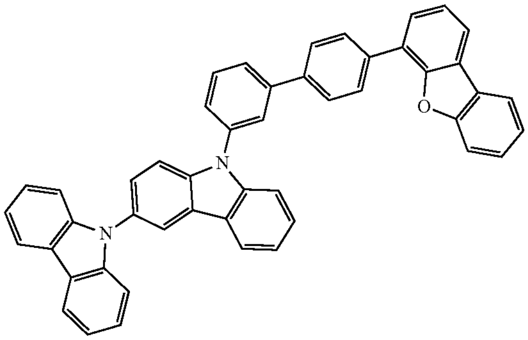
,
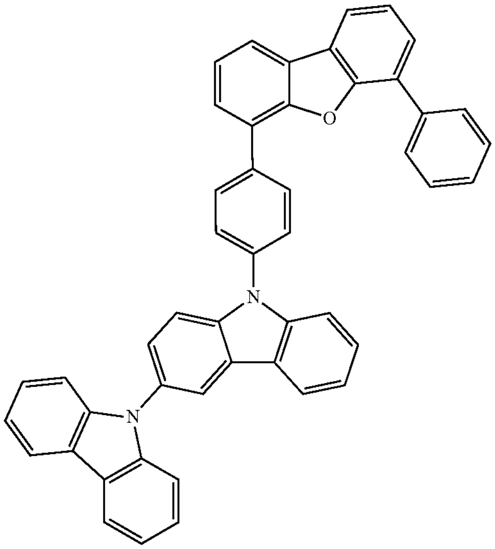
, -continued
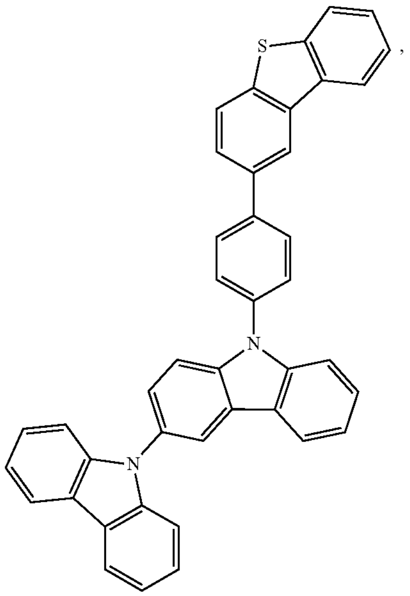
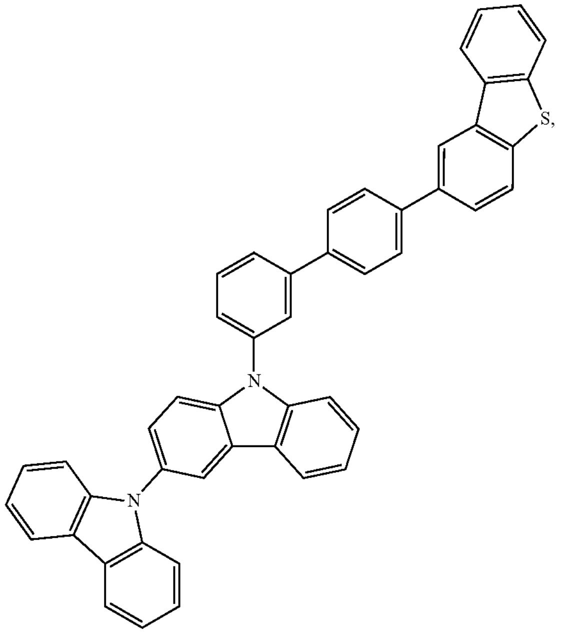
-continued
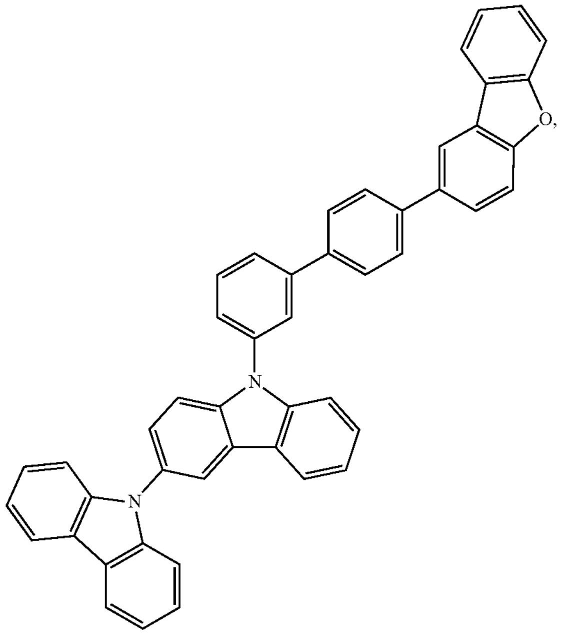
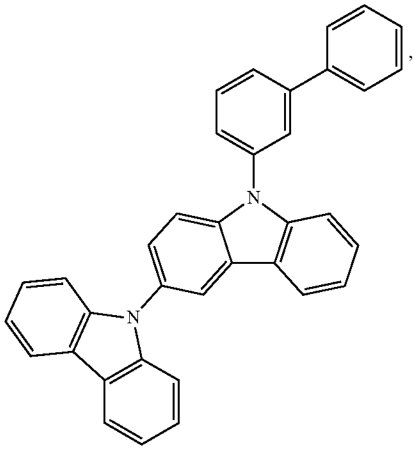
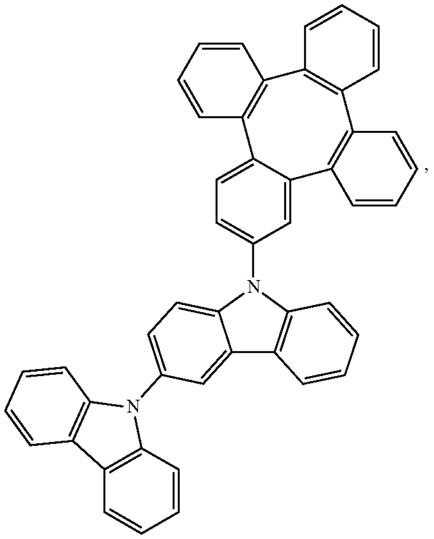

-continued
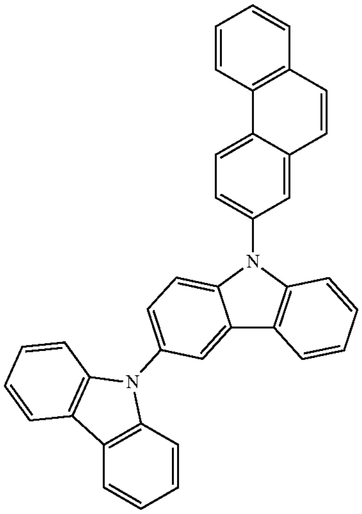
,
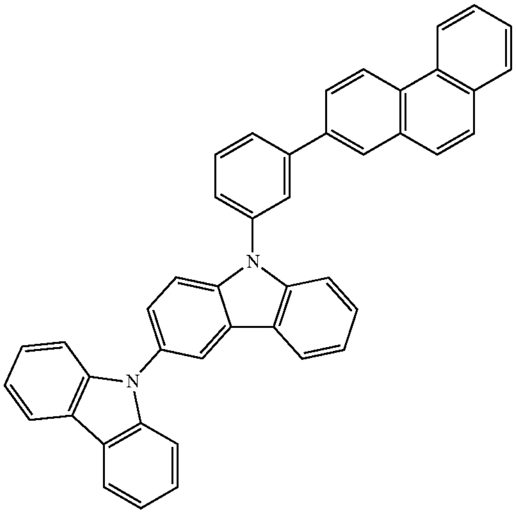
,
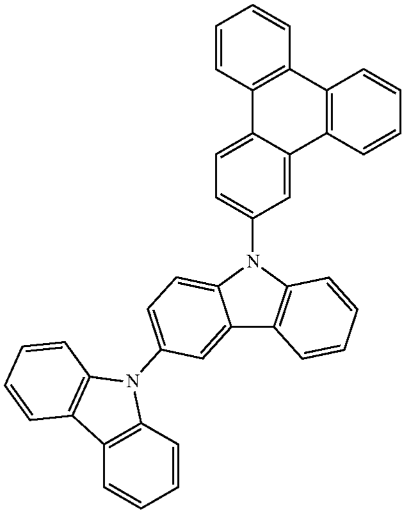
,
-continued
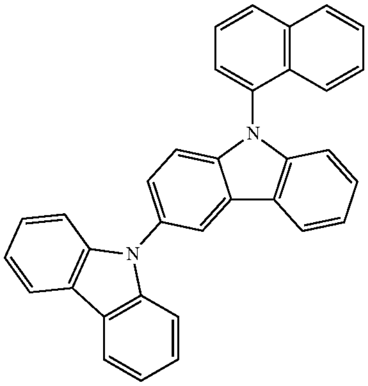
,
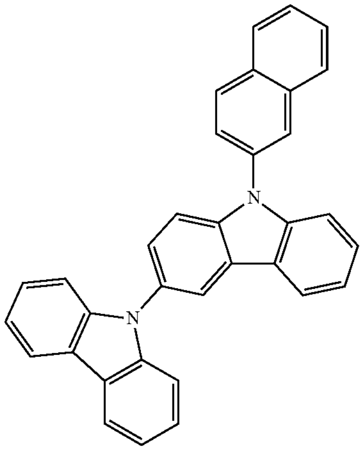
,
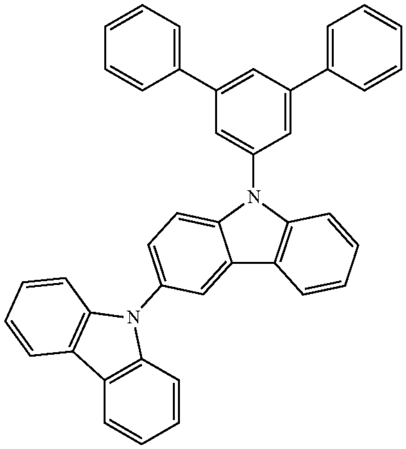
,
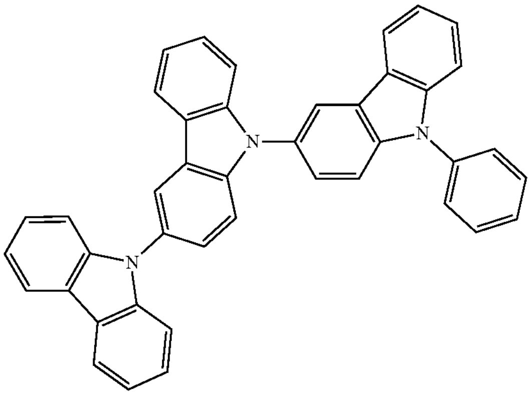
, -continued
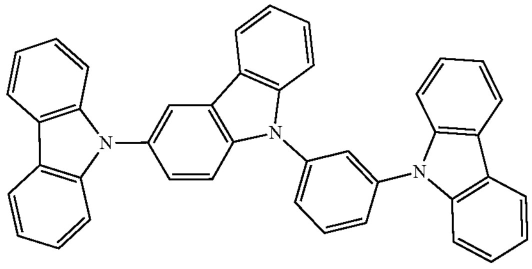
,
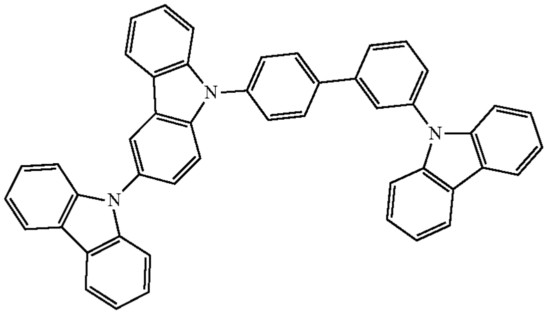
,
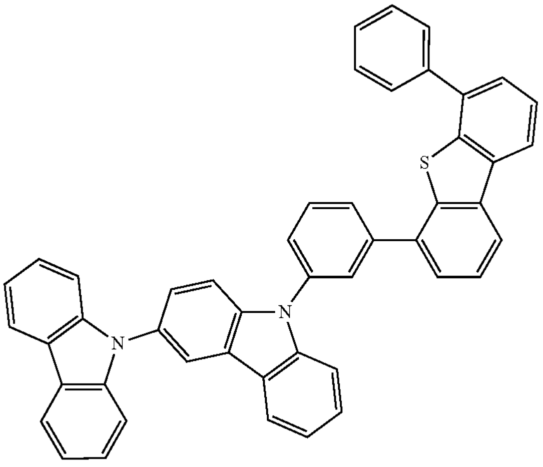
,
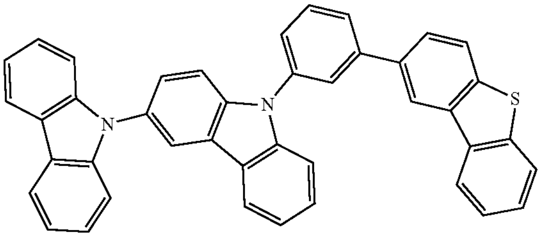
,
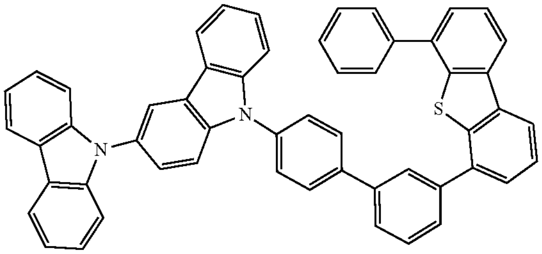
,
-continued
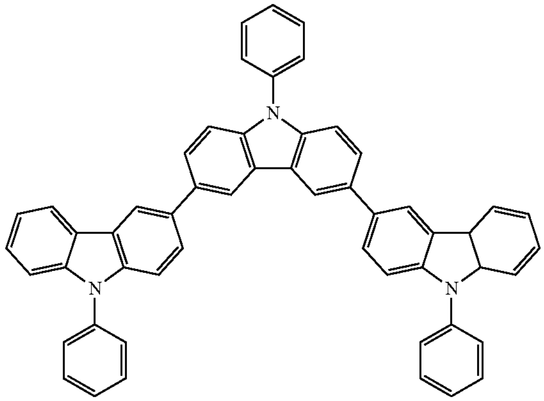
,
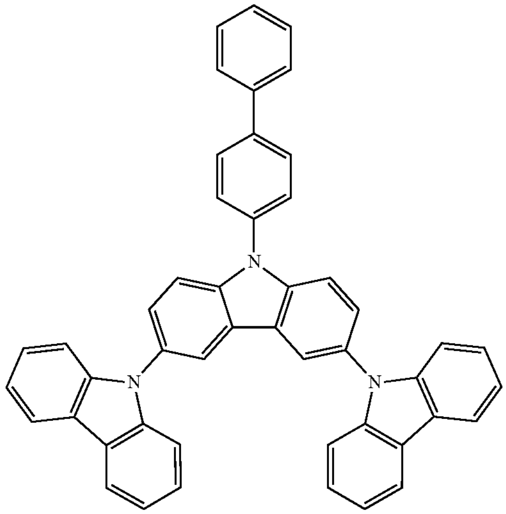
,
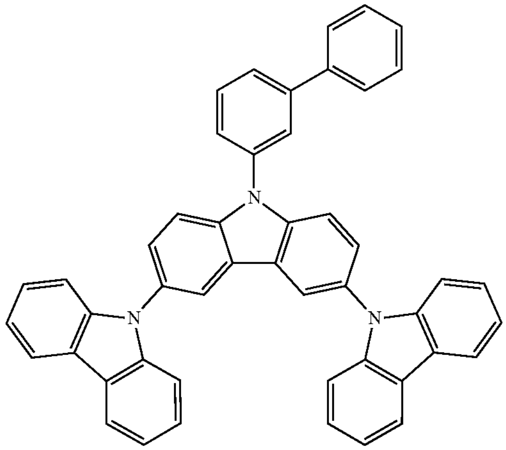
, -continued
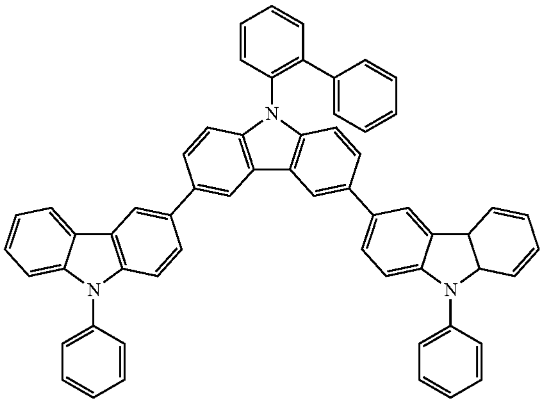
,
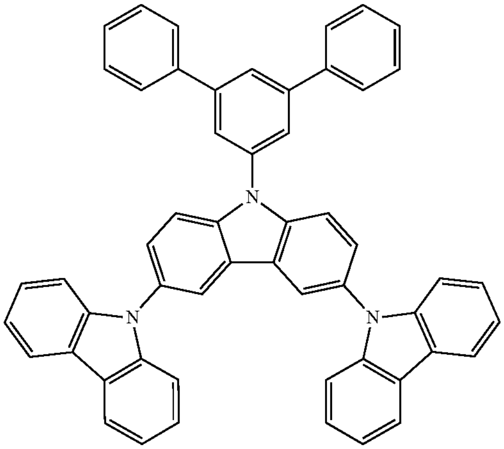
,
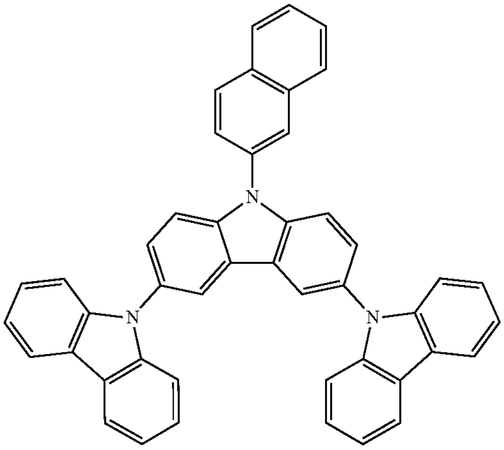
,
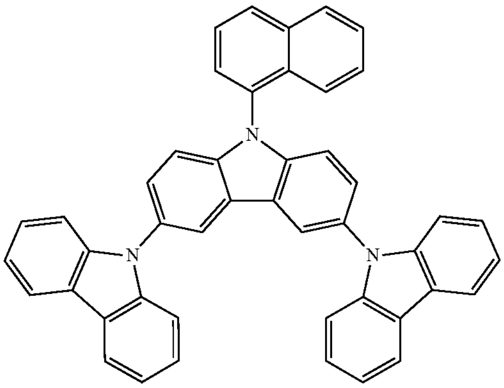
,
-continued
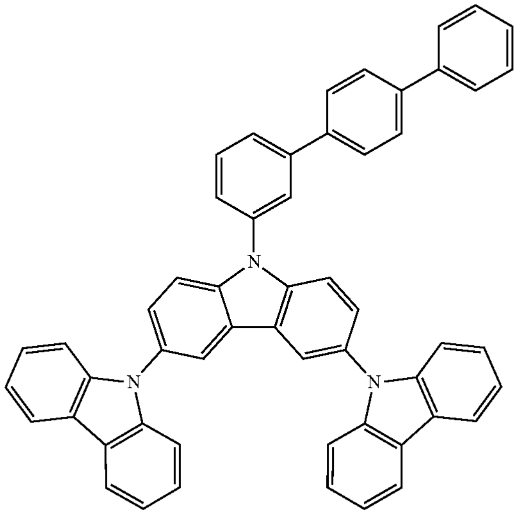
,
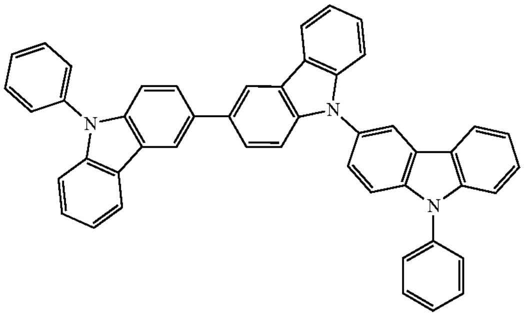
,
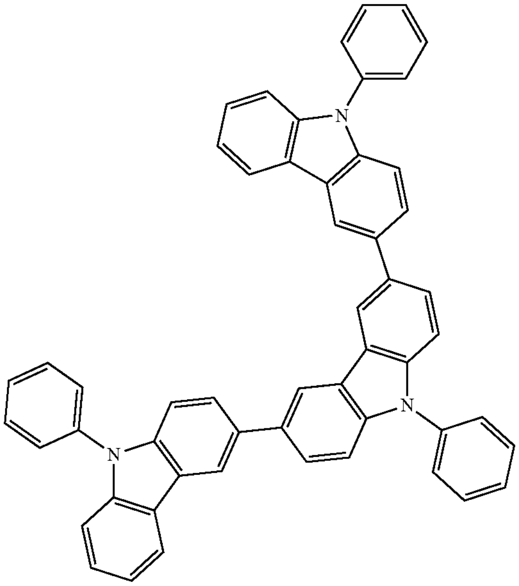
, -continued
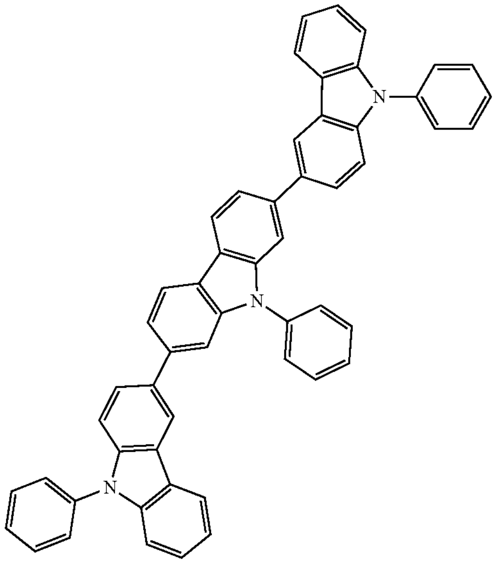
,
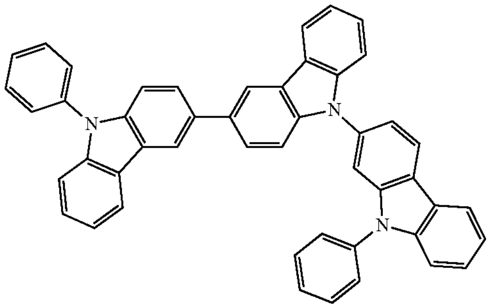
,
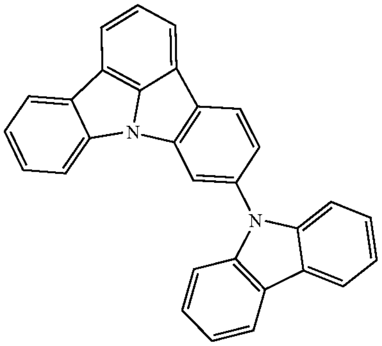
,
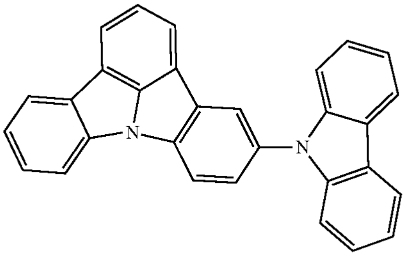
,
-continued
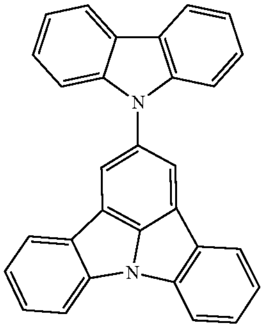
,
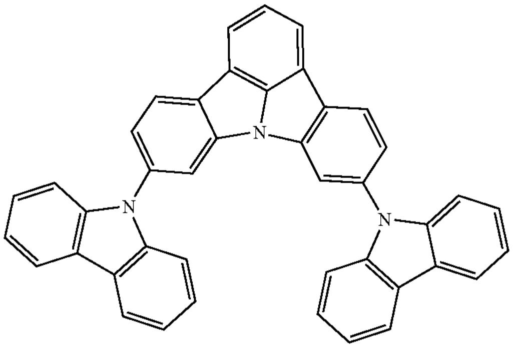
,
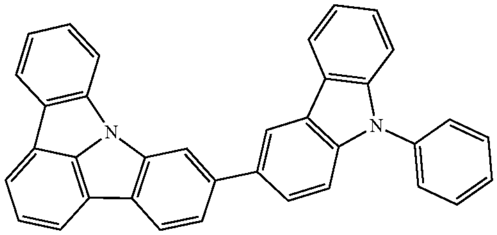
,
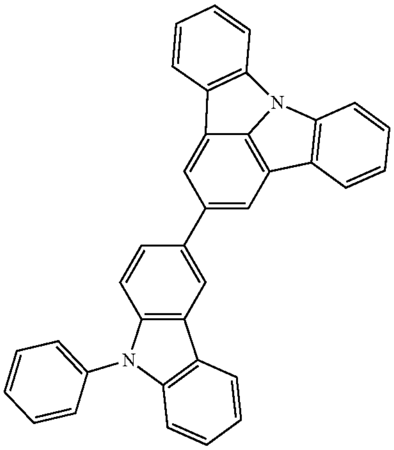
, -continued
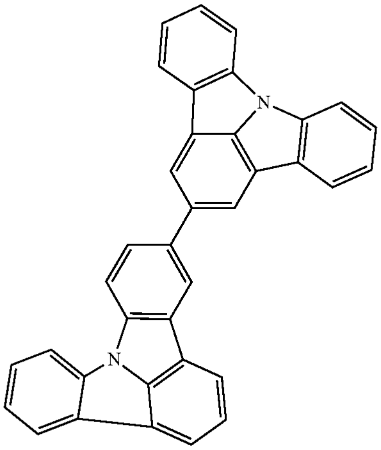
,
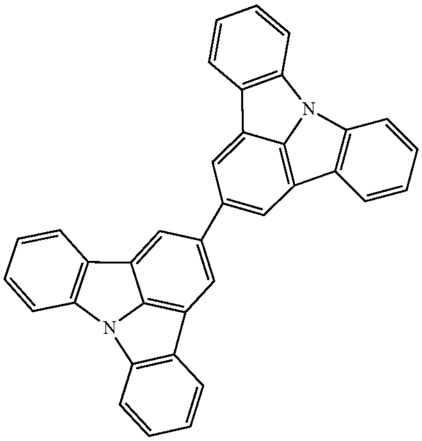
,
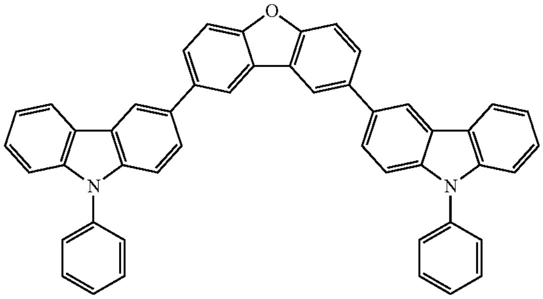
,
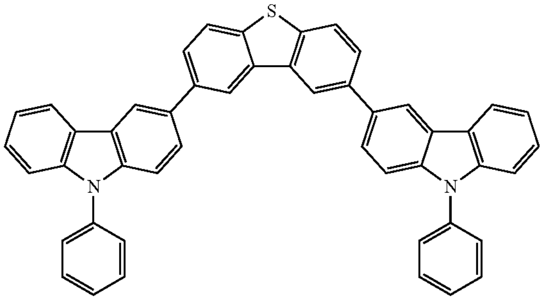
,
-continued
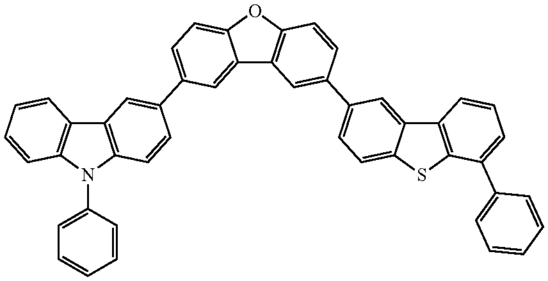
,
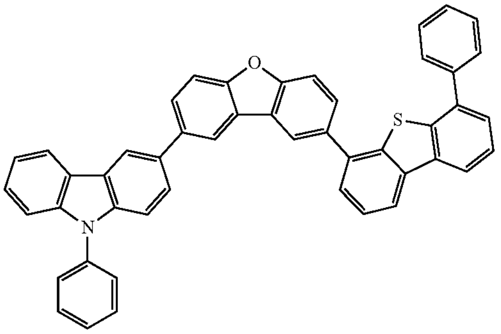
,
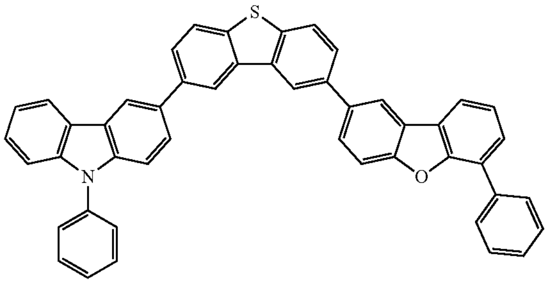
,
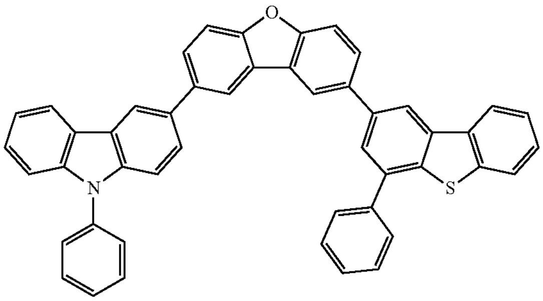
,
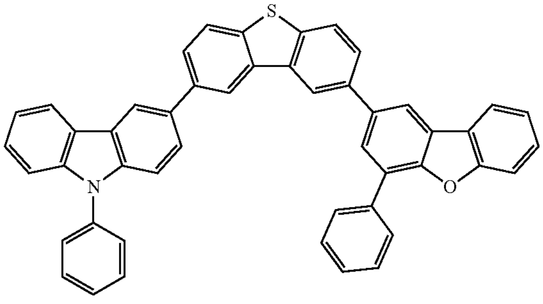
, -continued

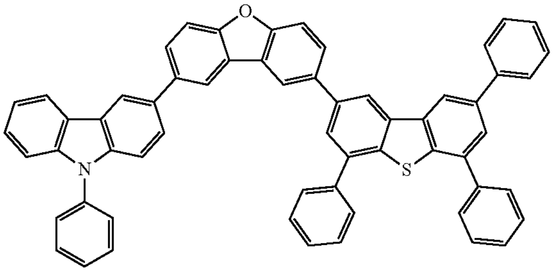

,

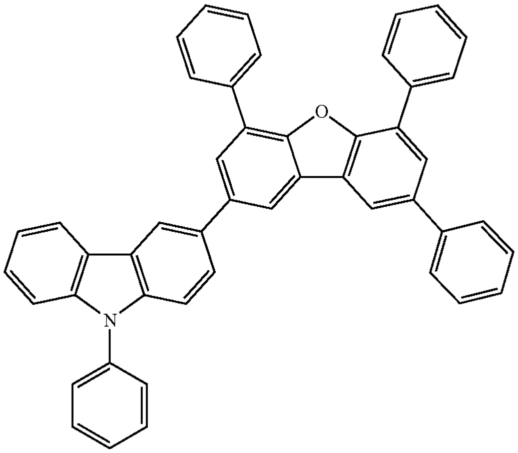

,

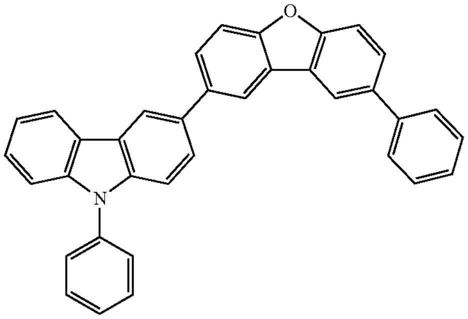

, and

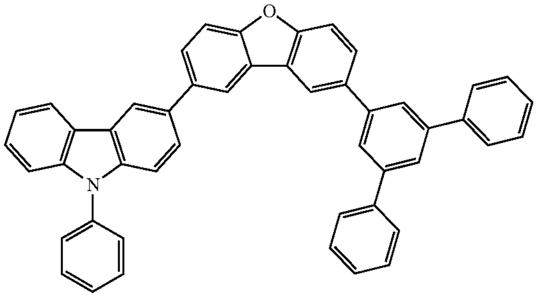

.

20. A formulation comprising a compound of Formula I

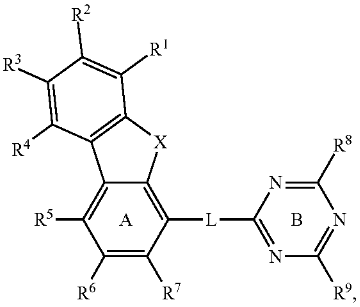

wherein:

each of $R^1$ to $R^7$ is independently a hydrogen or a substituent selected from the group consisting of phenyl, and a system consisting of two to ten phenyl groups connected to each other;

at least two of $R^1$ to $R^7$ are not hydrogen;

if $R^1$ and $R^3$ are not hydrogen, then at least one of the following is true: 1) $R^1$ and $R^3$ are different from each other; or 2) at least one of $R^1$ or $R^3$ is an unsubstituted phenyl;

if one of the at least two $R^1$ to $R^7$ that is not hydrogen is the system consisting of two to ten phenyl groups connected to each other, then the phenyl group directly bonded to the structure of Formula I having X bonds to exactly one phenyl group;

$R^8$ and $R^9$ are each independently selected from the group consisting of phenyl, and a system consisting of two to ten phenyl groups connected to each other;

X is selected from the group consisting of O, S, and Se; and

L is selected from the group consisting of direct bond and

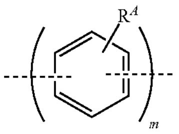

;

wherein m is an integer from 1 to 5, and $R^A$ is a hydrogen or a substituent selected from the group consisting of aromatic and heteroaromatic rings; and subject to the following provisos i) to iv):

i) if L is biphenyl, one phenyl of the biphenyl bonds to ring A and the other phenyl bonds to ring B;

ii) if X is O, then least one of $R^1$, $R^3$, or $R^5$ is H;

iii) if X is S, then at least one of $R^1$ or $R^6$ is H but if $R^6$ is H and $R^1$ is not H, then at least one of $R^3$ or $R^5$ is H; and iv) the following structures are excluded

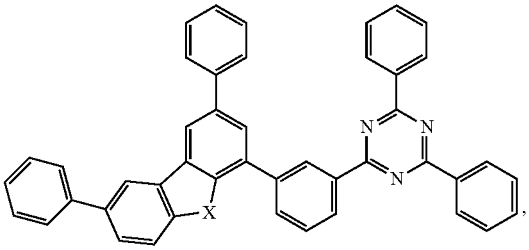

, and

-continued

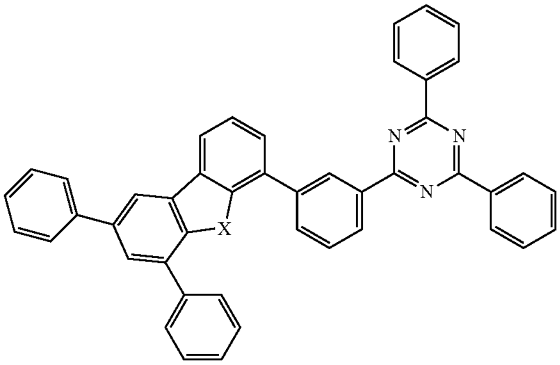

;

and wherein at least one of the following conditions 1) to 4) is true:

1) m is 1, ring A and ring B are meta to each other, and $R^1$ to $R^9$ comprise a total of at least 6 phenyl groups;

2) at least one of $R^1$ to $R^4$ is not hydrogen and at least one of $R^5$ to $R^7$ is not hydrogen;

3) $R^8$ is phenyl and $R^9$ is biphenyl; or

4) X is S; and an h-host selected from the group consisting of:

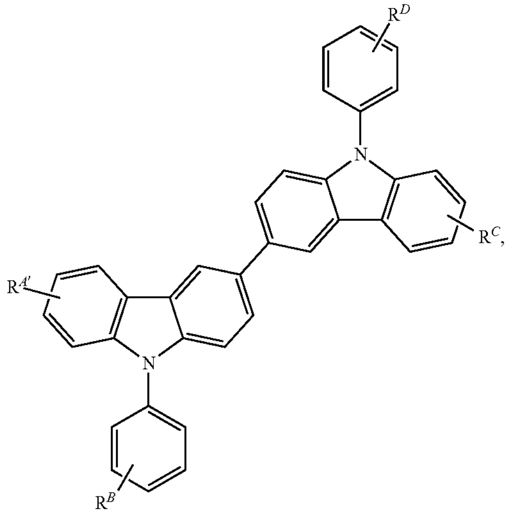

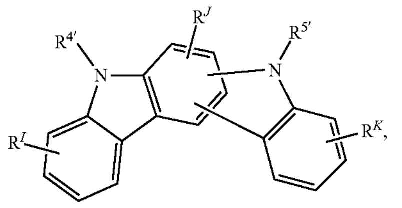

-continued

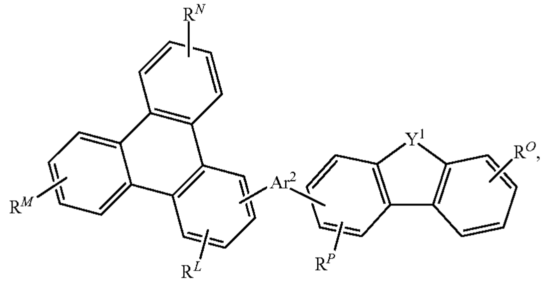

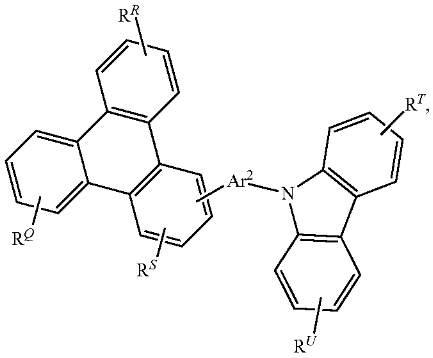

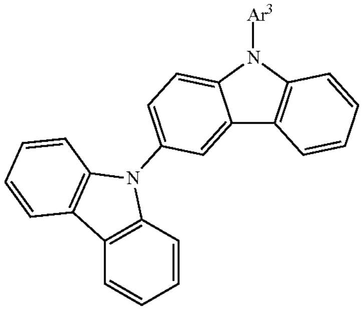

,

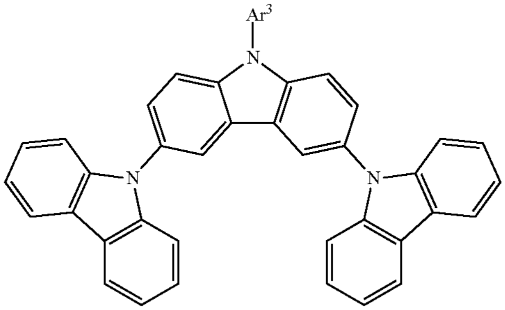

,

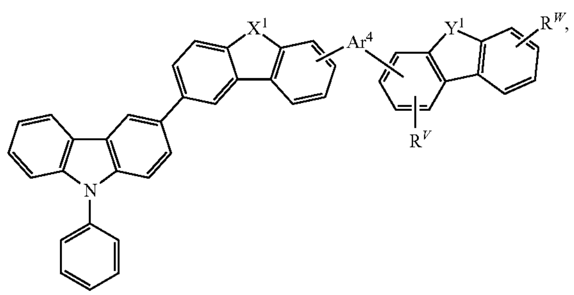

-continued
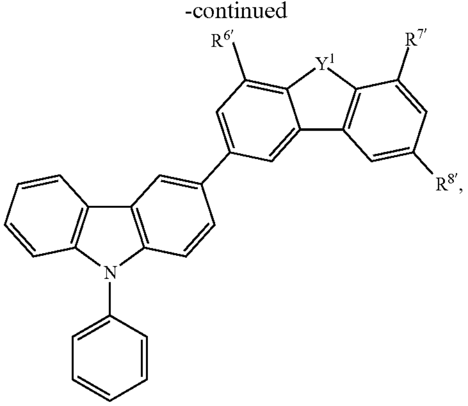
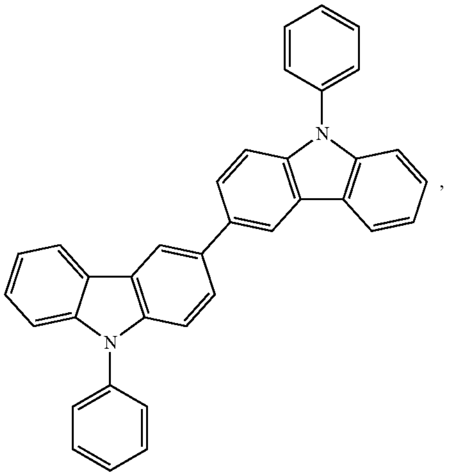
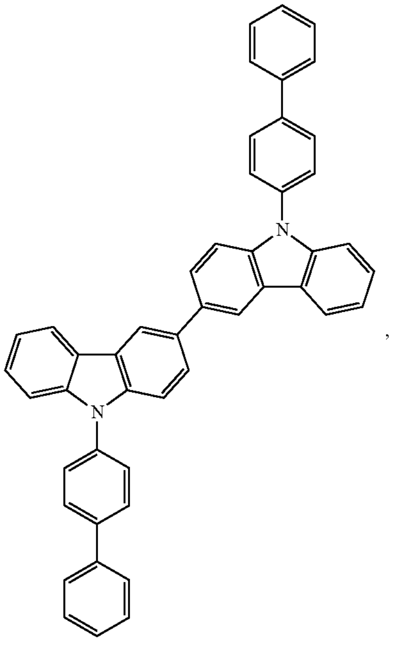
-continued
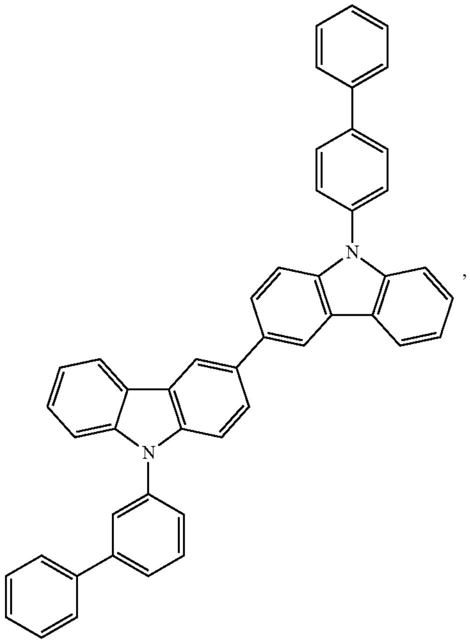
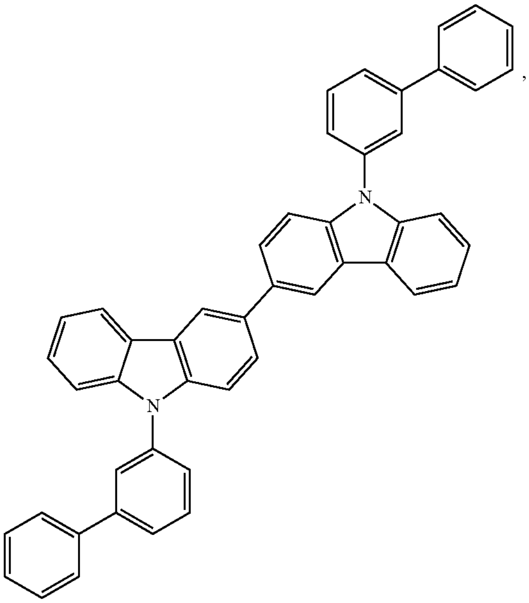

-continued
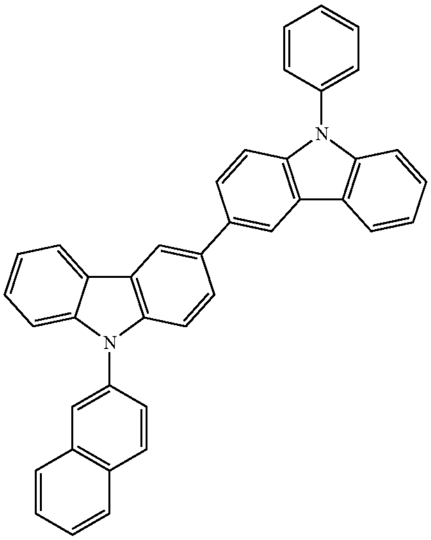
,
-continued
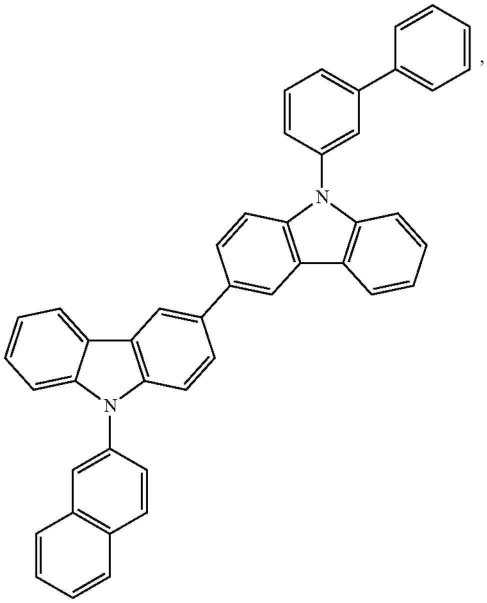
,
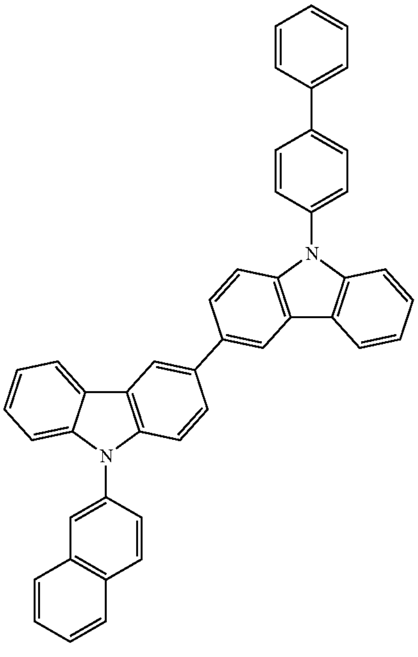
,
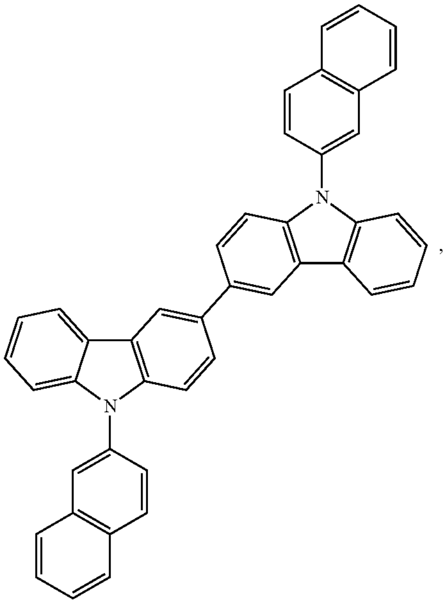
, -continued
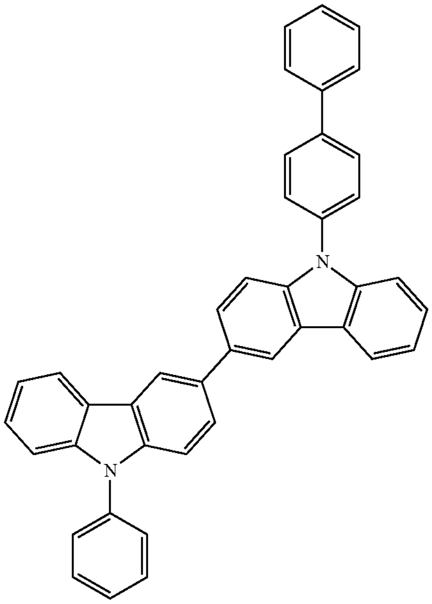
,
-continued
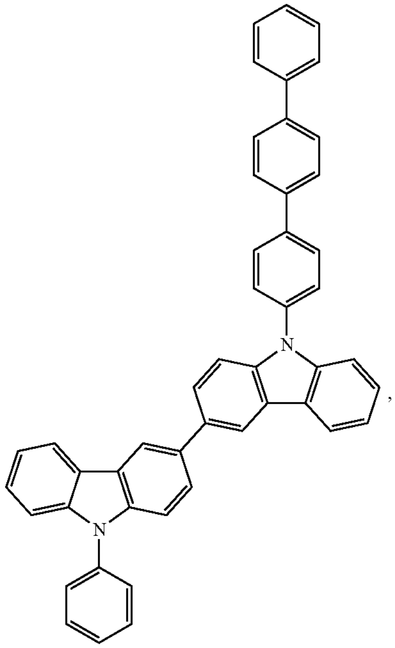
,
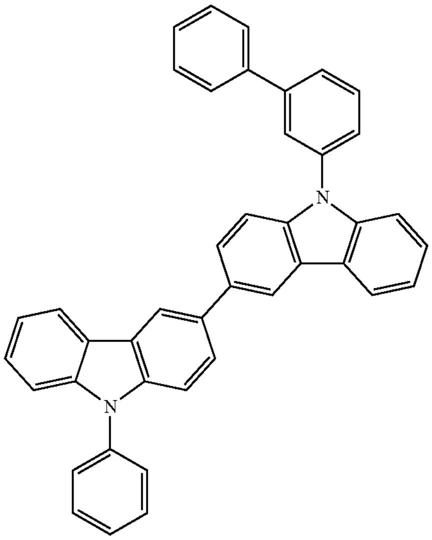
,
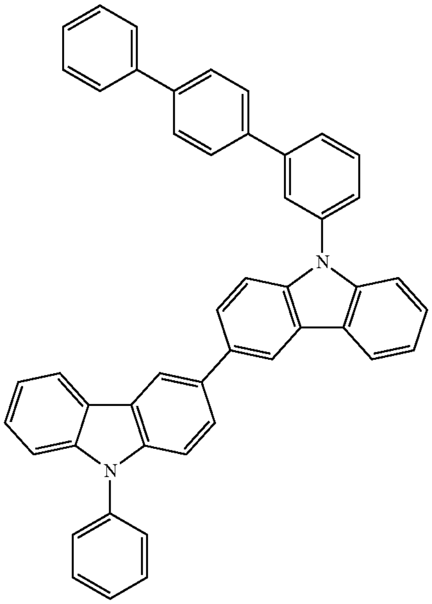
, -continued
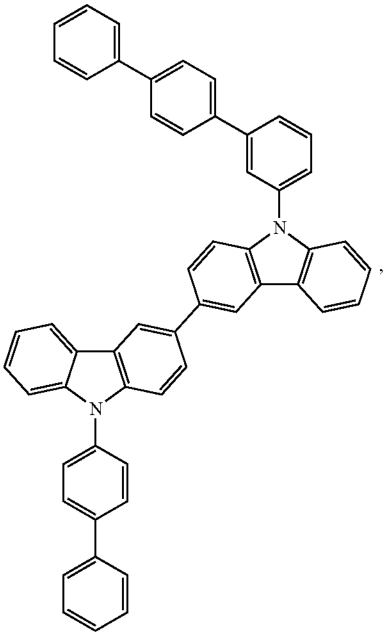
,
-continued
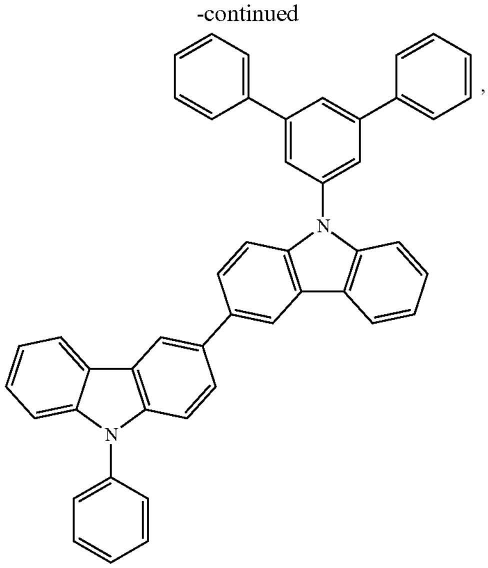
,
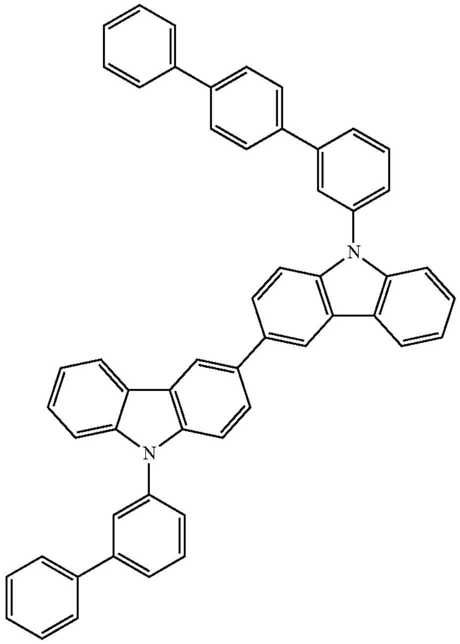
,
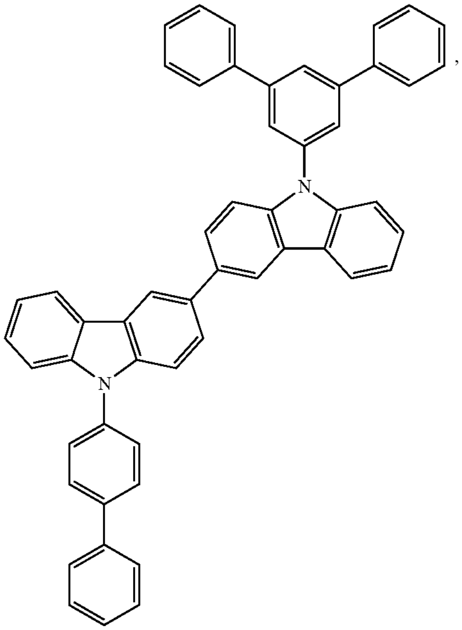
, -continued
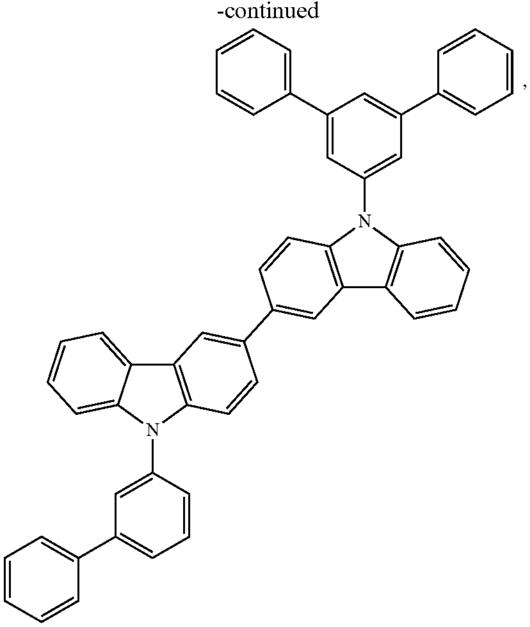
,
-continued
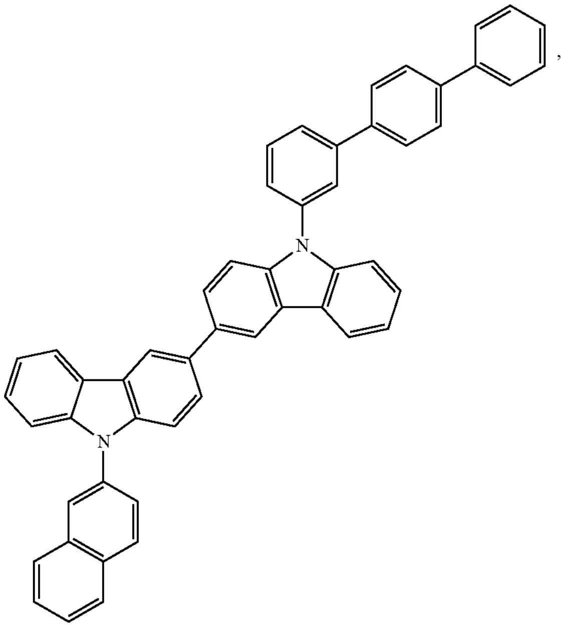
,
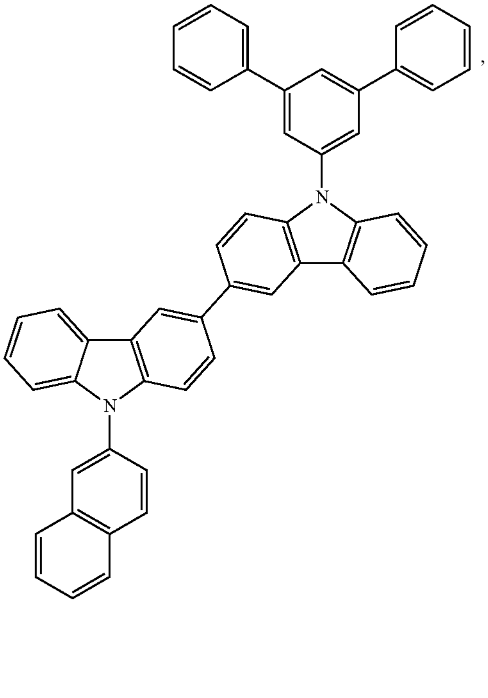
,
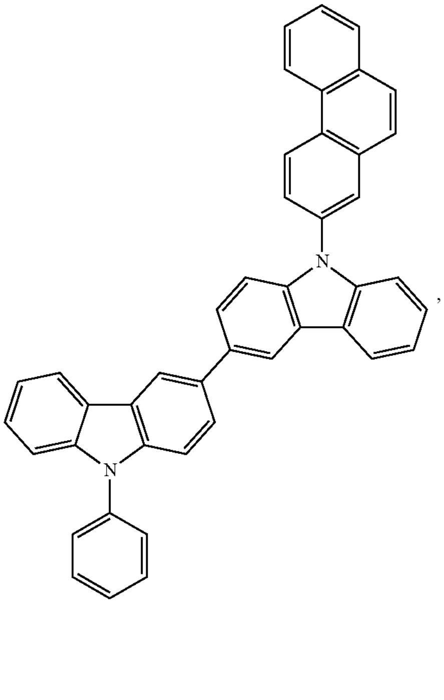
, -continued
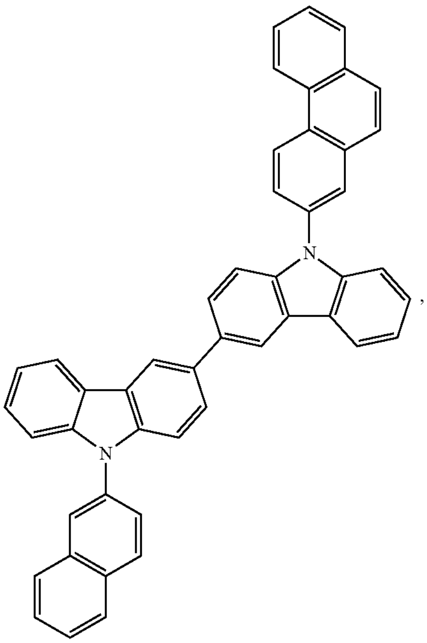
,
-continued
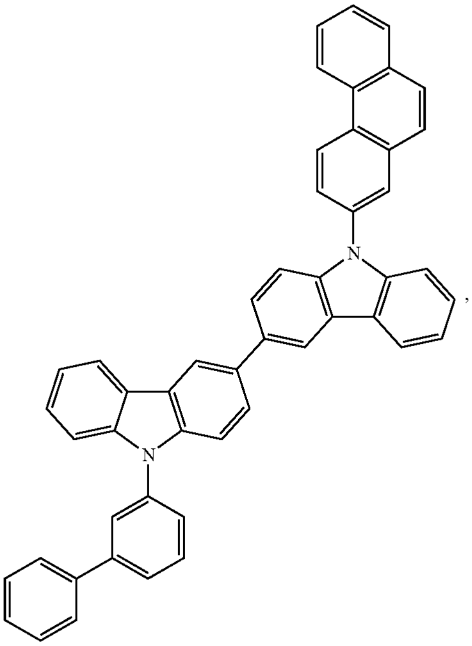
,
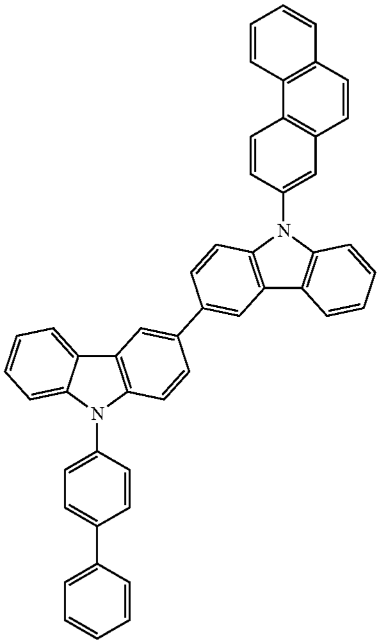
,
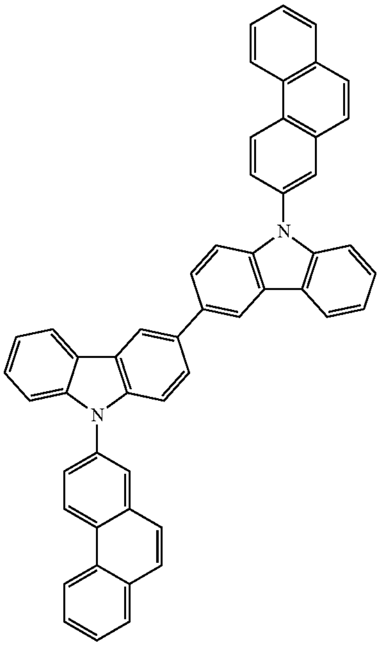
, -continued
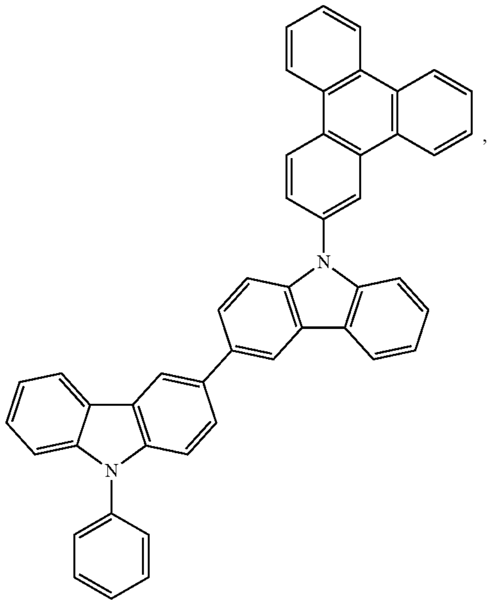
,
-continued
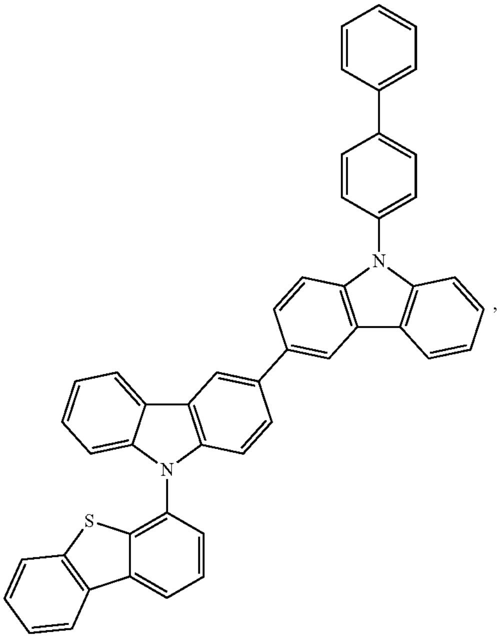
,
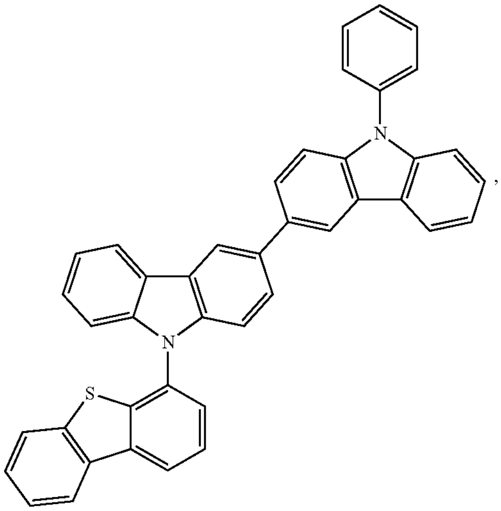
,
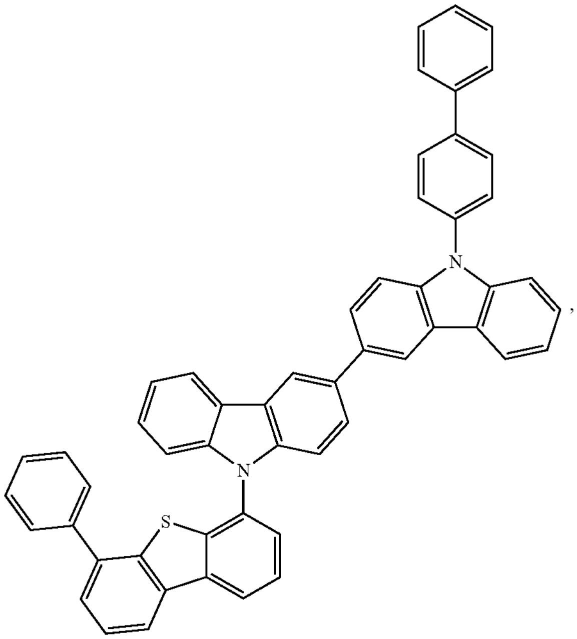
, -continued
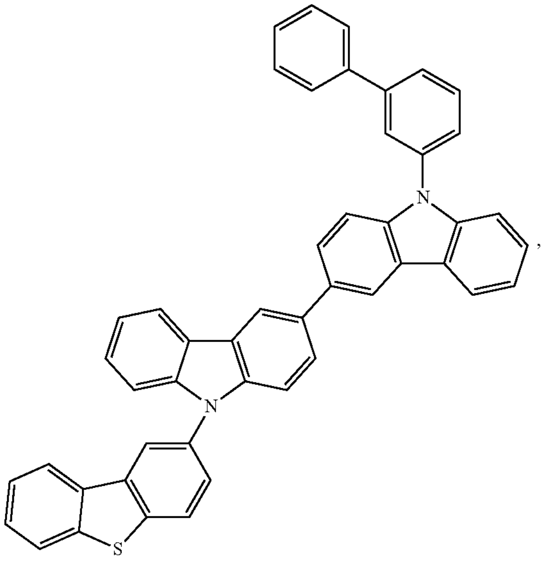
,
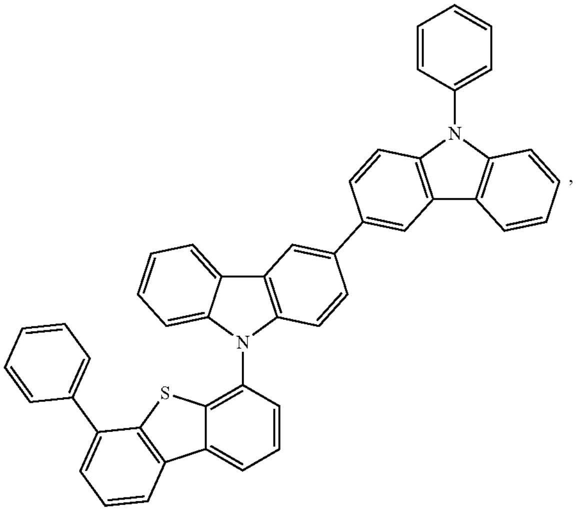
,
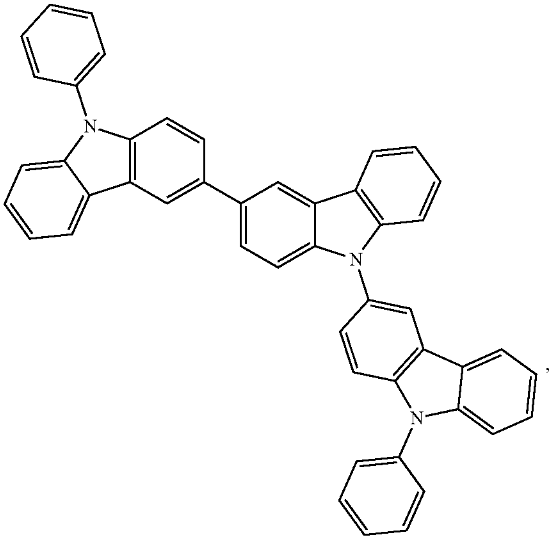
,
-continued
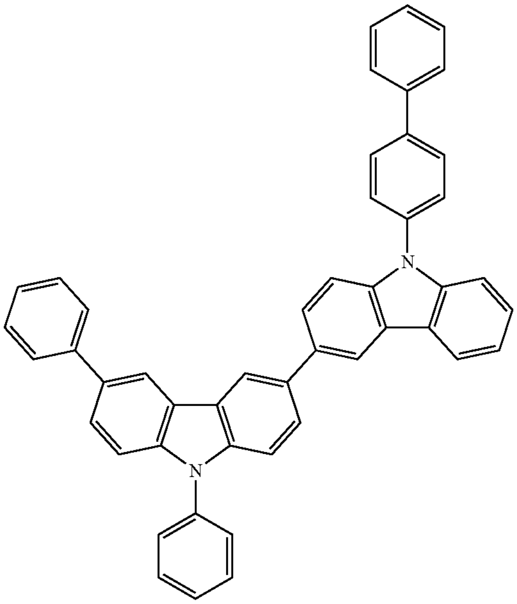
,
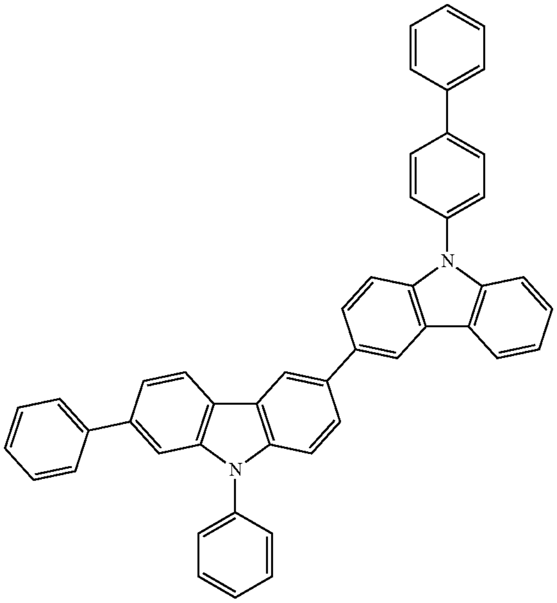
, -continued
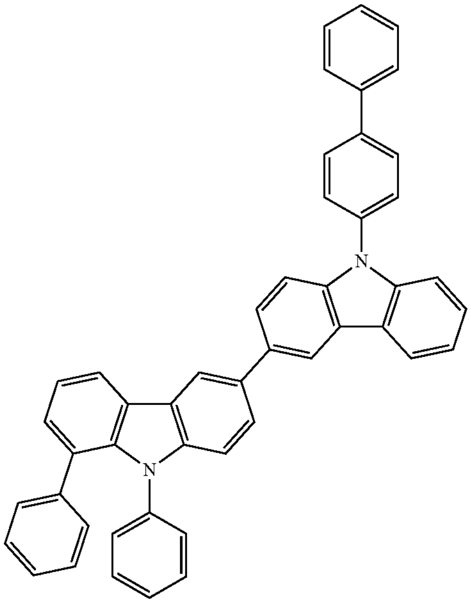
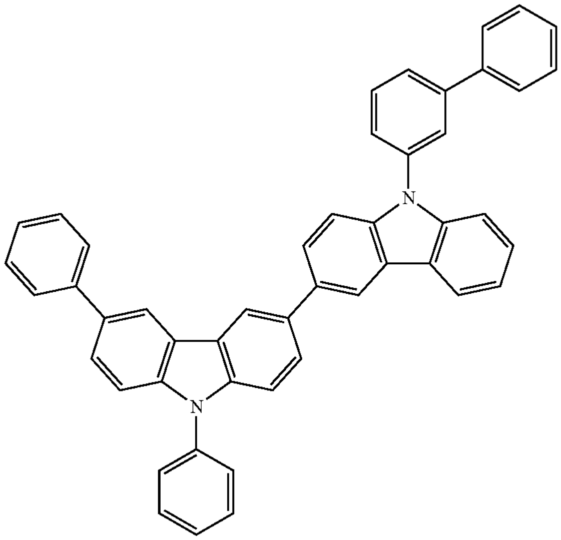
,
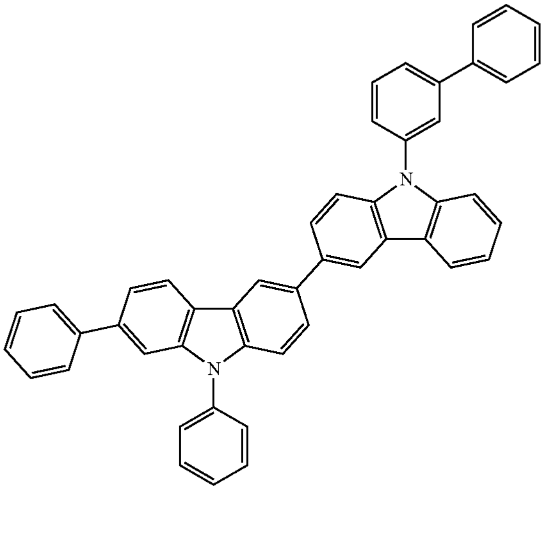
,
-continued
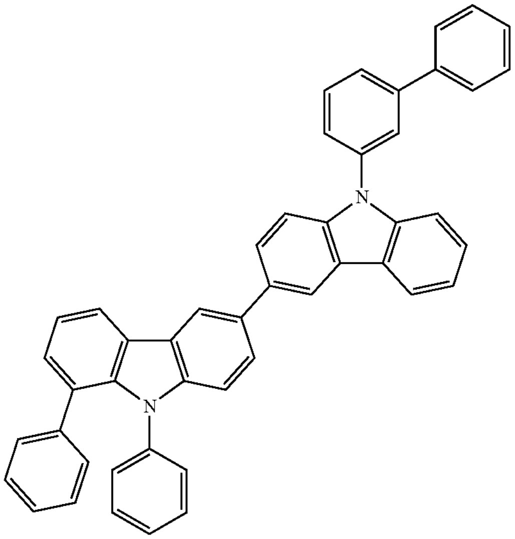
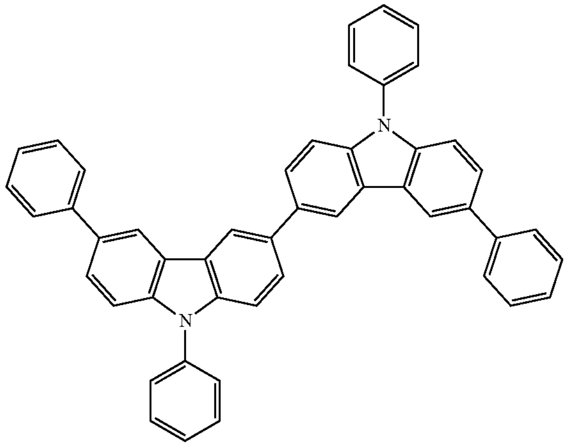
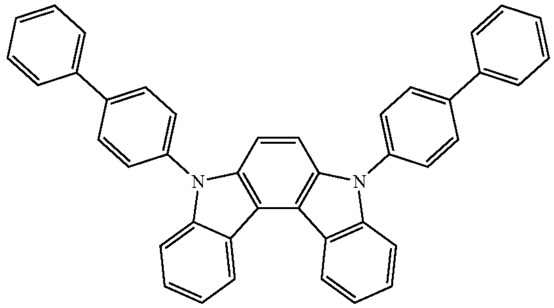
,
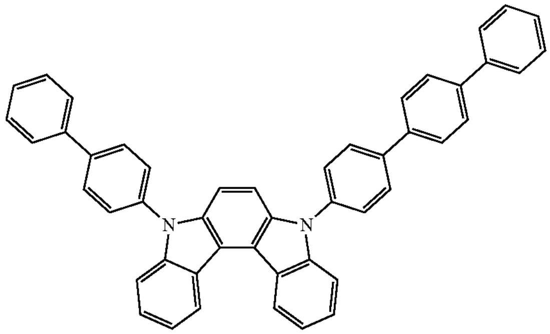
, -continued
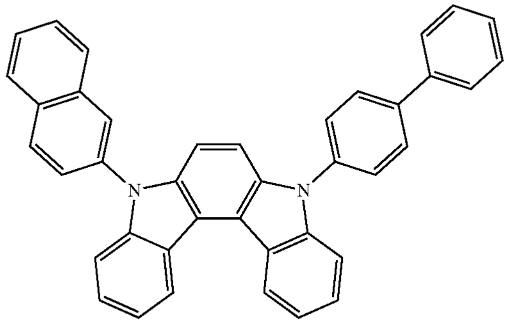
,
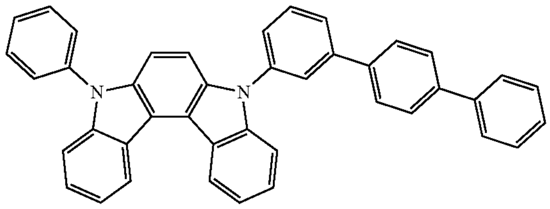
,
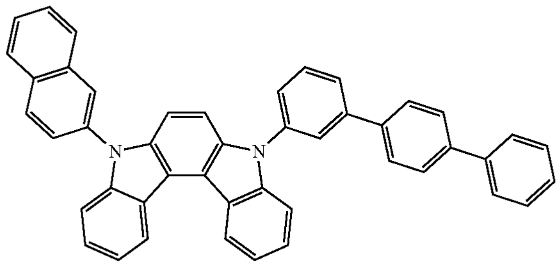
,
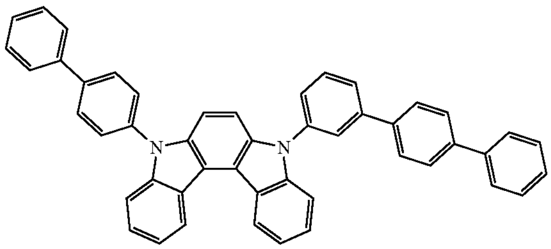
,
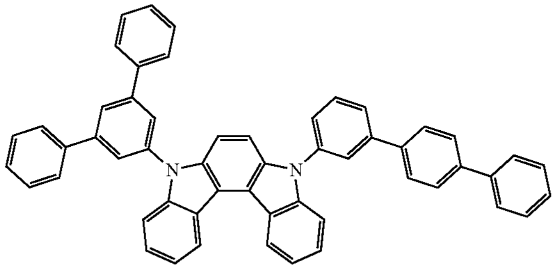
,
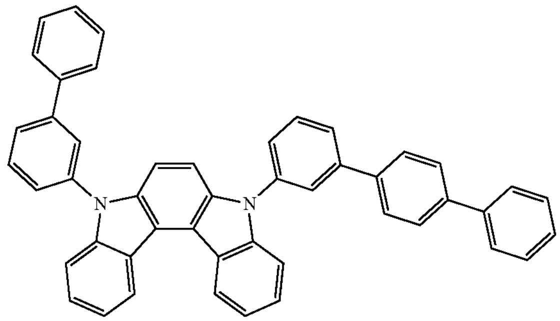
,
-continued
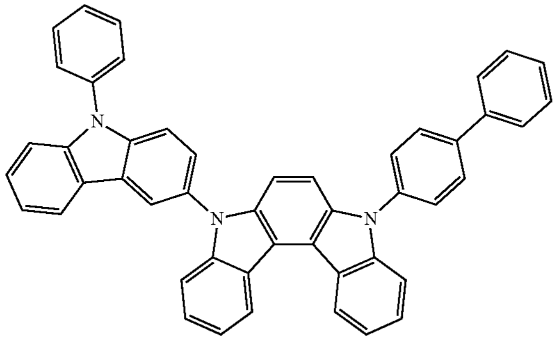
,
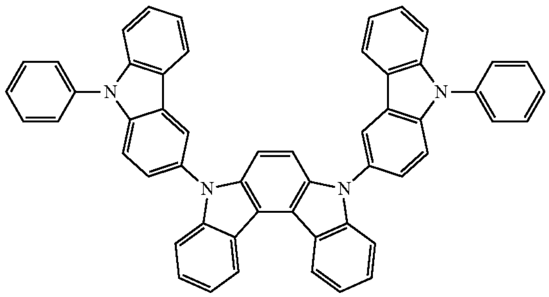
,
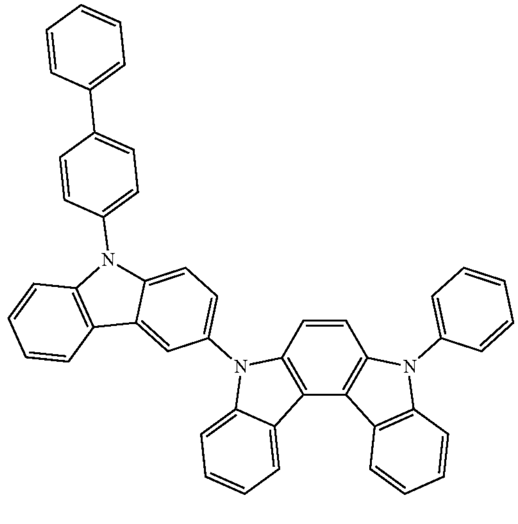
,
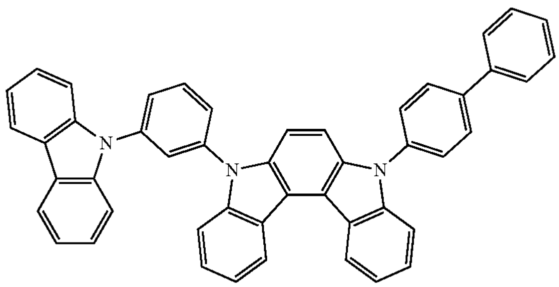
, -continued
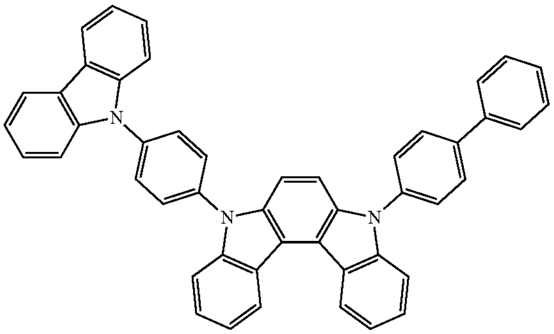
,
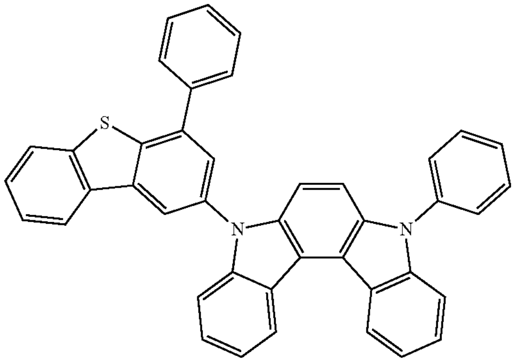
,
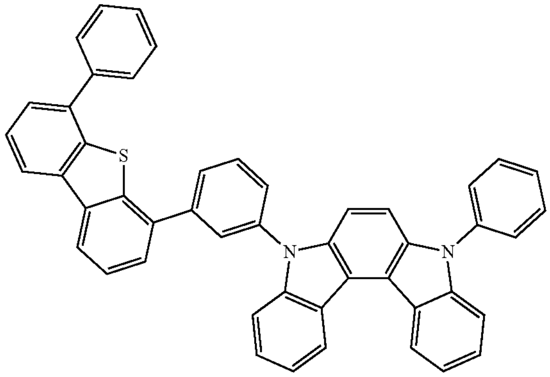
,
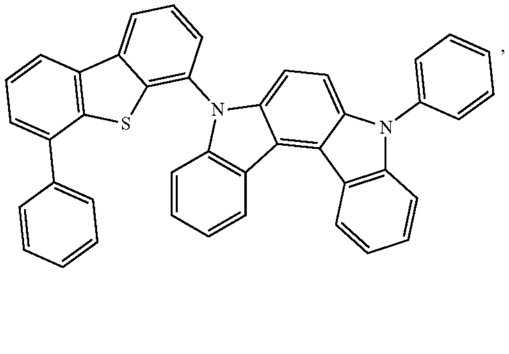
,
-continued
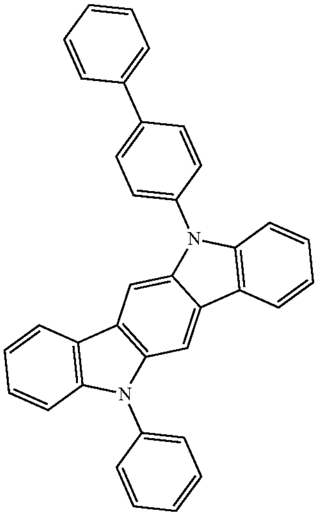
,
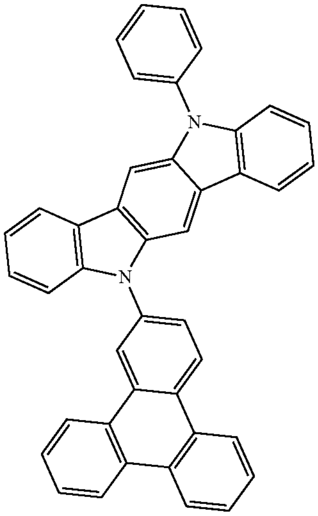
,
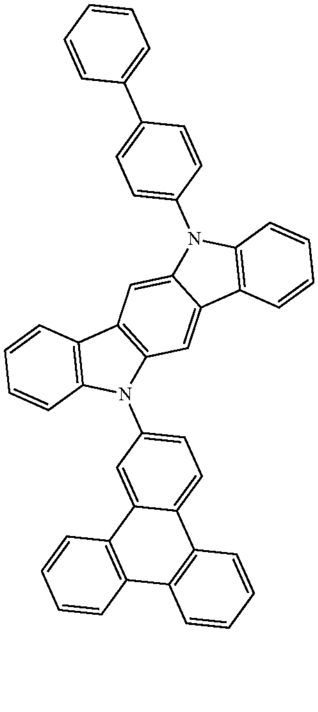
, -continued
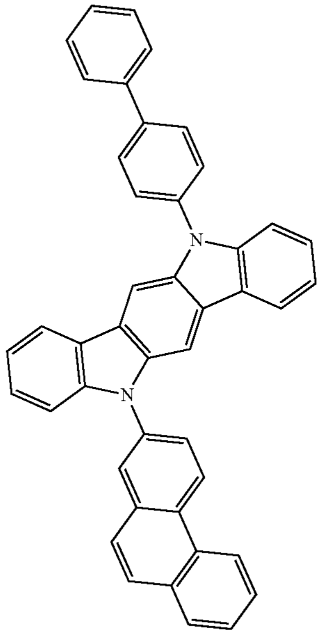
,
-continued
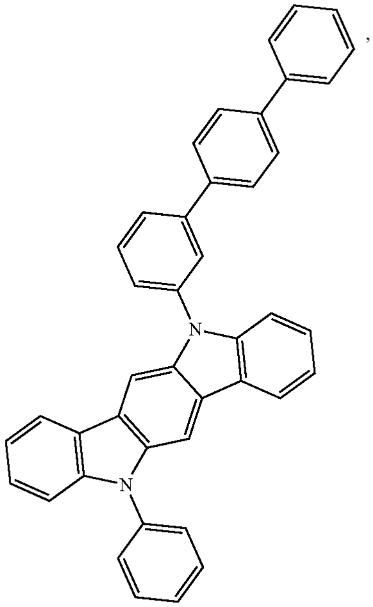
,
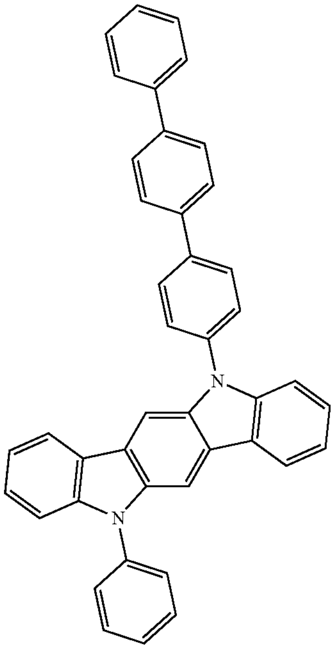
,
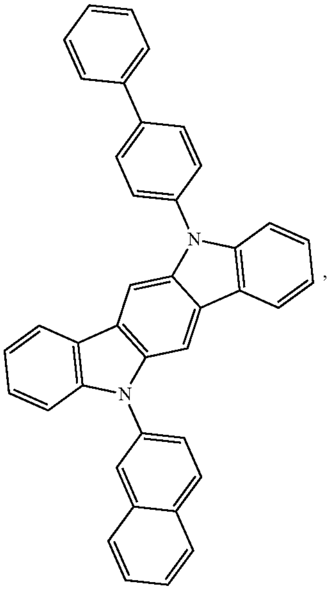
, -continued
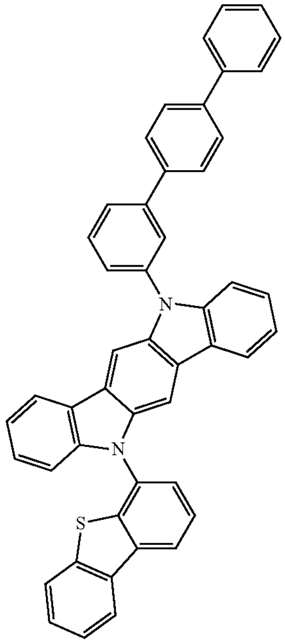
,
-continued
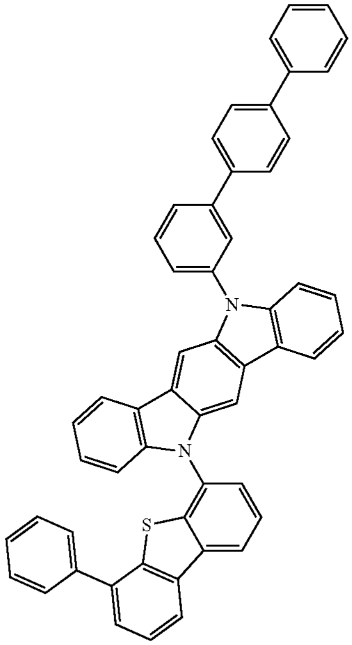
,
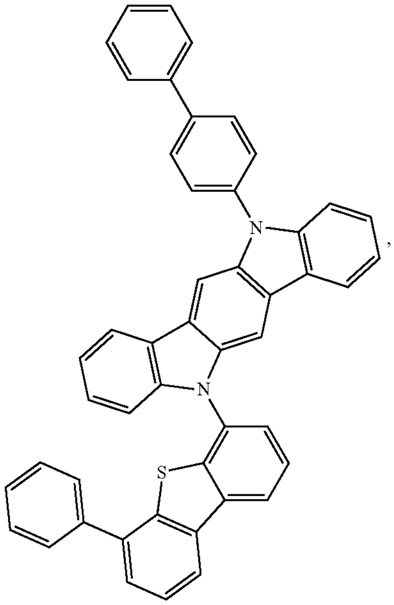
,
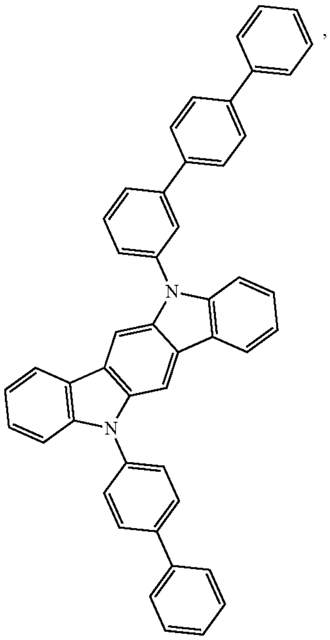
, -continued
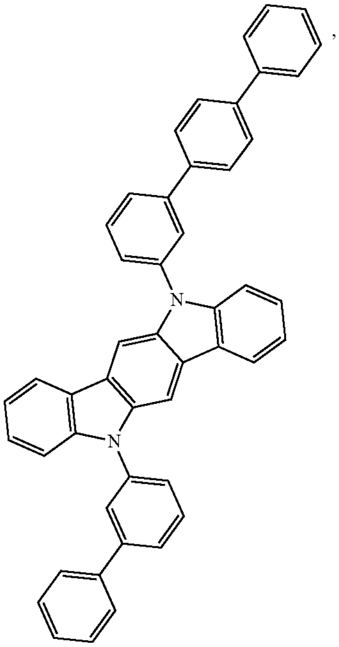
,
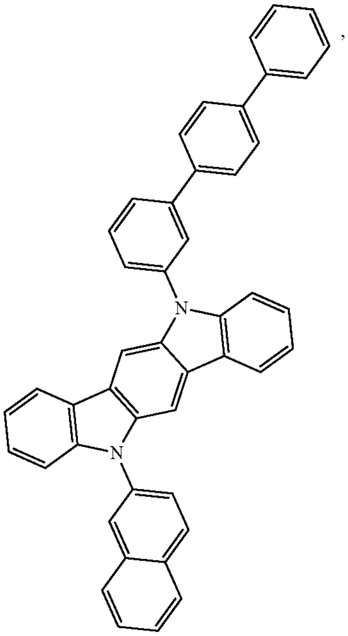
,
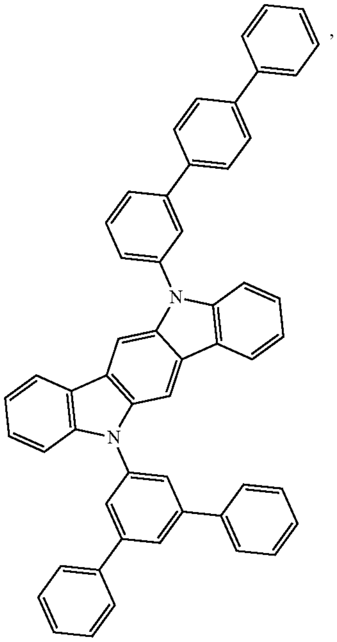
,
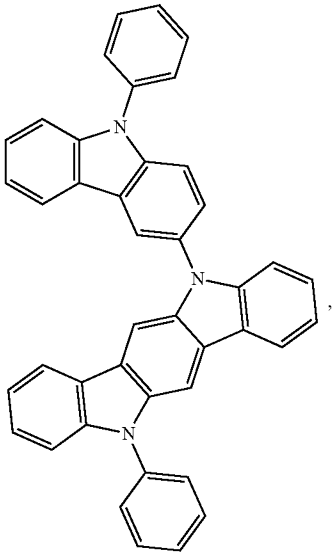
, -continued
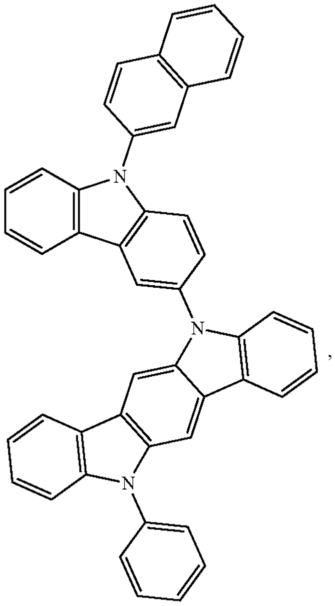
,
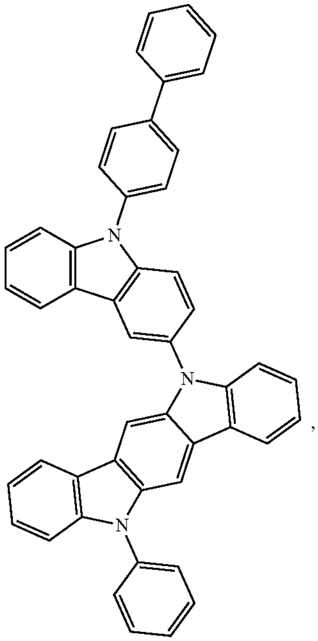
,
-continued
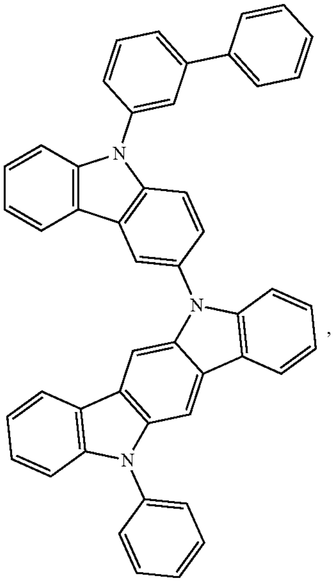
,
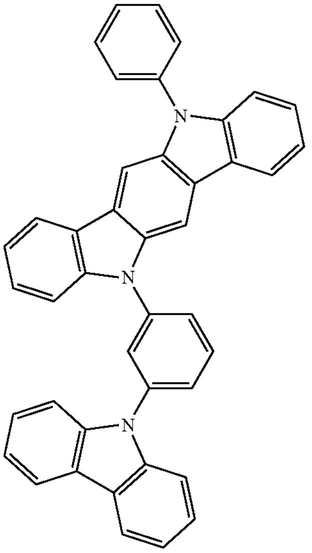
,
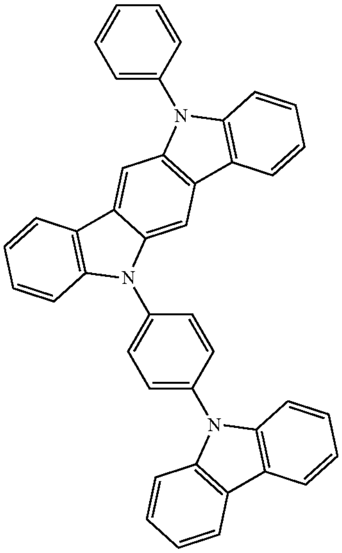
, -continued
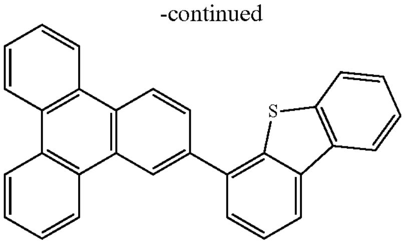
,
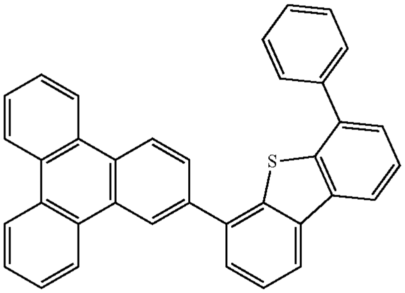
,
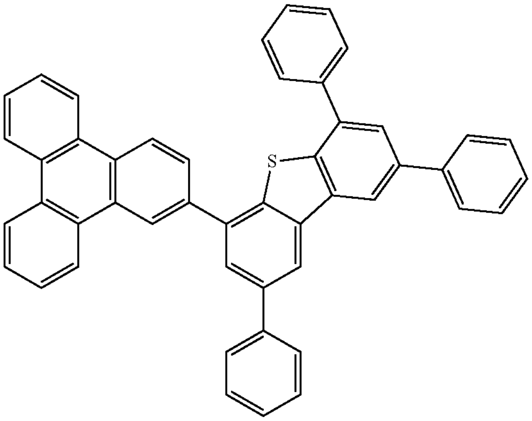
,
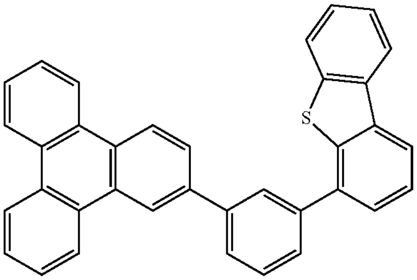
,
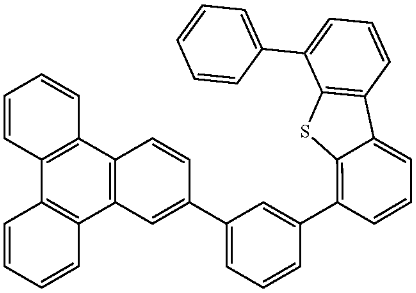
,
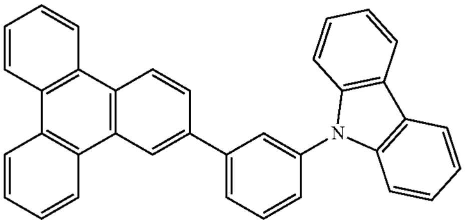
,
-continued
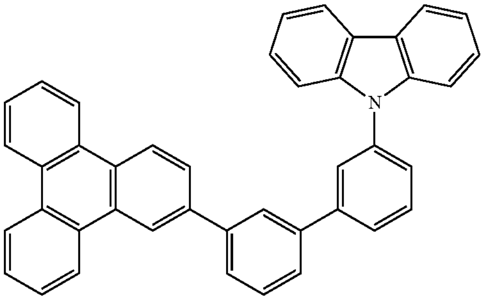
,
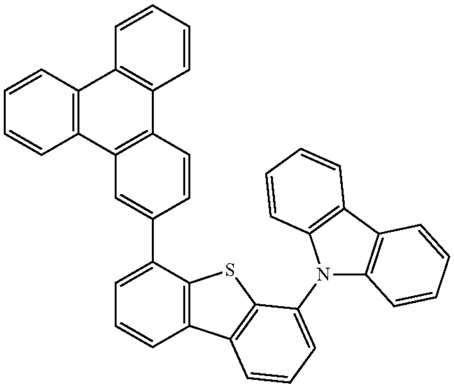
,
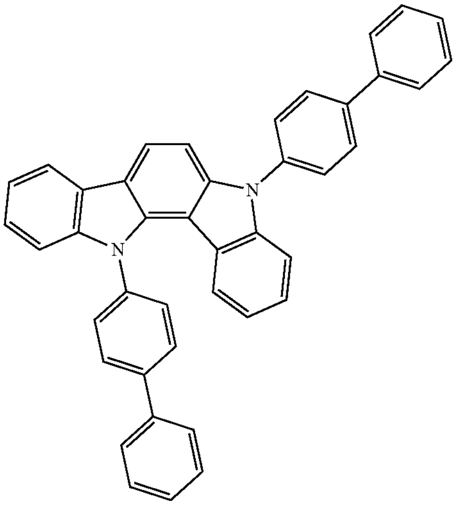
, -continued
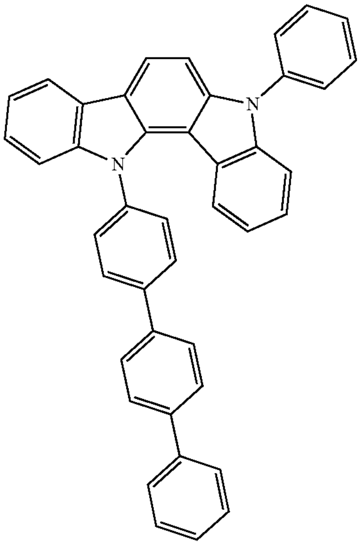
,
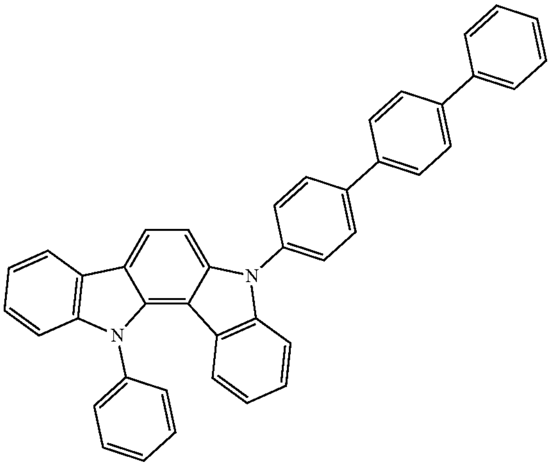
,
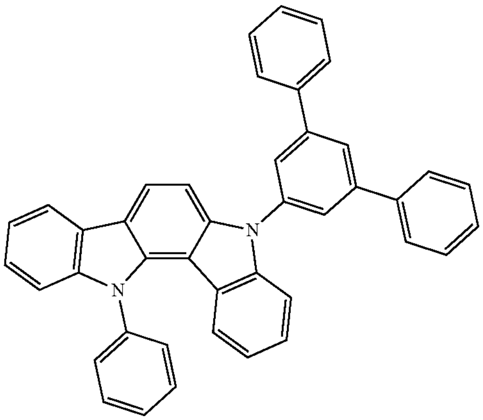
,
-continued
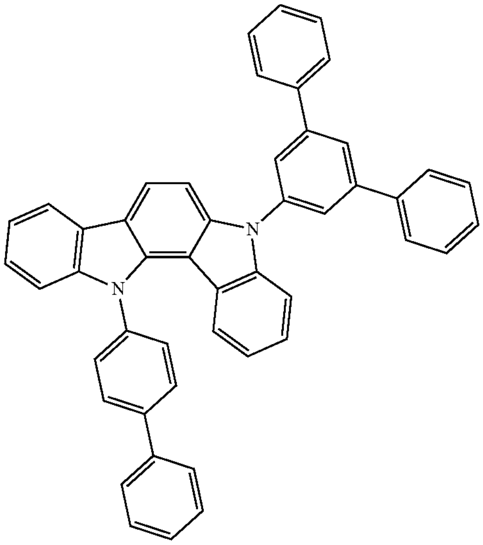
,
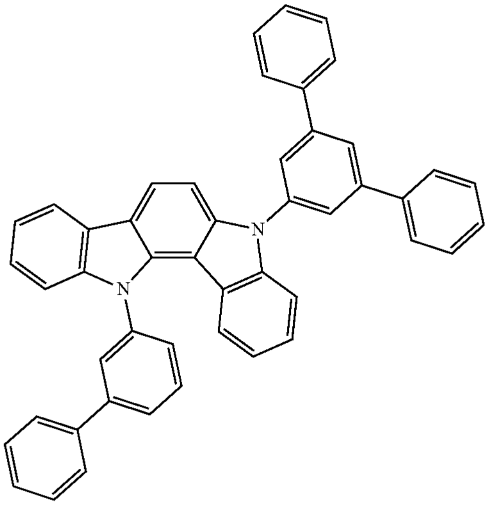
,
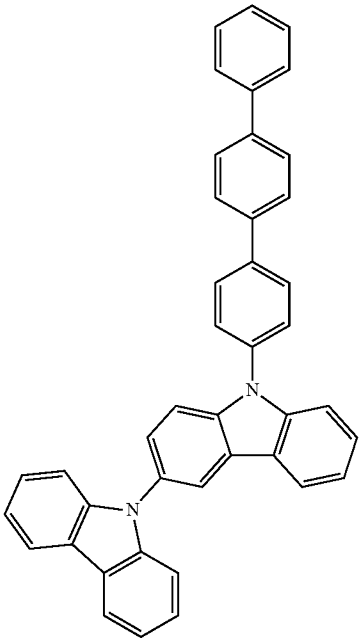
, -continued
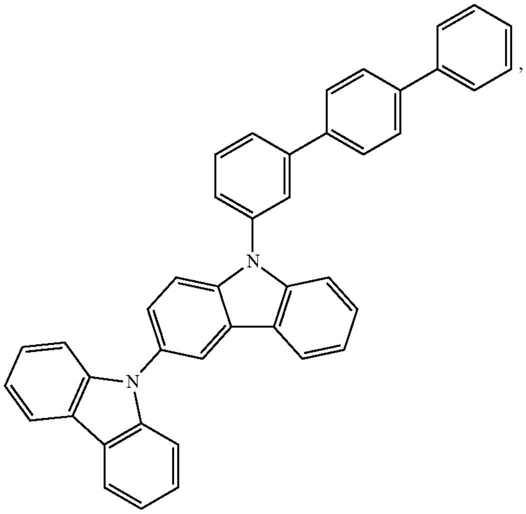
,
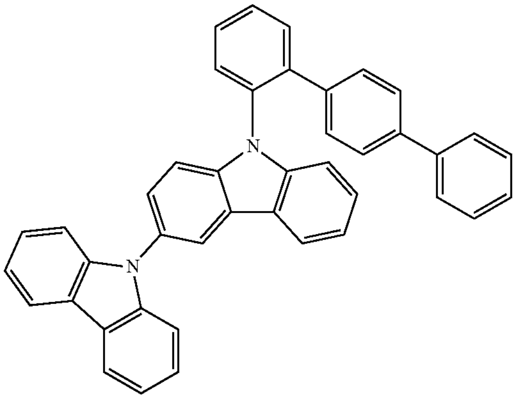
,
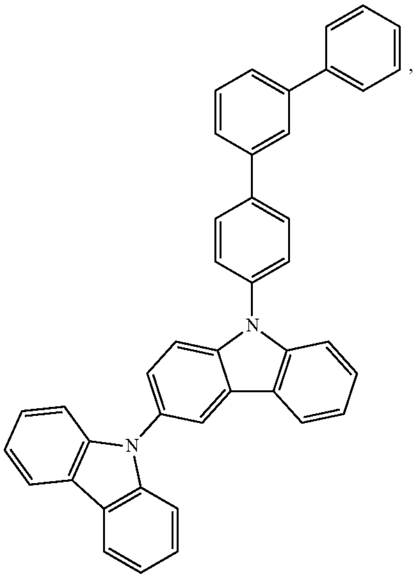
,
-continued
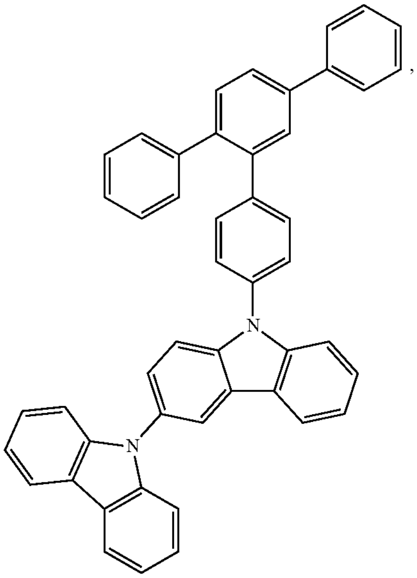
,
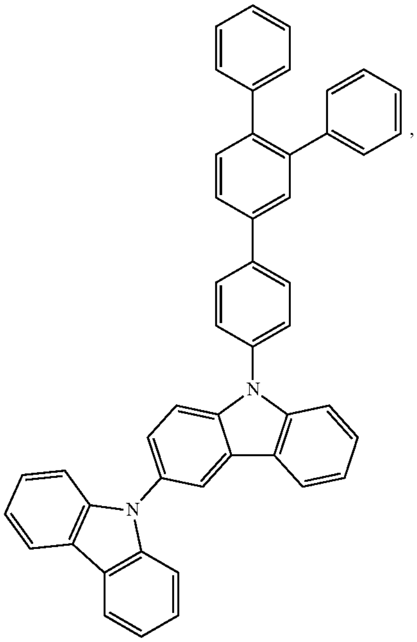
, -continued
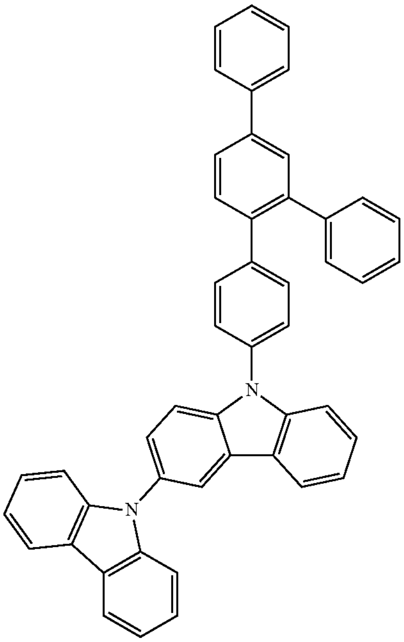
,
-continued
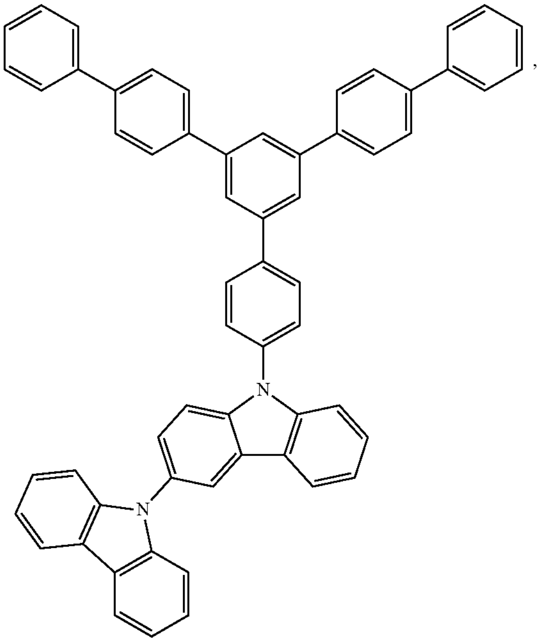
,
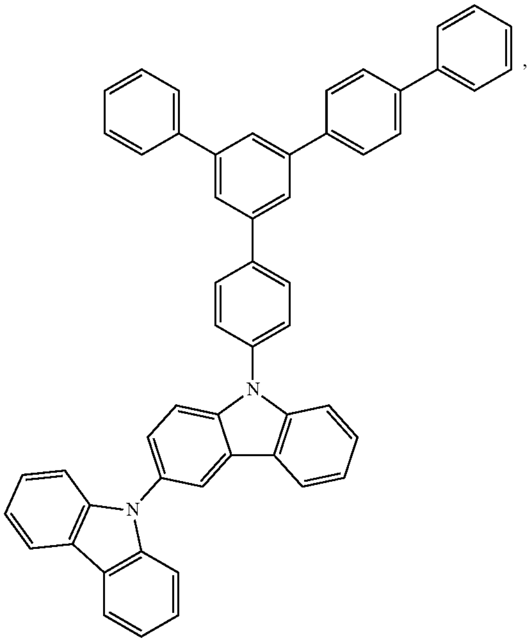
,
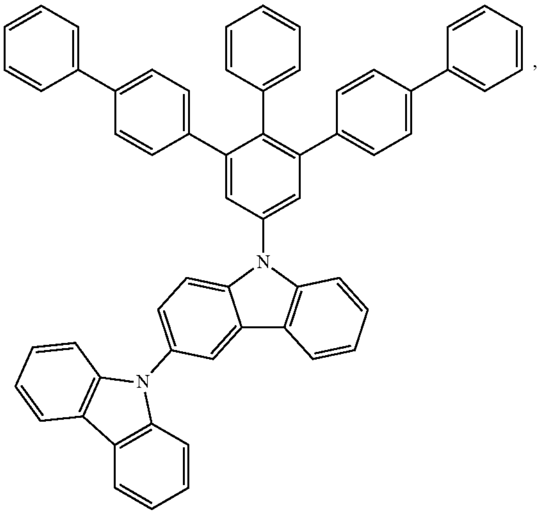
, -continued
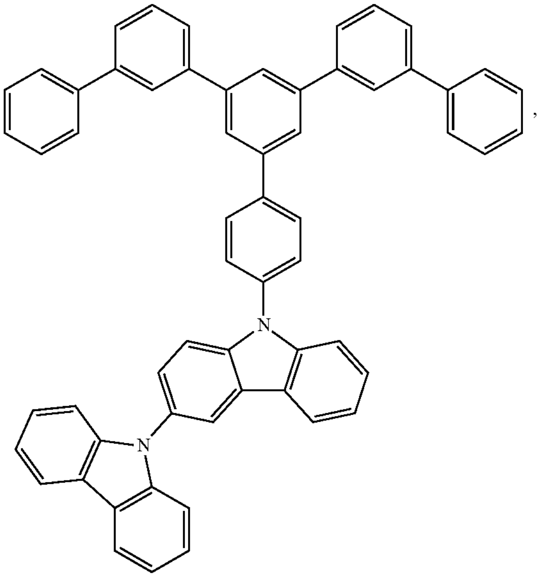
-continued
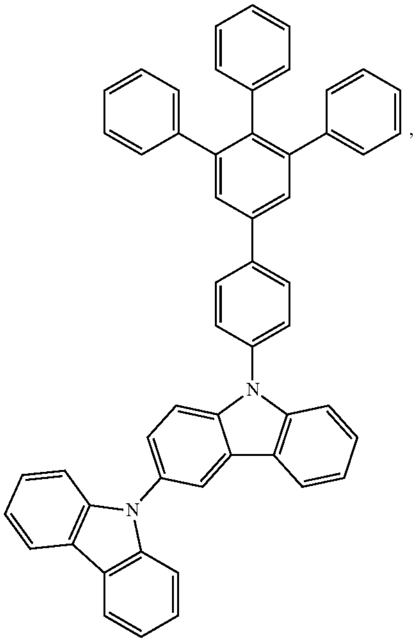
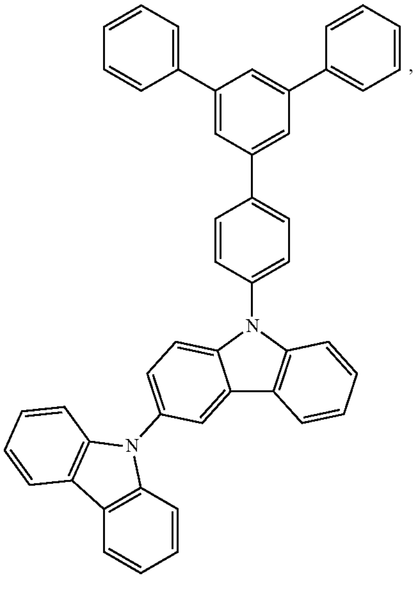
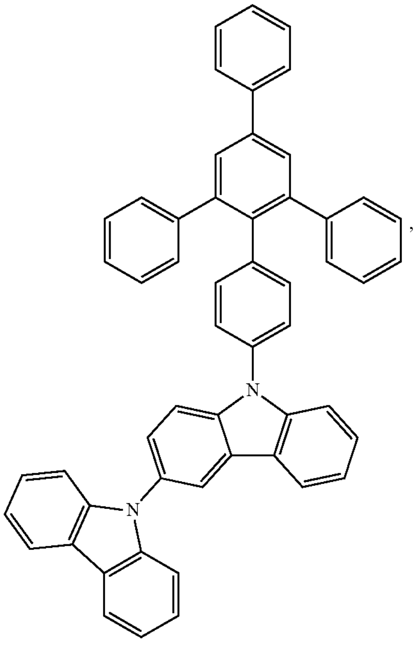

-continued
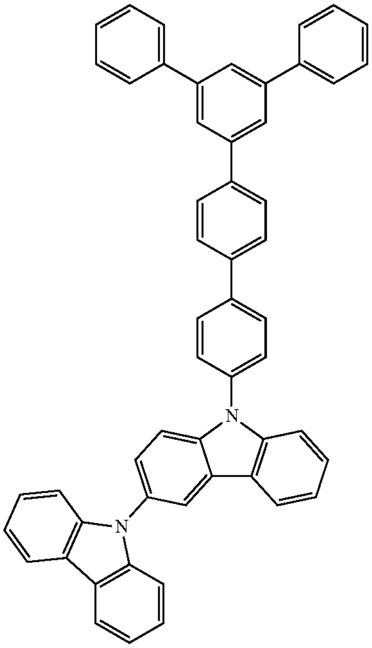
,
-continued
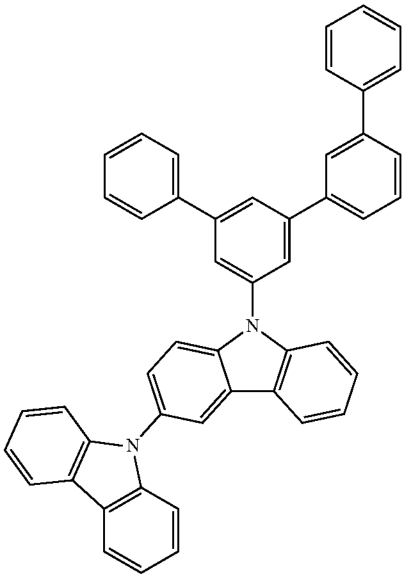
,
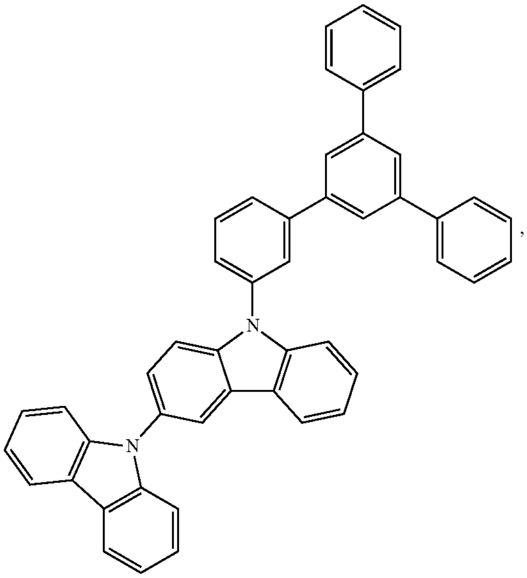
,
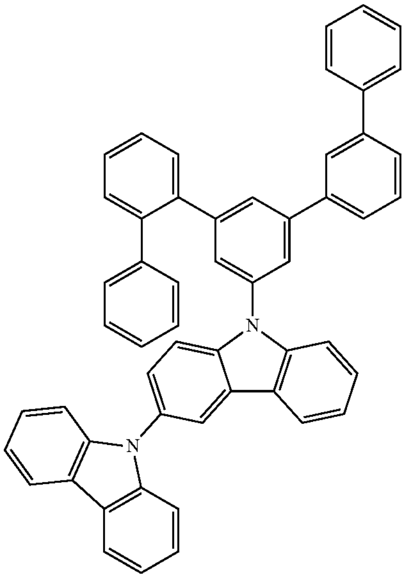
, -continued
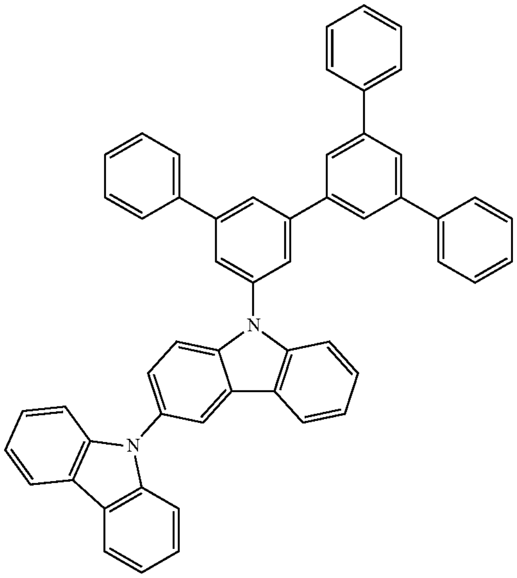
,
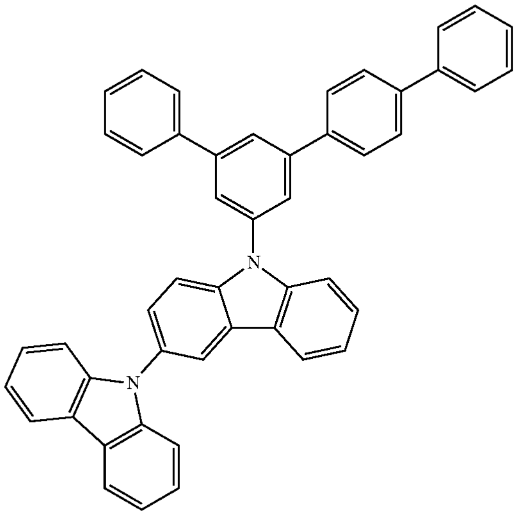
,
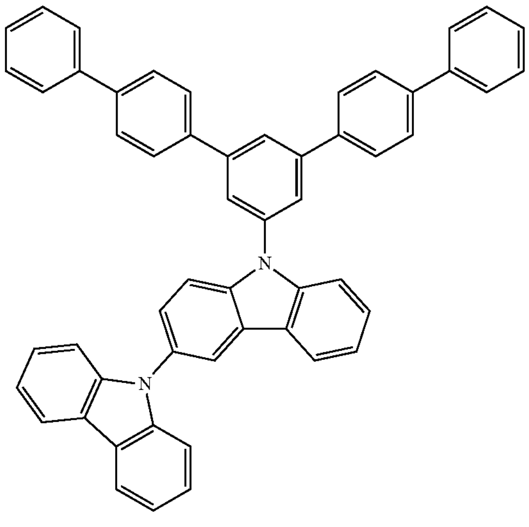
,
-continued
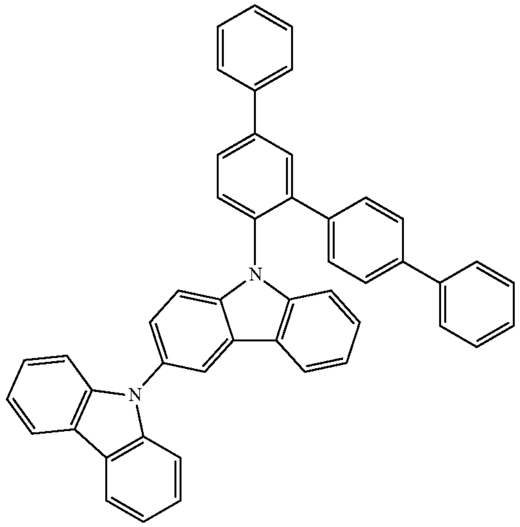
,
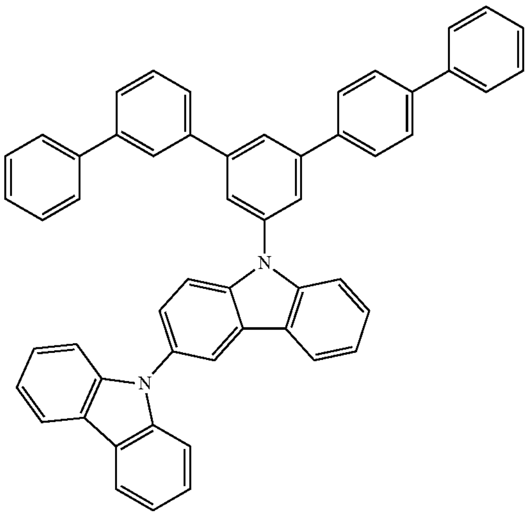
,
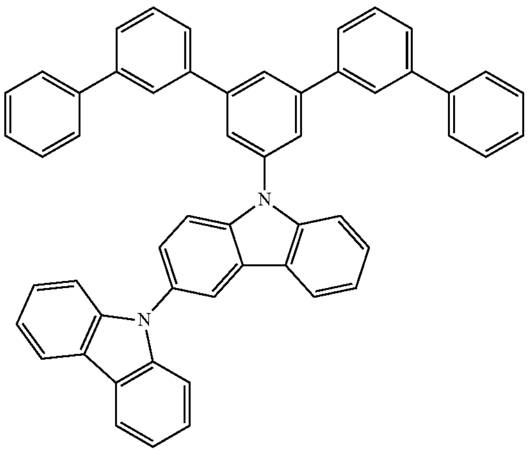
, -continued
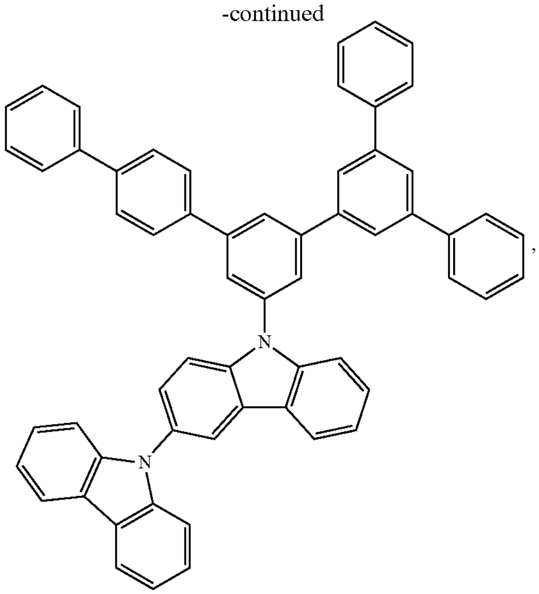
,
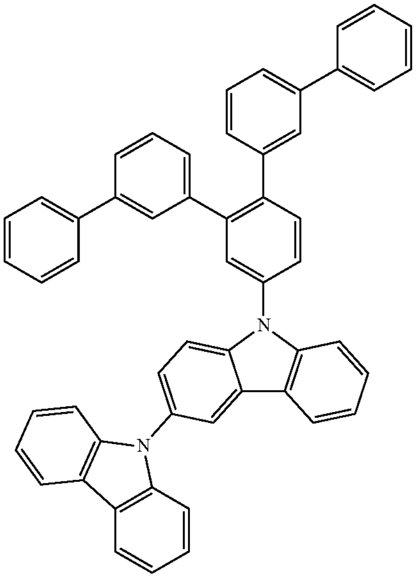
,
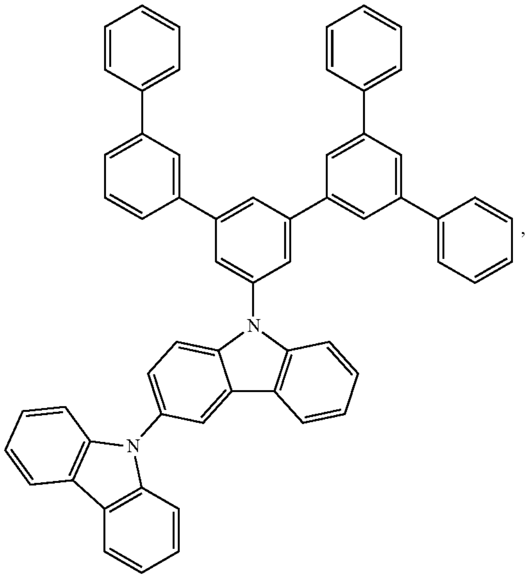
,
-continued
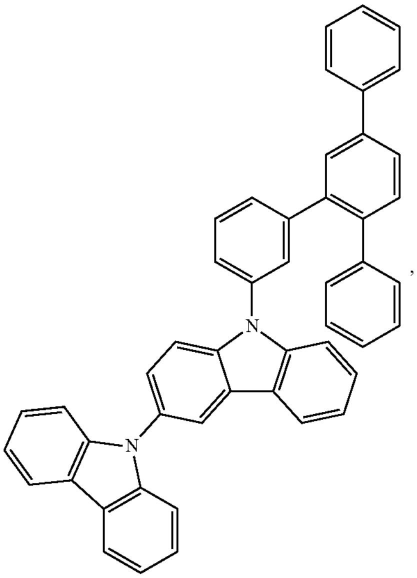
,
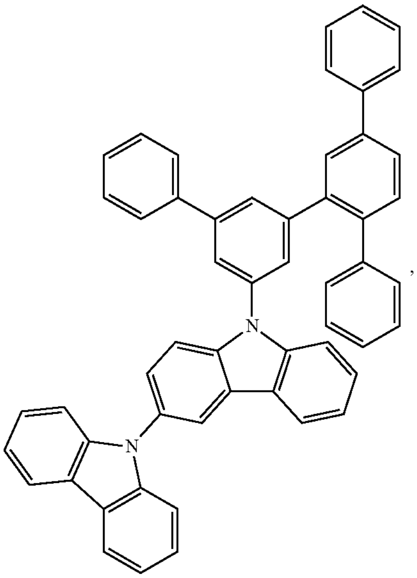
, -continued
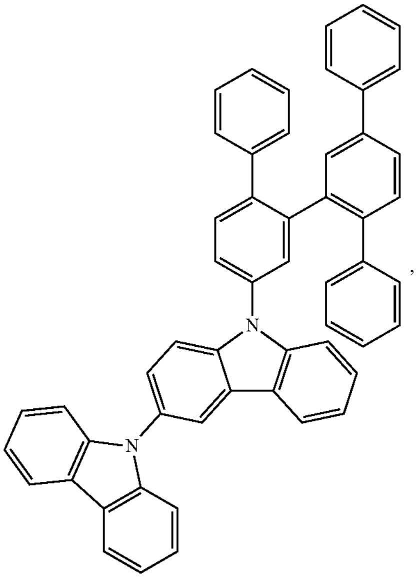
,
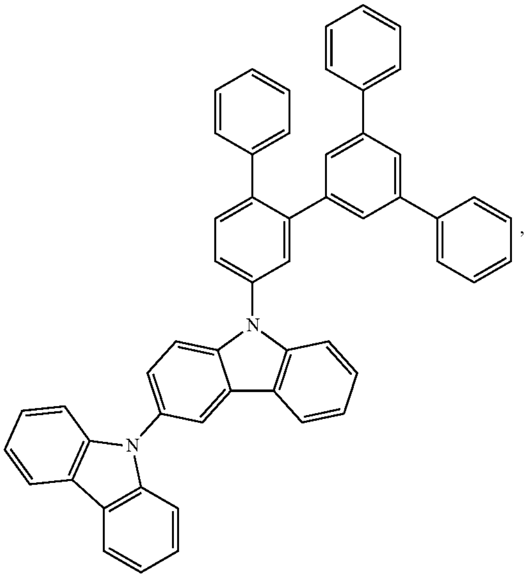
,
-continued
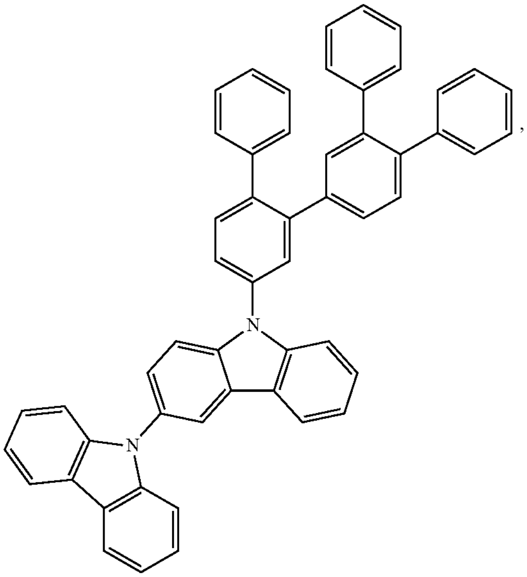
,
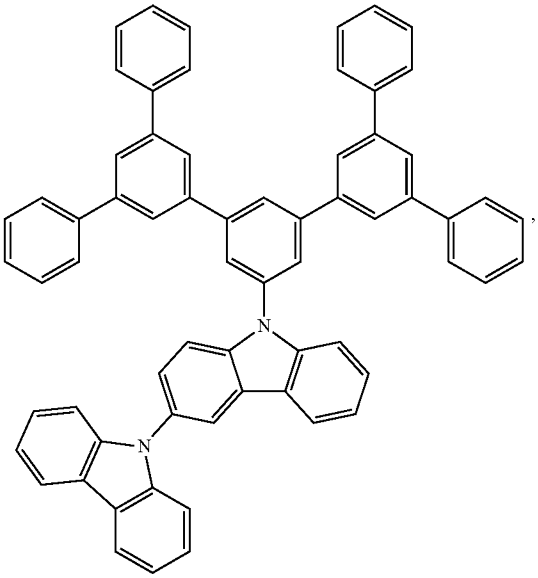
,
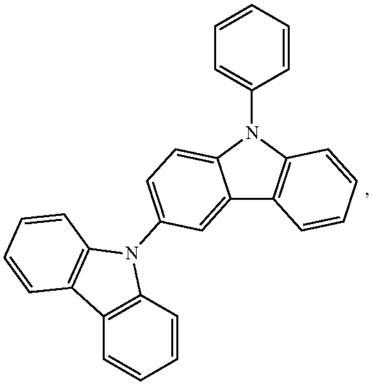
, -continued
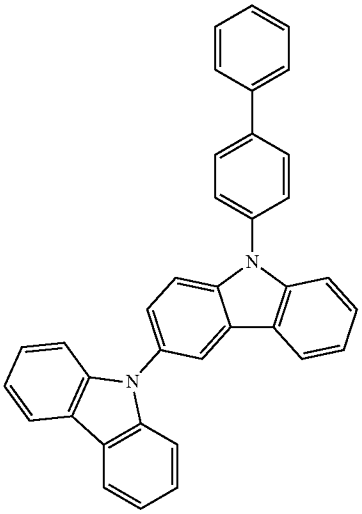
,
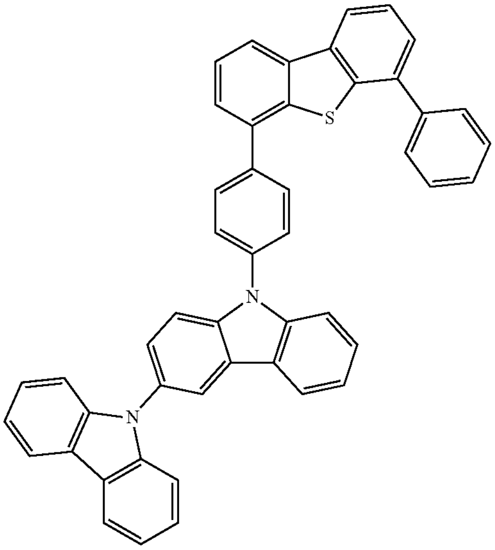
,
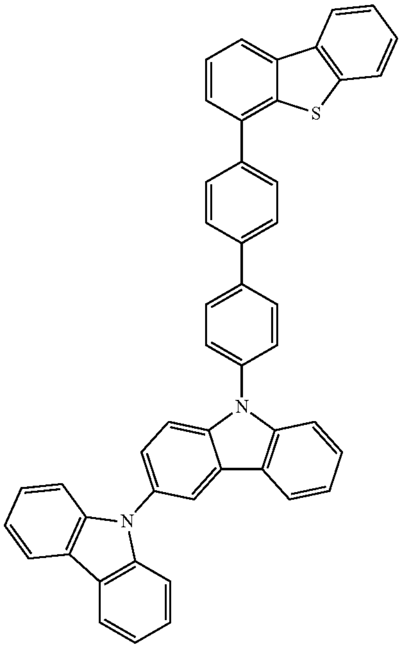
,
-continued
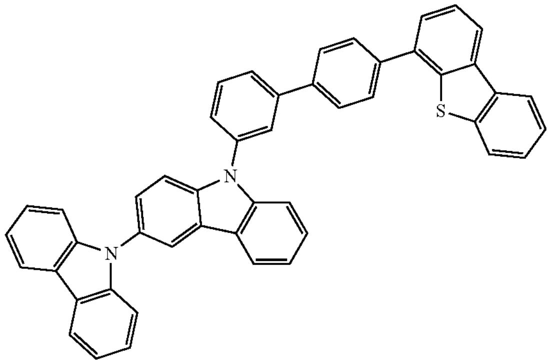
,
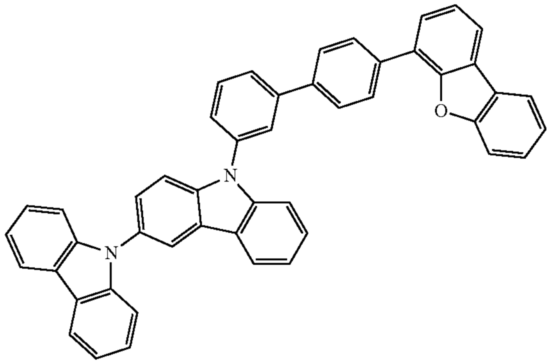
,
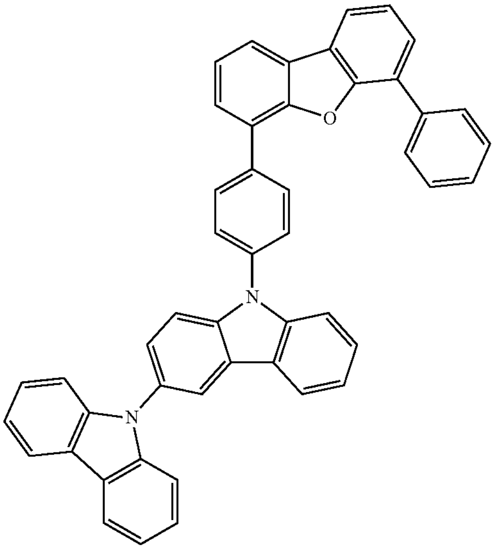
, -continued
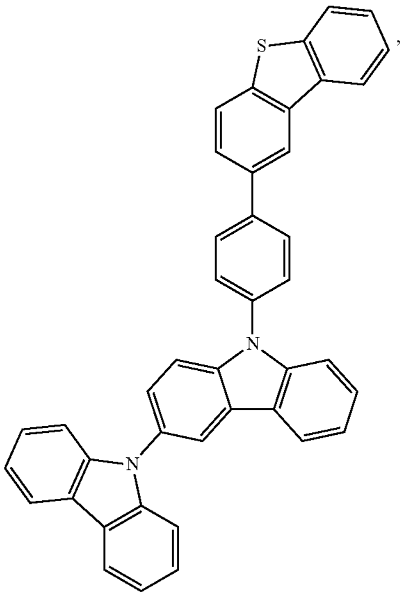
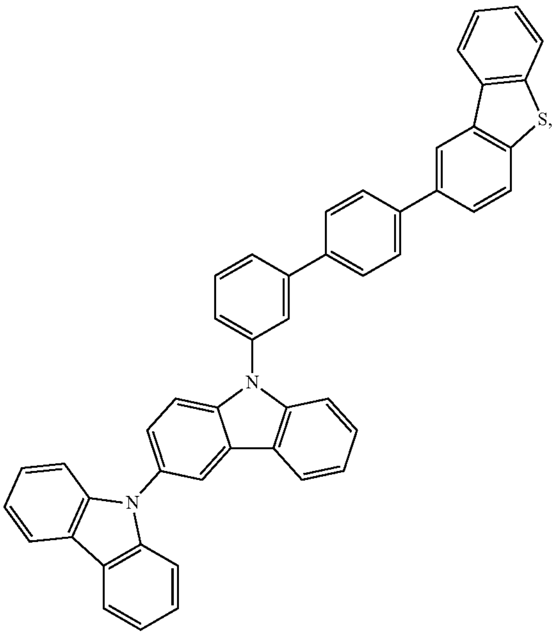
-continued
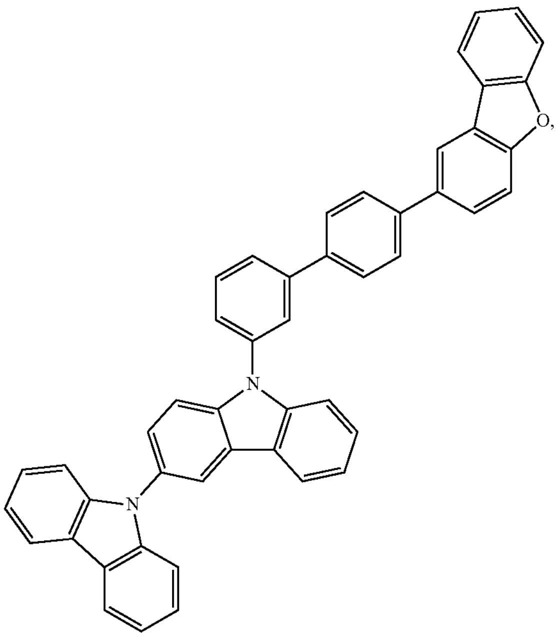
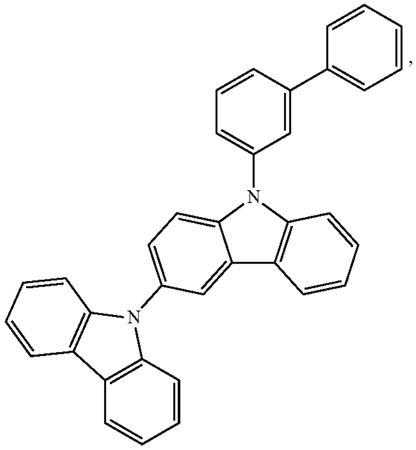
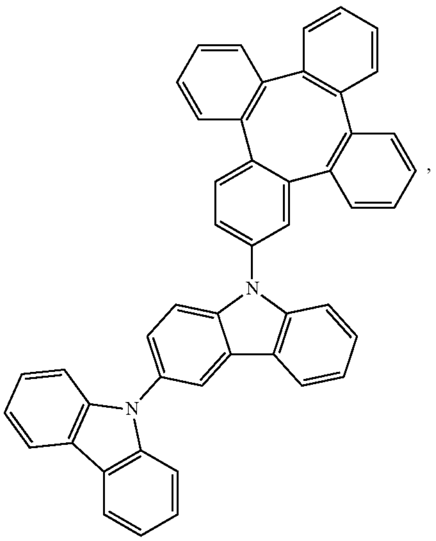

-continued
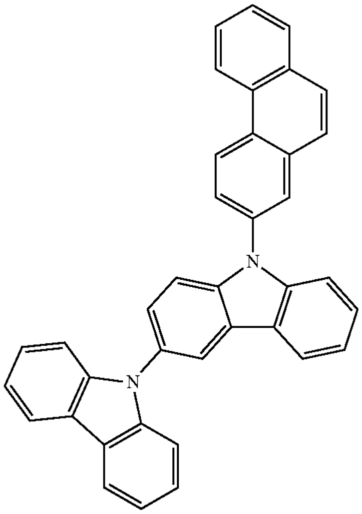
,
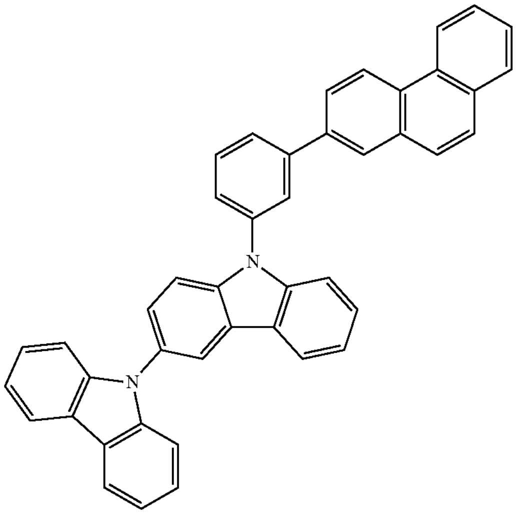
,
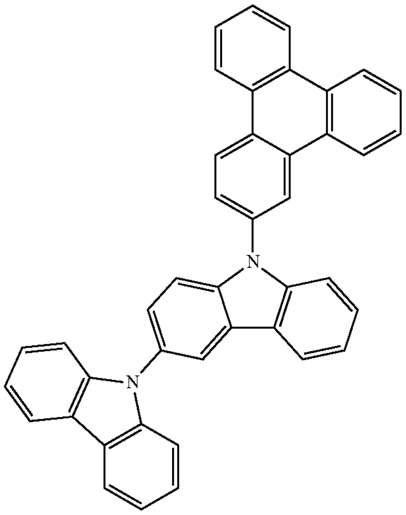
,
-continued
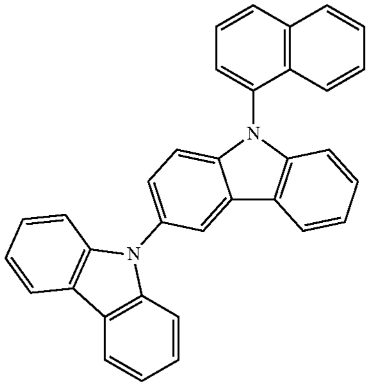
,
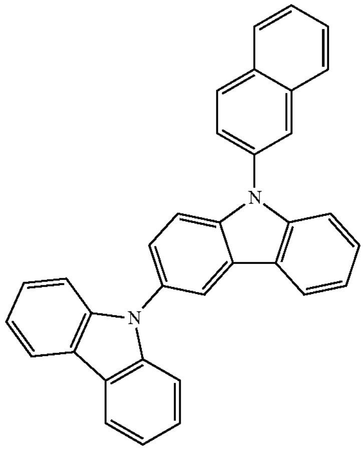
,
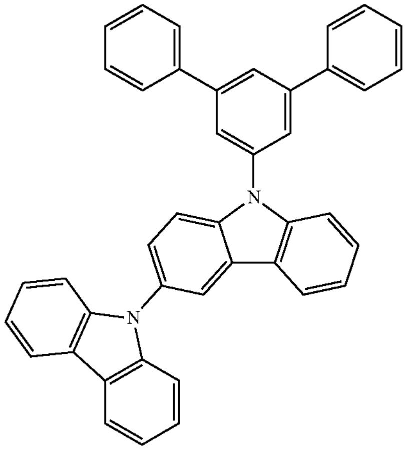
,
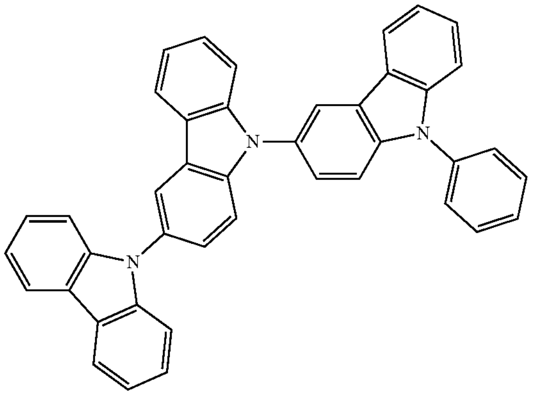
, -continued
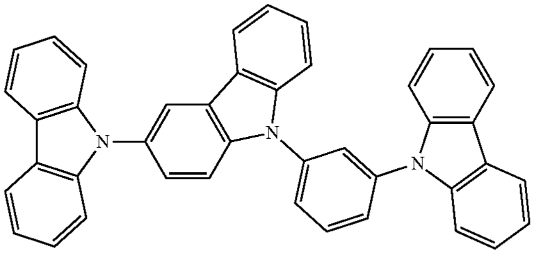
,
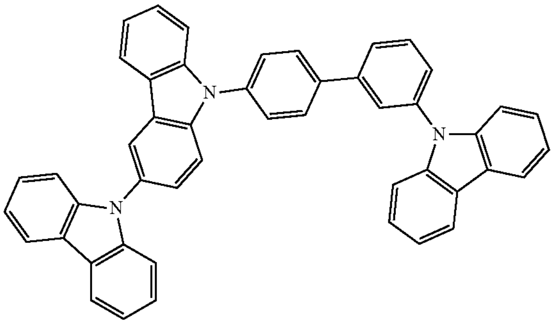
,
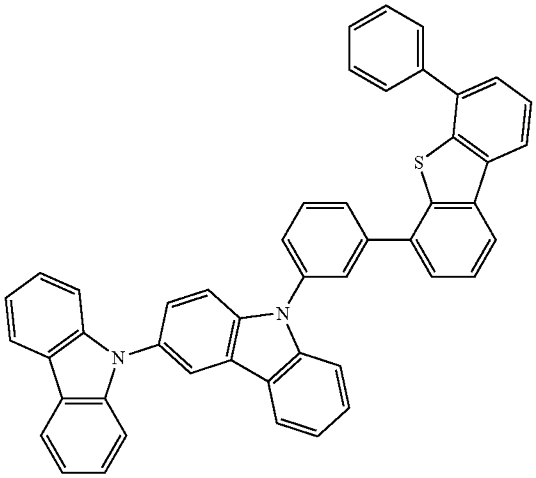
,
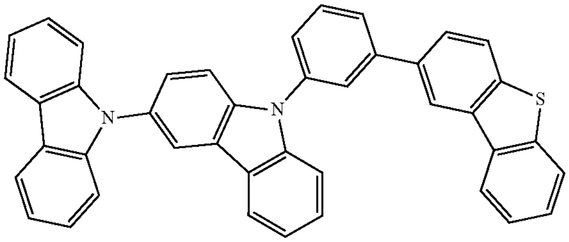
,
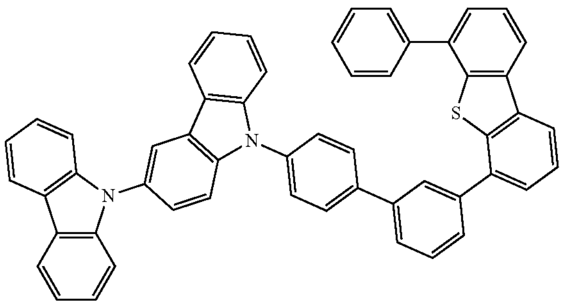
,
-continued
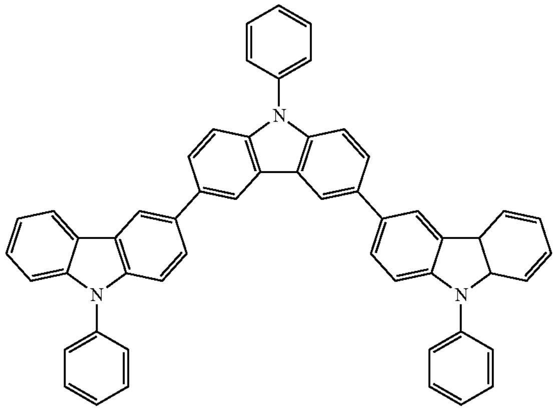
,
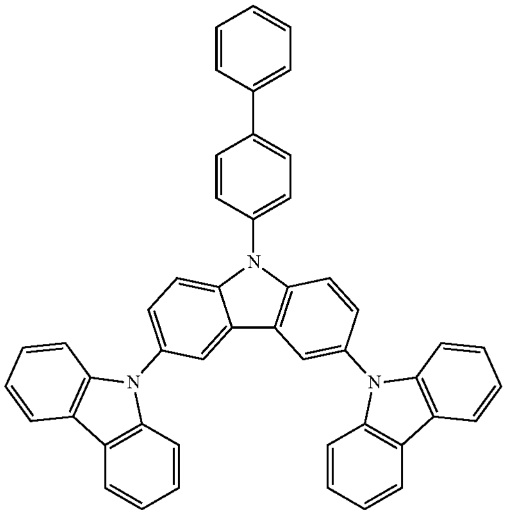
,
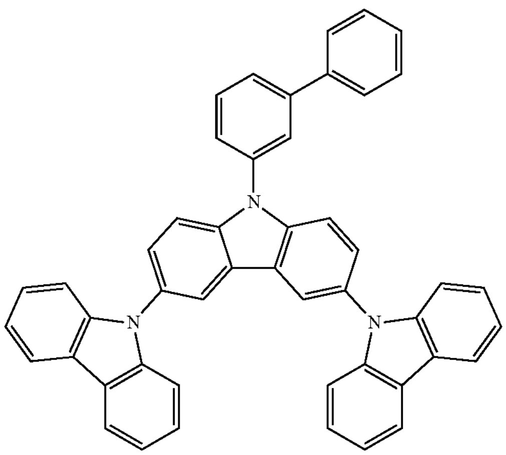
, -continued
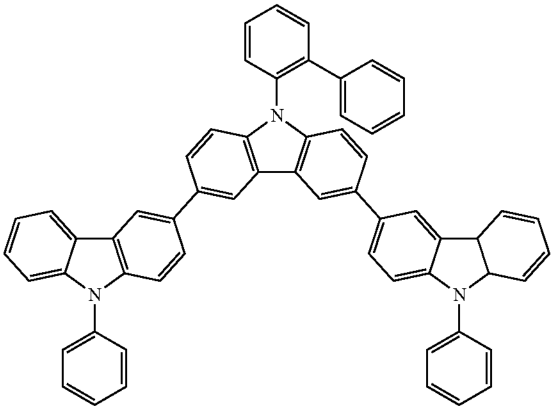
,
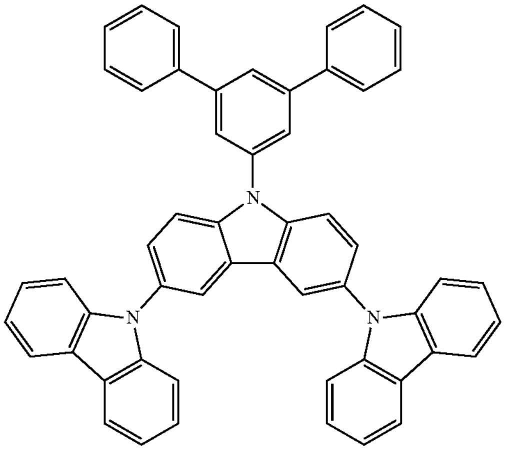
,
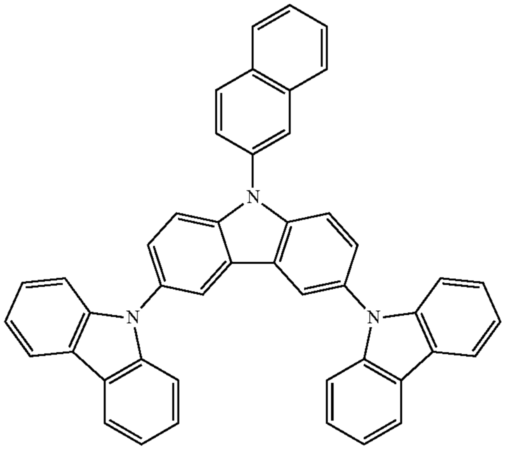
,
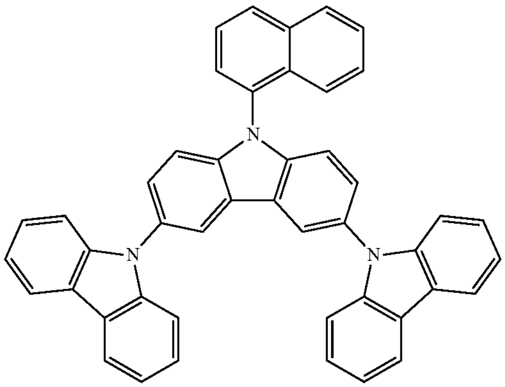
,
-continued
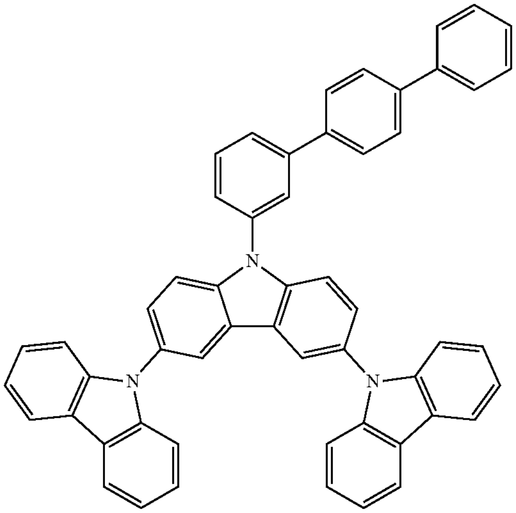
,
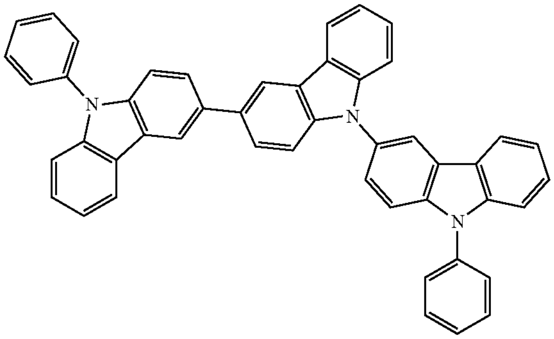
,
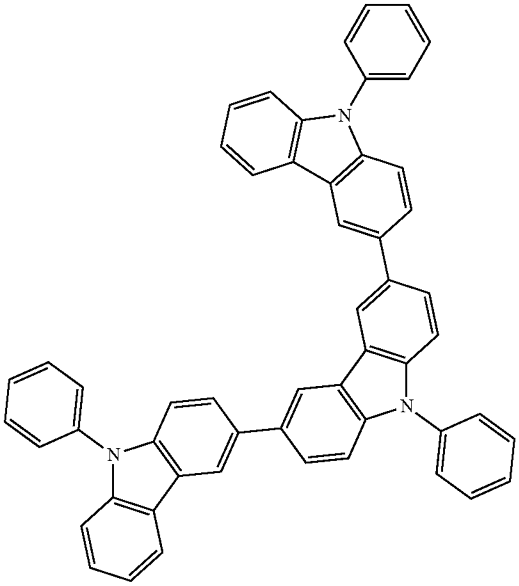
, -continued
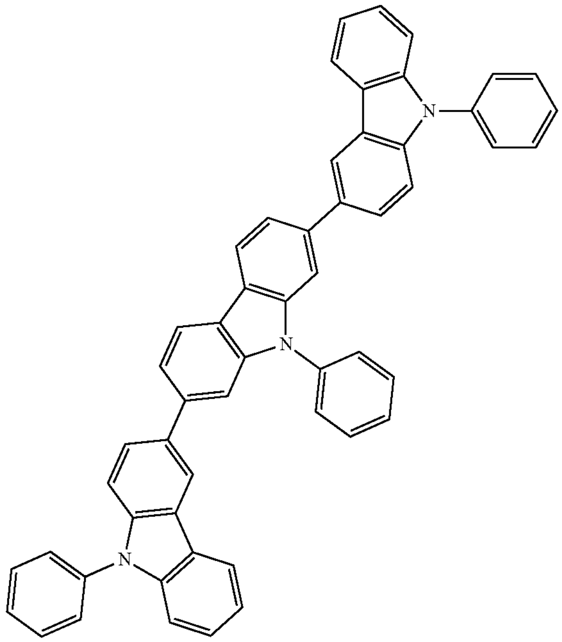
,
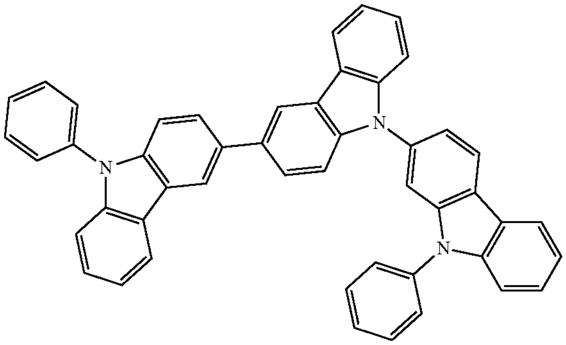
,
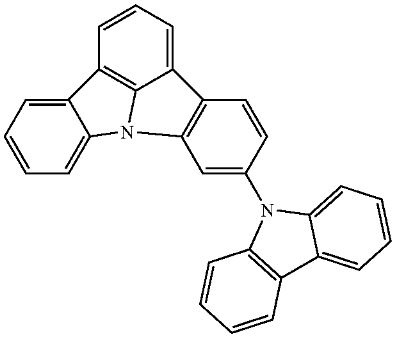
,
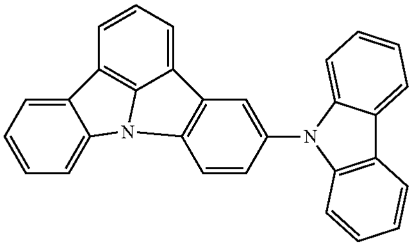
,
-continued
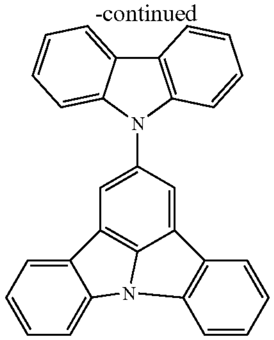
,
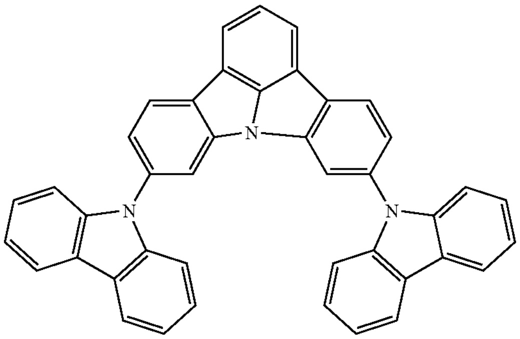
,
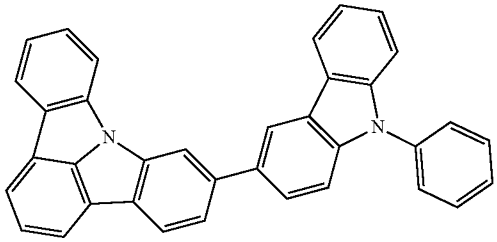
,
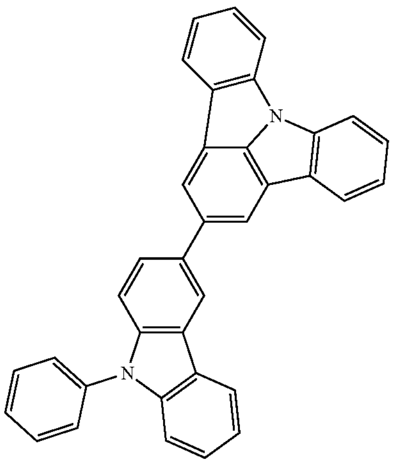
, -continued
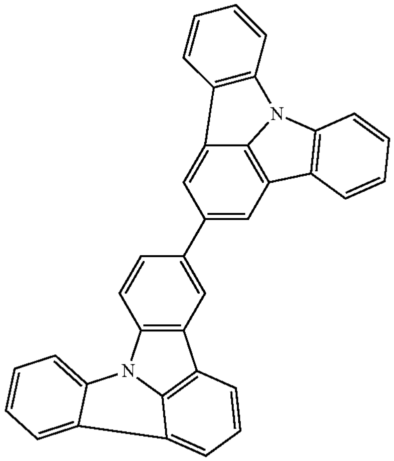
,
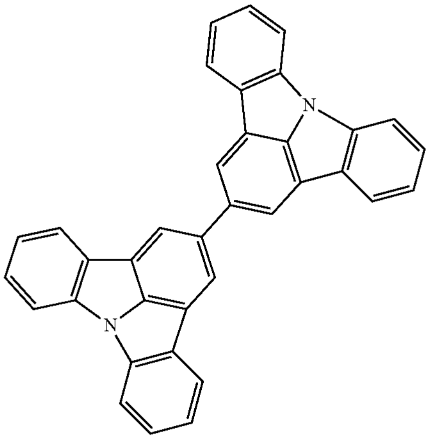
,
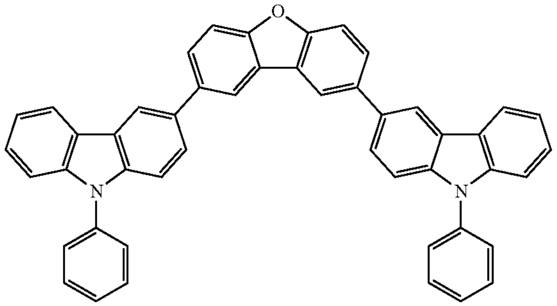
,
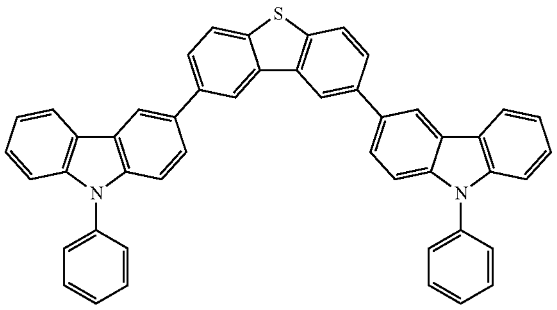
,
-continued
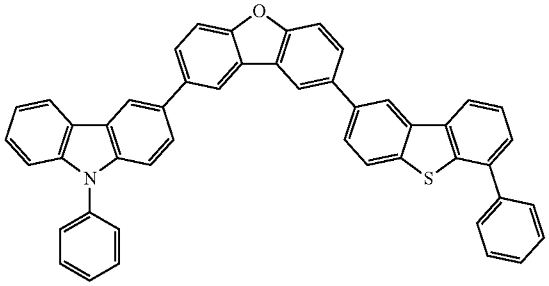
,
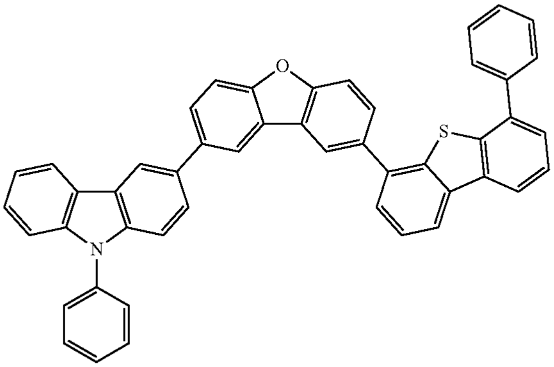
,
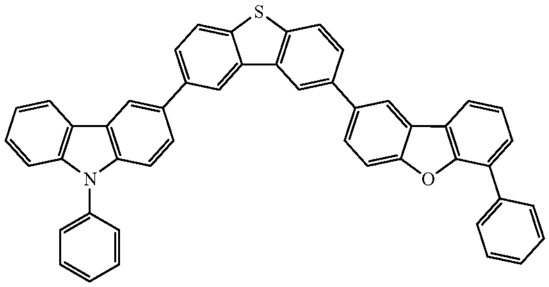
,
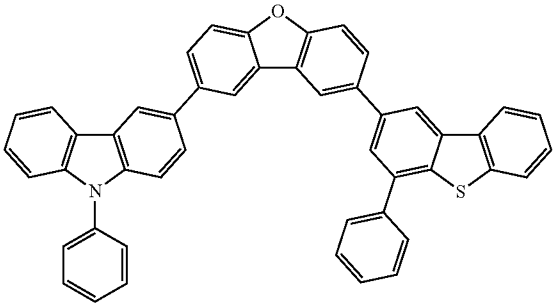
,
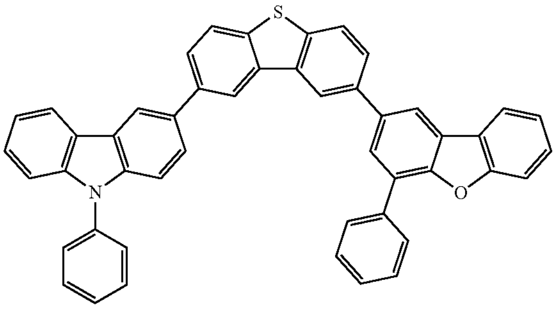

-continued

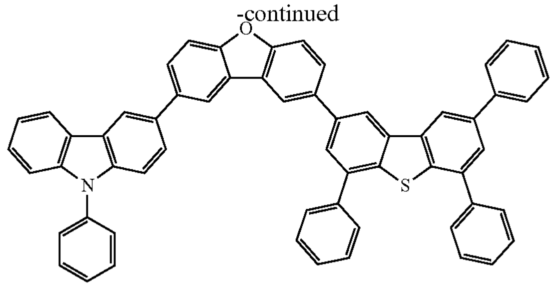

,

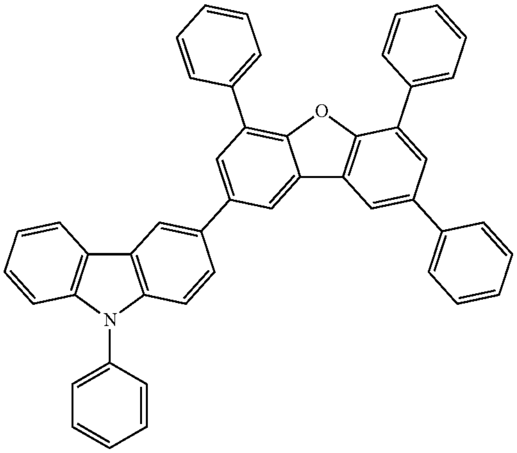

,

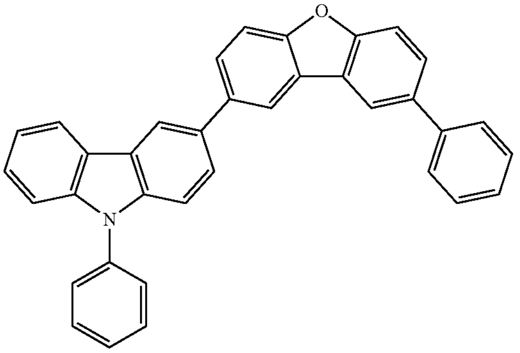

, and

-continued

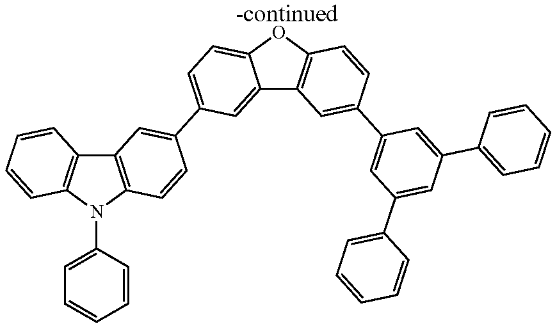

;

wherein:

each of $R^{A'}$, $R^B$, $R^C$, $R^D$, $R^I$, $R^J$, $R^K$, $R^L$, $R^M$, $R^N$, $R^O$, $R^P$, $R^Q$, $R^R$, $R^S$, $R^T$, $R^U$, $R^V$, and $R^W$ represent mono to the maximum allowable substitution, or no substitution;

each of $Ar^2$ and $Ar^4$ is a linker independently selected from the group consisting of a direct bond, aryl, and heteroaryl;

each of $X^1$ and $Y^1$ is independently selected from the group consisting of $BR_{e'}$, $NR_{e'}$, $PR_{e'}$, O, S, Se, C═O, S═O, $SO_2$, $CR_{e'}R_{f'}$, $SiR_{e'}R_{f'}$, and $GeR_{e'}R_{f'}$; and each $Ar^3$, $R^{4'}$, $R^{5'}$, $R^{6'}$, $R^{7'}$, $R^{8'}$, $R_{e'}$, $R_{f'}$, $R^{A'}$, $R^B$, $R^C$, $R^D$, $R^I$, $R^J$, $R^K$, $R^L$, $R^M$, $R^N$, $R^O$, $R^P$, $R^Q$, $R^R$, $R^S$, $R^T$, $R^U$, $R^V$, and $R^W$ is independently a hydrogen or a substituent selected from the group consisting of deuterium, halogen, alkyl, cycloalkyl, heteroalkyl, heterocycloalkyl, boryl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof.

* * * * *